US012636250B2

(12) United States Patent 
Tussey et al.

(10) Patent No.: US 12,636,250 B2
(45) Date of Patent: May 26, 2026

(54) MICRONEEDLE ARRAY PATCHES (MAPs), SYSTEMS, AND METHODS FOR MANUFACTURING AND USING SAME

(71) Applicant: Terrestrial Bio, Inc., Woburn, MA (US)

(72) Inventors: Lynda Tussey, Winston-Salem, NC (US); Matthew Dirckx, Medford, MA (US); Rebecca Crawley, Cambridge, MA (US); Bruce Kerwin, Cambridge, MA (US); Himabindu Nandivada Bailey, Cambridge, MA (US); Jane Maeng, Cambridge, MA (US); John Spiridigliozzi, Boston, MA (US); Jonathan A. Kluge, Cambridge, MA (US); Michael Isidoro, New Bedford, MA (US); Logan McElhinney, Cambridge, MA (US); Matthew Vargas, San Jose, CA (US)

(73) Assignee: Terrestrial Bio, Inc., Woburn, MA (US)

( * ) Notice: Subject to any disclaimer, the term of this patent is extended or adjusted under 35 U.S.C. 154(b) by 0 days.

(21) Appl. No.: 19/071,625

(22) Filed: Mar. 5, 2025

(65) Prior Publication Data

US 2025/0248925 A1 Aug. 7, 2025

Related U.S. Application Data

(63) Continuation of application No. 19/002,632, filed on Dec. 26, 2024.

(Continued)

(51) Int. Cl.
| | |
|---|---|
| *A61K 9/00* | (2006.01) |
| *A61K 31/198* | (2006.01) |

(Continued)

(52) U.S. Cl.
CPC .......... *A61K 9/0021* (2013.01); *A61K 31/198* (2013.01); *A61K 38/26* (2013.01); *A61K 47/32* (2013.01)

(58) Field of Classification Search
None
See application file for complete search history.

(56) References Cited

U.S. PATENT DOCUMENTS

| | | | |
|---|---|---|---|
| 387,413 A | 8/1888 | Griffin et al. | |
| 1,989,005 A | 1/1935 | Fink et al. | |

(Continued)

FOREIGN PATENT DOCUMENTS

| | | |
|---|---|---|
| AU | 2005228145 A1 | 10/2005 |
| AU | 2008209537 A1 | 7/2008 |

(Continued)

OTHER PUBLICATIONS

Ando et al. (Mechanical Chacterization of Dissolving Microneedles: Factors affecting physical strength of needles, Pharmaucetics, 2024, 16, 200). (Year: 2024).*

(Continued)

*Primary Examiner* — Melissa S Mercier
(74) *Attorney, Agent, or Firm* — McCarter & English, LLP; Maneesh Gulati

(57) ABSTRACT

Dispensable formulations, microneedles, microarray patches (MAPs), and systems that can facilitate simple, substantially pain-free, and consistent delivery of a wide range of active pharmaceutical ingredients (APIs) and doses, as well as methods of manufacturing and using the same are described herein.

30 Claims, 55 Drawing Sheets

Specification includes a Sequence Listing.

application tips disengage tips dissolve

Related U.S. Application Data

(60) Provisional application No. 63/723,023, filed on Nov. 20, 2024, provisional application No. 63/712,367, filed on Oct. 25, 2024, provisional application No. 63/701,470, filed on Sep. 30, 2024, provisional application No. 63/683,233, filed on Aug. 14, 2024, provisional application No. 63/623,084, filed on Jan. 19, 2024.

(51) Int. Cl.
 *A61K 38/26*       (2006.01)
 *A61K 47/32*       (2006.01)

(56) References Cited

U.S. PATENT DOCUMENTS

| | | |
|---|---|---|
| 3,270,960 A | 9/1966 | Phillips |
| 3,773,919 A | 11/1973 | Boswell et al. |
| 3,832,253 A | 8/1974 | DiPalma |
| 3,854,480 A | 12/1974 | Zaffaroni |
| 4,233,212 A | 11/1980 | Otoi et al. |
| 4,452,775 A | 6/1984 | Kent |
| 4,667,014 A | 5/1987 | Nestor, Jr. et al. |
| 4,675,189 A | 6/1987 | Kent et al. |
| 4,748,034 A | 5/1988 | de Rham |
| 4,787,738 A | 11/1988 | Joffe |
| 4,798,722 A | 1/1989 | Edman et al. |
| 4,806,355 A | 2/1989 | Goosen et al. |
| 4,818,291 A | 4/1989 | Iwatsuki et al. |
| 4,820,418 A | 4/1989 | Hirotsu et al. |
| 5,015,476 A | 5/1991 | Cochrum et al. |
| 5,047,507 A | 9/1991 | Buchegger et al. |
| 5,075,109 A | 12/1991 | Tice et al. |
| 5,093,489 A | 3/1992 | Diamantoglou |
| 5,118,666 A | 6/1992 | Habener |
| 5,120,712 A | 6/1992 | Habener |
| 5,133,974 A | 7/1992 | Paradissis et al. |
| 5,239,660 A | 8/1993 | Ooi |
| 5,245,012 A | 9/1993 | Lombari et al. |
| 5,252,285 A | 10/1993 | Lock |
| 5,263,992 A | 11/1993 | Guire |
| 5,270,419 A | 12/1993 | Domb |
| 5,290,494 A | 3/1994 | Coombes et al. |
| 5,346,481 A | 9/1994 | Bunin |
| 5,407,686 A | 4/1995 | Patel et al. |
| 5,576,881 A | 11/1996 | Doerr et al. |
| 5,606,019 A | 2/1997 | Cappello |
| 5,631,224 A | 5/1997 | Efendic et al. |
| 5,728,810 A | 3/1998 | Lewis et al. |
| 5,736,152 A | 4/1998 | Dunn |
| 5,766,620 A | 6/1998 | Heiber et al. |
| 5,770,193 A | 6/1998 | Vacanti et al. |
| 5,797,898 A | 8/1998 | Santini, Jr. et al. |
| 5,849,322 A | 12/1998 | Ebert et al. |
| 5,891,734 A | 4/1999 | Gill et al. |
| 5,900,238 A | 5/1999 | Gombotz et al. |
| 5,902,800 A | 5/1999 | Green et al. |
| 5,932,462 A | 8/1999 | Harris et al. |
| 5,994,099 A | 11/1999 | Lewis et al. |
| 6,009,753 A | 1/2000 | Tsang et al. |
| 6,106,816 A | 8/2000 | Hitchen |
| 6,110,590 A | 8/2000 | Zarkoob et al. |
| 6,123,819 A | 9/2000 | Peeters |
| 6,127,143 A | 10/2000 | Gunasekaran |
| 6,175,053 B1 | 1/2001 | Tsubouchi |
| 6,245,537 B1 | 6/2001 | Williams et al. |
| RE37,302 E | 7/2001 | Efendic et al. |
| 6,267,776 B1 | 7/2001 | O'Connell |
| 6,268,343 B1 | 7/2001 | Knudsen et al. |
| 6,302,848 B1 | 10/2001 | Larson et al. |
| 6,310,188 B1 | 10/2001 | Mukherjee |
| 6,325,810 B1 | 12/2001 | Hamilton et al. |
| 6,334,856 B1 | 1/2002 | Allen et al. |
| 6,337,198 B1 | 1/2002 | Levene et al. |
| 6,358,924 B1 | 3/2002 | Hoffmann |
| 6,372,244 B1 | 4/2002 | Antanavich et al. |
| 6,379,690 B2 | 4/2002 | Blanchard et al. |
| 6,387,413 B1 | 5/2002 | Miyata et al. |
| 6,395,734 B1 | 5/2002 | Tang et al. |
| 6,423,252 B1 | 7/2002 | Chun et al. |
| 6,451,987 B1 | 9/2002 | Staby |
| 6,503,231 B1 | 1/2003 | Prausnitz et al. |
| 6,592,623 B1 | 7/2003 | Bowlin et al. |
| 6,611,707 B1 | 8/2003 | Prausnitz et al. |
| 6,669,683 B2 | 12/2003 | Santini, Jr. et al. |
| 6,743,211 B1 | 6/2004 | Prausnitz et al. |
| 6,815,427 B2 | 11/2004 | Tsubouchi et al. |
| 6,844,321 B2 | 1/2005 | Arentsen |
| 6,849,708 B1 | 2/2005 | Habener |
| 6,902,932 B2 | 6/2005 | Altman et al. |
| 6,998,387 B1 | 2/2006 | Goke et al. |
| 7,041,797 B2 | 5/2006 | Vollrath |
| 7,052,488 B2 | 5/2006 | Uhland |
| 7,057,023 B2 | 6/2006 | Islam et al. |
| 7,060,260 B2 | 6/2006 | Fahnestock et al. |
| 7,226,439 B2 | 6/2007 | Prausnitz et al. |
| 7,285,637 B2 | 10/2007 | Armato et al. |
| 7,344,499 B1 | 3/2008 | Prausnitz et al. |
| 7,578,954 B2 | 8/2009 | Gartstein et al. |
| 7,582,080 B2 | 9/2009 | Santini, Jr. et al. |
| 7,595,293 B2 | 9/2009 | Engelund et al. |
| 7,611,481 B2 | 11/2009 | Cleary et al. |
| 7,635,755 B2 | 12/2009 | Kaplan et al. |
| 7,662,409 B2 | 2/2010 | Masters |
| 7,674,882 B2 | 3/2010 | Kaplan et al. |
| 7,727,575 B2 | 6/2010 | Kaplan et al. |
| 7,751,985 B2 | 7/2010 | Li et al. |
| 7,762,994 B2 | 7/2010 | Klint et al. |
| 7,763,203 B2 | 7/2010 | Arias et al. |
| 7,828,827 B2 | 11/2010 | Gartstein et al. |
| 7,842,780 B2 | 11/2010 | Kaplan et al. |
| 7,914,480 B2 | 3/2011 | Cleary et al. |
| 7,918,814 B2 | 4/2011 | Prausnitz et al. |
| 7,960,509 B2 | 6/2011 | Kaplan et al. |
| 8,071,722 B2 | 12/2011 | Kaplan et al. |
| 8,114,833 B2 | 2/2012 | Pedersen et al. |
| 8,114,959 B2 | 2/2012 | Juul-Mortensen |
| 8,129,343 B2 | 3/2012 | Lau et al. |
| 8,178,656 B2 | 5/2012 | Kaplan et al. |
| 8,187,616 B2 | 5/2012 | Wang et al. |
| 8,197,435 B2 | 6/2012 | Prausnitz et al. |
| 8,206,774 B2 | 6/2012 | Kaplan et al. |
| 8,257,324 B2 | 9/2012 | Prausnitz et al. |
| 8,318,159 B2 | 11/2012 | Adam et al. |
| 8,354,501 B2 | 1/2013 | Kaplan et al. |
| 8,361,617 B2 | 1/2013 | Kaplan et al. |
| 8,501,172 B2 | 8/2013 | Kaplan et al. |
| 8,506,530 B2 | 8/2013 | Laermer et al. |
| 8,506,980 B2 | 8/2013 | Takada |
| 8,530,625 B2 | 9/2013 | Kaplan et al. |
| 8,536,122 B2 | 9/2013 | Lau et al. |
| 8,614,293 B2 | 12/2013 | Kaplan et al. |
| 8,616,180 B2 | 12/2013 | Spitler et al. |
| 8,623,393 B2 | 1/2014 | Masters et al. |
| 8,636,713 B2 | 1/2014 | Prausnitz et al. |
| 8,684,969 B2 | 4/2014 | Moller et al. |
| 8,708,966 B2 | 4/2014 | Allen et al. |
| 8,742,069 B2 | 6/2014 | Kaplan et al. |
| 8,808,225 B2 | 8/2014 | Prausnitz et al. |
| 8,821,446 B2 | 9/2014 | Trautman et al. |
| 8,834,423 B2 | 9/2014 | Falo, Jr. et al. |
| 8,846,618 B2 | 9/2014 | Flink et al. |
| 8,911,749 B2 | 12/2014 | Ghartey-Tagoe et al. |
| 8,920,383 B2 | 12/2014 | Enggaard et al. |
| 9,040,073 B2 | 5/2015 | Boison et al. |
| 9,068,282 B2 | 6/2015 | Cannizzaro et al. |
| 9,084,840 B2 | 7/2015 | Kaplan et al. |
| 9,108,002 B2 | 8/2015 | Markussen |
| 9,114,238 B2 | 8/2015 | Singh et al. |
| 9,132,197 B2 | 9/2015 | Kaplan et al. |
| 9,132,239 B2 | 9/2015 | Moller et al. |
| 9,187,538 B2 | 11/2015 | Altman et al. |
| 9,233,067 B2 | 1/2016 | Lammel et al. |
| 9,278,123 B2 | 3/2016 | Sauerberg et al. |

(56)                    References Cited

U.S. PATENT DOCUMENTS

| | | |
|---|---|---|
| 9,302,903 B2 | 4/2016 | Park et al. |
| 9,339,545 B2 | 5/2016 | Prestrelski et al. |
| 9,452,280 B2 | 9/2016 | Singh et al. |
| 9,457,154 B2 | 10/2016 | Moller et al. |
| 9,498,524 B2 | 11/2016 | Ghartey-Tagoe et al. |
| 9,504,575 B2 | 11/2016 | Kaplan et al. |
| 9,511,012 B2 | 12/2016 | Altman et al. |
| 9,517,191 B2 | 12/2016 | Altman et al. |
| 9,522,107 B2 | 12/2016 | Altman et al. |
| 9,522,108 B2 | 12/2016 | Altman et al. |
| 9,545,369 B2 | 1/2017 | Altman et al. |
| 9,554,989 B2 | 1/2017 | Kaplan et al. |
| 9,599,891 B2 | 3/2017 | Kaplan et al. |
| RE46,363 E | 4/2017 | Moeller et al. |
| 9,623,147 B2 | 4/2017 | Kaplan et al. |
| 9,675,789 B2 | 6/2017 | Chen et al. |
| 9,687,611 B2 | 6/2017 | Moeller et al. |
| 9,687,640 B2 | 6/2017 | Trautman et al. |
| 9,687,641 B2 | 6/2017 | Singh et al. |
| 9,764,003 B2 | 9/2017 | Jensen |
| 9,775,953 B2 | 10/2017 | Enggaard et al. |
| 9,808,557 B2 | 11/2017 | Lovett et al. |
| 9,861,757 B2 | 1/2018 | Moller et al. |
| 9,925,299 B2 | 3/2018 | Kaplan et al. |
| 9,925,301 B2 | 3/2018 | Kaplan et al. |
| 9,944,019 B2 | 4/2018 | Falo, Jr. et al. |
| 9,962,534 B2 | 5/2018 | Chen et al. |
| 9,993,430 B2 | 6/2018 | Jensen et al. |
| 9,993,527 B2 | 6/2018 | Kaplan et al. |
| 10,022,436 B2 | 7/2018 | Henderson |
| 10,035,920 B2 | 7/2018 | Omenetto et al. |
| 10,086,047 B2 | 10/2018 | Sauerberg et al. |
| 10,166,177 B2 | 1/2019 | Altman et al. |
| 10,195,409 B2 | 2/2019 | Bourne et al. |
| 10,220,155 B2 | 3/2019 | Eiland et al. |
| 10,238,848 B2 | 3/2019 | Singh et al. |
| 10,245,422 B2 | 4/2019 | Le et al. |
| 10,265,384 B2 | 4/2019 | Nissen et al. |
| 10,265,511 B2 | 4/2019 | McAllister et al. |
| 10,278,923 B2 | 5/2019 | Nielsen et al. |
| 10,314,938 B2 | 6/2019 | Kaplan et al. |
| 10,322,185 B2 | 6/2019 | Kobayashi et al. |
| 10,335,462 B2 | 7/2019 | Jensen |
| 10,335,519 B2 | 7/2019 | Kaplan et al. |
| 10,357,616 B2 | 7/2019 | Moller et al. |
| 10,363,303 B2 | 7/2019 | Henderson |
| 10,376,615 B2 | 8/2019 | Lee et al. |
| 10,376,652 B2 | 8/2019 | Markussen |
| 10,384,045 B2 | 8/2019 | Ding et al. |
| 10,384,046 B2 | 8/2019 | Bayramov et al. |
| 10,441,768 B2 | 10/2019 | Falo, Jr. et al. |
| 10,463,608 B2 | 11/2019 | D'Souza |
| 10,548,981 B2 | 2/2020 | Kaplan et al. |
| 10,588,843 B2 | 3/2020 | Altman et al. |
| 10,610,478 B2 | 4/2020 | Altman et al. |
| 10,624,843 B2 | 4/2020 | Ding et al. |
| 10,736,840 B2 | 8/2020 | Mistilis et al. |
| 10,736,943 B2 | 8/2020 | Kaplan et al. |
| 10,737,083 B2 | 8/2020 | Falo, Jr. et al. |
| 10,828,478 B2 | 11/2020 | McAllister et al. |
| 10,835,580 B2 | 11/2020 | Young et al. |
| 10,857,093 B2 | 12/2020 | Shastry et al. |
| 10,888,605 B2 | 1/2021 | Moeller et al. |
| 10,905,744 B2 | 2/2021 | Föger et al. |
| 10,933,120 B2 | 3/2021 | Vilhelmsen et al. |
| 10,933,173 B2 | 3/2021 | Kaplan et al. |
| 10,940,301 B2 | 3/2021 | McAllister et al. |
| 10,946,180 B2 | 3/2021 | Trautman et al. |
| 10,960,052 B2 | 3/2021 | Sauerberg et al. |
| 11,033,499 B2 | 6/2021 | Jensen et al. |
| 11,052,231 B2 | 7/2021 | Ding et al. |
| 11,097,063 B2 | 8/2021 | Eiland et al. |
| 11,110,259 B2 | 9/2021 | Le et al. |
| 11,129,921 B2 | 9/2021 | Kaplan et al. |
| 11,311,679 B2 | 4/2022 | Markussen |
| 11,311,854 B2 | 4/2022 | Lee et al. |
| 11,312,744 B2 | 4/2022 | Yin et al. |
| 11,318,191 B2 | 5/2022 | Engelund et al. |
| 11,357,828 B2 | 6/2022 | Kwiatkowski et al. |
| 11,376,329 B2 | 7/2022 | Kluge et al. |
| 11,382,957 B2 | 7/2022 | Sauerberg et al. |
| 11,419,816 B2 | 8/2022 | Singh et al. |
| 11,439,802 B2 | 9/2022 | Shimizu et al. |
| 11,446,443 B2 | 9/2022 | Moeller et al. |
| 11,565,097 B2 | 1/2023 | Bayramov et al. |
| 11,622,996 B2 | 4/2023 | Bjerregaard et al. |
| 11,666,740 B2 | 6/2023 | Trautman et al. |
| 11,752,198 B2 | 9/2023 | Moeller et al. |
| 11,753,455 B2 | 9/2023 | Roed et al. |
| 11,759,501 B2 | 9/2023 | Vilhelmsen et al. |
| 11,759,502 B2 | 9/2023 | Vilhelmsen et al. |
| 11,759,503 B2 | 9/2023 | Vilhelmsen et al. |
| 11,833,189 B1 | 12/2023 | Bentz et al. |
| 11,865,213 B2 | 1/2024 | Zats et al. |
| 11,957,735 B2 | 4/2024 | Kwiatkowski et al. |
| 12,029,779 B2 | 7/2024 | Groenning et al. |
| 12,194,200 B2 | 1/2025 | Kaplan et al. |
| 12,280,101 B2 | 4/2025 | Kaplan et al. |
| 2002/0028243 A1 | 3/2002 | Masters |
| 2002/0138049 A1 | 9/2002 | Allen et al. |
| 2003/0007991 A1 | 1/2003 | Masters |
| 2003/0155670 A1 | 8/2003 | O'Brien |
| 2003/0183978 A1 | 10/2003 | Asakura |
| 2004/0005363 A1 | 1/2004 | Tsukada et al. |
| 2004/0096455 A1 | 5/2004 | Maa et al. |
| 2004/0133160 A1 | 7/2004 | Dalton |
| 2004/0170590 A1 | 9/2004 | Fahnestock et al. |
| 2004/0199241 A1 | 10/2004 | Gravett et al. |
| 2004/0219630 A1 | 11/2004 | Tsubouchi |
| 2004/0265260 A1 | 12/2004 | Tsubouchi et al. |
| 2004/0266992 A1 | 12/2004 | Migliaresi et al. |
| 2005/0112135 A1 | 5/2005 | Cormier et al. |
| 2005/0123565 A1 | 6/2005 | Subramony et al. |
| 2005/0124965 A1 | 6/2005 | Haywood |
| 2005/0147681 A1 | 7/2005 | Zhao |
| 2005/0255121 A1 | 11/2005 | Campbell et al. |
| 2007/0202057 A1 | 8/2007 | Fankhauser et al. |
| 2007/0212370 A1 | 9/2007 | Steinkasserer et al. |
| 2007/0212730 A1 | 9/2007 | Vepari et al. |
| 2008/0058400 A1 | 3/2008 | Yang et al. |
| 2008/0107706 A1 | 5/2008 | Lopez |
| 2008/0293919 A1 | 11/2008 | Kaplan et al. |
| 2009/0043280 A1 | 2/2009 | Dalton |
| 2009/0142836 A1 | 6/2009 | Wang et al. |
| 2009/0143724 A1 | 6/2009 | Cormier et al. |
| 2009/0155330 A1 | 6/2009 | Ghartey-Tagoe et al. |
| 2009/0171467 A1 | 7/2009 | Mann et al. |
| 2009/0182306 A1 | 7/2009 | Lee et al. |
| 2009/0202614 A1 | 8/2009 | Kaplan et al. |
| 2009/0232963 A1 | 9/2009 | Kaplan et al. |
| 2009/0297588 A1 | 12/2009 | Rheinnecker et al. |
| 2010/0028451 A1 | 2/2010 | Kaplan et al. |
| 2010/0046902 A1 | 2/2010 | Kaplan et al. |
| 2010/0063404 A1 | 3/2010 | Kaplan et al. |
| 2010/0065784 A1 | 3/2010 | Kaplan et al. |
| 2010/0068740 A1 | 3/2010 | Kaplan et al. |
| 2010/0070068 A1 | 3/2010 | Kaplan et al. |
| 2010/0095827 A1 | 4/2010 | Rheinnecker et al. |
| 2010/0096763 A1 | 4/2010 | Kaplan et al. |
| 2010/0120116 A1 | 5/2010 | Kaplan et al. |
| 2010/0178304 A1 | 7/2010 | Wang et al. |
| 2010/0191328 A1 | 7/2010 | Kaplan et al. |
| 2010/0279112 A1 | 11/2010 | Kaplan et al. |
| 2010/0292338 A1 | 11/2010 | Rheinnecker et al. |
| 2011/0046686 A1 | 2/2011 | Kaplan et al. |
| 2011/0063990 A1 | 3/2011 | Nogawa |
| 2011/0076384 A1 | 3/2011 | Cannizzaro et al. |
| 2011/0105402 A1 | 5/2011 | Kim et al. |
| 2011/0121485 A1 | 5/2011 | Rheinnecker et al. |
| 2011/0135697 A1 | 6/2011 | Omenetto et al. |
| 2011/0143947 A1 | 6/2011 | Chamberlin et al. |
| 2011/0152214 A1 | 6/2011 | Boison et al. |
| 2011/0171239 A1 | 7/2011 | Kaplan et al. |
| 2011/0172394 A1 | 7/2011 | Knight et al. |

(56)                    References Cited

U.S. PATENT DOCUMENTS

| | | | |
|---|---|---|---|
| 2011/0243988 A1 | 10/2011 | Ohtake et al. | |
| 2011/0305765 A1 | 12/2011 | Mathur et al. | |
| 2012/0052124 A1 | 3/2012 | Kaplan et al. | |
| 2012/0070427 A1 | 3/2012 | Kaplan et al. | |
| 2012/0121820 A1 | 5/2012 | Kaplan et al. | |
| 2012/0123519 A1 | 5/2012 | Lovett et al. | |
| 2012/0171770 A1 | 7/2012 | Numata et al. | |
| 2012/0187591 A1 | 7/2012 | Wang et al. | |
| 2012/0231499 A1 | 9/2012 | Lee et al. | |
| 2013/0165004 A1 | 6/2013 | Kaplan et al. | |
| 2013/0177611 A1 | 7/2013 | Kaplan et al. | |
| 2013/0195831 A1 | 8/2013 | Kaplan et al. | |
| 2014/0276474 A1 | 9/2014 | Ding et al. | |
| 2014/0287043 A1 | 9/2014 | Kaplan et al. | |
| 2014/0308362 A1 | 10/2014 | Bellas et al. | |
| 2015/0165092 A1 | 6/2015 | Kaplan et al. | |
| 2015/0183841 A1 | 7/2015 | Lo et al. | |
| 2015/0273021 A1 | 10/2015 | Kaplan et al. | |
| 2015/0366796 A1 | 12/2015 | Baudner et al. | |
| 2016/0046679 A1 | 2/2016 | Kluge et al. | |
| 2016/0235889 A1 | 8/2016 | Pallotta et al. | |
| 2016/0263208 A1 | 9/2016 | Skountzou et al. | |
| 2017/0014502 A1 | 1/2017 | Sumathy et al. | |
| 2017/0082585 A1 | 3/2017 | DeWitte et al. | |
| 2017/0120023 A1 | 5/2017 | Davis et al. | |
| 2017/0258889 A1 | 9/2017 | Kaplan et al. | |
| 2017/0296696 A1 | 10/2017 | Kaplan et al. | |
| 2018/0064920 A1 | 3/2018 | Desimone et al. | |
| 2018/0311338 A1 | 11/2018 | Henderson | |
| 2019/0046479 A1 | 2/2019 | Pathak | |
| 2019/0275136 A1 | 9/2019 | Kosuda et al. | |
| 2019/0381300 A1 | 12/2019 | Kobayashi et al. | |
| 2021/0085598 A1 | 3/2021 | Kosuda et al. | |
| 2021/0283597 A1 | 9/2021 | Kluge et al. | |
| 2022/0054704 A1 | 2/2022 | Kaplan et al. | |
| 2022/0257937 A1 | 8/2022 | Adachi et al. | |
| 2022/0339416 A1 | 10/2022 | Kosuda et al. | |
| 2023/0190911 A1 | 6/2023 | Kosuda et al. | |
| 2023/0270842 A1 | 8/2023 | Schrader et al. | |
| 2024/0082405 A1 | 3/2024 | Kluge et al. | |
| 2024/0091114 A1* | 3/2024 | Champredonde | A61K 8/898 |
| 2025/0009301 A1* | 1/2025 | Gross | A61B 5/685 |
| 2025/0109148 A1* | 4/2025 | Huang | C07D 519/04 |

FOREIGN PATENT DOCUMENTS

| | | | | | |
|---|---|---|---|---|---|
| AU | 2008241470 A1 | 10/2008 | | | |
| AU | 2009250998 A1 | 1/2010 | | | |
| AU | 2010238605 A1 | 11/2011 | | | |
| AU | 2011248108 A1 | 12/2012 | | | |
| AU | 2011248166 A1 | 1/2013 | | | |
| AU | 2014200648 A1 | 2/2014 | | | |
| AU | 2013364053 A1 | 7/2015 | | | |
| AU | 2014233541 A1 | 9/2015 | | | |
| AU | 2014237279 A1 | 9/2015 | | | |
| AU | 2014237357 A1 | 9/2015 | | | |
| AU | 2014237499 A1 | 9/2015 | | | |
| AU | 2014249471 A1 | 9/2015 | | | |
| AU | 2015308618 A1 | 3/2017 | | | |
| AU | 2019200645 A1 | 2/2019 | | | |
| AU | 2019261772 A1 | 11/2019 | | | |
| AU | 2020204234 A1 | 7/2020 | | | |
| BR | 112012028263 A2 | 11/2016 | | | |
| BR | 112015014969 A2 | 7/2017 | | | |
| BR | 112015022253 A2 | 7/2017 | | | |
| BR | 112015022432 A2 | 7/2017 | | | |
| BR | 122020006959 B1 | 4/2022 | | | |
| CA | 2405850 A1 | 10/2002 | | | |
| CA | 2517988 A1 | 9/2004 | | | |
| CA | 2560840 A1 | 10/2005 | | | |
| CA | 2608862 A1 | 12/2005 | | | |
| CA | 2676221 A1 | 7/2008 | | | |
| CA | 2686093 A1 | 10/2008 | | | |
| CA | 2759850 A1 | 10/2010 | | | |
| CA | 2801247 A1 | 11/2011 | | | |
| CA | 2896188 A1 | 6/2014 | | | |
| CA | 2903583 A1 | 9/2014 | | | |
| CA | 2903763 A1 | 9/2014 | | | |
| CA | 2904335 A1 | 9/2014 | | | |
| CA | 2905090 A1 | 9/2014 | | | |
| CA | 2906541 A1 | 9/2014 | | | |
| CA | 2903748 A1 | 10/2014 | | | |
| CN | 1467248 A | 1/2004 | | | |
| CN | 1483866 A | 3/2004 | | | |
| CN | 1541724 A | 11/2004 | | | |
| CN | 101445546 A | 6/2009 | | | |
| CN | 102917752 A | 2/2013 | | | |
| CN | 103260693 A | 8/2013 | | | |
| CN | 104027324 A | 9/2014 | | | |
| CN | 105188747 A | 12/2015 | | | |
| CN | 105833424 A | 8/2016 | | | |
| CN | 106422045 A | 2/2017 | | | |
| CN | 107356778 A | 11/2017 | | | |
| CN | 109200012 A | 1/2019 | | | |
| CN | 112399908 A | 2/2021 | | | |
| CN | 114306917 A * | 4/2022 | ............ | A61M 37/00 |
| DE | 202011100790 U1 | 10/2011 | | | |
| EP | 0290197 A2 | 11/1988 | | | |
| EP | 0361391 A2 | 4/1990 | | | |
| EP | 0404097 A2 | 12/1990 | | | |
| EP | 0920875 A1 | 6/1999 | | | |
| EP | 1088930 A2 | 4/2001 | | | |
| EP | 1123710 A1 | 8/2001 | | | |
| EP | 1440088 A2 | 7/2004 | | | |
| EP | 1599410 A2 | 11/2005 | | | |
| EP | 1613796 A2 | 1/2006 | | | |
| EP | 1725258 A2 | 11/2006 | | | |
| EP | 1737357 A2 | 1/2007 | | | |
| EP | 1844763 A1 | 10/2007 | | | |
| EP | 2121111 A2 | 11/2009 | | | |
| EP | 2146689 A2 | 1/2010 | | | |
| EP | 2429627 A2 | 3/2012 | | | |
| EP | 2566501 A2 | 3/2013 | | | |
| EP | 2566568 A2 | 3/2013 | | | |
| EP | 2578265 A1 | 4/2013 | | | |
| EP | 2664323 A1 | 11/2013 | | | |
| EP | 2934660 A1 | 10/2015 | | | |
| EP | 2967597 A1 | 1/2016 | | | |
| EP | 2968119 A1 | 1/2016 | | | |
| EP | 2968188 A1 | 1/2016 | | | |
| EP | 2968751 A2 | 1/2016 | | | |
| EP | 2968887 A1 | 1/2016 | | | |
| EP | 3193828 A1 | 7/2017 | | | |
| EP | 3215440 A1 | 9/2017 | | | |
| GB | 1182153 A | 2/1970 | | | |
| IL | 222803 A | 5/2016 | | | |
| IL | 241569 B | 5/2021 | | | |
| IL | 240930 B | 10/2021 | | | |
| IL | 239557 B | 1/2022 | | | |
| IN | 428743 | 12/2014 | | | |
| IN | 390534 | 7/2016 | | | |
| IN | 393040 | 7/2016 | | | |
| IN | 421691 | 7/2016 | | | |
| JP | 55-81589 A | 6/1980 | | | |
| JP | 55-139427 A | 10/1980 | | | |
| JP | 56-166235 A | 12/1981 | | | |
| JP | 58-38449 A | 8/1983 | | | |
| JP | 60-142259 A | 7/1985 | | | |
| JP | 60-259677 A | 12/1985 | | | |
| JP | 62-8054 A | 1/1987 | | | |
| JP | 63-93727 A | 4/1988 | | | |
| JP | 64-6220 A | 1/1989 | | | |
| JP | 1-118544 A | 5/1989 | | | |
| JP | 1-228472 A | 9/1989 | | | |
| JP | 1-254621 A | 10/1989 | | | |
| JP | 2-126247 A | 5/1990 | | | |
| JP | 2-311500 A | 12/1990 | | | |
| JP | 4-100975 A | 4/1992 | | | |
| JP | 4-263611 A | 9/1992 | | | |
| JP | 5-005275 A | 1/1993 | | | |
| JP | 5-43600 A | 2/1993 | | | |
| JP | 5-163132 A | 6/1993 | | | |
| JP | 5-195431 A | 8/1993 | | | |
| JP | 6-70702 A | 3/1994 | | | |

(56) References Cited

FOREIGN PATENT DOCUMENTS

| | | | |
|---|---|---|---|
| JP | 6-346314 | A | 12/1994 |
| JP | 7-60087 | A | 3/1995 |
| JP | 8-295697 | A | 11/1996 |
| JP | 9-188972 | A | 7/1997 |
| JP | 10-36676 | A | 2/1998 |
| JP | 11-49620 | A | 2/1999 |
| JP | 11-151438 | A | 6/1999 |
| JP | 11-180999 | A | 7/1999 |
| JP | 11-323735 | A | 11/1999 |
| JP | 2000-507963 | A | 6/2000 |
| JP | 2000-273264 | A | 10/2000 |
| JP | 2001-262470 | A | 9/2001 |
| JP | 2003-192807 | A | 7/2003 |
| JP | 2003-533468 | A | 11/2003 |
| JP | 2004-018757 | A | 1/2004 |
| JP | 2004-068161 | A | 3/2004 |
| JP | 2005-97229 | A | 4/2005 |
| JP | 4691025 | B2 | 6/2011 |
| JP | 4787738 | B2 | 10/2011 |
| JP | 5085317 | B2 | 11/2012 |
| JP | 5553612 | B2 | 7/2014 |
| JP | 5820805 | B2 | 11/2015 |
| JP | 5968875 | B2 | 8/2016 |
| JP | 6159770 | B2 | 7/2017 |
| JP | 6279662 | B2 | 2/2018 |
| JP | 6327852 | B2 | 5/2018 |
| JP | 6487899 | B2 | 3/2019 |
| JP | 2019-511255 | A | 4/2019 |
| JP | 6689187 | B2 | 4/2020 |
| JP | 6700170 | B2 | 5/2020 |
| JP | 6832969 | B2 | 2/2021 |
| JP | 6865524 | B2 | 4/2021 |
| JP | 6894455 | B2 | 6/2021 |
| JP | 7109188 | B2 | 7/2022 |
| JP | 7251885 | B2 | 4/2023 |
| KR | 101808635 | B1 | 12/2017 |
| KR | 102265808 | B1 | 6/2021 |
| KR | 102316739 | B1 | 10/2021 |
| KR | 102332671 | B1 | 11/2021 |
| KR | 102341601 | B1 | 12/2021 |
| MX | 351458 | B | 10/2017 |
| MX | 375307 | | 9/2020 |
| MX | 383605 | | 6/2021 |
| RU | 21271 | U1 | 1/2002 |
| RU | 2569029 | C2 | 11/2015 |
| RU | 2662432 | C2 | 7/2018 |
| RU | 2674083 | C2 | 12/2018 |
| RU | 2698095 | C2 | 8/2019 |
| RU | 2711567 | C2 | 1/2020 |
| WO | 1993/11161 | A1 | 6/1993 |
| WO | 1997/008315 | A1 | 3/1997 |
| WO | 1998/28000 | A1 | 7/1998 |
| WO | 1999/01089 | A1 | 1/1999 |
| WO | 1999/45964 | A1 | 9/1999 |
| WO | 1999/64580 | A1 | 12/1999 |
| WO | 2001/36531 | A1 | 5/2001 |
| WO | 2001/56626 | A1 | 8/2001 |
| WO | 2001/87267 | A1 | 11/2001 |
| WO | 2002/29141 | A1 | 4/2002 |
| WO | 2002/40242 | A1 | 5/2002 |
| WO | 2002/072931 | A1 | 9/2002 |
| WO | 2002/081793 | A1 | 10/2002 |
| WO | 2003/022909 | A1 | 3/2003 |
| WO | 2003/035124 | A2 | 5/2003 |
| WO | 2003/038033 | A2 | 5/2003 |
| WO | 2003/060099 | A2 | 7/2003 |
| WO | 2003/060207 | A1 | 7/2003 |
| WO | 2004/000255 | A1 | 12/2003 |
| WO | 2004/000389 | A2 | 12/2003 |
| WO | 2004/000915 | A2 | 12/2003 |
| WO | 2004/001103 | A2 | 12/2003 |
| WO | 2004/041845 | A2 | 5/2004 |
| WO | 2004/062697 | A2 | 7/2004 |
| WO | 2005/012606 | A2 | 2/2005 |
| WO | 2005/016239 | A2 | 2/2005 |
| WO | 2005/085327 | A1 | 9/2005 |
| WO | 2005/089794 | A2 | 9/2005 |
| WO | 2005/123114 | A2 | 12/2005 |
| WO | 2006/062685 | A2 | 6/2006 |
| WO | 2006/076711 | A2 | 7/2006 |
| WO | 2007/098951 | A2 | 9/2007 |
| WO | 2008/052755 | A2 | 5/2008 |
| WO | 2008/052775 | A2 | 5/2008 |
| WO | 2008/118133 | A2 | 10/2008 |
| WO | 2008/127401 | A2 | 10/2008 |
| WO | 2008/127402 | A2 | 10/2008 |
| WO | 2008/127405 | A2 | 10/2008 |
| WO | 2008/150861 | A1 | 12/2008 |
| WO | 2009/023615 | A1 | 2/2009 |
| WO | 2009/105564 | A2 | 8/2009 |
| WO | 2009/126689 | A2 | 10/2009 |
| WO | 2009/153140 | A2 | 12/2009 |
| WO | 2009/156226 | A2 | 12/2009 |
| WO | 2010/036992 | A2 | 4/2010 |
| WO | 2010/042798 | A2 | 4/2010 |
| WO | 2010/057142 | A2 | 5/2010 |
| WO | 2010/060600 | A1 | 6/2010 |
| WO | 2010/141133 | A2 | 12/2010 |
| WO | 2011/005381 | A2 | 1/2011 |
| WO | 2011/006133 | A2 | 1/2011 |
| WO | 2011/008842 | A2 | 1/2011 |
| WO | 2011/011347 | A2 | 1/2011 |
| WO | 2011/041395 | A2 | 4/2011 |
| WO | 2011/063990 | A2 | 6/2011 |
| WO | 2011/109691 | A2 | 9/2011 |
| WO | 2011/129120 | A1 | 10/2011 |
| WO | 2011/130335 | A2 | 10/2011 |
| WO | 2011/140240 | A2 | 11/2011 |
| WO | 2012/031144 | A2 | 3/2012 |
| WO | 2012/054582 | A2 | 4/2012 |
| WO | 2012/145739 | A1 | 10/2012 |
| WO | 2013/126799 | A1 | 8/2013 |
| WO | 2013/142119 | A1 | 9/2013 |
| WO | 2013/142611 | A2 | 9/2013 |
| WO | 2013/152265 | A1 | 10/2013 |
| WO | 2014/066884 | A1 | 5/2014 |
| WO | 2014/118305 | A1 | 8/2014 |
| WO | 2014/145002 | A2 | 9/2014 |
| WO | 2014/150069 | A1 | 9/2014 |
| WO | 2014/151654 | A1 | 9/2014 |
| WO | 2014/164314 | A1 | 10/2014 |
| WO | 2015/070108 | A1 | 5/2015 |
| WO | 2016/155082 | A1 | 10/2016 |
| WO | 2017/011320 | A1 | 1/2017 |
| WO | WO-2017037712 | A1 * | 3/2017 ......... A61K 31/575 |
| WO | 2018/053524 | A1 | 3/2018 |
| WO | 2019/195350 | A1 | 10/2019 |
| WO | 2022/111370 | A1 | 6/2022 |
| WO | 2022/152131 | A1 | 7/2022 |
| WO | 2023/052776 | A1 | 4/2023 |
| WO | 2023/055939 | A1 | 4/2023 |
| WO | 2023/159702 | A1 | 8/2023 |
| WO | 2023/174433 | A1 | 9/2023 |
| WO | WO-2023250117 | A2 * | 12/2023 ............ A61K 9/703 |
| WO | 2024/068848 | A1 | 4/2024 |
| WO | 2024/136035 | A1 | 6/2024 |
| WO | 2024/146049 | A1 | 7/2024 |

OTHER PUBLICATIONS

Megeed et al., Genetically engineered silk-elastinlike protein polymers for controlled drug delivery. Adv Drug Deliv Rev. Oct. 18, 2002;54(8):1075-91.

Mei et al., Use of filter paper for the collection and analysis of human whole blood specimens. J Nutr. May 2001;131 (5):1631S-6S.

Meier et al., Peptide Nucleic Acids(PNAs)-Unusual Properties of Nonionic Oligonucleotide Analogues. Angewandte Chemie International. Aug. 1992;31(8):1008-1010.

Meinel et al., Bone tissue engineering using human mesenchymal stem cells: effects of scaffold material and medium flow. Ann Biomed Eng. Jan. 2004;32(1):112-22.

(56)                    References Cited

OTHER PUBLICATIONS

Melson et al., What is the pipeline for future medications for obesity? Int J Obes (Lond). Mar. 2025;49(3):433-451.

Merck, M-M-R®II (Measles, Mumps, and Rubella Virus Vaccine Life). Package Insert, retrieved online at: https://www.fda.gov/vaccines-blood-biologics/vaccines/measles-mumps-and-rubella-virus-vaccine-live. Merck Sharp & Dohme LLC. 12 page, Aug. 2023.

Middaugh, Formulation and delivery of biopharmaceuticals. J Pharm Sci. Dec. 1996;85(12):1259-60.

Min et al., Regenerated silk fibroin nanofibers: water vapor-induced structural changes and their effects on the behavior of normal human cells. Macromol Biosci. Apr. 12, 2006;6(4):285-92.

Min et al., Preparation and Characterization of Crosslinked Porous Silk Fibroin Gel. Sen'i Gakkaishi. 1998;54(2):85-92.

Minoura et al., Fine structure and oxygen permeability of silk fibroin membrane treated with methanol. Polymer. Feb. 1990;31(2):265-269.

Mircamsy et al., Stabilizing effect of magnesium chloride and sucrose on Sabin live polio vaccine. Dev Biol Stand. 1978;41:255-7.

Mita et al., Highly repetitive structure and its organization of the silk fibroin gene. J Mol Evol. Jun. 1994;38(6):583-92.

Miyairi et al., Properties of beta-glucosidase immobilized in sericin membrane. J Ferment Technol. 1978;56(4):303-308.

Monath et al., Comparative safety and immunogenicity of two yellow fever 17D vaccines (Arilvax and YF-VAX) in a phase III multicenter, double-blind clinical trial. Am J Trop Med Hyg. May 2002;66(5):533-41.

Monti et al., Raman spectroscopic studies of silk fibroin from Bombyx mori. Journal of Raman Spectroscopy. Dec. 4, 1998;29(4):297-304.

Moss et al., Global measles elimination. Nat Rev Microbiol. Dec. 2006;4(12):900-8.

Murphy et al., Modification of silk fibroin using diazonium coupling chemistry and the effects on hMSC proliferation and differentiation. Biomaterials. Jul. 2008;29(19):2829-38.

Nakagawa et al., Characterization of the development of ectopic chondroid/bone matrix and chondrogenic/osteogenic cells during osteoinduction by rhBMP-2: a histochemical and ultrastructural study. Oral Dis. Sep. 2003;9(5):255-63.

Nakhasi et al., Specific binding of host cell proteins to the 3'-terminal stem-loop structure of rubella virus negative-strand RNA. J Virol. Nov. 1991;65(11):5961-7.

Nam et al., Morphology of regenerated silk fibroin: Effects of freezing temperature, alcohol addition, and molecular weight. Journal of Applied Polymer Science. Jul. 6, 2001;81(12):3008-3021.

Nazarov et al., Porous 3-D scaffolds from regenerated silk fibroin. Biomacromolecules. May-Jun. 2004;5(3):718-26.

Norman et al., Microneedle patches: usability and acceptability for self-vaccination against influenza. Vaccine. Apr. 1, 2014;32(16):1856-62.

Ochi et al., Rheology and dynamic light scattering of silk fibroin solution extracted from the middle division of Bombyx mori silkworm. Biomacromolecules. Nov.-Dec. 2002;3(6):1187-96.

Ohman et al., In vivo studies concerning a pH gradient in human stratum corneum and upper epidermis. Acta Derm Venereol. Sep. 1994;74(5):375-9.

Ohman et al., The pH gradient over the stratum corneum differs in X-linked recessive and autosomal dominant ichthyosis: a clue to the molecular origin of the "acid skin mantle"? J Invest Dermatol. Oct. 1998;111(4):674-7.

Ohtake et al., Arginine as a synergistic virucidal agent. Molecules. Mar. 8, 2010;15(3):1408-24.

Ohtake et al., Heat-stable measles vaccine produced by spray drying. Vaccine. Feb. 3, 2010;28(5):1275-84.

Ohtsuka et al., An alternative approach to deoxyoligonucleotides as hybridization probes by insertion of deoxyinosine at ambiguous codon positions. J Biol Chem. Mar. 10, 1985;260(5):2605-8.

Omenetto et al., New opportunities for an ancient material. Science. Jul. 30, 2010;329(5991):528-31.

Palmer et al., Characterization of factors affecting the stability of frozen heparinized plasma. Vox Sang. 1993;65(4):258-70.

Pandit et al., Studies on silk fibroin. I. Molecular weight, sedimentation coefficient, viscosity and optical rotation of silk fibroin from carbonate-extracted silk fiber. Arch Biochem Biophys. Mar. 1972;149(1):259-68.

Panilaitis et al., Macrophage responses to silk. Biomaterials. Aug. 2003;24(18):3079-85.

Park et al., Analysis of Mechanical Failure of Polymer Microneedles by Axial Force. J Korean Phys Soc. Apr. 2010;56(4):1223-1227.

Parsegian et al., Osmotic stress for the direct measurement of intermolecular forces. Methods Enzymol. 1986;127:400-16.

Peetermans et al., Stability of freeze-dried rubella virus vaccine (Cendehill® strain) at various temperatures. Journal of Biological Standardization. 1973;1(2):179-85.

Perry et al., Nano- and Micropatterning of Optically Transparent, Mechanically Robust, Biocompatible Silk Fibroin Films. Advanced Materials. Aug. 18, 2008;20(16):3070-2.

Petrini et al., Silk fibroin-polyurethane scaffolds for tissue engineering. J Mater Sci Mater Med. Oct.-Dec. 2001;12(10-12):849-53.

Pettit et al., The development of site-specific drug-delivery systems for protein and peptide biopharmaceuticals. Trends in Biotechnology. Dec. 1, 1998;16(8):343-349.

Pluckthun, Antibodies from *Escherichia coli*. The Pharmacology of Monoclonal Antibodies. Springer-Verlag, Berlin, Martin Rosenberg (Ed.). Chapter 11, pp. 269-315, (1994).

Potoczek et al., Manufacturing of highly porous calcium phosphate bioceramics via gel-casting using agarose. Ceramics International. Aug. 2009;35(6):2249-2254.

Preis et al., A single-step immunization by sustained antigen release. J Immunol Methods. 1979;28(1-2):193-7.

Preul et al., Application of a hydrogel sealant improves watertight closures of duraplasty onlay grafts in a canine craniotomy model. J Neurosurg. Sep. 2007;107(3):642-50.

Pritchard et al., Effect of silk protein processing on drug delivery from silk films. Macromol Biosci. Mar. 2013;13(3):311-20.

Pritchard et al., Incorporation of proteinase inhibitors into silk-based delivery devices for enhanced control of degradation and drug release. Biomaterials. Jan. 2011;32(3):909-18.

Pritchard et al., Physical and chemical aspects of stabilization of compounds in silk. Biopolymers. Jun. 2012;97(6):479-98.

Pritchard et al., Silk fibroin biomaterials for controlled release drug delivery. Expert Opin Drug Deliv. Jun. 2011;8(6):797-811.

Pritchard et al., Silk fibroin encapsulated powder reservoirs for sustained release of adenosine. J Control Release. Jun. 1, 2010;144(2):159-67.

Puren et al., Laboratory operations, specimen processing, and handling for viral load testing and surveillance. J Infect Dis. Apr. 15, 2010;201(Suppl 1):S27-36.

Qi et al., A Review of Structure Construction of Silk Fibroin Biomaterials from Single Structures to Multi-Level Structures. Int J Mol Sci. Mar. 3, 2017;18(3):237, 21 pages.

Radisic et al., High-density seeding of myocyte cells for cardiac tissue engineering. Biotechnol Bioeng. May 20, 2003;82(4):403-14.

Yamada et al., Preparation of undegraded native molecular fibroin solution from silkworm cocoons. Materials Science and Engineering: C. Aug. 15, 2001;14(1-2):41-46.

Yang et al., Hydroxyapatite scaffolds processed using a TBA-based freeze-gel casting/polymer sponge technique. J Mater Sci Mater Med. May 2010;21(5):1495-502.

Yao et al., Synthesis and structural characterization of silk-like materials incorporated with an elastic motif. J Biochem. Jan. 2003;133(1):147-54.

Yao et al., Temporal changes in matrix protein synthesis and mRNA expression during mineralized tissue formation by adult rat bone marrow cells in culture. J Bone Miner Res. Feb. 1994;9(2):231-40.

Yavuz et al., Silk Fibroin Microneedle Patches for the Sustained Release of Levonorgestrel. ACS Appl Bio Mater. Aug. 17, 2020;3(8):5375-5382.

Yildirim et al., Development of silk fibroin-based beads for immobilized cell fermentations. J Microencapsul. 2010;27(1):1-9.

(56)          References Cited

OTHER PUBLICATIONS

Yoshimizu et al., Preparation and characterization of silk fibroin powder and its application to enzyme immobilization. Journal of Applied Polymer Science. Jul. 1990;40(1-2):127-134.

You et al., Rapidly dissolving fibroin microneedles for transdermal drug delivery. Materials Science and Engineering C. 2011;31:1632-1636.

You et al., Rapidly dissolving silk protein microneedles for transdermal drug delivery. 2010 IEEE International Conference on Nano/Molecular Medicine and Engineering. Dec. 5-9, 2010;144-147.

Yu et al., Induced pluripotent stem cell lines derived from human somatic cells. Science. Dec. 21, 2007;318 (5858):1917-20.

Yucel et al., Non-equilibrium silk fibroin adhesives. J Struct Biol. May 2010;170(2):406-12.

Zapata et al., Engineering linear F(ab')2 fragments for efficient production in *Escherichia coli* and enhanced antiproliferative activity. Protein Eng. Oct. 1995;8(10):1057-62.

Zhang et al., Poly(alpha-hydroxyl acids)/hydroxyapatite porous composites for bone-tissue engineering. I. Preparation and morphology. J Biomed Mater Res. Mar. 15, 1999;44(4):446-55.

Zhang et al., Stabilization of vaccines and antibiotics in silk and eliminating the cold chain. Proc Natl Acad Sci U S A. Jun. 28, 2016;113(26):E3810. Retraction.

Zhang et al., Synthesis and characterization of macroporous chitosan/calcium phosphate composite scaffolds for tissue engineering. J Biomed Mater Res. Jun. 5, 2001;55(3):304-12.

Zhang et al., Synthesis, characterization and immunogenicity of silk fibroin-L-asparaginase bioconjugates. J Biotechnol. Nov. 21, 2005;120(3):315-26.

Zhang et al., Three-dimensional macroporous calcium phosphate bioceramics with nested chitosan sponges for load-bearing bone implants. J Biomed Mater Res. Jul. 2002;61(1):1-8.

Zhou et al., Exploring a novel long-acting glucagon-like peptide-1 receptor agonist built on the albumin-binding domain and XTEN scaffolds. Heliyon. Jan. 11, 2024;10(2):e24340, 9 pages.

Zhou et al., Preparation of a novel core-shell nanostructured gold colloid-silk fibroin bioconjugate by the protein in situ redox technique at room temperature. Chem Commun (Camb). Dec. 7, 2001;(23):2518-9.

Zhou et al., Silk fibroin: structural implications of a remarkable amino acid sequence. Proteins. Aug. 1, 2001;44 (2):119-22.

Zweig, Advances in vaccine stability monitoring technology. Vaccine. Aug. 14, 2006;24(33-34):5977-85.

Hamilton et al., Trimmed Spearman-Karber method for estimating median lethal concentrations in toxicity bioassays. Environ Sci Technol. 1977;11(7):714-9.

Hanawa et al., New oral dosage form for elderly patients. II. Release behavior of benfotiamine from silk fibroin gel. Chem Pharm Bull (Tokyo). May 1995;43(5):872-6.

Hanawa et al., New oral dosage form for elderly patients. III. Stability of trichlormethiazide in silk fibroin gel and various sugar solutions. Drug Dev Ind Pharm. Oct. 2000;26(10):1091-7.

Hanawa et al., New oral dosage form for elderly patients: preparation and characterization of silk fibroin gel. Chem Pharm Bull (Tokyo). Feb. 1995;43(2):284-8.

Hanson et al., Two-photon fluorescence lifetime imaging of the skin stratum corneum pH gradient. Biophys J. Sep. 2002;83(3):1682-90.

Harris et al., Open pore biodegradable matrices formed with gas foaming. J Biomed Mater Res. Dec. 5, 1998;42(3):396-402.

He et al., Silk I structure in Bombyx mori silk foams. Int J Biol Macromol. Mar.-Apr. 1999;24(2-3):187-95.

He et al., Stabilization of RNA Encapsulated in Silk. ACS Biomater Sci Eng. May 14, 2018;4(5):1708-1715. pre-publication edition.

Health Protection Agency, Foreign travel-associated illness, England, Wales, and Northern Ireland—2007 report. 103 pages, (2007).

Hersel et al., RGD modified polymers: biomaterials for stimulated cell adhesion and beyond. Biomaterials. Nov. 2003;24(24):4385-415.

Herzog et al., Plasticity of marrow-derived stem cells. Blood. Nov. 15, 2003;102(10):3483-93.

Hijirida et al., 13C NMR of Nephila clavipes major ampullate silk gland. Biophys J. Dec. 1996;71(6):3442-7.

Hinman et al., Synthetic spider silk: a modular fiber. Trends Biotechnol. Sep. 2000;18(9):374-9.

Hino et al., Change in secondary structure of silk fibroin during preparation of its microspheres by spray-drying and exposure to humid atmosphere. J Colloid Interface Sci. Oct. 1, 2003;266(1):68-73.

Hirai et al., Some comments on the penetration of water vapor into regenerated silk fibroin. Polymer. Jun. 2001;42 (12):5495-5499.

Hirschberg et al., Bioneedles as alternative delivery system for hepatitis B vaccine. J Control Release. Oct. 15, 2010;147(2):211-7.

Hofmann et al., Silk fibroin as an organic polymer for controlled drug delivery. J Control Release. Mar. 10, 2006;111(1-2):219-27.

Holliger et al., "Diabodies": small bivalent and bispecific antibody fragments. Proc Natl Acad Sci U S A. Jul. 15, 1993;90(14):6444-8.

Holmes, Novel peptide-based biomaterial scaffolds for tissue engineering. Trends Biotechnol. Jan. 2002;20(1):16-21.

Holy et al., Use of a biomimetic strategy to engineer bone. J Biomed Mater Res A. Jun. 15, 2003;65(4):447-53.

Horan et al., In vitro degradation of silk fibroin. Biomaterials. Jun. 2005;26(17):3385-93.

Hu et al., Effect of water on the thermal properties of silk fibroin. Thermochimica Acta. 2007;461:137-144.

Hu et al., Regulation of silk material structure by temperature-controlled water vapor annealing. Biomacromolecules. May 9, 2011;12(5):1686-96.

Huang et al., Engineered collagen-PEO nanofibers and fabrics. J Biomater Sci Polym Ed. 2001;12(9):979-93.

Huang et al., Generation of Synthetic Elastin-Mimetic Small Diameter Fibers and Fiber Networks. Macromolecules. 2000;33(8):2989-2997.

Hubschen et al., A multiplex TaqMan PCR assay for the detection of measles and rubella virus. J Virol Methods. May 2008; 149(2):246-50.

Ikushima et al., A Randomized Trial Investigating the Pharmacokinetics, Pharmacodynamics, and Safety of Subcutaneous Semaglutide Once-Weekly in Healthy Male Japanese and Caucasian Subjects. Adv Ther. Apr. 2018;35(4):531-544.

Jang et al., Restoration of peri-implant defects in immediate implant installations by Choukroun platelet-rich fibrin and silk fibroin powder combination graft. Oral Surg Oral Med Oral Pathol Oral Radiol Endod. Jun. 2010;109(6):831-6.

Jenkins et al., Clinical and experimental observations on the use of gelatin sponge or foam. Surgery. Jul. 1946;20(1):124-32.

Jiang et al., Tensile behavior and morphology of differently degummed silkworm (*Bombyx mori*) cocoon silk fibres. Materials Letters. Apr. 2006;60(7):919-925.

Jin et al., Biomaterial films of Bombyx mori silk fibroin with poly(ethylene oxide). Biomacromolecules. May-Jun. 2004;5 (3):711-7.

Jin et al., Electrospinning Bombyx mori silk with poly(ethylene oxide). Biomacromolecules. Nov.-Dec. 2002;3(6):1233-9.

Jin et al., Mechanism of silk processing in insects and spiders. Nature. Aug. 28, 2003;424(6952):1057-61.

Jin et al., Water-Stable Silk Films with Reduced beta-Sheet Content. Advanced Functional Materials. Jul. 1, 2005;15(8):1241-1247.

Jones et al., Isolation of Vgr-2, a novel member of the transforming growth factor-beta-related gene family. Mol Endocrinol. Nov. 1992;6(11):1961-8.

Kang et al., Effects of poloxamer on the gelation of silk fibroin. Macromolecular Rapid Communications. Jul. 2000;21 (11):788-791.

Karageorgiou et al., Porous silk fibroin 3-D scaffolds for delivery of bone morphogenetic protein-2 in vitro and in vivo. J Biomed Mater Res A. Aug. 2006;78(2):324-34.

Katoh et al., Novel approach to fabricate keratin sponge scaffolds with controlled pore size and porosity. Biomaterials. Aug. 2004;25(18):4255-62.

(56) References Cited

OTHER PUBLICATIONS

Kikuchi et al., Spectroscopic investigation of tertiary fold of staphylococcal protein A to explore its engineering application. Biomaterials. Apr. 1999;20(7):647-54.

Kim et al., Microneedle array delivered recombinant coronavirus vaccines: Immunogenicity and rapid translational development. EBioMedicine. May 2020;55:102743, 12 pages.

Kim et al., Structure and properties of silk hydrogels. Biomacromolecules. May-Jun. 2004;5(3):786-92.

Kingston et al., Structure of the nucleocapsid-binding domain from the mumps virus polymerase; an example of protein folding induced by crystallization. J Mol Biol. Jun. 13, 2008;379(4):719-31.

Kissmann et al., Stabilization of measles virus for vaccine formulation. Hum Vaccin. Sep.-Oct. 2008;4(5):350-9.

Kluge et al., Optimizing Molecular Weight of Lyophilized Silk as a Shelf-Stable Source Material. ACS Biomater Sci Eng. Apr. 11, 2016;2(4):595-605. pre-publication edition.

Kluge et al., Silk-based blood stabilization for diagnostics. Proc Natl Acad Sci U S A. May 24, 2016;113(21):5892-7.

Koppel, Analysis of Macromolecular Polydispersity in Intensity Correlation Spectroscopy: The Method of Cumulants. J Chem Phys. 1972;57:4814-20.

Koster, Sommerliche Umkehrdiffusion. Retrieved online at: http://www.bedachungen-koehler.de/sommerliche-umkehrdiffusion/. 6 pages, Sep. 27, 2016.

Kruger et al., Recognition of and steps to mitigate anxiety and fear of pain in injectable diabetes treatment. Diabetes Metab Syndr Obes. Jan. 16, 2015;8:49-56.

Kubar et al., Rapid and quantitative detection of mumps virus RNA by one-step real-time RT-PCR. Diagn Microbiol Infect Dis. Jun. 2004;49(2):83-8.

Kumakura, Effect of heat treatment on enzymes entrapped into polymer gels. Journal of Molecular Catalysis B: Enzymatic. Dec. 4, 1995;1(1):L1-L6.

Kumru et al., Vaccine instability in the cold chain: mechanisms, analysis and formulation strategies. Biologicals. Sep. 2014;42(5):237-59.

Kweon et al., Physical properties of silk fibroin/chitosan blend films. Journal of Applied Polymer Science. Mar. 2, 2001;80(7):928-934.

Kweon et al., Preparation of semi-interpenetrating polymer networks composed of silk fibroin and poly(ethylene glycol) macromer. Journal of Applied Polymer Science. Mar. 16, 2001;80(10):1848-1853.

Lammel et al., Controlling silk fibroin particle features for drug delivery. Biomaterials. Jun. 2010;31(16):4583-91.

Lau et al., Discovery of the Once-Weekly Glucagon-Like Peptide-1 (GLP-1) Analogue Semaglutide. J Med Chem. Sep. 24, 2015;58(18):7370-80.

Lau et al., Multilayered pyramidal dissolving microneedle patches with flexible pedestals for improving effective drug delivery. J Control Release. Nov. 10, 2017;265:113-119.

Lawrence et al., Silk film biomaterials for cornea tissue engineering. Biomaterials. Mar. 2009;30(7):1299-308.

Lazaris et al., Spider silk fibers spun from soluble recombinant silk produced in mammalian cells. Science. Jan. 18, 2002;295(5554):472-6. Supplemental Materials.

Lee et al., A combination graft of low-molecular-weight silk fibroin with Choukroun platelet-rich fibrin for rabbit calvarial defect. Oral Surg Oral Med Oral Pathol Oral Radiol Endod. May 2010;109(5):e33-8.

Lee et al., Hydrogels for Tissue Engineering. Chem Rev. 2001;101(7):1869-1880.

Leisk et al., Electrogelation for protein adhesives. Adv Mater. Feb. 9, 2010;22(6):711-5.

Letsinger et al., Phosphoramidate analogs of oligonucleotides. J Org Chem. Nov. 1970;35(11):3800-3.

Li et al., Chemical instability of protein pharmaceuticals: Mechanisms of oxidation and strategies for stabilization. Biotechnol Bioeng. Dec. 5, 1995;48(5):490-500.

Li et al., Effect of silicon on the formation of silk fibroin/calcium phosphate composite. J Mater Sci Mater Med. Feb. 2008; 19(2):577-82.

Li et al., Electrospun silk-BMP-2 scaffolds for bone tissue engineering. Biomaterials. Jun. 2006;27(16):3115-24.

Li et al., Fusion to an albumin-binding domain with a high affinity for albumin extends the circulatory half-life and enhances the in vivo antitumor effects of human TRAIL. J Control Release. Apr. 28, 2016;228:96-106.

Li et al., Silk-based stabilization of biomacromolecules. J Control Release. Dec. 10, 2015;219:416-430.

Li et al., Study on porous silk fibroin materials. I. Fine structure of freeze dried silk fibroin. Journal of Applied Polymer Science. Mar. 21, 2001;79(12):2185-2191.

Li et al., Study on porous silk fibroin materials. II. Preparation and characteristics of spongy porous silk fibroin materials. Journal of Applied Polymer Science. Jan. 16, 2001;79(12):2192-2199.

Li et al., The natural silk spinning process. A nucleation-dependent aggregation mechanism? Eur J Biochem. Dec. 2001;268(24):6600-6.

Liang et al., Improvements of the physical properties of fibroin membranes with sodium alginate. Journal of Applied Polymer Science. Aug. 15, 1992;45(11):1937-1943.

Liddle et al., How general practitioners store vaccines. A survey in south-western Sydney. Med J Aust. Apr. 3, 1995;162(7):366-8.

Lin et al., Microneedle patch with pure drug tips for delivery of liraglutide: pharmacokinetics in rats and minipigs. Drug Deliv Transl Res. Jan. 2025;15(1):216-230.

Lin et al., PEG hydrogels for the controlled release of biomolecules in regenerative medicine. Pharm Res. Mar. 2009;26(3):631-43.

Lintzeri et al., Epidermal thickness in healthy humans: a systematic review and meta-analysis. J Eur Acad Dermatol Venereol. Aug. 2022;36(8):1191-1200.

Lovett et al., Gel spinning of silk tubes for tissue engineering. Biomaterials. Dec. 2008;29(35):4650-7.

Lowe et al., Evaluation of the topical hemostatic efficacy and safety of TISSEEL VH S/D fibrin sealant compared with currently licensed TISSEEL VH in patients undergoing cardiac surgery: a phase 3, randomized, double-blind clinical study. J Cardiovasc Surg (Torino). Jun. 2007;48(3):323-31.

Lu et al., Stabilization of enzymes in silk films. Biomacromolecules. May 11, 2009;10(5):1032-42.

Lu et al., Water-insoluble silk films with silk I structure. Acta Biomater. Apr. 2010;6(4):1380-7.

Lucas et al., The silk fibroins. Adv Protein Chem. 1958;13:107-242.

Ma et al., Collagen/chitosan porous scaffolds with improved biostability for skin tissue engineering. Biomaterials. Nov. 2003;24(26):4833-41.

Ma et al., Microneedle, bio-microneedle and bio-inspired microneedle: A review. J Control Release. Apr. 10, 2017;251:11-23.

Macchetta et al., Fabrication of HA/TCP scaffolds with a graded and porous structure using a camphene-based freeze-casting method. Acta Biomater. May 2009;5(4):1319-27.

Mackay et al., Chondrogenic differentiation of cultured human mesenchymal stem cells from marrow. Tissue Eng. 1998 Winter;4(4):415-28.

Magoshi et al., Biospinning (Silk Fiber Formation, Multiple Spinning Mechanisms), Polymerics Materials Encyclopedia. Volume 1, A-B, Joseph C. Salamone (Ed.), CRC Press, Boca Raton. pp. 667-679, (1996).

Malvoisin et al., Measles virus glycoproteins: studies on the structure and interaction of the haemagglutinin and fusion proteins. J Gen Virol. Nov. 1993;74 ( Pt 11):2365-72.

Mancini-Bourgine et al., Induction or expansion of T-cell responses by a hepatitis B DNA vaccine administered to chronic HBV carriers. Hepatology. Oct. 2004;40(4):874-82.

Mandal et al., Cell proliferation and migration in silk fibroin 3D scaffolds. Biomaterials. May 2009;30(15):2956-65.

Mandal et al., High-strength silk protein scaffolds for bone repair. Proc Natl Acad Sci U S A. May 15, 2012;109(20):7699-704.

Manning et al., Stability of protein pharmaceuticals: an update. Pharm Res. Apr. 2010;27(4):544-75.

(56)         References Cited

OTHER PUBLICATIONS

Maquet et al., Porous poly(alpha-hydroxyacid)/Bioglass composite scaffolds for bone tissue engineering. I: Preparation and in vitro characterisation. Biomaterials. Aug. 2004;25(18):4185-94.

Marcovich et al., Comparison of 2-octyl cyanoacrylate adhesive, fibrin glue, and suturing for wound closure in the porcine urinary tract. Urology. Apr. 2001;57(4):806-10.

Marelli et al., Silk fibroin derived polypeptide-induced biomineralization of collagen. Biomaterials. Jan. 2012;33(1):102-8.

Martinez-Subiela et al., Effects of hemolysis, lipemia, hyperbilirubinemia, and anticoagulants in canine C-reactive protein, serum amyloid A, and ceruloplasmin assays. Can Vet J. Jul. 2005;46(7):625-9.

Marunaka, Roles of interstitial fluid pH in diabetes mellitus: Glycolysis and mitochondrial function. World J Diabetes. Feb. 15, 2015;6(1):125-35.

Mastrogiacomo et al., Role of scaffold internal structure on in vivo bone formation in macroporous calcium phosphate bioceramics. Biomaterials. Jun. 2006;27(17):3230-7.

Mathur et al., Silk fibroin-derived nanoparticles for biomedical applications. Nanomedicine (Lond). Jul. 2010;5(5):807-20.

McAleer et al., Stability on storage at various temperatures of live measles, mumps and rubella virus vaccines in new stabilizer. J Biol Stand. 1980;8(4):281-7.

McGovern, Non-Clinical Review(s). Center for Drug Evaluation and Research, Application No. 209637Orig1s000. 242 pages, Dec. 1, 2017.

MeGeed et al., Controlled release of plasmid DNA from a genetically engineered silk-elastinlike hydrogel. Pharm Res. Jul. 2002;19(7):954-9.

Torresi et al., Immunogenicity, safety and tolerability in adults of a new single-dose, live-attenuated vaccine against Japanese encephalitis: Randomised controlled phase 3 trials. Vaccine. Nov. 23, 2010;28(50):7993-8000.

Tsioris et al., Fabrication of Silk Microneedles for Controlled-Release Drug Delivery. Advanced Functional Materials. Jan. 25, 2012;22(2):330-5.

Tsukada et al., Preparation and application of porous silk fibroin materials. Journal of Applied Polymer Science. Oct. 24, 1994;54(4):507-514.

Tsukada et al., Structural changes of silk fibroin membranes induced by immersion in methanol aqueous solutions. Journal of Polymer Science, Part B, Polymer Physics. Apr. 15, 1994;32(5):961-968.

Tsukada et al., Structure and Compatibility of Poly(vinyl Alcohol)-Silk Fibroin (PVA/SF) Blend Films. Journal of Polymer Science Part B: Polymer Physics. Jan. 30, 1994;32(2):243-248.

Turner et al., Determination of the pH gradient across the stratum corneum. J Investig Dermatol Symp Proc. Aug. 1998;3(2):110-3.

Ueno et al., Accelerating effects of chitosan for healing at early phase of experimental open wound in dogs. Biomaterials. Aug. 1999;20(15):1407-14.

Um et al., Structural characteristics and properties of the regenerated silk fibroin prepared from formic acid. Int J Biol Macromol. Aug. 20, 2001;29(2):91-7.

Urquhart et al., Rate-controlled delivery systems in drug and hormone research. Annu Rev Pharmacol Toxicol. 1984;24:199-236.

Valluzzi et al., Methionine Redox Controlled Crystallization of Biosynthetic Silk Spidroin. J Phys Chem B. 1999;103(51):11382-11392.

Vander Straeten et al., A microneedle vaccine printer for thermostable COVID-19 mRNA vaccines. Nat Biotechnol. Apr. 24, 2023. doi: 10.1038/s41587-023-01774-z, with supplemental materials. 34 pages.

Vanderhooft et al., Synthesis and characterization of novel thiol-reactive poly(ethylene glycol) cross-linkers for extracellular-matrix-mimetic biomaterials. Biomacromolecules. Sep. 2007;8(9):2883-9.

Varma et al., Polymeric precursor route for the preparation of calcium phosphate compounds. Ceramics International. 1998;24(6):467-470.

Vepari et al., Silk as a Biomaterial. Prog Polym Sci. 2007;32(8-9):991-1007.

Vollrath et al., Silk production in a spider involves acid bath treatment. Proc Biol Sci. May 7, 1998;265(1398):817-820.

Vunjak-Novakovic et al., Dynamic cell seeding of polymer scaffolds for cartilage tissue engineering. Biotechnol Prog. Mar.-Apr. 1998;14(2):193-202.

Wallace et al., A tissue sealant based on reactive multifunctional polyethylene glycol. J Biomed Mater Res. 2001;58 (5):545-55.

Wang et al., A large family of putative transmembrane receptors homologous to the product of the Drosophila tissue polarity gene frizzled. J Biol Chem. Feb. 23, 1996;271(8):4468-76.

Wang et al., Biomaterial coatings by stepwise deposition of silk fibroin. Langmuir. Nov. 22, 2005;21(24):11335-41.

Wang et al., Controlled release from multilayer silk biomaterial coatings to modulate vascular cell responses. Biomaterials. Mar. 2008;29(7):894-903.

Wang et al., Enhanced Cancer Immunotherapy by Microneedle Patch-Assisted Delivery of Anti-PD1 Antibody. Nano Lett. Apr. 13, 2016;16(4):2334-40.

Wang et al., Growth factor gradients via microsphere delivery in biopolymer scaffolds for osteochondral tissue engineering. J Control Release. Mar. 4, 2009;134(2):81-90.

Wang et al., In vivo degradation of three-dimensional silk fibroin scaffolds. Biomaterials. Aug.-Sep. 2008;29(24-25):3415-28.

Wang et al., Silk Microneedle Patch Capable of On-Demand Multidrug Delivery to the Brain for Glioblastoma Treatment. Adv Mater. Jan. 2022;34(1):e2106606, 12 pages.

Wang et al., Silk nanospheres and microspheres from silk/pva blend films for drug delivery. Biomaterials. Feb. 2010;31(6):1025-35.

Wang et al., Sonication-induced gelation of silk fibroin for cell encapsulation. Biomaterials. Mar. 2008;29(8):1054-64.

Ward et al., Projected U.S. State-Level Prevalence of Adult Obesity and Severe Obesity. N Engl J Med. Dec. 19, 2019;381(25):2440-2450.

Warren et al., Highly efficient reprogramming to pluripotency and directed differentiation of human cells with synthetic modified mRNA. Cell Stem Cell. Nov. 5, 2010;7(5):618-30.

Waterman et al., Accelerated aging: prediction of chemical stability of pharmaceuticals. Int J Pharm. Apr. 11, 2005;293(1-2):101-25.

Wenk et al., Microporous silk fibroin scaffolds embedding PLGA microparticles for controlled growth factor delivery in tissue engineering. Biomaterials. May 2009;30(13):2571-81.

Wenk et al., Silk fibroin as a vehicle for drug delivery applications. J Control Release. Mar. 10, 2011;150(2):128-41.

Wenk et al., Silk fibroin spheres as a platform for controlled drug delivery. J Control Release. Nov. 24, 2008;132(1):26-34.

Wenk, Silk Fibroin as a Vehicle for Drug Delivery in Tissue Regeneration. A dissertation submitted to Eth Zurich for the Degree of Doctor of Sciences. 195 pages, (2009).

Wheat et al., Advances in bioadhesives, tissue sealants, and hemostatic agents. Urol Clin North Am. May 2009;36(2):265-75.

WHO, Health a Key to Prosperity, Success Stories in Developing Countries. Retrieved online at: https://apps.who.int/iris/bitstream/handle/10665/66616/WHO_CDS_2000.4.pdf?sequence=1&isAllowed=y. Communicable Diseases/World Health Organization, 62 pages, (2000).

WHO, Measles. Retrieved online at: http://who.int/mediacentre/factsheets/fs286/en/. 4 pages, Oct. 2011.

WHO, Requirements for measles, mumps and rubella vaccines and combined vaccine (live), (Requirements for Biological Substances No. 47). WHO Technical Report Series No. 840, Annex 3, retrieved online at: https://www.who.int/biologicals/publications/trs/areas/vaccines/mmr/WHO_TRS_840_A3.pdf, (1994).

WHO, Temperature sensitivity of vaccines. Retrieved online at: https://apps.who.int/iris/bitstream/handle/10665/69387/WHO_IVB_06.10_eng.pdf;jsessi. World Health Organization, 73 pages, Aug. 2006.

WHO, WHO Expert Committee on Biological Standardization, Thirty-second Report. Retrieved online at: https://apps.who.int/iris/bitstream/handle/10665/41534/WHO_TRS_673.pdf?sequence=1&isAllowed=y. World Health Organization Technical Report Series 673. 182 pages, (1982).

(56)  References Cited

OTHER PUBLICATIONS

Wightman et al., An investigation into the behaviour of air rifle pellets in ballistic gel and their interaction with bone. Forensic Sci Int. Jul. 15, 2010;200(1-3):41-9.

Wikipedia, Conjugate vaccine. Retrieved online at: https://en.wikipedia.org/wiki/Conjugate_vaccine, 4 pages, Dec. 18, 2019.

Wild et al., Measles virus: both the haemagglutinin and fusion glycoproteins are required for fusion. J Gen Virol. Feb. 1991;72 ( Pt 2):439-42.

Wilson et al., Building oligonucleotide therapeutics using non-natural chemistries. Current Opinion in Chemical Biology. Dec. 2006;10(6):607-614.

Wilson et al., Surface organization and nanopatterning of collagen by dip-pen nanolithography. Proc Natl Acad Sci U S A. Nov. 20, 2001;98(24):13660-4.

Woelk et al., Increased positive selection pressure in persistent (SSPE) versus acute measles virus infections. J Gen Virol. Jun. 2002;83(Pt 6):1419-1430.

Wolfson et al., Estimating the costs of achieving the WHO-UNICEF Global Immunization Vision and Strategy, 2006-2015. Bulletin of the World Health Organization. 2008;86:27-39.

Wong Po Foo et al., Genetic engineering of fibrous proteins: spider dragline silk and collagen. Adv Drug Deliv Rev. Oct. 18, 2002;54(8):1131-43.

Worrall et al., Xerovac: an ultra rapid method for the dehydration and preservation of live attenuated Rinderpest and Peste des Petits ruminants vaccines. Vaccine. Nov. 22, 2000;19(7-8):834-9.

Wray et al., Effect of processing on silk-based biomaterials: reproducibility and biocompatibility. J Biomed Mater Res B Appl Biomater. Oct. 2011;99(1):89-101.

Yamada et al., AFM observation of silk fibroin on mica substrates: morphologies reflecting the secondary structures. Thin Solid Films. Sep. 1, 2003;440(1-2):208-216.

Chothia et al., Canonical structures for the hypervariable regions of immunoglobulins. J Mol Biol. Aug. 20, 1987;196 (4):901-17.

Cirelli et al., Germinal center enhancement by extended antigen availability. Curr Opin Immunol. Aug. 2017;47:64-69.

Cirelli et al., Slow Delivery Immunization Enhances HIV Neutralizing Antibody and Germinal Center Responses via Modulation of Immunodominance. Cell. May 16, 2019;177(5):1153-1171.e28. pre-publication edition.

Colinet et al., A study of the stability of a bivalent measles—mumps vaccine. J Biol Stand. Oct. 1982;10(4):341-6.

Collins et al., Bone-like Resorbable Silk-based Scaffolds for Load-bearing Osteoregenerative Applications. Advanced Materials. Jan. 2, 2009;21(1):75-78.

Creighton et al., Protein folding. Biochem J. Aug. 15, 1990;270(1):1-16.

Curtis et al., Hydrophobic forces between protein molecules in aqueous solutions of concentrated electrolyte. Biophys Chem. Aug. 2, 2002;98(3):249-65.

Demura et al., Immobilization of biocatalysts with bombyx mori silk fibroin by several kinds of physical treatment and its application to glucose sensors. Biosensors. 1989;4(6):361-372.

Demura et al., Immobilization of glucose oxidase with Bombyx mori silk fibroin by only stretching treatment and its application to glucose sensor. Biotechnol Bioeng. Jan. 25, 1989;33(5):598-603.

Demura et al., Porous membrane of Bombyx mori silk fibroin: structure characterization, physical properties and application to glucose oxidase immobilization. Journal of Membrane Science. Jun. 15, 1991;59(1):39-52.

Demuth et al., Implantable silk composite microneedles for programmable vaccine release kinetics and enhanced immunogenicity in transcutaneous immunization. Adv Healthc Mater. Jan. 2014;3(1):47-58.

Deuel et al., Growth Factors. Principles and Practices, 2nd Edition. Robert Lanza (Ed.), Academic Press. Chapter 12, pp. 129-141. May 4, 2000.

Deville et al., Freeze casting of hydroxyapatite scaffolds for bone tissue engineering. Biomaterials. Nov. 2006;27 (32):5480-9.

Dinerman et al., Solute diffusion in genetically engineered silk-elastinlike protein polymer hydrogels. J Control Release. Aug. 21, 2002;82(2-3):277-87.

Dineva et al., Sample preparation: a challenge in the development of point-of-care nucleic acid-based assays for resource-limited settings. Analyst. Dec. 2007;132(12):1193-9.

Ding et al., Utility of GÃ¶ttingen minipigs for the prediction of human pharmacokinetic profiles after intravenous drug administration. Drug Metab Pharmacokinet. Dec. 2021;41:100408, 22 pages.

Division of Organic Chemistry American Chemical Society. Common Organic Solvents: Table of Properties. Retrieved online at: www.organicdivision.org/orig/organic_solvents.html. 2 pages, Oct. 5, 2016.

Division of Organic Chemistry, Common Organic Solvents: Table of Properties. Retrieved online at: https://www.orgnicdivision.org/orig/organic_solvents.html. 2 pages, Aug. 9, 2016.

Dorsett et al., Structure and function of the rubella virus proteins. Rev Infect Dis. Mar.-Apr. 1985;7 Suppl 1:S150-6.

Doshi et al., Electrospinning process and applications of electrospun fibers. Journal of Electrostatics. Aug. 1995;35 (2-3):151-160.

Dyakonov et al., Design and characterization of a silk-fibroin-based drug delivery platform using naproxen as a model drug. J Drug Deliv. 2012;2012:490514, 11 pages.

Edens et al., A microneedle patch containing measles vaccine is immunogenic in non-human primates. Vaccine. Sep. 8, 2015;33(37):4712-8.

Edens et al., Inactivated polio vaccination using a microneedle patch is immunogenic in the rhesus macaque. Vaccine. Sep. 8, 2015;33(37):4683-90.

Egholm et al., Peptide nucleic acids (PNA). Oligonucleotide analogs with an achiral peptide backbone. J Am Chem Soc. 1992;114(5):1895-1897.

Egholm et al., PNA hybridizes to complementary oligonucleotides obeying the Watson-Crick hydrogen-bonding rules. Nature. Oct. 7, 1993;365(6446):566-8.

Erickson, Size and Shape of Protein Molecules at the Nanometer Level Determined by Sedimentation, Gel Filtration, and Electron Microscopy. Biological Procedures Online. 2009;11:32-51.

Evans et al., Vaccine handling and storage in general practice. Health Trends. 1995;27:124-126.

Fedarko et al., Temporal regulation of hyaluronan and proteoglycan metabolism by human bone cells in vitro. J Biol Chem. Jul. 25, 1990;265(21):12200-9.

Ferguson et al., Does adult fracture repair recapitulate embryonic skeletal formation? Mech Dev. Sep. 1999;87(1-2):57-66.

Fernando et al., Safety, tolerability, acceptability and immunogenicity of an influenza vaccine delivered to human skin by a novel high-density microprojection array patch (Nanopatchâ‚‚c). Vaccine. Jun. 18, 2018;36(26):3779-3788.

Fisher et al., Proteoglycans of developing bone. J Biol Chem. May 25, 1983;258(10):6588-94.

Freddi et al., Silk Fibroin/Cellulose Blend Films: Preparation, Structure, and Physical Properties. Journal of Applied Polymer Science. Jun. 20, 1995;56(12):1537-1545.

Freshney, Culture of Animal Cells, a Manual of Basic Technique, Alan R. Liss, Inc., New York, NY. pp. 3-4, (1986).

Freshney, Maintenance of Primary and Early Passage Cultures, Methods of Tissue Engineering. Chapter 3, pp. 37-53, (2002).

Friedenstein et al., Bone marrow osteogenic stem cells: in vitro cultivation and transplantation in diffusion chambers. Cell Tissue Kinet. May 1987;20(3):263-72.

Friedenstein, Precursor cells of mechanocytes. Int Rev Cytol. 1976;47:327-59.

Friedrichsen et al., Results from three phase 1 trials of NNC9204-1177, a glucagon/GLP-1 receptor co-agonist: Effects on weight loss and safety in adults with overweight or obesity. Mol Metab. Dec. 2023;78:101801, 26 pages.

Fukui et al., Isolation and characterization of Xenopus follistatin and activins. Dev Biol. Sep. 1993;159(1):131-9.

Furst et al., Release of glutaraldehyde from an albumin-glutaraldehyde tissue adhesive causes significant in vitro and in vivo toxicity. Ann Thorac Surg. May 2005;79(5):1522-8.

(56)     References Cited

OTHER PUBLICATIONS

Gailhardou et al., Safety Overview of a Recombinant Live-Attenuated Tetravalent Dengue Vaccine: Pooled Analysis of Data from 18 Clinical Trials. PLoS Negl Trop Dis. Jul. 14, 2016;10(7):e0004821, 25 pages.

Galazka et al., Thermostability of vaccines. Global Programme for Vaccine and Immunization. WHO, World Health Organization. 64 pages, (1998).

Garg et al., Phase 1, randomized, rater and participant blinded placebo-controlled study of the safety, reactogenicity, tolerability and immunogenicity of H1N1 influenza vaccine delivered by VX-103 (a MIMIX microneedle patch [MAP] system) in healthy adults. PLoS One. Jun. 6, 2024;19(6):e0303450, 23 pages.

Gerber et al., VEGF couples hypertrophic cartilage remodeling, ossification and angiogenesis during endochondral bone formation. Nat Med. Jun. 1999;5(6):623-8.

Gill et al., Improved hemostasis during laparoscopic partial nephrectomy using gelatin matrix thrombin sealant. Urology. Mar. 2005;65(3):463-6.

Griffin et al., Safety, acceptability and tolerability of uncoated and excipient-coated high density silicon micro-projection array patches in human subjects. Vaccine. Dec. 4, 2017;35(48 Pt B):6676-6684.

Grigsby et al., Cloud-point temperatures for lysozyme in electrolyte solutions: effect of salt type, salt concentration and pH. Biophys Chem. Jul. 24, 2001;91(3):231-43.

Guziewicz et al., Lyophilized silk fibroin hydrogels for the sustained local delivery of therapeutic monoclonal antibodies. Biomaterials. Apr. 2011;32(10):2642-50.

Ha et al., Structural studies of Bombyx mori silk fibroin during regeneration from solutions and wet fiber spinning. Biomacromolecules. May-Jun. 2005;6(3):1722-31.

Haby, Atmospheric Water Vapor, retrieved online at: http://www.theweatherprediction.com/habyhints/40/. 1 page, Apr. 17, 2019.

Hall et al., Purification and characterization of measles virus. J Gen Virol. May 1973;19(2):175-88.

Rajkhowa et al., Molecular weight and secondary structure change in eri silk during alkali degumming and powdering. Journal of Applied Polymer Science. Aug. 18, 2010;119(3):1339-1347.

Ranheim et al., Development and application of a quantitative RT-PCR potency assay for a pentavalent rotavirus vaccine (RotaTeq). J Virol Methods. Feb. 2006;131(2):193-201.

Rapp et al., Protection of Measles Virus by Sulfate Ions Against Thermal Inactivation. J Bacteriol. Jul. 1965;90(1):132-5.

Reneker et al., Nanometre diameter fibres of polymer, produced by electrospinning. Nanotechnology. 1996;7:216-223 (1996).

Rexroad et al., Effect of pH and ionic strength on the physical stability of adenovirus type 5. J Pharm Sci. Feb. 2006;95(2):237-47.

Richardson, Coulson and Richardson's Chemical Engineering, Particle Technology and Separation Processes, vol. 2, 5th Edition. Butterworth Heinemann, Oxford. p. 126, (2002).

Roberts, Non-native protein aggregation kinetics. Biotechnol Bioeng. Dec. 1, 2007;98(5):927-38.

Robinson et al., The Effect of Concentrated Salt Solutions on the Activity Coefficient of Acetyltetraglycine Ethyl Ester. J Am Chem Soc. Jun. 5, 1965;87:2470-9.

Rockwood et al., Materials fabrication from Bombyx mori silk fibroin. Nat Protoc. Sep. 22, 2011;6(10):1612-31. pre-publication edition.

Rossolini et al., Use of deoxyinosine-containing primers vs degenerate primers for polymerase chain reaction based on ambiguous sequence information. Mol Cell Probes. Apr. 1994;8(2):91-8.

Rouphael et al., The safety, immunogenicity, and acceptability of inactivated influenza vaccine delivered by microneedle patch (TIV-MNP 2015): a randomised, partly blinded, placebo-controlled, phase 1 trial. Lancet. Aug. 12, 2017;390(10095):649-658.

Roy Chowdhury et al., Real-World Use of Oral and Subcutaneous Semaglutide in Routine Clinical Practice in the UK: A Single-Centre, Retrospective Observational Study. Diabetes Ther. Apr. 2024;15(4):869-881.

Roy et al., Freeze-drying of proteins: some emerging concerns. Biotechnol Appl Biochem. Apr. 2004;39(Pt 2):165-77.

Russell et al., The particle size of rubella virus. J Gen Virol. Jul. 1967;1(3):305-10.

Samal et al., Ultrasound Sonication Effects on Silk Fibroin Protein. Macromolecular Materials and Engineering. May 7, 2013;298(11):1201-1208. pre-publication edition.

Sanchez-Trasvina et al., Transdermal microneedle patches as a promising drug delivery system for anti-obesogenic molecules. Front Bioeng Biotechnol. Jun. 11, 2024;12:1380537, 13 pages.

Santin et al., In vitro evaluation of the inflammatory potential of the silk fibroin. J Biomed Mater Res. Sep. 5, 1999;46(3):382-9.

Sato et al., Animal Cell Culture. Principles of Tissue Engineering, Second Edition. Robert P. Lanza (Ed.). Academic Press, San Diego. Chapter 10, pp. 111-118, (2000).

Sawyer et al., Dextran therapy in thrombophlebitis. JAMA. Mar. 1, 1965;191:740-2.

Schaffner et al., Structure and function of RGD peptides involved in bone biology. Cell Mol Life Sci. Jan. 2003;60(1):119-32.

Schalk et al., Potency estimation of measles, mumps and rubella trivalent vaccines with quantitative PCR infectivity assay. Biologicals. Jun. 2005;33(2):71-9.

Scheibel, Spider silks: recombinant synthesis, assembly, spinning, and engineering of synthetic proteins. Microb Cell Fact. Nov. 16, 2004;3(1):14, 10 pages.

Scott et al., Personal medicine—the new banking crisis. Nat Biotechnol. Feb. 8, 2012;30(2):141-7.

Scriver, A simple phenylalanine method for detecting phenylketonuria in large populations of newborn infants, by Robert Guthrie and Ada Susi, Pediatrics, 1963;32:318-343. Pediatrics. Jul. 1998;102(1 Pt 2):236-7.

Sellers et al., Society of Toxicologic Pathology position paper: organ weight recommendations for toxicology studies. Toxicol Pathol. Aug. 2007;35(5):751-5.

Selvaraj et al., Formulation, Efficacy and Immunogenicity Studies of a Liquid State Rabies Vaccine with Magnesium Chloride as Stabilizer. J Vaccines Vaccin 2015;6(5)4 pages.

Serizawa et al., Enzymatic Hydrolysis of a Layer-by-Layer Assembly Prepared from Chitosan and Dextran Sulfate. Macromolecules. 2002;35(23):8656-8658.

Shi et al., Pharmacokinetics, Safety and Tolerability of Once-Weekly Subcutaneous Semaglutide in Healthy Chinese Subjects: A Double-Blind, Phase 1, Randomized Controlled Trial. Adv Ther. Jan. 2021;38(1):550-561.

Sigma-Aldrich, DMEM (Dulbecco's Modified Eagle Medium). Retrieved online at: https://www.sigmaaldrich.com/life-science/cell-culture/classical-media-salts/dmem.html. 2 pages, (2021).

Sikavitsas et al., Formation of three-dimensional cell/polymer constructs for bone tissue engineering in a spinner flask and a rotating wall vessel bioreactor. J Biomed Mater Res. Oct. 2002;62(1):136-48.

Silva et al., Genipin-modified silk-fibroin nanometric nets. Macromol Biosci. Aug. 11, 2008;8(8):766-74. pre-publication edition.

Singh et al., Physiological properties and differential glycosylation of phosphorylated and nonphosphorylated forms of osteopontin secreted by normal rat kidney cells. J Biol Chem. Oct. 25, 1990;265(30):18696-701.

Singh et al., Single-Administration Self-Boosting Microneedle Patch for the Treatment of Obesity. Adv Ther (Weinh). Sep. 2024;7(9):2400028, 9 pages.

Soffer et al., Silk-based electrospun tubular scaffolds for tissue-engineered vascular grafts. J Biomater Sci Polym Ed. 2008;19(5):653-64.

Sofia et al., Functionalized silk-based biomaterials for bone formation. J Biomed Mater Res. Jan. 2001;54(1):139-48.

Soon et al., Compressive strength and processing of camphene-based freeze cast calcium phosphate scaffolds with aligned pores. Materials Letters. 2009;63:1548-1550.

Spain et al., Self-reported Barriers to Adherence and Persistence to Treatment With Injectable Medications for Type 2 Diabetes. Clin Ther. Jul. 2016;38(7):1653-1664.

Spotnitz et al., Hemostats, sealants, and adhesives: components of the surgical toolbox. Transfusion. Jul. 2008;48 (7):1502-16.

(56)  References Cited

OTHER PUBLICATIONS

Stinson et al., Enhancing influenza vaccine immunogenicity and efficacy through infection mimicry using silk microneedles. Vaccine. https://www.sciencedirect.com/science/article/pii/S0264410X21009579. 12 pages, Aug. 2021.
Stinson et al., Thin silk fibroin films as a dried format for temperature stabilization of inactivated polio vaccine. Vaccine. Feb. 11, 2020;38(7):1652-1660.
Stricker-Krongrad et al., The importance of minipigs in dermal safety assessment: an overview. Cutan Ocul Toxicol. Jun. 2017;36(2):105-113.
Sullivan et al., Minimally invasive protein delivery with rapidly dissolving polymer microneedles. Adv Mater. Mar. 2008;20(5):933-938.
Takahashi et al., Induction of pluripotent stem cells from adult human fibroblasts by defined factors. Cell. Nov. 30, 2007;131(5):861-72.
Tam et al., Sustained antigen availability during germinal center initiation enhances antibody responses to vaccination. Proc Natl Acad Sci U S A. Oct. 25, 2016;113(43):E6639-E6648. pre-publication edition.
Tamada et al., New process to form a silk fibroin porous 3-D structure. Biomacromolecules. Nov.-Dec. 2005;6(6):3100-6.
Tan et al., Albumin-binding domain extends half-life of glucagon-like peptide-1. Eur J Pharmacol. Jan. 5, 2021;890:173650, 18 pages.
Tanaka et al., Properties of Silk Fibroin/Poly(vinyl alcohol) Blend Solutions and Peculiar Structure Found in Heterogeneous Blend Films. Polymer International. Mar. 26, 1999;42(1):107-111.
Thomson et al., Hydroxyapatite fiber reinforced poly(alpha-hydroxy ester) foams for bone regeneration. Biomaterials. Nov. 1998;19(21):1935-43.
Thomson et al., Polymer Scaffold Processing. Principles of Tissue Engineering, Second Edition. Academic Press. Chapter 21, pp. 251-262, (2000).
Torchiana, Polyethylene glycol based synthetic sealants: potential uses in cardiac surgery. J Card Surg. Nov.-Dec. 2003;18(6):504-6.
U.S. Appl. No. 17/714,025, filed Apr. 5, 2022, 2022-0339416, Published.
U.S. Appl. No. 16/334,215, filed Mar. 18, 2019, 2019-0275136, Abandoned.
U.S. Appl. No. 17/958,148, filed Sep. 30, 2022, 2023-0190911, Published.
U.S. Appl. No. 14/112,769, filed Jun. 12, 2014, 2014-0287043, Abandoned.
U.S. Appl. No. 15/858,239, filed Dec. 29, 2017, U.S. Pat. No. 12,280,101, Issued.
U.S. Appl. No. 15/492,363, filed Apr. 20, 2017, 2017-0258889, Abandoned.
U.S. Appl. No. 19/076,476, filed Mar. 11, 2025, Pending.
U.S. Appl. No. 14/775,200, filed Sep. 11, 2015, 2016-0046679, Abandoned.
U.S. Appl. No. 15/068,083, filed Mar. 11, 2016, U.S. Pat. No. 11,376,329, Issued.
U.S. Appl. No. 17/829,271, filed May 31, 2022, 2024-0082405, Published.
U.S. Appl. No. 11/247,358, filed Oct. 11, 2005, U.S. Pat. No. 7,635,4755, Issued.
U.S. Appl. No. 12/611,256, filed Nov. 3, 2009, U.S. Pat. No. 8,614,293, Issued.
U.S. Appl. No. 14/293,308, filed Jun. 2, 2014, U.S. Pat. No. 9,623,147, Issued.
U.S. Appl. No. 16/406,538, filed May 8, 2019, U.S. Pat. No. 11,129,921, Issued.
U.S. Appl. No. 12/425,541, filed Apr. 17, 2009, U.S. Pat. No. 9,084,840, Issued.
U.S. Appl. No. 13/778,480, filed Feb. 27, 2013, 2013-0165004, Abandoned.
U.S. Appl. No. 13/827,304, filed Mar. 14, 2013, U.S. Pat. No. 8,742,069, Issued.
U.S. Appl. No. 15/434,484, filed Feb. 16, 2017, U.S. Pat. No. 10,314,938, Issued.
U.S. Appl. No. 17/466,239, filed Sep. 3, 2021, 2022-0054704, Abandoned.
U.S. Appl. No. 13/880,592, filed Sep. 3, 2013, U.S. Pat. No. 10,933,173, Issued.
U.S. Appl. No. 17/173,289, filed Feb. 11, 2021, U.S. Pat. No. 12,194,200, Issued.
U.S. Appl. No. 18/968,134, filed Dec. 4, 2024, Pending.
U.S. Appl. No. 17/157,451, filed Jan. 25, 2021, 2021-0283597, Abandoned.
U.S. Appl. No. 18/792,439, filed Aug. 1, 2024, Abandoned.
U.S. Appl. No. 17/044,439, filed Oct. 1, 2020, 2021-0085598, Published.
U.S. Appl. No. 11/020,650, filed Dec. 23, 2004, U.S. Pat. No. 7,674,882, Issued.
U.S. Appl. No. 12/688,014, filed Jan. 15, 2010, U.S. Pat. No. 8,071,722, Issued.
U.S. Appl. No. 11/628,930, filed Oct. 23, 2007, U.S. Pat. No. 8,178,656, Issued.
U.S. Appl. No. 13/443,264, filed Apr. 10, 2012, U.S. Pat. No. 8,530,625, Issued.
U.S. Appl. No. 13/783,485, filed Mar. 4, 2013, 2013-0177611, Abandoned.
U.S. Appl. No. 13/826,598, filed Mar. 14, 2013, 2013-0195831, Abandoned.
U.S. Appl. No. 14/095,366, filed Dec. 3, 2013, U.S. Pat. No. 10,548,981, Issued.
U.S. Appl. No. 14/437,881, filed Apr. 23, 2015, U.S. Pat. No. 9,925,299, Issued.
U.S. Appl. No. 17/991,525, filed Nov. 21, 2022, 2023-0270842, Published.
U.S. Appl. No. 19/002,632, filed Dec. 26, 2024, Pending.
Abdullahi et al., Animal models in burn research. Cell Mol Life Sci. Sep. 2014;71(17):3241-55.
Acharya et al., Performance evaluation of a silk protein-based matrix for the enzymatic conversion of tyrosine to L-Dopa. Biotechnol J. Feb. 2008;3(2):226-33.
Adler, Challenges in the Development of Pre-filled Syringes for Biologics from a Formulation Scientist's Point of View. American Pharmaceutical Review. Retrieved online at: https://www.americanpharmaceuticalreview.com/Featured-Articles/38372-Challenges-in-the-Development-of-Pre-filled-Syringes-for-Biologics-from-a-Formulation-Scientist-s-Point-of-View/. 8 pages, Feb. 1, 2012.
Adu et al., Live viral vaccine potency: an index for assessing the cold chain system. Public Health. Nov. 1996;110(6):325-30.
Agarwal et al., Effect of Moisture Absorption on the Thermal Properties of Bombyx mori Silk Fibroin Films. J Appl Polym Sci. 1997;63:401-410.
Ajisawa, Dissolution of silk fibroin with calciumchloride/ethanol aqueous solution. The Journal of Sericultural Science of Japan. 1998;67(2):91-94.
Altman et al., Silk matrix for tissue engineered anterior cruciate ligaments. Biomaterials. Oct. 2002;23(20):4131-41.
Altman et al., Silk-based biomaterials. Biomaterials. Feb. 2003;24(3):401-16.
Ando et al., Piezoelectric and Related Properties of Hydrated Silk Fibroin. Reports on Progress in Polymer Physics in Japan. 1980;XXIII:775-778.
Andreotti et al., Correlation between HIV-1 viral load quantification in plasma, dried blood spots, and dried plasma spots using the Roche COBAS Taqman assay. J Clin Virol. Jan. 2010;47(1):4-7.
Aoi et al., Importance of pH homeostasis in metabolic health and diseases: crucial role of membrane proton transport. Biomed Res Int. 2014;2014:598986, 16 pages.
Arora et al., Micro-scale devices for transdermal drug delivery. Int J Pharm. Dec. 8, 2008;364(2):227-36.
Arvanitoyannis et al., Physico-chemical studies of chitosan-poly(vinyl alcohol) blends plasticized with sorbitol and sucrose. Carbohydrate Polymers. Dec. 5, 1997;34(1-2):9-19.
Arya et al., Tolerability, usability and acceptability of dissolving microneedle patch administration in human subjects. Biomaterials. Jun. 2017;128:1-7.

(56)            References Cited

OTHER PUBLICATIONS

Arya, Stabilization of vaccines: to be or not to be. Vaccine. Oct. 15, 2000;19(4-5):595-7.

Asakura et al., An ESR study of spin-labeled silk fibroin membranes and spin-labeled glucose oxidase immobilized in silk fibroin membranes. Biotechnol Bioeng. Mar. 5, 1990;35(5):511-7.

Asakura et al., Conformational characterization of Bombyx mori silk fibroin in the solid state by high-frequency carbon-13 cross polarization-magic angle spinning NMR, x-ray diffraction, and infrared spectroscopy. Macromolecules. 1985;18(10):1841-1845.

Asakura et al., NMR of Silk Fibroin. 2. C NMR Study of the Chain Dynamics and Solution Structure of Bombyx mori Silk Fibroin. Macromolecules. 1984;17:1075-1081.

Asakura et al., Silk Production and Processing. Encyclopedia of Agricultural Science, vol. 4, 1st Edition. Charles J. Arntzen (Ed.), Academic Press. pp. 1-11, Nov. 28, 1994.

Ausar et al., Conformational stability and disassembly of Norwalk virus-like particles. Effect of pH and temperature. J Biol Chem. Jul. 14, 2006;281(28):19478-88.

Ayub et al., Mechanism of the Gelation of Fibroin Solution. Bioscience, Biotechnology, and Biochemistry. 1993;57(11):1910-1912.

Batzer et al., Enhanced evolutionary PCR using oligonucleotides with inosine at the 3'-terminus. Nucleic Acids Res. Sep. 25, 1991;19(18):5081.

Bayraktar et al., Silk fibroin as a novel coating material for controlled release of theophylline. Eur J Pharm Biopharm. Aug. 2005;60(3):373-81.

Beaucage et al., The Functionalization of Oligonucleotides via Phosphoramidite Derivatives. Tetrahedron. Mar. 5, 1993;49(10)1925-1963.

Beauchamp et al., Temperature and the storage of vaccines. N Z Med J. Apr. 8, 1992;105(931):135.

Bini et al., Mapping domain structures in silks from insects and spiders related to protein assembly. J Mol Biol. Jan. 2, 2004;335(1):27-40.

Bishai et al., Vaccine storage practices in pediatric offices. Pediatrics. Feb. 1992;89(2):193-6.

Bolon et al., STP position paper: Recommended practices for sampling and processing the nervous system (brain, spinal cord, nerve, and eye) during nonclinical general toxicity studies. Toxicol Pathol. 2013;41(7):1028-48.

Boopathy et al., Enhancing humoral immunity via sustained-release implantable microneedle patch vaccination. Proc Natl Acad Sci U S A. Aug. 13, 2019;116(33):16473-16478. pre-publication edition.

Brandau et al., Thermal stability of vaccines. J Pharm Sci. Feb. 2003;92(2):218-31.

Braun et al., Modelling self assembly of natural silk solutions. Int J Biol Macromol. Sep. 2003;32(3-5):59-65.

Bregman et al., Recommended tissue list for histopathologic examination in repeat-dose toxicity and carcinogenicity studies: a proposal of the Society of Toxicologic Pathology (STP). Toxicol Pathol. Mar.-Apr. 2003;31(2):252-3.

Burckbuchler et al., Rheological and syringeability properties of highly concentrated human polyclonal immunoglobulin solutions. Eur J Pharm Biopharm. Nov. 2010;76(3):351-6.

Cai et al., Fabrication of Chitosan/Silk Fibroin Composite Nanofibers for Wound-dressing Applications. Int J Mol Sci. 2010;11(9):3529-3539.

Caplan, The mesengenic process. Clin Plast Surg, an International Quarterly, Bone Repair and Regeneration. Jul. 1994;21(3):429-35.

Cappello et al., In-situ self-assembling protein polymer gel systems for administration, delivery, and release of drugs. J Control Release. Apr. 30, 1998;53(1-3):105-17.

CDC, MMWR, Morbidity and Mortality Weekly Report. Center for Disease Control. Jun. 21, 1996;45(24):505-524.

Chang et al., C-reactive protein binds to both oxidized LDL and apoptotic cells through recognition of a common ligand: Phosphorylcholine of oxidized phospholipids. Proc Natl Acad Sci U S A. Oct. 1, 2002;99(20):13043-8.

Chao et al., Silk hydrogel for cartilage tissue engineering. J Biomed Mater Res B Appl Biomater. Oct. 2010;95(1):84-90.

Chen et al., Conformation transition kinetics of Bombyx mori silk protein. Proteins. Jul. 1, 2007;68(1):223-31.

Chen et al., Human bone marrow stromal cell and ligament fibroblast responses on RGD-modified silk fibers. J Biomed Mater Res A. Nov. 1, 2003;67(2):559-70.

Chen et al., Improvement of physicochemical stabilities of emulsions containing oil droplets coated by non-globular protein-beet pectin complex membranes. Food Research International. Jun. 2011;44(5):1468-1475.

Chen et al., Opportunities and challenges of developing thermostable vaccines. Expert Rev Vaccines. May 2009;8(5):547-57.

Chen et al., pH sensitivity and ion sensitivity of hydrogels based on complex-forming chitosan/silk fibroin interpenetrating polymer network. Journal of Applied Polymer Science. Dec. 7, 1998;65(11):2257-2262.

Chen et al., Rheological characterization of nephila spidroin solution. Biomacromolecules. Jul.-Aug. 2002;3(4):644-8.

Chen et al., Separation of alcohol-water mixture by pervaporation through a novel natural polymer blend membrane-chitosan/silk fibroin blend membrane. Journal of Applied Polymer Science. Aug. 8, 1999;73(6):975-980.

Chen et al., Transport of pharmaceuticals through silk fibroin membrane. Polymer. Jun. 1994;35(13):2853-2856.

Chen, Polymeric drug delivery systems: lidocaine microspheres for prolonged and localized in vivo anesthetic effects and light-induced drug release from polymeric device mediated by bacteriorhodopsin. Thesis abstract. 2 pages, (2004).

Cheriyan, Monitoring the vaccine cold chain. Arch Dis Child. Nov. 1993;69(5):600-1.

Cheyne, Vaccine delivery management. Rev Infect Dis. May-Jun. 1989;11 Suppl 3:S617-22.

International Search Report and Written Opinion for Application No. PCT/US2024/062002, dated May 12, 2025, 26 pages.

* cited by examiner application    tips disengage    tips dissolve

FIG. 3
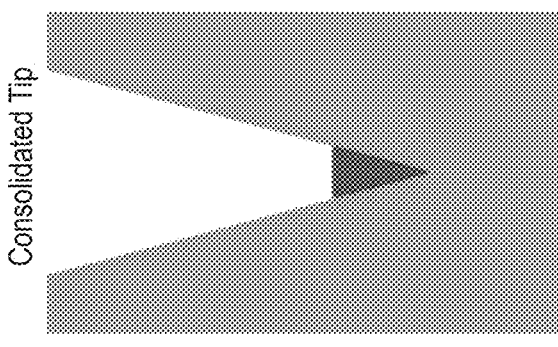
Consolidated Tip
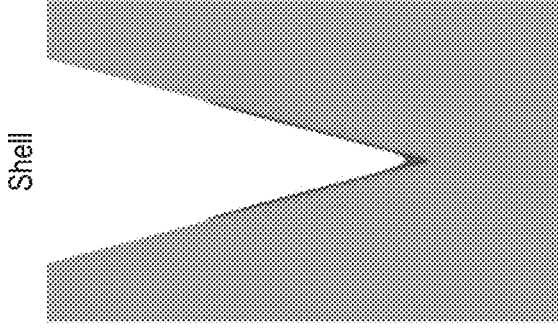
Shell
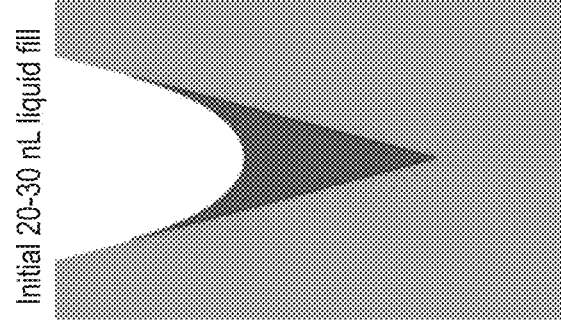
Initial 20-30 nL liquid fill

FIG. 4

Interfacial Tension (adhesion)

↑Adhesion ↓Consolidation

- Hydrophilic/polar vs –phobic/non-polar (PDMS is non-polar)
  - Surfactants & Proteins have -philic and -phobic regions
- Charge interactions (silicone mold is slight neg charge )
- *pI of ingredients, pH of form through drying*
  - Salts, charge shielding?
- Contact line "pinning"
  - Microscale roughness, or precipitated solids can cause pinning

Viscosity

↑ *Viscosity* ↑ Resistance to flow ↓Flow rate ↓Resistance ↑ Consolidation

Fluid flow

- Solids Content and viscosity increase during drying – at some point viscosity rises to a point such that flow is no longer possible
- Intrinsic viscosity – lower is probably better (printability may have different optimum)
- *Solubility* / precipitation of ingredients during drying a consideration
- Protein-protein interactions / aggregation increase viscosity?
- Plasticization (i.e. reduce viscosity at low %water)
  - Non-volatile liquids e.g. Tween-20, Glycerol, Triton-X, Low MW PEG
  - Less-volatile solvents e.g. DMSO, Propanediol
- Water retention / *hygroscopicity* (e.g. sucrose, maybe PVP), water is also a plasticizer

Evaporation

↑Evaporation rate ↑Material flow rate

- Evaporation affected by:
  - *Temperature*
  - *Humidity* (water)
  - Volatility (other solvents)
  - Diffusion gradient within needle cavity
  - Convection at mold surface

Colloidal diffusion

↑*Particle size* ↓Diffusion ↓Consolidation (?)

- Increased solvent viscosity also reduces diffusion. Sucrose, Tween, polymers could be counterproductive in this mechanism

Surface Tension (cohesion)

Many things that plasticize also reduce surface tension, so there may be trade-offs or optimal windows ↑*Surface Tension* ↑Consolidation

- Water vs other solvents
- Surfactants ↓ST
- Proteins, polymers slightly ↓ST
- Salts very slightly ↑ST
- Printability, mold filling may have different optimal range vs. consolidation

Contact line
We want this to recede (de-wetting)

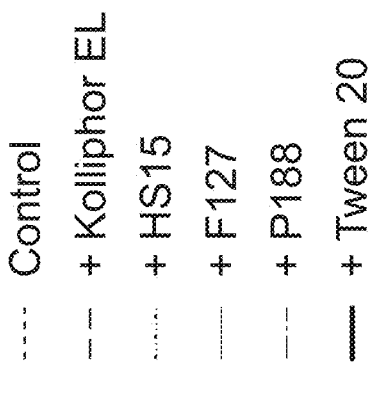
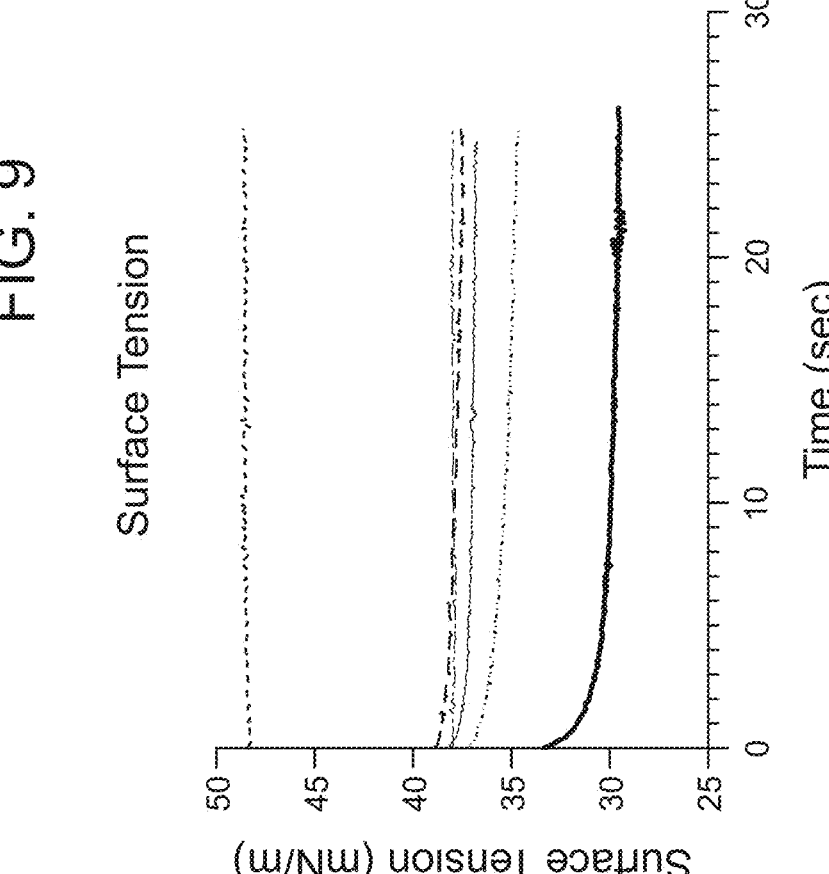

FIG. 12

Deployment depth (um)- VX-103 vs GLP-1

FIG. 13B

Force / extension curves of GLP-1 MAPs vs VX-103 MAPs

Base Ultimate Strength

Sample Types

Questions:
Can dextran and/or higher loading of PVP K17 improve tip strength?

Experimental details:
- Dextran (3%) and PVP K17 (6%) compared to the control group
- Formulation: 1.37% Arg-HCl + 180 mg/mL API + 100 mM MOPS pH 7.5 + 0.1% Kalliphor EL + 0.1mg/mL AF-647 dye
- 20 nL target fill volume

Conclusions:
- Higher concentration of PVP or 3% Dextran do not improve structural strength of the needle
- Dextran may be a viable option

Next steps:
- Add salt to improve dextran tips

Key Results and Takeaways:
- Dextran tips had longer shells than PVP
- Instron compression testing shows no significant difference in peak force (N) between the groups

| | Control: 1% PVP K17 | Dextran (3%) | High PVP (6%) |
|---|---|---|---|
| tip length (um) | 394.1 | 413.0 | 388.6 |
| shell length (um) | 91.92 | 128.91 | 55.24 |
| %consolidation | 76.7% | 68.8% | 85.8% |

Tip length, %consolidation and tip strength were comparable

| | 100 mM MOPS (pH 7.9) | 100 mM Tris-HCl (pH 8.2) |
|---|---|---|
| Fill per needle (nL) | 19.60 | 19.36 |
| Tip length (um) | 368.2 | 366.2 |
| Shell length (um) | 52.57 | 56.14 |
| %Consolidation | 85.7% | 84.7% |

Failure force/needle

FIG. 18

| | Arg-HCl (1.37%) | Histidine (0.5%) | Proline (0.75%) |
|---|---|---|---|
| Tip length (um) | 392.3 | 415.0 | 381.3 |
| Shell length (um) | 96.6 | 134.6 | 82.4 |
| %Consolidation | 75.4% | 67.6% | 78.4% |

FIG. 19
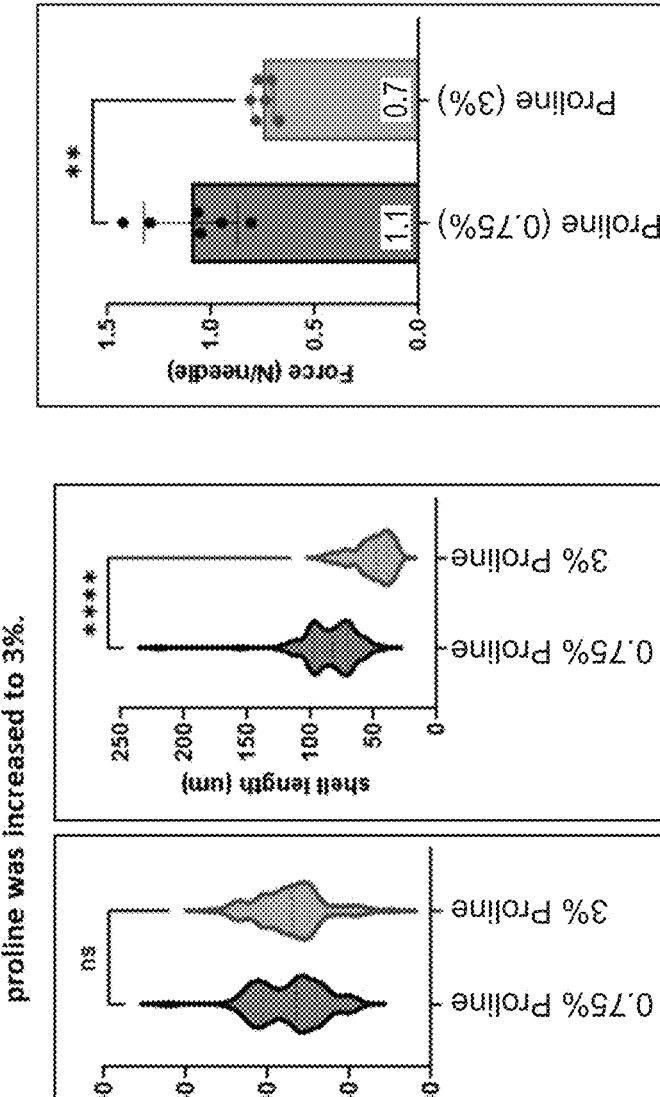
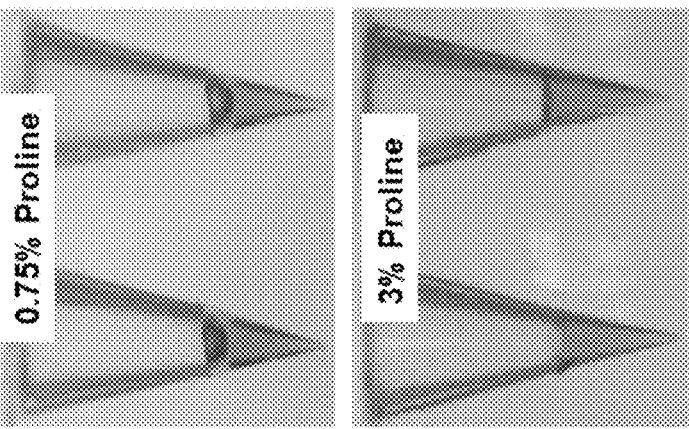

| | NaCl (0.9%) | MgCl2 (1%) | MgCl2 (0.5%) | Control (GLP-060) |
|---|---|---|---|---|
| tip length (um) | 378.1 | 340.8 | 378.1 | 397.5 |
| shell length (um) | 55.2 | 59.8 | 55.2 | 80.5 |
| %consolidation | 85.4% | 82.4% | 85.4% | 79.7% |

|  | 0.75% Proline + 0.9% NaCl | 0.75% Proline |
|---|---|---|
| tip length (um) | 381.2 | 385.9 |
| shell length (um) | 55.82 | 85.33 |
| %consolidation | 85.4% | 77.9% |

FIG. 22
GLP-136
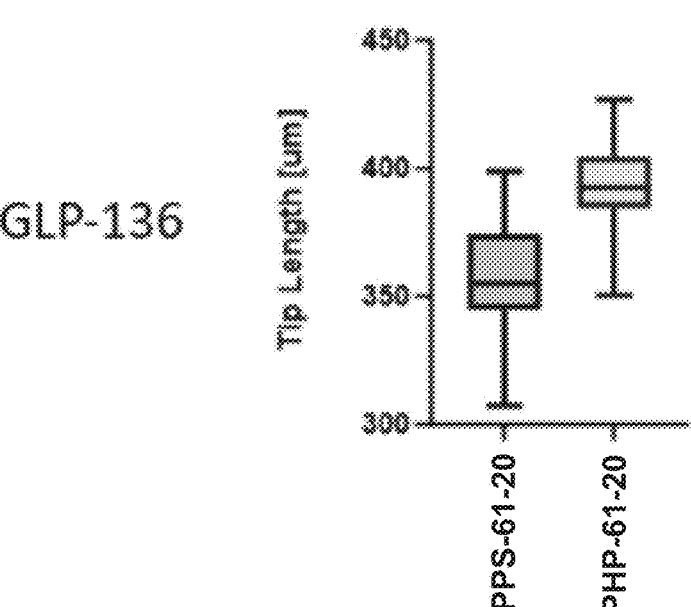
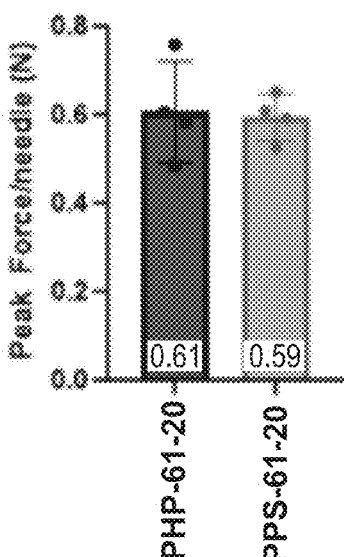
GLP-142
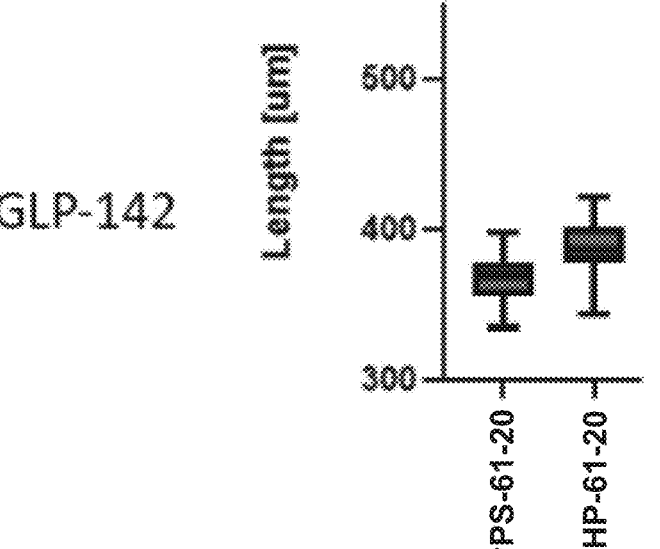
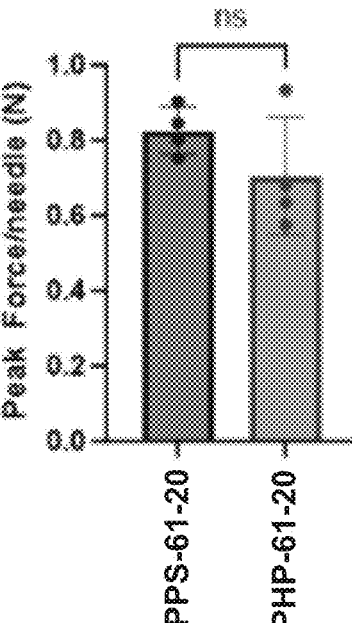

FIG. 23A

Compiled PD-IVR Results

60 Needles

90 Needles

Rectangular sub-arrays

Filled needles are indicated by an X, all other mold cavities are left empty

Circular sub-arrays

Filled needles are indicated by an X, all other mold cavities are left empty

FIG. 25C
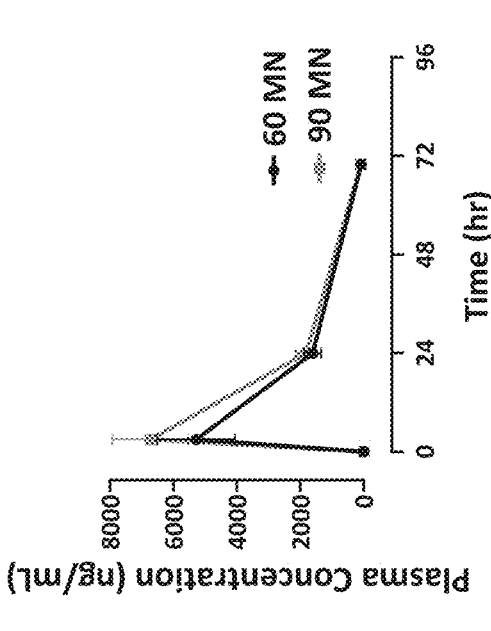
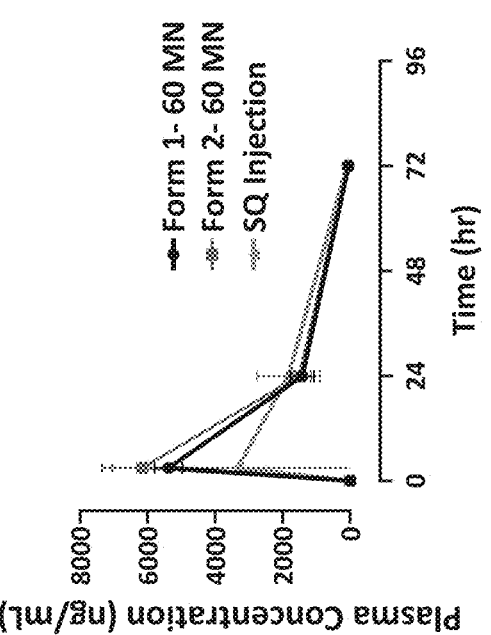
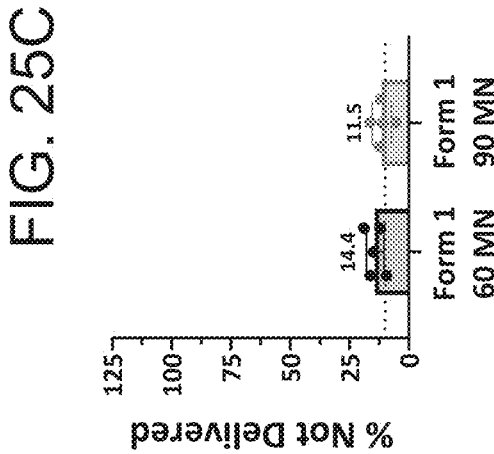
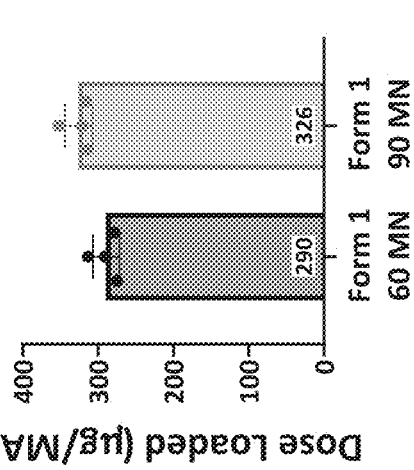
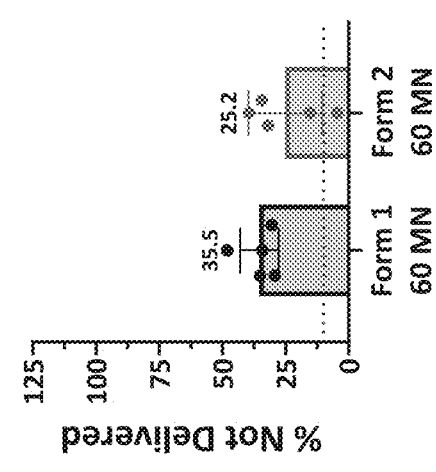
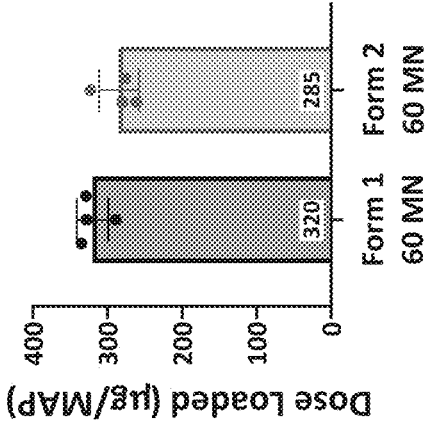

FIG. 27

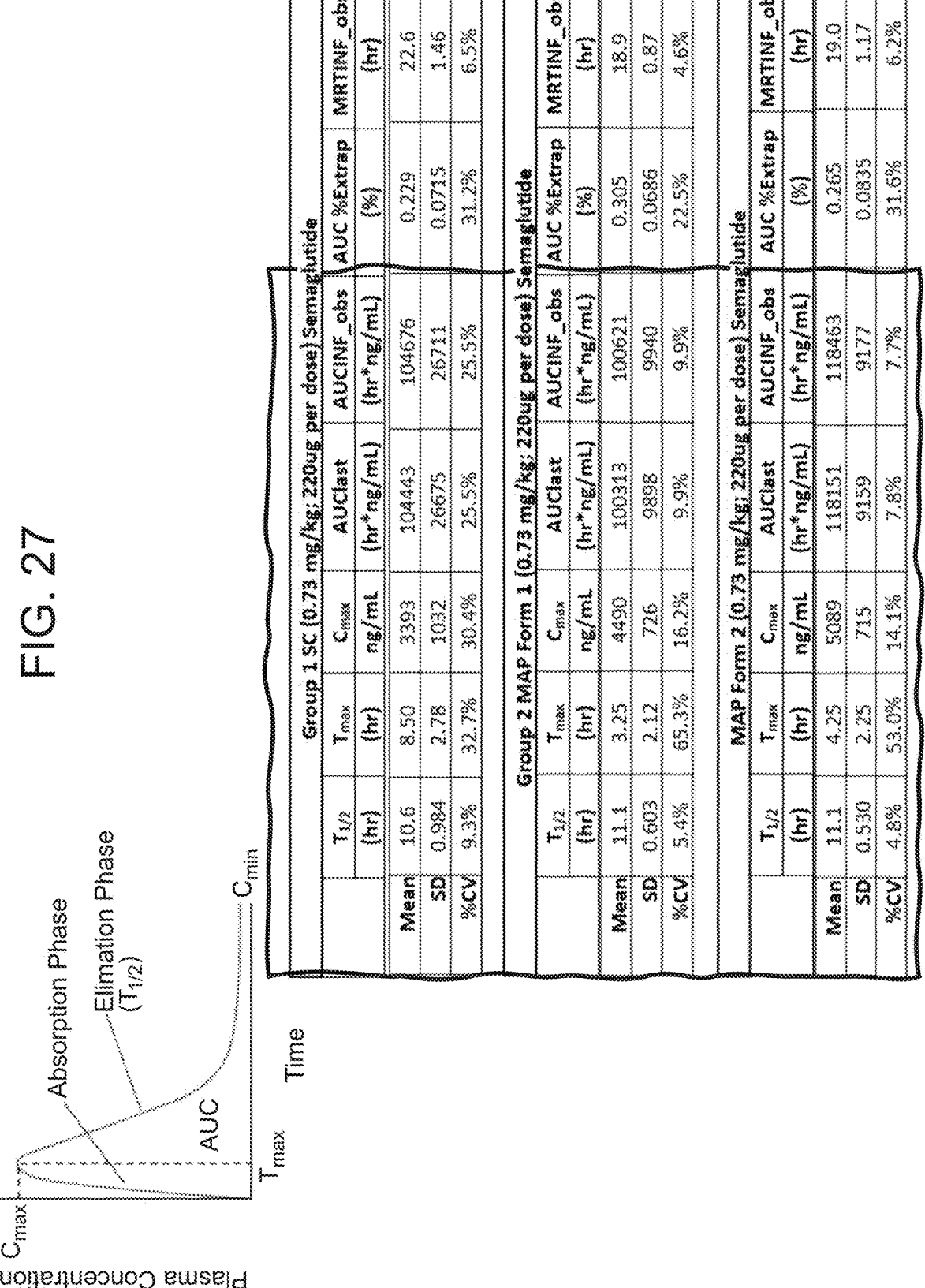

Group 1 SC (0.73 mg/kg; 220ug per dose) Semaglutide

|  | T$_{1/2}$ (hr) | T$_{max}$ (hr) | C$_{max}$ ng/mL | AUClast (hr*ng/mL) | AUCINF_obs (hr*ng/mL) | AUC %Extrap (%) | MRTINF_obs (hr) |
|---|---|---|---|---|---|---|---|
| Mean | 10.6 | 8.50 | 3393 | 104443 | 104676 | 0.229 | 22.6 |
| SD | 0.984 | 2.78 | 1032 | 26675 | 26711 | 0.0715 | 1.46 |
| %CV | 9.3% | 32.7% | 30.4% | 25.5% | 25.5% | 31.2% | 6.5% |

Group 2 MAP Form 1 (0.73 mg/kg; 220ug per dose) Semaglutide

|  | T$_{1/2}$ (hr) | T$_{max}$ (hr) | C$_{max}$ ng/mL | AUClast (hr*ng/mL) | AUCINF_obs (hr*ng/mL) | AUC %Extrap (%) | MRTINF_obs (hr) |
|---|---|---|---|---|---|---|---|
| Mean | 11.1 | 3.25 | 4490 | 100313 | 100621 | 0.305 | 18.9 |
| SD | 0.603 | 2.12 | 726 | 9898 | 9940 | 0.0686 | 0.87 |
| %CV | 5.4% | 65.3% | 16.2% | 9.9% | 9.9% | 22.5% | 4.6% |

MAP Form 2 (0.73 mg/kg; 220ug per dose) Semaglutide

|  | T$_{1/2}$ (hr) | T$_{max}$ (hr) | C$_{max}$ ng/mL | AUClast (hr*ng/mL) | AUCINF_obs (hr*ng/mL) | AUC %Extrap (%) | MRTINF_obs (hr) |
|---|---|---|---|---|---|---|---|
| Mean | 11.1 | 4.25 | 5089 | 118151 | 118463 | 0.265 | 19.0 |
| SD | 0.530 | 2.25 | 715 | 9159 | 9177 | 0.0835 | 1.17 |
| %CV | 4.8% | 53.0% | 14.1% | 7.8% | 7.7% | 31.6% | 6.2% |

FIG. 28B

| Route | Group | Subject | Test Article | Dose (ug) | Rsq | T$_{1/2}$ (h) | T$_{max}$ (h) | C$_{max}$ (ng/mL) | T$_{last}$ (h) | AUC$_{last}$ (h*ng/mL) | AUC$_{INF}$ (h*ng/mL) | AUC%Extrap (%) |
|---|---|---|---|---|---|---|---|---|---|---|---|---|
| MAP | 1 | 1001 | 61 MN | 220 | 0.986 | 91.7 | 8.00 | 114 | 168 | 8370 | 11300 | 26.1 |
| | 1 | 1002 | 61 MN | 220 | 0.977 | 83.3 | 12.0 | 72.6 | 168 | 6540 | 8910 | 26.6 |
| | 1 | 1103 | 61 MN | 220 | 0.994 | 92.9 | 24.0 | 79.7 | 168 | 7220 | 10000 | 27.9 |
| | 1 | 1104 | 61 MN | 220 | 0.966 | 70.0 | 8.00 | 101 | 168 | 6790 | 8400 | 19.2 |
| | | | | Mean | 0.981 | 84.5 | 13.0 | 91.8 | 168 | 7230 | 9660 | 25.0 |
| | | | | SD | 0.0119 | 10.6 | 7.57 | 19.1 | 0 | 811 | 1300 | 3.90 |
| | | | | CV% | 1.2 | 12.5 | 58.2 | 20.8 | 0 | 11.2 | 13.4 | 15.6 |

| Route | Group | Subject | Test Article | Dose (ug) | Rsq | T$_{1/2}$ (h) | T$_{max}$ (h) | C$_{max}$ (ng/mL) | T$_{last}$ (h) | AUC$_{last}$ (h*ng/mL) | AUC$_{INF}$ (h*ng/mL) | AUC%Extrap (%) |
|---|---|---|---|---|---|---|---|---|---|---|---|---|
| MAP | 2 | 2101 | 41 MN | 220 | 0.995 | 65.3 | 6.0 | 67.5 | 168 | 6230 | 7520 | 17.2 |
| | 2 | 2102 | 41 MN | 220 | 0.951 | 92.1 | 12.0 | 83.6 | 168 | 6770 | 9160 | 26.1 |
| | 2 | 2103 | 41 MN | 220 | 0.979 | 102 | 12.0 | 101 | 168 | 6730 | 8960 | 24.9 |
| | | | | Mean | 0.975 | 86.5 | 10.0 | 84.0 | 168 | 6580 | 8550 | 22.7 |
| | | | | SD | 0.0223 | 18.8 | 3.46 | 16.8 | 0 | 302 | 896 | 4.84 |
| | | | | CV% | 2.3 | 21.8 | 34.6 | 19.9 | 0 | 4.6 | 10.5 | 21.3 |

| Route | Group | Subject | Test Article | Dose (ug) | Rsq | T$_{1/2}$ (h) | T$_{max}$ (h) | C$_{max}$ (ng/mL) | T$_{last}$ (h) | AUC$_{last}$ (h*ng/mL) | AUC$_{INF}$ (h*ng/mL) | AUC%Extrap (%) |
|---|---|---|---|---|---|---|---|---|---|---|---|---|
| SC | 3 | 3001 | SubQ | 220 | 0.954 | 88.4 | 24.0 | 74.0 | 168 | 7110 | 9590 | 25.9 |
| | 3 | 3102 | SubQ | 220 | 0.917 | 83.9 | 12.0 | 75.3 | 168 | 6530 | 8630 | 24.3 |
| | 3 | 3003 | SubQ | 220 | 1.00 | 86.8 | 4.00 | 65.6 | 168 | 6760 | 9380 | 27.9 |
| | | | | Mean | 0.957 | 86.3 | 13.3 | 71.6 | 168 | 6800 | 9200 | 26.0 |
| | | | | SD | 0.0416 | 2.29 | 10.1 | 5.27 | 0 | 289 | 508 | 1.82 |
| | | | | CV% | 4.4 | 2.7 | 75.5 | 7.35 | 0 | 4.3 | 5.5 | 7.0 |

FIG. 29A

| Defect Type | Description | Exemplary Images of Defects |
|---|---|---|
| Missing Tip & Base | The entire needle including the base portion and tip portion are not present on the demolded patch. | |
| Missing Tip | The base portion of a needle has been demolded onto the patch, however, there is no tip attached to the base portion. | |
| Other | Any other abnormality (specify) | |

Subcutaneous (SQ) Injection - Luciferin (Day 1)

Intramuscular (IM) or MAP Luc-Encoding mRNA (Day 0)

Luminescence IVIS Imaging (30min after luciferin injection)

FIG. 34

Rapidly dissolving base

Encapsualtion efficiency via RiboGreen

B)

mRNA Integrity via CE

Baseline 4C 1 Month 25C 1 Month

SEQUENCE LISTING

```
Sequence total quantity: 1
SEQ ID NO: 1          moltype = AA  length = 31
FEATURE               Location/Qualifiers
source                1..31
                      mol_type = protein
                      note = human GLP-1 (7-37)
                      organism = Homo sapiens
SEQUENCE: 1
HAEGTFTSDV SSYLEGQAAK EFIAWLVKGR G                              31
```

MICRONEEDLE ARRAY PATCHES (MAPs), SYSTEMS, AND METHODS FOR MANUFACTURING AND USING SAME

RELATED APPLICATIONS

This application is a continuation of U.S. patent application Ser. No. 19/002,632, filed on Dec. 26, 2024, which claims priority to U.S. Provisional Patent Application No. 63/723,023 filed on Nov. 20, 2024, U.S. Provisional Patent Application No. 63/712,367 filed on Oct. 25, 2024, U.S. Provisional Patent Application No. 63/701,470 filed on Sep. 30, 2024, U.S. Provisional Patent Application No. 63/683, 233 filed on Aug. 14, 2024, and U.S. Provisional Patent Application No. 63/623,084 filed on Jan. 19, 2024, the contents of which are incorporated herein by reference in their entirety.

GOVERNMENT SUPPORT

This invention was made with government support under 1R43DK142429-01 awarded by the National Institute of Diabetes and Digestive and Kidney Diseases. The government has certain rights in the invention.

REFERENCE TO SEQUENCE LISTING

The instant application contains a Sequence Listing which has been submitted electronically in XML format and is hereby incorporated by reference in its entirety. Said XML copy, created on Apr. 17, 2025, is named "132296-02405_Sequence_Listing.xml" and is 2,203 bytes in size.

BACKGROUND

Conventional methods of administering active pharmaceutical ingredients (APIs) often involves painful injections, leading to discomfort and challenges with patient compliance and dosing errors. A promising alternative to these conventional methods is transdermal delivery of APIs using microarray patches (MAPs), which offer a more comfortable way to deliver APIs through the patient's skin. However, there exists significant technical and commercial challenges to the clinical adoption of microneedles for API delivery, including dosage calibration, pharmacodynamics, biocompatibility, patient compliance, sterilization, mass production, and regulatory oversight.

Current microneedles can be characterized by a limited dosing capacity, given that the microneedles' size can restrict the total amount of API that they can carry. Current microneedles can also be characterized by inconsistent pharmacokinetics, due in part to factors related to the architecture of human skin which can impede microneedle insertion and lead to inconsistent API delivery. Safety concerns related to the selection of safe and biocompatible materials also remains an important yet challenging aspect of microneedle development. Moreover, large-scale manufacturing of microneedles remains costly due to expensive, but important, processing steps to ensure sterilization and batch consistency.

There exists a need for improved microneedles and manufacturing processes that address the current technical and commercial challenges to the clinical adoption of microneedle array patches (MAPs) for API delivery.

SUMMARY

Microneedles and microneedle array patches (MAPs) are promising alternatives to conventional methods of administering active pharmaceutical ingredients (APIs), but their clinical adoption for API delivery has been limited due to significant technical and commercial challenges related to, for example, loading capacity, dosing accuracy, pharmacodynamics, biocompatibility, patient compliance, sterilization, mass production, and regulatory oversight. The present disclosure relates to dispensable formulations, microneedles, microneedle array patches (MAPs), and systems for delivery of active pharmaceutical ingredients (APIs) that provide inter alia improved API delivery consistency and pharmacodynamics.

The present disclosure is based, at least in part, on Applicant's surprising discovery of specific combinations of water-soluble excipients that can, for example, effectively (1) enhance the stability of a high concentration of active pharmaceutical ingredients (API) for delivery of an effective dose of the API using a microneedle and/or a microarray patch (MAP) described herein; (2) enhance the fluid properties of a composition, such as a dispensable formulation, for manufacturing a microneedle and/or a microarray patch (MAP) described herein using, e.g., a liquid dispensing system; (3) enhance the consolidation of the API into the apex of the microneedle tip during manufacturing; (4) enhance the strength of the microneedle, e.g., to resist deformation during deployment; and/or (5) minimize, or eliminate, manufacturing defects, such as shell formation and microneedle tip dislodgement, that negatively affect microneedle morphology, strength, deployment efficiency, API delivery consistency, and pharmacodynamics.

The present disclosure is further based, at least in part, on Applicant's surprising discovery of a microneedle and/or a microarray patch (MAP) capable of effectively delivering a clinically relevant dose of an active pharmaceutical ingredient (API), such as a glucagon-like peptide-1 (GLP-1) receptor agonist (RA). GLP-1 receptor agonists (also referred to as "GLP-1 RA" or simply "GLP-1" herein), such as semaglutide, are important to Type 2 diabetes (T2D) and obesity treatments. GLP-1 works in the gastrointestinal system and in appetite centers of the brain to control glucose homeostasis, energy homeostasis, and satiety. However, the half-life of the GLP-1 polypeptide is relatively short at 1 to 2 minutes, making it difficult to use as a drug. Currently, some of the most effective T2D and obesity treatments, e.g., GLP-1 RAs, such as semaglutide, utilize a delivery strategy of attaching a half-life extending moiety (e.g., a fatty acid moiety), to the GLP-1 polypeptide that supports reversible binding to serum albumin and limits renal excretion and enzymatic degradation. While these modifications have reduced treatment frequency from daily to weekly, poor adherence linked to perceived treatment complexity and needle fear remains a general problem. These barriers highlight the need for new modes of GLP-1 RA delivery. The microneedles, microarray patches (MAPs), and systems described herein can be used to address several unmet needs associated with current delivery approaches for APIs, such as GLP-1 RAs, e.g., semaglutide, including, for example, treatment adherence and hesitancy associated with needle and syringe delivery and the low bioavailability associated with orally delivered APIs, such as GLP-1 RAs, e.g., semaglutide.

Without wishing to be bound by theory, a higher dose of a glucagon-like peptide-1 (GLP-1) receptor agonist, such as semaglutide, may be required to treat obesity relative to the dose required to treat Type 2 diabetes (T2D). For example, in some embodiments, approximately twice the dose of semaglutide is required for the treatment of obesity as compared to Type 2 diabetes (T2D). This is believed to be due, at least in part, to the need to achieve high concentrations and longer residence times of a glucagon-like peptide-1 (GLP-1) receptor agonist in the appetite centers of the brain. Accordingly, Applicant has developed compositions, including dispensable formulations comprising a water-soluble excipient, and methods for making a microneedle and/or a microarray patch (MAP), suitable for the treatment of, e.g., Type 2 diabetes (T2D) and/or obesity. In one aspect, the present disclosure provides a microneedle and/or a microarray patch (MAP) comprising a glucagon-like peptide-1 (GLP-1) receptor agonist, e.g., semaglutide, and a water-soluble excipient. In some embodiments, the microneedle and/or the microarray patch (MAP) can include less than about 1 mg (e.g., less than about 1000 μg) of a glucagon-like peptide-1 (GLP-1) receptor agonist, e.g., semaglutide, per microneedle and/or per consolidated microneedle tip. In some embodiments, the microneedle and/or the microarray patch (MAP) can include about 0.001 μg to about 1000 μg of a glucagon-like peptide-1 (GLP-1) receptor agonist, e.g., semaglutide, per microneedle and/or per consolidated microneedle tip. In some embodiments, the microneedle and/or the microarray patch (MAP) can include about 1 μg to about 20 μg of a glucagon-like peptide-1 (GLP-1) receptor agonist, e.g., semaglutide, per microneedle. In some embodiments, the microneedle and/or the microarray patch (MAP) can include about 1 μg to about 20 μg of a glucagon-like peptide-1 (GLP-1) receptor agonist, e.g., semaglutide, per consolidated microneedle tip. In some embodiments, the microarray patch (MAP) can include an array size of about 10 to about 1000 microneedles. In some embodiments, the microarray patch (MAP) can include an array size of about 10 to about 600 microneedles. In some embodiments, the microarray patch (MAP) can include an array size of about 10 to about 300 microneedles. In some embodiments, the microarray patch (MAP) can include an array size of about 200 to about 600 microneedles. In some embodiments, the microarray patch (MAP) can include a total dose of about 0.01 mg to about 10 mg of a glucagon-like peptide-1 (GLP-1) receptor agonist, e.g., semaglutide. In some embodiments, the microarray patch (MAP) can include a total dose of about 1 mg to about 10 mg of a glucagon-like peptide-1 (GLP-1) receptor agonist, e.g., semaglutide.

In some embodiments, the microneedles, microarray patches (MAPs), and systems described herein may be referred to as being a part of the "MIMIX" platform or as being a "MIMIX" device. Accordingly, in one aspect, the present disclosure provides improved MIMIX microneedles, MIMIX microarray patches (MAPs), and MIMIX systems. Such improved microneedles, microarray patches (MAPs), and systems can be used to enhance the delivery of active pharmaceutical ingredients (APIs), including, e.g., therapeutic proteins, that may be characterized by unwanted immunogenicity, that is, the ability to provoke an unwanted immune response against itself. Such immunogenicity may be triggered by components that are intrinsic to an API, such as specific amino acid sequences present within a therapeutic protein; to host-cell proteins (HCPs) that may co-purify, or "hitchhike," with an API produced in a biological expression system and which may be difficult to detect and remove during downstream processing (DSP); and/or to components, such as excipients (e.g., silk fibroin), that may be present in a pharmaceutical formulation. It is generally known in the art that unwanted immune responses to APIs, and the presence of anti-drug antibodies (ADAs), can pose problems for both clinical safety and efficacy of therapeutic products. For example, immunologically based adverse events, including, but not limited to, anaphylaxis, cytokine release syndrome, and cross-reactive neutralization of endogenous proteins, can cause a sponsor to terminate clinical development of what otherwise may have been an efficacious therapeutic product. Without wishing to be bound by theory, the immunogenicity of an API, and the detection of ADAs, can play an important role in the clinical development process, e.g., because the clinical effects of unwanted immune responses can affect the pharmacokinetics (PK), pharmacodynamics (PD), safety, and/or efficacy of the API. In addition, the route of administration, dose, and frequency can also affect immunogenicity. For example, in some instances, a lower dose administered intermittently may be more immunogenic than a larger dose administered without interruption. In general, a frequent or chronic dosage regimen may be considered to have a higher immunogenicity risk than a single dose regimen because multiple and/or chronic administration of APIs, may allow for the 'prime and boost' phenomenon often utilized in vaccine development. Accordingly, in one aspect, the present disclosure provides microneedles, microarray patches (MAPs), and systems that can address the problems associated with unwanted immunogenicity and/or repeated administration. In some embodiments, the present disclosure provides microneedles, microarray patches (MAPs), and systems that can reduce the clinical effects of unwanted immune responses and/or can improve the pharmacokinetics (PK), pharmacodynamics (PD), safety, and/or efficacy of an API, e.g., compared to a commercially approved formulation of the API.

In one aspect, the present disclosure provides, a microneedle, comprising a consolidated microneedle tip formed from a dispensable formulation, wherein the dispensable formulation comprises: (i) an active pharmaceutical ingredient (API); and (ii) a water-soluble excipient at a concentration of about 0.01% (w/v) to about 90% (w/v). In some embodiments, the dispensable formulation comprises an active pharmaceutical ingredient (API) at a concentration of greater than about 100 mg/mL. In some embodiments, the dispensable formulation comprises a water-soluble excipient at a concentration of about 0.01% (w/v) to about 30% (w/v). In some embodiments, the dispensable formulation comprises a water-soluble excipient selected from the group consisting of a polymer, a sugar, a sugar alcohol, an amino acid, an antioxidant, a buffer, a surfactant, a salt, and combinations thereof. In some embodiments, the dispensable formulation comprises a glucagon-like peptide-1 (GLP-1) receptor agonist. In one aspect, the present disclosure provides, a microneedle, comprising a consolidated microneedle tip formed from a dispensable formulation, wherein the dispensable formulation comprises: (i) a glucagon-like peptide-1 (GLP-1) receptor agonist at a concentration of greater than about 100 mg/mL; and (ii) a water-soluble excipient selected from the group consisting of an amino acid, a surfactant, and combinations thereof. In one aspect, the present disclosure provides, a microneedle, comprising a consolidated microneedle tip formed from a dispensable formulation, wherein the dispensable formulation comprises: (i) a glucagon-like peptide-1 (GLP-1) receptor agonist at a concentration of greater than about 100 mg/ml; and (ii) a water-soluble excipient at a concentration of about 0.01% (w/v) to about 10% (w/v). In some embodiments, the water-soluble excipient is selected from the group consisting of an amino acid, a surfactant, and combinations thereof. In some embodiments, the water-soluble excipient comprises an amino acid. In some embodiments, the water-soluble comprises a surfactant. In some embodiments, the dispensable formulation comprises a water-soluble excipient selected from the group consisting of a povidone polymer, a polyvinyl alcohol (PVA) polymer, and combinations thereof. In some embodiments, the water-soluble excipient comprises a polymer selected from the group consisting of (i) a polyvinylpyrrolidone (PVP) polymer (povidone), optionally wherein the PVP polymer (povidone) is selected from the group consisting of Povidone K 12 (PVP K12), Povidone K 17 (PVP K17), Povidone K 30 (PVP K30), and combinations thereof; (ii) a polyvinyl alcohol (PVA) polymer, optionally wherein the PVA polymer comprises PVA 4-88; (iii) a vinylpyrrolidone-vinyl acetate (VP-VA) copolymer (copovidone), optionally wherein the VP-VA copolymer (copovidone) is selected from the group consisting of Kollidon® VA 64, Plasdone® S-630, and combinations thereof; (iv) a polyvinyl alcohol-poly-ethylene glycol (PEG-PVA) graft copolymer, optionally wherein the PEG-PVA graft polymer comprises Kollicoat® Protect; (v) a polysaccharide, optionally wherein the polysaccharide is selected from the group consisting of Pullulan, Dextran 40, Methyl Cellulose (MC), Hydroxypropyl Methylcellulose (HPMC), Carboxymethyl cellulose (CMC), and combinations thereof; (vi) a fibroin protein, optionally wherein the fibroin protein comprise a silk fibroin protein; and (vii) combinations thereof. In some embodiments, the water-soluble excipient is selected from the group consisting of (i) the polymer is selected from the group consisting of silk fibroin, Povidone K 12 (PVP K12), Povidone K 17 (PVP K17), Povidone K 30 (PVP K30), PVA 4-88, Kollidon® VA 64, Dextran 40, Methyl Cellulose (MC), Hydroxypropyl Methylcellulose (HPMC), Carboxymethyl cellulose (CMC), Plasdone® S-630, Pullulan, Kollicoat® Protect, and combinations thereof; (ii) the sugar is selected from the group consisting of sucrose, trehalose, lactose, and combinations thereof; (iii) the sugar alcohol is selected from the group consisting of mannitol, xylitol, sorbitol, glyercol, and combinations thereof; (iv) the amino acid is selected from the group consisting of arginine-HCl, proline, histidine, methionine, aspartic acid, glutamic acid, and combinations thereof; (v) the antioxidant is selected from the group consisting of sodium metabisulfite, sodium pyruvate, sodium ascorbate, and combinations thereof; (v) the buffer is selected from the group consisting of Tris-HCl, PBS, TE, 3-(N-Morpholino) propanesulfonic acid (MOPS), Phosphate, Bis-tris, HEPES, and combinations thereof; (vi) the surfactant is selected from the group consisting of Kolliphor® EL (Polyoxyl 35 Castor Oil), Kolliphor® HS 15 (Polyoxyl 15 Hydrostearate), Pluronic® F-127 (Poloxamer 407), Pluronic® F-68 (Poloxamer 188), Tween® 20 (polysorbate 20), Tween® 80 (polysorbate 80), Soluplus®, P124, CHAPS, and combinations thereof; and/or (vii) the salt is selected from the group consisting of NaCl, CaCl$_2$), ZnCl$_2$, MgCl$_2$, urea, and combinations thereof. In some embodiments, of any one of the microneedles described herein, wherein: the silk fibroin is present in the printable tip formulation at about 0% w/v to about 2% w/v; the PVP K12 is present in the printable tip formulation at about 0% w/v to about 70% w/v; the PVP K17 is present in the printable tip formulation at about 0% w/v to about 70% w/v; the PVP K30 is present in the printable tip formulation at about 0% w/v to about 50% w/v; the PVA 4-88 is present in the printable tip formulation at about 0% w/v to about 20% w/v; the Kollidon® VA 64 is present in the printable tip formulation at about 0% w/v to about 70% w/v; the Dextran 40 is present in the printable tip formulation at about 0% w/v to about 30% w/v; the Methyl Cellulose is present in the printable tip formulation at about 0% w/v to about 8% w/v; the Hydroxypropyl Methylcellulose is present in the printable tip formulation at about 0% w/v to about 14% w/v; the Carboxymethyl cellulose is present in the printable tip formulation at about 0% w/v to about 4% w/v; the Plasdone® S-630 is present in the printable tip formulation at about 0% w/v to about 70% w/v; the Pullulan is present in the printable tip formulation at about 0% w/v to about 10% w/v; the Kollicoat® Protect is present in the printable tip formulation at about 0% w/v to about 10% w/v; the Sucrose is present in the printable tip formulation at about 0% w/v to about 60% w/v; the Trehalose is present in the printable tip formulation at about 0% w/v to about 20% w/v; the Lactose is present in the printable tip formulation at about 0% w/v to about 20% w/v; the Mannitol is present in the printable tip formulation at about 0% w/v to about 10% w/v; the Xylitol is present in the printable tip formulation at about 0% w/v to about 10% w/v; the Sorbitol is present in the printable tip formulation at about 0% w/v to about 10% w/v; the Glyercol is present in the printable tip formulation at about 0% w/v to about 10% w/v; the Arginine-HCl is present in the printable tip formulation at about 0% w/v to about 20% w/v; the Proline is present in the printable tip formulation at about 0% w/v to about 6% w/v; the Histidine is present in the printable tip formulation at about 0% w/v to about 6% w/v; the Methionine is present in the printable tip formulation at about 0% w/v to about 6% w/v; the Aspartic Acid is present in the printable tip formulation at about 0% w/v to about 6% w/v; the Glutamic Acid is present in the printable tip formulation at about 0% w/v to about 6% w/v; the Sodium metabisulfite is present in the printable tip formulation at about 0% w/v to about 2% w/v; the Sodium pyruvate is present in the printable tip formulation at about 0% w/v to about 2% w/v; the Sodium ascorbate is present in the printable tip formulation at about 0% w/v to about 2% w/v; the Tris-HCl is present in the printable tip formulation at about 0 mM to about 350 mM; the PBS is present in the printable tip formulation at about 0X to about 2X; the TE is present in the printable tip formulation at about 0X to about 2X; the MOPS is present in the printable tip formulation at about 0 mM to about 350 mM; the Phosphate is present in the printable tip formulation at about 0 mM to about 350 mM; the Bis-tris is present in the printable tip formulation at about 0 mM to about 350 mM; the HEPES is present in the printable tip formulation at about 0 mM to about 350 mM; the Kolliphor® EL is present in the printable tip formulation at about 0% w/v to about 2% w/v; the Kolliphor® HS 15 is present in the printable tip formulation at about 0% w/v to about 2% w/v; the Pluronic® F-127 (Poloxamer 407) is present in the printable tip formulation at about 0% w/v to about 2% w/v; the Pluronic® F-68 (Poloxamer 188) is present in the printable tip formulation at about 0% w/v to about 2% w/v; the Tween® 20 (polysorbate 20) is present in the printable tip formulation at about 0% w/v to about 2% w/v; the Tween® 80 (polysorbate 80) is present in the printable tip formulation at about 0% w/v to about 2% w/v; the Soluplus® is present in the printable tip formulation at about 0% w/v to about 10% w/v; the P124 is present in the printable tip formulation at about 0% w/v to about 2% w/v; the CHAPS is present in the printable tip formulation at about 0% w/v to about 2% w/v; the NaCl is present in the printable tip formulation at about 0% w/v to about 2% w/v; the CaCl$_2$) is present in the printable tip formulation at about 0% w/v to about 2% w/v; the ZnCl$_2$ is present in the printable tip formulation at about 0% w/v to about 2% w/v; the MgCl$_2$ is present in the printable tip formulation at about 0% w/v to about 2% w/v; and/or the Urea is present in the printable tip formulation at about 0% w/v to about 2% w/v. In some embodiments, the glucagon-like peptide-1 (GLP-1)

7 receptor agonist is present in the dispensable formulation at a concentration of about 150 mg/mL to about 300 mg/mL, or wherein the glucagon-like peptide-1 (GLP-1) receptor agonist is present in the dispensable formulation at a concentration of about 180 mg/mL. In some embodiments, the glucagon-like peptide-1 (GLP-1) receptor agonist is selected from the group consisting of semaglutide; dulaglutide; exenatide; liraglutide; lixisenatide; tirzepatide; albiglutide; taspoglutide; pharmaceutically acceptable salts thereof; derivatives thereof; and combinations thereof. In some embodiments, the glucagon-like peptide-1 (GLP-1) receptor agonist comprises Semaglutide, a pharmaceutically acceptable salt thereof, or a derivative thereof. In some embodiments, the microneedle further comprises an additional active pharmaceutical ingredient (API), wherein the additional API is selected from the group consisting of (i) an antidiabetic agent, (ii) an anti-obesity agent, (iii) an anti-cardiovascular disease agent, and (iv) combinations thereof. In some embodiments, of any one of the microneedles described herein, wherein: (i) the water-soluble excipient is present in the dispensable formulation at a concentration of about 0.01% (w/v) to about 10% (w/v); (ii) the amino acid is present in the dispensable formulation at a concentration of about 0.5% to about 5%; (iii) the surfactant is present in the printable tip formulation at a concentration of about 0.01% (w/v) to about 1% (w/v); (iv) the dispensable formulation further comprises a povidone polymer present at a concentration of about 0.5% (w/v) to about 5% (w/v); (v) the dispensable formulation further comprises a polyvinyl alcohol (PVA) polymer present at a concentration of about 0.5% (w/v) to about 5% (w/v); (vi) the dispensable formulation further comprises a fibroin protein present at a concentration of about 0.1% (w/v) to about 2% (w/v); (vii) the dispensable formulation further comprises a salt present at a concentration of about 0.5% (w/v) to about 5% (w/v); (viii) the dispensable formulation further comprises a sugar present at a concentration of about 10% (w/v) to about 30% (w/v); and/or (ix) the dispensable formulation further comprises a buffer present at a concentration of about 50 mM to about 150 mM. In some embodiments, the consolidated tip comprises a proline amino acid, or a derivative thereof. In some embodiments, the consolidated tip comprises a polyoxyl 35 castor oil surfactant, or a derivative thereof. In some embodiments, the consolidated tip comprises a Polysorbate 80 surfactant, or a derivative thereof. In some embodiments, the consolidated tip comprises a povidone K 17 (PVP K17) polymer, or a derivative thereof. In some embodiments, the consolidated tip comprises a polyvinyl alcohol (PVA) 4-88 polymer, or a derivative thereof. In some embodiments, the consolidated tip comprises a silk fibroin protein, or a derivative thereof. In some embodiments, the consolidated tip comprises a NaCl salt. In some embodiments, the consolidated tip comprises a sucrose sugar. In some embodiments, the consolidated tip comprises a Tris-HCl buffer. In some embodiments, of any one of the microneedles described herein, further comprising a microneedle base formed from a dispensable formulation, optionally wherein the dispensable formulation comprises at least one selected from the group consisting of (i) a water-soluble excipient comprising a povidone polymer present at a concentration of about 10% (w/v) to about 70% (w/v); (ii) a water-soluble excipient comprising a polyvinyl alcohol (PVA) polymer present at a concentration of about 0.1% (w/v) to about 20% (w/v); (iii) a water-soluble excipient comprising a sugar present at a concentration of about 10% (w/v) to about 30% (w/v); (iv) a water-soluble excipient comprising a surfactant present at a concentration of about 0.01% (w/v) to about 1% (w/v); (v) a water-soluble excipient comprising a buffer present at a concentration of about 5 mM to about 25 mM (w/v); and (vi) combinations thereof. In some embodiments, the microneedle base comprises: (i) a povidone K 17 (PVP K17) polymer, or a derivative thereof; (ii) a PVA 4-88 polymer, or a derivative thereof; and (iii) a 1x TE buffer. In some embodiments, the microneedle base comprises: (i) a povidone K 17 (PVP K17) polymer, or a derivative thereof; (ii) a PVA 4-88 polymer, or a derivative thereof; (iii) a sucrose sugar; and (iv) a Tris buffer. In some embodiments, of any one of the microneedle described herein, wherein: the PVP K12 is present in the printable base formulation at about 0% w/v to about 90% w/v; the PVP K17 is present in the printable base formulation at about 0% w/v to about 90% w/v; the Kollidon® VA 64 is present in the printable base formulation at about 0% w/v to about 90% w/v; the Dextran is present in the printable base formulation at about 0% w/v to about 90% w/v; the PVA 4-88 is present in the printable base formulation at about 0% w/v to about 40% w/v; the PVA 4-88 is present in the printable base formulation at about 0% w/v to about 2% w/v; the Tris-HCl is present in the printable base formulation at about 0% w/v to about 40 mM % w/v; the MOPS is present in the printable base formulation at about 0 mM to about 50 mM; the Tris-EDTA is present in the printable base formulation at about 0X to about 2X; the Kolliphor EL is present in the printable base formulation at about 0% w/v to about 2% w/v; the Pluronic® F-68 (Poloxamer 188) is present in the printable base formulation at about 0% w/v to about 2% w/v; the Kolliphor® HS 15 is present in the printable base formulation at about 0% w/v to about 2% w/v; the F-127 is present in the printable base formulation at about 0% w/v to about 2% w/v; the Tween® 20 (polysorbate 20) is present in the printable base formulation at about 0% w/v to about 2% w/v; the Triton-X-100 is present in the printable base formulation at about 0% w/v to about 2% w/v; the Sucrose is present in the printable base formulation at about 0% w/v to about 60% w/v; the Trehalose is present in the printable base formulation at about 0% w/v to about 40% w/v; the Glycerol is present in the printable base formulation at about 0% w/v to about 8% w/v; the Carboxymethylcellulose is present in the printable base formulation at about 0% w/v to about 8% w/v; the Methyl Cellulose is present in the printable base formulation at about 0% w/v to about 8% w/v; and/or the Hydroxypropyl Methylcellulose is present in the printable base formulation at about 0% w/v to about 8% w/v. In some embodiments, the active pharmaceutical ingredient (API) comprises at least one selected from the group consisting of a small molecule, a biological molecule, a nucleotide, an oligonucleotide, a nucleic acid, a DNA, an RNA, an mRNA, a mRNA-loaded lipid nanoparticle (mRNA-LNP), an amino acid, a peptide, a polypeptide, a protein, a hormone, an antigen, a vaccine, a virus-like particle (VLP), a mimetic, an agonist, an antagonist, an inhibitor, a biologic, an antibody or antigen-binding fragment thereof, pharmaceutically acceptable salts thereof, derivatives thereof, and combinations thereof. In some embodiments, the active pharmaceutical ingredient (API) comprises an mRNA, a mRNA-loaded lipid nanoparticle (mRNA-LNP), or combinations thereof.

In one aspect, the present disclosure provides, a microarray patch (MAP), comprising a plurality of microneedles, optionally wherein each of the plurality of microneedles comprises a consolidated microneedle tip and a microneedle base, wherein the consolidated microneedle tip and the microneedle base are independently configured to withstand and propagate an impact energy applied by an applicator to each of the plurality of microneedles during deployment without deformation, and wherein the applicator is config-
ured to apply substantially the same amount of impact
energy to each of the plurality of microneedles to achieve
deployment of at least about 70% of the consolidate tips in
the MAP to a delivery depth of at least about 400 µm below
the surface of the subject's skin.

In one aspect, the present disclosure provides, a microar-
ray patch (MAP), comprising: a plurality of microneedles,
wherein each of the plurality of microneedles comprises a
consolidated microneedle tip formed from a dispensable
formulation, wherein the dispensable formulation com-
prises: (i) an active pharmaceutical ingredient (API); and (ii)
a water-soluble excipient at a concentration of about 0.01%
(w/v) to about 90% (w/v). In some embodiments, the
dispensable formulation comprises an active pharmaceutical
ingredient (API) at a concentration of greater than about 100
mg/mL. In some embodiments, the dispensable formulation
comprises a water-soluble excipient at a concentration of
about 0.01% (w/v) to about 30% (w/v). In some embodi-
ments, the dispensable formulation comprises a water-
soluble excipient selected from the group consisting of a
polymer, a sugar, a sugar alcohol, an amino acid, an anti-
oxidant, a buffer, a surfactant, a salt, and combinations
thereof. In some embodiments, the dispensable formulation
comprises a glucagon-like peptide-1 (GLP-1) receptor ago-
nist.

In one aspect, the present disclosure provides, a microar-
ray patch (MAP), comprising: a plurality of microneedles,
wherein each of the plurality of microneedles comprises a
consolidated microneedle tip formed from a dispensable
formulation, wherein the dispensable formulation com-
prises: (i) a glucagon-like peptide-1 (GLP-1) receptor ago-
nist at a concentration of greater than about 100 mg/mL; and
(ii) a water-soluble excipient selected from the group con-
sisting of an amino acid, a surfactant, and combinations
thereof.

In one aspect, the present disclosure provides, a microar-
ray patch (MAP), comprising: a plurality of microneedles,
wherein each of the plurality of microneedles comprises a
consolidated microneedle tip formed from a dispensable
formulation, wherein the dispensable formulation com-
prises: (i) a glucagon-like peptide-1 (GLP-1) receptor ago-
nist at a concentration of greater than about 100 mg/mL; and
(ii) a water-soluble excipient selected from the group con-
sisting of an amino acid, a surfactant, and combinations
thereof. In some embodiments, the glucagon-like peptide-1
(GLP-1) receptor agonist is present in the dispensable for-
mulation at a concentration of about 150 mg/mL to about
300 mg/mL, or wherein the glucagon-like peptide-1 (GLP-
1) receptor agonist is present at a concentration of about 180
mg/mL. In some embodiments, the glucagon-like peptide-1
(GLP-1) receptor agonist comprises Semaglutide, a phar-
maceutically acceptable salt thereof, or a derivative thereof.
In some embodiments, the microarray patch (MAP) further
comprises an additional active pharmaceutical ingredient
(API), wherein the additional API is selected from the group
consisting of (i) an antidiabetic agent, (ii) an anti-obesity
agent, (iii) an anti-cardiovascular disease agent, and (iv)
combinations thereof. In some embodiments, of any one of
the microarray patches (MAPs) described herein, wherein:
(i) the water-soluble excipient is present in the dispensable
formulation at a concentration of about 0.01% (w/v) to about
10% (w/v); (ii) the amino acid is present in the dispensable
formulation at a concentration of about 0.5% to about 5%;
(iii) the surfactant is present in the printable tip formulation
at a concentration of about 0.01% (w/v) to about 1% (w/v);
(iv) the dispensable formulation further comprises a povidone polymer present at a concentration of about 0.5% (w/v)
to about 5% (w/v); (v) the dispensable formulation further
comprises a polyvinyl alcohol (PVA) polymer present at a
concentration of about 0.5% (w/v) to about 5% (w/v); (vi)
the dispensable formulation further comprises a fibroin
protein present at a concentration of about 0.1% (w/v) to
about 2% (w/v); (vii) the dispensable formulation further
comprises a salt present at a concentration of about 0.5%
(w/v) to about 5% (w/v); (viii) the dispensable formulation
further comprises a sugar present at a concentration of about
10% (w/v) to about 30% (w/v); and/or (ix) the dispensable
formulation further comprises a buffer present at a concen-
tration of about 50 mM to about 150 mM. In some embodi-
ments, the consolidated tip comprises a proline amino acid,
or a derivative thereof. In some embodiments, the consoli-
dated tip comprises a polyoxyl 35 castor oil surfactant, or a
derivative thereof. In some embodiments, the consolidated
tip comprises a Polysorbate 80 surfactant, or a derivative
thereof. In some embodiments, the consolidated tip com-
prises a povidone K 17 (PVP K17) polymer, or a derivative
thereof. In some embodiments, the consolidated tip com-
prises a polyvinyl alcohol (PVA) 4-88 polymer, or a deriva-
tive thereof. In some embodiments, the consolidated tip
comprises a silk fibroin protein, or a derivative thereof. In
some embodiments, the consolidated tip comprises a NaCl
salt. In some embodiments, the consolidated tip comprises a
sucrose sugar. In some embodiments, the consolidated tip
comprises a Tris-HCl buffer. In some embodiments, the
microarray patch (MAP), further comprises a microneedle
base formed from a dispensable formulation, optionally
wherein the dispensable formulation comprises at least one
selected from the group consisting of (i) a water-soluble
excipient comprising a povidone polymer present at a con-
centration of about 10% (w/v) to about 70% (w/v); (ii) a
water-soluble excipient comprising a polyvinyl alcohol
(PVA) polymer present at a concentration of about 0.1%
(w/v) to about 20% (w/v); (iii) a water-soluble excipient
comprising a sugar present at a concentration of about 10%
(w/v) to about 30% (w/v); (iv) a water-soluble excipient
comprising a surfactant present at a concentration of about
0.01% (w/v) to about 1% (w/v); (v) a water-soluble excipi-
ent comprising a buffer present at a concentration of about
5 mM to about 25 mM (w/v); and (vi) combinations thereof.
In some embodiments, the microneedle base comprises: (i)
a povidone K 17 (PVP K17) polymer, or a derivative thereof;
(ii) a PVA 4-88 polymer, or a derivative thereof; and (iii) a
1x TE buffer. In some embodiments, the microneedle base
comprises: (i) a povidone K 17 (PVP K17) polymer, or a
derivative thereof; (ii) a PVA 4-88 polymer, or a derivative
thereof; (iii) a sucrose sugar; and (iv) a Tris buffer. In some
embodiments, of any one of the microarray patches (MAPs)
described herein, wherein: the PVP K12 is present in the
printable base formulation at about 0% w/v to about 90%
w/v; the PVP K17 is present in the printable base formula-
tion at about 0% w/v to about 90% w/v; the Kollidon® VA
64 is present in the printable base formulation at about 0%
w/v to about 90% w/v; the Dextran is present in the printable
base formulation at about 0% w/v to about 90% w/v; the
PVA 4-88 is present in the printable base formulation at
about 0% w/v to about 40% w/v; the PVA 4-88 is present in
the printable base formulation at about 0% w/v to about 2%
w/v; the Tris-HCl is present in the printable base formulation
at about 0% w/v to about 40 mM % w/v; the MOPS is
present in the printable base formulation at about 0 mM to
about 50 mM; the Tris-EDTA is present in the printable base
formulation at about 0X to about 2X; the Kolliphor EL is
present in the printable base formulation at about 0% w/v to about 2% w/v; the Pluronic® F-68 (Poloxamer 188) is present in the printable base formulation at about 0% w/v to about 2% w/v; the Kolliphor® HS 15 is present in the printable base formulation at about 0% w/v to about 2% w/v; the F-127 is present in the printable base formulation at about 0% w/v to about 2% w/v; the Tween® 20 (polysorbate 20) is present in the printable base formulation at about 0% w/v to about 2% w/v; the Triton-X-100 is present in the printable base formulation at about 0% w/v to about 2% w/v; the Sucrose is present in the printable base formulation at about 0% w/v to about 60% w/v; the Trehalose is present in the printable base formulation at about 0% w/v to about 40% w/v; the Glycerol is present in the printable base formulation at about 0% w/v to about 8% w/v; the Carboxymethylcellulose is present in the printable base formulation at about 0% w/v to about 8% w/v; the Methyl Cellulose is present in the printable base formulation at about 0% w/v to about 8% w/v; and/or the Hydroxypropyl Methylcellulose is present in the printable base formulation at about 0% w/v to about 8% w/v. In some embodiments, the active pharmaceutical ingredient (API) comprises at least one selected from the group consisting of a small molecule, a biological molecule, a nucleotide, an oligonucleotide, a nucleic acid, a DNA, an RNA, an mRNA, a mRNA-loaded lipid nanoparticle (mRNA-LNP), an amino acid, a peptide, a polypeptide, a protein, a hormone, an antigen, a vaccine, a virus-like particle (VLP), a mimetic, an agonist, an antagonist, an inhibitor, a biologic, an antibody or antigen-binding fragment thereof, pharmaceutically acceptable salts thereof, derivatives thereof, and combinations thereof. In some embodiments, the active pharmaceutical ingredient (API) comprises an mRNA, a mRNA-loaded lipid nanoparticle (mRNA-LNP), or combinations thereof.

In one aspect, the present disclosure provides, a microarray patch (MAP), comprising: a plurality of microneedles, wherein each of the plurality of microneedles comprises a three-dimensional (3D) printed structure selected from the group consisting of a consolidated microneedle tip, a microneedle base, and combinations thereof, wherein the consolidated microneedle tip is formed from a printable tip formulation comprising: (i) an active pharmaceutical ingredient (API); (ii) a water-soluble povidone polymer, or a water-soluble polyvinyl alcohol (PVA) polymer, present at a concentration of about 0.5% (w/v) to about 5% (w/v); and (iii) a water-soluble excipient present at a concentration of about 0.01% (w/v) to about 30% (w/v), wherein the water-soluble excipient is selected from the group consisting of a polymer, a sugar, a sugar alcohol, an amino acid, an antioxidant, a buffer, a surfactant, a salt, and combinations thereof. In some embodiments, the printable tip formulation further comprises at least one selected from the group consisting of a polymer comprising Povidone K 17 (PVP K17), an amino acid comprising proline, a surfactant comprising Kolliphor® EL, a salt comprising NaCl, a sugar comprising sucrose, a buffer comprising Tris-HCl, and combinations thereof. In some embodiments, the active pharmaceutical ingredient (API) comprises a glucagon-like peptide-1 (GLP-1) receptor agonist. In some embodiments, the glucagon-like peptide-1 (GLP-1) receptor agonist is selected from the group consisting of selected from the group consisting of Semaglutide; Dulaglutide; Exenatide; Liraglutide; Lixisenatide; Tirzepatide; Albiglutide; Taspoglutide; pharmaceutically acceptable salts thereof; derivatives thereof; and combinations thereof. In some embodiments, the glucagon-like peptide-1 (GLP-1) receptor agonist comprises Semaglutide, a pharmaceutically acceptable salt thereof, or a derivative thereof. In some embodiments, the printable tip formulation comprises about 100 mg/mL to about 300 mg/mL of the glucagon-like peptide-1 (GLP-1) agonist, about 0.1% w/v to about 2% w/v PVP K17, about 0.1% w/v to about 6% w/v Proline, about 0.01% w/v to about 0.5% w/v Kolliphor EL, about 50 mM to about 250 mM Tris-HCl buffer, and optionally about 0.1% w/v to about 2% w/v NaCl. In some embodiments, the printable tip formulation comprises about 180 mg/mL of the glucagon-like peptide-1 (GLP-1) agonist, about 1% w/v PVP K17, about 0.75% w/v Proline, about 0.1% w/v Kolliphor EL, about 0.9% w/v NaCl, and about 100 mM Tris-HCl buffer. In some embodiments, the printable tip formulation comprises about 180 mg/mL of the glucagon-like peptide-1 (GLP-1) agonist, about 1% w/v PVP K17, about 3% w/v Proline, about 0.1% w/v Kolliphor EL, and about 100 mM Tris-HCl buffer. In some embodiments, the microarray patch (MAP) comprises about 0.1 mg to about 30 mg of the glucagon-like peptide-1 (GLP-1) receptor agonist. In some embodiments, the microarray patch (MAP) comprises about 0.25 mg to about 2.4 mg of Semaglutide, a pharmaceutically acceptable salt thereof, or a derivative thereof. In some embodiments, the glucagon-like peptide-1 (GLP-1) receptor agonist is present in an amount of about 1 µg to about 20 µg per consolidated microneedle tip. In some embodiments, of any one of the microneedles, or the microarray patches (MAPs) described herein, wherein Semaglutide (Ozempic®, Rybelsus®, Wegovy®), a pharmaceutically acceptable salt thereof, or a derivative thereof, is present in an amount of at least about 2 µg per consolidated microneedle tip. In some embodiments, the active pharmaceutical ingredient (API) comprises a lipid nanoparticle-mRNA (LNP-mRNA) formulation. In some embodiments, the printable tip formulation comprises about 0.1% w/v to about 2% w/v PVA 4-88, about 3% w/v to about 7% w/v PVA PVP K17, about 8% w/v to about 12% w/v sucrose, and about 1X TE buffer. In some embodiments, the printable tip formulation comprises about 1% w/v PVA 4-88, about 5% w/v PVA PVP K17, about 10% w/v sucrose, and about 1X TE buffer. In some embodiments, the microarray patch (MAP) is configured for deployment onto the skin of a subject by using an applicator, wherein the MAP and the applicator are independently configured to function as a system to provide a consistent dose delivery of the active pharmaceutical ingredient (API), optionally wherein the active pharmaceutical ingredient (API) comprises a glucagon-like peptide-1 (GLP-1) receptor agonist. In some embodiments, the consolidated microneedle tip and the microneedle base are independently configured to withstand and propagate an impact energy applied by an applicator to each of the plurality of microneedles during deployment without deformation, wherein the applicator is configured to apply substantially the same amount of impact energy to each of the plurality of microneedles to achieve deployment of at least about 70% of the consolidate tips in the MAP to a delivery depth of at least about 400 µm below the surface of the subject's skin. In some embodiments, of any one of the microarray patches (MAPs) described herein, wherein: (i) each of the plurality of microneedles is characterized by a needle strength of at least about 0.1 N, at least about 0.2 N, at least about 0.3 N, at least about 0.4 N, and/or at least about 0.5 N yield load to minimize deformation and to maximize delivery depth of the consolidated microneedle tip during deployment, optionally wherein each of the plurality of microneedles is characterized by a needle strength of about 0.1 N to about 0.5 yield load; (ii) each of the plurality of microneedles is characterized by a tip strength and/or a failure force of at least about 0.1 N, at least about 0.2 N, at least about 0.3 N, at least about 0.4 N, and/or at least about 0.5 N per microneedle; (iii) each of the plurality of microneedles comprises about 0.001 µg to about 20 µg of the glucagon-like peptide-1 (GLP-1) receptor agonist per consolidated microneedle tip; (iv) each of the plurality of microneedles is characterized by a primary needle height (also referred to as "a pre-deployment needle height") of about 700 µm to about 1,250 µm; (v) the consolidated microneedle tip is characterized by a tip length of about 200 µm to about 500 µm; (vi) the consolidated microneedle tip is formed from about 10 nL to about 50 nL of the dispensable formulation; (vii) the consolidated microneedle tip is characterized by a substantially flat meniscus; (viii) no more than about 20% of the plurality of microneedles comprises a defect; and/or (ix) no more than about 10% of the plurality of microneedles comprises a consolidated microneedle tip characterized by a tip length greater than about 400 µm. In some embodiments, the microarray patch (MAP) comprises a microneedle array attached to a backing by an adhesive, wherein the microneedle array comprises a plurality of microneedles arranged in an array configuration, wherein each of the plurality of microneedles independently comprises the consolidated microneedle tip and the base, optionally wherein the adhesive is selected from the group consisting of an acrylic adhesive; an acrylate adhesive; a tackified adhesive, optionally a tackified acrylic adhesive and/or a tackified acrylate adhesive; a pressure sensitive adhesive; a synthetic rubber adhesive, optionally a pressure sensitive synthetic rubber adhesive; and combinations thereof. In some embodiments, the microarray patch (MAP) comprises a microneedle array characterized by an array size of about 50 to about 1,000 microneedles, optionally wherein the microneedle array is characterized by an array configuration that enables microneedle insertion and deployment of the consolidated microneedle tip to a consistent delivery depth of at least about 400 µm below the skin surface. In some embodiments, the MAP and the applicator are independently configured to provide an in vitro recovery of at least about 70% of the active pharmaceutical ingredient (API), optionally a glucagon-like peptide-1 (GLP-1) receptor agonist; and an ex vivo dose delivery efficiency of at least about 70% of the active pharmaceutical ingredient (API), optionally a glucagon-like peptide-1 (GLP-1) receptor agonist, wherein less than about 30% of the active pharmaceutical ingredient (API), optionally a glucagon-like peptide-1 (GLP-1) receptor agonist, is not delivered upon deployment.

In one aspect, the present disclosure provides, a method of treating a disease or a condition, comprising deploying onto the skin of a subject the microneedle, or the microarray patch (MAP) as described herein.

In one aspect, the present disclosure provides, a method of treating at least one condition selected from the group consisting of type 2 diabetes, overweight, obesity, cardiovascular disease, and combinations, comprising deploying onto the skin of a subject a microarray patch (MAP), comprising: a plurality of microneedles, wherein each of the plurality of microneedles comprises a consolidated microneedle tip formed from a dispensable formulation, wherein the dispensable formulation comprises: (i) a glucagon-like peptide-1 (GLP-1) receptor agonist at a concentration of greater than about 100 mg/mL; and (ii) a water-soluble excipient selected from the group consisting of an amino acid, a surfactant, and combinations thereof. In some embodiments, the microneedle or the microarray patch (MAP) sustains the release of the active pharmaceutical ingredient (API), optionally a glucagon-like peptide-1 (GLP-1) receptor agonist. In some embodiments, the microneedle or the microarray patch (MAP) is configured for daily, weekly, or monthly administration, optionally wherein the microneedle or the microarray patch (MAP) is configured for once daily, once weekly, or once monthly administration, optionally wherein the microneedle or the microarray patch (MAP) is configured for multiple daily, multiple weekly, or multiple monthly administrations.

In one aspect, the present disclosure provides, a high-throughput screening method for selecting a dispensable formulation suitable for microarray patch (MAP) manufacturing, comprising: providing a model air-dried film system comprising: (i) a printable tip formulation comprising an active pharmaceutical ingredient (API) formulation and a water-soluble excipient, and/or (ii) a printable base formulation comprising a water-soluble excipient, wherein the model air-dried film system was generated using a predefined printability parameter, optionally wherein the predefined printability parameter is selected from the group consisting of temperature, humidity, viscosity, solid content, dispense volume, dispense velocity, and combinations thereof.

In one aspect, the present disclosure provides, a method wherein the dispensable formulation suitable for microarray patch (MAP) manufacturing is selected when the fluid properties of the dispensable formulation enable microarray patch (MAP) a manufacturing process, such that a microarray patch (MAP) generated using the predefined printability parameter is characterized by a morphology substantially free of defects, optionally wherein no more than about 0% to about 30% of the microneedles in the microarray patch (MAP) comprise a defect, and/or no more than about 0% to about 30% of the microneedles in the microarray patch (MAP) comprise a consolidated tip length of greater than 400 µm. In one aspect, the present disclosure provides, a method wherein the dispensable formulation suitable for microarray patch (MAP) manufacturing is selected when the fluid properties of the dispensable formulation enables (i) formation of a consolidated microneedle tip and/or a microneedle base configured to withstand and propagate an impact energy applied by an applicator to each of the plurality of microneedles during deployment of without deformation, wherein the applicator is configured to apply substantially the same amount of impact energy to each of the plurality of microneedles to achieve deployment of at least about 70% of the consolidate tips in the MAP to a delivery depth of at least about 400 µm below the surface of the subject's skin; (ii) an in vitro recovery of at least about 70% of the active pharmaceutical ingredient (API), optionally a glucagon-like peptide-1 (GLP-1) receptor agonist; and/or (iii) an ex vivo dose delivery efficiency of at least about 70% of the active pharmaceutical ingredient (API), optionally a glucagon-like peptide-1 (GLP-1) receptor agonist, wherein less than about 30% of the active pharmaceutical ingredient (API), optionally a glucagon-like peptide-1 (GLP-1) receptor agonist, is not delivered upon deployment.

In one aspect, the present disclosure provides, a method of manufacturing a microarray patch (MAP), comprising: (i) providing: (a) a microarray mold comprising a plurality of cavities which are characterized by a predefined criteria selected from the group consisting of: a microneedle height, a microneedle spacing, a microneedle base size, a microneedle tip size, an array size, and combinations thereof; (b) at least one print solution selected from the group consisting of a printable tip formulation, a printable base formulation, and a combination thereof, and (c) an active pharmaceutical ingredient (API), wherein the API is independently present or absent in the at least one print solution; (ii) printing a plurality of microneedles by independently filling at least one cavity of the plurality of cavities with a predefined dispense volume of the print solution, thereby forming a plurality of printed microneedles; (iii) applying a backing to a surface of the plurality of microneedles; and (iv) demolding the plurality of microneedles, thereby generating a microarray patch (MAP).

In one aspect, the present disclosure provides, a microarray patch (MAP), comprising a plurality of microneedles described herein.

In one aspect, the present disclosure provides, a microarray patch (MAP) system, comprising: (i) a microarray patch (MAP) described herein, wherein the MAP comprises a plurality of microneedles, wherein each of the plurality of microneedles comprises a consolidated microneedle tip and a microneedle base, wherein the consolidated microneedle tip and the microneedle base are independently configured to withstand and propagate an impact energy applied by an applicator to each of the plurality of microneedles during deployment without deformation; and (ii) an applicator configured to apply substantially the same amount of impact energy to each of the plurality of microneedles to achieve deployment of at least about 70% of the consolidate tips in the MAP to a delivery depth of at least about 400 µm below the surface of the subject's skin.

The present invention is further illustrated by the following detailed description and drawings.

BRIEF DESCRIPTION OF THE DRAWINGS

FIG. 3 shows a schematic of MIMIX MAP Tip drying. 20-30 nL of print solution are typically dispensed into each mold cavity and allowed to dry. Extreme shell formation is depicted in the middle figure, while full consolidation into the Tip is shown on the right.

FIG. 4 shows important parameters impacting MIMIX MAP Tip drying and consolidation. Tip formulation development aims to ensure high concentrations of payload avoid pinning while drying and consolidate to the tip of each mold cavity.

FIG. 9 shows surface tension over time as measured by the pendant drop method for tip formulations including various surfactants in GLP-045.

Figure 12:
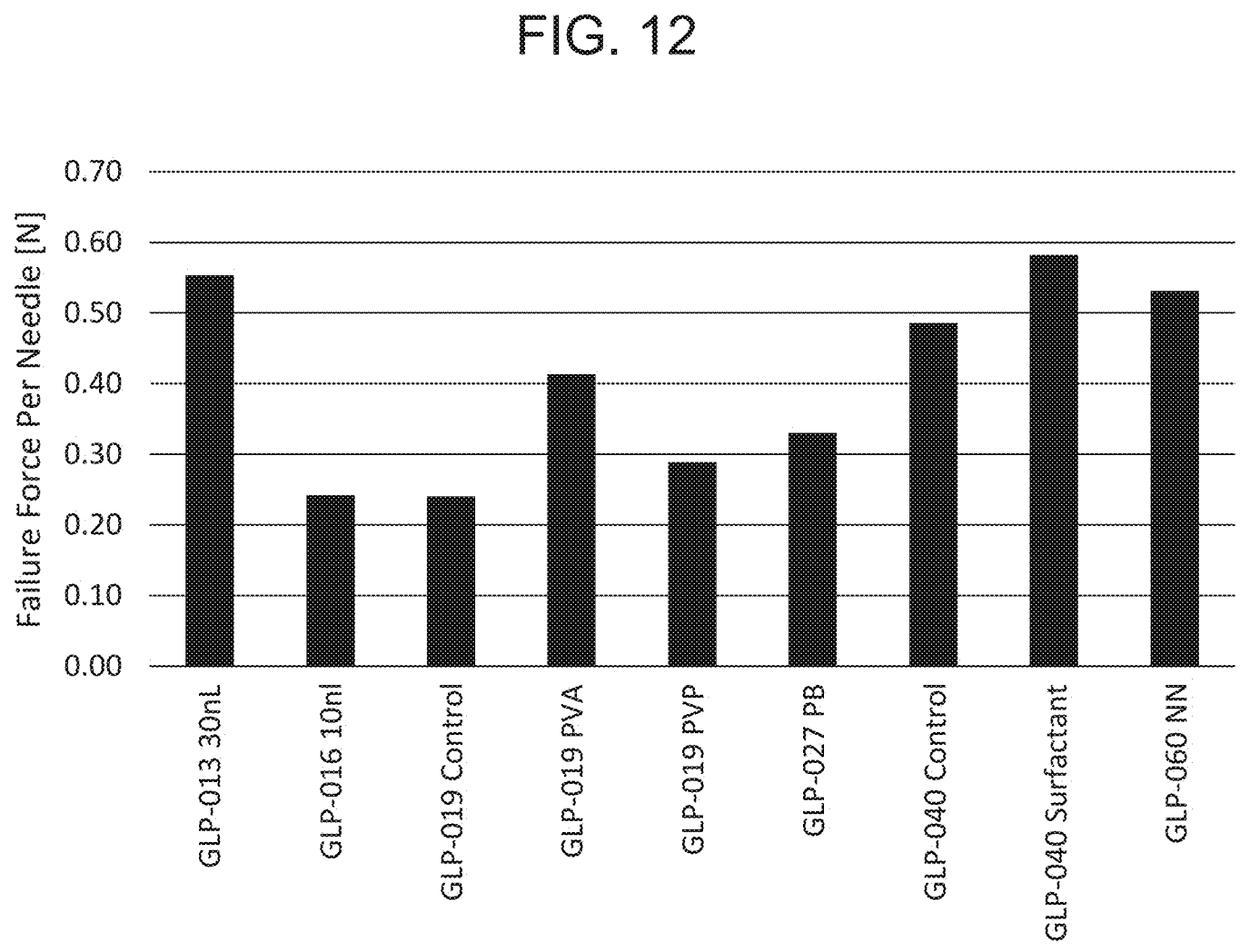

FIG. 12 shows a summary of Mechanical strength of MAPs during the feasibility evaluation phase. Mechanical strength was infrequently measured during this phase, but was often below 0.4 N per needle.

FIG. 13A-13E shows shallow delivery of microneedles and microneedle dimensions using the Feasibility Formulation and comparison with VX103 MAPs. FIG. 13A shows the ex vivo deployment results of the 3 separate ex vivo deployment sample sets of GLP-1 277 array MAPs compared to historical measurements of VX103 ex vivo deployments (VX103-245 and VX103-332, "2 drop" respectively). In a separate analysis, GLP-1 tip lengths (GLP-019-042) were compared against historical values for VX103 tip lengths. While the tip lengths are measured in two different ways, FIG. 13B, shows that there is a significant difference between the two groups. FIG. 13C shows unpaired t test comparison of Air Gap and Needle Height Lost deployment outcomes for 241-array VX103 and GLP-1 MAP's. FIG. 13D shows the resultant load displacement curves of VX-103 MAPs compared to GLP-1 MAPs (left panel), and that the stiffness (middle panel) and ultimate strength (right panel) of the VX103 MAPs is higher than the GLP-1 MAPs. FIG. 13E shows the comparison of the compressive strengths of the MAPs constructed of the VX103 and GLP-1 base formulations only.

FIG. 14 shows the GLP-067 Study Summary. Film studies show that PVP K17 (at all the concentrations tested) and 3% Dextran are compatible with GLP-1.

FIG. 15 shows the GLP-073 Study Summary. A MAP study shows that higher concentrations of PVP K17 and 3% Dextran do not impact the mechanical strength of the GLP-1 Tip.

FIG. 18 shows incorporation of 0.75% Proline lowers the shell length and significantly improves Tip strength in the instron crush test.

FIG. 19 shows incorporation of 3% Proline improves Tip consolidation but reduces Tip strength.

FIG. 22 shows tip length and tip strength data for GLP-136 and GLP-142 for MAPs containing two different formulations (PPS and PHP).

FIG. 23A-B show that the PPS and PHP formulations lead to less variable, lower Tip (FIG. 23A) and Shell (FIG. 23B) lengths.

FIG. 25C pilot rat PK studies show similar PK profiles for differing array sizes and Form 1 and 2. Top panel: shows comparable PK profile for delivery of semaglutide formulated in the PPS formulation (Form 1) for two different array sizes delivering the same total dose. Bottom panel: shows PPS (Form 1) and PHP (Form 2) formulations have similar PK profiles with potentially higher BA for both MAP formulations relative to SQ delivery.

FIG. 27 shows a comparison of PK parameters for MAP delivery of GLP-1 formulated in Form 1 (PPS) or Form 2 (PHP) versus subcutaneous delivery of GLP-1 formulated in 100 mM Tris (pH 7.5).

FIG. 28B shows Minipig PK analyses show a similar $T_{max}$, modestly higher $C_{max}$, comparable $T_{1/2}$ and comparable AUC.

FIG. 29A shows exemplary defective tips.

Deploy onto the skin using the applicator 3) wear the MAP for 5 minutes 4) peel off adhesive backing. The middle panel shows a MIMIX system preloaded with a MAP, and the right panel shows a description of MIMIX components as tips could be modified.

Figure 32A:
FIG. 32A shows (left panel) a simple four-step application of a MAP: 1) Open the pouch and take out the product 2)
Figure 32B:
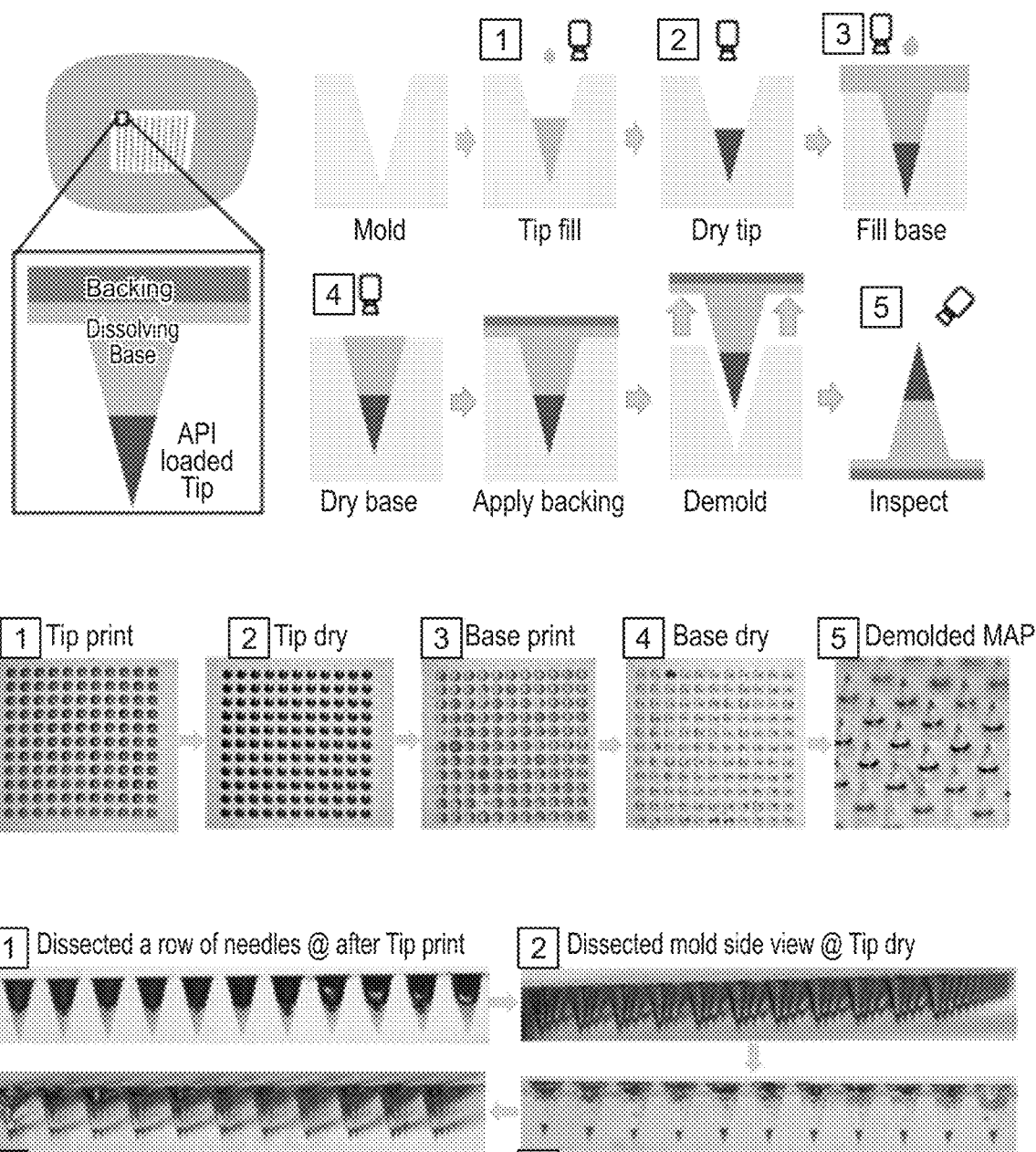

FIG. 32B shows (top panels) a schematic of an exemplary MAP fabrication process, (middle panels) top-down view of a mold, and (bottom panels) side view and cross-sectioned mold throughout the process.

Figure 33:
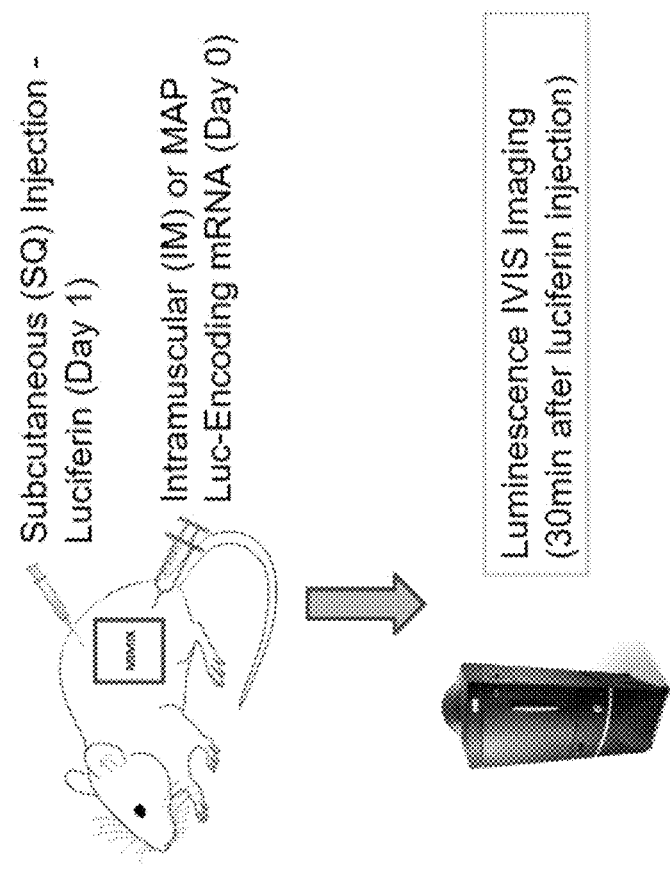

FIG. 33 shows a MAP in vivo potency IVIS workflow.

Figure 34:
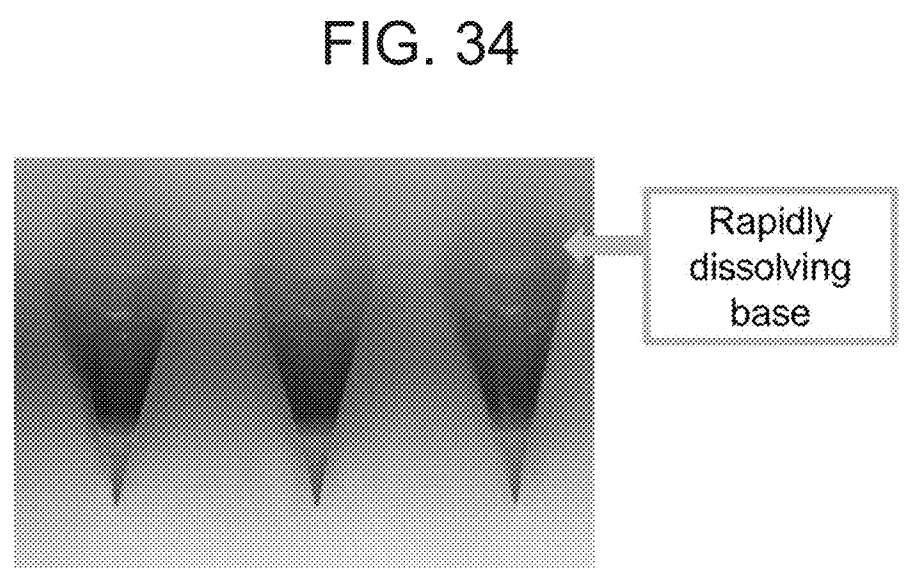

FIG. 34 shows fluorescence imaging was used to verify tip consolidation in a MAP and how the dried tip and base interact in a needle. The tips were filled at the distal end of needles, and the fluorescence was distributed evenly throughout the consolidated tips indicating the tips dried uniformly.

Figure 35A:
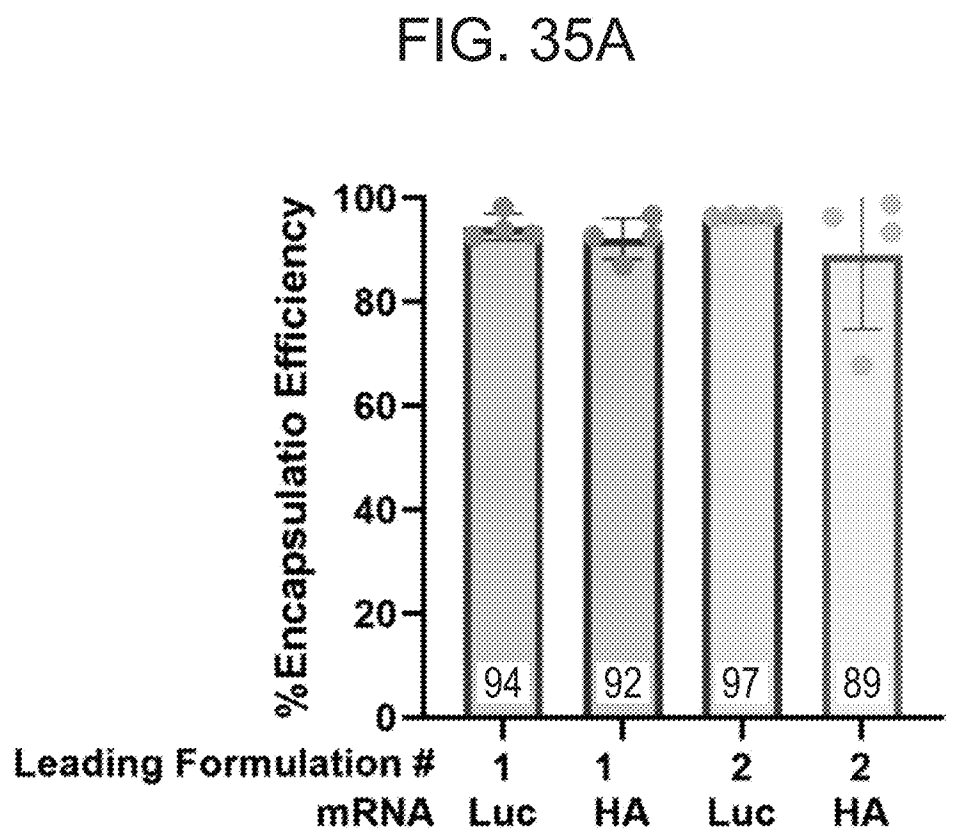

FIG. 35A shows encapsulation efficiency was used to measure the stability of LNPs throughout the MAP drying process. N=4 MAPs from each of the two leading tip formulations were dissolved in buffer and subsequently assayed using the RiboGreen assay. The MIMIX platform was compatible with both leading tip formulations and different mRNA cargos (luciferase and hemagglutinin (HA)-encoding mRNA)

Figure 35B:
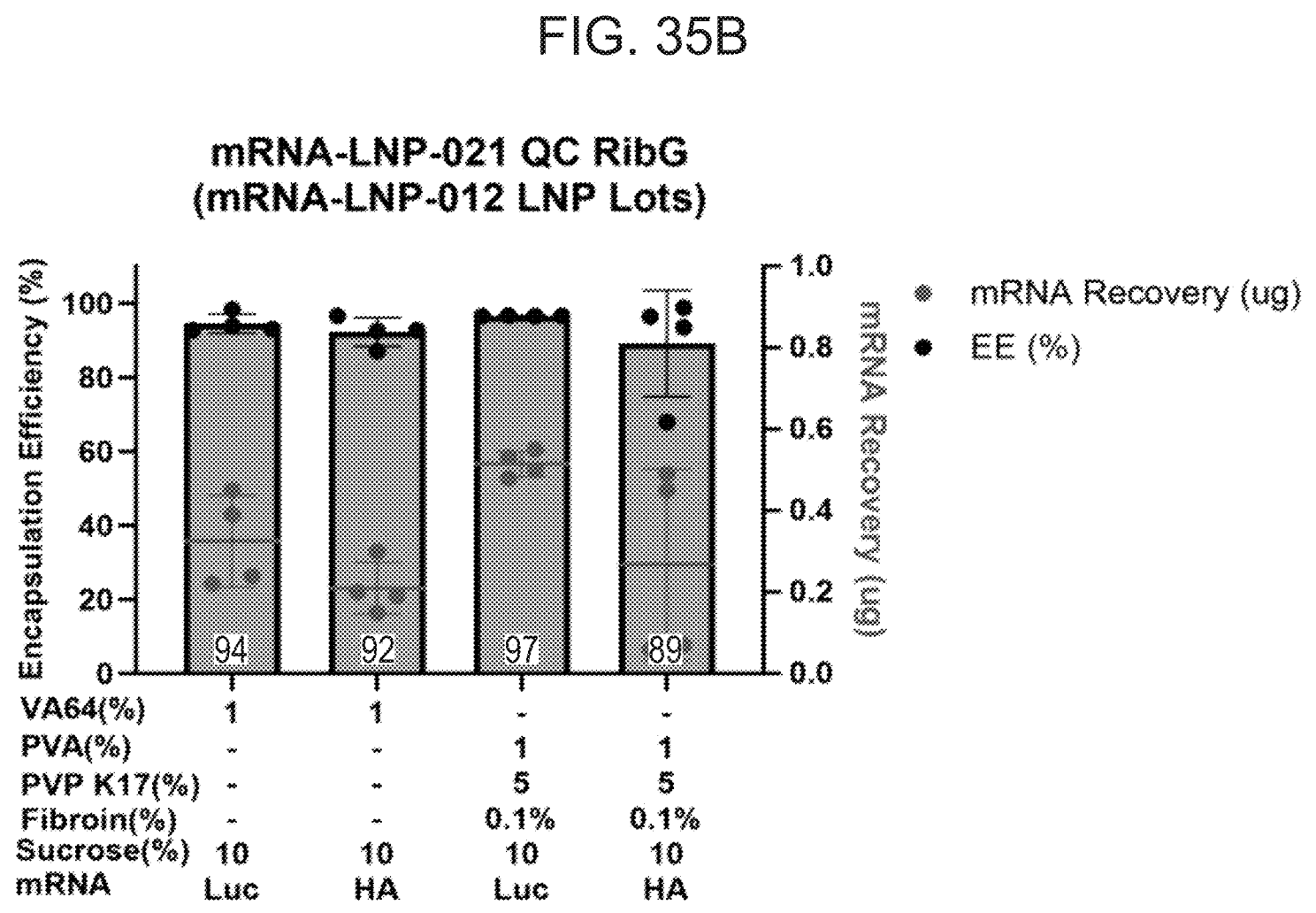

FIG. 35B represents the data shown in FIG. 35A with additional labels indicating the formulation components evaluated. Formulation details are also summarized in Table 12.

Figure 36A:
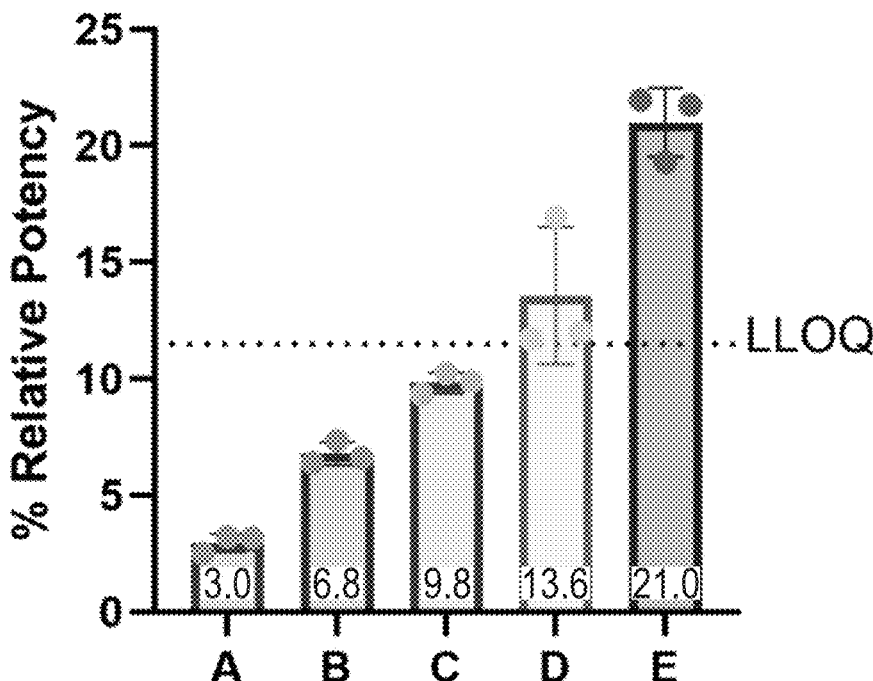

FIG. 36A shows MAPs containing mRNA-LNPs encoding for luciferase were solubilized and eluate was transfected into BHK-21 cells to determine in vitro potency. Five different groups varying tip and base formulations and drying conditions were evaluated. Stepwise improvements to in vitro potency were observed with optimized formulations and drying conditions, from 3% to 21%, compared to the liquid control.

Figure 36B:
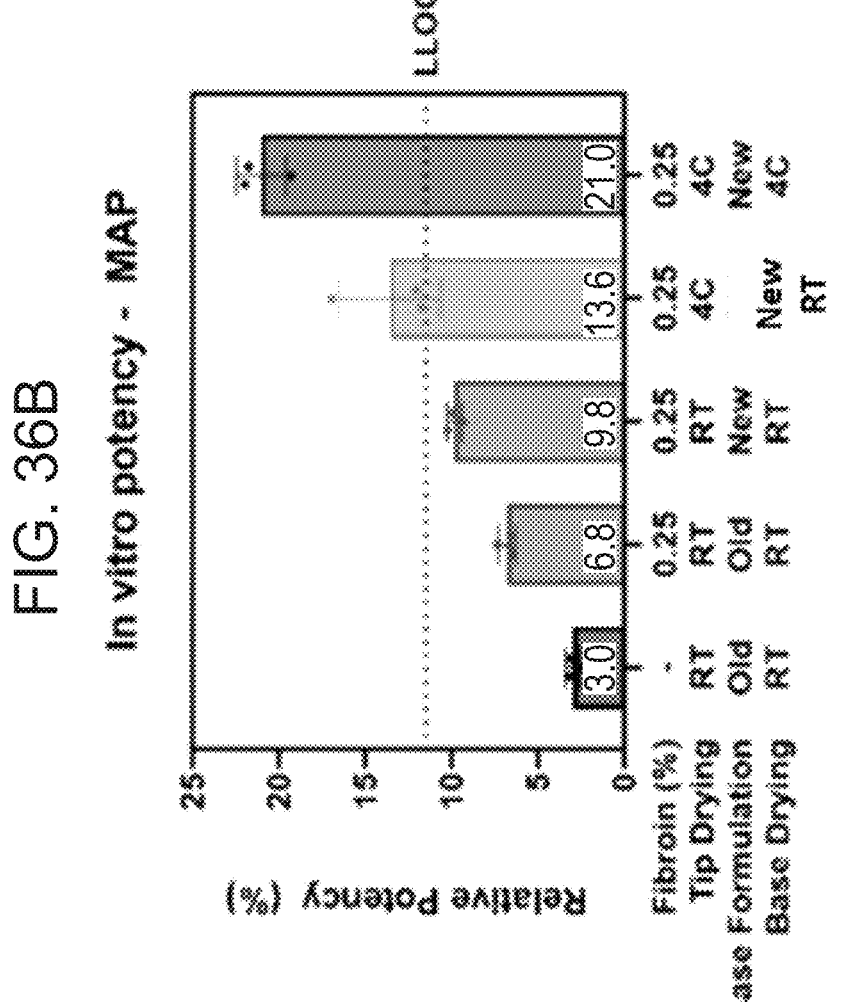

FIG. 36B represents the data shown in FIG. 36A with additional labels indicating the formulation components evaluated. Formulation details are also summarized in Table 13.

Figure 37:
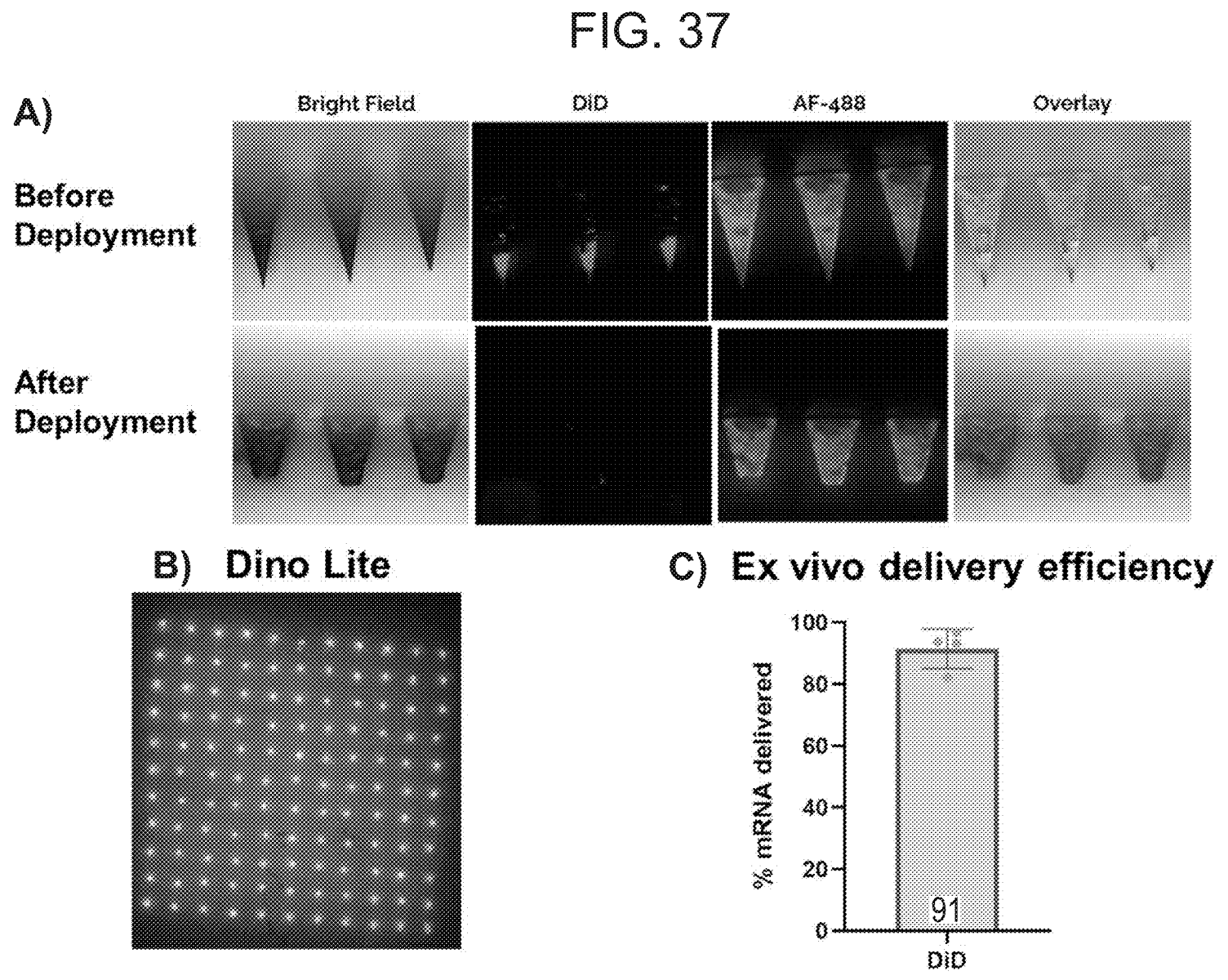

FIG. 37 shows MAPs containing DiD-labelled LNP tip formulation and AlexaFluor 488 base formulation were fabricated, deployed into excised vivo porcine skin, and characterized to evaluate deployment efficiency. A) Fluorescent side-view imaging shows MAPs clearly deployed well, with little to no dye remaining in tip post-deployment. B) The deployed MAPs showed distinct and bright tips that were embedded within the skin, demonstrating compatibility of the labeled antigen with this method. C) Quantitative fluorescence revealed only an average of 9% DiD remaining on MAPs, indicating 91% of LNP was successfully delivered into the porcine skin.

Figure 38:
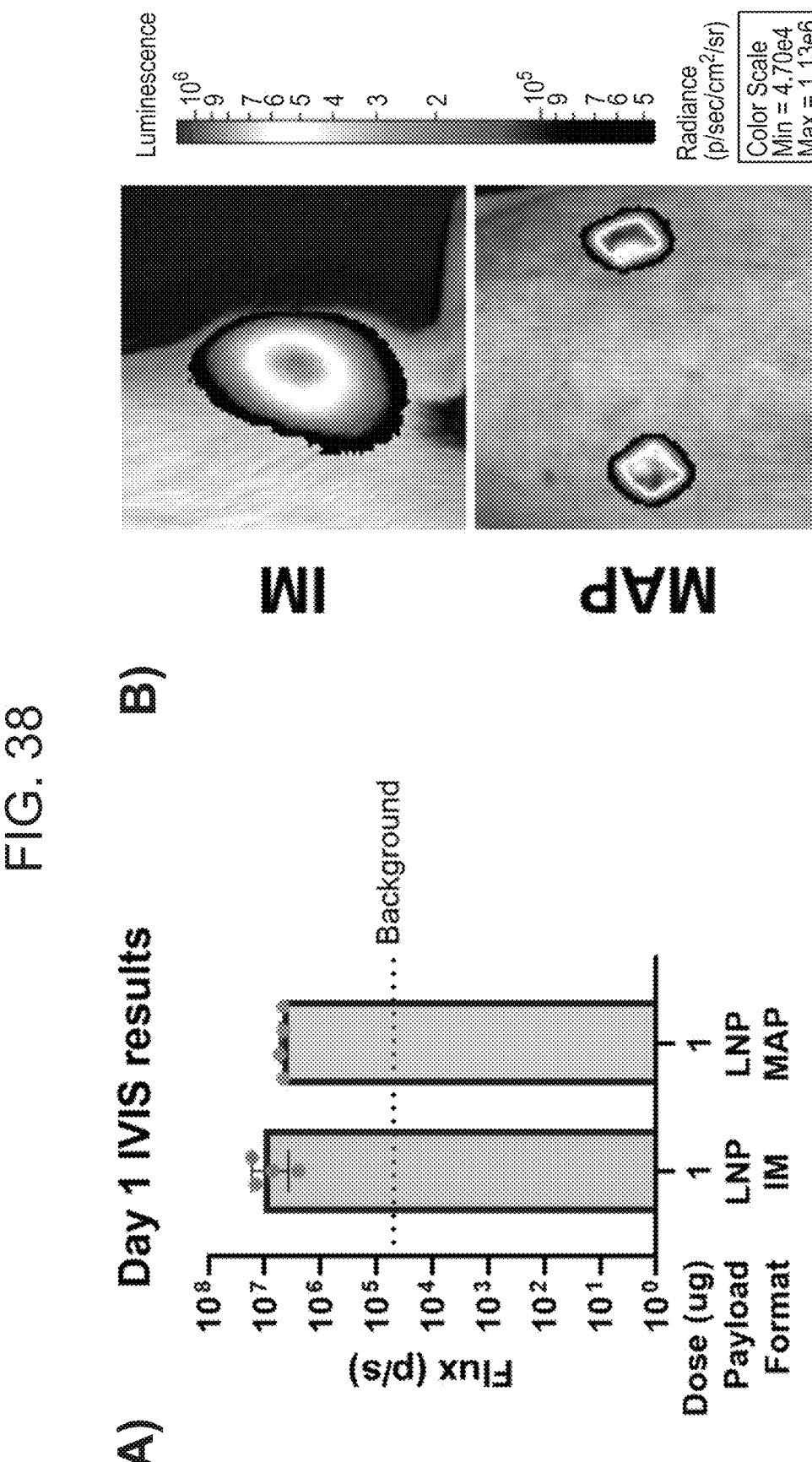

FIG. 38 shows the potency of MAPs by IVIS in comparison to the same dose (Intramuscular) IM A) MAPs exhibited similar in vivo luciferase expression compared to IM. Delayed release kinetics from MAPs may also contribute to differences in expression B) Representative IVIS images.

Figure 39:
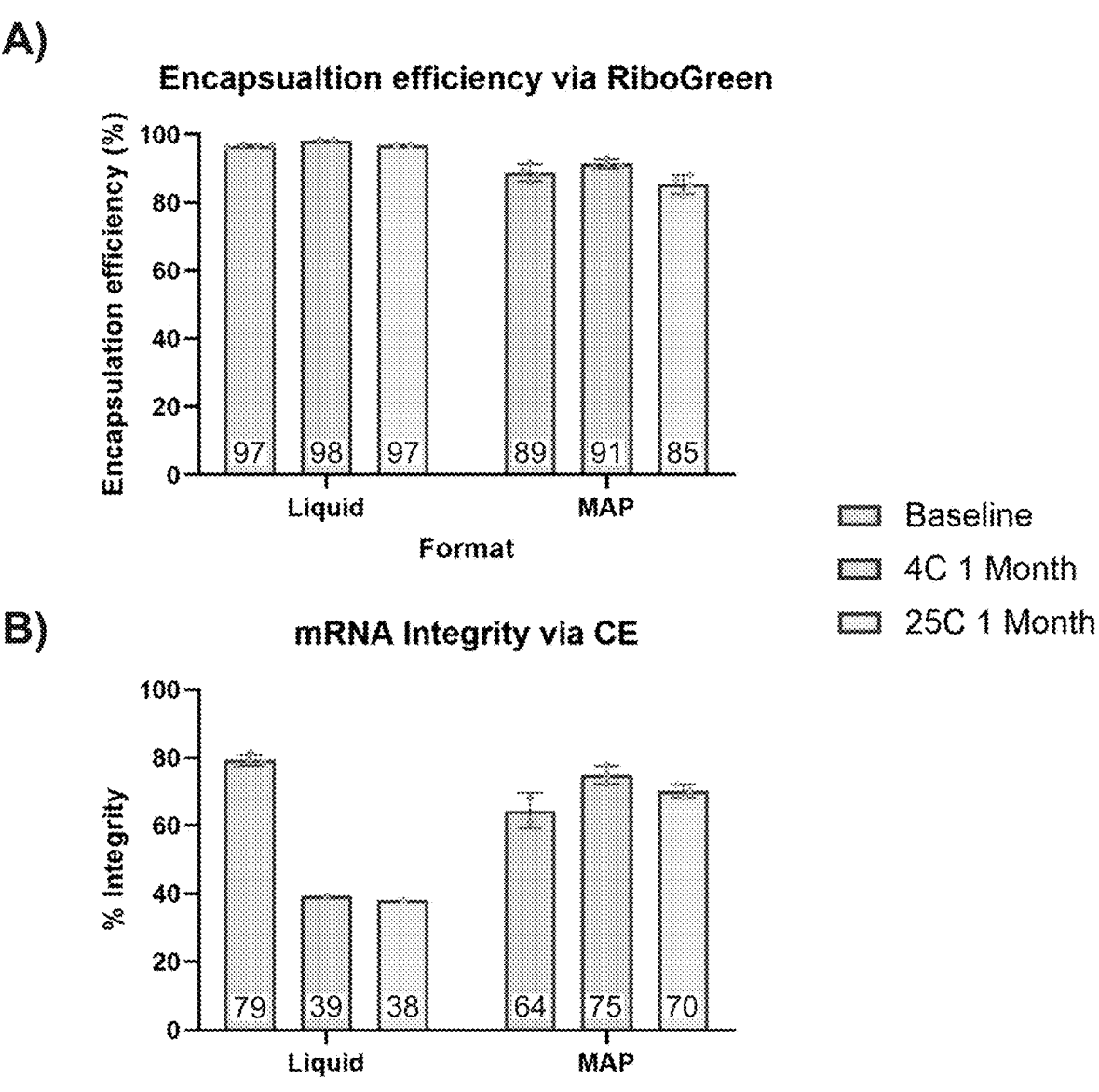

FIG. 39 shows HA-encoding mRNA MAPs were fabricated and stored for 1 month at 4C or 25C to determine mRNA stability via RiboGreen or CE. A) Encapsulation efficiency was retained in both liquid controls and MAPs at all temperature and time points, suggesting encapsulation efficiency likely not a good measure of mRNA stability. B) Significant loss in mRNA integrity observed in liquid format after 1 month storage. Largest contributor of degradation was due to mRNA aggregation/secondary structure formation. While there was some mRNA integrity loss through the manufacturing process, mRNA stored in the MAP format exhibited enhanced stability over liquid control, with no additional mRNA degradation observed after 1 month storage.

DETAILED DESCRIPTION

Definitions

In order that the present invention may be more readily understood, certain terms are first defined. Unless defined otherwise, all technical and scientific terms used herein have the same meaning as commonly understood by one of ordinary skill in the art to which the invention pertains. In addition, it should be noted that whenever a value or range of values are recited, it is intended that values and ranges intermediate to the recited values are also intended to be part of this invention.

As used in this specification and the appended claims, the singular forms "a," "an," and "the" include plural references unless the content clearly dictates otherwise.

The articles "a" and "an" are used herein to refer to one or to more than one (i.e., to at least one) of the grammatical object of the article. By way of example, "an element" means one element or more than one element, e.g., a plurality of elements.

The use of the alternative (e.g., "or") should be understood to mean either one, both, or any combination thereof of the alternatives. The term "or" is used herein to mean, and is used interchangeably with, the term "and/or," unless context clearly indicates otherwise.

As used herein, the term "about," when referring to a measurable value such as an amount, a temporal duration, and the like, is meant to encompass variations of ±20%, or ±10%, more preferably ±5%, even more preferably ±1%, and still more preferably ±0.1% from the specified value, as such variations are appropriate to perform the disclosed methods.

As used herein, any concentration range, percentage range, ratio range, or integer range is to be understood to include the value of any integer within the recited range and, when appropriate, fractions thereof (such as one tenth and one hundredth of an integer), unless otherwise indicated.

As used herein, "comprise," "comprising," "comprises," and "comprised of" are meant to be synonymous with "include," "including," "includes," or "contain," "containing," "contains" and are inclusive or open-ended terms that specifies the presence of what follows, e.g., component and do not exclude or preclude the presence of additional, non-recited components, features, element, members, steps, known in the art or disclosed therein. By way of example, the term "including" is used herein to mean, and is used interchangeably with, the phrase "including but not limited to."

As used herein, the terms "such as," "for example," and the like are intended to refer to exemplary embodiments and not to limit the scope of the present disclosure.

As used herein, the terms "preventing" or "prevention" refer to a reduction in risk of acquiring a disease, disorder, and/or condition (e.g., causing at least one of the clinical symptoms of the disease, disorder, and/or condition not to develop in a subject that may be exposed to and/or predisposed to the disease, disorder, and/or condition but does not yet experience or display symptoms of the disease, disorder, and/or condition).

As used herein, the terms "treating" or "treatment" refer to a beneficial or desired result including, but not limited to, slowing, stopping, and/or reversing of the progression of a disease, disorder, and/or condition. As such, in some embodiments, "treating" means an application or administration of the methods, compositions, e.g., microneedles and/or microarray patches (MAP), and/or systems described herein to a subject in need thereof, e.g., a subject suffering from a disease, disorder, condition, and/or symptom thereof, where the purpose is to cure, heal, alleviate, relieve, alter, remedy, ameliorate, improve, or affect the disease, disorder, condition, and/or symptom thereof. In some embodiments, the beneficial or desired result of treatment can be the alleviation and/or amelioration of one or more symptoms of the disease, disorder, and/or condition. In some embodiments, the beneficial or desired result of treatment can be to diminish the extent of the disease, disorder, and/or condition. In some embodiments, the beneficial or desired result of treatment can be a stabilized (e.g., not worsening) state of the disease, disorder, and/or condition. In some embodiments, the beneficial or desired result of treatment can be amelioration or palliation of the disease, disorder, and/or condition, whether detectable or undetectable. In some embodiments, "treatment" can also mean prolonging survival as compared to expected survival in the absence of treatment.

As used interchangeably herein, the terms "dose," "total dose," and "total dose delivered," in the context of a microarray patch (MAP), may refer to the total amount, e.g., by weight, of an API that is present in a MAP. In some embodiments, the "total dose delivered" by a MAP can be determined by the amount of an API ("payload") that can be loaded onto and/or into each microneedle multiplied by the total number of microneedles present in the MAP. In some embodiments, the "total dose delivered" by a MAP can be determined by the amount of an API ("payload") that can be loaded onto and/or into each consolidated microneedle tip multiplied by the total number of microneedles comprising said consolidated microneedle tip present in the MAP. In some embodiments, the "total dose delivered" by a MAP can be determined by the amount of an API ("payload") that can be loaded onto and/or into each microneedle base multiplied by the total number of microneedles comprising said microneedle base present in the MAP. In some embodiments, an API ("payload") may be loaded onto and/or into both the consolidated microneedle tip and the microneedle base.

As used interchangeably herein, the terms "dose," "total dose," and "total dose delivered," in the context of a microneedle, may refer to the total amount, e.g., by weight, of an API that is present in a microneedle (e.g., a single microneedle).

As used interchangeably herein, the terms "dose," "total dose," and "total dose delivered," in the context of a dispensable formulation, may refer to the total amount, e.g., by weight, of an API that is present in a dispense volume of the dispensable formulation, such as a tip fill volume and/or a base fill volume. In some embodiments, when the concentration of an API in the dispensable formulation can be defined, the "dose" may be expressed as a volume, e.g., a dispense volume of the dispensable formulation, such as a tip fill volume and/or a base fill volume.

As used herein, the term "prophylactically effective amount," is intended to include the amount of an active agent that, when administered to a subject who does not yet experience or display symptoms of a condition, disease, and/or disorder, but who may be predisposed to the condition, disease, and/or disorder, is sufficient to prevent or ameliorate the condition, disease, and/or disorder or one or more symptoms of the condition, disease, and/or disorder. Ameliorating the condition, disease, and/or disorder includes slowing the course of the condition, disease, and/or disorder or reducing the severity of later-developing condition, disease, and/or disorder. The "prophylactically effective amount" may vary depending on the active agent, how the active agent is administered, the degree of risk of condition, disease, and/or disorder, and the history, age, weight, family history, genetic makeup, the types of preceding or concomitant treatments, if any, and other individual characteristics of the patient to be treated.

A "therapeutically effective amount" or "prophylactically effective amount" also includes an amount of an active agent that produces some desired local or systemic effect at a reasonable benefit/risk ratio applicable to any treatment. Active agents employed in the methods of the present invention may be administered in a sufficient amount to produce a reasonable benefit/risk ratio applicable to such treatment.

As used herein, the term "administering" to a subject includes dispensing, delivering or applying a composition as described herein to a subject by any suitable route for delivery of the composition to the subject, including delivery by deploying a microneedle and/or a microarray patch (MAP) described herein. Exemplary modes of administration include, but are not limited to, injection, infusion, instillation, inhalation, or ingestion. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In preferred embodiments, the compositions are administered intradermally and/or transdermally by a microneedle and/or a microarray patch (MAP) described herein. Alternatively or in combination, delivery can be by any route such as by the topical, parenteral or oral route, intracerebral injection, intramuscular injection, subcutaneous, intradermal injection, intravenous injection, buccal administration, transdermal delivery and administration by the rectal, colonic, vaginal, intranasal, and/or respiratory tract route.

In some embodiments, the term "administering" to a subject includes dispensing, delivering, or applying a microneedle and/or a microarray patch (MAP) described herein to the skin of a subject at any suitable site on the body (e.g., arm, abdomen, back, buttock, and/or upper torso) for delivery of the composition to the subject. In some embodiments, the microneedle and/or the microarray patch (MAP) can be applied to a dry, flat skin area on the upper arm, abdomen, back, buttock, and/or upper torso. In some embodiments, the site of application on the skin is substantially free of oils, scars, cuts, burns, and/or irritation. In some embodiments, the microneedle and/or the microarray patch (MAP) should not be applied to areas of the skin that have received prior treatment with the API and/or another therapy.

As used herein, the term "adjust" or "modulate" and grammatical equivalents thereof means to alter (e.g., increase and/or decrease). In some embodiments, the term describes a level, an amount, and/or a concentration of a parameter, such as any physical and/or chemical property. In some embodiments, the term describes an alteration relative to a "control" or a "reference," such as, for example, a control sample, a control subject, a control formulation, a reference drug, a reference level, and/or a reference parameter. As used herein, the terms "control" or "reference" generally refer to a standard of comparison. In some embodiments, alterations may be made to a level, an amount, and/or a concentration of, for example, a formulation component, such as an active pharmaceutical ingredient (API) and/or a water-soluble excipient, described herein. In some embodiments, alterations may be made to enhance a physical property and/or a chemical property of the microneedles and/or microarray patches (MAPs) described herein. Such alterations may include, for example, alterations to a dispensable formulation, such as a dispensable tip and/or a dispensable base formulation described herein. In some embodiments, alterations may be made to a manufacturing feasibility criteria, a printability parameter, and/or a process output to enhance a physical property and/or a chemical property of the microneedles and/or microarray patches (MAPs) described herein.

The term "increase" refers to any increase, for example, an increase by at least about 1%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, at least about 99%, or up to and including an increase of at least about 100% or more (e.g., substantially above levels of detection), or any increase between about 1% to about 100% or more, as compared to a reference, e.g., a reference level. In some embodiments, an increase may be determined by a method that achieves, e.g., statistical significance (p<0.05).

The term "decrease" or "reduce" refers to any decrease, for example, a decrease by at least about 1%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, at least about 99%, or up to and including a decrease of at least about 100% or more (e.g., below levels of detection), or any decrease between about 1% to about 100% or more, as compared to a reference, e.g., a reference level. In some embodiments, a decrease may be determined by a method that achieves, e.g., statistical significance (p<0.05).

As used herein, the term "active agent" refers to a compound, macromolecule, drug, element, substance, or mixture that when administered to a subject, alone or in combination with another compound, macromolecule, drug, element, substance, or mixture, confers, directly or indirectly, a physiological effect on the subject. In some embodiments, salts, solvates (including hydrates), esters, analogues, derivatives, and/or prodrugs of the active agent are contemplated herein. In some embodiments, crystalline forms, non-crystalline forms, polymorphs, and any pseudopolymorphs of the active agent are also contemplated herein. In some embodiments, "active agent" and "active pharmaceutical ingredient" and "API" are used interchangeably.

As used herein, the term "pharmacokinetic profile" has its ordinary meaning as understood by those skilled in the art and thus includes, by way of non-limiting example, a characteristic of the curve that results from plotting blood serum concentration of a API over time, following administration of the API to a subject. A pharmacokinetic profile thus includes a pharmacokinetic parameter or set of parameters that can be used to characterize the pharmacokinetics of a particular API or dosage form (e.g., a microneedle and/or a MAP described herein) when administered to a suitable patient population. Various pharmacokinetic parameters are known to those skilled in the art. In some embodiments, "pharmacokinetic parameters" refers to the in vivo characteristics of an API (or a reference drug) over time, such as plasma concentration (C), $C_{max}$, $C_n$, $C_{24}$, $T_{max}$, and AUC. In some embodiments, "$C_{max}$" refers to the measured concentration of the API, e.g., in the plasma, at the point of maximum concentration. In some embodiments, "$C_n$" refers to the measured concentration of an API, e.g., in the plasma, at about n hours after administration. In some embodiments, "$C_{24}$" refers to the measured concentration of an API, e.g., in the plasma, at about 24 hours after administration. In some embodiments, "$T_{max}$" refers to the time at which the measured concentration of an API, e.g., in the plasma, is the highest (i.e., $C_{max}$) after administration of the API. In some embodiments, "AUC" refers to the area under the curve of a graph of the measured concentration of an API (e.g., plasma concentration) versus time, measured from one time point to another time point. For example, "$AUC_{0-t}$" refers to the area under the curve of API concentration (e.g., plasma concentration) versus time from time 0 to time t. In some embodiments, "$AUC_{0-INF}$" refers to the calculated area under the curve of API concentration (e.g., plasma concentration) versus time from time 0 to time infinity. AUClast indicates the area under the blood plasma concentration versus time curve from the time of administration until the time of the last measurable concentration. Pharmacokinetic parameters may be measured in various ways known to those skilled in the art, e.g., single dosage or steady-state. Differences in one or more of the pharmacokinetic profiles (e.g., $C_{max}$) may indicate pharmacokinetic distinctness between two formulations.

Those skilled in the art will understand that pharmacokinetic parameters may be determined by comparison to a reference standard using clinical trial methods known and accepted by those skilled in the art, e.g., as described in the examples set forth herein. Since the pharmacokinetics of a API can vary from patient to patient, such clinical trials generally involve multiple patients and appropriate statistical analyses of the resulting data (typically ANOVA at 90% confidence). Comparisons of pharmacokinetic parameters are on a dose-adjusted basis, as understood by those skilled in the art.

As used herein, the term "bioavailability" generally means that the extent or rate at which an active pharmaceutical ingredient (API) is absorbed into a living system or is made available at the site of physiological activity. Bioavailability can be characterized by one or more pharmacokinetic parameters, as described herein. Generally, the term bioavailability refers to the fraction of an administered dose of the API, such as a GLP-1 peptide comprised in a pharmaceutical composition (e.g., a microneedle and/or a MAP) described herein, that reaches the systemic circulation unchanged. For example, when an API is administered intravenously, its bioavailability can be 100%. However, when an API is administered via other routes, e.g., orally, its bioavailability may decrease due to incomplete absorption and/or first-pass metabolism occurring in the gastrointestinal (GI) tract and liver. Transdermal and/or intradermal delivery of an API by a microneedle and/or a MAP described herein can bypass first-pass metabolism by allowing the API to enter the systemic circulation directly.

As used herein, the term "bioequivalence" generally means the absence of a significant difference in the rate and extent to which an active pharmaceutical ingredient (API) (or a reference drug) in pharmaceutical equivalents or pharmaceutical alternatives becomes available at the site of action when administered in an appropriately designed study, such as a pharmacokinetic (PK) study described herein.

As used herein, the term "stabilized" or "stable," in the context of a pharmaceutical composition comprising an API, such as a microneedle and/or a MAP described herein, refers to a pharmaceutical composition with increased chemical stability, increased physical stability or increased chemical and physical stability relative to a pharmaceutical composition without all the ingredients (e.g., water-soluble excipients) of the pharmaceutical composition of the present disclosure. In some embodiments, the term "stability," in the context of a pharmaceutical composition comprising an API, such as a microneedle and/or a MAP described herein, refers to the shelf life of the composition.

As used herein, the term "shelf stability" can refer to the longest length of time in the labeling or approval documentation accompanying a commercially approved formulation of an active pharmaceutical ingredient (API). A product's "shelf stability" or "shelf life" generally means the length of time expected for a product to look and act as expected and to stay safe for use. In some embodiments, the labeling or approval documentation originates from the European Medicines Agency. In some embodiments, the labeling or approval documentation originates from the U.S. Food and Drug Agency (FDA). In some embodiments, "shelf stability" can refer to either room temperature shelf conditions and/or cold-chain shelf conditions.

As used herein, the terms "reference drug," "reference listed drug (RLD)," and "reference standard" can refer to an active pharmaceutical ingredient (API) product as described in the U.S. Federal Food and Drug Administration's (FDA) Orange Book, Approved Drug Products with Therapeutic Equivalence Evaluations and/or the European Medicines Agency (EMEA) document "Note for Guidance on the Investigation of Bioavailability and Bioequivalence. In some embodiments, the reference drug comprises a GLP-1 receptor agonist, such as semaglutide, dulaglutide, exenatide, liraglutide, lixisenatide, tirzepatide, albiglutide, and/or taspoglutide.

As used herein, the term "anti-drug antibody" or "ADA" refers to an antibody produced by the immune system of a subject that can specifically bind to an epitope on an active pharmaceutical ingredient (API), such as an epitope on a therapeutic protein. ADAs can be classified as either neutralizing antibodies (NAbs) or non-neutralizing antibodies (nNAbs). ADAs may affect the safety and efficacy of an API, and as such may be monitored when administering an API, such as a therapeutic protein, to a subject. Although an API (e.g., a therapeutic protein) may be therapeutically effective in various diseases, disorders, and/or conditions, its administration (or repeated administration) can also be highly immunogenic (e.g., inducing high titers of ADAs) and may elicit an undesirable immune response to the API (e.g., the therapeutic protein). The formation of an ADA immune response can interfere with the activity of the API or neutralize it, thereby altering the API's pharmacokinetic (PK) and pharmacodynamic (PD) properties and reducing its efficacy, and/or causing an adverse event in a subject. Immune-based adverse effects may be acute and/or delayed. A possible life-threatening consequence of ADA formation against an API (e.g., a therapeutic protein) is cross-reactivity with an endogenous protein that inhibits or neutralizes its activity when the protein has a non-redundant role in mediating important physiological functions. An additional potential consequence of cross-reactivity to an endogenous protein can result from antibody responses to an API that is a counterpart of an endogenous cell surface receptor or a counterpart of an endogenous cytokine that is membrane-expressed. Such ADAs may cross-reactively bind to the respective cell surface receptors or proteins, causing cyto-kine release and/or other undesirable manifestations of cel-lular activation. In general, the development of neutralizing ADA activity and/or the presence of sustained ADA titers may lead to loss of efficacy and/or an increased risk of an adverse reaction. In some embodiments, the microneedles, microarray patches (MAPs), and systems described herein can decrease the potential for and/or the risk associated with an unwanted immune response developing to an API, such as a therapeutic protein. In some embodiments, the microneedles, microarray patches (MAPs), and systems described herein can improve the immunogenicity profile, clinical safety, and/or efficacy of an API, such as a thera-peutic protein. In some embodiments, the microneedles, microarray patches (MAPs), and systems described herein can reduce the occurrence and/or severity of immunologi-cally based adverse events, including, but not limited to, anaphylaxis, cytokine release syndrome, and cross-reactive neutralization of endogenous proteins. In some embodi-ments, the microneedles, microarray patches (MAPs), and systems described herein can enhance the delivery of high-risk therapeutic protein products (e.g., therapeutic counter-parts of nonredundant endogenous proteins), e.g., by reduc-ing unwanted immunogenicity. In some embodiments, the microneedles, microarray patches (MAPs), and systems described herein can reduce the development of neutralizing ADA activity, decrease the presence of sustained ADA titers that may lead to loss of efficacy, and/or reduce the risk of an adverse reaction. In some embodiments, the microneedles, microarray patches (MAPs), and systems described herein can increase immune tolerance, e.g., when severe conse-quences result from immunogenicity. In some rare instances, an ADA may act as a carrier and enhance the half-life of an API and/or prolong its therapeutic effects. In some embodi-ments, the microneedles, microarray patches (MAPs), and systems described herein can help promote the development of an ADA with beneficial effects, such as a ADA that can act as a carrier and enhance the half-life of an API, such as a therapeutic protein (e.g., a GLP-1 receptor agonist) and/or prolong its therapeutic effects.

As used herein, the term "neutralizing antibody" or "NAb" refers to a subset of anti-drug antibodies (ADAs) that can bind to an active pharmaceutical ingredient (API), such as a therapeutic protein, in a manner that can inhibit or neutralize its activity. In some embodiments, a neutralizing antibody may inhibit the activity of an API, such as a therapeutic protein, by binding to an epitope (e.g., a neu-tralizing epitope) within or close to an active site of the molecule or by causing conformational changes, thereby physically interfering with the ability of the API to bind its target. In some embodiments, a neutralizing antibody may inhibit the binding of an API to its target, thereby rendering the API partially or completely inactive. In some embodi-ments, a neutralizing antibody may block and/or interfere with an API's ability to bind its target, thereby rendering the API partially or completely inactive. For example, in some instances, a neutralizing antibody may block and/or interfere with the ability of an API, such as a soluble ligand drug (e.g., a GLP-1 receptor agonist), to bind its receptor (e.g., a GLP-1 receptor). In some embodiments, the microneedles, microar-ray patches (MAPs), and systems described herein can reduce the development of and/or effects of a neutralizing antibody that can block and/or interfere with the ability of an API, such as a soluble ligand drug (e.g., a GLP-1 receptor agonist), to bind its receptor (e.g., a GLP-1 receptor). In some embodiments, the microneedles, microarray patches (MAPs), and systems described herein can reduce the devel-opment of and/or the effects of a cross-reactive antibody to an endogenous counterpart of an API (e.g., an endogenous GLP-1). Neutralizing antibodies may affect the safety and efficacy of an API, and as such may be monitored when administering an API, such as a therapeutic protein, to a subject.

As used herein, the term "non-neutralizing antibody" or "nNAb" refers to a subset of anti-drug antibodies (ADAs) that can bind to an active pharmaceutical ingredient (API), such as a therapeutic protein, in a manner that may modulate its activity. In some embodiments, a non-neutralizing anti-body may modulate the activity of a API, such as a thera-peutic protein, by binding to an epitope (e.g., a non-neu-tralizing epitope) that does not affect the API-target interaction (e.g., does not physically interfere with the ability of the API to bind its target). While non-neutralizing antibodies may not necessarily affect the API-target inter-action, non-neutralizing antibodies may affect the safety of an API, e.g., by causing adverse events, such as hypersen-sitivity reactions and inflammatory responses; and/or may affect the efficacy of an API, e.g., by altering its clearance, cellular uptake, and/or half-life. Non-neutralizing antibodies may affect the safety and efficacy of an API, and as such may be monitored when administering an API, such as a thera-peutic protein, to a subject.

Amounts: throughout this disclosure, various aspects of the invention can be presented in a percent concentration format. The percent concentration of a material (e.g., an API and/or excipient described herein) in solution (e.g., a dis-pensable formulation described herein) can be expressed in several ways depending on how the material and solution are measured. Accordingly, the description of a percent concen-tration should be considered to have specifically disclosed all the possible ways the material and solution may be measured, unless the content clearly dictates otherwise. For example, the amount of a component, such as an API and/or a water-soluble excipient, present in a dispensable formu-lation (e.g., a dispense volume of a dispensable formulation) may be a weight per weight (% w/w), a weight per volume (% w/v), and/or a volume per volume (% v/v) percent concentration, unless the content clearly dictates otherwise. In should also be understood that the amount of a compo-nent, such as an API and/or a water-soluble excipient, present in a microneedle and/or a MAP described herein may relate to the amount of the component present in the dispensable formulation (e.g., in the dispense volume of the dispensable formulation) from which the microneedle and/ or the MAP was formed. For example, the amount of a component, such as an API and/or a water-soluble excipient, present in a dispensable tip and/or base formulation (e.g., a dispense volume of a dispensable tip and/or base formula-tion) from which a microneedle and/or a MAP may be formed. In some embodiments, the amount of a component, such as an API and/or a water-soluble excipient, present in a microneedle and/or a MAP described herein may be determined, e.g., after drying.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. As another example, a range such as 95-99% identity, includes something with 95%, 96%, 97%, 98% or 99% identity, and includes subranges such as 96-99%, 96-98%, 96-97%, 97-99%, 97-98% and 98-99% identity. This applies regardless of the breadth of the range.

Compositions

Dispensable Formulations, Microneedles, and Microarray Patches (MAPs)

The present disclosure relates, in one aspect, to microneedles and/or microarray patches (MAPs) that can facilitate simple, substantially pain-free, and consistent delivery of a wide range of active pharmaceutical ingredients (APIs) and doses. The microneedles and/or microarray patches (MAPs) can be formed from a dispensable formulation described herein, comprising at least one selected from the group consisting of an active pharmaceutical ingredient (API), a water-soluble excipient, and combinations thereof. As disclosed herein, Applicant has surprisingly discovered specific combinations of water-soluble excipients that can, for example, effectively (1) enhance the stability of a high concentration of active pharmaceutical ingredients (API) for delivery of an effective dose of the API using a microneedle and/or a microarray patch (MAP) described herein; (2) enhance the fluid properties of a composition, such as a dispensable formulation, for manufacturing a microneedle and/or a microarray patch (MAP) described herein using, e.g., a liquid dispensing system; (3) enhance the consolidation of the API into the apex of a microneedle tip (e.g., a consolidated microneedle tip) during manufacturing; (4) enhance the strength of the microneedle, e.g., to resist deformation during deployment; and/or (5) minimize, or eliminate, manufacturing defects, such as shell formation and microneedle tip dislodgement, that can negatively affect microneedle morphology, strength, deployment efficiency, API delivery consistency, and pharmacodynamics.

Accordingly, in one aspect, the present disclosure provides a composition, such as a dispensable formulation, comprising at least one selected from the group consisting of an active pharmaceutical ingredient (API), a water-soluble excipient, and combinations thereof. In some embodiments, the dispensable formulation can be used for producing a microneedle and/or a microarray patch (MAP).

Accordingly, in one aspect, the disclosure further provides a composition, such as a pharmaceutical composition, comprising an active pharmaceutical ingredient (API) and a water soluble excipient. Such compositions, e.g., pharmaceutical compositions, can be in the form of a microneedle and/or a microarray patch (MAP). In one embodiment, the present disclosure provides microneedles and/or microarray patches (MAPs), comprising an active pharmaceutical ingredient (API) and a water soluble excipient, demonstrating consistent dosing, extended shelf stability, therapeutically relevant dosing, and/or therapeutically relevant bioavailability. In one embodiment, the present disclosure provides microneedles and/or microarray patches (MAPs), comprising an active pharmaceutical ingredient (API) and a water soluble excipient, demonstrating bioequivalence to commercially approved formulations of the API.

Accordingly, in one aspect, the disclosure provides a microneedle and/or a microarray patch (MAP), comprising at least one selected from the group consisting of an active pharmaceutical ingredient (API), a water-soluble excipient, and combinations thereof. In particular embodiments, the microneedle and/or the microarray patch (MAP), comprises an active pharmaceutical ingredient (API) and a water-soluble excipient. In particular embodiments, the microneedle and/or the microarray patch (MAP), comprises an active pharmaceutical ingredient (API) and a plurality of water-soluble excipients.

The microneedles and/or microarray patches (MAPs) can be configured to deliver one or more active pharmaceutical ingredients (APIs) (e.g., small molecules, biologics, peptides, proteins, nucleic acids, mRNA, lipid nanoparticles (LNPs), vaccines, virus-like particles (VLPs), live attenuated viruses, inactivated viruses, adjuvanted vaccines, and combinations thereof) through the skin of a subject, and to provide release of the API immediately and/or over a prolonged period of time.

In some embodiments, the microneedles and/or microarray patches (MAPs) can further comprise a consolidated microneedle tip. In some embodiments, the microneedles and/or microarray patches (MAPs) can further comprise a microneedle base. In some embodiments, the microneedles and/or microarray patches (MAPs) can further comprise a consolidated microneedle tip and a microneedle base. The consolidated microneedle tip and/or the microneedle base can be formed, independently, from a dispensable formulation (e.g., a dispensable tip formulation and/or a dispensable base formulation, respectively), comprising at least one selected from the group consisting of an active pharmaceutical ingredient (API), a water-soluble excipient, and combinations thereof. In some embodiments, the consolidated microneedle tip and/or the microneedle base can be formed, independently, from the same or different dispensable formulation. As such, in some embodiments, the consolidated microneedle tip and the microneedle base can comprise, independently, the same or different combination and/or amount of components (e.g., API and/or water-soluble excipient). The amount of a component (e.g., API and/or water-soluble excipient) can be based, for example, on the amount of the component (e.g., API and/or water-soluble excipient) present in a dispensable formulation (e.g., a dispensable tip formulation and/or a dispensable base formulation, respectively).

Additional features and non-limiting examples of the dispensable formulations, microneedles, and microarray patches (MAPs) of the present disclosure are disclosed below.

Dispensable Formulations

According to one aspect, the disclosure provides a dispensable formulation, e.g., comprising at least one selected from the group consisting of an active pharmaceutical ingredient (API), a water-soluble excipient, and combinations thereof. Such dispensable formulations can be used to produce a microneedle and/or a microarray patch (MAP) described herein. In some embodiments, the present disclosure provides a dispensable formulation, e.g., comprising at least one selected from the group consisting of an active pharmaceutical ingredient (API), a water-soluble excipient, and combinations thereof, that can be used to form a consolidated microneedle tip and/or a microneedle base.

As used herein, the term "dispensable formulation" is intended to broadly encompass any composition, such as a liquid composition, that can be dispensed (e.g., printed, ejected, jetted, and/or sprayed) from a liquid handling device. In some embodiments, it is desirable to provide a dispensable formulation, comprising at least one selected from the group consisting of an active pharmaceutical ingredient (API), a water-soluble excipient, and combinations thereof for manufacturing a microneedle and/or a microarray patch (MAP), described herein, e.g., using a liquid dispensing system. In some embodiments, a dispensable formulation comprising an active pharmaceutical ingredient (API) and a water-soluble excipient can be used to form a consolidated microneedle tip (also referred to herein as a "tip formulation"). In some embodiments, a dispensable formulation comprising a water-soluble excipient may be used to form a microneedle base (also referred to herein as a "base formulation").

As used herein, the term "liquid dispensing system" refers to any device that can transfer a predefined amount of a liquid, e.g., a dispensable formulation described herein, to a target site, such as into a cavity, e.g., a microprojection shaped cavity, of a mold that defines the shape of a microneedle and/or a microarray patch (MAP). In some embodiment, the amount of liquid, e.g., dispensable formulation described herein, dispensed and the rate at which the liquid dispensing system dispenses the liquid to a target site may be adjusted manually and/or automatically.

In some embodiment, the amount of a liquid, e.g., a dispensable formulation, that is dispensed to fill, or to partially fill, a microprojection shaped cavity of a mold that defines the shape of a microneedle and/or a microarray patch (MAP) may be about 1 nl to about 1000 nL (e.g., about 1 nL, about 5 nL, about 10 nL, about 15 nL, about 20 nL, about 25 nL, about 30 nL, about 35 nL, about 40 nL, about 45 nL, about 50 nL, about 55 nL, about 60 nL, about 65 nL, about 70 nL, about 75 nL, about 80 nL, about 85 nL, about 90 nL, about 95 nL, about 100 nL, about 105 nL, about 110 nL, about 115 nL, about 120 nL, about 125 nL, about 130 nL, about 135 nL, about 140 nL, about 145 nL, about 150 nL, about 155 nL, about 160 nL, about 165 nL, about 170 nL, about 175 nL, about 180 nL, about 185 nL, about 190 nL, about 195 nL, about 200 nL, about 205 nL, about 210 nL, about 215 nL, about 220 nL, about 225 nL, about 230 nL, about 235 nL, about 240 nL, about 245 nL, about 250 nL, about 255 nL, about 260 nL, about 265 nL, about 270 nL, about 275 nL, about 280 nL, about 285 nL, about 290 nL, about 295 nL, about 300 nL, about 305 nL, about 310 nL, about 315 nL, about 320 nL, about 325 nL, about 330 nL, about 335 nL, about 340 nL, about 345 nL, about 350 nL, about 355 nL, about 360 nL, about 365 nL, about 370 nL, about 375 nL, about 380 nL, about 385 nL, about 390 nL, about 395 nL, about 400 nL, about 405 nL, about 410 nL, about 415 nL, about 420 nL, about 425 nL, about 430 nL, about 435 nL, about 440 nL, about 445 nL, about 450 nL, about 455 nL, about 460 nL, about 465 nL, about 470 nL, about 475 nL, about 480 nL, about 485 nL, about 490 nL, about 495 nL, about 500 nL, about 505 nL, about 510 nL, about 515 nL, about 520 nL, about 525 nL, about 530 nL, about 535 nL, about 540 nL, about 545 nL, about 550 nL, about 555 nL, about 560 nL, about 565 nL, about 570 nL, about 575 nL, about 580 nL, about 585 nL, about 590 nL, about 595 nL, about 600 nL, about 605 nL, about 610 nL, about 615 nL, about 620 nL, about 625 nL, about 630 nL, about 635 nL, about 640 nL, about 645 nL, about 650 nL, about 655 nL, about 660 nL, about 665 nL, about 670 nL, about 675 nL, about 680 nL, about 685 nL, about 690 nL, about 695 nL, about 700 nL, about 705 nL, about 710 nL, about 715 nL, about 720 nL, about 725 nL, about 730 nL, about 735 nL, about 740 nL, about 745 nL, about 750 nL, about 755 nL, about 760 nL, about 765 nL, about 770 nL, about 775 nL, about 780 nL, about 785 nL, about 790 nL, about 795 nL, about 800 nL, about 805 nL, about 810 nL, about 815 nL, about 820 nL, about 825 nL, about 830 nL, about 835 nL, about 840 nL, about 845 nL, about 850 nL, about 855 nL, about 860 nL, about 865 nL, about 870 nL, about 875 nL, about 880 nL, about 885 nL, about 890 nL, about 895 nL, about 900 nL, about 905 nL, about 910 nL, about 915 nL, about 920 nL, about 925 nL, about 930 nL, about 935 nL, about 940 nL, about 945 nL, about 950 nL, about 955 nL, about 960 nL, about 965 nL, about 970 nL, about 975 nL, about 980 nL, about 985 nL, about 990 nL, about 995 nL, or about 1000 nL). In some embodiments, the predefined amount of the liquid, e.g., the dispensable formulation, that is dispensed into the microprojection shaped cavity of the mold forms a consolidated microneedle tip. In some embodiment, the predefined amount of the liquid, e.g., the dispensable formulation, that is dispensed into the microprojection shaped cavity of the mold forms a microneedle base.

As used herein, the term "target site" refers to a specific position on a solid support that can contain a liquid, e.g., a dispensable formulation. In some embodiments, the target site may be a specific microprojection shaped cavity of a mold that defines the shape of a microneedle array. Such a mold may contain one or more target sites, e.g., one or more microprojection shaped cavities, which may be arranged randomly or in an ordered array or other pattern.

In some embodiments, the liquid dispensing system may be a vision-guided dispensing system capable of accurately dispensing a liquid, e.g., a dispensable formulation, in complex patterns and/or to specific target sites, such as to fill, or to partially fill, a microprojection shaped cavity of a mold that defines the shape of a microneedle array.

In some embodiments, the liquid dispensing system may be a low-volume dispensing system. As used herein, the term "low-volume dispensing" refers to any dispensing process with volumes in the nanoliter (nL) and/or picoliter (pL) range. In some embodiments, low-volume dispensing encompasses dispensing single liquid drops in the volume range of about 0.1 pL to more than about 1 μL.

In some embodiments, the liquid dispensing system may be configured to provide dropwise dispensing. The term "dropwise," as used herein, means that a liquid, e.g., a dispensable formulation, is provided in a drop-by-drop fashion. The terms "dropwise" and "drop-by-drop" are generally intended to mean that one discrete drop of a liquid, e.g., a dispensable formulation, irrespective of its drop size (e.g., diameter and/or volume) is provided or dispensed at a time and/or that a plurality of drops is provided in a consecutive manner, one at a time. In some embodiments, dropwise dispensing of a liquid, e.g., a dispensable formulation, is provided to fill, or to partially fill, a microprojection shaped cavity of a mold that defines the shape of a microneedle array.

The term "progressive fill," as used herein, refers to a dropwise manner of dispensing a dispensable formulation, such as a dispensable tip formulation and/or a dispensable base formulation described herein. In some embodiments, the term "progressive fill" refers to a dropwise manner of dispensing one or more drops of a dispensable formulation, such as a dispensable tip formulation and/or a dispensable base formulation described herein, into a microprojection shaped cavity of a mold that defines the shape of a microneedle and/or a microarray patch (MAP).

In particular embodiments, the term "progressive fill" refers to a dropwise manner of dispensing a dispensable formulation, such as a dispensable tip formulation and/or a dispensable base formulation described herein, that may include an intervening drying step between the dispense of one or more drops. For example, in some embodiments, a progressive fill may comprise the steps of (1) dispensing one or more drops of a dispensable formulation, such as a dispensable tip formulation and/or a dispensable base formulation described herein, into a microprojection shaped cavity of a mold that defines the shape of a microneedle and/or a microarray patch (MAP); (2) drying the dispensed volume of the dispensable formulation for a predetermined period of time (e.g., one or more seconds, minutes, hours, and/or days) at predetermined environmental conditions (e.g., ambient temperature and/or relative humidity) to form a dried or partially dried portion of a consolidated microneedle tip and/or microneedle base; (3) dispensing one or more drops of the dispensable formulation onto the dried or partially dried portion of the consolidated microneedle tip and/or the microneedle base; and optionally (4) repeating step (2) and/or (3) to fully form a consolidated microneedle tip and/or a microneedle base, thereby generating a microneedle and/or the microarray patch (MAP) described herein. In some embodiments, using a progressive fill to form a consolidated microneedle tip and/or a microneedle base may reduce and/or eliminate the occurrence of a defect during manufacturing of a microneedle and/or a microarray patch (MAP) described herein. In some embodiments, the term "progressive base fill," refers to a dropwise manner of dispensing a dispensable base formulation. In some embodiments, subsequent to the formation of a consolidated microneedle tip, a microneedle base applied to the consolidated microneedle tip may be formed using a progressive base fill. It may be understood that the term "subsequent to the formation of a consolidated microneedle tip" encompasses, for example, the formation of a dried or partially dried consolidated microneedle tip from a dispensable tip formulation prior to the dispensing of one or more drops of a dispensable base formulation. For example, in some embodiments, a progressive base fill may comprise the steps of (1) dispensing one or more drops of a dispensable base formulation onto a dried or partially dried consolidated microneedle tip in a microprojection shaped cavity of a mold that defines the shape of a microneedle and/or a microarray patch (MAP); (2) optionally drying the dispensed volume of the dispensable base formulation for a predetermined period of time (e.g., one or more seconds, minutes, hours, and/or days) at predetermined environmental conditions (e.g., ambient temperature and/or relative humidity) to form a dried or partially dried portion of a microneedle base; (3) optionally dispensing one or more drops of the dispensable base formulation onto the dried or partially dried portion of the consolidated microneedle tip and/or the microneedle base; and optionally (4) repeating step (2) and/or (3) to fully form a consolidated microneedle tip and/or a microneedle base, thereby generating a microneedle and/or the microarray patch (MAP) described herein. In some embodiments, using a progressive base fill to form a consolidated microneedle tip and/or a microneedle base may reduce and/or eliminate the occurrence of a defect during manufacturing of a microneedle and/or a microarray patch (MAP) described herein.

As used herein, the terms "defect" and "manufacturing defect" and the like are broadly intended to encompass any kind of anomaly, imperfection, or undesirable feature formed on or within a microneedle and/or a microarray patch (MAP) described herein, e.g., during manufacturing. In some embodiments, the terms refer to an abnormality on the surface or within the volume of a material, such as a dispensable formulation, intended to form the consolidated microneedle tip and/or the microneedle base of a microneedle and/or a microarray patch (MAP) described herein. Defects may include non-uniformities, non-conformities, misalignments, flaws, damages, aberrations, and irregularities in the material or product.

In some embodiments, the defect may alter the morphology, the strength, and/or the deployment efficiency of a microneedle and/or a microarray patch (MAP) described herein. In some embodiments, the defect comprises a shell or shell-like structure formed, e.g., from the dispensable tip formulation, an incomplete consolidated microneedle tip, a missing consolidated microneedle tip, a missing base, a dislodgement of the consolidated microneedle tip (e.g., all or a portion of the consolidated microneedle tip is dislodged into the microneedle base), and/or resolubilization of the microneedle tip, that can negatively affect microneedle morphology, strength, and/or deployment efficiency.

As used herein, the term "drop size" refers to the size of the drop dispensed, and may be expressed in units of volume and/or diameter. In some embodiments, drop size may be measured in microliters ($\mu$L). In some embodiments, drop size may be measured in microns ($\mu$m). In some embodiments, drop size may be measured in nanoliters (nL). In some embodiments, drop size may be measured in nanometers (nm). In some embodiments, drop size may be measured in picoliters (pL). In some embodiments, drop size may be measured in picometers (pm). In some embodiments, drop size may be inferred based on a determination of the speed of the dispensed drop, as larger drops are generally characterized by greater speed.

In some embodiments, the drop size may be about 1 pL to about 1000 nL (e.g., about 1 pL to about 50 pL; about 1 pL to about 100 pL; about 1 pL to about 150 pL; about 1 pL to about 200 pL; about 1 pL to about 250 pL; about 1 pL to about 300 pL; about 1 pL to about 350 pL; about 1 pL to about 400 pL; about 1 pL to about 450 pL; about 1 pL to about 500 pL; about 1 pL to about 550 pL; about 1 pL to about 600 pL; about 1 pL to about 650 pL; about 1 pL to about 700 pL; about 1 pL to about 750 pL; about 1 pL to about 800 pL; about 1 pL to about 850 pL; about 1 pL to about 900 pL; about 1 pL to about 950 pL; about 1 pL to about 1000 pL; about 1 nL to about 50 nL; about 1 nL to about 100 nL; about 1 nL to about 150 nL; about 1 nL to about 200 nL; about 1 nL to about 250 nL; about 1 nL to about 300 nL; about 1 nL to about 350 nL; about 1 nL to about 400 nL; about 1 nL to about 450 nL; about 1 nL to about 500 nL; about 1 nL to about 550 nL; about 1 nL to about 600 nL; about 1 nL to about 650 nL; about 1 nL to about 700 nL; about 1 nL to about 750 nL; about 1 nL to about 800 nL; about 1 nL to about 850 nL; about 1 nL to about 900 nL; about 1 nL to about 950 nL; or about 1 nL to about 1000 nL).

In some embodiments, the drop size may be about 1 pL to about 1000 pL (e.g., about 1 pL, about 5 pL, about 10 pL, about 15 pL, about 20 pL, about 25 pL, about 30 pL, about 35 pL, about 40 pL, about 45 pL, about 50 pL, about 55 pL, about 60 pL, about 65 pL, about 70 pL, about 75 pL, about 80 pL, about 85 pL, about 90 pL, about 95 pL, about 100 pL, about 105 pL, about 110 pL, about 115 pL, about 120 pL, about 125 pL, about 130 pL, about 135 pL, about 140 pL, about 145 pL, about 150 pL, about 155 pL, about 160 pL, about 165 pL, about 170 pL, about 175 pL, about 180 pL, about 185 pL, about 190 pL, about 195 pL, about 200 pL, about 205 pL, about 210 pL, about 215 pL, about 220 pL, about 225 pL, about 230 pL, about 235 pL, about 240 pL, about 245 pL, about 250 pL, about 255 pL, about 260 pL, about 265 pL, about 270 pL, about 275 pL, about 280 pL, about 285 pL, about 290 pL, about 295 pL, about 300 pL, about 305 pL, about 310 pL, about 315 pL, about 320 pL, about 325 pL, about 330 pL, about 335 pL, about 340 pL, about 345 pL, about 350 pL, about 355 pL, about 360 pL, about 365 pL, about 370 pL, about 375 pL, about 380 pL, about 385 pL, about 390 pL, about 395 pL, about 400 pL, about 405 pL, about 410 pL, about 415 pL, about 420 pL, about 425 pL, about 430 pL, about 435 pL, about 440 pL, about 445 pL, about 450 pL, about 455 pL, about 460 pL, about 465 pL, about 470 pL, about 475 pL, about 480 pL, about 485 pL, about 490 pL, about 495 pL, about 500 pL, about 505 pL, about 510 pL, about 515 pL, about 520 pL, about 525 pL, about 530 pL, about 535 pL, about 540 pL, about 545 pL, about 550 pL, about 555 pL, about 560 pL, about 565 pL, about 570 pL, about 575 pL, about 580 pL, about 585 pL, about 590 pL, about 595 pL, about 600 pL, about 605 pL, about 610 pL, about 615 pL, about 620 pL, about 625 pL, about 630 pL, about 635 pL, about 640 pL, about 645 pL, about 650 pL, about 655 pL, about 660 pL, about 665 pL, about 670 pL, about 675 pL, about 680 pL, about 685 pL, about 690 pL, about 695 pL, about 700 pL, about 705 pL, about 710 pL, about 715 pL, about 720 pL, about 725 pL, about 730 pL, about 735 pL, about 740 pL, about 745 pL, about 750 pL, about 755 pL, about 760 pL, about 765 pL, about 770 pL, about 775 pL, about 780 pL, about 785 pL, about 790 pL, about 795 pL, about 800 pL, about 805 pL, about 810 pL, about 815 pL, about 820 pL, about 825 pL, about 830 pL, about 835 pL, about 840 pL, about 845 pL, about 850 pL, about 855 pL, about 860 pL, about 865 pL, about 870 pL, about 875 pL, about 880 pL, about 885 pL, about 890 pL, about 895 pL, about 900 pL, about 905 pL, about 910 pL, about 915 pL, about 920 pL, about 925 pL, about 930 pL, about 935 pL, about 940 pL, about 945 pL, about 950 pL, about 955 pL, about 960 pL, about 965 pL, about 970 pL, about 975 pL, about 980 pL, about 985 pL, about 990 pL, about 995 pL, or about 1000 pL).

In some embodiments, the drop size may be about 1 nL to about 1000 nL (e.g., about 1 nL, about 5 nL, about 10 nL, about 15 nL, about 20 nL, about 25 nL, about 30 nL, about 35 nL, about 40 nL, about 45 nL, about 50 nL, about 55 nL, about 60 nL, about 65 nL, about 70 nL, about 75 nL, about 80 nL, about 85 nL, about 90 nL, about 95 nL, about 100 nL, about 105 nL, about 110 nL, about 115 nL, about 120 nL, about 125 nL, about 130 nL, about 135 nL, about 140 nL, about 145 nL, about 150 nL, about 155 nL, about 160 nL, about 165 nL, about 170 nL, about 175 nL, about 180 nL, about 185 nL, about 190 nL, about 195 nL, about 200 nL, about 205 nL, about 210 nL, about 215 nL, about 220 nL, about 225 nL, about 230 nL, about 235 nL, about 240 nL, about 245 nL, about 250 nL, about 255 nL, about 260 nL, about 265 nL, about 270 nL, about 275 nL, about 280 nL, about 285 nL, about 290 nL, about 295 nL, about 300 nL, about 305 nL, about 310 nL, about 315 nL, about 320 nL, about 325 nL, about 330 nL, about 335 nL, about 340 nL, about 345 nL, about 350 nL, about 355 nL, about 360 nL, about 365 nL, about 370 nL, about 375 nL, about 380 nL, about 385 nL, about 390 nL, about 395 nL, about 400 nL, about 405 nL, about 410 nL, about 415 nL, about 420 nL, about 425 nL, about 430 nL, about 435 nL, about 440 nL, about 445 nL, about 450 nL, about 455 nL, about 460 nL, about 465 nL, about 470 nL, about 475 nL, about 480 nL, about 485 nL, about 490 nL, about 495 nL, about 500 nL, about 505 nL, about 510 nL, about 515 nL, about 520 nL, about 525 nL, about 530 nL, about 535 nL, about 540 nL, about 545 nL, about 550 nL, about 555 nL, about 560 nL, about 565 nL, about 570 nL, about 575 nL, about 580 nL, about 585 nL, about 590 nL, about 595 nL, about 600 nL, about 605 nL, about 610 nL, about 615 nL, about 620 nL, about 625 nL, about 630 nL, about 635 nL, about 640 nL, about 645 nL, about 650 nL, about 655 nL, about 660 nL, about 665 nL, about 670 nL, about 675 nL, about 680 nL, about 685 nL, about 690 nL, about 695 nL, about 700 nL, about 705 nL, about 710 nL, about 715 nL, about 720 nL, about 725 nL, about 730 nL, about 735 nL, about 740 nL, about 745 nL, about 750 nL, about 755 nL, about 760 nL, about 765 nL, about 770 nL, about 775 nL, about 780 nL, about 785 nL, about 790 nL, about 795 nL, about 800 nL, about 805 nL, about 810 nL, about 815 nL, about 820 nL, about 825 nL, about 830 nL, about 835 nL, about 840 nL, about 845 nL, about 850 nL, about 855 nL, about 860 nL, about 865 nL, about 870 nL, about 875 nL, about 880 nL, about 885 nL, about 890 nL, about 895 nL, about 900 nL, about 905 nL, about 910 nL, about 915 nL, about 920 nL, about 925 nL, about 930 nL, about 935 nL, about 940 nL, about 945 nL, about 950 nL, about 955 nL, about 960 nL, about 965 nL, about 970 nL, about 975 nL, about 980 nL, about 985 nL, about 990 nL, about 995 nL, or about 1000 nL).

As used herein, the term "dispense volume" refers to the total amount of liquid dispensed in a single drop and/or in a plurality of drops. In some embodiments, dispense volume may be measured in microliters (μL). In some embodiments, dispense volume may be measured in nanoliters (nL). In some embodiments, dispense volume may be measured in picoliters (pL). In some embodiments, the terms drop size and dispense volume may be used interchangeably.

In some embodiments, the dispense volume may be about 1 pL to about 1000 nL (e.g., about 1 pL to about 50 pL; about 1 pL to about 100 pL; about 1 pL to about 150 pL; about 1 pL to about 200 pL; about 1 pL to about 250 pL; about 1 pL to about 300 pL; about 1 pL to about 350 pL; about 1 pL to about 400 pL; about 1 pL to about 450 pL; about 1 pL to about 500 pL; about 1 pL to about 550 pL; about 1 pL to about 600 pL; about 1 pL to about 650 pL; about 1 pL to about 700 pL; about 1 pL to about 750 pL; about 1 pL to about 800 pL; about 1 pL to about 850 pL; about 1 pL to about 900 pL; about 1 pL to about 950 pL; about 1 pL to about 1000 pL; about 1 nL to about 50 nL; about 1 nL to about 100 nL; about 1 nL to about 150 nL; about 1 nL to about 200 nL; about 1 nL to about 250 nL; about 1 nL to about 300 nL; about 1 nL to about 350 nL; about 1 nL to about 400 nL; about 1 nL to about 450 nL; about 1 nL to about 500 nL; about 1 nL to about 550 nL; about 1 nL to about 600 nL; about 1 nL to about 650 nL; about 1 nL to about 700 nL; about 1 nL to about 750 nL; about 1 nL to about 800 nL; about 1 nL to about 850 nL; about 1 nL to about 900 nL; about 1 nL to about 950 nL; or about 1 nL to about 1000 nL).

In some embodiments, the dispense volume may be about 1 pL to about 1000 pL (e.g., about 1 pL, about 5 pL, about 10 pL, about 15 pL, about 20 pL, about 25 pL, about 30 pL, about 35 pL, about 40 pL, about 45 pL, about 50 pL, about 55 pL, about 60 pL, about 65 pL, about 70 pL, about 75 pL, about 80 pL, about 85 pL, about 90 pL, about 95 pL, about 100 pL, about 105 pL, about 110 pL, about 115 pL, about 120 pL, about 125 pL, about 130 pL, about 135 pL, about 140 pL, about 145 pL, about 150 pL, about 155 pL, about 160 pL, about 165 pL, about 170 pL, about 175 pL, about 180 pL, about 185 pL, about 190 pL, about 195 pL, about 200 pL, about 205 pL, about 210 pL, about 215 pL, about 220 pL, about 225 pL, about 230 pL, about 235 pL, about 240 pL, about 245 pL, about 250 pL, about 255 pL, about 260 pL, about 265 pL, about 270 pL, about 275 pL, about 280 pL, about 285 pL, about 290 pL, about 295 pL, about 300 pL, about 305 pL, about 310 pL, about 315 pL, about 320 pL, about 325 pL, about 330 pL, about 335 pL, about 340 pL, about 345 pL, about 350 pL, about 355 pL, about 360 pL, about 365 pL, about 370 pL, about 375 pL, about 380 pL, about 385 pL, about 390 pL, about 395 pL, about 400 pL, about 405 pL, about 410 pL, about 415 pL, about 420 pL, about 425 pL, about 430 pL, about 435 pL, about 440 pL, about 445 pL, about 450 pL, about 455 pL, about 460 pL, about 465 pL, about 470 pL, about 475 pL, about 480 pL, about 485 pL, about 490 pL, about 495 pL, about 500 pL, about 505 pL, about 510 pL, about 515 pL, about 520 pL, about 525 pL, about 530 pL, about 535 pL, about 540 pL, about 545 pL, about 550 pL, about 555 pL, about 560 pL, about 565 pL, about 570 pL, about 575 pL, about 580 pL, about 585 pL, about 590 pL, about 595 pL, about 600 pL, about 605 pL, about 610 pL, about 615 pL, about 620 pL, about 625 pL, about 630 pL, about 635 pL, about 640 pL, about 645 pL, about 650 pL, about 655 pL, about 660 pL, about 665 pL, about 670 pL, about 675 pL, about 680 pL, about 685 pL, about 690 pL, about 695 pL, about 700 pL, about 705 pL, about 710 pL, about 715 pL, about 720 pL, about 725 pL, about 730 pL, about 735 pL, about 740 pL, about 745 pL, about 750 pL, about 755 pL, about 760 pL, about 765 pL, about 770 pL, about 775 pL, about 780 pL, about 785 pL, about 790 pL, about 795 pL, about 800 pL, about 805 pL, about 810 pL, about 815 pL, about 820 pL, about 825 pL, about 830 pL, about 835 pL, about 840 pL, about 845 pL, about 850 pL, about 855 pL, about 860 pL, about 865 pL, about 870 pL, about 875 pL, about 880 pL, about 885 pL, about 890 pL, about 895 pL, about 900 pL, about 905 pL, about 910 pL, about 915 pL, about 920 pL, about 925 pL, about 930 pL, about 935 pL, about 940 pL, about 945 pL, about 950 pL, about 955 pL, about 960 pL, about 965 pL, about 970 pL, about 975 pL, about 980 pL, about 985 pL, about 990 pL, about 995 pL, or about 1000 pL).

In some embodiments, the dispense volume may be about 1 nL to about 1000 nL (e.g., about 1 nL, about 5 nL, about 10 nL, about 15 nL, about 20 nL, about 25 nL, about 30 nL, about 35 nL, about 40 nL, about 45 nL, about 50 nL, about 55 nL, about 60 nL, about 65 nL, about 70 nL, about 75 nL, about 80 nL, about 85 nL, about 90 nL, about 95 nL, about 100 nL, about 105 nL, about 110 nL, about 115 nL, about 120 nL, about 125 nL, about 130 nL, about 135 nL, about 140 nL, about 145 nL, about 150 nL, about 155 nL, about 160 nL, about 165 nL, about 170 nL, about 175 nL, about 180 nL, about 185 nL, about 190 nL, about 195 nL, about 200 nL, about 205 nL, about 210 nL, about 215 nL, about 220 nL, about 225 nL, about 230 nL, about 235 nL, about 240 nL, about 245 nL, about 250 nL, about 255 nL, about 260 nL, about 265 nL, about 270 nL, about 275 nL, about 280 nL, about 285 nL, about 290 nL, about 295 nL, about 300 nL, about 305 nL, about 310 nL, about 315 nL, about 320 nL, about 325 nL, about 330 nL, about 335 nL, about 340 nL, about 345 nL, about 350 nL, about 355 nL, about 360 nL, about 365 nL, about 370 nL, about 375 nL, about 380 nL, about 385 nL, about 390 nL, about 395 nL, about 400 nL, about 405 nL, about 410 nL, about 415 nL, about 420 nL, about 425 nL, about 430 nL, about 435 nL, about 440 nL, about 445 nL, about 450 nL, about 455 nL, about 460 nL, about 465 nL, about 470 nL, about 475 nL, about 480 nL, about 485 nL, about 490 nL, about 495 nL, about 500 nL, about 505 nL, about 510 nL, about 515 nL, about 520 nL, about 525 nL, about 530 nL, about 535 nL, about 540 nL, about 545 nL, about 550 nL, about 555 nL, about 560 nL, about 565 nL, about 570 nL, about 575 nL, about 580 nL, about 585 nL, about 590 nL, about 595 nL, about 600 nL, about 605 nL, about 610 nL, about 615 nL, about 620 nL, about 625 nL, about 630 nL, about 635 nL, about 640 nL, about 645 nL, about 650 nL, about 655 nL, about 660 nL, about 665 nL, about 670 nL, about 675 nL, about 680 nL, about 685 nL, about 690 nL, about 695 nL, about 700 nL, about 705 nL, about 710 nL, about 715 nL, about 720 nL, about 725 nL, about 730 nL, about 735 nL, about 740 nL, about 745 nL, about 750 nL, about 755 nL, about 760 nL, about 765 nL, about 770 nL, about 775 nL, about 780 nL, about 785 nL, about 790 nL, about 795 nL, about 800 nL, about 805 nL, about 810 nL, about 815 nL, about 820 nL, about 825 nL, about 830 nL, about 835 nL, about 840 nL, about 845 nL, about 850 nL, about 855 nL, about 860 nL, about 865 nL, about 870 nL, about 875 nL, about 880 nL, about 885 nL, about 890 nL, about 895 nL, about 900 nL, about 905 nL, about 910 nL, about 915 nL, about 920 nL, about 925 nL, about 930 nL, about 935 nL, about 940 nL, about 945 nL, about 950 nL, about 955 nL, about 960 nL, about 965 nL, about 970 nL, about 975 nL, about 980 nL, about 985 nL, about 990 nL, about 995 nL, or about 1000 nL).

In some embodiments, the dispensable formulation can be characterized by a fluid property that enhances the mechanical properties of a microneedle and/or microneedle tip consolidation. Such fluid properties can also be referred to as "printability parameters" and can be selected from the group consisting of viscosity, surface tension, density, solids content, and combinations thereof.

In some embodiments, a dispensable formulation, and/or the microneedle and/or MAP formed from the dispensable formulation, can be characterized by a process parameter for the dispense system that can be adjusted to enhance the mechanical and/or morphological properties of a microneedle and/or microneedle, such as tip consolidation. Such process parameters may also be referred to as "process inputs" or "process outputs." In some embodiments, "process inputs" can be selected from the group consisting of temperature, humidity, and combinations thereof, and may be related to the environmental conditions present and/or the equipment settings utilized during microneedle and/or MAP manufacturing. In some embodiments, "process outputs" can be selected from the group consisting of dispense volume, dispense velocity, and combinations thereof. In some embodiments, the dispensable formulation can be characterized by a fluid property that can be adjusted to improve manufacturing precision, quality, efficiency and/or yield. In some embodiments, the dispensable formulation can be characterized by a fluid property that can be adjusted to improve formability of the microneedle and/or the microarray patch (MAP). In some embodiments, the dispensable formulation can be characterized by a fluid property that can be adjusted to improve a structural property of the microneedle and/or the microarray patch (MAP). In some embodiments, the dispensable formulation can be characterized by a fluid property that can be adjusted to enhance the deployability of the microneedle and/or the microarray patch (MAP).

Viscosity

In some embodiments, in the context of manufacturing a microneedle and/or a microarray patch (MAP), a dispensable formulation (e.g., a tip formulation and/or a base formulation), comprising at least one selected from the group consisting of an active pharmaceutical ingredient (API), a water-soluble excipient, and combinations thereof, can be characterized by a viscosity of about 1 cP to about 1750 cP (e.g., about 1 cP, about 25 cP, about 50 cP, about 75 cP, about 100 cP, about 125 cP, about 150 cP, about 175 cP, about 200 cP, about 225 cP, about 250 cP, about 275 cP, about 300 cP, about 325 cP, about 350 cP, about 375 cP, about 400 cP, about 425 cP, about 450 cP, about 475 cP, about 500 cP, about 525 cP, about 550 cP, about 575 cP, about 600 cP, about 625 cP, about 650 cP, about 675 cP, about 700 cP, about 725 cP, about 750 cP, about 775 cP, about 800 cP, about 825 cP, about 850 cP, about 875 cP, about 900 cP, about 925 cP, about 950 cP, about 975 cP, about 1000 cP, about 1025 cP, about 1050 cP, about 1075 cP, about 1100 cP, about 1125 cP, about 1150 cP, about 1175 cP, about 1200 cP, about 1225 cP, about 1250 cP, about 1275 cP, about 1300 cP, about 1325 cP, about 1350 cP, about 1375 cP, about 1400 cP, about 1425 cP, about 1450 cP, about 1475 cP, about 1500 cP, about 1525 cP, about 1550 cP, about 1575 cP, about 1600 cP, about 1625 cP, about 1650 cP, about 1675 cP, about 1700 cP, about 1725 cP, or about 1750 cP).

In some embodiments, a dispensable tip formulation, e.g., comprising an API and a water-soluble excipient, can be characterized by a viscosity of about 1 cP to about 1750 cP (e.g., about 1 cP, about 25 cP, about 50 cP, about 75 cP, about 100 cP, about 125 cP, about 150 cP, about 175 cP, about 200 cP, about 225 cP, about 250 cP, about 275 cP, about 300 cP, about 325 cP, about 350 cP, about 375 cP, about 400 cP, about 425 cP, about 450 cP, about 475 cP, about 500 cP, about 525 cP, about 550 cP, about 575 cP, about 600 cP, about 625 cP, about 650 cP, about 675 cP, about 700 cP, about 725 cP, about 750 cP, about 775 cP, about 800 cP, about 825 cP, about 850 cP, about 875 cP, about 900 cP, about 925 cP, about 950 cP, about 975 cP, about 1000 cP, about 1025 cP, about 1050 cP, about 1075 cP, about 1100 cP, about 1125 cP, about 1150 cP, about 1175 cP, about 1200 cP, about 1225 cP, about 1250 cP, about 1275 cP, about 1300 cP, about 1325 cP, about 1350 cP, about 1375 cP, about 1400 cP, about 1425 cP, about 1450 cP, about 1475 cP, about 1500 cP, about 1525 cP, about 1550 cP, about 1575 cP, about 1600 cP, about 1625 cP, about 1650 cP, about 1675 cP, about 1700 cP, about 1725 cP, or about 1750 cP).

In some embodiments, a dispensable base formulation, e.g., comprising a water-soluble excipient, can be characterized by a viscosity of about 1 cP to about 1750 cP (e.g., about 1 cP, about 25 cP, about 50 cP, about 75 cP, about 100 cP, about 125 cP, about 150 cP, about 175 cP, about 200 cP, about 225 cP, about 250 cP, about 275 cP, about 300 cP, about 325 cP, about 350 cP, about 375 cP, about 400 cP, about 425 cP, about 450 cP, about 475 cP, about 500 cP, about 525 cP, about 550 cP, about 575 cP, about 600 cP, about 625 cP, about 650 cP, about 675 cP, about 700 cP, about 725 cP, about 750 cP, about 775 cP, about 800 cP, about 825 cP, about 850 cP, about 875 cP, about 900 cP, about 925 cP, about 950 cP, about 975 cP, about 1000 cP, about 1025 cP, about 1050 cP, about 1075 cP, about 1100 cP, about 1125 cP, about 1150 cP, about 1175 cP, about 1200 cP, about 1225 cP, about 1250 cP, about 1275 cP, about 1300 cP, about 1325 cP, about 1350 cP, about 1375 cP, about 1400 cP, about 1425 cP, about 1450 cP, about 1475 cP, about 1500 cP, about 1525 cP, about 1550 cP, about 1575 cP, about 1600 cP, about 1625 cP, about 1650 cP, about 1675 cP, about 1700 cP, about 1725 cP, or about 1750 cP).

In some embodiments, in the context of manufacturing a microneedle and/or a microarray patch (MAP), a dispensable formulation (e.g., a tip formulation and/or a base formulation), comprising at least one selected from the group consisting of an active pharmaceutical ingredient (API), a water-soluble excipient, and combinations thereof, can be characterized by a viscosity of about 1 cP to about 10 cP (e.g., about 1 cP, about 1.25 cP, about 1.5 cP, about 1.75 cP, about 2 cP, about 2.25 cP, about 2.5 cP, about 2.75 cP, about 3 cP, about 3.25 cP, about 3.5 cP, about 3.75 cP, about 4 cP, about 4.25 cP, about 4.5 cP, about 4.75 cP, about 5 cP, about 5.25 cP, about 5.5 cP, about 5.75 cP, about 6 cP, about 6.25 cP, about 6.5 cP, about 6.75 cP, about 7 cP, about 7.25 cP, about 7.5 cP, about 7.75 cP, about 8 cP, about 8.25 cP, about 8.5 cP, about 8.75 cP, about 9 cP, about 9.25 cP, about 9.5 cP, about 9.75 cP, or about 10 cP).

In some embodiments, a dispensable tip formulation, e.g., comprising an API and a water-soluble excipient, can be characterized by a viscosity of about 1 cP to about 10 cP (e.g., about 1 cP, about 1.25 cP, about 1.5 cP, about 1.75 cP, about 2 cP, about 2.25 cP, about 2.5 cP, about 2.75 cP, about 3 cP, about 3.25 cP, about 3.5 cP, about 3.75 cP, about 4 cP, about 4.25 cP, about 4.5 cP, about 4.75 cP, about 5 cP, about 5.25 cP, about 5.5 cP, about 5.75 cP, about 6 cP, about 6.25 cP, about 6.5 cP, about 6.75 cP, about 7 cP, about 7.25 cP, about 7.5 cP, about 7.75 cP, about 8 cP, about 8.25 cP, about 8.5 cP, about 8.75 cP, about 9 cP, about 9.25 cP, about 9.5 cP, about 9.75 cP, or about 10 cP).

In some embodiments, a dispensable base formulation, e.g., comprising a water-soluble excipient, can be characterized by a viscosity of about 1 cP to about 10 cP (e.g., about 1 cP, about 1.25 cP, about 1.5 cP, about 1.75 cP, about 2 cP, about 2.25 cP, about 2.5 cP, about 2.75 cP, about 3 cP, about 3.25 cP, about 3.5 cP, about 3.75 cP, about 4 cP, about 4.25 cP, about 4.5 cP, about 4.75 cP, about 5 cP, about 5.25 cP, about 5.5 cP, about 5.75 cP, about 6 cP, about 6.25 cP, about 6.5 cP, about 6.75 cP, about 7 cP, about 7.25 cP, about 7.5 cP, about 7.75 cP, about 8 cP, about 8.25 cP, about 8.5 cP, about 8.75 cP, about 9 cP, about 9.25 cP, about 9.5 cP, about 9.75 cP, or about 10 cP).

In some embodiments, in the context of manufacturing a microneedle and/or a microarray patch (MAP), a dispensable formulation (e.g., a tip formulation and/or a base formulation), comprising at least one selected from the group consisting of an active pharmaceutical ingredient (API), a water-soluble excipient, and combinations thereof, can be characterized by a viscosity of about 1 cP to about 100 cP (e.g., about 1 cP, about 2 cP, about 3 cP, about 4 cP, about 5 cP, about 6 cP, about 7 cP, about 8 cP, about 9 cP, about 10 cP, about 11 cP, about 12 cP, about 13 cP, about 14 cP, about 15 cP, about 16 cP, about 17 cP, about 18 cP, about 19 cP, about 20 cP, about 21 cP, about 22 cP, about 23 cP, about 24 cP, about 25 cP, about 26 cP, about 27 cP, about 28 cP, about 29 cP, about 30 cP, about 31 cP, about 32 cP, about 33 cP, about 34 cP, about 35 cP, about 36 cP, about 37 cP, about 38 cP, about 39 cP, about 40 cP, about 41 cP, about 42 cP, about 43 cP, about 44 cP, about 45 cP, about 46 cP, about 47 cP, about 48 cP, about 49 cP, about 50 cP, about 51 cP, about 52 cP, about 53 cP, about 54 cP, about 55 cP, about 56 cP, about 57 cP, about 58 cP, about 59 cP, about 60 cP, about 61 cP, about 62 cP, about 63 cP, about 64 cP, about 65 cP, about 66 cP, about 67 cP, about 68 cP, about 69 cP, about 70 cP, about 71 cP, about 72 cP, about 73 cP, about 74 cP, about 75 cP, about 76 cP, about 77 cP, about 78 cP, about 79 cP, about 80 cP, about 81 cP, about 82 cP, about 83 cP, about 84 cP, about 85 cP, about 86 cP, about 87 cP, about 88 cP, about 89 cP, about 90 cP, about 91 cP, about 92 cP, about 93 cP, about 94 cP, about 95 cP, about 96 cP, about 97 cP, about 98 cP, about 99 cP, or about 100 cP).

In some embodiments, a dispensable tip formulation, e.g., comprising an API and a water-soluble excipient, can be characterized by a viscosity of about 1 cP to about 100 cP (e.g., about 1 cP, about 2 cP, about 3 cP, about 4 cP, about 5 cP, about 6 cP, about 7 cP, about 8 cP, about 9 cP, about 10 cP, about 11 cP, about 12 cP, about 13 cP, about 14 cP, about 15 cP, about 16 cP, about 17 cP, about 18 cP, about 19 cP, about 20 cP, about 21 cP, about 22 cP, about 23 cP, about 24 cP, about 25 cP, about 26 cP, about 27 cP, about 28 cP, about 29 cP, about 30 cP, about 31 cP, about 32 cP, about 33 cP, about 34 cP, about 35 cP, about 36 cP, about 37 cP, about 38 cP, about 39 cP, about 40 cP, about 41 cP, about 42 cP, about 43 cP, about 44 cP, about 45 cP, about 46 cP, about 47 cP, about 48 cP, about 49 cP, about 50 cP, about 51 cP, about 52 cP, about 53 cP, about 54 cP, about 55 cP, about 56 cP, about 57 cP, about 58 cP, about 59 cP, about 60 cP, about 61 cP, about 62 cP, about 63 cP, about 64 cP, about 65 cP, about 66 cP, about 67 cP, about 68 cP, about 69 cP, about 70 cP, about 71 cP, about 72 cP, about 73 cP, about 74 cP, about 75 cP, about 76 cP, about 77 cP, about 78 cP, about 79 cP, about 80 cP, about 81 cP, about 82 cP, about 83 cP, about 84 cP, about 85 cP, about 86 cP, about 87 cP, about 88 cP, about 89 cP, about 90 cP, about 91 cP, about 92 cP, about 93 cP, about 94 cP, about 95 cP, about 96 cP, about 97 cP, about 98 cP, about 99 cP, or about 100 cP).

In some embodiments, a dispensable base formulation, e.g., comprising a water-soluble excipient, can be characterized by a viscosity of about 1 cP to about 100 cP (e.g., about 1 cP, about 2 cP, about 3 cP, about 4 cP, about 5 cP, about 6 cP, about 7 cP, about 8 cP, about 9 cP, about 10 cP, about 11 cP, about 12 cP, about 13 cP, about 14 cP, about 15 cP, about 16 cP, about 17 cP, about 18 cP, about 19 cP, about 20 cP, about 21 cP, about 22 cP, about 23 cP, about 24 cP, about 25 cP, about 26 cP, about 27 cP, about 28 cP, about 29 cP, about 30 cP, about 31 cP, about 32 cP, about 33 cP, about 34 cP, about 35 cP, about 36 cP, about 37 cP, about 38 cP, about 39 cP, about 40 cP, about 41 cP, about 42 cP, about 43 cP, about 44 cP, about 45 cP, about 46 cP, about 47 cP, about 48 cP, about 49 cP, about 50 cP, about 51 cP, about 52 cP, about 53 cP, about 54 cP, about 55 cP, about 56 cP, about 57 cP, about 58 cP, about 59 cP, about 60 cP, about 61 cP, about 62 cP, about 63 cP, about 64 cP, about 65 cP, about 66 cP, about 67 cP, about 68 cP, about 69 cP, about 70 cP, about 71 cP, about 72 cP, about 73 cP, about 74 cP, about 75 cP, about 76 cP, about 77 cP, about 78 cP, about 79 cP, about 80 cP, about 81 cP, about 82 cP, about 83 cP, about 84 cP, about 85 cP, about 86 cP, about 87 cP, about 88 cP, about 89 cP, about 90 cP, about 91 cP, about 92 cP, about 93 cP, about 94 cP, about 95 cP, about 96 cP, about 97 cP, about 98 cP, about 99 cP, or about 100 cP).

In some embodiments, in the context of manufacturing a microneedle and/or a microarray patch (MAP), a dispensable formulation (e.g., a tip formulation and/or a base formulation), comprising at least one selected from the group consisting of an active pharmaceutical ingredient (API), a water-soluble excipient, and combinations thereof, can be characterized by a viscosity of about 100 cP to about 1500 cP (e.g., about 100 cP, about 110 cP, about 120 cP, about 130 cP, about 140 cP, about 150 cP, about 160 cP, about 170 cP, about 180 cP, about 190 cP, about 200 cP, about 210 cP, about 220 cP, about 230 cP, about 240 cP, about 250 cP, about 260 cP, about 270 cP, about 280 cP, about 290 cP, about 300 cP, about 310 cP, about 320 cP, about 330 cP, about 340 cP, about 350 cP, about 360 cP, about 370 cP, about 380 cP, about 390 cP, about 400 cP, about 410 cP, about 420 cP, about 430 cP, about 440 cP, about 450 cP, about 460 cP, about 470 cP, about 480 cP, about 490 cP, about 500 cP, about 510 cP, about 520 cP, about 530 cP, about 540 cP, about 550 cP, about 560 cP, about 570 cP, about 580 cP, about 590 cP, about 600 cP, about 610 cP, about 620 cP, about 630 cP, about 640 cP, about 650 cP, about 660 cP, about 670 cP, about 680 cP, about 690 cP, about 700 cP, about 710 cP, about 720 cP, about 730 cP, about 740 cP, about 750 cP, about 760 cP, about 770 cP, about 780 cP, about 790 cP, about 800 cP, about 810 cP, about 820 cP, about 830 cP, about 840 cP, about 850 cP, about 860 cP, about 870 cP, about 880 cP, about 890 cP, about 900 cP, about 910 cP, about 920 cP, about 930 cP, about 940 cP, about 950 cP, about 960 cP, about 970 cP, about 980 cP, about 990 cP, about 1000 cP, about 1010 cP, about 1020 cP, about 1030 cP, about 1040 cP, about 1050 cP, about 1060 cP, about 1070 cP, about 1080 cP, about 1090 cP, about 1100 cP, about 1110 cP, about 1120 cP, about 1130 cP, about 1140 cP, about 1150 cP, about 1160 cP, about 1170 cP, about 1180 cP, about 1190 cP, about 1200 cP, about 1210 cP, about 1220 cP, about 1230 cP, about 1240 cP, about 1250 cP, about 1260 cP, about 1270 cP, about 1280 cP, about 1290 cP, about 1300 cP, about 1310 cP, about 1320 cP, about 1330 cP, about 1340 cP, about 1350 cP, about 1360 cP, about 1370 cP, about 1380 cP, about 1390 cP, about 1400 cP, about 1410 cP, about 1420 cP, about 1430 cP, about 1440 cP, about 1450 cP, about 1460 cP, about 1470 cP, about 1480 cP, about 1490 cP, or about 1500 cP).

about 570 cP, about 580 cP, about 590 cP, about 600 cP, about 610 cP, about 620 cP, about 630 cP, about 640 cP, about 650 cP, about 660 cP, about 670 cP, about 680 cP, about 690 cP, about 700 cP, about 710 cP, about 720 cP, about 730 cP, about 740 cP, about 750 cP, about 760 cP, about 770 cP, about 780 cP, about 790 cP, about 800 cP, about 810 cP, about 820 cP, about 830 cP, about 840 cP, about 850 cP, about 860 cP, about 870 cP, about 880 cP, about 890 cP, about 900 cP, about 910 cP, about 920 cP, about 930 cP, about 940 cP, about 950 cP, about 960 cP, about 970 cP, about 980 cP, about 990 cP, about 1000 cP, about 1010 cP, about 1020 cP, about 1030 cP, about 1040 cP, about 1050 cP, about 1060 cP, about 1070 cP, about 1080 cP, about 1090 cP, about 1100 cP, about 1110 cP, about 1120 cP, about 1130 cP, about 1140 cP, about 1150 cP, about 1160 cP, about 1170 cP, about 1180 cP, about 1190 cP, about 1200 cP, about 1210 cP, about 1220 cP, about 1230 cP, about 1240 cP, about 1250 cP, about 1260 cP, about 1270 cP, about 1280 cP, about 1290 cP, about 1300 cP, about 1310 cP, about 1320 cP, about 1330 cP, about 1340 cP, about 1350 cP, about 1360 cP, about 1370 cP, about 1380 cP, about 1390 cP, about 1400 cP, about 1410 cP, about 1420 cP, about 1430 cP, about 1440 cP, about 1450 cP, about 1460 cP, about 1470 cP, about 1480 cP, about 1490 cP, or about 1500 cP).

In some embodiments, a dispensable tip formulation, e.g., comprising an API and a water-soluble excipient, can be characterized by a viscosity of about 100 cP to about 1500 cP (e.g., about 100 cP, about 110 cP, about 120 cP, about 130 cP, about 140 cP, about 150 cP, about 160 cP, about 170 cP, about 180 cP, about 190 cP, about 200 cP, about 210 cP, about 220 cP, about 230 cP, about 240 cP, about 250 cP, about 260 cP, about 270 cP, about 280 cP, about 290 cP, about 300 cP, about 310 cP, about 320 cP, about 330 cP, about 340 cP, about 350 cP, about 360 cP, about 370 cP, about 380 cP, about 390 cP, about 400 cP, about 410 cP, about 420 cP, about 430 cP, about 440 cP, about 450 cP, about 460 cP, about 470 cP, about 480 cP, about 490 cP, about 500 cP, about 510 cP, about 520 cP, about 530 cP, about 540 cP, about 550 cP, about 560 cP, about 570 cP, about 580 cP, about 590 cP, about 600 cP, about 610 cP, about 620 cP, about 630 cP, about 640 cP, about 650 cP, about 660 cP, about 670 cP, about 680 cP, about 690 cP, about 700 cP, about 710 cP, about 720 cP, about 730 cP, about 740 cP, about 750 cP, about 760 cP, about 770 cP, about 780 cP, about 790 cP, about 800 cP, about 810 cP, about 820 cP, about 830 cP, about 840 cP, about 850 cP, about 860 cP, about 870 cP, about 880 cP, about 890 cP, about 900 cP, about 910 cP, about 920 cP, about 930 cP, about 940 cP, about 950 cP, about 960 cP, about 970 cP, about 980 cP, about 990 cP, about 1000 cP, about 1010 cP, about 1020 cP, about 1030 cP, about 1040 cP, about 1050 cP, about 1060 cP, about 1070 cP, about 1080 cP, about 1090 cP, about 1100 cP, about 1110 cP, about 1120 cP, about 1130 cP, about 1140 cP, about 1150 cP, about 1160 cP, about 1170 cP, about 1180 cP, about 1190 cP, about 1200 cP, about 1210 cP, about 1220 cP, about 1230 cP, about 1240 cP, about 1250 cP, about 1260 cP, about 1270 cP, about 1280 cP, about 1290 cP, about 1300 cP, about 1310 cP, about 1320 cP, about 1330 cP, about 1340 cP, about 1350 cP, about 1360 cP, about 1370 cP, about 1380 cP, about 1390 cP, about 1400 cP, about 1410 cP, about 1420 cP, about 1430 cP, about 1440 cP, about 1450 cP, about 1460 cP, about 1470 cP, about 1480 cP, about 1490 cP, or about 1500 cP).

In some embodiments, a dispensable base formulation, e.g., comprising a water-soluble excipient, can be characterized by a viscosity of about 100 cP to about 1500 cP (e.g., about 100 cP, about 110 cP, about 120 cP, about 130 cP, about 140 cP, about 150 cP, about 160 cP, about 170 cP, about 180 cP, about 190 cP, about 200 cP, about 210 cP, about 220 cP, about 230 cP, about 240 cP, about 250 cP, about 260 cP, about 270 cP, about 280 cP, about 290 cP, about 300 cP, about 310 cP, about 320 cP, about 330 cP, about 340 cP, about 350 cP, about 360 cP, about 370 cP, about 380 cP, about 390 cP, about 400 cP, about 410 cP, about 420 cP, about 430 cP, about 440 cP, about 450 cP, about 460 cP, about 470 cP, about 480 cP, about 490 cP, about 500 cP, about 510 cP, about 520 cP, about 530 cP, about 540 cP, about 550 cP, about 560 cP, about 570 cP, about 580 cP, about 590 cP, about 600 cP, about 610 cP, about 620 cP, about 630 cP, about 640 cP, about 650 cP, about 660 cP, about 670 cP, about 680 cP, about 690 cP, about 700 cP, about 710 cP, about 720 cP, about 730 cP, about 740 cP, about 750 cP, about 760 cP, about 770 cP, about 780 cP, about 790 cP, about 800 cP, about 810 cP, about 820 cP, about 830 cP, about 840 cP, about 850 cP, about 860 cP, about 870 cP, about 880 cP, about 890 cP, about 900 cP, about 910 cP, about 920 cP, about 930 cP, about 940 cP, about 950 cP, about 960 cP, about 970 cP, about 980 cP, about 990 cP, about 1000 cP, about 1010 cP, about 1020 cP, about 1030 cP, about 1040 cP, about 1050 cP, about 1060 cP, about 1070 cP, about 1080 cP, about 1090 cP, about 1100 cP, about 1110 cP, about 1120 cP, about 1130 cP, about 1140 cP, about 1150 cP, about 1160 cP, about 1170 cP, about 1180 cP, about 1190 cP, about 1200 cP, about 1210 cP, about 1220 cP, about 1230 cP, about 1240 cP, about 1250 cP, about 1260 cP, about 1270 cP, about 1280 cP, about 1290 cP, about 1300 cP, about 1310 cP, about 1320 cP, about 1330 cP, about 1340 cP, about 1350 cP, about 1360 cP, about 1370 cP, about 1380 cP, about 1390 cP, about 1400 cP, about 1410 cP, about 1420 cP, about 1430 cP, about 1440 cP, about 1450 cP, about 1460 cP, about 1470 cP, about 1480 cP, about 1490 cP, or about 1500 cP).

Surface Tension

In some embodiments, in the context of manufacturing a microneedle and/or a microarray patch (MAP), a dispensable formulation (e.g., a tip formulation and/or a base formulation), comprising at least one selected from the group consisting of an active pharmaceutical ingredient (API), a water-soluble excipient, and combinations thereof, can be characterized by a surface tension of less than about 75 mN/m (e.g., less than about 5 mN/m, less than about 10 mN/m, less than about 15 mN/m, less than about 20 mN/m, less than about 25 mN/m, less than about 30 mN/m, less than about 35 mN/m, less than about 40 mN/m, less than about 45 mN/m, less than about 50 mN/m, less than about 55 mN/m, less than about 60 mN/m, less than about 65 mN/m, less than about 70 mN/m, or less than about 75 mN/m).

In some embodiments, a dispensable tip formulation, e.g., comprising an API and a water-soluble excipient, can be characterized by a surface tension of less than about 75 mN/m (e.g., less than about 5 mN/m, less than about 10 mN/m, less than about 15 mN/m, less than about 20 mN/m, less than about 25 mN/m, less than about 30 mN/m, less than about 35 mN/m, less than about 40 mN/m, less than about 45 mN/m, less than about 50 mN/m, less than about 55 mN/m, less than about 60 mN/m, less than about 65 mN/m, less than about 70 mN/m, or less than about 75 mN/m).

In some embodiments, a dispensable base formulation, e.g., comprising a water-soluble excipient, can be characterized by a surface tension of less than about 75 mN/m (e.g., less than about 5 mN/m, less than about 10 mN/m, less than about 15 mN/m, less than about 20 mN/m, less than about 25 mN/m, less than about 30 mN/m, less than about 35 mN/m, less than about 40 mN/m, less than about 45 mN/m, less than about 50 mN/m, less than about 55 mN/m, less than about 60 mN/m, less than about 65 mN/m, less than about 70 mN/m, or less than about 75 mN/m).

In some embodiments, in the context of manufacturing a microneedle and/or a microarray patch (MAP), a dispensable formulation (e.g., a tip formulation and/or a base formulation), comprising at least one selected from the group consisting of an active pharmaceutical ingredient (API), a water-soluble excipient, and combinations thereof, can be characterized by a surface tension of about 1 mN/m to about 75 mN/m (e.g., about 1 mN/m, about 2 mN/m, about 3 mN/m, about 4 mN/m, about 5 mN/m, about 6 mN/m, about 7 mN/m, about 8 mN/m, about 9 mN/m, about 10 mN/m, about 11 mN/m, about 12 mN/m, about 13, mN/m, about 14 mN/m, about 15 mN/m, about 16 mN/m, about 17 mN/m, about 18 mN/m, about 19 mN/m, about 20 mN/m, about 21 mN/m, about 22 mN/m, about 23 mN/m, about 24 mN/m, about 25 mN/m, about 26 mN/m, about 27 mN/m, about 28 mN/m, about 29 mN/m, about 30 mN/m, about 31 mN/m, about 32 mN/m, about 33 mN/m, about 34 mN/m, about 35 mN/m, about 36 mN/m, about 37 mN/m, about 38 mN/m, about 39 mN/m, about 40 mN/m, about 41 mN/m, about 42 mN/m, about 43 mN/m, about 44 mN/m, about 45 mN/m, about 46 mN/m, about 47 mN/m, about 48 mN/m, about 49 mN/m, about 50 mN/m, about 51 mN/m, about 52 mN/m, about 53 mN/m, about 54 mN/m, about 55 mN/m, about 56 mN/m, about 57 mN/m, about 58 mN/m, about 59 mN/m, about 60 mN/m, about 61 mN/m, about 62 mN/m, about 63 mN/m, about 64 mN/m, about 65 mN/m, about 66 mN/m, about 67 mN/m, about 68 mN/m, about 69 mN/m, about 70 mN/m, about 71 mN/m, about 72 mN/m, about 73 mN/m, about 74 mN/m, or about 75 mN/m).

In some embodiments, a dispensable tip formulation, e.g., comprising an API and a water-soluble excipient, can be characterized by a surface tension of about 1 mN/m to about 75 mN/m (e.g., about 1 mN/m, about 2 mN/m, about 3 mN/m, about 4 mN/m, about 5 mN/m, about 6 mN/m, about 7 mN/m, about 8 mN/m, about 9 mN/m, about 10 mN/m, about 11 mN/m, about 12 mN/m, about 13 mN/m, about 14 mN/m, about 15 mN/m, about 16 mN/m, about 17 mN/m, about 18 mN/m, about 19 mN/m, about 20 mN/m, about 21 mN/m, about 22 mN/m, about 23 mN/m, about 24 mN/m, about 25 mN/m, about 26 mN/m, about 27 mN/m, about 28 mN/m, about 29 mN/m, about 30 mN/m, about 31 mN/m, about 32 mN/m, about 33 mN/m, about 34 mN/m, about 35 mN/m, about 36 mN/m, about 37 mN/m, about 38 mN/m, about 39 mN/m, about 40 mN/m, about 41 mN/m, about 42 mN/m, about 43 mN/m, about 44 mN/m, about 45 mN/m, about 46 mN/m, about 47 mN/m, about 48 mN/m, about 49 mN/m, about 50 mN/m, about 51 mN/m, about 52 mN/m, about 53 mN/m, about 54 mN/m, about 55 mN/m, about 56 mN/m, about 57 mN/m, about 58 mN/m, about 59 mN/m, about 60 mN/m, about 61 mN/m, about 62 mN/m, about 63 mN/m, about 64 mN/m, about 65 mN/m, about 66 mN/m, about 67 mN/m, about 68 mN/m, about 69 mN/m, about 70 mN/m, about 71 mN/m, about 72 mN/m, about 73 mN/m, about 74 mN/m, or about 75 mN/m).

In some embodiments, a dispensable base formulation, e.g., comprising a water-soluble excipient, can be characterized by a surface tension of about 1 mN/m to about 75 mN/m (e.g., about 1 mN/m, about 2 mN/m, about 3 mN/m, about 4 mN/m, about 5 mN/m, about 6 mN/m, about 7 mN/m, about 8 mN/m, about 9 mN/m, about 10 mN/m, about 11 mN/m, about 12 mN/m, about 13 mN/m, about 14 mN/m, about 15 mN/m, about 16 mN/m, about 17 mN/m, about 18 mN/m, about 19 mN/m, about 20 mN/m, about 21 mN/m, about 22 mN/m, about 23 mN/m, about 24 mN/m, about 25 mN/m, about 26 mN/m, about 27 mN/m, about 28 mN/m, about 29 mN/m, about 30 mN/m, about 31 mN/m, about 32 mN/m, about 33 mN/m, about 34 mN/m, about 35 mN/m, about 36 mN/m, about 37 mN/m, about 38 mN/m, about 39 mN/m, about 40 mN/m, about 41 mN/m, about 42 mN/m, about 43 mN/m, about 44 mN/m, about 45 mN/m, about 46 mN/m, about 47 mN/m, about 48 mN/m, about 49 mN/m, about 50 mN/m, about 51 mN/m, about 52 mN/m, about 53 mN/m, about 54 mN/m, about 55 mN/m, about 56 mN/m, about 57 mN/m, about 58 mN/m, about 59 mN/m, about 60 mN/m, about 61 mN/m, about 62 mN/m, about 63 mN/m, about 64 mN/m, about 65 mN/m, about 66 mN/m, about 67 mN/m, about 68 mN/m, about 69 mN/m, about 70 mN/m, about 71 mN/m, about 72 mN/m, about 73 mN/m, about 74 mN/m, or about 75 mN/m).

Density

In some embodiments, in the context of manufacturing a microneedle and/or a microarray patch (MAP), a dispensable formulation (e.g., a tip formulation and/or a base formulation), comprising at least one selected from the group consisting of an active pharmaceutical ingredient (API), a water-soluble excipient, and combinations thereof, can be characterized by a density of about 0.5 g/mL to about 1.5 g/mL (e.g., about 0.5 g/mL, about 0.55 g/mL, about 0.6 g/mL, about 0.65 g/mL, about 0.7 g/mL, about 0.75 g/mL, about 0.8 g/mL, about 0.85 g/mL, about 0.9 g/mL, about 0.95 g/mL, about 1 g/mL, about 1.05 g/mL, about 1.1 g/mL, about 1.15 g/mL, about 1.2 g/mL, about 1.25 g/mL, about 1.3 g/mL, about 1.35 g/mL, about 1.4 g/mL, about 1.45 g/mL, or about 1.5 g/mL).

In some embodiments, a dispensable tip formulation, e.g., comprising an API and a water-soluble excipient, can be characterized by a density of about 0.5 g/mL to about 1.5 g/mL (e.g., about 0.5 g/mL, about 0.55 g/mL, about 0.6 g/mL, about 0.65 g/mL, about 0.7 g/mL, about 0.75 g/mL, about 0.8 g/mL, about 0.85 g/mL, about 0.9 g/mL, about 0.95 g/mL, about 1 g/mL, about 1.05 g/mL, about 1.1 g/mL, about 1.15 g/mL, about 1.2 g/mL, about 1.25 g/mL, about 1.3 g/mL, about 1.35 g/mL, about 1.4 g/mL, about 1.45 g/mL, or about 1.5 g/mL).

In some embodiments, a dispensable base formulation, e.g., comprising a water-soluble excipient, can be characterized by a density of about 0.5 g/mL to about 1.5 g/mL (e.g., about 0.5 g/mL, about 0.55 g/mL, about 0.6 g/mL, about 0.65 g/mL, about 0.7 g/mL, about 0.75 g/mL, about 0.8 g/mL, about 0.85 g/mL, about 0.9 g/mL, about 0.95 g/mL, about 1 g/mL, about 1.05 g/mL, about 1.1 g/mL, about 1.15 g/mL, about 1.2 g/mL, about 1.25 g/mL, about 1.3 g/mL, about 1.35 g/mL, about 1.4 g/mL, about 1.45 g/mL, or about 1.5 g/mL).

In some embodiments, in the context of manufacturing a microneedle and/or a microarray patch (MAP), a dispensable formulation (e.g., a tip formulation and/or a base formulation), comprising at least one selected from the group consisting of an active pharmaceutical ingredient (API), a water-soluble excipient, and combinations thereof, can be characterized by a density of about 1 g/mL to about 1.1 g/mL (e.g., about 1 g/mL, about 1.01 g/mL, about 1.02 g/mL, about 1.03 g/mL, about 1.04 g/mL, about 1.05 g/mL, about 1.06 g/mL, about 1.07 g/mL, about 1.08 g/mL, about 1.09 g/mL, or about 1.1 g/mL).

In some embodiments, a dispensable tip formulation, e.g., comprising an API and a water-soluble excipient, can be characterized by a density of about 1 g/mL to about 1.1 g/mL (e.g., about 1 g/mL, about 1.01 g/mL, about 1.02 g/mL, about 1.03 g/mL, about 1.04 g/mL, about 1.05 g/mL, about 1.06 g/mL, about 1.07 g/mL, about 1.08 g/mL, about 1.09 g/mL, or about 1.1 g/mL).

In some embodiments, a dispensable base formulation, e.g., comprising a water-soluble excipient, can be characterized by a density of about 1 g/mL to about 1.1 g/mL (e.g., about 1 g/mL, about 1.01 g/mL, about 1.02 g/mL, about 1.03 g/mL, about 1.04 g/mL, about 1.05 g/mL, about 1.06 g/mL, about 1.07 g/mL, about 1.08 g/mL, about 1.09 g/mL, or about 1.1 g/mL).

Solids Content

In some embodiments, in the context of manufacturing a microneedle and/or a microarray patch (MAP), a dispensable formulation (e.g., a tip formulation and/or a base formulation), comprising at least one selected from the group consisting of an active pharmaceutical ingredient (API), a water-soluble excipient, and combinations thereof, can be characterized by a solid content of about 1% to about 75% (e.g., about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, or about 75%).

In some embodiments, a dispensable tip formulation, e.g., comprising an API and a water-soluble excipient, can be characterized by a solid content of about 1% to about 75% (e.g., about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, or about 75%).

In some embodiments, a dispensable base formulation, e.g., comprising a water-soluble excipient, can be characterized by a solid content of about 1% to about 75% (e.g., about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, or about 75%).

Microneedles and Microarray Patches (MAPs)

According to one aspect, the disclosure provides a microneedle and/or a microarray patch (MAP), e.g., comprising an active pharmaceutical ingredient (API) and a water soluble excipient. In one aspect, the disclosure provides a microneedle, comprising an active pharmaceutical ingredient (API) and a water soluble excipient. In one aspect, the disclosure provides a microarray patch (MAP), comprising an active pharmaceutical ingredient (API) and a water soluble excipient. In some embodiments, the microneedles and/or microarray patches (MAPs), e.g., comprising an active pharmaceutical ingredient (API) and a water soluble excipient, can be configured and utilized to provide consistent dosing, extended shelf stability, therapeutically relevant dosing, and/or therapeutically relevant bioavailability. Such microneedles and/or microarray patches (MAPs) may demonstrate bioequivalence to a commercially approved formulation of the API and/or a reference drug.

In some embodiments, the microneedles and/or microarray patches (MAPs), e.g., comprising an active pharmaceutical ingredient (API) and a water soluble excipient, can be configured and utilized to provide bioequivalent pharmacokinetics to delivery of a similar dose of the API and/or a reference drug using a different dosage form and/or a different route of administration. In some embodiments, the microneedles and/or microarray patches (MAPs) can provide bioequivalent pharmacokinetics to a commercially approved formulation of the API and/or a reference drug. In some embodiments, the microneedles and/or microarray patches (MAPs) can provide bioequivalent pharmacokinetics to delivery via other routes of administration (e.g., via parenteral, subcutaneous, intravenous, intramuscular, and/or oral administration) of a similar dose of the API and/or a reference drug.

As used interchangeably herein, the terms "microneedle" and "microprojection" refer to a three-dimensional (3D) microstructure, such as a micron-sized needle or needle-like structure, that can be configured to penetrate or cut through a biological barrier, a tissue, and/or a cell. Microneedles can be configured and utilized for various applications, including, e.g., biomedical applications, such as drug delivery, biosensing, biomolecular and cellular sampling, disease diagnosis, disease mitigation, disease treatment, disease prevention, and/or health monitoring; and cosmetic applications, such as nutrient and/or cosmeceutical delivery. In particular embodiments, the microneedles described herein can comprise a consolidated microneedle tip and a microneedle base.

As used interchangeably herein, the terms "microarray patch (MAP)" and "microneedle array patch (MAP)" refer to a device comprising a plurality of microneedles arranged in a random or predefined two-dimensional or three-dimensional configuration, such as an array. In some embodiments, the configuration of the microneedles can be regular or irregular according to a repeating geometric pattern. Suitable geometric patterns include, e.g., hexagonal grids, square grids, triangular grids, and staggered arrays. In some embodiments, the microarray patch (MAP) comprises a plurality of microneedles arranged in a hexagonal grid. In some embodiments, the microarray patch (MAP) comprises a plurality of microneedles arranged in a square grid. In some embodiments, the microarray patch (MAP) comprises a plurality of microneedles arranged in a triangular grid. In some embodiments, the microarray patch (MAP) comprises a plurality of microneedles arranged in a staggered array. In some embodiments, a staggered array can be used, for example, to achieve different penetration depths by varying the needle lengths within the array. In some embodiments, the microarray patch (MAP) comprises a plurality of microneedles comprising one or more active pharmaceutical ingredients (APIs).

Conventional microneedles can be characterized by a limited dosing capacity, given that the microneedles' size can restrict the total amount of an active pharmaceutical ingredient (API) that they can carry. Conventional microneedles can also be characterized by inconsistent pharmacokinetics, due in part to factors related to the architecture of human skin which can impede microneedle insertion, leading to inconsistent delivery of an active pharmaceutical ingredient (API). The architecture of human skin can have clinical relevance, because specific features of human skin can affect how the skin responds to external stimuli, such as the insertion of microneedles. Specific features of the skin, e.g., thickness of the stratum corneum, spread or expansion of the subcutaneous adipose layer, and density of skin appendages, such as hair follicles, sweat, and sebaceous glands, can also vary at different body sites. Ensuring reproducible insertion of microneedles into the skin of a subject can also be challenging because individual microneedles in a microarray patch (MAP) can exhibit, e.g., different insertion behaviors, such as deformation, based on their specific position within the microarray, leading to inconsistent delivery of an active pharmaceutical ingredient (API). Without wishing to be bound by theory, the insertion behavior of microneedles, e.g., in a microarray patch (MAP), is based, at least in part, upon the mechanical properties of the skin, microneedle material, the microarray geometry, and the distribution of the microneedles in the microarray.

As disclosed herein, Applicant has surprisingly discovered specific combinations of water-soluble excipients that can, for example, effectively (1) enhance the stability of a high concentration of active pharmaceutical ingredients (API) for delivery of an effective dose of the API using a microneedle and/or a microarray patch (MAP) described herein; (2) enhance the fluid properties of a composition, such as a dispensable formulation, for manufacturing a microneedle and/or a microarray patch (MAP) described herein using, e.g., a liquid dispensing system; (3) enhance the consolidation of the API into the apex of a microneedle tip (e.g., a consolidated microneedle tip) during manufacturing; (4) enhance the strength of the microneedle, e.g., to resist deformation during deployment; and/or (5) minimize, or eliminate, manufacturing defects, such as shell formation and microneedle tip dislodgement, that can negatively affect microneedle morphology, strength, deployment efficiency, API delivery consistency, and pharmacodynamics.

In some embodiments, the microarray patch (MAP) comprises a backing. In some embodiments, the microarray patch (MAP) comprises about 10 to about 10000 microneedles (e.g., about 10, about 50, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2150, 2200, 2250, 2300, 2350, 2400, 2450, 2500, 2550, 2600, 2650, 2700, 2750, 2800, 2850, 2900, 2950, 3000, 3050, 3100, 3150, 3200, 3250, 3300, 3350, 3400, 3450, 3500, 3550, 3600, 3650, 3700, 3750, 3800, 3850, 3900, 3950, 4000, 4050, 4100, 4150, 4200, 4250, 4300, 4350, 4400, 4450, 4500, 4550, 4600, 4650, 4700, 4750, 4800, 4850, 4900, 4950, 5000, 5050, 5100, 5150, 5200, 5250, 5300, 5350, 5400, 5450, 5500, 5550, 5600, 5650, 5700, 5750, 5800, 5850, 5900, 5950, 6000, 6050, 6100, 6150, 6200, 6250, 6300, 6350, 6400, 6450, 6500, 6550, 6600, 6650, 6700, 6750, 6800, 6850, 6900, 6950, 7000, 7050, 7100, 7150, 7200, 7250, 7300, 7350, 7400, 7450, 7500, 7550, 7600, 7650, 7700, 7750, 7800, 7850, 7900, 7950, 8000, 8050, 8100, 8150, 8200, 8250, 8300, 8350, 8400, 8450, 8500, 8550, 8600, 8650, 8700, 8750, 8800, 8850, 8900, 8950, 9000, 9050, 9100, 9150, 9200, 9250, 9300, 9350, 9400, 9450, 9500, 9550, 9600, 9650, 9700, 9750, 9800, 9850, 9900, 9950, or 10000 microneedles). In some embodiments, the microarray patch (MAP) comprises about 10 to about 9000 microneedles. In some embodiments, the microarray patch (MAP) comprises about 10 to about 8000 microneedles. In some embodiments, the microarray patch (MAP) comprises about 10 to about 7000 microneedles. In some embodiments, the microarray patch (MAP) comprises about 10 to about 6000 microneedles. In some embodiments, the microarray patch (MAP) comprises about 10 to about 5000 microneedles. In some embodiments, the microarray patch (MAP) comprises about 10 to about 4000 microneedles. In some embodiments, the microarray patch (MAP) comprises about 10 to about 3000 microneedles. In some embodiments, the microarray patch (MAP) comprises about 10 to about 2000 microneedles. In some embodiments, the microarray patch (MAP) comprises about 10 to about 1000 microneedles (e.g., about 10, 25, 50, 75, 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, or 1000 microneedles). In some embodiments, the microarray patch (MAP) comprises about 10 to about 500 microneedles (e.g., about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, or 500 microneedles). In some embodiments, the microarray patch (MAP) comprises about 10 to about 400 microneedles. In some embodiments, the microarray patch (MAP) comprises about 10 to about 300 microneedles. In some embodiments, the microarray patch (MAP) comprises about 10 to about 200 microneedles. In some embodiments, the microarray patch (MAP) comprises about 10 to about 100 microneedles. In some embodiments, the microarray patch (MAP) comprises about 10 to about 50 microneedles. The number of microneedles in the microarray patch (MAP) can also be referred to as the "array size."

As used herein, the term "backing" refers to a material that is suitable for attaching to a component of a microneedle. In some embodiments, a backing material is suitable for attaching to the base of a microneedle described herein. Exemplary backing materials that can be used in the fabrication of a microneedle and/or a MAP described herein include, but are not limited to, a solid support, e.g., a paper-based material, a plastic material, a polymeric material, or a polyester-based material (e.g., a Whatman 903 paper, a polymeric tape, a plastic tape, an adhesive-backed polyester tape, or other medical tape). In some embodiments, the backing comprises a Whatman 903 paper. In some embodiments, the backing comprises a polyester tape. In some embodiments, the polyester tape comprises an adhesive-backed polyester tape. In some embodiments, the backing material may be coated (e.g., at least on one side) with an adhesive suitable for bonding to and/or adhering to the microneedle base described herein. In some embodiments, a backing can be attached to the microneedle by an adhesive, such as an adhesive compatible with the active pharmaceutical ingredients (API). The term "compatible with the active pharmaceutical ingredients (API)" means an adhesive that may be in contact with the microneedle and/or the microarray patch (MAP) for an extended period of time without significantly damaging and/or degrading the active pharmaceutical ingredient (API). The backing may include an adhesive to improve contact with the skin.

The backing materials used in the microneedles of the invention may have various properties, including, but not limited to, the ability to bond and/or adhere to the dissolving base layer to permit demolding. A backing material must be strong enough for the backing to maintain patch integrity, e.g., if the dissolving base layer has cracks or discontinuities. The backing material may be sufficiently flexible so as to conform, for example, to a non-flat surface, such as a skin surface. In particular, the backing must be flexible enough during wear time, such as after the patch is applied (e.g., pressed into) the skin. The backing may comprise and/or consist of a non-dissolving material, such that the backing maintains its integrity after patch application to a skin surface and during patch removal from a skin surface. The backing may have any suitable dimension, e.g., to accommodate the microneedle array, and/or to better suit the intended site of application.

Microneedles can be made from a variety of materials, which can affect the microneedle's biocompatibility, mechanical properties, and other characteristics. Microneedles can be classified based on fabrication process, shapes, types, active pharmaceutical ingredients (API) delivery approaches, and materials. Microneedles can be formed to have a variety of different geometric shapes, for example, cylinder, cone, pyramid, tapered, spear, spherical pedestal, candle-like, bullet shaped, spike, lancet, domed, beveled, and the like. Based on the types and API delivery approach, microneedles can be classified, for example, as solid microneedles, hollow microneedles, coated microneedles, dissolvable/dissolving microneedles, and hydrogel-forming microneedles. In some embodiments, solid microneedles can be configured to be inserted into the skin to generate pores that enable active pharmaceutical ingredients (API) to be released into the body, e.g., by diffusion. In some embodiments, coated microneedles can include solid microneedles coated with active pharmaceutical ingredients (API). In some embodiments, the coating of active pharmaceutical ingredients (API) can be applied by a film coating process, e.g., spraying. In some embodiments, hollow microneedles can be configured to have a hollow path for carrying and delivering active pharmaceutical ingredients (API). In some embodiments, dissolving microneedles can be configured to dissolved over a predetermined period of time once inserted into the skin.

In some embodiments, the active pharmaceutical ingredients (API) release profile of the microneedles can be configured based on the type of microneedles and/or the microneedle materials. In some embodiments, the microneedles can be configured to release a predefined amount of an active pharmaceutical ingredients (API) (e.g., about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100% of the API) in a predefined period of time (e.g., about 5 seconds, about 10 seconds, about 15 seconds, about 20 seconds, about 25 seconds, about 30 seconds, about 35 seconds, about 40 seconds, about 45 seconds, about 50 seconds, about 55 seconds, or about 60 seconds; or about 5 minutes, about 10 minutes, about 15 minutes, about 20 minutes, about 25 minutes, about 30 minutes, about 35 minutes, about 40 minutes, about 45 minutes, about 50 minutes, about 55 minutes, or about 60 minutes; or about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, or about 24 hours; or about 1 day, about 2 days, about 3 days, about 4 days, about 5 days, about 6 days, or about 7 days; or about 1 week, about 2 weeks, about 3 weeks, about 4 weeks; or about 1 month, about 2 months, about 3 months, about 4 months, about 5 months, about 6 months, about 7 months, about 8 months, about 9 months, about 10 months, about 11 months, or about 12 months; or about 1 year, about 2 years, about 3 years, about 4 years, or about 5 years or more). In some embodiments, the microneedles can be configured to release a predefined amount of active pharmaceutical ingredients (API) in a predefined period of time though a dissolution-diffusion mechanism. In some embodiments, the microneedles can be configured to release a predefined amount of active pharmaceutical ingredients (API) though an immediate-release mechanism. In some embodiments, the microneedles can be configured to release a predefined amount of active pharmaceutical ingredients (API) in a predefined period of time though a modified-release mechanism. Exemplary modified release mechanisms can include, e.g., controlled-release, sustained-release, and/or long-acting API products and/or microneedle formulations.

The distinct characteristic of each type of microneedle can allow a variety of clinical applications, including diagnosis and treatment.

The microneedles described herein can be used for intradermal and/or transdermal delivery of an active pharmaceutical ingredient (API). In particular, the microneedles can be configured to penetrate the surface of the skin (i.e., the stratum corneum) of a subject, so as to allow an API to reach a deeper layer of the skin, such as the underlying epidermis layer, or epidermis and dermis layers, rich in blood vessels and lymphatics for localized and/or systemic absorption. As such, the microneedles, microarray patches (MAPs), and systems described herein can provide precise and consistent delivery of an API, including both small and large molecules, and can facilitate both localized and/or systemic therapeutic effects. The microneedles and microarray patches (MAPs) described herein can be configured to have different structural and functional characteristics depending on their application. In some embodiments, the microneedle and/or the microarray patch (MAP) can be configured to have any dimension and/or geometry to enable the deployment of a microneedle tip (e.g., a consolidated microneedle tip) at a depth of at least about 100 μm to about 1000 μm (e.g., about 100 μm, about 125 μm, about 150 μm, about 175 μm, about 200 μm, about 225 μm, about 250 μm, about 275 μm, about 300 μm, about 325 μm, about 350 μm, about 375 μm, about 400 μm, about 425 μm, about 450 μm, about 475 μm, about 500 μm, about 525 μm, about 550 μm, about 575 μm, about 600 μm, about 625 μm, about 650 μm, about 675 μm, about 700 μm, about 725 μm, about 750 μm, about 775 μm, about 800 μm, about 825 μm, about 850 μm, about 875 μm, about 900 μm, about 925 μm, about 950 μm, about 975 μm, or about 1000 μm) below the surface of the skin of a subject for release of an active pharmaceutical ingredient (API).

In some embodiments, the specific dimensions and geometries of the microneedle and/or the microarray patch (MAP) can be expressed as an average value. In some embodiments, the specific dimensions and geometries of the microneedle and/or the microarray patch (MAP) can be expressed as a mean value.

In some embodiments, the microneedle and/or the microarray patch (MAP) can be characterized by a pre-deployment needle height (or "needle height"), an air gap, a post-deployment needle height, a deployed tip depth, and/or a height delivered.

As used herein, the terms "pre-deployment needle height," "primary needle height," "microneedle height," and "needle height" interchangeably refer to the full height of undeployed microneedles. In some embodiments, the "primary needle height" may be calculated using the formula: Primary Needle Height=Consolidated Microneedle Tip Length+Base Length. In some embodiments, the microneedle and/or the microarray patch (MAP) can be characterized by a pre-deployment needle height (or "needle height") of about 25 μm to about 3000 μm (e.g., about 25 μm, about 50 μm, about 75 μm, about 100 μm, about 125 μm, about 150 μm, about 175 μm, about 200 μm, about 225 μm, about 250 μm, about 275 μm, about 300 μm, about 325 μm, about 350 μm, about 375 μm, about 400 μm, about 425 μm, about 450 μm, about 475 μm, about 500 μm, about 525 μm, about 550 μm, about 575 μm, about 600 μm, about 625 μm, about 650 μm, about 675 μm, about 700 μm, about 725 μm, about 750 μm, about 775 μm, about 800 μm, about 825 μm, about 850 μm, about 875 μm, about 900 μm, about 925 μm, about 950 μm, about 975 μm, about 1000 μm, about 1025 μm, about 1050 μm, about 1075 μm, about 1100 μm, about 1125 μm, about 1150 μm, about 1175 μm, about 1200 μm, about 1225 μm, about 1250 μm, about 1275 μm, about 1300 μm, about 1325 μm, about 1350 μm, about 1375 μm, about 1400 μm, about 1425 μm, about 1450 μm, about 1475 μm, about 1500 μm, about 1525 μm, about 1550 μm, about 1575 μm, about 1600 μm, about 1625 μm, about 1650 μm, about 1675 μm, about 1700 μm, about 1725 μm, about 1750 μm, about 1775 μm, about 1800 μm, about 1825 μm, about 1850 μm, about 1875 μm, about 1900 μm, about 1925 μm, about 1950 μm, about 1975 μm, about 2000 μm, about 2025 μm, about 2050 μm, about 2075 μm, about 2100 μm, about 2125 μm, about 2150 μm, about 2175 μm, about 2200 μm, about 2225 μm, about 2250 μm, about 2275 μm, about 2300 μm, about 2325 μm, about 2350 μm, about 2375 μm, about 2400 μm, about 2425 μm, about 2450 μm, about 2475 μm, about 2500 μm, about 2525 μm, about 2550 μm, about 2575 μm, about 2600 μm, about 2625 μm, about 2650 μm, about 2675 μm, about 2700 μm, about 2725 μm, about 2750 μm, about 2775 μm, about 2800 μm, about 2825 μm, about 2850 μm, about 2875 μm, about 2900 μm, about 2925 μm, about 2950 μm, about 2975 μm, or about 3000 μm). In some embodiments, the needle height can be measured from the apex of the consolidated microneedle tip to the bottom of the microneedle base. In some embodiments, at least about 25%, about 30%, about 35%, about 40%, about 45%, about 50%, about 55%, about 60%, about 65%, about 70%, about 75%, about 80%, about 85%, about 90%, about 95%, or about 100% of the microneedle height can be inserted into the skin of a subject upon deployment.

As used herein, the term "air gap" refers to the space between the bottom of the adhesive of the MAP backing and the skin surface, measured while the MAP is deployed. In some embodiments, the microneedle and/or the microarray patch (MAP) can be characterized by an air gap of about 100 μm to about 600 μm (e.g., about 100 μm, about 105 μm, about 110 μm, about 115 μm, about 120 μm, about 125 μm, about 130 μm, about 135 μm, about 140 μm, about 145 μm, about 150 μm, about 155 μm, about 160 μm, about 165 μm, about 170 μm, about 175 μm, about 180 μm, about 185 μm, about 190 μm, about 195 μm, about 200 μm, about 205 μm, about 210 μm, about 215 μm, about 220 μm, about 225 μm, about 230 μm, about 235 μm, about 240 μm, about 245 μm, about 250 μm, about 255 μm, about 260 μm, about 265 μm, about 270 μm, about 275 μm, about 280 μm, about 285 μm, about 290 μm, about 295 μm, about 300 μm, about 305 μm, about 310 μm, about 315 μm, about 320 μm, about 325 μm, about 330 μm, about 335 μm, about 340 μm, about 345 μm, about 350 μm, about 355 μm, about 360 μm, about 365 μm, about 370 μm, about 375 μm, about 380 μm, about 385 μm, about 390 μm, about 395 μm, about 400 μm, about 405 μm, about 410 μm, about 415 μm, about 420 μm, about 425 μm, about 430 μm, about 435 μm, about 440 μm, about 445 μm, about 450 μm, about 455 μm, about 460 μm, about 465 μm, about 470 μm, about 475 μm, about 480 μm, about 485 μm, about 490 μm, about 495 μm, about 500 μm, about 505 μm, about 510 μm, about 515 μm, about 520 μm, about 525 μm, about 530 μm, about 535 μm, about 540 μm, about 545 μm, about 550 μm, about 555 μm, about 560 μm, about 565 μm, about 570 μm, about 575 μm, about 580 μm, about 585 μm, about 590 μm, about 595 μm, or about 600 μm).

As used herein, the term "post-deployment needle height" or "residual needle height" refers to the height of needles after the MAP has been removed from tissue following deployment. In some embodiments, the microneedle and/or the microarray patch (MAP) can be characterized by a post-deployment needle height of about 0 μm to about 600 μm (e.g., about 0 μm, about 1 μm, about 5 μm, about 10 μm, about 15 μm, about 20 μm, about 25 μm, about 30 μm, about 35 μm, about 40 μm, about 45 μm, about 50 μm, about 55 μm, about 60 μm, about 65 μm, about 70 μm, about 75 μm, about 80 μm, about 85 μm, about 90 μm, about 95 μm, about 100 μm, about 105 μm, about 110 μm, about 115 μm, about 120 μm, about 125 μm, about 130 μm, about 135 μm, about 140 μm, about 145 μm, about 150 μm, about 155 μm, about 160 μm, about 165 μm, about 170 μm, about 175 μm, about 180 μm, about 185 μm, about 190 μm, about 195 μm, about 200 μm, about 205 μm, about 210 μm, about 215 μm, about 220 μm, about 225 μm, about 230 μm, about 235 μm, about 240 μm, about 245 μm, about 250 μm, about 255 μm, about 260 μm, about 265 μm, about 270 μm, about 275 μm, about 280 μm, about 285 μm, about 290 μm, about 295 μm, about 300 μm, about 305 μm, about 310 μm, about 315 μm, about 320 μm, about 325 μm, about 330 μm, about 335 μm, about 340 μm, about 345 μm, about 350 μm, about 355 μm, about 360 μm, about 365 μm, about 370 μm, about 375 μm, about 380 μm, about 385 μm, about 390 μm, about 395 μm, about 400 μm, about 405 μm, about 410 μm, about 415 μm, about 420 μm, about 425 μm, about 430 μm, about 435 μm, about 440 μm, about 445 μm, about 450 μm, about 455 μm, about 460 μm, about 465 μm, about 470 μm, about 475 μm, about 480 μm, about 485 μm, about 490 μm, about 495 μm, about 500 μm, about 505 μm, about 510 μm, about 515 μm, about 520 μm, about 525 μm, about 530 μm, about 535 μm, about 540 μm, about 545 μm, about 550 μm, about 555 μm, about 560 μm, about 565 μm, about 570 μm, about 575 μm, about 580 μm, about 585 μm, about 590 μm, about 595 μm, or about 600 μm).

In some embodiments, the microneedle and/or the microarray patch (MAP) can be characterized by a post-deployment needle height of less than about 600 μm (e.g., less than about 25 μm, less than about 50 μm, less than about 75 μm, less than about 100 μm, less than about 125 μm, less than about 150 μm, less than about 175 μm, less than about 200 μm, less than about 225 μm, less than about 250 μm, less than about 275 μm, less than about 300 μm, less than about 325 μm, less than about 350 μm, less than about 375 μm, less than about 400 μm, less than about 425 μm, less than about 450 μm, less than about 475 μm, less than about 500 μm, less than about 525 μm, less than about 550 μm, less than about 575 μm, or less than about 600 μm).

In some embodiments, the microneedle and/or the microarray patch (MAP) can be characterized by a percentage of needle height lost of about 30% to about 60% (e.g., about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, or about 60%).

In some embodiments, the microneedle and/or the microarray patch (MAP) can be characterized by a percentage of undeployed API not delivered which is measured following MAP deployment by dissolving the MAP in vitro and measuring residual API by RP-HPLC (or other) API specific assay (e.g., average % Post Deployment—In Vitro Release (PD-IVR), e.g., by RP-HPLC) of about 1% to about 50% (e.g., about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, or about 50%).

In some embodiments, the microneedle and/or the microarray patch (MAP) can be characterized by a dose delivered per needle (or dispense volume loaded into each needle) of about 0.1 nL to about 10 nL (e.g., about 0.1 nL, about 0.2 nL, about 0.3 nL, about 0.4 nL, about 0.5 nL, about 0.6 nL, about 0.7 nL, about 0.8 nL, about 0.9 nL, about 1 nL, about 1.1 nL, about 1.2 nL, about 1.3 nL, about 1.4 nL, about 1.5 nL, about 1.6 nL, about 1.7 nL, about 1.8 nL, about 1.9 nL, about 2 nL, about 2.1 nL, about 2.2 nL, about 2.3 nL, about 2.4 nL, about 2.5 nL, about 2.6 nL, about 2.7 nL, about 2.8 nL, about 2.9 nL, about 3 nL, about 3.1 nL, about 3.2 nL, about 3.3 nL, about 3.4 nL, about 3.5 nL, about 3.6 nL, about 3.7 nL, about 3.8 nL, about 3.9 nL, about 4 nL, about 4.1 nL, about 4.2 nL, about 4.3 nL, about 4.4 nL, about 4.5 nL, about 4.6 nL, about 4.7 nL, about 4.8 nL, about 4.9 nL, about 5 nL, about 5.1 nL, about 5.2 nL, about 5.3 nL, about 5.4 nL, about 5.5 nL, about 5.6 nL, about 5.7 nL, about 5.8 nL, about 5.9 nL, about 6 nL, about 6.1 nL, about 6.2 nL, about 6.3 nL, about 6.4 nL, about 6.5 nL, about 6.6 nL, about 6.7 nL, about 6.8 nL, about 6.9 nL, about 7 nL, about 7.1 nL, about 7.2 nL, about 7.3 nL, about 7.4 nL, about 7.5 nL, about 7.6 nL, about 7.7 nL, about 7.8 nL, about 7.9 nL, about 8 nL, about 8.1 nL, about 8.2 nL, about 8.3 nL, about 8.4 nL, about 8.5 nL, about 8.6 nL, about 8.7 nL, about 8.8 nL, about 8.9 nL, about 9 nL, about 9.1 nL, about 9.2 nL, about 9.3 nL, about 9.4 nL, about 9.5 nL, about 9.6 nL, about 9.7 nL, about 9.8 nL, about 9.9 nL, or about 10 nL) of an active pharmaceutical ingredient (API), e.g., described herein.

As used herein, the terms "deployed tip depth," "deployment depth," and "penetration depth" interchangeably refer to the length between the skin surface and the apex of a deployed tip, such as a tip deployed into the skin of a subject, measured post-deployment after the MAP is removed. In some embodiments, the "penetration depth" may be calculated using the formula: Penetration Depth=Primary Needle Height-Air Gap. In some embodiments, the microneedle and/or the microarray patch (MAP) can be characterized by a deployed tip depth of about at least about 250 μm, e.g., about 250 μm to about 1000 μm (e.g., about 250 μm, about 255 μm, about 260 μm, about 265 μm, about 270 μm, about 275 μm, about 280 μm, about 285 μm, about 290 μm, about 295 μm, about 300 μm, about 305 μm, about 310 μm, about 315 μm, about 320 μm, about 325 μm, about 330 μm, about 335 μm, about 340 μm, about 345 μm, about 350 μm, about 355 μm, about 360 μm, about 365 μm, about 370 μm, about 375 μm, about 380 μm, about 385 μm, about 390 μm, about 395 μm, about 400 μm, about 405 μm, about 410 μm, about 415 μm, about 420 μm, about 425 μm, about 430 μm, about 435 μm, about 440 μm, about 445 μm, about 450 μm, about 455 μm, about 460 μm, about 465 μm, about 470 μm, about 475 μm, about 480 μm, about 485 μm, about 490 μm, about 495 μm, about 500 μm, about 505 μm, about 510 μm, about 515 μm, about 520 μm, about 525 μm, about 530 μm, about 535 μm, about 540 μm, about 545 μm, about 550 μm, about 555 μm, about 560 μm, about 565 μm, about 570 μm, about 575 μm, about 580 μm, about 585 μm, about 590 μm, about 595 μm, about 600 μm, about 605 μm, about 610 μm, about 615 μm, about 620 μm, about 625 μm, about 630 μm, about 635 μm, about 640 μm, about 645 μm, about 650 μm, about 655 μm, about 660 μm, about 665 μm, about 670 μm, about 675 μm, about 680 μm, about 685 μm, about 690 μm, about 695 μm, about 700 μm, about 705 μm, about 710 μm, about 715 μm, about 720 μm, about 725 μm, about 730 μm, about 735 μm, about 740 μm, about 745 μm, about 750 μm, about 755 μm, about 760 μm, about 765 μm, about 770 μm, about 775 μm, about 780 μm, about 785 μm, about 790 μm, about 795 μm, about 800 μm, about 805 μm, about 810 μm, about 815 μm, about 820 μm, about 825 μm, about 830 μm, about 835 μm, about 840 μm, about 845 μm, about 850 μm, about 855 μm, about 860 μm, about 865 μm, about 870 μm, about 875 μm, about 880 μm, about 885 μm, about 890 μm, about 895 μm, about 900 μm, about 905 μm, about 910 μm, about 915 μm, about 920 μm, about 925 μm, about 930 μm, about 935 μm, about 940 μm, about 945 μm, about 950 μm, about 955 μm, about 960 μm, about 965 μm, about 970 μm, about 975 μm, about 980 μm, about 985 μm, about 990 μm, about 995 μm, or about 1000 μm). In some embodiments, the microneedle and/or the microarray patch (MAP) can be characterized by a deployed tip depth of about 250 μm to about 600 μm. In some embodiments, the microneedle and/or the microarray patch (MAP) can be characterized by a deployed tip depth of about 250 μm to about 500 μm. In some embodiments, the microneedle and/or the microarray patch (MAP) can be characterized by a deployed tip depth of about 300 μm to about 400 μm.

As used herein, the term "height delivered" refers to the difference between the pre-deployment needle height and post-deployment needle height measurements, representing the length of the needle that has been deployed and left behind. In some embodiments, the microneedle and/or the microarray patch (MAP) can be characterized by a height delivered of about 50 μm to about 1000 μm (e.g., about 50 μm, about 75 μm, about 100 μm, about 125 μm, about 150 μm, about 175 μm, about 200 μm, about 225 μm, about 250 μm, about 275 μm, about 300 μm, about 325 μm, about 350 μm, about 375 μm, about 400 μm, about 425 μm, about 450 μm, about 475 μm, about 500 μm, about 525 μm, about 550 μm, about 575 μm, about 600 μm, about 625 μm, about 650 μm, about 675 μm, about 700 μm, about 725 μm, about 750 μm, about 775 μm, about 800 μm, about 825 μm, about 850 μm, about 875 μm, about 900 μm, about 925 μm, about 950 μm, about 975 μm, or about 1000 μm). In some embodiments, the microneedle and/or the microarray patch (MAP) can be characterized by a height delivered of about 50 μm to about 600 μm (e.g., about 50 μm, about 55 μm, about 60 μm, about 65 μm, about 70 μm, about 75 μm, about 80 μm, about 85 μm, about 90 μm, about 95 μm, about 100 μm, about 105 μm, about 110 μm, about 115 μm, about 120 μm, about 125 μm, about 130 μm, about 135 μm, about 140 μm, about 145 μm, about 150 μm, about 155 μm, about 160 μm, about 165 μm, about 170 μm, about 175 μm, about 180 μm, about 185 μm, about 190 μm, about 195 μm, about 200 μm, about 205 μm, about 210 μm, about 215 μm, about 220 μm, about 225 μm, about 230 μm, about 235 μm, about 240 μm, about 245 μm, about 250 μm, about 255 μm, about 260 μm, about 265 μm, about 270 μm, about 275 μm, about 280 μm, about 285 μm, about 290 μm, about 295 μm, about 300 μm, about 305 μm, about 310 μm, about 315 μm, about 320 μm, about 325 μm, about 330 μm, about 335 μm, about 340 μm, about 345 μm, about 350 μm, about 355 μm, about 360 μm, about 365 μm, about 370 μm, about 375 μm, about 380 μm, about 385 μm, about 390 μm, about 395 μm, about 400 μm, about 405 μm, about 410 μm, about 415 μm, about 420 μm, about 425 μm, about 430 μm, about 435 μm, about 440 μm, about 445 μm, about 450 μm, about 455 μm, about 460 μm, about 465 μm, about 470 μm, about 475 μm, about 480 μm, about 485 μm, about 490 μm, about 495 μm, about 500 μm, about 505 μm, about 510 μm, about 515 μm, about 520 μm, about 525 μm, about 530 μm, about 535 μm, about 540 μm, about 545 μm, about 550 μm, about 555 μm, about 560 μm, about 565

μm, about 570 μm, about 575 μm, about 580 μm, about 585 μm, about 590 μm, about 595 μm, or about 600 μm).

In some embodiments, the microneedle and/or the microarray patch (MAP) can be characterized by a microneedle dimension comprising a width of about 1 μm to about 650 μm (e.g., about 1 μm, about 2 μm, about 3 μm, about 4 μm, about 5 μm, about 6 μm, about 7 μm, about 8 μm, about 9 μm, about 10 μm, about 15 μm, about 25 μm, about 30 μm, about 35 μm, about 40 μm, about 45 μm, about 50 μm, about 55 μm, about 60 μm, about 65 μm, about 70 μm, about 75 μm, about 80 μm, about 85 μm, about 90 μm, about 95 μm, about 100 μm, about 105 μm, about 110 μm, about 115 μm, about 120 μm, about 125 μm, about 130 μm, about 135 μm, about 140 μm, about 145 μm, about 150 μm, about 155 μm, about 160 μm, about 165 μm, about 170 μm, about 175 μm, about 180 μm, about 185 μm, about 190 μm, about 195 μm, about 200 μm, about 205 μm, about 210 μm, about 215 μm, about 220 μm, about 225 μm, about 230 μm, about 235 μm, about 240 μm, about 245 μm, about 250 μm, about 255 μm, about 260 μm, about 265 μm, about 270 μm, about 275 μm, about 280 μm, about 285 μm, about 290 μm, about 295 μm, about 300 μm, about 305 μm, about 310 μm, about 315 μm, about 320 μm, about 325 μm, about 330 μm, about 335 μm, about 340 μm, about 345 μm, about 350 μm, about 355 μm, about 360 μm, about 365 μm, about 370 μm, about 375 μm, about 380 μm, about 385 μm, about 390 μm, about 395 μm, about 400 μm, about 405 μm, about 410 μm, about 415 μm, about 420 μm, about 425 μm, about 430 μm, about 435 μm, about 440 μm, about 445 μm, about 450 μm, about 455 μm, about 460 μm, about 465 μm, about 470 μm, about 475 μm, about 480 μm, about 485 μm, about 490 μm, about 495 μm, about 500 μm, about 505 μm, about 510 μm, about 515 μm, about 520 μm, about 525 μm, about 530 μm, about 535 μm, about 540 μm, about 545 μm, about 550 μm, about 555 μm, about 560 μm, about 565 μm, about 570 μm, about 575 μm, about 580 μm, about 585 μm, about 590 μm, about 595 μm, about 600 μm, about 605 μm, about 610 μm, about 615 μm, about 620 μm, about 625 μm, about 630 μm, about 635 μm, about 640 μm, about 645 μm, or about 650 μm). The width may be measured at any point along the length of the microneedle. In some embodiments, the width can be measured across the base of the microneedle. In some embodiments, the width can be measured across the consolidated tip of the microneedle.

Width of the array is related to needle spacing and number of needles. Tested array widths range from about 3 mm to about 29 mm wide. In some embodiments, the width of an array can be about 2 mm to about 200 mm (e.g., about 5 mm, about 10 mm, about 15 mm, about 20 mm, about 25 mm, about 30 mm, about 35 mm, about 40 mm, about 45 mm, about 50 mm, about 55 mm, about 60 mm, about 65 mm, about 70 mm, about 75 mm, about 80 mm, about 85 mm, about 90 mm, about 95 mm, about 100 mm, about 105 mm, about 110 mm, about 115 mm, about 120 mm, about 125 mm, about 130 mm, about 135 mm, about 140 mm, about 145 mm, about 150 mm, about 155 mm, about 160 mm, about 165 mm, about 170 mm, about 175 mm, about 180 mm, about 185 mm, about 190 mm, about 195 mm, or about 200 mm).

In some embodiments, the microneedle and/or the microarray patch (MAP) can be characterized by spacing between the microneedles of about 25 μm to about 3000 μm (e.g., about 25 μm, about 50 μm, about 75 μm, about 100 μm, about 125 μm, about 150 μm, about 175 μm, about 200 μm, about 225 μm, about 250 μm, about 275 μm, about 300 μm, about 325 μm, about 350 μm, about 375 μm, about 400 μm, about 425 μm, about 450 μm, about 475 μm, about 500 μm, about 525 μm, about 550 μm, about 575 μm, about 600 μm, about 625 μm, about 650 μm, about 675 μm, about 700 μm, about 725 μm, about 750 μm, about 775 μm, about 800 μm, about 825 μm, about 850 μm, about 875 μm, about 900 μm, about 925 μm, about 950 μm, about 975 μm, about 1000 μm, about 1025 μm, about 1050 μm, about 1075 μm, about 1100 μm, about 1125 μm, about 1150 μm, about 1175 μm, about 1200 μm, about 1225 μm, about 1250 μm, about 1275 μm, about 1300 μm, about 1325 μm, about 1350 μm, about 1375 μm, about 1400 μm, about 1425 μm, about 1450 μm, about 1475 μm, about 1500 μm, about 1525 μm, about 1550 μm, about 1575 μm, about 1600 μm, about 1625 μm, about 1650 μm, about 1675 μm, about 1700 μm, about 1725 μm, about 1750 μm, about 1775 μm, about 1800 μm, about 1825 μm, about 1850 μm, about 1875 μm, about 1900 μm, about 1925 μm, about 1950 μm, about 1975 μm, about 2000 μm, about 2025 μm, about 2050 μm, about 2075 μm, about 2100 μm, about 2125 μm, about 2150 μm, about 2175 μm, about 2200 μm, about 2225 μm, about 2250 μm, about 2275 μm, about 2300 μm, about 2325 μm, about 2350 μm, about 2375 μm, about 2400 μm, about 2425 μm, about 2450 μm, about 2475 μm, about 2500 μm, about 2525 μm, about 2550 μm, about 2575 μm, about 2600 μm, about 2625 μm, about 2650 μm, about 2675 μm, about 2700 μm, about 2725 μm, about 2750 μm, about 2775 μm, about 2800 μm, about 2825 μm, about 2850 μm, about 2875 μm, about 2900 μm, about 2925 μm, about 2950 μm, about 2975 μm, or about 3000 μm). In some embodiments, the microneedles can be evenly spaced. In some embodiments, the spacing between the microneedles can be measured from the center of the microneedle (also referred to as "center-to-center spacing). In some embodiments, the spacing between the microneedles can be measured from the tip of the microneedle (also referred to as "tip-to-tip spacing"). In some embodiments, the spacing between the microneedles can be measured from the edge of the microneedle base (also referred to as "edge-to-edge" spacing).

In some embodiments, the microneedle and/or the microarray patch (MAP) can be configured to deliver the consolidated microneedle tip to a depth of at least about 250 μm below the surface of the subject's skin, e.g., about 200 μm to about 1000 μm (e.g., about 200 μm, about 205 μm, about 210 μm, about 215 μm, about 220 μm, about 225 μm, about 230 μm, about 235 μm, about 240 μm, about 245 μm, about 250 μm, about 255 μm, about 260 μm, about 265 μm, about 270 μm, about 275 μm, about 280 μm, about 285 μm, about 290 μm, about 295 μm, about 300 μm, about 305 μm, about 310 μm, about 315 μm, about 320 μm, about 325 μm, about 330 μm, about 335 μm, about 340 μm, about 345 μm, about 350 μm, about 355 μm, about 360 μm, about 365 μm, about 370 μm, about 375 μm, about 380 μm, about 385 μm, about 390 μm, about 395 μm, about 400 μm, about 405 μm, about 410 μm, about 415 μm, about 420 μm, about 425 μm, about 430 μm, about 435 μm, about 440 μm, about 445 μm, about 450 μm, about 455 μm, about 460 μm, about 465 μm, about 470 μm, about 475 μm, about 480 μm, about 485 μm, about 490 μm, about 495 μm, about 500 μm, about 505 μm, about 510 μm, about 515 μm, about 520 μm, about 525 μm, about 530 μm, about 535 μm, about 540 μm, about 545 μm, about 550 μm, about 555 μm, about 560 μm, about 565 μm, about 570 μm, about 575 μm, about 580 μm, about 585 μm, about 590 μm, about 595 μm, about 600 μm, about 605 μm, about 610 μm, about 615 μm, about 620 μm, about 625 μm, about 630 μm, about 635 μm, about 640 μm, about 645 μm, about 650 μm, about 655 μm, about 660 μm, about 665 μm, about 670 μm, about 675 μm, about 680 μm, about 685 μm, about 690 μm, about 695 μm, about 700 μm, about 705 μm, about 710 μm, about 715 μm, about 720 μm, about 725 μm, about 730 μm, about 735 μm, about 740 μm, about 745 μm, about 750 μm, about 755 μm, about 760 μm, about 765 μm, about 770 μm, about 775 μm, about 780 μm, about 785 μm, about 790 μm, about 795 μm, about 800 μm, about 805 μm, about 810 μm, about 815 μm, about 820 μm, about 825 μm, about 830 μm, about 835 μm, about 840 μm, about 845 μm, about 850 μm, about 855 μm, about 860 μm, about 865 μm, about 870 μm, about 875 μm, about 880 μm, about 885 μm, about 890 μm, about 895 μm, about 900 μm, about 905 μm, about 910 μm, about 915 μm, about 920 μm, about 925 μm, about 930 μm, about 935 μm, about 940 μm, about 945 μm, about 950 μm, about 955 μm, about 960 μm, about 965 μm, about 970 μm, about 975 μm, about 980 μm, about 985 μm, about 990 μm, about 995 μm, or about 1000 μm).

In some embodiments, the microneedle and/or the microarray patch (MAP) can comprise a plurality of layers, wherein each layer is independently formed from a dispensable formulation described herein. In some embodiments, the microneedle comprises at least 2 layers, wherein each layer is independently formed from a dispensable formulation described herein. In some embodiments, the microneedle comprises 2, 3, 4, 5, 6, 7, 8, 9, 10, 11, 12, 13, 14, 15, 16, 17, 18, 19, 20, 21, 22, 23, 24, or 25 or more layers, wherein each layer is independently formed from a dispensable formulation described herein. In some embodiments, each layer can independently be formed from a predefined volume of the dispensable formulation. In some embodiments, the predefined volume of the dispensable formulation can be about 1 nL to about 1000 nL (e.g., about 1 nL, about 5 nL, about 10 nL, about 15 nL, about 20 nL, about 25 nL, about 30 nL, about 35 nL, about 40 nL, about 45 nL, about 50 nL, about 55 nL, about 60 nL, about 65 nL, about 70 nL, about 75 nL, about 80 nL, about 85 nL, about 90 nL, about 95 nL, about 100 nL, about 105 nL, about 110 nL, about 115 nL, about 120 nL, about 125 nL, about 130 nL, about 135 nL, about 140 nL, about 145 nL, about 150 nL, about 155 nL, about 160 nL, about 165 nL, about 170 nL, about 175 nL, about 180 nL, about 185 nL, about 190 nL, about 195 nL, about 200 nL, about 205 nL, about 210 nL, about 215 nL, about 220 nL, about 225 nL, about 230 nL, about 235 nL, about 240 nL, about 245 nL, about 250 nL, about 255 nL, about 260 nL, about 265 nL, about 270 nL, about 275 nL, about 280 nL, about 285 nL, about 290 nL, about 295 nL, about 300 nL, about 305 nL, about 310 nL, about 315 nL, about 320 nL, about 325 nL, about 330 nL, about 335 nL, about 340 nL, about 345 nL, about 350 nL, about 355 nL, about 360 nL, about 365 nL, about 370 nL, about 375 nL, about 380 nL, about 385 nL, about 390 nL, about 395 nL, about 400 nL, about 405 nL, about 410 nL, about 415 nL, about 420 nL, about 425 nL, about 430 nL, about 435 nL, about 440 nL, about 445 nL, about 450 nL, about 455 nL, about 460 nL, about 465 nL, about 470 nL, about 475 nL, about 480 nL, about 485 nL, about 490 nL, about 495 nL, about 500 nL, about 505 nL, about 510 nL, about 515 nL, about 520 nL, about 525 nL, about 530 nL, about 535 nL, about 540 nL, about 545 nL, about 550 nL, about 555 nL, about 560 nL, about 565 nL, about 570 nL, about 575 nL, about 580 nL, about 585 nL, about 590 nL, about 595 nL, about 600 nL, about 605 nL, about 610 nL, about 615 nL, about 620 nL, about 625 nL, about 630 nL, about 635 nL, about 640 nL, about 645 nL, about 650 nL, about 655 nL, about 660 nL, about 665 nL, about 670 nL, about 675 nL, about 680 nL, about 685 nL, about 690 nL, about 695 nL, about 700 nL, about 705 nL, about 710 nL, about 715 nL, about 720 nL, about 725 nL, about 730 nL, about 735 nL, about 740 nL, about 745 nL, about 750 nL, about 755 nL, about 760 nL, about 765 nL, about 770 nL, about 775 nL, about 780 nL, about 785 nL, about 790 nL, about 795 nL, about 800 nL, about 805 nL, about 810 nL, about 815 nL, about 820 nL, about 825 nL, about 830 nL, about 835 nL, about 840 nL, about 845 nL, about 850 nL, about 855 nL, about 860 nL, about 865 nL, about 870 nL, about 875 nL, about 880 nL, about 885 nL, about 890 nL, about 895 nL, about 900 nL, about 905 nL, about 910 nL, about 915 nL, about 920 nL, about 925 nL, about 930 nL, about 935 nL, about 940 nL, about 945 nL, about 950 nL, about 955 nL, about 960 nL, about 965 nL, about 970 nL, about 975 nL, about 980 nL, about 985 nL, about 990 nL, about 995 nL, or about 1000 nL). In some embodiments, each layer can independently be formed from a single drop of the dispensable formulation.

Consolidated Microneedle Tip

In some embodiments, the microneedle comprises a consolidated microneedle tip, comprising an active pharmaceutical ingredient (API) and a water-soluble excipient.

As used herein, the term "consolidated microneedle tip" refers to the apical portion, or apex, of the microneedle within which a predefined amount of an active pharmaceutical ingredient (API) can be concentrated, e.g., to reduce the risk of delivery of an insufficient amount of API if needle insertion fails and/or if partial needle penetration occurred. In some embodiments, the term "apex" refers to the end of the body of the microneedle that is furthest from the microneedle base. In some embodiments, the term "apex" refers to the sharpest portion of a microneedle, which can be characterized by, e.g., a tip radius, a tip diameter, and/or a tip angle. In some embodiments, the term "tip radius" or "consolidated tip radius" may refer to the radius of a circle equivalent in cross-sectional area to the smallest aspect of a microneedle, e.g., at the apex. In some embodiments, the term "tip diameter" or "consolidated tip diameter" may refer to the radius of a circle equivalent in cross-sectional area to the smallest aspect of a microneedle, e.g., at the apex. In some embodiments, the term "apex" refers to the portion of the microneedle that can be delivered to the deepest depth below the surface of the subject's skin, such that an indicated deployment depth "below the surface of the subject's skin" may refer to a portion of the microneedle having a three-dimensional structure defined by a "length" or a "percentage of the pre-deployment needle height" corresponding to the distance between the apex of the inserted microneedle (e.g., delivered to the deepest depth below the surface of the subject's skin) and the surface of the subject's skin. In some embodiments, an indicated deployment depth "below the surface of the subject's skin" may be expressed as a single value and/or as a range of values related to the "length" or the "percentage of the pre-deployment needle height" of the microneedle inserted into, that is "below the surface" of the subject's skin. Thus, it may be understood that API present within such a portion of the deployed microneedle may be effectively delivered to the subject by an appropriate release mechanism, while API present in portions of the microneedle (e.g., portions of the consolidated microneedle tip and/or microneedle base) that are not inserted may not be delivered to the subject. Accordingly, the consistency of deployment may be related to the number of and/or percentage of microneedles in a MAP that can be reliably inserted "below the surface" of the subject's skin to achieve delivery of an API. In some embodiments, the consistency of deployment may also be related to the percentage of the pre-deployment needle height that can be reliably inserted "below the surface" of the subject's skin to achieve delivery of an API. In some embodiments, a defect such as a shell or shell-like structure formed, e.g., from the dispensable tip formulation comprising an API, can lead to delivery of an insufficient amount of API if needle insertion fails and/or if partial needle penetration occurs.

In some embodiments, the consolidated microneedle tip may be characterized by a meniscus. In general, the term "meniscus" refers to the convex surface of liquid which is formed by surface tension. In the context of a meniscus, "concavity" refers to the curved, downward facing shape of the liquid surface, where the liquid appears to "curve up" the sides of the container, creating a concave appearance; this typically happens when the liquid molecules are more attracted to the container walls than to each other. In some embodiments, the consolidated microneedle tip may be characterized by a meniscus having a substantially concave shape. In the context of a meniscus, "convexity" refers to a curved upward surface of a liquid where the liquid molecules are more attracted to each other than to the container walls, causing the liquid to curve upwards, creating a dome-like shape. In some embodiments, the consolidated microneedle tip, e.g., after drying, may be characterized by a meniscus having a substantially convex shape. In some embodiments, the consolidated microneedle tip is characterized by a substantially flat meniscus. A "meniscus curvature angle" may refer to the angle formed by the curve of a meniscus, which may be the curved surface of a liquid within a container, generally describing how much the liquid curves at the edge of the container, and may be primarily influenced by the surface tension of the liquid and its adhesion to the container walls; a larger angle may indicate a more pronounced curve, while a smaller angle may indicate a flatter meniscus. A "flatter meniscus" or a "substantially flat meniscus" may have a meniscus curvature angle closer to 90 degrees, meaning that the contact angle between the liquid and the container wall is nearly perpendicular, resulting in a relatively flat surface at the liquid-air interface; generally, a flatter meniscus may indicate a contact angle approaching 90 degrees. In some embodiments, the consolidated microneedle tip is characterized by contact angles approaching 90 degrees. In some embodiments, the consolidated microneedle tip is characterized by contact angles of about 60 degrees to about 120 degrees (e.g., about 60 degrees, about 61 degrees, about 62 degrees, about 63 degrees, about 64 degrees, about 65 degrees, about 66 degrees, about 67 degrees, about 68 degrees, about 69 degrees, about 70 degrees, about 71 degrees, about 72 degrees, about 73 degrees, about 74 degrees, about 75 degrees, about 76 degrees, about 77 degrees, about 78 degrees, about 79 degrees, about 80 degrees, about 81 degrees, about 82 degrees, about 83 degrees, about 84 degrees, about 85 degrees, about 86 degrees, about 87 degrees, about 88 degrees, about 89 degrees, about 90 degrees, about 91 degrees, about 92 degrees, about 93 degrees, about 94 degrees, about 95 degrees, about 96 degrees, about 97 degrees, about 98 degrees, about 99 degrees, about 100 degrees, about 101 degrees, about 102 degrees, about 103 degrees, about 104 degrees, about 105 degrees, about 106 degrees, about 107 degrees, about 108 degrees, about 109 degrees, about 110 degrees, about 111 degrees, about 112 degrees, about 113 degrees, about 114 degrees, about 115 degrees, about 116 degrees, about 117 degrees, about 118 degrees, about 119 degrees, or about 120 degrees). In some embodiments, the consolidated microneedle tip is characterized by contact angles of about 70 degrees to about 110 degrees.

The meniscus curvature angle and/or the meniscus shape may be related to the liquid-air interface of a meniscus at the point where it touches the wall of a microprojection shaped cavity of a mold that defines the shape of a microneedle and/or a microarray patch (MAP) described herein during manufacturing. In some embodiments, the consolidated microneedle tip is characterized by a meniscus curvature angle and/or a meniscus shape that enhances the formation of the consolidated microneedle tip. In some embodiments, the meniscus curvature angle and/or the meniscus shape may be related to the formation of a defect, such as a shell or shell-like structure formed, e.g., from the dispensable tip formulation comprising an API, and which can lead to delivery of an insufficient amount of API if needle insertion fails and/or if partial needle penetration occurs. In particular embodiments, the consolidated microneedle tip does not comprise a shell and/or a shell-like structure. In some embodiments, the meniscus curvature angle and/or the meniscus shape may be determined before and/or after drying.

Without wishing to be bound by theory, Applicant has surprisingly discovered that specific combinations of water-soluble excipients can enhance, e.g., the consolidation of the API into the apex of the microneedle tip during manufacturing.

In some embodiments, the consolidated microneedle tip can be configured to release a predefined amount of an active pharmaceutical ingredients (API) (e.g., about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100% of the API) in a predefined period of time (e.g., about 5 seconds, about 10 seconds, about 15 seconds, about 20 seconds, about 25 seconds, about 30 seconds, about 35 seconds, about 40 seconds, about 45 seconds, about 50 seconds, about 55 seconds, or about 60 seconds; or about 5 minutes, about 10 minutes, about 15 minutes, about 20 minutes, about 25 minutes, about 30 minutes, about 35 minutes, about 40 minutes, about 45 minutes, about 50 minutes, about 55 minutes, or about 60 minutes; or about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, or about 24 hours; or about 1 day, about 2 days, about 3 days, about 4 days, about 5 days, about 6 days, or about 7 days; or about 1 week, about 2 weeks, about 3 weeks, about 4 weeks; or about 1 month, about 2 months, about 3 months, about 4 months, about 5 months, about 6 months, about 7 months, about 8 months, about 9 months, about 10 months, about 11 months, or about 12 months; or about 1 year, about 2 years, about 3 years, about 4 years, or about 5 years or more). In some embodiments, the consolidated microneedle tip can be configured to release a predefined amount of an active pharmaceutical ingredients (API) in a predefined period of time though a dissolution-diffusion mechanism. In some embodiments, the consolidated microneedle tip can be configured to release a predefined amount of an active pharmaceutical ingredients (API) though an immediate-release mechanism. In some embodiments, the consolidated microneedle tip can be configured to release a predefined amount of an active pharmaceutical ingredients (API) in a predefined period of time though a modified-release mechanism. Exemplary modified release mechanisms can include, e.g., controlled-release, sustained-release, and/or long-acting API products and/or consolidated microneedle tip formulations.

In some embodiments, the microneedle and/or the microarray patch (MAP) can be characterized by a consolidated microneedle tip length of about 200 μm to about 500 μm (e.g., about 200 μm, about 205 μm, about 210 μm, about 215 μm, about 220 μm, about 225 μm, about 230 μm, about 235 μm, about 240 μm, about 245 μm, about 250 μm, about 255 μm, about 260 μm, about 265 μm, about 270 μm, about 275 μm, about 280 μm, about 285 μm, about 290 μm, about 295 μm, about 300 μm, about 305 μm, about 310 μm, about 315 μm, about 320 μm, about 325 μm, about 330 μm, about 335 μm, about 340 μm, about 345 μm, about 350 μm, about 355 μm, about 360 μm, about 365 μm, about 370 μm, about 375 μm, about 380 μm, about 385 μm, about 390 μm, about 395 μm, about 400 μm, about 405 μm, about 410 μm, about 415 μm, about 420 μm, about 425 μm, about 430 μm, about 435 μm, about 440 μm, about 445 μm, about 450 μm, about 455 μm, about 460 μm, about 465 μm, about 470 μm, about 475 μm, about 480 μm, about 485 μm, about 490 μm, about 495 μm, or about 500 μm).

In some embodiments, the microneedle and/or the microarray patch (MAP) can be characterized by a consolidated microneedle tip length of greater than about 300 μm, e.g., about 300 μm to about 500 μm (e.g., about 300 μm, about 301 μm, about 302 μm, about 303 μm, about 304 μm, about 305 μm, about 306 μm, about 307 μm, about 308 μm, about 309 μm, about 310 μm, about 311 μm, about 312 μm, about 313 μm, about 314 μm, about 315 μm, about 316 μm, about 317 μm, about 318 μm, about 319 μm, about 320 μm, about 321 μm, about 322 μm, about 323 μm, about 324 μm, about 325 μm, about 326 μm, about 327 μm, about 328 μm, about 329 μm, about 330 μm, about 331 μm, about 332 μm, about 333 μm, about 334 μm, about 335 μm, about 336 μm, about 337 μm, about 338 μm, about 339 μm, about 340 μm, about 341 μm, about 342 μm, about 343 μm, about 344 μm, about 345 μm, about 346 μm, about 347 μm, about 348 μm, about 349 μm, about 350 μm, about 351 μm, about 352 μm, about 353 μm, about 354 μm, about 355 μm, about 356 μm, about 357 μm, about 358 μm, about 359 μm, about 360 μm, about 361 μm, about 362 μm, about 363 μm, about 364 μm, about 365 μm, about 366 μm, about 367 μm, about 368 μm, about 369 μm, about 370 μm, about 371 μm, about 372 μm, about 373 μm, about 374 μm, about 375 μm, about 376 μm, about 377 μm, about 378 μm, about 379 μm, about 380 μm, about 381 μm, about 382 μm, about 383 μm, about 384 μm, about 385 μm, about 386 μm, about 387 μm, about 388 μm, about 389 μm, about 390 μm, about 391 μm, about 392 μm, about 393 μm, about 394 μm, about 395 μm, about 396 μm, about 397 μm, about 398 μm, about 399 μm, about 400 μm, about 401 μm, about 402 μm, about 403 μm, about 404 μm, about 405 μm, about 406 μm, about 407 μm, about 408 μm, about 409 μm, about 410 μm, about 411 μm, about 412 μm, about 413 μm, about 414 μm, about 415 μm, about 416 μm, about 417 μm, about 418 μm, about 419 μm, about 420 μm, about 421 μm, about 422 μm, about 423 μm, about 424 μm, about 425 μm, about 426 μm, about 427 μm, about 428 μm, about 429 μm, about 430 μm, about 431 μm, about 432 μm, about 433 μm, about 434 μm, about 435 μm, about 436 μm, about 437 μm, about 438 μm, about 439 μm, about 440 μm, about 441 μm, about 442 μm, about 443 μm, about 444 μm, about 445 μm, about 446 μm, about 447 μm, about 448 μm, about 449 μm, about 450 μm, about 451 μm, about 452 μm, about 453 μm, about 454 μm, about 455 μm, about 456 μm, about 457 μm, about 458 μm, about 459 μm, about 460 μm, about 461 μm, about 462 μm, about 463 μm, about 464 μm, about 465 μm, about 466 μm, about 467 μm, about 468 μm, about 469 μm, about 470 μm, about 471 μm, about 472 μm, about 473 μm, about 474 μm, about 475 μm, about 476 μm, about 477 μm, about 478 μm, about 479 μm, about 480 μm, about 481 μm, about 482 μm, about 483 μm, about 484 μm, about 485 μm, about 486 μm, about 487 μm, about 488 μm, about 489 μm, about 490 μm, about 491 μm, about 492 μm, about 493 μm, about 494 μm, about 495 μm, about 496 μm, about 497 μm, about 498 μm, about 499 μm, or about 500 μm).

In some embodiments, the microneedle and/or the microarray patch (MAP) can be characterized by a consolidated microneedle tip length of greater than about 400 μm, e.g., about 400 μm to about 500 μm (e.g., about 400 μm, about 401 μm, about 402 μm, about 403 μm, about 404 μm, about 405 μm, about 406 μm, about 407 μm, about 408 μm, about 409 μm, about 410 μm, about 411 μm, about 412 μm, about 413 μm, about 414 μm, about 415 μm, about 416 μm, about 417 μm, about 418 μm, about 419 μm, about 420 μm, about 421 μm, about 422 μm, about 423 μm, about 424 μm, about 425 μm, about 426 μm, about 427 μm, about 428 μm, about 429 μm, about 430 μm, about 431 μm, about 432 μm, about 433 μm, about 434 μm, about 435 μm, about 436 μm, about 437 μm, about 438 μm, about 439 μm, about 440 μm, about 441 μm, about 442 μm, about 443 μm, about 444 μm, about 445 μm, about 446 μm, about 447 μm, about 448 μm, about 449 μm, about 450 μm, about 451 μm, about 452 μm, about 453 μm, about 454 μm, about 455 μm, about 456 μm, about 457 μm, about 458 μm, about 459 μm, about 460 μm, about 461 μm, about 462 μm, about 463 μm, about 464 μm, about 465 μm, about 466 μm, about 467 μm, about 468 μm, about 469 μm, about 470 μm, about 471 μm, about 472 μm, about 473 μm, about 474 μm, about 475 μm, about 476 μm, about 477 μm, about 478 μm, about 479 μm, about 480 μm, about 481 μm, about 482 μm, about 483 μm, about 484 μm, about 485 μm, about 486 μm, about 487 μm, about 488 μm, about 489 μm, about 490 μm, about 491 μm, about 492 μm, about 493 μm, about 494 μm, about 495 μm, about 496 μm, about 497 μm, about 498 μm, about 499 μm, or about 500 μm).

In some embodiments, the microneedle and/or the microarray patch (MAP) can be characterized by a consolidated tip diameter of about 0.25 μm to about 50 μm (e.g., about 0.25 μm, about 0.5 μm, about 1 μm, about 2 μm, about 3 μm, about 4 μm, about 5 μm, about 6 μm, about 7 μm, about 8 μm, about 9 μm, about 10 μm, about 11 μm, about 12 μm, about 13 μm, about 14 μm, about 15 μm, about 16 μm, about 17 μm, about 18 μm, about 19 μm, about 20 μm, about 21 μm, about 22 μm, about 23 μm, about 24 μm, about 25 μm, about 26 μm, about 27 μm, about 28 μm, about 29 μm, about 30 μm, about 31 μm, about 32 μm, about 33 μm, about 34 μm, about 35 μm, about 36 μm, about 37 μm, about 38 μm, about 39 μm, about 40 μm, about 41 μm, about 42 μm, about 43 μm, about 44 μm, about 45 μm, about 46 μm, about 47 μm, about 48 μm, about 49 μm, or about 50 μm). In some embodiments, the microneedles described herein can be characterized by a consolidated tip diameter of about 1 μm to about 25 μm. In some embodiments, the microneedle and/or the microarray patch (MAP) can be characterized by a consolidated tip diameter of about 1 μm to about 15 μm. In some embodiments, the microneedle and/or the microarray patch (MAP) can be characterized by a consolidated tip diameter of about 1 μm to about 5 μm.

In some embodiments, the microneedles and/or microarray patches (MAPs) described can be characterized by a consolidated tip angle of about 5° to about 50° (e.g., about 5°, about 6°, about 7°, about 8°, about 9°, about 10°, about 11°, about 12°, about 13°, about 14°, about 15°, about 16°, about 17°, about 18°, about 19°, about 20°, about 21°, about 22°, about 23°, about 24°, about 25°, about 26°, about 27°, about 28°, about 29°, about 30°, about 31°, about 32°, about 33°, about 34°, about 35°, about 36°, about 37°, about 38°, about 39°, about 40°, about 41°, about 42°, about 43°, about 44°, about 45°, about 46°, about 47°, about 48°, about 49°, or about) 50°.

In some embodiments, the consolidated microneedle tip comprises a plurality of layers, wherein each layer is independently formed from a dispensable formulation described herein. In some embodiments, the consolidated microneedle tip comprises at least 2 layers, wherein each layer is independently formed from a dispensable formulation described herein. In some embodiments, the consolidated microneedle tip comprises 2, 3, 4, 5, 6, 7, 8, 9, 10, 11, 12, 13, 14, 15, 16, 17, 18, 19, 20, 21, 22, 23, 24, or 25 or more layers, wherein each layer is independently formed from a dispensable formulation described herein. In some embodiments, each layer can independently be formed from a predefined volume of the dispensable formulation. In some embodiments, the predefined volume of the dispensable formulation can be about 1 nL to about 1000 nL (e.g., about 1 nL, about 5 nL, about 10 nL, about 15 nL, about 20 nL, about 25 nL, about 30 nL, about 35 nL, about 40 nL, about 45 nL, about 50 nL, about 55 nL, about 60 nL, about 65 nL, about 70 nL, about 75 nL, about 80 nL, about 85 nL, about 90 nL, about 95 nL, about 100 nL, about 105 nL, about 110 nL, about 115 nL, about 120 nL, about 125 nL, about 130 nL, about 135 nL, about 140 nL, about 145 nL, about 150 nL, about 155 nL, about 160 nL, about 165 nL, about 170 nL, about 175 nL, about 180 nL, about 185 nL, about 190 nL, about 195 nL, about 200 nL, about 205 nL, about 210 nL, about 215 nL, about 220 nL, about 225 nL, about 230 nL, about 235 nL, about 240 nL, about 245 nL, about 250 nL, about 255 nL, about 260 nL, about 265 nL, about 270 nL, about 275 nL, about 280 nL, about 285 nL, about 290 nL, about 295 nL, about 300 nL, about 305 nL, about 310 nL, about 315 nL, about 320 nL, about 325 nL, about 330 nL, about 335 nL, about 340 nL, about 345 nL, about 350 nL, about 355 nL, about 360 nL, about 365 nL, about 370 nL, about 375 nL, about 380 nL, about 385 nL, about 390 nL, about 395 nL, about 400 nL, about 405 nL, about 410 nL, about 415 nL, about 420 nL, about 425 nL, about 430 nL, about 435 nL, about 440 nL, about 445 nL, about 450 nL, about 455 nL, about 460 nL, about 465 nL, about 470 nL, about 475 nL, about 480 nL, about 485 nL, about 490 nL, about 495 nL, about 500 nL, about 505 nL, about 510 nL, about 515 nL, about 520 nL, about 525 nL, about 530 nL, about 535 nL, about 540 nL, about 545 nL, about 550 nL, about 555 nL, about 560 nL, about 565 nL, about 570 nL, about 575 nL, about 580 nL, about 585 nL, about 590 nL, about 595 nL, about 600 nL, about 605 nL, about 610 nL, about 615 nL, about 620 nL, about 625 nL, about 630 nL, about 635 nL, about 640 nL, about 645 nL, about 650 nL, about 655 nL, about 660 nL, about 665 nL, about 670 nL, about 675 nL, about 680 nL, about 685 nL, about 690 nL, about 695 nL, about 700 nL, about 705 nL, about 710 nL, about 715 nL, about 720 nL, about 725 nL, about 730 nL, about 735 nL, about 740 nL, about 745 nL, about 750 nL, about 755 nL, about 760 nL, about 765 nL, about 770 nL, about 775 nL, about 780 nL, about 785 nL, about 790 nL, about 795 nL, about 800 nL, about 805 nL, about 810 nL, about 815 nL, about 820 nL, about 825 nL, about 830 nL, about 835 nL, about 840 nL, about 845 nL, about 850 nL, about 855 nL, about 860 nL, about 865 nL, about 870 nL, about 875 nL, about 880 nL, about 885 nL, about 890 nL, about 895 nL, about 900 nL, about 905 nL, about 910 nL, about 915 nL, about 920 nL, about 925 nL, about 930 nL, about 935 nL, about 940 nL, about 945 nL, about 950 nL, about 955 nL, about 960 nL, about 965 nL, about 970 nL, about 975 nL, about 980 nL, about 985 nL, about 990 nL, about 995 nL, or about 1000 nL). In some embodiments, each layer can independently be formed from a single drop of the dispensable formulation.

Microneedle Base

In some embodiments, the microneedle comprises a microneedle base, comprising a water-soluble excipient.

As used herein, the term "microneedle base" refers to the portion of the microneedle that functions as a support or pedestal for the consolidated microneedle tip, and/or that functions to connect adjacent microneedles to form a continuous microarray patch (MAP). In some embodiments, the microneedle base is dissolvable. In some embodiments, at least about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100% of the microneedle base is dissolved upon application to the skin of a subject in a predefined period of time (e.g., about 5 seconds, about 10 seconds, about 15 seconds, about 20 seconds, about 25 seconds, about 30 seconds, about 35 seconds, about 40 seconds, about 45 seconds, about 50 seconds, about 55 seconds, or about 60 seconds; or about 5 minutes, about 10 minutes, about 15 minutes, about 20 minutes, about 25 minutes, or about 30 minutes). In some embodiments, at least about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100% of the microneedle base is inserted into the skin of a subject upon deployment. In some embodiments, the microneedle base comprises a material that can dissolve into the skin, e.g., within the intended wear time (e.g., about five minutes). In some embodiments, the at least about 10%, 20%, 30%, 40%, 50%, 60%, 70%, 80%, 90%, or 100% of the dissolvable base layer is dissolved after application, e.g., to the skin, within the intended wear time (e.g., about 1 minute, about 2 minutes, about 3 minutes, about 4 minutes, about 5 minutes, about 6 minutes, about 7 minutes, about 8 minutes, about 9 minutes, or about 10 minutes or more).

In some embodiments, the microneedle base comprises less than 100% (e.g., less than about 1%, less than about 5%, less than about 10%, less than about 15%, less than about 20%, less than about 25%, less than about 30%, less than about 35%, less than about 40%, less than about 45%, less than about 50%, less than about 55%, less than about 60%, less than about 65%, less than about 70%, less than about 75%, less than about 80%, less than about 85%, less than about 90%, less than about 95%, or less than about 100%) of the total amount (e.g., dose) of a API loaded into the microneedle and/or the MAP. In some embodiments, the microneedle base does not comprise, e.g., a detectable amount of an API. In some embodiments, the microneedle base is formulated to limit and/or reduce the amount of API leakage (e.g., diffusion) from the consolidated microneedle tip into the microneedle base.

In some embodiments, the microneedle base comprises a material that can dissolve into the skin, e.g., within the intended wear time (e.g., about five minutes). In some embodiments, at least about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% of the microneedle base is dissolved after application, e.g., to the skin, within the intended wear time (e.g., about 1 minute, about 2 minutes, about 3 minutes, about 4 minutes, about 5 minutes, about 6 minutes, about 7 minutes, about 8 minutes, about 9 minutes, or about 10 minutes or more).

In some embodiments, the consolidated microneedle tip comprises a material that can dissolve into the skin, e.g., within the intended wear time (e.g., about five minutes). In some embodiments, at least about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% of the consolidated microneedle tip is dissolved after application, e.g., to the skin, within the intended wear time (e.g., about 1 minute, about 2 minutes, about 3 minutes, about 4 minutes, about 5 minutes, about 6 minutes, about 7 minutes, about 8 minutes, about 9 minutes, or about 10 minutes or more).

In some embodiments, the microneedle and/or the microarray patch (MAP) can be characterized by a base length of about 25 μm to about 2500 μm (e.g., about 25 μm, about 50 μm, about 75 μm, about 100 μm, about 125 μm, about 150 μm, about 175 μm, about 200 μm, about 225 μm, about 250 μm, about 275 μm, about 300 μm, about 325 μm, about 350 μm, about 375 μm, about 400 μm, about 425 μm, about 450 μm, about 475 μm, about 500 μm, about 525 μm, about 550 μm, about 575 μm, about 600 μm, about 625 μm, about 650 μm, about 675 μm, about 700 μm, about 725 μm, about 750 μm, about 775 μm, about 800 μm, about 825 μm, about 850 μm, about 875 μm, about 900 μm, about 925 μm, about 950 μm, about 975 μm, about 1000 μm, about 1025 μm, about 1050 μm, about 1075 μm, about 1100 μm, about 1125 μm, about 1150 μm, about 1175 μm, about 1200 μm, about 1225 μm, about 1250 μm, about 1275 μm, about 1300 μm, about 1325 μm, about 1350 μm, about 1375 μm, about 1400 μm, about 1425 μm, about 1450 μm, about 1475 μm, about 1500 μm, about 1525 μm, about 1550 μm, about 1575 μm, about 1600 μm, about 1625 μm, about 1650 μm, about 1675 μm, about 1700 μm, about 1725 μm, about 1750 μm, about 1775 μm, about 1800 μm, about 1825 μm, about 1850 μm, about 1875 μm, about 1900 μm, about 1925 μm, about 1950 μm, about 1975 μm, about 2000 μm, about 2025 μm, about 2050 μm, about 2075 μm, about 2100 μm, about 2125 μm, about 2150 μm, about 2175 μm, about 2200 μm, about 2225 μm, about 2250 μm, about 2275 μm, about 2300 μm, about 2325 μm, about 2350 μm, about 2375 μm, about 2400 μm, about 2425 μm, about 2450 μm, about 2475 μm, or about 2500 μm).

In some embodiments, the microneedle base comprises a plurality of layers, wherein each layer is independently formed from a dispensable formulation described herein. In some embodiments, the microneedle base comprises at least 2 layers, wherein each layer is independently formed from a dispensable formulation described herein. In some embodiments, the microneedle base comprises 2, 3, 4, 5, 6, 7, 8, 9, 10, 11, 12, 13, 14, 15, 16, 17, 18, 19, 20, 21, 22, 23, 24, or 25 or more layers, wherein each layer is independently formed from a dispensable formulation described herein. In some embodiments, each layer can independently be formed from a predefined volume of the dispensable formulation. In some embodiments, the predefined volume of the dispensable formulation can be about 1 nL to about 1000 nL (e.g., about 1 nL, about 5 nL, about 10 nL, about 15 nL, about 20 nL, about 25 nL, about 30 nL, about 35 nL, about 40 nL, about 45 nL, about 50 nL, about 55 nL, about 60 nL, about 65 nL, about 70 nL, about 75 nL, about 80 nL, about 85 nL, about 90 nL, about 95 nL, about 100 nL, about 105 nL, about 110 nL, about 115 nL, about 120 nL, about 125 nL, about 130 nL, about 135 nL, about 140 nL, about 145 nL, about 150 nL, about 155 nL, about 160 nL, about 165 nL, about 170 nL, about 175 nL, about 180 nL, about 185 nL, about 190 nL, about 195 nL, about 200 nL, about 205 nL, about 210 nL, about 215 nL, about 220 nL, about 225 nL, about 230 nL, about 235 nL, about 240 nL, about 245 nL, about 250 nL, about 255 nL, about 260 nL, about 265 nL, about 270 nL, about 275 nL, about 280 nL, about 285 nL, about 290 nL, about 295 nL, about 300 nL, about 305 nL, about 310 nL, about 315 nL, about 320 nL, about 325 nL, about 330 nL, about 335 nL, about 340 nL, about 345 nL, about 350 nL, about 355 nL, about 360 nL, about 365 nL, about 370 nL, about 375 nL, about 380 nL, about 385 nL, about 390 nL, about 395 nL, about 400 nL, about 405 nL, about 410 nL, about 415 nL, about 420 nL, about 425 nL, about 430 nL, about 435 nL, about 440 nL, about 445 nL, about 450 nL, about 455 nL, about 460 nL, about 465 nL, about 470 nL, about 475 nL, about 480 nL, about 485 nL, about 490 nL, about 495 nL, about 500 nL, about 505 nL, about 510 nL, about 515 nL, about 520 nL, about 525 nL, about 530 nL, about 535 nL, about 540 nL, about 545 nL, about 550 nL, about 555 nL, about 560 nL, about 565 nL, about 570 nL, about 575 nL, about 580 nL, about 585 nL, about 590 nL, about 595 nL, about 600 nL, about 605 nL, about 610 nL, about 615 nL, about 620 nL, about 625 nL, about 630 nL, about 635 nL, about 640 nL, about 645 nL, about 650 nL, about 655 nL, about 660 nL, about 665 nL, about 670 nL, about 675 nL, about 680 nL, about 685 nL, about 690 nL, about 695 nL, about 700 nL, about 705 nL, about 710 nL, about 715 nL, about 720 nL, about 725 nL, about 730 nL, about 735 nL, about 740 nL, about 745 nL, about 750 nL, about 755 nL, about 760 nL, about 765 nL, about 770 nL, about 775 nL, about 780 nL, about 785 nL, about 790 nL, about 795 nL, about 800 nL, about 805 nL, about 810 nL, about 815 nL, about 820 nL, about 825 nL, about 830 nL, about 835 nL, about 840 nL, about 845 nL, about 850 nL, about 855 nL, about 860 nL, about 865 nL, about 870 nL, about 875 nL, about 880 nL, about 885 nL, about 890 nL, about 895 nL, about 900 nL, about 905 nL, about 910 nL, about 915 nL, about 920 nL, about 925 nL, about 930 nL, about 935 nL, about 940 nL, about 945 nL, about 950 nL, about 955 nL, about 960 nL, about 965 nL, about 970 nL, about 975 nL, about 980 nL, about 985 nL, about 990 nL, about 995 nL, or about 1000 nL). In some embodiments, each layer can independently be formed from a single drop of the dispensable formulation.

In some embodiments, the microneedles and/or microarray patches (MAPs) described herein can be formed from a dispensable formulation, such as a dispensable tip formulation and/or a dispensable base formulation described herein.

In some embodiments, the consolidated microneedle tip can be formed from about 10 nL to about 100 nL (e.g., about 10 nL, about 11 nL, about 12 nL, about 13 nL, about 14 nL, about 15 nL, about 16 nL, about 17 nL, about 18 nL, about 19 nL, about 20 nL, about 21 nL, about 22 nL, about 23 nL, about 24 nL, about 25 nL, about 26 nL, about 27 nL, about 28 nL, about 29 nL, about 30 nL, about 31 nL, about 32 nL, about 33 nL, about 34 nL, about 35 nL, about 36 nL, about 37 nL, about 38 nL, about 39 nL, about 40 nL, about 41 nL, about 42 nL, about 43 nL, about 44 nL, about 45 nL, about 46 nL, about 47 nL, about 48 nL, about 49 nL, about 50 nL, about 51 nL, about 52 nL, about 53 nL, about 54 nL, about 55 nL, about 56 nL, about 57 nL, about 58 nL, about 59 nL, about 60 nL, about 61 nL, about 62 nL, about 63 nL, about 64 nL, about 65 nL, about 66 nL, about 67 nL, about 68 nL, about 69 nL, about 70 nL, about 71 nL, about 72 nL, about 73 nL, about 74 nL, about 75 nL, about 76 nL, about 77 nL, about 78 nL, about 79 nL, about 80 nL, about 81 nL, about 82 nL, about 83 nL, about 84 nL, about 85 nL, about 86 nL, about 87 nL, about 88 nL, about 89 nL, about 90 nL, about 91 nL, about 92 nL, about 93 nL, about 94 nL, about 95 nL, about 96 nL, about 97 nL, about 98 nL, about 99 nL, or about 100 nL) of a dispensable tip formulation described herein (also referred to herein as the "tip fill volume"). In some embodiments, the tip fill volume may be dispensed to fill, or to partially fill, a microprojection shaped cavity of a mold that defines the shape of a microneedle and/or a microarray patch (MAP) described herein. In some embodiments, the tip fill volume is dispensed to fill, or to partially fill, a microprojection shaped cavity of a mold that defines the shape of a microneedle and/or a microarray patch (MAP) prior to, or concurrently with, the base fill volume. In some embodiments, the tip fill volume is dispensed to fill, or to partially fill, a microprojection shaped cavity of a mold that defines the shape of a microneedle and/or a microarray patch (MAP) in a single drop. In some embodiments, the tip fill volume is dispensed to fill, or to partially fill, a microprojection shaped cavity of a mold that defines the shape of a microneedle and/or a microarray patch (MAP) in a dropwise manner.

In some embodiments, the microneedle base can be formed from about 50 nL to about 5000 nL (e.g., 50 nL, about 75 nL, about 100 nL, about 125 nL, about 150 nL, about 175 nL, about 200 nL, about 225 nL, about 250 nL, about 275 nL, about 300 nL, about 325 nL, about 350 nL, about 375 nL, about 400 nL, about 425 nL, about 450 nL, about 475 nL, about 500 nL, about 525 nL, about 550 nL, about 575 nL, about 600 nL, about 625 nL, about 650 nL, about 675 nL, about 700 nL, about 725 nL, about 750 nL, about 775 nL, about 800 nL, about 825 nL, about 850 nL, about 875 nL, about 900 nL, about 925 nL, about 950 nL, about 975 nL, about 1000 nL, about 1025 nL, about 1050 nL, about 1075 nL, about 1100 nL, about 1125 nL, about 1150 nL, about 1175 nL, about 1200 nL, about 1225 nL, about 1250 nL, about 1275 nL, about 1300 nL, about 1325 nL, about 1350 nL, about 1375 nL, about 1400 nL, about 1425 nL, about 1450 nL, about 1475 nL, about 1500 nL, about 1525 nL, about 1550 nL, about 1575 nL, about 1600 nL, about 1625 nL, about 1650 nL, about 1675 nL, about 1700 nL, about 1725 nL, about 1750 nL, about 1775 nL, about 1800 nL, about 1825 nL, about 1850 nL, about 1875 nL, about 1900 nL, about 1925 nL, about 1950 nL, about 1975 nL, about 2000 nL, about 2025 nL, about 2050 nL, about 2075 nL, about 2100 nL, about 2125 nL, about 2150 nL, about 2175 nL, about 2200 nL, about 2225 nL, about 2250 nL, about 2275 nL, about 2300 nL, about 2325 nL, about 2350 nL, about 2375 nL, about 2400 nL, about 2425 nL, about 2450 nL, about 2475 nL, about 2500 nL, about 2525 nL, about 2550 nL, about 2575 nL, about 2600 nL, about 2625 nL, about 2650 nL, about 2675 nL, about 2700 nL, about 2725 nL, about 2750 nL, about 2775 nL, about 2800 nL, about 2825 nL, about 2850 nL, about 2875 nL, about 2900 nL, about 2925 nL, about 2950 nL, about 2975 nL, about 3000 nL, about 3025 nL, about 3050 nL, about 3075 nL, about 3100 nL, about 3125 nL, about 3150 nL, about 3175 nL, about 3200 nL, about 3225 nL, about 3250 nL, about 3275 nL, about 3300 nL, about 3325 nL, about 3350 nL, about 3375 nL, about 3400 nL, about 3425 nL, about 3450 nL, about 3475 nL, about 3500 nL, about 3525 nL, about 3550 nL, about 3575 nL, about 3600 nL, about 3625 nL, about 3650 nL, about 3675 nL, about 3700 nL, about 3725 nL, about 3750 nL, about 3775 nL, about 3800 nL, about 3825 nL, about 3850 nL, about 3875 nL, about 3900 nL, about 3925 nL, about 3950 nL, about 3975 nL, about 4000 nL, about 4025 nL, about 4050 nL, about 4075 nL, about 4100 nL, about 4125 nL, about 4150 nL, about 4175 nL, about 4200 nL, about 4225 nL, about 4250 nL, about 4275 nL, about 4300 nL, about 4325 nL, about 4350 nL, about 4375 nL, about 4400 nL, about 4425 nL, about 4450 nL, about 4475 nL, about 4500 nL, about 4525 nL, about 4550 nL, about 4575 nL, about 4600 nL, about 4625 nL, about 4650 nL, about 4675 nL, about 4700 nL, about 4725 nL, about 4750 nL, about 4775 nL, about 4800 nL, about 4825 nL, about 4850 nL, about 4875 nL, about 4900 nL, about 4925 nL, about 4950 nL, about 4975 nL, or about 5000 nL) of a dispensable base formulation described herein (also referred to herein as the "base fill volume"). In some embodiments, the base fill volume may be dispensed to fill, or to partially fill, a microprojection shaped cavity of a mold that defines the shape of a microneedle and/or a microarray patch (MAP) described herein. In some embodiments, the base fill volume is dispensed to fill, or to partially fill, a microprojection shaped cavity of a mold that defines the shape of a microneedle and/or a microarray patch (MAP) concurrently with, or subsequent to, the tip fill volume. In some embodiments, the base fill volume is dispensed to fill, or to partially fill, a microprojection shaped cavity of a mold that defines the shape of a microneedle and/or a microarray patch (MAP) in a dropwise manner, e.g., using a progressive base fill. In some embodiments, the base fill volume is dispensed to fill, or to partially fill, a microprojection shaped cavity of a mold that defines the shape of a microneedle and/or a microarray patch (MAP) in a single drop.

Microneedle and Microarray Patch (MAP) Systems

The microneedles and/or microarray patches (MAPs) described herein can be applied, e.g., to the skin of a subject, using a device, such as an applicator. Accordingly, in one aspect, the disclosure provides a system, comprising: (i) a microneedle and/or a MAP; and (ii) a device, such as an applicator. The device, e.g., the applicator, can be configured to facilitate consistent deployment of the microneedles and/or MAPs described herein to achieve effective API delivery. Exemplary devices, applicators, and systems are described, for example, in International Publication No. WO2023/250117, International Application No. PCT/US2024/034901, and International Application No. PCT/US2024/062002 filed Dec. 26, 2024, the contents of which are incorporated herein by reference in their entirety.

It is generally known in the art that microneedles can often suffer from insufficient skin insertion. This can occur when microneedles are not able to sufficiently puncture and penetrate into the skin, leading to inconsistent delivery of an active pharmaceutical ingredient (API). In some instances, deformation, fracture, or breakage of microneedles during or after patch administration can alter the release profile of the API, which may lead to changes in the pharmacokinetics of the API. Numerous factors can affect the efficiency of microneedle insertion, including, but not limited to the materials and processes that are used to form the microneedle, microneedle geometry, needle type, density, size, shape, tip and base diameters, height, needle density, indentation forces, minimum curvature radius to pierce the stratum corneum, skin thickness, and/or skin elasticity. The mechanical strength of the microneedles may also be altered by the presence of an API and/or water-soluble excipient. Moreover, while the ability to insert efficiently is an important factor when manufacturing microneedles, other factors should also be considered, such as cost, biocompatibility, and batch production capabilities. As such, microneedles that readily insert into the skin may not necessarily be considered viable for clinical applications due to the combination of these other factors. One of skill in the art will appreciate that the dispensable formulations, systems, and methods provided herein can be used to achieve the desired mechanical properties and consistent deployment of the microneedles and/or MAPs described herein to achieve effective API delivery for specific clinical applications. In certain embodiments, the applicator can be specifically configured to provide a predetermined force (e.g., impact energy) sufficient to achieve skin penetration and deployment of a consolidated microneedle tip (e.g., formed from a dispensable tip formulation described herein), e.g., at a sufficient depth within or beneath the surface of a subject's skin for successful API delivery.

In order to improve consistency and effectiveness of MAP application, an automated applicator device may be desirable. Accordingly, in some embodiments, the present disclosure provides an applicator device having one or more features or advantages over existing devices or simple manual application. The disclosed devices may be configured for repeated or single use, and the devices may be pre-loaded with a MAP (i.e., as a kit or system product including applicator and MAP). Alternatively, the applicator may be separate from a MAP, and a MAP may be selected and loaded to the device (e.g., based on desired APIs, patient characteristics, or need for additional applications for more than one patient or for a patient that needs more than one MAP). In some embodiments, the applicator can improve MAP application by one or more of (1) properly holding, stretching, and/or pre-tensioning skin to receive the MAP, (2) applying a reliable degree of force and/or depth of force against the skin to ensure proper microneedle placement, and/or (3) controlling distribution of application force across the MAP and/or microneedles.

As used herein, the term "consistent" in the context of the deployment of the microneedles and/or MAPs described herein generally refers to the repeatability of achieving the appropriate level of microneedle penetration required for successful API delivery. In some embodiments, such consistency is more easily achieved by utilizing the system, comprising: (i) a microneedle and/or a MAP; and (ii) a device, such as an applicator, described herein. In certain embodiments, the applicator can be specifically configured to provide a predetermined force (e.g., impact energy) sufficient to achieve skin penetration and deployment of at least about 50% of the consolidated microneedle tips present in a microarray patch (MAP), e.g., at a sufficient depth within or beneath the surface of a subject's skin for successful API delivery. In some embodiments, the sufficiency of deployment of the microneedles and/or the MAPs may be characterized by a pre-deployment needle height (or "needle height"), an air gap, a post-deployment needle height, a deployed tip depth, and/or a height delivered that can be achieved in using the system with applicator described herein.

In some embodiments, the microneedles and/or microarray patches (MAPs) can be applied, e.g., to the skin of a subject, using an applicator characterized by a piston velocity of about 0.5 m/s to about 20 m/s (e.g., about 0.5 m/s, about 1 m/s, about 1.5 m/s, about 2 m/s, about 2.5 m/s, about 3 m/s, about 3.5 m/s, about 4 m/s, about 4.5 m/s, about 5 m/s, about 5.5 m/s, about 6 m/s, about 6.5 m/s, about 7 m/s, about 7.5 m/s, about 8 m/s, about 8.5 m/s, about 9 m/s, about 9.5 m/s, about 10 m/s, about 10.5 m/s, about 11 m/s, about 11.5 m/s, about 12 m/s, about 12.5 m/s, about 13 m/s, about 13.5 m/s, about 14 m/s, about 14.5 m/s, about 15 m/s, about 15.5 m/s, about 16 m/s, about 16.5 m/s, about 17 m/s, about 17.5 m/s, about 18 m/s, about 18.5 m/s, about 19 m/s, about 19.5 m/s, or about 20 m/s).

In some embodiments, the microneedles and/or microarray patches (MAPs) can be applied, e.g., to the skin of a subject, using an applicator characterized by an energy per needle of about 0.1 mJ to about 5 mJ (e.g., about 0.1 mJ, about 0.2 mJ, about 0.3 mJ, about 0.4 mJ, about 0.5 mJ, about 0.6 mJ, about 0.7 mJ, about 0.8 mJ, about 0.9 mJ, about 1 mJ, about 1.1 mJ, about 1.2 mJ, about 1.3 mJ, about 1.4 mJ, about 1.5 mJ, about 1.6 mJ, about 1.7 mJ, about 1.8 mJ, about 1.9 mJ, about 2 mJ, about 2.1 mJ, about 2.2 mJ, about 2.3 mJ, about 2.4 mJ, about 2.5 mJ, about 2.6 mJ, about 2.7 mJ, about 2.8 mJ, about 2.9 mJ, about 3 mJ, about 3.1 mJ, about 3.2 mJ, about 3.3 mJ, about 3.4 mJ, about 3.5 mJ, about 3.6 mJ, about 3.7 mJ, about 3.8 mJ, about 3.9 mJ, about 4 mJ, about 4.1 mJ, about 4.2 mJ, about 4.3 mJ, about 4.4 mJ, about 4.5 mJ, about 4.6 mJ, about 4.7 mJ, about 4.8 mJ, about 4.9 mJ, or about 5 mJ).

In some embodiments, the applicator can be specifically configured to apply substantially the same amount of force (e.g., impact energy) to each of the plurality of microneedles in a microarray patch (MAP) to achieve a sufficient deployment depth below the surface of the subject's skin to then achieve transdermal and/or intradermal delivery of at least about 75% or more (e.g., about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100%) of the API from the MAP to a subject. In some embodiments, the applicator can be specifically configured to apply substantially the same amount of force (e.g., impact energy) to each of the plurality of microneedles in a microarray patch (MAP) to achieve a deployment depth of at least about 400 μm below the surface of the subject's skin to then achieve delivery of at least about 80% of the API from the MAP to a delivery depth of at least about 300 μm below the surface of the subject's skin.

According to one aspect, the disclosure provides a microneedle and/or a microarray patch (MAP), e.g., comprising an active pharmaceutical ingredient (API) and a water soluble excipient. In one aspect, the disclosure provides a microneedle, comprising an active pharmaceutical ingredient (API) and a water soluble excipient. In one aspect, the disclosure provides a microarray patch (MAP), comprising an active pharmaceutical ingredient (API) and a water soluble excipient.

Accordingly, the present disclosure provides improved systems comprising devices for application of medical patches, including biodegradable MAPs described herein. The systems can allow reliable application of a MAP, including even and reliable application such that a sufficient force and/or depth of skin penetration is achieved to ensure that needle-like portions of the patch are positioned at a desired depth within or beneath a portion of the skin. The applicator can be configured to provide a predetermined force to quickly and reliably apply the patch to a desired location, thereby helping to improve delivery of APIs (e.g., drugs, vaccines, biologics, or other materials) using the selected MAP. In some embodiments, the applicator may include a top portion having a top surface and a sidewall, wherein the top portion includes an activation mechanism; a bottom portion having a bottom surface and a sidewall; a middle portion connected to the top portion and the bottom portion; a piston portion connected to the top portion and the middle portion; and a compressible member positioned between the middle portion and the piston portion and configured to apply downward pressure to the piston portion, wherein when the activation mechanism is activated, the piston portion is released from the top portion and the middle portion and moves towards the bottom surface; wherein a MAP can be held in a patch holder near the bottom surface of the bottom portion, and when the piston portion moves downwards, the MAP is released from the patch holder and pushed downward by the piston portion through the patch holder onto subject's skin.

Active Pharmaceutical Ingredients (APIs)

The present disclosure provides, in some embodiments, dispensable formulations, microneedles and/or microarray patches (MAPs) comprising an active pharmaceutical ingredient (API). The present disclosure also provides combination treatment methods for administering a microneedle and/or a microarray patch (MAP) disclosed herein with an additional therapy.

As used herein, the term "active pharmaceutical ingredient (API)" (also referred to as a "drug," an "active agent," or a "therapeutic agent") refers to any type of pharmaceutically active compound or derivative that is useful in the prevention, diagnosis, stabilization, treatment, or management of a condition, disorder or disease. The term "an active pharmaceutical ingredient (API)" generally refers to an agent that is administered to a subject to treat a disease, disorder, or other clinically recognized condition, or for prophylactic purposes, and has a therapeutic and/or clinically significant effect on the body of the subject to treat, prevent, and/or diagnose the disease, disorder, or condition. The active pharmaceutical ingredient may be delivered to a subject in a quantity greater than a trace amount to affect a therapeutic response in the subject. In some embodiments, an active pharmaceutical ingredient (API) may include, but is not limited to, any synthetic or naturally occurring biologically active compound or composition of matter which, when administered to a subject (e.g., a human or nonhuman animal), induces a desired pharmacologic, immunogenic, and/or physiologic effect by local and/or systemic action. Examples of APIs are described in well-known literature references such as the Merck Index, the Physician's Desk Reference, and The Pharmacological Basis of Therapeutics, and they include, without limitation, medicaments; vitamins; mineral supplements; substances used for the treatment, prevention, diagnosis, cure or mitigation of a disease or illness; substances which affect the structure or function of the body; or pro-drugs, which become biologically active or more active after they have been placed in a physiological environment. Various forms of an API may be used which are capable of being released from the microneedles and/or the microarray patches (MAPs) described herein into adjacent tissues and/or fluids upon administration, e.g., to the skin of a subject. Accordingly, it should be understood that the APIs described herein are not limited to any particular type of API.

In some embodiments, "active pharmaceutical ingredient (API)" refers to an agent that possesses therapeutic, prophylactic, or diagnostic properties in vivo, for example when administered to a human subject or an animal, including mammals and domestic animals. Examples of active agents include, but are not limited to, amino acids, proteins, peptides, hormones, biologics, antibodies, growth factors, nucleic acids, such as DNA, RNA, and mRNA, gene constructs, and vectors, lipid nanoparticles (LNPs), sugars, antigens, vaccines, viruses, live attenuated viruses, inactivated viruses, adjuvanted vaccines, viral-like particles, enzymes, cells, small molecules, antibiotics, drugs, and any combination thereof. The term "active agent" or "active pharmaceutical ingredient" or "API" includes the compound(s), pharmaceutically acceptable salts thereof, isomers, solvates, prodrugs, derivatives, complexes and hydrates, anhydrous forms thereof, and any polymorphic or amorphous forms or combinations thereof.

In some embodiments, the dispensable formulation, the microneedle and/or the microarray patch (MAP) can comprise and/or can be administered in combination with a therapeutically effective amount and/or or a prophylactically effective amount of an active pharmaceutical ingredient (API). In some embodiments, the dispensable formulation, the microneedle and/or the microarray patch (MAP) can comprise and/or can be administered in combination with an active pharmaceutical ingredient (API) in an amount that produces some desired local and/or systemic effect at a reasonable benefit/risk ratio applicable to any treatment. APIs employed in the methods of the present disclosure may be administered in a sufficient amount to produce a reasonable benefit/risk ratio applicable to such treatment using a microneedle and/or a microarray patch (MAP) described herein.

In some embodiments, a dispensable formulation (e.g., a dispense volume of a dispensable formulation), a microneedle (e.g., a single microneedle), and/or a MAP (e.g., a plurality of microneedles) can comprise about 0.001 μg to about 1000 mg of an API. In some embodiments, the amount of API present in a dispensable formulation (e.g., a dispense volume of a dispensable formulation), a microneedle (e.g., a single microneedle), and/or a MAP (e.g., a plurality of microneedles) can be (% w/w) weight by weight, (% w/v) weight by volume, and/or (% v/v) volume by volume.

In some embodiments, the dispensable formulation, the microneedle and/or the microarray patch (MAP) can comprise about 0.1 μg to about 1000 ug (e.g., about 0.1 μg, about 1 μg, about 5 μg, about 10 μg, about 15 μg, about 20 μg, about 25 μg, about 30 μg, about 35 μg, about 40 μg, about 45 μg, about 50 μg, about 55 μg, about 60 μg, about 65 μg, about 70 μg, about 75 μg, about 80 μg, about 85 μg, about 90 μg, about 95 μg, about 100 μg, about 105 μg, about 110 μg, about 115 μg, about 120 μg, about 125 μg, about 130 μg, about 135 μg, about 140 μg, about 145 μg, about 150 μg, about 155 μg, about 160 μg, about 165 μg, about 170 μg, about 175 μg, about 180 μg, about 185 μg, about 190 μg, about 195 μg, about 200 μg, about 205 μg, about 210 μg, about 215 μg, about 220 μg, about 225 μg, about 230 μg, about 235 μg, about 240 μg, about 245 μg, about 250 μg, about 255 μg, about 260 μg, about 265 μg, about 270 μg, about 275 μg, about 280 μg, about 285 μg, about 290 μg, about 295 μg, about 300 μg, about 305 μg, about 310 μg, about 315 μg, about 320 μg, about 325 μg, about 330 μg, about 335 μg, about 340 μg, about 345 μg, about 350 μg, about 355 μg, about 360 μg, about 365 μg, about 370 μg, about 375 μg, about 380 μg, about 385 μg, about 390 μg, about 395 μg, about 400 μg, about 405 μg, about 410 μg, about 415 μg, about 420 μg, about 425 μg, about 430 μg, about 435 μg, about 440 μg, about 445 μg, about 450 μg, about 455 μg, about 460 μg, about 465 μg, about 470 μg, about 475 μg, about 480 μg, about 485 μg, about 490 μg, about 495 μg, about 500 μg, about 505 μg, about 510 μg, about 515 μg, about 520 μg, about 525 μg, about 530 μg, about 535 μg, about 540 μg, about 545 μg, about 550 μg, about 555 μg, about 560 μg, about 565 μg, about 570 μg, about 575 μg, about 580 μg, about 585 μg, about 590 μg, about 595 μg, about 600 μg, about 605 μg, about 610 μg, about 615 μg, about 620 μg, about 625 μg, about 630 μg, about 635 μg, about 640 μg, about 645 μg, about 650 μg, about 655 μg, about 660 μg, about 665 μg, about 670 μg, about 675 μg, about 680 μg, about 685 μg, about 690 μg, about 695 μg, about 700 μg, about 705 μg, about 710 μg, about 715 μg, about 720 μg, about 725 μg, about 730 μg, about 735 μg, about 740 μg, about 745 μg, about 750 μg, about 755 μg, about 760 μg, about 765 μg, about 770 μg, about 775 μg, about 780 μg, about 785 μg, about 790 μg, about 795 μg, about 800 μg, about 805 μg, about 810 μg, about 815 μg, about 820 μg, about 825 μg, about 830 μg, about 835 μg, about 840 μg, about 845 μg, about 850 μg, about 855 μg, about 860 μg, about 865 μg, about 870 μg, about 875 μg, about 880 μg, about 885 μg, about 890 μg, about 895 μg, about 900 μg, about 905 μg, about 910 μg, about 915 μg, about 920 μg, about 925 μg, about 930 μg, about 935 μg, about 940 μg, about 945 μg, about 950 μg, about 955 μg, about 960 μg, about 965 μg, about 970 μg, about 975 μg, about 980 μg, about 985 μg, about 990 μg, about 995 μg, or about 1000 μg) of an active pharmaceutical ingredient (API), e.g., described herein. In some embodiments, a dispense volume of a dispensable formulation, such as a dispensable tip formulation and/or a dispensable base formulation described herein, can comprise about 0.1 μg to about 1000 mg of the active pharmaceutical ingredient (API). In some embodiments, a microneedle, e.g., a microneedle present in a microarray patch (MAP), can comprise about 0.1 μg to about 1000 mg of the API. In some embodiments, each microneedle in a microarray patch (MAP) can independently comprise about 0.1 μg to about 1000 mg of an active pharmaceutical ingredient (API), e.g., per microneedle. In some embodiments, the microarray patch (MAP) can comprise a total amount of about 0.1 μg to about 1000 mg of an active pharmaceutical ingredient (API), e.g., per MAP.

In some embodiments, the dispensable formulation, the microneedle and/or the microarray patch (MAP) can comprise about 0.1 mg to about 1000 mg (e.g., about 0.1 mg, about 1 mg, about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 105 mg, about 110 mg, about 115 mg, about 120 mg, about 125 mg, about 130 mg, about 135 mg, about 140 mg, about 145 mg, about 150 mg, about 155 mg, about 160 mg, about 165 mg, about 170 mg, about 175 mg, about 180 mg, about 185 mg, about 190 mg, about 195 mg, about 200 mg, about 205 mg, about 210 mg, about 215 mg, about 220 mg, about 225 mg, about 230 mg, about 235 mg, about 240 mg, about 245 mg, about 250 mg, about 255 mg, about 260 mg, about 265 mg, about 270 mg, about 275 mg, about 280 mg, about 285 mg, about 290 mg, about 295 mg, about 300 mg, about 305 mg, about 310 mg, about 315 mg, about 320 mg, about 325 mg, about 330 mg, about 335 mg, about 340 mg, about 345 mg, about 350 mg, about 355 mg, about 360 mg, about 365 mg, about 370 mg, about 375 mg, about 380 mg, about 385 mg, about 390 mg, about 395 mg, about 400 mg, about 405 mg, about 410 mg, about 415 mg, about 420 mg, about 425 mg, about 430 mg, about 435 mg, about 440 mg, about 445 mg, about 450 mg, about 455 mg, about 460 mg, about 465 mg, about 470 mg, about 475 mg, about 480 mg, about 485 mg, about 490 mg, about 495 mg, about 500 mg, about 505 mg, about 510 mg, about 515 mg, about 520 mg, about 525 mg, about 530 mg, about 535 mg, about 540 mg, about 545 mg, about 550 mg, about 555 mg, about 560 mg, about 565 mg, about 570 mg, about 575 mg, about 580 mg, about 585 mg, about 590 mg, about 595 mg, about 600 mg, about 605 mg, about 610 mg, about 615 mg, about 620 mg, about 625 mg, about 630 mg, about 635 mg, about 640 mg, about 645 mg, about 650 mg, about 655 mg, about 660 mg, about 665 mg, about 670 mg, about 675 mg, about 680 mg, about 685 mg, about 690 mg, about 695 mg, about 700 mg, about 705 mg, about 710 mg, about 715 mg, about 720 mg, about 725 mg, about 730 mg, about 735 mg, about 740 mg, about 745 mg, about 750 mg, about 755 mg, about 760 mg, about 765 mg, about 770 mg, about 775 mg, about 780 mg, about 785 mg, about 790 mg, about 795 mg, about 800 mg, about 805 mg, about 810 mg, about 815 mg, about 820 mg, about 825 mg, about 830 mg, about 835 mg, about 840 mg, about 845 mg, about 850 mg, about 855 mg, about 860 mg, about 865 mg, about 870 mg, about 875 mg, about 880 mg, about 885 mg, about 890 mg, about 895 mg, about 900 mg, about 905 mg, about 910 mg, about 915 mg, about 920 mg, about 925 mg, about 930 mg, about 935 mg, about 940 mg, about 945 mg, about 950 mg, about 955 mg, about 960 mg, about 965 mg, about 970 mg, about 975 mg, about 980 mg, about 985 mg, about 990 mg, about 995 mg, about 1000 mg) of an active pharmaceutical ingredient (API), e.g., described herein.

In some embodiments, the dispensable formulation, the microneedle and/or the microarray patch (MAP) can comprise about 0.1% (w/v) to about 100% (w/v) (e.g., about 0.1% (w/v), about 1% (w/v), about 2% (w/v), about 3% (w/v), about 4% (w/v), about 5% (w/v), about 6% (w/v), about 7% (w/v), about 8% (w/v), about 9% (w/v), about 10% (w/v), about 11% (w/v), about 12% (w/v), about 13% (w/v), about 14% (w/v), about 15% (w/v), about 16% (w/v), about 17% (w/v), about 18% (w/v), about 19% (w/v), about 20% (w/v), about 21% (w/v), about 22% (w/v), about 23% (w/v), about 24% (w/v), about 25% (w/v), about 26% (w/v), about 27% (w/v), about 28% (w/v), about 29% (w/v), about 30% (w/v), about 31% (w/v), about 32% (w/v), about 33% (w/v), about 34% (w/v), about 35% (w/v), about 36% (w/v), about 37% (w/v), about 38% (w/v), about 39% (w/v), about 40%

(w/v), about 41% (w/v), about 42% (w/v), about 43% (w/v), about 44% (w/v), about 45% (w/v), about 46% (w/v), about 47% (w/v), about 48% (w/v), about 49% (w/v), about 50% (w/v), about 51% (w/v), about 52% (w/v), about 53% (w/v), about 54% (w/v), about 55% (w/v), about 56% (w/v), about 57% (w/v), about 58% (w/v), about 59% (w/v), about 60% (w/v), about 61% (w/v), about 62% (w/v), about 63% (w/v), about 64% (w/v), about 65% (w/v), about 66% (w/v), about 67% (w/v), about 68% (w/v), about 69% (w/v), about 70% (w/v), about 71% (w/v), about 72% (w/v), about 73% (w/v), about 74% (w/v), about 75% (w/v), about 76% (w/v), about 77% (w/v), about 78% (w/v), about 79% (w/v), about 80% (w/v), about 81% (w/v), about 82% (w/v), about 83% (w/v), about 84% (w/v), about 85% (w/v), about 86% (w/v), about 87% (w/v), about 88% (w/v), about 89% (w/v), about 90% (w/v), about 91% (w/v), about 92% (w/v), about 93% (w/v), about 94% (w/v), about 95% (w/v), about 96% (w/v), about 97% (w/v), about 98% (w/v), about 99% (w/v), about 100% (w/v)) of an active pharmaceutical ingredient (API), e.g., described herein.

In some embodiments, the dispensable formulation, the microneedle and/or the microarray patch (MAP) can comprise about 0.1 nL to about 10 nL (e.g., about 0.1 nL, about 0.2 nL, about 0.3 nL, about 0.4 nL, about 0.5 nL, about 0.6 nL, about 0.7 nL, about 0.8 nL, about 0.9 nL, about 1 nL, about 1.1 nL, about 1.2 nL, about 1.3 nL, about 1.4 nL, about 1.5 nL, about 1.6 nL, about 1.7 nL, about 1.8 nL, about 1.9 nL, about 2 nL, about 2.1 nL, about 2.2 nL, about 2.3 nL, about 2.4 nL, about 2.5 nL, about 2.6 nL, about 2.7 nL, about 2.8 nL, about 2.9 nL, about 3 nL, about 3.1 nL, about 3.2 nL, about 3.3 nL, about 3.4 nL, about 3.5 nL, about 3.6 nL, about 3.7 nL, about 3.8 nL, about 3.9 nL, about 4 nL, about 4.1 nL, about 4.2 nL, about 4.3 nL, about 4.4 nL, about 4.5 nL, about 4.6 nL, about 4.7 nL, about 4.8 nL, about 4.9 nL, about 5 nL, about 5.1 nL, about 5.2 nL, about 5.3 nL, about 5.4 nL, about 5.5 nL, about 5.6 nL, about 5.7 nL, about 5.8 nL, about 5.9 nL, about 6 nL, about 6.1 nL, about 6.2 nL, about 6.3 nL, about 6.4 nL, about 6.5 nL, about 6.6 nL, about 6.7 nL, about 6.8 nL, about 6.9 nL, about 7 nL, about 7.1 nL, about 7.2 nL, about 7.3 nL, about 7.4 nL, about 7.5 nL, about 7.6 nL, about 7.7 nL, about 7.8 nL, about 7.9 nL, about 8 nL, about 8.1 nL, about 8.2 nL, about 8.3 nL, about 8.4 nL, about 8.5 nL, about 8.6 nL, about 8.7 nL, about 8.8 nL, about 8.9 nL, about 9 nL, about 9.1 nL, about 9.2 nL, about 9.3 nL, about 9.4 nL, about 9.5 nL, about 9.6 nL, about 9.7 nL, about 9.8 nL, about 9.9 nL, or about 10 nL) of an active pharmaceutical ingredient (API), e.g., described herein.

In some embodiments, the dispensable formulation, the microneedle and/or the microarray patch (MAP) can comprise about 0.1 mg/ml to about 500 mg/ml (e.g., about 0.1 mg/mL, about 1 mg/mL, about 5 mg/mL, about 10 mg/mL, about 15 mg/mL, about 20 mg/mL, about 25 mg/mL, about 30 mg/mL, about 35 mg/mL, about 40 mg/mL, about 45 mg/mL, about 50 mg/mL, about 55 mg/mL, about 60 mg/mL, about 65 mg/mL, about 70 mg/mL, about 75 mg/mL, about 80 mg/mL, about 85 mg/mL, about 90 mg/mL, about 95 mg/mL, about 100 mg/mL, about 105 mg/mL, about 110 mg/mL, about 115 mg/mL, about 120 mg/mL, about 125 mg/mL, about 130 mg/mL, about 135 mg/mL, about 140 mg/mL, about 145 mg/mL, about 150 mg/mL, about 155 mg/mL, about 160 mg/mL, about 165 mg/mL, about 170 mg/mL, about 175 mg/mL, about 180 mg/mL, about 185 mg/mL, about 190 mg/mL, about 195 mg/mL, about 200 mg/mL, about 205 mg/mL, about 210 mg/mL, about 215 mg/mL, about 220 mg/mL, about 225 mg/mL, about 230 mg/mL, about 235 mg/mL, about 240 mg/mL, about 245 mg/mL, about 250 mg/mL, about 255 mg/mL, about 260 mg/mL, about 265 mg/mL, about 270 mg/mL, about 275 mg/mL, about 280 mg/mL, about 285 mg/mL, about 290 mg/mL, about 295 mg/mL, about 300 mg/mL, about 305 mg/mL, about 310 mg/mL, about 315 mg/mL, about 320 mg/mL, about 325 mg/mL, about 330 mg/mL, about 335 mg/mL, about 340 mg/mL, about 345 mg/mL, about 350 mg/mL, about 355 mg/mL, about 360 mg/mL, about 365 mg/mL, about 370 mg/mL, about 375 mg/mL, about 380 mg/mL, about 385 mg/mL, about 390 mg/mL, about 395 mg/mL, about 400 mg/mL, about 405 mg/mL, about 410 mg/mL, about 415 mg/mL, about 420 mg/mL, about 425 mg/mL, about 430 mg/mL, about 435 mg/mL, about 440 mg/mL, about 445 mg/mL, about 450 mg/mL, about 455 mg/mL, about 460 mg/mL, about 465 mg/mL, about 470 mg/mL, about 475 mg/mL, about 480 mg/mL, about 485 mg/mL, about 490 mg/mL, about 495 mg/ml, about 500 mg/mL) of an active pharmaceutical ingredient (API), e.g., described herein.

Additional non-limiting examples of active pharmaceutical ingredient (API) which can be incorporated into the dispensable formulations, microneedles and/or a microarray patches (MAPs) of the present disclosure, and/or that can be administered as a combination therapy are disclosed below.

Peptides

In some embodiments, the active pharmaceutical ingredient (API) comprises an amino acid, a peptide, a polypeptide, and/or a protein.

As used herein, the term "peptide" refers to a compound of two or more subunit amino acids, amino acid analogs, or peptidomimetics. The subunits may be linked by peptide bonds or by other bonds (e.g., as esters, ethers, and the like). The term "peptide" is used herein generically to refer to peptides (e.g., polyamino acids of from 2 to about 20 residues), polypeptides (e.g., peptides of from about 20 residues to about 100 residues), and/or proteins (e.g., peptides having about 100 or more residues).

In some embodiments, the peptide is a protein therapeutic. In some embodiments, the terms "protein therapeutic," "therapeutic protein," and the like refer to a peptide and/or a protein that has a biological effect in the body, or on a region in the body on which it directly acts, or on a region of the body on which it remotely acts via intermediates, etc. Examples of therapeutic proteins include, but are not limited to, peptides; proteins; enzymes; receptors; receptor fusions; soluble receptors; soluble receptor fusions; antibodies (e.g., monoclonal antibodies (mAbs) and/or polyclonal antibodies); antigen-binding fragments of an antibody; Fc fusion proteins; cytokines; hormones; incretins, regulatory factors; growth factors; coagulation and/or clotting factors; blood proteins; plasma proteins; serum proteins; albumins; globulins; fibrinogens; regulatory proteins; antigen-binding agents; glucagon-like peptide-1 (GLP-1) polypeptides, such as a GLP-1 receptor agonist, a GLP-1 analogue, a GLP-1 derivative, and/or a salt thereof; a gastric inhibitory polypeptide (GIP), also known as a glucose-dependent insulinotropic polypeptide, such as a GIP receptor agonist, a GIP analogue, a GIP derivative, and/or a salt thereof; glucagon receptor agonists (GCGs); amylin receptor agonists (Amylins); Y1 and Y2 receptor agonists (PYYs); insulin; insulin analogues, insulin-like growth factor 1 (IGF-1). The above list of proteins is merely exemplary in nature, and is not intended to be a limiting recitation.

In some embodiments, the active pharmaceutical ingredient (API) comprises an antibody. The term "antibody" as used herein refers to a polypeptide or a protein complex that specifically binds an epitope of an antigen. An antibody includes an intact antibody, or a binding fragment thereof that competes with the intact antibody for specific binding and includes chimeric, humanized, fully human, and bispecific antibodies. Binding fragments include, but are not limited to, Fab, Fab', F(ab')2, Fv, and single-chain antibodies. In some embodiments, an antibody is referred to as an immunoglobulin and includes the various classes and isotypes, such as IgA (IgA1 and IgA2), IgD, IgE, IgM, and IgG (IgG1, IgG3 and IgG4) etc. In some embodiments, the antibody is polyclonal or monoclonal. In some embodiments, the antibody is from any origin, such as mouse or human, including a chimeric antibody thereof. In some embodiments, the antibody is humanized.

In some embodiments, the active pharmaceutical ingredient (API) comprises an amino acid. As used herein, the term "amino acid" refers to either natural and/or unnatural or synthetic amino acids, including glycine and both D or L optical isomers, and amino acid analogs and peptidomimetics. A peptide of three or more amino acids is commonly called an oligopeptide if the peptide chain is short. While the term "protein" encompasses the term "polypeptide", a "polypeptide" may be less than a full-length protein, e.g., a biologically active fragment of a polypeptide. The term "biologically active fragment", "biologically active form", "biologically active equivalent", and "functional derivative" of a wild-type protein, means a substance that possesses a biological activity that is at least substantially equal (e.g., not significantly different from) the biological activity of the wild type protein as measured using an assay suitable for detecting the activity.

Glucagon-like peptide-1 (GLP-1) polypeptides and GLP-1 receptor agonists

In some embodiments, the active pharmaceutical ingredient (API) comprises a glucagon-like peptide-1 (GLP-1) polypeptide, such as a GLP-1 receptor agonist, a GLP-1 analogue, a GLP-1 derivative, and/or a salt thereof. In some embodiments, the dispensable formulation, the microneedle and/or the microarray patch (MAP) can comprise and/or can be administered in combination with a GLP-1 polypeptide, such as a GLP-1 receptor agonist, a GLP-1 analogue, a GLP-1 derivative, and/or a salt thereof.

As used herein, the term "GLP-1 polypeptide" refers to a polypeptide which is capable of binding to a GLP-1 receptor and/or to activating a GLP-1 receptor. In some embodiments, a GLP-1 polypeptide is a polypeptide which has GLP-1 activity. In some embodiments, a GLP-1 polypeptide is a GLP-1 receptor agonist.

As used herein, the term "GLP-1 receptor agonist" refers to a compound which is capable of binding to a GLP-1 receptor and/or to activating a GLP-1 receptor. Such a GLP-1 receptor agonist may be characterized as having "GLP-1 activity." A GLP-1 receptor agonist may be based on any type of molecular scaffold, including, for example, a polypeptide, a protein, a small molecule, an antibody, a fusion protein, or any combination hereof. In some embodiments, the GLP-1 receptor agonist can comprise one or more moieties which are capable of binding to a GLP-1 receptor and/or to activating a GLP-1 receptor. Exemplary GLP-1 receptor agonists include, without limitation, semaglutide; dulaglutide; exenatide; liraglutide; lixisenatide; tirzepatide; albiglutide; taspoglutide; pharmaceutically acceptable salts thereof; derivatives thereof; analogues thereof; and combinations thereof.

As used herein, the term "GLP-1 activity" refers to the capability of a compound to activate a GLP-1 receptor. Accordingly, a GLP-1 polypeptide, such as a GLP-1 receptor agonist, a GLP-1 analogue, a GLP-1 derivative, and/or a salt thereof, can be characterized by "GLP-1 activity" which refers to the ability of the compound to bind to the GLP-1 receptor and initiate a signal transduction pathway resulting in, e.g., insulinotropic action or other physiological effects as is known in the art. In some embodiments the "GLP-1 agonist" binds to a GLP-1 receptor, e.g., with an affinity constant (KD) or activate the receptor with a potency (EC50) of below about 1 pM, e.g., below about 100 nM as measured by methods known in the art and exhibits insulinotropic activity, where insulinotropic activity may be measured in vivo or in vitro assays known to those of ordinary skill in the art. For example, the GLP-1 agonist may be administered to an animal with increased blood glucose (e.g., obtained using an Intravenous Glucose Tolerance Test (IVGTT). A person skilled in the art will be able to determine a suitable glucose dosage and a suitable blood sampling regime, e.g., depending on the species of the animal, for the IVGTT and measure the plasma insulin concentration over time.

As used herein, the term "GLP-1 analogue" refers to an analogue (or variant) of a GLP-1 polypeptide. In some embodiments, a GLP-1 analogue comprises an analogue (or variant) of the human glucagon-like peptide-1 (GLP-1 (7-37)). The amino acid sequence of human GLP-1 (7-37) is HAEGTFTSDVSSYLEGQAAKEFIAWLVKGRG (SEQ ID NO: 1). In some embodiments, the amino acid sequence of a GLP-1 analogue can comprise one or more amino acid changes as compared to GLP-1 (7-37). In some embodiments, the amino acid changes may include amino acid additions, substitutions, and or deletions. In some embodiments, the term GLP-1 analogue is characterized by about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or more sequence identity to GLP-1 (7-37). In some embodiments, the GLP-1 analogue comprises the amino acid sequence of semaglutide.

As used herein, the term "GLP-1 derivative" refers to a chemically modified GLP-1 polypeptide, in which one or more substituents have been covalently attached to the GLP-1 polypeptide. In some embodiments, the GLP-1 derivative comprises a GLP-1 analogue to which one or more substituents are covalently linked. In some embodiments, the GLP-1 derivative comprises semaglutide.

In some embodiments, the active pharmaceutical ingredient (API) comprises a glucagon-like peptide-1 (GLP-1) agonist and/or similar agonists. For example, it may be understood that the API may encompass APIs relevant to the treatment of T2D, obesity, NASH (Nonalcoholic steatohepatitis), MASH (Metabolic dysfunction-associated steatohepatitis), NAFLD (nonalcoholic fatty liver disease), short bowel syndrome, Alzheimer's, chronic heart failure, chronic kidney disease, osteoarthritis, obstructive sleep apnea, psoriasis and other inflammatory cutaneous diseases, and drug addiction.

Accordingly, in one aspect, the present disclosure provides a composition (e.g., a dispensable formulation, a microneedle and/or a microarray patch (MAP)), comprising: (i) a glucagon-like peptide-1 (GLP-1) receptor agonist at a concentration of greater than about 100 mg/mL; and (ii) a water-soluble excipient selected from the group consisting of an amino acid, a surfactant, and combinations thereof.

In one aspect, the present disclosure provides a composition (e.g., a dispensable formulation, a microneedle and/or a microarray patch (MAP)), comprising: (i) a glucagon-like peptide-1 (GLP-1) receptor agonist at a concentration of greater than about 100 mg/ml; and (ii) a water-soluble excipient at a concentration of about 0.01% (w/v) to about 10% (w/v).

In one aspect, the present disclosure provides a microneedle, comprising a consolidated microneedle tip formed from a dispensable formulation, wherein the dispensable formulation comprises: (i) a glucagon-like peptide-1 (GLP-1) receptor agonist at a concentration of greater than about 100 mg/ml; and (ii) a water-soluble excipient selected from the group consisting of an amino acid, a surfactant, and combinations thereof.

In one aspect, the present disclosure provides a microneedle, comprising a consolidated microneedle tip formed from a dispensable formulation, wherein the dispensable formulation comprises: (i) a glucagon-like peptide-1 (GLP-1) receptor agonist at a concentration of greater than about 100 mg/mL; and (ii) a water-soluble excipient at a concentration of about 0.01% (w/v) to about 10% (w/v).

In some embodiments, the glucagon-like peptide-1 (GLP-1) receptor agonist is present in the dispensable formulation at a concentration of about 150 mg/mL to about 300 mg/mL, or wherein the glucagon-like peptide-1 (GLP-1) receptor agonist is present in the dispensable formulation at a concentration of about 180 mg/mL. In some embodiments, the glucagon-like peptide-1 (GLP-1) receptor agonist comprises semaglutide, a pharmaceutically acceptable salt thereof, or a derivative thereof. In some embodiments, the composition (e.g., a dispensable formulation, a microneedle and/or a microarray patch (MAP)), further comprises an additional active pharmaceutical ingredient (API), wherein the additional API is selected from the group consisting of (i) an antidiabetic agent, (ii) an anti-obesity agent, (iii) an anti-cardiovascular disease agent, and (iv) combinations thereof. In some embodiments, the microneedle comprises (i) the water-soluble excipient is present in the dispensable formulation at a concentration of about 0.01% (w/v) to about 10% (w/v); (ii) the amino acid is present in the dispensable formulation at a concentration of about 0.5% to about 5%; (iii) the surfactant is present in the printable tip formulation at a concentration of about 0.01% (w/v) to about 1% (w/v); (iv) the dispensable formulation further comprises a povidone polymer present at a concentration of about 0.5% (w/v) to about 5% (w/v); (v) the dispensable formulation further comprises a salt present at a concentration of about 0.5% (w/v) to about 5% (w/v); and/or (vi) the dispensable formulation further comprises a buffer present at a concentration of about 50 mM to about 150 mM. In some embodiments, the consolidated tip comprises a proline amino acid, or a derivative thereof. In some embodiments, the consolidated tip comprises a polyoxyl 35 castor oil surfactant, or a derivative thereof. In some embodiments, the consolidated tip comprises a povidone K 17 (PVP K17) polymer, or a derivative thereof. In some embodiments, the consolidated tip comprises a NaCl salt. In some embodiments, the consolidated tip comprises a Tris-HCl buffer. In some embodiments, the microneedle further comprises a microneedle base formed from a dispensable formulation, wherein the dispensable formulation comprises at least one selected from the group consisting of (i) a water-soluble excipient comprising a povidone polymer present at a concentration of about 30% (w/v) to about 90% (w/v); (ii) a water-soluble excipient comprising a polyvinyl alcohol (PVA) polymer present at a concentration of about 0.1% (w/v) to about 3% (w/v); (iii) a water-soluble excipient comprising a buffer present at a concentration of about 5 mM to about 25 mM (w/v); and (iv) combinations thereof. In some embodiments, the microneedle base comprises at least one selected from the group consisting of (i) a povidone K 17 (PVP K17) polymer, or a derivative thereof; (ii) a PVA 4-88 polymer, or a derivative thereof; (iii) a 1x TE buffer; and (iv) combinations thereof.

In one aspect, the present disclosure provides a microarray patch (MAP), comprising: a plurality of microneedles, wherein each of the plurality of microneedles comprises a consolidated microneedle tip formed from a dispensable formulation, wherein the dispensable formulation comprises: (i) a glucagon-like peptide-1 (GLP-1) receptor agonist at a concentration of greater than about 100 mg/mL; and (ii) a water-soluble excipient selected from the group consisting of an amino acid, a surfactant, and combinations thereof.

In some embodiments, the microarray patch (MAP) of claim 14, wherein the glucagon-like peptide-1 (GLP-1) receptor agonist is present in the dispensable formulation at a concentration of about 150 mg/mL to about 300 mg/mL, or wherein the glucagon-like peptide-1 (GLP-1) receptor agonist is present at a concentration of about 180 mg/mL. In some embodiments, the glucagon-like peptide-1 (GLP-1) receptor agonist comprises Semaglutide, a pharmaceutically acceptable salt thereof, or a derivative thereof. In some embodiments, the microarray patch (MAP) further comprises an additional active pharmaceutical ingredient (API), wherein the additional API is selected from the group consisting of (i) an antidiabetic agent, (ii) an anti-obesity agent, (iii) an anti-cardiovascular disease agent, and (iv) combinations thereof. In some embodiments, the microarray patch (MAP) comprises (i) the water-soluble excipient is present in the dispensable formulation at a concentration of about 0.01% (w/v) to about 10% (w/v); (ii) the amino acid is present in the dispensable formulation at a concentration of about 0.5% to about 5%; (iii) the surfactant is present in printable tip formulation at a concentration of about 0.01% (w/v) to about 1% (w/v); (iv) the dispensable formulation further comprises a povidone polymer present at a concentration of about 0.5% (w/v) to about 5% (w/v); (iii) the dispensable formulation further comprises a salt present at a concentration of about 0.5% (w/v) to about 5% (w/v); and/or (iv) the dispensable formulation further comprises a buffer present at a concentration of about 50 mM to about 150 mM. In some embodiments, the consolidated tip comprises a proline amino acid, or a derivative thereof. In some embodiments, the consolidated tip comprises a polyoxyl 35 castor oil surfactant, or a derivative thereof. In some embodiments, the consolidated tip comprises a povidone K 17 (PVP K17) polymer, or a derivative thereof. In some embodiments, the consolidated tip comprises a NaCl salt. In some embodiments, the MAP comprises a Tris-HCl buffer. In some embodiments, (a) each of the plurality of microneedles of the MAP further comprises a microneedle base formed from a dispensable formulation, wherein the dispensable formulation comprises at least one selected from the group consisting of (i) a water-soluble excipient comprising a povidone polymer present at a concentration of about 30% (w/v) to about 90% (w/v); (ii) a water-soluble excipient comprising a polyvinyl alcohol (PVA) polymer present at a concentration of about 0.1% (w/v) to about 3% (w/v); (iii) a water-soluble excipient comprising a buffer present at a concentration of about 5 mM to about 25 mM (w/v); and (iv)

combinations thereof; and/or (b) the microarray patch (MAP) further comprises a backing attached to the plurality of microneedles, wherein the backing is attached with an adhesive that is compatible with the glucagon-like peptide-1 (GLP-1) receptor agonist. In some embodiments, the microneedle base comprises at least one selected from the group consisting of (i) a povidone K 17 (PVP K17) polymer, or a derivative thereof; (ii) a PVA 4-88 polymer, or a derivative thereof; (iii) a 1x TE buffer; and (iv) combinations thereof. In some embodiments, the microarray patch (MAP) is configured for deployment onto the skin of a subject by using an applicator, wherein the MAP and the applicator are independently configured to function as a system to provide a consistent dose delivery of the glucagon-like peptide-1 (GLP-1) receptor agonist. In some embodiments, the consolidated microneedle tip and the microneedle base are independently configured to withstand and propagate an impact energy applied by an applicator to each of the plurality of microneedles during deployment without deformation, wherein the applicator is configured to apply substantially the same amount of impact energy to each of the plurality of microneedles to achieve deployment of at least about 80% of the consolidate tips in the MAP to a delivery depth of at least about 400 µm at least about 400 µm below the surface of the subject's skin. In some embodiments, (i) each of the plurality of microneedles is characterized by a total array strength of at least about 50 N yield load to minimize deformation and to maximize delivery depth of the consolidated microneedle tip during deployment; (ii) each of the plurality of microneedles is characterized by a tip strength of at least about 0.4 N per microneedle and a failure force of at least about 0.3 N per microneedle; (iii) each of the plurality of microneedles comprises about 1 µg to about 20 µg of the glucagon-like peptide-1 (GLP-1) receptor agonist per consolidated microneedle tip; (iv) each of the plurality of microneedles is characterized by a primary needle height (also referred to as "a pre-deployment needle height") of about 700 µm to about 1,250 µm; (v) the consolidated microneedle tip is characterized by a tip length of about 200 µm to about 500 µm; (vi) the consolidated microneedle tip is formed from about 10 nL to about 50 nL of the dispensable formulation; (vii) the consolidated microneedle tip is characterized by a flat meniscus; (viii) no more than about 20% of the plurality of microneedles comprises a defect; and/or (ix) no more than about 10% of the plurality of microneedles comprises a consolidated microneedle tip characterized by a tip length greater than about 400 µm. In some embodiments, the MAP and the applicator are independently configured to provide an in vitro recovery of at least about 70% of the glucagon-like peptide-1 (GLP-1) receptor agonist; and an ex vivo dose delivery efficiency of at least about 70% of the glucagon-like peptide-1 (GLP-1) receptor agonist, wherein less than about 20% of the glucagon-like peptide-1 (GLP-1) receptor agonist is not delivered upon deployment.

In one aspect, the present disclosure provides a method of treating at subject in need thereof, comprising deploying onto the skin of the subject a microarray patch (MAP), comprising: a plurality of microneedles, wherein each of the plurality of microneedles comprises a consolidated microneedle tip formed from a dispensable formulation, wherein the dispensable formulation comprises: (i) a glucagon-like peptide-1 (GLP-1) receptor agonist at a concentration of greater than about 100 mg/mL; and (ii) a water-soluble excipient selected from the group consisting of an amino acid, a surfactant, and combinations thereof. In some embodiments, the subject is suffering from a disease or condition selected from the group consisting of type 2 diabetes, overweight, obesity, and/or cardiovascular disease.

Nucleic Acids

In some embodiments, the active pharmaceutical ingredient (API) comprises a nucleic acid. In some embodiments, the dispensable formulation, the microneedle, and/or the microarray patch (MAP) can comprise and/or can be administered in combination with a nucleic acid.

As used herein, the term "nucleic acid" refers to any compound and/or any substance that is or can be incorporated into a polynucleotide chain. In some embodiments, "nucleic acid" refers to a compound and/or a substance that is or can be incorporated into a polynucleotide chain, e.g., via a phosphodiester linkage. In some embodiments, "nucleic acid" refers to an individual nucleic acid residue (e.g., a nucleotide and/or a nucleoside). In some embodiments, "nucleic acid" refers to a polynucleotide chain comprising individual nucleic acid residues. In some embodiments, "nucleic acid" refers to any compound and/or any substance comprising a nucleic acid, such as a deoxyribonucleic acid (DNA) and/or a ribonucleic acid (RNA). In some embodiments, "nucleic acid" refers to a single-stranded nucleic acid, a double-stranded nucleic acid, and/or a triple-stranded nucleic acid (also referred to as a "triple-helical nucleic acid"). In some embodiments, "nucleic acid" refers to a single-stranded RNA, a double-stranded RNA, a triple-stranded RNA, a single-stranded DNA, a double-stranded DNA, a triple-stranded DNA, and/or a complementary DNA (cDNA). In some embodiments, "nucleic acid" refers to an isolated nucleic acid, such as an isolated deoxyribonucleic acid (DNA) and/or an isolated ribonucleic acid (RNA). In some embodiments, "nucleic acid" refers to an isolated DNA, e.g., of any sequence. In some embodiments, "nucleic acid" refers to an isolated RNA, e.g., of any sequence.

In some embodiments, "nucleic acid" refers to a recombinant nucleic acid, such as a recombinant polynucleotide. In some embodiments, "nucleic acid" refers to a branched polynucleotide. In some embodiments, "nucleic acid" refers to an aptamer. In some embodiments, "nucleic acid" refers to a plasmid. In some embodiments, "nucleic acid" refers to a vector. In some embodiments, "nucleic acid" refers to a gene, or a gene fragment. In some embodiments, "nucleic acid" refers to a exon. In some embodiments, "nucleic acid" refers to an intron. In some embodiments, "nucleic acid" refers to a catalytic nucleic acid.

In some embodiments, "nucleic acid" refers to a viral vector, such as an adeno-associated viral (AAV) vector, a adenoviral vector, a lentiviral vector, a retroviral vector, a herpes simplex virus vector, and/or a chimeric viral vector.

In some embodiments, "nucleic acid" refers to a nucleic acid conjugate. In some embodiments, the term "nucleic acid conjugate" refers to a nucleic acid molecule (e.g., a DNA and/or an RNA) that can be chemically linked to another molecule, e.g., a peptide, such as a cell penetrating peptide (CPP); an antibody; a small molecule; a lipid; a fatty acid; a cholesterol; a sugar, such as a N-acetylgalactosamine (GalNAc); and/or a polymer, such as a poly(ethylene glycol) (PEG), a poly(propylene oxide) (PPO), a poly(isoprene) (PI), a poly(methyl acrylate) (pMA) a poly(methyl methacrylate) (pMMA), a poly(N-isopropylacrylamide) (pNIPAM), a poly(ethylene oxide methyl ether methacrylate) (PEOMA), a poly(diacetoneacrylamide) (pDAAm), and/or a polystyrene (PS).

In some embodiments, "nucleic acid" refers to an antisense nucleic acid. In some embodiments, "antisense nucleic acid" refers to a nucleic acid, such as a single-stranded oligonucleotide and/or a double-stranded oligonucleotide, that is complementary to a specific nucleic acid sequence (e.g., a complementary sequence of DNA and/or RNA). In some embodiments, "antisense nucleic acid" refers to a nucleic acid that can bind to a messenger RNA (mRNA), e.g., to prevent ribosomes from attaching and/or to attract an enzyme that can break down the mRNA. In some embodiments, "antisense nucleic acid" refers to a nucleic acid that can reduce the levels of an mRNA and/or a protein in a cell, e.g., in the nucleus and/or cytoplasm of the cell.

In some embodiments, "nucleic acid" refers to a nucleic acid probe. In some embodiments, "nucleic acid probe" refers to a nucleic acid, such as a single-stranded DNA and/or a single-stranded RNA, that can bind to, be used to detect, and/or be used to identify a specific nucleic acid sequence (e.g., a complementary sequence of DNA and/or RNA) in a sample and/or organism.

In some embodiments, "nucleic acid" refers to a primer. In some embodiments, the terms "primer," "oligonucleotide," and "oligo," refer to any nucleic acid that can hybridize to a target nucleic acid sequence of interest. In some embodiments, "primer" refers to a single-stranded nucleic acid having a length of about 15 to about 35 nucleotides (e.g., about 15, about 16, about 17, about 18, about 19, about 20, about 21, about 22, about 23, about 24, about 25, about 26, about 27, about 28, about 29, about 30, about 31, about 32, about 33, about 34, or about 35 nucleotides) that can be used, e.g., to initiate DNA synthesis.

In some embodiments, "nucleic acid" encompasses a ribonucleic acid (RNA). Exemplary RNA include, but are not limited to, an RNA-based therapeutic, an interference RNA (RNAi), a small interfering RNA (siRNA), a repeat-associated short interfering RNA (rasiRNA), a short hairpin RNA (shRNA), an antisense RNA (aRNA), a messenger RNA (mRNA), a modified messenger RNA (mmRNA), a RNA vector, a transfer RNA (tRNA), a transfer-messenger RNA (tmRNA), a self-amplifying RNA, a cis-natural antisense transcript (cis-NAT), a ribosomal RNA (rRNA), a small nuclear RNA (snRNA), a small nucleolar RNA (snoRNA), an SmY RNA, a small Cajal body-specific RNA (scaRNA), a long non-coding RNA (lncRNA), a micro-RNA (miRNA), a circular RNA (circRNA), a naked RNA, a retrotransposon, a PIWI-interacting RNA (piRNA), a multimeric coding nucleic acid (MCNA), a polymeric coding nucleic acid (PCNA), an RNA oligonucleotide, a recombinant RNA, a RNA aptamer, an RNA virus, a viral genome, a viral vector, a viroid, an RNA vaccine, a satellite RNA, a transacting siRNA (tasiRNA), a guide RNA (gRNA), a CRISPR RNA (crRNA), a spliced leader RNA (SL RNA), a Y RNA, a telomerase RNA component (TERC), a ribozyme, a gene therapy, a signal recognition particle RNA, derivatives thereof, and combinations thereof.

In some embodiments, "nucleic acid" encompasses a deoxyribonucleic acid (DNA). Exemplary DNA include, but are not limited to, an DNA-based therapeutic, a single-stranded DNA (ssDNA), a double-stranded DNA (dsDNA), a complementary DNA (cDNA), a plasmid DNA, an DNA oligonucleotide, a recombinant DNA, an antisense DNA, a gene, a transgene, a gene therapy, a DNA aptamer, a DNA virus, a viral genome, a viral vector, a DNA vaccine, a mitochondrial DNA (mtDNA), a circular DNA, an artificial chromosome, a chromosomal DNA (chrDNA), a extrachromosomal DNA (ecDNA), an extrachromosomal circular DNA (eccDNA), an extrachromosomal rDNA circles (ERC), a telomeric circle (e.g., a duplex (t-circle) and/or a single-stranded (c-circle)), a deoxyribozyme (DNAzyme), a small polydispersed DNA (spcDNA), a naked DNA, a microDNA, derivatives thereof, and combinations thereof.

In some embodiments, the active pharmaceutical ingredient (API) comprises a nucleic acid molecule, such as a polynucleotide or an oligonucleotide. In some embodiments, the dispensable formulation, the microneedle and/or the microarray patch (MAP) can comprise and/or can be administered in combination with a nucleic acid molecule, such as a polynucleotide or an oligonucleotide.

As used interchangeably herein, the terms "polynucleotide" and "nucleic acid" refer to polymeric forms of nucleotides of any length. The polynucleotides may contain deoxyribonucleotides, ribonucleotides, and/or their analogs. Nucleotides may have any three-dimensional structure, and may perform any function, known or unknown. The term "polynucleotide" includes, for example, single-, double-stranded and triple helical molecules, a gene or gene fragment, exons, introns, mRNA, tRNA, rRNA, siRNA, ribozymes, antisense molecules, cDNA, recombinant polynucleotides, branched polynucleotides, aptamers, plasmids, vectors, isolated DNA of any sequence, isolated RNA of any sequence, nucleic acid probes, and primers. A nucleic acid molecule may also comprise modified nucleic acid molecules (e.g., comprising modified bases, sugars, and/or internucleotide linkages). In some embodiments, the active pharmaceutical ingredient (API) comprises a nucleic acid molecule, such as a deoxyribonucleic acid (DNA) molecule and/or a ribonucleic acid (RNA) molecule.

In some embodiments, the active pharmaceutical ingredient (API) comprises an mRNA. e.g., encapsulated in a lipid nanoparticle. In some embodiments, the dispensable formulation, the microneedle and/or the microarray patch (MAP) can comprise and/or can be administered in combination with an mRNA, e.g., encapsulated in a lipid nanoparticle.

mRNA and Lipid Nanoparticles

In some embodiments, the active pharmaceutical ingredient (API) comprises a messenger RNA (mRNA). In some embodiments, the dispensable formulation, the microneedle and/or the microarray patch (MAP) can comprise and/or can be administered in combination with an mRNA.

As used herein, the term "messenger RNA (mRNA)" refers to a polynucleotide that encodes at least one polypeptide. mRNA as used herein encompasses both modified and unmodified RNA. mRNA may contain one or more coding and non-coding regions. mRNA can be purified from natural sources, produced using recombinant expression systems and optionally purified, chemically synthesized, etc. Where appropriate, e.g., in the case of chemically synthesized molecules, mRNA can comprise nucleoside analogs such as analogs having chemically modified bases or sugars, backbone modifications, etc. An mRNA sequence is presented in the 5' to 3' direction unless otherwise indicated. In some embodiments, an mRNA is or comprises natural nucleosides (e.g., adenosine, guanosine, cytidine, uridine); nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O (6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N- phosphoramidite linkages). In some embodiments, a nucleic acid is a mRNA encoding a protein.

In some embodiments, a lipid nanoparticle (LNP) formulation comprises an mRNA-LNP formulation. As used herein, the term "mRNA-LNP formulation" refers to a composition or formulation comprising one or more mRNA molecules encapsulated in LNPs. As used herein, the terms "lipid nanoparticle," or "LNP" refers to a particle having at least one dimension (e.g., diameter) on the order of nanometers (e.g., about 1 nm to about 1,000 nm) and comprising one or more lipids, e.g., one or more ionizable lipids. In some embodiments, an LNP can comprise one or more ionizable lipids. In some embodiments, an LNP can comprise one or more ionizable lipids and one or more other lipids, such as neutral lipids, charged lipids, steroids, and polymer conjugated lipids. In some embodiments, an LNP can comprise one or more ionizable lipids and one or more helper lipids. Such helper lipids can be included in the LNP to improve the properties of the nanoparticle, such as particle stability, polydispersity index (PDI), encapsulation efficiency, delivery efficacy, tolerability, and biodistribution. In general, an LNP can comprise an ionizable lipid, such as an ionizable cationic lipid, and a helper lipid, such as a cholesterol molecule, a phospholipid, and a poly(ethylene glycol)-lipid (PEG-lipid) conjugate. The LNPs described herein can further comprise an active pharmaceutical ingredient (API), such as a nucleic acid molecule described herein. In some embodiments, the LNP can comprise an mRNA.

In some embodiments, an LNP can comprise one or more ionizable lipids and an active pharmaceutical ingredient (API), such as a nucleic acid molecule (e.g., an mRNA). In some embodiments, an LNP can comprise one or more ionizable lipids, one or more other lipids, such as neutral lipids, charged lipids, steroids, and polymer conjugated lipids, and an active pharmaceutical ingredient (API), such as a nucleic acid molecule. In some embodiments, an LNP can comprise one or more ionizable lipids, one or more helper lipids, and an active pharmaceutical ingredient (API), such as a nucleic acid molecule.

In some embodiments, an LNP can comprise one or more ionizable lipids selected from the group consisting of (CAS #parenthetical): CKK-E12 (1432494-65-9), TT3 (1821214-50-9), C12-200 (1220890-25-4), SM-102 (2089251-47-6), ALC-0315 (2036272-55-4), DLin-MC3-DMA (1224606 Jun. 7), Lipid 5 (2089251-33-0), and combinations thereof. In some embodiments, the first three (e.g., CKK-E12, TT3 and C12-200) may represent a class of generally symmetric "lipidoids," while the latter four (e.g., SM-102, ALC-0315, DLin-MC3-DMA, and Lipid 5) may be the more canonical asymmetric lipids, three of which are components in FDA-approved drugs (e.g., SM-102 in SpikeVax, ALC-0315 in Comirnaty, and DLin-MC3-DMA in Onpattro). In some embodiments, an LNP can comprise a combination of the following helper/stabilizing lipid components in varying amounts: DOPE, DSPC, DOPC, Cholesterol, DMG-PEG2000, DMPE-PEG2000, ALC-0159, and combinations thereof. In some embodiments, an LNP can comprise quaternary amine/fixed charge cationic lipids, such as DOTAP, DDAB, and/or DOTMA. In some embodiments, an LNP can comprise early generation ionizable lipids, such as DOBAQ, DODMA, and/or DODAP. In some embodiments, an LNP can comprise multivalent cationic lipids, such as MVL5, GL67, and/or DOSPA. In some embodiments, an LNP can comprise SS-OP, SS-EC, Genevant CL1, Acuitas Lipid A9 (CAS #2036272-50-9), Alnylam L319, Arcturus ATX-0114, and/or MIT Lipid 6 (CAS #3037332-21-8). In some embodiments, an LNP can comprise helper lipids, such as beta-sitosterol, stigmasterol, sitostanol, campesterol, campestanol, DSPG, DOPG, DSPE, DSPE-PEG2000-Mannose, DSPE-PEG2000, DMG-PEG1000, DMPE-PEG1000, DMG-pSar25 (pSar refers to polySarcosine), DOPE-pSar25, N-dodecyl-pSar25, DMG-pCBMA (CBMA refers to carboxybetaine methacrylate), DSPE-pCBMA, DMPE-pCBMA, DMG-pSBMA (SBMA refers to sulfobetaine methacrylate), DSPE-pSBMA, and/or DMPE-pSBMA.

The LNPs described herein can be included in a composition, such as a dispensable formulation, microneedle, and/or a microarray patch (MAP) described herein. Such compositions can be used to deliver an active pharmaceutical ingredient (API), such as a nucleic acid (e.g., an mRNA), to a subject. In some embodiments, lipid nanoparticles can be included in a composition, such as a dispensable formulation, microneedle, and/or a microarray patch (MAP) described herein, that can be used to deliver an active pharmaceutical ingredient (API), such as a nucleic acid (e.g., an mRNA), to a target site of interest (e.g., a cell, a tissue, an organ, a tumor, and the like). The term "polydispersity index" or "PDI" refers to a ratio that describes the homogeneity of the particle size distribution of a system, e.g., a lipid nanoparticle composition. A small value, e.g., less than 0.3, indicates a narrow particle size distribution.

As used herein, "encapsulated" by a lipid refers a therapeutic agent, such as a nucleic acid (e.g., mRNA), that is fully or partially encapsulated by a lipid nanoparticle, in some embodiments, the therapeutic agent such as a nucleic acid (e.g., mRNA) is fully encapsulated in a lipid nanoparticle.

The efficiency of the encapsulation of a therapeutic and/or prophylactic agent in a lipid nanoparticle composition describes the amount of the therapeutic and/or prophylactic agent that is encapsulated or otherwise associated with the lipid nanoparticles after preparation, relative to the initial amount provided. The encapsulation efficiency is desired to be high (e.g., close to 100%). The encapsulation efficiency may be measured, for example, by comparing the amount of the therapeutic and/or prophylactic agent in a solution containing a loaded LNP before and after breaking up the loaded LNP with one or more organic solvents or detergents. Fluorescence may be used to measure the amount of free therapeutic and/or prophylactic (e.g., RNA) in a solution. For instance, the encapsulation efficiency may be evaluated using an assay known to one skilled in the art. In some embodiments, the encapsulation efficiency of an API is at least 50%, for example 50%, 55%, 60%, 65%, 70%, 75%, 80%, 85%, 90%, 91%, 92%, 93%, 94%, 95%, 96%, 97%, 98%, 99%, or 100%. In some embodiments, the encapsulation efficiency is at least 80%. In some embodiments, the encapsulation efficiency is at least 90%. In some embodiments, the encapsulation efficiency of the therapeutic and/or prophylactic agent is between 80% and 100%.

In some embodiments, the present disclosure features microneedles and microneedle devices characterized by tips comprising copovidone (e.g., copovidone K25-31 or Kollidon VA 64) and configured for delivery of mRNA, e.g., encapsulated in a lipid nanoparticle, to a subject. The devices and methods disclosed herein can provide, e.g., a means to treat and/or prevent diseases associated with an infectious agent, such as viruses. It has been found that utilizing microneedles characterized by tips comprising copovidone (e.g., copovidone K25-31) results in more efficacious delivery of mRNA and/or enhanced immunogenic effect as compared to alternative microneedles free of copovidone (e.g., copovidone K25-31) and/or by alternative means of delivery, e.g., intradermal or intramuscular delivery.

Accordingly, in one aspect, the present disclosure provides a microneedle device (e.g., a microarray patch) comprising at least one microneedle, optionally a plurality of microneedles, wherein the microneedle comprises copovidone and an mRNA for delivery to a subject. In some embodiments, the microneedle device comprises at least one microneedle comprises: (i) a backing; (ii) a microneedle base, such as a dissolvable base, applied to the backing; and (iii) a consolidated microneedle tip (e.g., an implantable tip), applied to the base, wherein the consolidated microneedle tip (e.g., the implantable tip) comprises copovidone and contains the mRNA. In some embodiments, the microneedle device comprises a lipid nanoparticle (LNP) formulation which encapsulates the mRNA. In some embodiments, the consolidated microneedle tip (e.g., the implantable tip) is substantially free of or does not comprise silk fibroin, optionally, a regenerated silk fibroin and/or silk fibroin. In some embodiments, the consolidated microneedle tip (e.g., the implantable tip) comprises silk fibroin, optionally, a regenerated silk fibroin and/or silk fibroin, optionally wherein the consolidated microneedle tip (e.g., the implantable tip) comprises about 0.01% to about 5% silk fibroin.

In some embodiments, the mRNA encodes an antigen for delivery to the subject, optionally, in an amount sufficient to induce an immune response, optionally, a humoral and/or cellular immune response. In some embodiments, the mRNA encodes an antigen to induce an immune response to Cholera, COVID-19, Dengue fever, Diphtheria, Ebola, *Haemophilus influenzae* type b, Hepatitis A, Hepatitis B, Hepatitis E, Human papillomavirus infection, Influenza, Japanese encephalitis, Malaria, Measles, Meningococcal disease, Monkeypox, Mumps, Pneumococcal disease, Pertussis, Poliomyelitis, Rabies, Rotavirus gastroenteritis, Rubella, Smallpox, Tetanus, Tick-borne encephalitis, Tuberculosis, Typhoid fever, Varicella, Yellow fever, human metapneumovirus (hMPV), Respiratory syncytial virus (RSV), Cytomegalovirus (CMV), Nipah virus, Lyme disease and/or Shingles (Herpes Zoster). In some embodiments, the microneedle device further comprises a second plurality of microneedles comprising an active agent which is different from the mRNA. In some embodiments, the microneedle device is configured for immediate release of the mRNA. In some embodiments, the microneedle device is configured for controlled or sustained release of the mRNA. In some embodiments, the microneedle device is not configured for controlled or sustained release of the mRNA.

In some embodiments, the microneedle base comprises at least one of: a polysaccharide (e.g., dextran); a disaccharide (e.g., sucrose, maltose, and trehalose); a polymer (e.g., methyl cellulose, polyethylene glycol (PEG), carboxymethylcellulose (CMC), hydroxypropyl methylcellulose (HPMC), polyvinylpyrrolidone (PVP), polyvinyl alcohol (PVA), and hyaluronate); a protein (e.g., gelatin); a plasticizer (e.g., glycerol, propanediol); and a surfactant (e.g., an octyl phenol ethoxylate (e.g., Triton-X), a polysorbate, a poloxamers, and/or a polyethoxylated alcohol). In some embodiments, the microneedle base comprises one or more of copovidone, gelatin, dextran, glycerol, polyethylene glycol (PEG) (e.g., including low molecular weight PEG), sucrose, trehalose, maltose, carboxymethylcellulose (CMC), polyvinylpyrrolidone (PVP), polyvinyl alcohol (PVA), hyaluronate, methyl cellulose, and/or a surfactant (e.g., a octyl phenol ethoxylate (e.g., Triton-X), polysorbate, poloxamers, such as P188, and/or a polyethoxylated alcohol). In some embodiments, the microneedle base comprises PVA and/or PVP, optionally wherein: (i) the base comprises about 0.1% to about 5% PVA; (ii) the base comprises about 10% to about 90% PVP; (iii) the PVP is selected from the group consisting of PVP K17, PVP K12, and combinations thereof; and/or (iv) the PVA is PVA 4-88. In some embodiments, the consolidated microneedle tip (e.g., the implantable tip) further comprises: (i) a disaccharide (e.g., sucrose, maltose, and trehalose); (ii) a polymer (e.g., methyl cellulose, polyethylene glycol (PEG), carboxymethylcellulose (CMC), polyvinylpyrrolidone (PVP), polyvinyl alcohol (PVA), hyaluronate); (iii) an amino acid (e.g., threonine); (iv) a plasticizer (e.g., glycerol, propanediol); (v) a buffer (e.g., PBS, 1X TE); (vi) a surfactant (e.g., an octyl phenol ethoxylate (e.g., Triton-X), a polysorbate (e.g., Tween 20), a poloxamers, and/or a polyethoxylated alcohol); and/or (vii) an adjuvant. In some embodiments, the copovidone comprises copovidone K25-31 (Kollidon VA 64). In some embodiments, the consolidated microneedle tip (e.g., the implantable tip) comprises about 0.1% to about 5%, about 0.2% to about 3%, about 0.4% to about 2% or about 0.5 to about 1.5% copovidone. In some embodiments, the consolidated microneedle tip (e.g., the implantable tip) comprise about 1% of copovidone. In some embodiments, the consolidated microneedle tip (e.g., the implantable tip) is substantially free of or does not comprise arginine, PVA and/or PVP, optionally wherein: (i) the tip comprises about 0.1% to about 5% PVA; (ii) the tip comprises about 1% to about 10% PVP; (iii) the PVP is selected from the group consisting of PVP K17, PVP K12, and combinations thereof; and/or (iv) the PVA is PVA 4-88. In some embodiments, the consolidated microneedle tip (e.g., the implantable tip) further comprises sucrose, optionally wherein the consolidated microneedle tip (e.g., the implantable tip) further comprises about 1% to about 20% sucrose. In some embodiments, (i) the base comprises about 17.7% sucrose, about 17.7% PVA 4-88, and about 17.7% PVP K-17; (ii) the base comprises about 50% PVP K12 and 0.5% PVA 4-88; and/or (iii) the consolidated microneedle tip (e.g., the implantable tip) comprises about 1% PVA 4-88, about 5% PVP K17, and about 10% sucrose.

In some embodiments, the microneedle (e.g., the microneedle tip) further comprises, and/or is configured to release, a non-vaccine molecule, e.g., a molecule useful to confirm dose delivery, e.g., a dye molecule (e.g., a biocompatible dye molecule), or a reporter molecule, that can be visualized (e.g., by illuminating with UV irradiation).

Accordingly, in one aspect, the present disclosure provides a method of providing immunity, e.g., broad spectrum immunity, in a subject comprising contacting the skin of the subject with a microneedle device described herein.

Accordingly, in one aspect, the present disclosure provides a method of delivery of an antigen or a vaccine preparation thereof to a subject, comprising contacting the skin of the subject with a microneedle device described herein.

Accordingly, in one aspect, the present disclosure provides a method of increasing an immune response to a virus in a subject comprising contacting the skin of the subject with a microneedle device described herein.

Vaccines and Virus-Like Particles

In some embodiments, the active pharmaceutical ingredient (API) comprises a vaccine, a virus, a virus-like particle (VLP), an antigen, and/or an immunogen. In some embodiments, the dispensable formulation, the microneedle and/or the microarray patch (MAP) can comprise and/or can be administered in combination with a vaccine, a virus, a virus-like particle (VLP), an antigen, and/or an immunogen.

As used herein, the term "antigen" or "immunogen" refers to any molecule or substance capable of inducing an immune response, such as a humoral immune response and/or acellular immune response, e.g., leading to the activation of B and/or T lymphocytes and/or innate immune cells and/or antigen presenting cells. Any macromolecule, including proteins or peptides, can be an antigen. Antigens can also be derived from genomic and/or recombinant DNA. For example, any DNA comprising a nucleotide sequence or a partial nucleotide sequence that encodes a protein capable of eliciting an immune response encodes an "antigen." In some embodiments, an antigen does not need to be encoded solely by a full length nucleotide sequence of a gene, nor does an antigen need to be encoded by a gene at all. In some embodiments, an antigen can be synthesized or can be derived from a biological sample, e.g., a tissue sample, a tumor sample, a cell, or a fluid with other biological components. In some embodiments, an antigen can be derived from a virus, e.g., an inactivated virus, a viral like particle, or a viral vector. Antigens as used herein may also be mixtures of several individual antigens. Exemplary antigens include, without limitation, a gene product, a protein, a peptide, a protein, a pathogen fragment, a whole pathogen, a viral vector, a viral particle, and the like.

As used herein, the term "vaccine" refers to any composition that will elicit a protective immune response in a subject that has been exposed to the composition. An immune response may include induction of antibodies and/ or induction of a T-cell response. Usually, an "immune response" includes but is not limited to one or more of the following effects: the production or activation of antibodies, B cells, helper T cells, suppressor T cells, and/or cytotoxic T cells, directed specifically to an antigen or antigens included in or derived from the composition or vaccine of interest. Preferably, the subject will display either a therapeutic or a protective immunological (memory) response such that resistance to new infection will be enhanced and/or the clinical severity of the disease reduced. Such protection will be demonstrated by either a reduction in number or severity of, or lack of one or more of the clinical signs associated with the infection of the pathogen, in the delay of onset of viremia, in a reduced viral persistence, in a reduction of the overall viral load and/or in a reduction of viral excretion. In some embodiments, a "vaccine" refers to any preparation of an antigen or an immunogen (including subunit antigens, toxoid antigens, conjugate antigens, or other types of antigenic molecules, or nucleic acid molecules encoding the same) or a killed or live attenuated microorganism that, when introduced into a subject's body, affects the immune response to the specific antigen or microorganism by causing activation of the immune system against the specific antigen or microorganism (e.g., inducing antibody formation, T-cell responses, and/or B-cell responses). Generally, vaccines against microorganisms are directed toward at least part of a virus, bacteria, parasite, mycoplasma, or other infectious agent.

Examples of vaccines that can be included in the dispensable formulation, the microneedle and/or the microarray patch (MAP) described herein include, but are not limited to, BIOTHRAX® (anthrax vaccine adsorbed, Emergent Biosolutions, Rockville, Md.); TICE® BCG Live (Bacillus Calmette-Guerin for intravesical use, Organon Tekina Corp. LLC, Durham, N.C.); MYCOBAX® BCG Live (Sanofi Pasteur Inc); DAPTACEL® (diphtheria and tetanus toxoids and acellular pertussis [DTaP] vaccine adsorbed, Sanofi Pasteur Inc.); INFANRIX® (DTaP vaccine adsorbed, GlaxoSmithKline); TRIPEDIA® (DTaP vaccine, Sanofi Pasteur); TRIHIBIT®(DTaP/Hib #, sanofi pasteur); KINRIX® (diphtheria and tetanus toxoids, acellular pertussis adsorbed and inactivated poliovirus vaccine, GlaxoSmithKline); PEDIARIX® (DTaP-HepB-IPV, GlaxoSmithKline); PENTACEL® (diphtheria and tetanus toxoids and acellular pertussis adsorbed, inactivated poliovirus and Haemophilus b conjugate [tetanus toxoid conjugate] vaccine, sanofi pasteur); Diphtheria and Tetanus Toxoids, adsorbed (for pediatric use, Sanofi Pasteur); DECAVAC® (diphtheria and tetanus toxoids adsorbed, for adult use, Sanofi Pasteur); ACTHIB® (Haemophilus b tetanus toxoid conjugate vaccine, Sanofi Pasteur); PEDVAXHIB® (Hib vaccine, Merck); Hiberix (Haemophilus b tetanus toxoid conjugate vaccine, booster dose, GlaxoSmithKline); COMVAX® (Hepatitis B-Hib vaccine, Merck); HAVRIX® (Hepatitis A vaccine, pediatric, GlaxoSmithKline); VAQTA® (Hepatitis A vaccine, pediatric, Merck); ENGERIX-BR (Hep B, pediatric, adolescent, GlaxoSmithKline); RECOMBIVAX HB® (hepatitis B vaccine, Merck); TWINRIX® (HepA/HepB vaccine, 18 years and up, GlaxoSmithKline); CERVARIX® (human papillomavirus bivalent [types 16 and 18] vaccine, recombinant, GlaxoSmithKline); GARDASIL® (human papillomavirus bivalent [types 6, 11, 16 and 18] vaccine, recombinant, Merck); AFLURIA® (Influenza vaccine, 18 years and up, CSL); AGRIFLU™ (influenza virus vaccine for intramuscular injection, Novartis Vaccines); FLUARIX® (Influenza vaccine, 18 years and up, GaxoSmithKline); FLULAVAL® (Influenza vaccine, 18 years and up, GaxoSmithKline); FLUVIRIN® (Influenza vaccine, 4 years and up, Novartis Vaccine); FLUZONE® (Influenza vaccine, 6 months and up, Sanofi Pasteur); FLUMIST® (Influenza vaccine, 2 years and up, Medimmune); IPOL® (e-IPV polio vaccine, sanofi Pasteur); JE VAX® (Japanese encephalitis virus vaccine inactivated, BIKEN, Japan); IXIARO® (Japanese encephalitis virus vaccine inactivated, Novarits); MENACTRA® (Meningococcal [Groups A, C, Y and W-135] and diphtheria vaccine, Sanofi Pasteur); MENOMUNE®-A/C/Y/W-135 (Meningococcal polysaccharide vaccine, sanofi pasteur); MMRII® (MMR vaccine, Merck); MENVEO® (Meningococcal [Groups A, C, Y and W-135] oligosaccharide diphtheria CRM197 conjugate vaccine, Novartis Vaccines); PROQUAD® (MMR and varicella vaccine, Merck); PNEUMOVAX 23® (pneumococcal polysaccharide vaccine, Merck); PREVNAR® (pneumococcal vaccine, 7-valent, Wyeth/Lederle); PREVNAR®-13® (pneumococcal vaccine, 13-valent, Wyeth/Lederle); POLIOVAX™ (poliovirus inactivated, sanofi pasteur); IMOVAX® (Rabies vaccine, Sanofi Pasteur); RABAVERT™ (Rabies vaccine, Chiron); ROTATEQ® (Rotavirus vaccine, live, oral pentavalent, Merck); ROTARIX® (Rotavirus, live, oral vaccine, GlaxoSmithKline); DECAVAC™ (tetanus and diphtheria toxoids vaccine, sanofi pasteur); Td (generic) (tetanus and diphtheria toxoids, adsorbed, Massachusetts Biol. Labs); TYPHIMVI® (typhoid Vi polysaccharide vaccine, Sanofi Pasteur); ADACEL® (tetanus toxoid, reduced diphtheria toxoid and acellular pertussis, sanofi pasteur); BOOSTRIX® (tetanus toxoid, reduced diphtheria toxoid and acellular pertussis, GlaxoSmithKline); VIVOTIF® (typhoid vaccine live oral Ty21a, Berna Biotech); ACAM2000™ (Smallpox (vaccinia) vaccine, live, Acambis, Inc.); DRYVAX® (Smallpox (vaccinia) vaccine); VARIVAX® (varicella [live] vaccine, Merck); YF-VAX® (Yellow fever vaccine, Sanofi Pasteur); ZOSTAVAX® (Varicella zoster, Merck); or combinations thereof. Any vaccine products listed in database of Center for Disease Control and Prevention (CDC) can also be included in the compositions described herein.

The term "virus-like particle (VLP)" as used herein, refers to a non-replicative or non-infectious, preferably a non-replicative and non-infectious virus particle, or refers to a non-replicative or non-infectious, preferably a non-replicative and non-infectious structure resembling a virus particle, preferably a capsid of a virus. The term "non-replicative", as used herein, refers to being incapable of replicating the genome comprised by the VLP. The term "non-infectious", as used herein, refers to being incapable of entering the host cell.

As used herein, the term "virus" refers to an infectious agent composed of, e.g., a nucleic acid encapsidated in a protein. Such infectious agents are incapable of autonomous replication (i.e., replication requires the use of the host cell's machinery). Viral genomes can be single-stranded (ss) or double-stranded (ds), RNA or DNA, and can or cannot use reverse transcriptase (RT). Additionally, ssRNA viruses can be either sense (+) or antisense (−). Exemplary viruses include, but are not limited to, dsDNA viruses (e.g., Adenoviruses, Herpesviruses, Poxviruses), ssDNA viruses (e.g., Parvoviruses), dsRNA viruses (e.g., Reo viruses), (+) ssRNA viruses (e.g., Picornaviruses, Toga viruses, Coronaviruses), (−) ssRNA viruses (e.g., Orthomyxoviruses, Rhabdoviruses), ssRNA-RT viruses, i.e., (+) sense RNA with DNA intermediate in life-cycle (e.g., Retroviruses), and dsDNA-RT viruses (e.g., Hepadnaviruses). In some embodiments, viruses can also include wild-type (natural) viruses, killed viruses, live attenuated viruses, modified viruses, recombinant viruses or any combinations thereof. Exemplary retroviruses include human immunodeficiency virus (HIV). Other examples of viruses include, but are not limited to, enveloped viruses, respiratory syncytial viruses, non-enveloped viruses (e.g., human papillomavirus (HPV)), bacteriophages, recombinant viruses, and viral vectors. The term "bacteriophages" as used herein refers to viruses that infect bacteria.

In some embodiments, the active pharmaceutical ingredient (API) comprises a vaccine, a virus, a virus-like particle (VLP), an antigen, and/or an immunogen related to or derived from Cholera, COVID-19, Dengue fever, Diphtheria, Ebola, *Haemophilus influenzae* type b, Hepatitis A, Hepatitis B, Hepatitis E, Human papillomavirus infection, Influenza, Japanese encephalitis, Malaria, Measles, Meningococcal disease, Monkeypox, Mumps, Pneumococcal disease, Pertussis, Poliomyelitis, Rabies, Rotavirus gastroenteritis, Rubella, Smallpox, Tetanus, Tick-borne encephalitis, Tuberculosis, Typhoid fever, Varicella, Yellow fever, human metapneumovirus (hMPV), Respiratory syncytial virus (RSV), Cytomegalovirus (CMV), Nipah virus, Lyme disease and/or Shingles (Herpes Zoster).

In some embodiments, an antigen or immunogen is capable of inducing an immunological response against itself after administration to a mammalian subject. The term "immunological" as used herein with respect to an immunological response, refers to the development of a humoral (antibody mediated) and/or a cellular (mediated by antigen-specific T cells or their secretion products) response directed against an immunogen in a recipient subject. Such a response can be an active response induced by administration of an immunogen or immunogenic peptide to a subject or a passive response induced by administration of antibody or primed T cells that are directed towards the immunogen.

In some embodiments, an immunogen is a coronavirus antigen. In some embodiments, an immunogen is a coronavirus.

As used herein, the term "coronavirus" refers to a positive-sense ssRNA virus within the Corona viridae family. A coronavirus may be an alphacoronavirus, a betacoronavirus, a gammacoronavirus, or a deltacoronavirus. A coronavirus can be a live wild-type virus, a live attenuated virus, an inactivated virus (e.g., a UV-inactivated virus), a chimeric virus, or a recombinant virus. Coronaviruses are known to infect humans and other animals (e.g., birds and mammals). Examples of coronaviruses include severe acute respiratory syndrome coronavirus (SARS-COV), severe acute respiratory syndrome virus 2 (SARS-COV-2), Middle East respiratory syndrome coronavirus (MERS-COV), human coronavirus 229E (HCoV-229E), human coronavirus NL63 (HCoV-NL63), human coronavirus OC43 (HCoV-OC43), and human coronavirus HKU1 (HCoV-HKLH).

In some embodiments, an immunogen is an influenza virus.

As used herein, the term "influenza virus" refers to a negative-sense ssRNA virus within the Orthomyxoviridae family. An influenza virus can be a live wild-type virus, a live attenuated virus, an inactivated virus, a chimeric virus, or a recombinant virus. Examples of influenza viruses include influenza A, influenza B, influenza C, and influenza D.

In some embodiments, an immunogen is a viral vaccine (e.g., a monovalent (also called univalent) or a multivalent (also called polyvalent) vaccine, such as for coronavirus and/or influenza). In some embodiments, the vaccine (e.g., coronavirus vaccine and/or influenza vaccine) may be monovalent, bivalent, trivalent, quadrivalent (also called tetravalent), or pentavalent. In some embodiments, the immunogen is a replicating or non-replicating vaccine vector (e.g., comprises an adenovirus vector, an adeno-associated virus vector, an alpha virus vector, a herpesvirus vector, a measles virus vector, a poxvirus vector, or a vesicular stomatitis virus vector).

In some embodiments, the active pharmaceutical ingredient (API) comprises an amino acid molecule, such as a peptide, a polypeptide, and/or a protein. In some embodiments, the active pharmaceutical ingredient (API) comprises a recombinant protein. In some embodiments, the active pharmaceutical ingredient (API) comprises a recombinant protein vaccine.

In some embodiments, the active pharmaceutical ingredient (API) comprises a nucleic acid based vaccine, such as a DNA-based vaccine and/or a RNA-based vaccine. In some embodiments, the active pharmaceutical ingredient (API) comprises an mRNA. In some embodiments, the active pharmaceutical ingredient (API) comprises an mRNA-based vaccine.

In some embodiments, the active pharmaceutical ingredient (API) comprises a lipid nanoparticle (LNP) formulation.

Anti-Cancer Agents

In some embodiments, the active pharmaceutical ingredient (API) comprises an anti-cancer agent. In some embodiments, the dispensable formulation, the microneedle and/or the microarray patch (MAP) can comprise and/or can be administered in combination with an anti-cancer agent.

In some embodiments, the active pharmaceutical ingredient (API) comprises a low or small molecular weight chemotherapeutic agent. In some embodiments, the dispensable formulation, the microneedle and/or the microarray patch (MAP) can comprise and/or can be administered in combination with a low or small molecular weight chemotherapeutic agent.

Exemplary low or small molecular weight chemotherapeutic agents include, but not limited to, 13-cis-retinoic acid (isotretinoin, ACCUTANE®), 2-CdA (2-chlorodeoxyadenosine, cladribine, LEUSTATIN™), 5-azacitidine (azacitidine, VIDAZA®), 5-fluorouracil (5-FU, fluorouracil, ADRUCIL®), 6-mercaptopurine (6-MP, mercaptopurine, PURINETHOL®), 6-TG (6-thioguanine, thioguanine, THIOGUANINE TABLOID®), abraxane (paclitaxel protein-bound), actinomycin-D (dactinomycin, COSMEGEN®), alitretinoin (PANRETIN®), all-transretinoic acid (ATRA, tretinoin, VESANOID®), altretamine (hexamethylmelamine, HMM, HEXALEN®), amethopterin (methotrexate, methotrexate sodium, MTX, TREXALL™, RHEUMATREX®), amifostine (ETHYOL®), arabinosylcytosine (Ara-C, cytarabine, CYTOSAR-U®), arsenic trioxide (TRISENOX®), asparaginase (*Erwinia* L-asparaginase, L-asparaginase, ELSPAR®, KIDROLASE®), BCNU (carmustine, BICNU®), bendamustine (TREANDA®), bexarotene (TARGRETIN®), bleomycin (BLENOXANE®), busulfan (BUSULFEX®, MYLERAN®), calcium leucovorin (Citrovorum Factor, folinic acid, leucovorin), camptothecin-11 (CPT-11, irinotecan, CAMPTOSAR®), capecitabine (XELODA®), carboplatin (PARAPLATIN®), carmustine wafer (prolifeprospan 20 with carmustine implant, GLIADEL® wafer), CCI-779 (temsirolimus, TORISEL®), CCNU (lomustine, CeeNU), CDDP (cisplatin, PLATINOL®, PLATINOL-AQ®), chlorambucil (leukeran), cyclophosphamide (CYTOXAN®, NEOSAR®), dacarbazine (DIC, DTIC, imidazole carboxamide, DTIC-DOME®), daunomycin (daunorubicin, daunorubicin hydrochloride, rubidomycin hydrochloride, CERUBIDINE®), decitabine (DACOGEN®), dexrazoxane (ZINECARD®), DHAD (mitoxantrone, NOVANTRONE®), docetaxel (TAXOTERE®), doxorubicin (ADRIAMYCIN®, RUBEX®), epirubicin (ELLENCE™), eribulin (HALAVEN®), estramustine (EMCYT®), etoposide (VP-16, etoposide phosphate, TOPOSAR®, VEPESID®, ETOPOPHOS®), floxuridine (FUDR®), fludarabine (FLUDARA®), fluorouracil (cream) (CARAC™, EFUDEX®, FLUOROPLEX®), gemcitabine (GEMZAR®), hydroxyurea (HYDREA®, DROXIA™, MYLOCEL™), idarubicin (IDAMYCIN®), ifosfamide (IFEX®), ixabepilone (IXEMPRA™), LCR (leurocristine, vincristine, VCR, ONCOVIN®, VINCASAR PFS®), L-PAM (L-sarcolysin, melphalan, phenylalanine mustard, ALKERAN®), mechlorethamine (mechlorethamine hydrochloride, mustine, nitrogen mustard, MUSTARGEN®), mesna (MESNEXT), mitomycin (mitomycin-C, MTC, MUTAMYCIN®), nelarabine (ARRANON®), oxaliplatin (ELOXATIN™), paclitaxel (TAXOL®, ONXAL™), pegaspargase (PEG-L-asparaginase, ONCOSPAR®), PEMETREXED (ALIMTA®), pentostatin (NIPENT®), procarbazine (MATULANE®), streptozocin (ZANOSAR®), temozolomide (TEMODAR®), teniposide (VM-26, VUMON®), TESPA (thiophosphoamide, thiotepa, TSPA, THIOPLEX®), topotecan (HYCAMTIN®), vinblastine (vinblastine sulfate, vincaleukoblastine, VLB, ALKABAN-AQ®, VELBAN®), vinorelbine (vinorelbine tartrate, NAVELBINE®), and vorinostat (ZOLINZA®).

In some embodiments, the dispensable formulation, the microneedle and/or the microarray patch (MAP) can comprise and/or can be administered in combination with an FDA approved targeted therapy. For example, for the treatment of a melanoma a silk fibroin-based microneedle of the present disclosure can comprise and/or can be administered in combination with Binimetinib (MEKTOVI®), Cobimetinib (COTELLIC®), Dabrafenib (TAFINLAR®), Encorafenib (BRAFTOVI®), Trametinib (MEKINIST®), and/or Vemurafenib (ZELBORAF®).

In some embodiments, for the treatment of a basal cell carcinoma the dispensable formulation, the microneedle and/or the microarray patch (MAP) can comprise and/or can be administered in combination with Sonidegib (ODOMZO®) and/or Vismodegib (Erivedge®).

In some embodiments, for the treatment of a breast cancer the dispensable formulation, the microneedle and/or the microarray patch (MAP) can comprise and/or can be administered in combination with Abemaciclib (VERZENIO®), Alpelsib (PIQRAY®), Olaparib (LYNPARZA®), Palbociclib (IBRANCE®), Ribociclib (KISQALI®), and/or Talazoparib (TALZENNA®).

In some embodiments, the dispensable formulation, the microneedle and/or the microarray patch (MAP) can comprise and/or can be administered in combination with a biologic. Biologics useful in the treatment of cancers are known in the art and the dispensable formulation, the microneedle and/or the microarray patch (MAP), as described herein, may be administered, for example, in conjunction with such known biologics. For example, the FDA has approved the following biologics for the treatment of breast cancer: HERCEPTIN® (trastuzumab, Genentech Inc., South San Francisco, Calif.; a humanized monoclonal antibody that has anti-tumor activity in HER2-positive breast cancer); FASLODEX® (fulvestrant, AstraZeneca Pharmaceuticals, LP, Wilmington, Del.; an estrogen-receptor antagonist used to treat breast cancer); ARIMIDEX® (anastrozole, AstraZeneca Pharmaceuticals, LP; a nonsteroidal aromatase inhibitor which blocks aromatase, an enzyme needed to make estrogen); AROMASIN® (exemestane, Pfizer Inc., New York, N.Y.; an irreversible, steroidal aromatase inactivator used in the treatment of breast cancer); FEMARA® (letrozole, Novartis Pharmaceuticals, East Hanover, N.J.; a nonsteroidal aromatase inhibitor approved by the FDA to treat breast cancer); and NOLVADEX® (tamoxifen, AstraZeneca Pharmaceuticals, LP; a nonsteroidal antiestrogen approved by the FDA to treat breast cancer). Other biologics with which the the dispensable formulation, the microneedle and/or the microarray patch (MAP) may be combined include: AVASTIN® (bevacizumab, Genentech Inc.; the first FDA-approved therapy designed to inhibit angiogenesis); and ZEVALIN® (ibritumomab tiuxetan, Biogen Idec, Cambridge, Mass.; a radiolabeled monoclonal antibody currently approved for the treatment of B-cell lymphomas).

In addition, the FDA has approved the following biologics for the treatment of colorectal cancer: AVASTIN®; ERBITUX® (cetuximab, ImClone Systems Inc., New York, N.Y., and Bristol-Myers Squibb, New York, N.Y.; is a monoclonal antibody directed against the epidermal growth factor receptor (EGFR)); GLEEVEC® (imatinib mesylate; a protein kinase inhibitor); and ERGAMISOL® (levamisole hydrochloride, Janssen Pharmaceutica Products, LP, Titusville, N.J.; an immunomodulator approved by the FDA in 1990 as an adjuvant treatment in combination with 5-fluorouracil after surgical resection in patients with Dukes' Stage C colon cancer).

For the treatment of lung cancer, exemplary biologics include TARCEVA® (erlotinib HCL, OSI Pharmaceuticals Inc., Melville, N.Y.; a small molecule designed to target the human epidermal growth factor receptor 1 (HER1) pathway).

For the treatment of multiple myeloma, exemplary biologics include VELCADE® Velcade (bortezomib, Millennium Pharmaceuticals, Cambridge Mass.; a proteasome inhibitor). Additional biologics include THALIDOMID® (thalidomide, Clegene Corporation, Warren, N.J.; an immunomodulatory agent and appears to have multiple actions, including the ability to inhibit the growth and survival of myeloma cells and anti-angiogenesis).

Additional exemplary cancer therapeutic antibodies include, but are not limited to, 3F8, abagovomab, adecatumumab, ado-trastuzumab emtansine (KADCYLA®), afutuzumab, alacizumab pegol, alemtuzumab (CAMPATH®, MABCAMPATH®), altumomab pentetate (HYBRI-CEAKER®), anatumomab mafenatox, anrukinzumab (IMA-638), apolizumab, arcitumomab (CEA-SCAN®), atezolizumab (TECENTRIQ®), avelumab (BAVENCIO®), bavituximab, bectumomab (LYMPHOSCAN®), belimumab (BENLYSTA®, LYMPHOSTAT-B®), besilesomab (SCIN-TIMUN®), bevacizumab (AVASTIN®), bivatuzumab mertansine, blinatumomab, brentuximab vedotin, cantuzumab mertansine, capromab pendetide (PROSTASCINT®), catumaxomab (REMOVAB®), CC49, cemiplimab-rwlc (LIBTAYO®) cetuximab (C225, ERBITUX®), citatuzumab bogatox, cixutumumab, clivatuzumab tetraxetan, conatumumab, dacetuzumab, denosumab (PROLIA®), detumomab, ecromeximab, edrecolomab (PANOREX®), elotuzumab, epitumomab cituxetan, epratuzumab, ertumaxomab (REXOMUN®), etaracizumab, farletuzumab, figitumumab, fresolimumab, galiximab, gemtuzumab ozogamicin (MYLOTARG®), girentuximab, glembatumumab vedotin, ibritumomab (ibritumomab tiuxetan, ZEVALIN®), igovomab (INDIMACIS-125®), intetumumab, inotuzumab ozogamicin, ipilimumab, iratumumab, labetuzumab (CEA-CIDE®), lexatumumab, lintuzumab, lucatumumab, lumiliximab, mapatumumab, matuzumab, milatuzumab, minretumomab, mitumomab, nacolomab tafenatox, naptumomab estafenatox, necitumumab, nimotuzumab (THER-ACIM®, THERALOC®), nofetumomab merpentan (VER-LUMA®), ofatumumab (ARZERRA®), olaratumab, oportuzumab monatox, oregovomab (OVAREX®), panitumumab (VECTIBIX®), pemtumomab (THERAGYN®), pertuzumab (OMNITARG®), pintumomab, pritumumab, ramucirumab, ranibizumab (LUCENTIS®), rilotumumab, rituximab (MABTHERA®, RITUXAN®), robatumumab, satumomab pendetide, sibrotuzumab, siltuximab, sontuzumab, tacatuzumab tetraxetan (AFP-CIDE®), taplitumomab paptox, tenatumomab, TGN1412, ticilimumab (tremelimumab), tigatuzumab, TNX-650, tositumomab (BEXXAR®), trastuzumab (HERCEPTIN®), trastuzumab and hyaluronidase-oysk (HERCEPTIN HYLECTA®), tremelimumab, tucotuzumab celmoleukin, veltuzumab, volociximab, votumumab (HUMASPECT®), zalutumumab (HUMAX-EGFR®), and zanolimumab (HUMAX-CD4®).

In other embodiments, the dispensable formulation, the microneedle and/or the microarray patch (MAP) can comprise and/or can be administered in combination with a viral cancer therapeutic agent. Exemplary viral cancer therapeutic agents include, but are not limited to, vaccinia virus (vvDD-CDSR), carcinoembryonic antigen-expressing measles virus, recombinant vaccinia virus (TK-deletion plus GM-CSF), Seneca Valley virus-001, Newcastle virus, coxsackie virus A21, GL-ONC1, EBNA1 C-terminal/LMP2 chimeric protein-expressing recombinant modified vaccinia Ankara vaccine, carcinoembryonic antigen-expressing measles virus, G207 oncolytic virus, modified vaccinia virus Ankara vaccine expressing p53, OncoVEX GM-CSF modified herpes-simplex 1 virus, fowlpox virus vaccine vector, recombinant vaccinia prostate-specific antigen vaccine, human papillomavirus 16/18 L1 virus-like particle/AS04 vaccine, MVA-EBNA1/LMP2 Inj. vaccine, quadrivalent HPV vaccine, quadrivalent human papillomavirus (types 6, 11, 16, 18) recombinant vaccine (GARDASIL®), recombinant fowlpox-CEA (6D)/TRICOM vaccine; recombinant vaccinia-CEA (6D)-TRICOM vaccine, recombinant modified vaccinia Ankara-5T4 vaccine, recombinant fowlpox-TRICOM vaccine, oncolytic herpes virus NV1020, HPV L1 VLP vaccine V504, human papillomavirus bivalent (types 16 and 18) vaccine (CERVARIX®), herpes simplex virus HF10, Ad5CMV-p53 gene, recombinant vaccinia DF3/MUC1 vaccine, recombinant vaccinia-MUC-1 vaccine, recombinant vaccinia-TRICOM vaccine, ALVAC MART-1 vaccine, replication-defective herpes simplex virus type I (HSV-1) vector expressing human Preproenkephalin (NP2), wild-type reovirus, reovirus type 3 Dearing (REOLYSIN®), oncolytic virus HSV1716, recombinant modified vaccinia Ankara (MVA)-based vaccine encoding Epstein-Barr virus target antigens, recombinant fowlpox-prostate specific antigen vaccine, recombinant vaccinia prostate-specific antigen vaccine, recombinant vaccinia-B7.1 vaccine, rAd-p53 gene, Ad5-delta24RGD, HPV vaccine 580299, JX-594 (thymidine kinase-deleted vaccinia virus plus GM-CSF), HPV-16/18 L1/AS04, fowlpox virus vaccine vector, vaccinia-tyrosinase vaccine, MEDI-517 HPV-16/18 VLP AS04 vaccine, adenoviral vector containing the thymidine kinase of herpes simplex virus TK99UN, HspE7, FP253/Fludarabine, ALVAC (2) melanoma multi-antigen therapeutic vaccine, ALVAC-hB7.1, canarypox-hIL-12 melanoma vaccine, Ad-REIC/Dkk-3, rAd-IFN SCH 721015, TIL-Ad-INFg, Ad-ISF35, and coxsackievirus A21 (CVA21, CAVATAK®). In other embodiments, the dispensable formulation, the microneedle and/or the microarray patch (MAP) can comprise and/or can be administered in combination with Talimogene Laherparepvec (IMLYGIC®), an FDA approved melanoma treatment.

In other embodiments, the dispensable formulation, the microneedle and/or the microarray patch (MAP) can comprise and/or can be administered in combination with a neoantigen vaccine. In certain embodiments, a neoantigen vaccine can be prepared as described, for example, in Schumacher et al. Science. 348 (6230): 69-74, 2015, incorporated herein by reference in its entirety. In some embodiments, a microneedle disclosed herein can be used in a method for identifying a neoantigen, and/or in a method of preparing a neoantigen vaccine. Without wishing to be bound by theory, cancer neoantigens derived from random somatic mutations in tumor tissue represent an attractive type of target for cancer immunotherapies including cancer vaccines. Vaccination against the tumor-specific neoantigens minimizes the potential induction of central and peripheral tolerance as well as the risk of autoimmunity. (See e.g., Guo et al. Frontiers in Immunology. Vol. 9 Article 1499, 2018, which is incorporated herein by reference in its entirety). In certain embodiments, the application of a microneedle of the present disclosure to a tumor can result in the subject's immune system being exposed to tumor-specific neoantigens, and result in the development of a vaccination and immunity to cancers having the same, or similar, tumor-specific neoantigens.

In other embodiments, the dispensable formulation, the microneedle and/or the microarray patch (MAP) can comprise and/or can be administered in combination with a nanopharmaceutical. Exemplary cancer nanopharmaceuticals include, but are not limited to, ABRAXANE® (paclitaxel bound albumin nanoparticles), CRLX101 (camptothecin (CPT) conjugated to a linear cyclodextrin-based polymer), CRLX288 (conjugating docetaxel to the biodegradable polymer poly(lactic-co-glycolic acid)), cytarabine liposomal (liposomal Ara-C, DEPOCYT™), daunorubicin liposomal (DAUNOXOME®), doxorubicin liposomal (DOXIL®, CAELYX®), encapsulated-daunorubicin citrate liposome (DAUNOXOME®), and PEG anti-VEGF aptamer (MACUGEN®).

In some embodiments, the dispensable formulation, the microneedle and/or the microarray patch (MAP) can comprise and/or can be administered in combination with paclitaxel or a paclitaxel formulation, e.g., TAXOL®, protein-bound paclitaxel (e.g., ABRAXANE®). Exemplary paclitaxel formulations include, but are not limited to, nanoparticle albumin-bound paclitaxel (ABRAXANE®, marketed by Abraxis Bioscience), docosahexaenoic acid bound-paclitaxel (DHA-paclitaxel, Taxoprexin, marketed by Protarga), polyglutamate bound-paclitaxel (PG-paclitaxel, paclitaxel poliglumex, CT-2103, XYOTAX, marketed by Cell Therapeutic), the tumor-activated prodrug (TAP), ANG105 (Angiopep-2 bound to three molecules of paclitaxel, marketed by ImmunoGen), paclitaxel-EC-1 (paclitaxel bound to the erbB2-recognizing peptide EC-1; see Li et al., Biopolymers (2007) 87:225-230), and glucose-conjugated paclitaxel (e.g., 2'-paclitaxel methyl 2-glucopyranosyl succinate (see, e.g., Liu et al., *Bioorganic & Medicinal Chemistry Letters* (2007) 17:617-620).

Exemplary RNAi and antisense RNA agents for treating cancer include, but not limited to, CALAA-01, siG12D LODER (Local Drug EluteR), and ALN-VSP02.

Other cancer therapeutic agents include, but not limited to, cytokines (e.g., aldesleukin (IL-2, Interleukin-2, PRO-LEUKIN®), alpha Interferon (IFN-alpha, Interferon alfa, INTRON® A (Interferon alfa-2b), ROFERON-A® (Interferon alfa-2a)), Epoetin alfa (PROCRIT®), filgrastim (G-CSF, Granulocyte-Colony Stimulating Factor, NEUPO-GEN®), GM-CSF (Granulocyte Macrophage Colony Stimulating Factor, sargramostim, LEUKINE™), IL-11 (Interleukin-11, oprelvekin, NEUMEGA®), Interferon alfa-2b (PEG conjugate) (PEG interferon, PEG-INTRON™), and pegfilgrastim (NEULASTA™)), hormone therapy agents (e.g., aminoglutethimide (CYTADREN®), anastrozole (ARIMIDEX®), bicalutamide (CASODEX®), exemestane (AROMASIN®), fluoxymesterone (HALOTESTIN®), flutamide (EULEXIN®), fulvestrant (FASLODEX®), goserelin (ZOLADEX®), letrozole (FEMARA®), leuprolide (ELIGARD™, LUPRON®, LUPRON DEPOT®, VIADUR™), megestrol (megestrol acetate, MEGACE®), nilutamide (ANANDRON®, NILANDRON®), octreotide (octreotide acetate, SANDOSTATIN®, SANDOSTATIN LAR®), raloxifene (EVISTA®), romiplostim (NPLATE®), tamoxifen (NOVALDEX®), and toremifene (FARESTON®)), phospholipase A2 inhibitors (e.g., anagrelide (AGRYLIN®)), biologic response modifiers (e.g., BCG (THERACYS®, TICE®), and Darbepoetin alfa (ARANESP®)), target therapy agents (e.g., bortezomib (VELCADE®), dasatinib (SPRYCEL™), denileukin diftitox (ONTAK®), erlotinib (TARCEVA®), everolimus (AFINITOR®), gefitinib (IRESSA®), imatinib mesylate (STI-571, GLEEVEC™), lapatinib (TYKERB®), sorafenib (NEXAVAR®), and SU11248 (sunitinib, SUTENT®)), immunomodulatory and antiangiogenic agents (e.g., CC-5013 (lenalidomide, REVLIMID®), and thalidomide (THALOMID®)), glucocorticosteroids (e.g., cortisone (hydrocortisone, hydrocortisone sodium phosphate, hydrocortisone sodium succinate, ALA-CORT®, HYDROCORT ACETATE®, hydrocortone phosphate LANACORT®, SOLU-CORTEF®), decadron (dexamethasone, dexamethasone acetate, dexamethasone sodium phosphate, DEXASONE®, DIODEX®, HEXADROL®, MAXIDEX®), methylprednisolone (6-methylprednisolone, methylprednisolone acetate, methylprednisolone sodium succinate, DURAL-ONE®, MEDRALONE®, MEDROL®, M-PREDNISOL®, SOLU-MEDROL®), prednisolone (DELTA-CORTEF®, ORAPRED®, PEDIAPRED®, PRELONE®), and prednisone (DELTASONE®, LIQUID PRED®, METI-CORTEN®, ORASONE®)), and bisphosphonates (e.g., pamidronate (AREDIA®), and zoledronic acid (ZO-META®))

In some embodiments, the dispensable formulation, the microneedle and/or the microarray pacth (MAP) can comprise and/or can be administered in combination with a tyrosine kinase inhibitor (e.g., a receptor tyrosine kinase (RTK) inhibitor). Exemplary tyrosine kinase inhibitor include, but are not limited to, an epidermal growth factor (EGF) pathway inhibitor (e.g., an epidermal growth factor receptor (EGFR) inhibitor), a vascular endothelial growth factor (VEGF) pathway inhibitor (e.g., an antibody against VEGF, a VEGF trap, a vascular endothelial growth factor receptor (VEGFR) inhibitor (e.g., a VEGFR-1 inhibitor, a VEGFR-2 inhibitor, a VEGFR-3 inhibitor)), a platelet derived growth factor (PDGF) pathway inhibitor (e.g., a platelet derived growth factor receptor (PDGFR) inhibitor (e.g., a PDGFR-β inhibitor)), a RAF-1 inhibitor, a KIT inhibitor and a RET inhibitor. In some embodiments, the anti-cancer agent used in combination with the AHCM agent is selected from the group consisting of: axitinib (AG013736), bosutinib (SKI-606), cediranib (RECENTIN™, AZD2171), dasatinib (SPRYCEL®, BMS-354825), erlotinib (TARCEVA®), gefitinib (IRESSA®), imatinib (Gleevec®, CGP57148B, STI-571), lapatinib (TYKERB®, TYVERB®), lestaurtinib (CEP-701), neratinib (HKI-272), nilotinib (TASIGNA®), semaxanib (semaxinib, SU5416), sunitinib (SUTENT®, SU11248), toceranib (PALLA-DIA®), vandetanib (ZACTIMA®, ZD6474), vatalanib (PTK787, PTK/ZK), trastuzumab (HERCEPTIN®), bevacizumab (AVASTIN®), rituximab (RITUXAN®), cetuximab (ERBITUX®), panitumumab (VECTIBIX®), ranibizumab (Lucentis®), nilotinib (TASIGNA®), sorafenib (NEXAVAR®), alemtuzumab (CAMPATH®), gemtuzumab ozogamicin (MYLOTARG®), ENMD-2076, PCI-32765, AC220, dovitinib lactate (TKI258, CHIR-258), BIBW 2992 (TOVOK™), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, XL228, AEE788, AG-490, AST-6, BMS-599626, CUDC-101, PD153035, pelitinib (EKB-569), vandetanib (zactima), WZ3146, WZ4002, WZ8040, ABT-869 (linifanib), AEE788, AP24534 (ponatinib), AV-951 (tivozanib), axitinib, BAY 73-4506 (regorafenib), brivanib alaninate (BMS-582664), brivanib (BMS-540215), cediranib (AZD2171), CHIR-258 (dovitinib), CP 673451, CYC116, E7080, Ki8751, masitinib (AB1010), MGCD-265, motesanib diphosphate (AMG-706), MP-470, OSI-930, Pazopanib Hydrochloride, PD173074, nSorafenib Tosylate (Bay 43-9006), SU 5402, TSU-68 (SU6668), vatalanib, XL880 (GSK1363089, EXEL-2880). Selected tyrosine kinase inhibitors are chosen from sunitinib, erlotinib, gefitinib, or sorafenib. In one embodiment, the tyrosine kinase inhibitor is sunitinib.

In some embodiments, the dispensable formulation, the microneedle and/or the microarray pacth (MAP) can comprise and/or can be administered in combination with one of more of: an anti-angiogenic agent, or a vascular targeting agent or a vascular disrupting agent. Exemplary anti-angiogenic agents include, but are not limited to, vascular endothelial growth factor (VEGF) inhibitors (e.g., anti-VEGF antibodies (e.g., bevacizumab); VEGF receptor inhibitors (e.g., itraconazole); inhibitors of cell proliferatin and/or migration of endothelial cells (e.g., carboxyamido-triazole, TNP-470); inhibitors of angiogenesis stimulators (e.g., suramin), among others. A vascular-targeting agent (VTA) or vascular disrupting agent (VDA) is designed to damage the vasculature (blood vessels) of cancer tumors causing central necrosis (reviewed in, e.g., Thorpe, P. E. (2004) Clin. Cancer Res. Vol. 10:415-427). VTAs can be small-molecules. Exemplary small-molecule VTAs include, but are not limited to, microtubule destabilizing drugs (e.g., combretastatin A-4 disodium phosphate (CA4P), ZD6126, AVE8062, Oxi 4503); and vadimezan (ASA404).

In certain embodiments, the anti-cancer agent described herein can be formulated in a sustained release particle.

Immunomodulatory Agents

In some embodiments, the active pharmaceutical ingredient (API) comprises an immunomodulatory agent. In some embodiments, the dispensable formulation, the microneedle and/or the microarray pacth (MAP) can comprise and/or can be administered in combination with an immunomodulatory agent.

Checkpoint Inhibitors

In some embodiments, the dispensable formulation, the microneedle and/or the microarray pacth (MAP) can comprise and/or can be administered in combination with an immune checkpoint inhibitor. For example, in certain embodiments, a silk fibroin-based microneedle can be used to locally administer a therapeutic agent (e.g., ant anti-cancer agent and/or an immunomodulatory agent) to a tumor in a subject in combination with systemic administration (e.g., by injection) of a checkpoint inhibitor (e.g., an anti-PD1 antibody).

In embodiments, an immune checkpoint inhibitor inhibits a checkpoint molecule. Exemplary checkpoint molecules include but are not limited to CTLA4, PD1, PD-L1, PD-L2, TIM3, LAG3, CD160, 2B4, CD80, CD86, B7-H3 (CD276), B7-H4 (VTCN1), HVEM (TNFRSF14 or CD270), BTLA, KIR, MHC class I, MHC class II, GAL9, VISTA, BTLA, TIGIT, LAIR1, and A2aR. See, e.g., Pardoll. Nat. Rev. Cancer 12.4 (2012): 252-64, incorporated herein by reference.

In some embodiments, the immune checkpoint inhibitor is a PD-1 inhibitor, e.g., an anti-PD-1 antibody such as Nivolumab, Pembrolizumab or Pidilizumab. Nivolumab (also called MDX-1106, MDX-1106-04, ONO-4538, or BMS-936558) is a fully human IgG4 monoclonal antibody that specifically inhibits PD1. See, e.g., U.S. Pat. No. 8,008,449 and WO2006/121168. Pembrolizumab (also called Lambrolizumab, MK-3475, MK03475, SCH-900475 or KEYTRUDA®; Merck) is a humanized IgG4 monoclonal antibody that binds to PD-1. (See, e.g., Hamid, O. et al. (2013) New England Journal of Medicine 369 (2): 134-44, U.S. Pat. No. 8,354,509 and WO2009/114335). Pidilizumab (also called CT-011 or Cure Tech) is a humanized IgG1k monoclonal antibody that binds to PD1. (See, e.g., WO2009/101611). In one embodiment, the inhibitor of PD-1 is an antibody molecule having a sequence substantially identical or similar thereto, e.g., a sequence at least 85%, 90%, 95% identical or higher to the sequence of Nivolumab, Pembrolizumab or Pidilizumab. Additional anti-PD1 antibodies, e.g., AMP 514 (Amplimmune), are described, e.g., in U.S. Pat. No. 8,609,089, US2010028330, and/or US20120114649.

In some embodiments, the PD-1 inhibitor is an immuno-adhesin, e.g., an immunoadhesin comprising an extracellular/PD-1 binding portion of a PD-1 ligand (e.g., PD-L1 or PD-L2) that is fused to a constant region (e.g., an Fc region of an immunoglobulin). In embodiments, the PD-1 inhibitor is AMP-224 (B7-DCIg, e.g., described in WO2011/066342 and WO2010/027827), a PD-L2 Fc fusion soluble receptor that blocks the interaction between B7-H1 and PD-1.

In some embodiments, the immune checkpoint inhibitor is a PD-L1 inhibitor, e.g., an antibody molecule. In some embodiments, the PD-L1 inhibitor is YW243.55.S70, MPDL3280A, MEDI-4736, MSB-0010718C, or MDX-1105. In some embodiments, the anti-PD-L1 antibody is MSB0010718C (also called A09-246-2; Merck Serono), which is a monoclonal antibody that binds to PD-L1. Exemplary humanized anti-PD-L1 antibodies are described, e.g., in WO2013/079174. In one embodiment, the PD-L1 inhibitor is an anti-PD-L1 antibody, e.g., YW243.55.S70. The YW243.55.S70 antibody is described, e.g., in WO 2010/077634. In one embodiment, the PD-L1 inhibitor is MDX-1105 (also called BMS-936559), which is described, e.g., in WO2007/005874. In one embodiment, the PD-L1 inhibitor is MDPL3280A (Genentech/Roche), which is a human Fc-optimized IgG1 monoclonal antibody against PD-L1. See, e.g., U.S. Pat. No. 7,943,743 and U.S Publication No.: 20120039906. In one embodiment, the inhibitor of PD-L1 is an antibody molecule having a sequence substantially identical or similar thereto, e.g., a sequence at least 85%, 90%, 95% identical or higher to the sequence of YW243.55.S70, MPDL3280A, MEDI-4736, MSB-0010718C, or MDX-1105.

In embodiments, the immune checkpoint inhibitor is a PD-L2 inhibitor, e.g., AMP-224 (which is a PD-L2 Fc fusion soluble receptor that blocks the interaction between PD1 and B7-H1. See, e.g., WO2010/027827 and WO2011/066342.

In one embodiment, the immune checkpoint inhibitor is a LAG-3 inhibitor, e.g., an anti LAG-3 antibody molecule. In embodiments, the anti-LAG-3 antibody is BMS-986016 (also called BMS986016; Bristol-Myers Squibb). BMS-986016 and other humanized anti-LAG-3 antibodies are described, e.g., in US 2011/0150892, WO2010/019570, and WO2014/008218.

In embodiments, the immune checkpoint inhibitor is a TIM-3 inhibitor, e.g., anti-TIM3 antibody molecule, e.g., described in U.S. Pat. No. 8,552,156, WO 2011/155607, EP 2581113 and U.S Publication No.: 2014/044728.

In embodiments, the immune checkpoint inhibitor is a CTLA-4 inhibitor, e.g., anti-CTLA-4 antibody molecule. Exemplary anti-CTLA4 antibodies include Tremelimumab (IgG2 monoclonal antibody from Pfizer, formerly known as ticilimumab, CP-675,206); and Ipilimumab (also called MDX-010, CAS No. 477202-00-9). Other exemplary anti-CTLA-4 antibodies are described, e.g., in U.S. Pat. No. 5,811,097.

TLR Agonists

In some embodiments, the dispensable formulation, the microneedle and/or the microarray pacth (MAP) can comprise and/or can be administered in combination with a Toll-like receptor (TLR) agonist.

TLRs are a family of pattern recognition receptors that were initially identified as sensors of the innate immune system that recognize microbial pathogens. In humans, the TLRs include TLR-1, TLR-2, TLR-3, TLR-4, TLR-5, TLR-6, TLR-7, TLR-8, TLR-9, and TLR-10. TLR-1, -2, -4, -5, and -6, are expressed on the surface of cells and TLR-3, -7/8, and -9 are expressed with the ER compartment. Human dendritic cell subsets can be identified on the basis of distinct TLR expression patterns. The myeloid or "conventional" subset of human dendritic cells express TLRs 1-8 and the plasmacytoid subset of dendritic cells express only TLR-7 and TLR-9. Ligand binding to TLRs invokes a cascade of intra-cellular signaling pathways that induce the production of factors involved in inflammation and immunity. Upon stimulation, the myeloid subset and the plasmacytoid subset of human dendritic cells result in antigen-specific CD4+ and CD8+ T cell priming and activation of NK cells and T-cells, respectively.

In some embodiments, the TLR agonist is chosen from one or more of a TLR-1 agonist, a TLR-2 agonist, a TLR-3 agonist, a TLR-4 agonist, a TLR-5 agonist, a TLR-6 agonist, a TLR-7 agonist, a TLR-8 agonist, a TLR-9 agonist, a TLR-10 agonist, a TLR-1/2 agonist, a TLR-2/6 agonist, or a TLR-7/8 agonist. In one embodiment, the TLR agonist is a TLR7 agonist.

In some embodiments, the TLR agonist is imiquimod or 3-(2-methylpropyl)-3,5,8-triazatricyclo[7.4.0.02,6]trideca-1 (9),2(6),4,7,10,12-hexaen-7-amine. Imiquimod or 3-(2-methylpropyl)-3,5,8-triazatricyclo[7.4.0.02,6]trideca-1 (9),2 (6),4,7,10,12-hexaen-7-amine can bind to and activate TLR-7 and/or TLR-8.

In some embodiments, the TLR agonist is 852A. 852A is disclosed, e.g., in Inglefield et al. *J Interferon Cytokine Res.* 2008; 28 (4): 253-63. 852A can bind to and activate TLR-7 and/or TLR-8.

In some embodiments, the TLR agonist is Bacille Calmette-Guérin (BCG). BCG can bind to and activate TLR-9.

In some embodiments, the TLR agonist is EMD 120108. EMD 120108 is a synthetic oligonucleotide containing phosphorothioate oligodeoxynucleotide. EMD 1201081 can bind to and activate TLR-9, e.g., in monocytes/macrophages, plasmacytoid dendritic cells (DCs) and B cells, initiating immune signaling pathways, activating B cells and inducing T-helper cell cytokine production.

In some embodiments, the TLR agonist is IMO-2055. IMO-2055 is a synthetic oligonucleotide containing unmethylated CpG dinucleotides. Mimicking unmethylated CpG sequences in bacterial DNA, IMO-2055 can bind to and activate TLR-9, e.g., in monocytes/macrophages, plasmacytoid dendritic cells (DCs) and B cells, initiating immune signaling pathways and activating B cells and DCs and inducing T-helper cell cytokine production.

Other exemplary TLR agonists that can be used in the combination include, e.g., TLR-1/2 agonists (e.g., Pam3Cys), TLR-2 agonists (e.g., CFA, MALP2, Pam2Cys, FSL-1, or Hib-OMPC), TLR-3 agonists (e.g., polyribosinic: polyribocytidic acid (Poly I: C), polyadenosine-polyuridylic acid (poly AU), polyinosinic-polycytidylic acid stabilized with poly-L-lysine and carboxymethylcellulose (Hiltonol®)), TLR-4 agonists (e.g., monophosphoryl lipid A (MPL), LPS, sialyl-Tn (STn)), TLR-5 agonists (e.g., bacterial flagellin), TLR-7 agonists (e.g., imiquimod), TLR-7/8 agonists (e.g., resiquimod or loxoribine), and TLR-9 agonists (e.g., unmethylated CpG dinucleotide (CpG-ODN)).

In another embodiment, the TLR agonist is used in combination with a GITR agonist, e.g., as described in WO2004/060319, and International Publication No.: WO2014/012479.

STING Agonists

In some embodiments, the dispensable formulation, the microneedle and/or the microarray pacth (MAP) can comprise and/or can be administered in combination with a STING agonist.

In some embodiments, the STING agonist is cyclic dinucleotide, e.g., a cyclic dinucleotide comprising purine or pyrimidine nucleobases (e.g., adenosine, guanine, uracil, thymine, or cytosine nucleobases). In some embodiments, the nucleobases of the cyclic dinucleotide comprise the same nucleobase or different nucleobases.

In some embodiments, the STING agonist comprises an adenosine or a guanosine nucleobase. In some embodiments, the STING agonist comprises one adenosine nucleobase and one guanosine nucleobase. In some embodiments, the STING agonist comprises two adenosine nucleobases or two guanosine nucleobases.

In some embodiments, the STING agonist comprises a modified cyclic dinucleotide, e.g., comprising a modified nucleobase, a modified ribose, or a modified phosphate linkage. In some embodiments, the modified cyclic dinucleotide comprises a modified phosphate linkage, e.g., a thiophosphate.

In some embodiments, the STING agonist comprises a cyclic dinucleotide (e.g., a modified cyclic dinucleotide) with 2',5' or 3',5' phosphate linkages. In some embodiments, the STING agonist comprises a cyclic dinucleotide (e.g., a modified cyclic dinucleotide) with Rp or Sp stereochemistry around the phosphate linkages.

Figure 7:
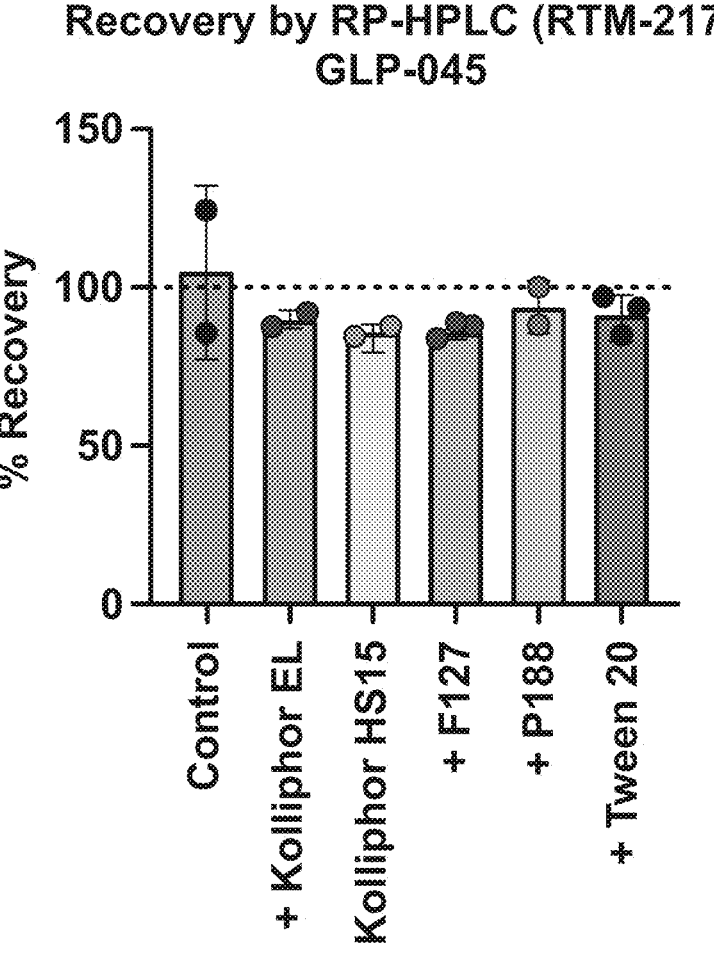
FIG. 7 shows the percent recovery of inactive semaglutide by RP-HPLC. Films containing various surfactants with the background formulation of 180 mg/mL GLP-1+1% PVP K17+1.37% Arg-HCl+0.1 mg/mL AF-647 in 100 mM MOPS from GLP-045.
Figure 8:
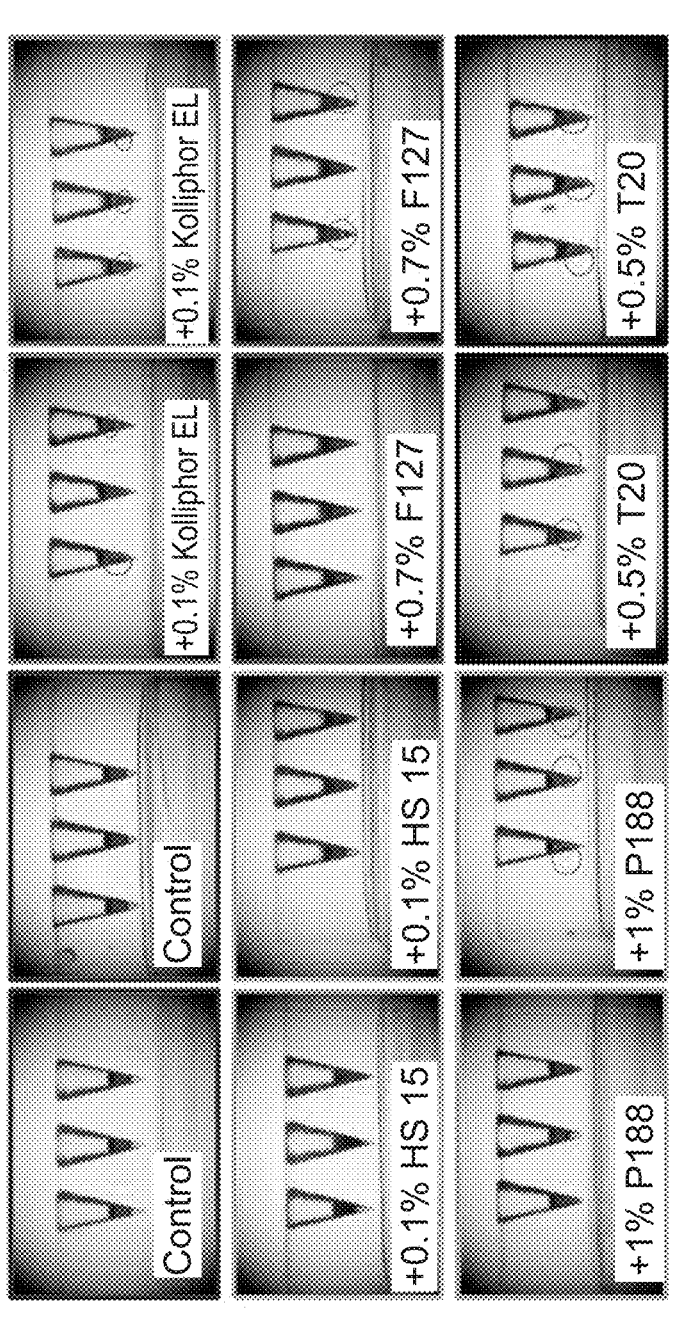
FIG. 8 shows visible light micrographs of dry tips in a macromold model system in GLP-045. Each needle cavity in the macromold is 5 mm long and is filled with about 2.4 µL of formulation by pipette and centrifugation. Kolliphor EL and P188 have relatively better dry tip morphology.
Figure 10:
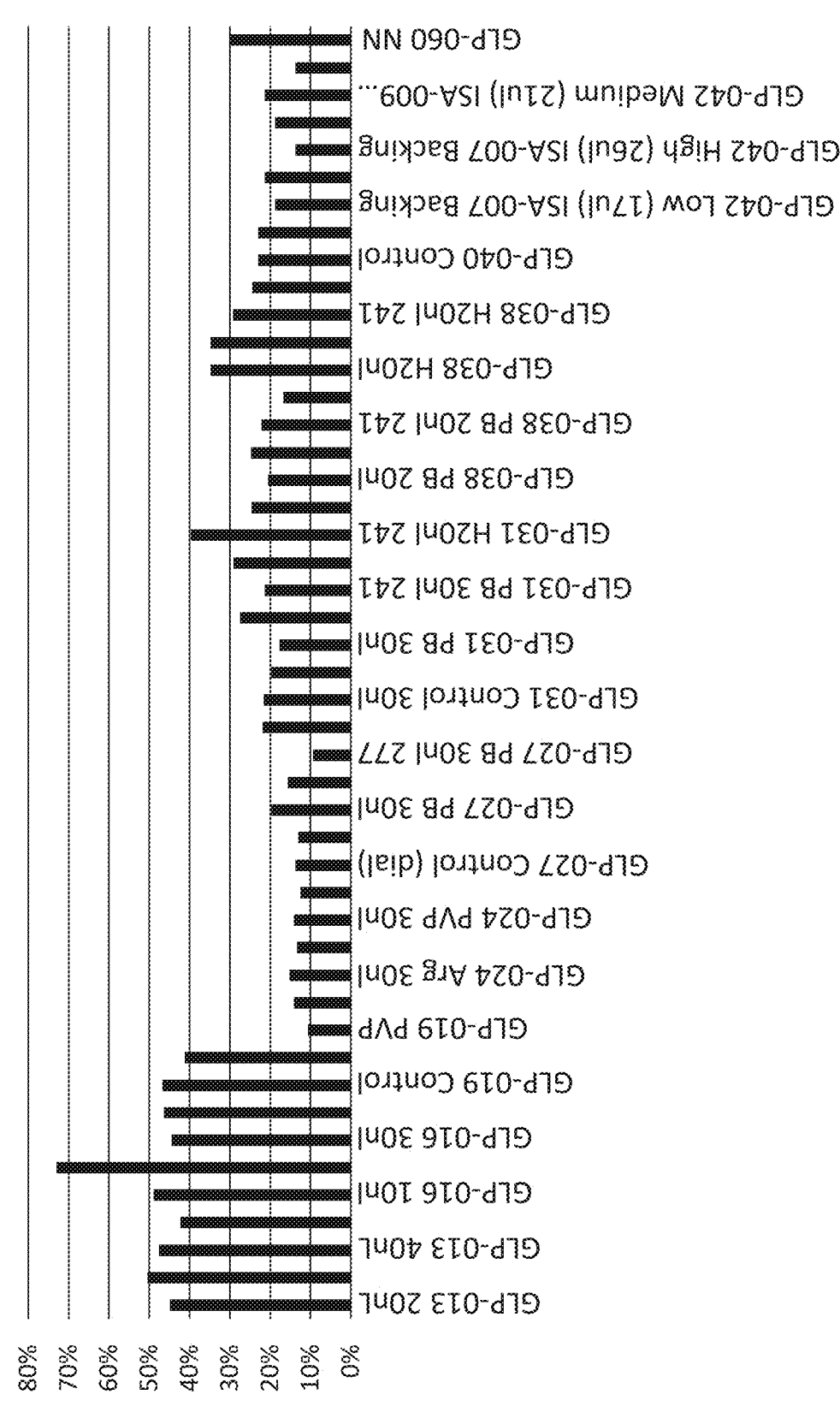
FIG. 10 shows a summary of shell length as a portion of overall tip length during the feasibility evaluation phase of the program using inactivated semaglutide API. There is a drastic reduction in shell length after the introduction of PVP into the formulation in study GLP-019, however the shell length is still variable and is ideally minimized.
Figure 11:
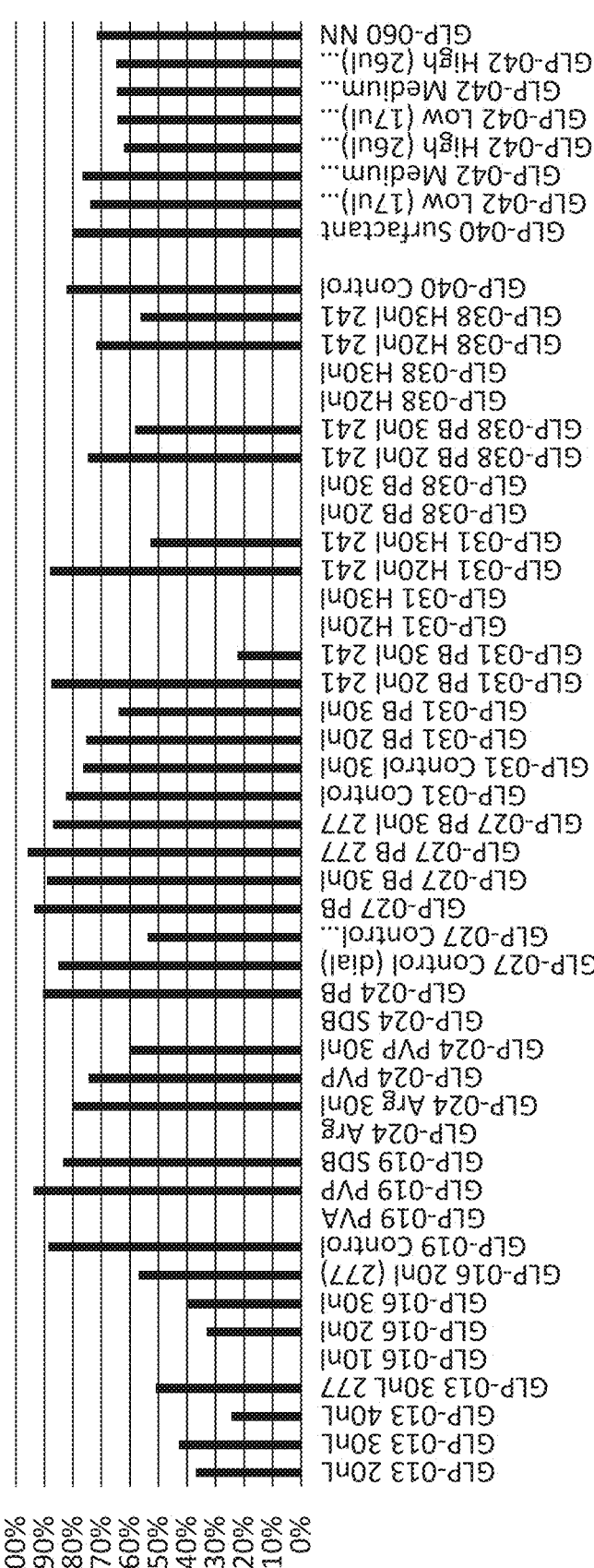
FIG. 11 shows the percent (%) delivered from MAPs after deployment on ex vivo porcine skin. This test was not run on all groups throughout the feasibility phase of the program, often due to low yields. This is an important readout because it relates to the delivery efficiency of the platform. Results are highly variable, and may be below the desired target of >80%.

In some embodiments, the STING agonist is Rp, Rp dithio 2',3' c-di-AMP (e.g., Rp,Rp-dithio c-[A (2',5')pA(3', 5')p]), or a cyclic dinucleotide analog thereof. In some embodiments, the STING agonist is a compound depicted in U.S. Patent Publication No. US2015/0056224 (e.g., a compound in FIG. 2c, e.g., compound 21 or compound 22). In some embodiments, the STING agonist is c-[G (2',5')pG(3', 5')p], a dithio ribose O-substituted derivative thereof, or a compound depicted in FIG. 4 of PCT Publication Nos. WO 2014/189805 and WO 2014/189806. In some embodiments, the STING agonist is c-[A (2',5')pA(3',5')p] or a dithio ribose O-substitued derivative thereof, or is a compound depicted in FIG. 5 of PCT Publication Nos. WO 2014/189805 and WO 2014/189806. In some embodiments, the STING agonist is c-[G (2',5')pA(3',5')p], or a dithio ribose O-substitued derivative thereof, or is a compound depicted in FIG. 5 of PCT Publication Nos. WO 2014/189805 and WO 2014/189806. In some embodiments, the STING agonist is 2'-0-propargyl-cyclic-[A(2',5')pA(3',5')p] (2'-0-propargyl-ML-CDA) or a compound depicted in FIG. 7 of PCT Publication No. WO 2014/189806.

Other exemplary STING agonists are disclosed, e.g., in PCT Publication Nos. WO 2014/189805 and WO 2014/189806, and U.S. Publication No. 2015/0056225.

RIG Agonists

In some embodiments, the dispensable formulation, the microneedle and/or the microarray pacth (MAP) can comprise and/or can be administered in combination with a RIG agonist (i.e., agonists of retinoic acid-inducible gene I (RIG-I), encoded by the gene DDX58). Exemplary RIG agonists are described in Elion et al. Oncotarget. 9 (48): 29007-29017, 2018, which is incorporated herein by reference in its entirety.

Cytokines

In some embodiments, the dispensable formulation, the microneedle and/or the microarray pacth (MAP) can comprise and/or can be administered in combination with a cytokine.

The cytokines are generally polypeptides that influence cellular activity, for example, through signal transduction pathways. Accordingly, a cytokine is useful and can be associated with receptor-mediated signaling that transmits a signal from outside the cell membrane to modulate a response within the cell. Cytokines are proteinaceous signaling compounds that are mediators of the immune response. They control many different cellular functions including proliferation, differentiation and cell survival/apoptosis; cytokines are also involved in several pathophysiological processes including viral infections and autoimmune diseases. Cytokines are synthesized under various stimuli by a variety of cells of both the innate (monocytes, macrophages, dendritic cells) and adaptive (T- and B-cells) immune systems. Cytokines can be classified into two groups: pro- and anti-inflammatory. Pro-inflammatory cytokines, including IFNγ, IL-1, IL-6 and TNF-alpha, are predominantly derived from the innate immune cells and Th1 cells. Anti-inflammatory cytokines, including IL-10, IL-4, IL-13 and IL-5, are synthesized from Th2 immune cells.

Accordingly, in some embodiments, the cytokine molecule is an interleukin or a variant thereof, e.g., a functional variant thereof. In some embodiments the interleukin is a proinflammatory interleukin. In some embodiments the interleukin is chosen from interleukin-2 (IL-2), interleukin-12 (IL-12), interleukin-15 (IL-15), interleukin-18 (IL-18), interleukin-21 (IL-21), interleukin-7 (IL-7), or interferon gamma. In some embodiments, the cytokine molecule is a proinflammatory cytokine. In an embodiment, the cytokine molecule is IL-18.

The cytokine may be wild-type (e.g., wild-type recombinant) or genetically engineered (e.g., to introduce one or more mutations). In some embodiments, the cytokine is an engineered cytokine, e.g., an engineered interleukin. In some embodiments, the engineered cytokine comprises one or more mutations, e.g., to afford different biological properties relative to the wild type variant. For example, the cytokine molecule may be an engineered 'decoy-resistant' interleukin (e.g., decoy-resistant IL-18), as described by Zhou et al. (Nature (2020) 583:609-614; incorporated herein by reference in its entirety). In some embodiments, the cytokine is an engineered interleukin (e.g., engineered IL-2, or engineered IL-18).

In some embodiments, the cytokine is engineered to improve one or more pharmacokinetic properties. In some embodiments, the engineered cytokine comprises a cytokine fused to another molecule (e.g., an antibody), e.g., to increase the serum half-life of the cytokine. In some embodiments, the cytokine is fused to a long-half-life protein or protein domain (e.g., Fc fusion, transferrin [Tf] fusion, or albumin fusion). In some embodiments, the cytokine is fused to an inert polypeptide (e.g., XTEN or recombinant PEG (rPEG); a homo-amino acid polymer (HAP; e.g., by HAPylation); a proline-alanine-serine polymer (PAS; e.g., by PASylation); or an elastin-like peptide (ELP; e.g., by ELPylation)). In some embodiments, the cytokine is conjugated to repeat chemical moieties (e.g., a polymer, e.g., PEG by PEGylation; or hyaluronic acid), e.g., to increase the hydrodynamic radius of the cytokine. In some embodiments, the negative charge of the cytokine is increased, e.g., by polysialylation of the cytokine, or by fusing a negatively charged, highly sialylated peptide (e.g., carboxy-terminal peptide [CTP; of chorionic gonadotropin (CG) β-chain]) to the cytokine. In some embodiments, the cytokine is non-covalently bound to a long-half-life protein, e.g., HSA, human IgG, or transferrin. In some embodiments, the cytokine is chemically conjugated to long-half-life proteins, e.g., a human IgG, an Fc moietie, or HSA. Methods for preparing and using fusion proteins, and similarly modified proteins, e.g., for half-life extension, has been described (see, e.g., Strohl et al. *BioDrugs* (2015) 29:215-239; and references cited therein).

Engineered cytokines (e.g., engineered interleukins) may be produced by known methods, e.g., by a directed evolution technique (see, e.g., Zhou et al., vide supra). Examples of engineered cytokines (e.g., engineered interleukins) have been described (see, e.g., WO 2012/107417; WO 2009/061853; U.S. Pat. No. 9,580,486; Minsahwi et al. *Front Immunol.* 2020 (11); 1794; Tang et al. *Cytokine X* (2019) 100001; Mitra et al. *Immunity* (2015) 42:826-838; Casadesus et al. *Oncolmmunology* (2020) 9:1770565; Zhou et al, vide supra; each of which are incorporated herein by reference in their entirety).

Without wishing to be bound by theory, engineered cytokines (e.g., 'decoy-resistant' interleukins, e.g., decoy resistant IL-18) can have beneficial properties compared to their wild-type counterparts. By way of example, decoy-resistant IL-18 can maintain signaling potential but remain impervious to inhibition by IL-18 binding protein (IL-18BP). In some embodiments; the engineered cytokine has improved stability compared to the wild-type cytokine (e.g., improved temperature-dependent stability, pH-dependent stability, or both). In some embodiments, the engineered cytokine has improved serum half-life, relative to the wild-type cytokine. In some embodiments, the engineered cytokine has modified affinity (e.g., enhanced affinity) for a receptor, different to the wild-type cytokine. In some embodiments, the engineered cytokine has lower toxicity, relative to the wild-type cytokine.

In certain embodiments, the cytokine is a single chain cytokine. In certain embodiments, the cytokine is a multichain cytokine (e.g., the cytokine comprises 2 or more (e.g., 2) polypeptide chains. An exemplary multichain cytokine is IL-12.

Examples of useful cytokines include, but are not limited to, GM-CSF, IL-1α, IL-1β, IL-2, IL-3, IL-4, IL-5, IL-6, IL-7, IL-8, IL-10, IL-12, IL-18, IL-21, IFN-α, IFN-β, IFN-γ, MIP-1α, MIP-1β, TGF-β, TNF-α, and TNFβ. In one embodiment the cytokine of the multispecific or multifunctional polypeptide is a cytokine selected from the group of GM-CSF, IL-2, IL-7, IL-8, IL-10, IL-12, IL-15, IL-18, IL-21, IFN-α, IFN-γ, MIP-1α, MIP-1β and TGF-β. In one embodiment the cytokine of the multispecific or multifunctional polypeptide is a cytokine selected from the group of GM-CSF, IL-2, IL-7, IL-8, IL-10, IL-12, IL-15, IL-21, IFN-α, IFN-γ, MIP-1α, MIP-1β and TGF-β. In one embodiment the cytokine of the multispecific or multifunctional polypeptide is a cytokine selected from the group of IL-2, IL-7, IL-10, IL-12, IL-15, IL-18, IFN-α, and IFN-γ. In one embodiment the cytokine of the multispecific or multifunctional polypeptide is a cytokine selected from the group of IL-2, IL-7, IL-10, IL-12, IL-15, IFN-α, and IFN-γ. In certain embodiments the cytokine is mutated to remove N- and/or O-glycosylation sites. Elimination of glycosylation can increase homogeneity of the product obtainable in recombinant production.

In one embodiment, the cytokine is IL-2. In a specific embodiment, the IL-2 cytokine can elicit one or more of the cellular responses selected from the group consisting of: proliferation in an activated T lymphocyte cell, differentiation in an activated T lymphocyte cell, cytotoxic T cell (CTL) activity, proliferation in an activated B cell, differentiation in an activated B cell, proliferation in a natural killer (NK) cell, differentiation in a NK cell, cytokine secretion by an activated T cell or an NK cell, and NK/lymphocyte activated killer (LAK) antitumor cytotoxicity.

In another embodiment the cytokine is IL-12. In a specific embodiment said IL-12 cytokine is a single chain IL-12 cytokine. In one embodiment, the IL-12 cytokine can elicit one or more of the cellular responses selected from the group consisting of: proliferation in a NK cell, differentiation in a NK cell, proliferation in a T cell, and differentiation in a T cell.

In another embodiment the cytokine is IL-10. In another specific embodiment the IL-10 cytokine is a monomeric IL-10 cytokine. In one embodiment, the IL-10 cytokine can elicit one or more of the cellular responses selected from the group consisting of: inhibition of cytokine secretion, inhibition of antigen presentation by antigen presenting cells, reduction of oxygen radical release, and inhibition of T cell proliferation.

In a specific embodiment said IL-15 cytokine is a mutant IL-15 cytokine having reduced binding affinity to the α-subunit of the IL-15 receptor. Without wishing to be bound by theory, a mutant IL-15 polypeptide with reduced binding to the α-subunit of the IL-15 receptor has a reduced ability to bind to fibroblasts throughout the body, resulting in improved pharmacokinetics and toxicity profile, compared to a wild-type IL-15 polypeptide.

In one embodiment, the IL-15 cytokine can elicit one or more of the cellular responses selected from the group consisting of: proliferation in an activated T lymphocyte cell, differentiation in an activated T lymphocyte cell, cytotoxic T cell (CTL) activity, proliferation in an activated B cell, differentiation in an activated B cell, proliferation in a natural killer (NK) cell, differentiation in a NK cell, cytokine secretion by an activated T cell or an NK cell, and NK/lymphocyte activated killer (LAK) antitumor cytotoxicity.

In another embodiment the cytokine is interleukin-18 (IL-18). In one embodiment, the cytokine is an IL-18 variant polypeptide. In one embodiment said IL-18 cytokine is a decoy-resistant IL-18 (see, e.g., U.S. Patent Publication No.: 2019/0070262; and Zhou et al. vide supra, each of which are incorporated herein by reference in their entirety). In one embodiment, the IL-18 cytokine can elicit one or more of the cellular responses selected from the group consisting of: proliferation in a NK cell, differentiation in a NK cell, proliferation in a T cell, differentiation in a T cell, and simulation of lymphocytes (e.g., innate lymphocytes). Without wishing to be bound by theory, IL-18 can be used as an effective immunotherapeutic, and is well tolerated in humans (see, e.g., Robertson et al. Clin. Cancer Res. (2006) 12:4265-4273). In some embodiments, IL-18 (e.g., decoy-resistant IL-18) increases the population of precursor T cells (e.g., CD8 T cells) that express a transcription factor (e.g., Tcf1) with anti-tumor function. In some embodiments, IL-18 (e.g., decoy-resistant IL-18) promotes the differentiation of T-cells towards a highly active polyfunctional effector phenotype. In some embodiments, IL-18 (e.g., decoy-resistant IL-18) decreases the prevalence of exhausted CD8+ T cells (e.g., those that express the transcriptional regulator of exhaustion TOX). In some embodiments, IL-18 (e.g., decoy-resistant IL-18) enhances the activity and/or maturation of NK cells.

In some embodiments, the cytokine is a decoy-resistant interleukin IL-18. In some embodiments, the cytokine is an IL-18 variant polypeptide, wherein the IL-18 variant polypeptide specifically binds to IL-18 receptor (IL-18R) and wherein, compared to wild type (WT) IL-18, the IL-18 variant polypeptide comprises at least one mutation and exhibits substantially reduced binding to IL-18 binding protein (IL-18BP). In some embodiments, the cytokine is an IL-18 variant polypeptide comprising at least one mutation selected from the group consisting of Y1X, L5X, K8X, M51X, K53X, S55X, Q56X, P57X, G59X, M60X, E77X, Q103X, S105X, D110X, N111X, M113X, V153X, and N155X, relative to a wild-type IL-18 sequence, e.g., SEQ ID NO: 30 of US2019/0070262. In some embodiments, the cytokine is an IL-18 variant polypeptide comprising at least one mutation selected from the group consisting of Y1H, Y1R, L5H, L51, L5Y, K8Q, K8R, M51T, M51K, M51D, M51N, M51E, M51R, K53R, K53G, K53S, K53T, S55K, S55R, Q56E, Q56A, Q56R, Q56V, Q56G, Q56K, Q56L, P57L, P57G, P57A, P57K, G59T, G59A, M60K, M60Q, M60R, M60L, E77D, Q103E, Q103K, Q103P, Q103A, Q103R, S105R, S105D, S105K, S105N, S105A, D110H, D110K, D110N, D110Q, D110E, D110S, D110G, N111H, N111Y, N111D, N111R, N111S, N111G, M113V, M113R, M113T, M113K, V1531, V153T, V153A, N155K, and N155H, relative to a wild-type IL-18 sequence, e.g., SEQ ID NO: 30 of US2019/0070262. In some embodiments, the cytokine is an IL-18 variant polypeptide comprising at least 6 mutations selected from: Y1X, L5X, K8X, M51X, K53X, 555X, Q56X, P57X, G59X, M60X, E77X, Q103X, S105X, D110X, N111X, M113X, V153X, and N155X, relative to a wild-type IL-18 sequence, e.g., SEQ ID NO: 30 of US2019/ 0070262. In some embodiments, the cytokine is an IL-18 variant polypeptide comprising mutations at positions M51, K53, Q56 D110, and N111, relative to a wild-type IL-18 sequence, e.g., SEQ ID NO: 30 of US2019/0070262. In some embodiments, the cytokine is an IL-18 variant polypeptide sequence comprising the following five mutations: (i) M51E, M51R, M51K, M51T, M51D, or M51N; (ii) K53G, K53S, K53T, or K53R; (iii) Q56G, Q56R, Q56L, Q56E, Q56A, Q56V, or Q56K; (iv) D110S, D110N, D110G, D110K, D110H, D110Q, or D110E; and (v) N111G, N111R, N111S, N111D, N111H, or N111Y; relative to a wild-type IL-18 sequence, e.g., SEQ ID NO: 30 of US2019/0070262. In some embodiments, the cytokine is an IL-18 variant polypeptide further comprising mutations at positions P57 and M60, relative to a wild-type IL-18 sequence, e.g., SEQ ID NO: 30 of US2019/0070262. In some embodiments, the cytokine is an IL-18 variant polypeptide comprising the following seven mutations: (i) M51E, M51R, M51K, M51T, M51D, or M51N; (ii) K53G, K53S, K53T, or K53R; (iii) Q56G, Q56R, Q56L, Q56E, Q56A, Q56V, or Q56K; (iv) D110S, D110N, D110G, D110K, D110H, D110Q, or D110E; (v) N111G, N111R, N111S, N111D, N111H, or N111Y; (vi) P57A, P57L, P57G, or P57K; and (vii) M60L, M60R, M60K, or M600; relative to a wild-type IL-18 sequence, e.g., SEQ ID NO: 30 of US2019/0070262. In some embodiments, the cytokine is an IL-18 variant polypeptide sequence comprising a polypeptide sequence described US2019/0070262 (e.g., one of SEQ ID NOs.: 34-59, 60-72, 73-91, 191-193, or a fragment thereof).

Without wishing to be bound by theory, an IL-18 variant protein (e.g., a decoy-resistant IL-18) can avoid potential attenuation of activity due to the presence of IL-18 binding proteins, such as IL-18BP. Without wishing to be bound by theory, an IL-18 variant protein (e.g., decoy-resistant IL-18) can evade IL-18BP, and can further promote innate antitumor immunity by stimulating NK cell activity and/or enhancing NK cell maturation, and can exert anti-tumor immunity against tumors that are resistant to canonical immune checkpoint blockade therapy (e.g., anti-PD-1 plus anti-CLTA-4) due to loss of MHC class I surface expression.

Mutant cytokine molecules useful as effector moieties can be prepared by deletion, substitution, insertion or modification using genetic or chemical methods well known in the art. Genetic methods may include site-specific mutagenesis of the encoding DNA sequence, PCR, gene synthesis, and the like. The correct nucleotide changes can be verified for example by sequencing. Substitution or insertion may involve natural as well as non-natural amino acid residues. Amino acid modification includes well known methods of chemical modification such as the addition or removal of glycosylation sites or carbohydrate attachments, and the like.

In one embodiment, the cytokine is GM-CSF. In a specific embodiment, the GM-CSF cytokine can elicit proliferation and/or differentiation in a granulocyte, a monocyte or a dendritic cell.

In one embodiment, the cytokine is IFN-α. In a specific embodiment, the IFN-α cytokine can elicit one or more of the cellular responses selected from the group consisting of: inhibiting viral replication in a virus-infected cell, and upregulating the expression of major histocompatibility complex I (MHC I). In another specific embodiment, the IFN-α cytokine can inhibit proliferation in a tumor cell. In one embodiment the cytokine, particularly a single-chain cytokine, is IFNγ. In a specific embodiment, the IFN-γ cytokine can elicit one or more of the cellular responses selected from the group of: increased macrophage activity, increased expression of MHC molecules, and increased NK cell activity.

In one embodiment the cytokine, particularly a single-chain cytokine, is IL-7. In a specific embodiment, the IL-7 cytokine can elicit proliferation of T and/or B lymphocytes.

In one embodiment, the cytokine is IL-8. In a specific embodiment, the IL-8 cytokine can elicit chemotaxis in neutrophils. In one embodiment, the cytokine, particularly a single-chain cytokine, is MIP-1α. In a specific embodiment, the MIP-1a cytokine can elicit chemotaxis in monocytes and T lymphocyte cells. In one embodiment, the cytokine is MIP-1β. In a specific embodiment, the MIP-1β cytokine can elicit chemotaxis in monocytes and T lymphocyte cells. In one embodiment, the cytokine is TGF-β. In a specific embodiment, the TGF-β cytokine can elicit one or more of the cellular responses selected from the group consisting of: chemotaxis in monocytes, chemotaxis in macrophages, upregulation of IL-1 expression in activated macrophages, and upregulation of IgA expression in activated B cells.

In some embodiments, the microneedle or combination treatment disclosed herein includes a cytokine. In embodiments, the cytokine includes a full length, a fragment or a variant of a cytokine; a cytokine receptor domain, e.g., a cytokine receptor dimerizing domain; or an agonist of a cytokine receptor, e.g., an antibody molecule (e.g., an agonistic antibody) to a cytokine receptor.

In some embodiments the cytokine is chosen from IL-2, IL-12, IL-15, IL-18, IL-7, IL-21, or interferon gamma, or a fragment or variant thereof, or a combination of any of the aforesaid cytokines. The cytokine molecule can be a monomer or a dimer. In embodiments, the cytokine molecule can further include a cytokine receptor dimerizing domain.

In other embodiments, the cytokine molecule is an agonist of a cytokine receptor, e.g., an antibody molecule (e.g., an agonistic antibody) to a cytokine receptor chosen from an IL-15Ra or IL-21R.

Other immunomodulatory agents include, but are not limited to cancer vaccines, such as a viral cancer therapeutic agent and/or a cancer vaccine which comprises a tumor antigen, such as a neoantigen.

Water-Soluble Excipients

The present disclosure provides, in some embodiments, dispensable formulations, microneedles and/or microarray patches (MAPs) comprising a water-soluble excipient.

As used herein, the term "water-soluble excipient" refers to any pharmaceutically acceptable excipient which is dissolvable, or substantially dissolvable, in an aqueous solution, such as water. In the present context, if not stated otherwise, the term "water-soluble" refers to the solubility of an excipient in water or in an aqueous salt or aqueous buffer solution, or in an aqueous solution containing other components.

As disclosed herein, Applicant has surprisingly discovered specific combinations of water-soluble excipients that can, for example, effectively (1) enhance the stability of a high concentration of active pharmaceutical ingredients (API) for delivery of an effective dose of the API using a microneedle and/or a microarray patch (MAP) described herein; (2) enhance the fluid properties of a composition, such as a dispensable formulation, for manufacturing a microneedle and/or a microarray patch (MAP) described herein using, e.g., a liquid dispensing system; (3) enhance the consolidation of the API into the apex of a microneedle tip (e.g., a consolidated microneedle tip) during manufacturing; (4) enhance the strength of the microneedle, e.g., to resist deformation during deployment; and/or (5) minimize, or eliminate, manufacturing defects, such as shell formation and microneedle tip dislodgement, that can negatively affect microneedle morphology, strength, deployment efficiency, API delivery consistency, and pharmacodynamics. In some embodiments, the water-soluble excipient may be any substance or mixture of substances that may be used to enhance microneedle tip consolidation. In some embodiments, the water-soluble excipient may be any substance or mixture of substances that may be used to modify a fluid property of a composition, such as a dispensable formulation described herein, for manufacturing a microneedle and/or a microarray patch (MAPs) using e.g., a liquid dispensing system. In some embodiments, the water-soluble excipient may be any substance or mixture of substances that may be used to enhance the solubility of an active pharmaceutical ingredient (API) for manufacturing a microneedle and/or a microarray patch (MAPs) using e.g., a liquid dispensing system.

The terms "water-soluble excipient," "excipient," and "pharmaceutically acceptable excipient" may be used interchangeably herein to refer to any component other than an active pharmaceutical ingredient (API) which can be used in a composition for delivery of an active therapeutic agent to a subject or combined with an active therapeutic agent (e.g., to create a pharmaceutical composition, such as a microneedle and/or a microarray patch (MAPs)) to improve its handling or storage properties or to permit or facilitate formation of a dose unit of the composition (e.g., a microneedle and/or a microarray patch (MAPs)). Excipients include, but are not limited to, solvents, penetration enhancers, wetting agents, antioxidants, lubricants, polymers, sugars, sugar alcohols, amino acids, antioxidants, buffers, salts, surfactants, emollients, and substances added to improve morphology, appearance, or texture of the microneedle and/or the microarray patch (MAP) and any substances used to form the microneedle and/or the microarray patch (MAP). Any such excipients can be used in any dosage forms, e.g., microneedles and/or the microarray patches (MAPs) described herein. The foregoing classes of excipients are not meant to be exhaustive but merely illustrative as a person of ordinary skill in the art would recognize that additional types and combinations of excipients could be used to achieve the desired goals for delivery of an API. The excipient can be an inert substance, an inactive substance, and/or a not medicinally active substance. The excipient can serve various purposes. For example, the excipient may be added to a pharmaceutical composition to further facilitate administration of an API.

The term "pharmaceutically acceptable excipient" means an excipient that is useful in preparing a pharmaceutical composition, e.g., a microneedle and/or a microarray patch (MAP), that is generally safe, non-toxic and includes excipients that are acceptable for human pharmaceutical use. In some embodiments, the term "excipient" refers to any pharmaceutically acceptable component, such as an additive, a carrier, a diluent, an adjuvant, an ingredient, or combination thereof, other than an active pharmaceutical ingredient (API), which may be included in a composition described herein.

In terms of total weight, excipients may constitute over 50% of a microneedle and/or a microarray patch (MAPs) and over 90% of a liquid composition, such as a dispensable formulation, described herein.

Without wishing to be bound by theory, a water-soluble excipient may be selected from the group consisting of a polymer, a sugar, a sugar alcohol, an amino acid, an antioxidant, a buffer, a surfactant, a salt, and combinations thereof.

In some embodiments, the water-soluble excipient may be selected from the group consisting of (i) a polymer is selected from the group consisting of silk fibroin, Povidone K 12 (PVP K12), Povidone K 17 (PVP K17), Povidone K 30 (PVP K30), PVA 4-88, Kollidon® VA 64, Dextran 40, Methyl Cellulose (MC), Hydroxypropyl Methylcellulose (HPMC), Carboxymethyl cellulose (CMC), Plasdone® S-630, Pullulan, Kollicoat® Protect, and combinations thereof; (ii) a sugar is selected from the group consisting of sucrose, trehalose, lactose, and combinations thereof; (iii) a sugar alcohol is selected from the group consisting of mannitol, xylitol, sorbitol, glyercol, and combinations thereof; (iv) an amino acid is selected from the group consisting of arginine-HCl, proline, histidine, methionine, aspartic acid, glutamic acid, and combinations thereof; (v) an antioxidant is selected from the group consisting of sodium metabisulfite, sodium pyruvate, sodium ascorbate, and combinations thereof; (v) the buffer is selected from the group consisting of Tris-HCl, PBS, TE, MOPS, Phosphate, Bis-tris, HEPES, and combinations thereof; (vi) the surfactant is selected from the group consisting of Kolliphor® EL, Kolliphor® HS 15, Pluronic® F-127 (Poloxamer 407), Pluronic® F-68 (Poloxamer 188), Tween® 20 (polysorbate 20), Tween® 80 (polysorbate 80), Soluplus®, P124, CHAPS, and combinations thereof; and/or (vii) the salt is selected from the group consisting of NaCl, CaCl$_2$), ZnCl$_2$, MgCl$_2$, urea, and combinations thereof.

The water-soluble excipient may be present in a composition described herein at a concentration of about 0% (w/v) to about 100% (w/v). In some embodiments, the water-soluble excipient may be present in a composition, e.g., a dispensable formulation, at a concentration of about 0% (w/v), about 0.001% (w/v), about 0.01% (w/v), about 0.1% (w/v), about 0.2% (w/v), about 0.3% (w/v), about 0.4% (w/v), about 0.5% (w/v), about 0.6% (w/v), about 0.7% (w/v), about 0.8% (w/v), about 0.9% (w/v), about 1% (w/v), about 2% (w/v), about 3% (w/v), about 4% (w/v), about 5% (w/v), about 6% (w/v), about 7% (w/v), about 8% (w/v), about 9% (w/v), about 10% (w/v), about 11% (w/v), about 12% (w/v), about 13% (w/v), about 14% (w/v), about 15% (w/v), about 16% (w/v), about 17% (w/v), about 18% (w/v), about 19% (w/v), about 20% (w/v), about 21% (w/v), about 22% (w/v), about 23% (w/v), about 24% (w/v), about 25% (w/v), about 26% (w/v), about 27% (w/v), about 28% (w/v), about 29% (w/v), about 30% (w/v), about 31% (w/v), about 32% (w/v), about 33% (w/v), about 34% (w/v), about 35% (w/v), about 36% (w/v), about 37% (w/v), about 38% (w/v), about 39% (w/v), about 40% (w/v), about 41% (w/v), about 42% (w/v), about 43% (w/v), about 44% (w/v), about 45%

(w/v), about 46% (w/v), about 47% (w/v), about 48% (w/v), about 49% (w/v), about 50% (w/v), about 51% (w/v), about 52% (w/v), about 53% (w/v), about 54% (w/v), about 55% (w/v), about 56% (w/v), about 57% (w/v), about 58% (w/v), about 59% (w/v), about 60% (w/v), about 61% (w/v), about 62% (w/v), about 63% (w/v), about 64% (w/v), about 65% (w/v), about 66% (w/v), about 67% (w/v), about 68% (w/v), about 69% (w/v), about 70% (w/v), about 71% (w/v), about 72% (w/v), about 73% (w/v), about 74% (w/v), about 75% (w/v), about 76% (w/v), about 77% (w/v), about 78% (w/v), about 79% (w/v), about 80% (w/v), about 81% (w/v), about 82% (w/v), about 83% (w/v), about 84% (w/v), about 85% (w/v), about 86% (w/v), about 87% (w/v), about 88% (w/v), about 89% (w/v), about 90% (w/v), about 91% (w/v), about 92% (w/v), about 93% (w/v), about 94% (w/v), about 95% (w/v), about 96% (w/v), about 97% (w/v), about 98% (w/v), about 99% (w/v), or about 100% (w/v).

Polymers

The present disclosure provides, in some embodiments, dispensable formulations, microneedles and/or microarray patches (MAPs) comprising a polymer. In some embodiments, a polymer may be present in a composition described herein at a concentration of about 0% (w/v) to about 100% (w/v).

In some embodiments, the polymer may be selected from the group consisting of a polyvinylpyrrolidone (PVP) polymer (also referred to as a "povidone" polymer), a polyvinyl alcohol (PVA) polymer, a vinylpyrrolidone-vinyl acetate (VP-VA) copolymer (also referred to as a "copovidone" polymer), a polyvinyl alcohol-poly-ethylene glycol (PEG-PVA) graft copolymer, a polysaccharide, a fibroin protein, and combinations thereof.

In some embodiments, the polymer comprises a povidone polymer, such as a povidone polymer selected from the group consisting of Povidone K 12 (PVP K12), Povidone K 17 (PVP K17), Povidone K 30 (PVP K30), and combinations thereof.

In some embodiments, the polymer comprises a polyvinyl alcohol (PVA) polymer, such as PVA 4-88.

In some embodiments, the polymer comprises a copovidone polymer, such as a copovidone polymer selected from the group consisting of Kollidon® VA 64, Plasdone® S-630, and combinations thereof.

In some embodiments, the polymer comprises a polyvinyl alcohol-poly-ethylene glycol (PEG-PVA) graft copolymer, optionally wherein the PEG-PVA graft polymer comprises Kollicoat® Protect.

In some embodiments, the polymer comprises a polysaccharide, optionally wherein the polysaccharide is selected from the group consisting of Pullulan, Dextran 40, Methyl Cellulose (MC), Hydroxypropyl Methylcellulose (HPMC), Carboxymethyl cellulose (CMC), and combinations thereof.

In some embodiments, the polymer comprises a fibroin protein, optionally wherein the fibroin protein comprises a silk fibroin protein.

In some embodiments, the polymer may be present in a composition, e.g., a dispensable formulation, at a concentration of about 0% (w/v), about 0.001% (w/v), about 0.01% (w/v), about 0.1% (w/v), about 0.2% (w/v), about 0.3% (w/v), about 0.4% (w/v), about 0.5% (w/v), about 0.6% (w/v), about 0.7% (w/v), about 0.8% (w/v), about 0.9% (w/v), about 1% (w/v), about 2% (w/v), about 3% (w/v), about 4% (w/v), about 5% (w/v), about 6% (w/v), about 7% (w/v), about 8% (w/v), about 9% (w/v), about 10% (w/v), about 11% (w/v), about 12% (w/v), about 13% (w/v), about 14% (w/v), about 15% (w/v), about 16% (w/v), about 17% (w/v), about 18% (w/v), about 19% (w/v), about 20% (w/v), about 21% (w/v), about 22% (w/v), about 23% (w/v), about 24% (w/v), about 25% (w/v), about 26% (w/v), about 27% (w/v), about 28% (w/v), about 29% (w/v), about 30% (w/v), about 31% (w/v), about 32% (w/v), about 33% (w/v), about 34% (w/v), about 35% (w/v), about 36% (w/v), about 37% (w/v), about 38% (w/v), about 39% (w/v), about 40% (w/v), about 41% (w/v), about 42% (w/v), about 43% (w/v), about 44% (w/v), about 45% (w/v), about 46% (w/v), about 47% (w/v), about 48% (w/v), about 49% (w/v), about 50% (w/v), about 51% (w/v), about 52% (w/v), about 53% (w/v), about 54% (w/v), about 55% (w/v), about 56% (w/v), about 57% (w/v), about 58% (w/v), about 59% (w/v), about 60% (w/v), about 61% (w/v), about 62% (w/v), about 63% (w/v), about 64% (w/v), about 65% (w/v), about 66% (w/v), about 67% (w/v), about 68% (w/v), about 69% (w/v), about 70% (w/v), about 71% (w/v), about 72% (w/v), about 73% (w/v), about 74% (w/v), about 75% (w/v), about 76% (w/v), about 77% (w/v), about 78% (w/v), about 79% (w/v), about 80% (w/v), about 81% (w/v), about 82% (w/v), about 83% (w/v), about 84% (w/v), about 85% (w/v), about 86% (w/v), about 87% (w/v), about 88% (w/v), about 89% (w/v), about 90% (w/v), about 91% (w/v), about 92% (w/v), about 93% (w/v), about 94% (w/v), about 95% (w/v), about 96% (w/v), about 97% (w/v), about 98% (w/v), about 99% (w/v), or about 100% (w/v).

Sugars

The present disclosure provides, in some embodiments, dispensable formulations, microneedles and/or microarray patches (MAPs) comprising a sugar. In some embodiments, the sugar can be selected from the group consisting of sucrose, trehalose, lactose, and combinations thereof. In some embodiments, a sugar may be present in a composition described herein at a concentration of about 0% (w/v) to about 100% (w/v). In some embodiments, the sugar may be present in a composition, e.g., a dispensable formulation, at a concentration of about 0% (w/v), about 0.001% (w/v), about 0.01% (w/v), about 0.1% (w/v), about 0.2% (w/v), about 0.3% (w/v), about 0.4% (w/v), about 0.5% (w/v), about 0.6% (w/v), about 0.7% (w/v), about 0.8% (w/v), about 0.9% (w/v), about 1% (w/v), about 2% (w/v), about 3% (w/v), about 4% (w/v), about 5% (w/v), about 6% (w/v), about 7% (w/v), about 8% (w/v), about 9% (w/v), about 10% (w/v), about 11% (w/v), about 12% (w/v), about 13% (w/v), about 14% (w/v), about 15% (w/v), about 16% (w/v), about 17% (w/v), about 18% (w/v), about 19% (w/v), about 20% (w/v), about 21% (w/v), about 22% (w/v), about 23% (w/v), about 24% (w/v), about 25% (w/v), about 26% (w/v), about 27% (w/v), about 28% (w/v), about 29% (w/v), about 30% (w/v), about 31% (w/v), about 32% (w/v), about 33% (w/v), about 34% (w/v), about 35% (w/v), about 36% (w/v), about 37% (w/v), about 38% (w/v), about 39% (w/v), about 40% (w/v), about 41% (w/v), about 42% (w/v), about 43% (w/v), about 44% (w/v), about 45% (w/v), about 46% (w/v), about 47% (w/v), about 48% (w/v), about 49% (w/v), about 50% (w/v), about 51% (w/v), about 52% (w/v), about 53% (w/v), about 54% (w/v), about 55% (w/v), about 56% (w/v), about 57% (w/v), about 58% (w/v), about 59% (w/v), about 60% (w/v), about 61% (w/v), about 62% (w/v), about 63% (w/v), about 64% (w/v), about 65% (w/v), about 66% (w/v), about 67% (w/v), about 68% (w/v), about 69% (w/v), about 70% (w/v), about 71% (w/v), about 72% (w/v), about 73% (w/v), about 74% (w/v), about 75% (w/v), about 76% (w/v), about 77% (w/v), about 78% (w/v), about 79% (w/v), about 80% (w/v), about 81% (w/v), about 82% (w/v), about 83% (w/v), about 84% (w/v), about 85% (w/v), about 86% (w/v), about 87% (w/v), about 88% (w/v), about 89% (w/v), about 90% (w/v), about 91% (w/v), about 92% (w/v), about 93% (w/v), about 94% (w/v), about 95% (w/v), about 96% (w/v), about 97% (w/v), about 98% (w/v), about 99% (w/v), or about 100% (w/v).

Sugar Alcohols

The present disclosure provides, in some embodiments, dispensable formulations, microneedles and/or microarray patches (MAPs) comprising a sugar alcohol. In some embodiments, the sugar alcohol can be selected from the group consisting of mannitol, xylitol, sorbitol, glyercol, and combinations thereof. In some embodiments, a sugar alcohol may be present in a composition described herein at a concentration of about 0% (w/v) to about 100% (w/v). In some embodiments, the sugar alcohol may be present in a composition, e.g., a dispensable formulation, at a concentration of about 0% (w/v), about 0.001% (w/v), about 0.01% (w/v), about 0.1% (w/v), about 0.2% (w/v), about 0.3% (w/v), about 0.4% (w/v), about 0.5% (w/v), about 0.6% (w/v), about 0.7% (w/v), about 0.8% (w/v), about 0.9% (w/v), about 1% (w/v), about 2% (w/v), about 3% (w/v), about 4% (w/v), about 5% (w/v), about 6% (w/v), about 7% (w/v), about 8% (w/v), about 9% (w/v), about 10% (w/v), about 11% (w/v), about 12% (w/v), about 13% (w/v), about 14% (w/v), about 15% (w/v), about 16% (w/v), about 17% (w/v), about 18% (w/v), about 19% (w/v), about 20% (w/v), about 21% (w/v), about 22% (w/v), about 23% (w/v), about 24% (w/v), about 25% (w/v), about 26% (w/v), about 27% (w/v), about 28% (w/v), about 29% (w/v), about 30% (w/v), about 31% (w/v), about 32% (w/v), about 33% (w/v), about 34% (w/v), about 35% (w/v), about 36% (w/v), about 37% (w/v), about 38% (w/v), about 39% (w/v), about 40% (w/v), about 41% (w/v), about 42% (w/v), about 43% (w/v), about 44% (w/v), about 45% (w/v), about 46% (w/v), about 47% (w/v), about 48% (w/v), about 49% (w/v), about 50% (w/v), about 51% (w/v), about 52% (w/v), about 53% (w/v), about 54% (w/v), about 55% (w/v), about 56% (w/v), about 57% (w/v), about 58% (w/v), about 59% (w/v), about 60% (w/v), about 61% (w/v), about 62% (w/v), about 63% (w/v), about 64% (w/v), about 65% (w/v), about 66% (w/v), about 67% (w/v), about 68% (w/v), about 69% (w/v), about 70% (w/v), about 71% (w/v), about 72% (w/v), about 73% (w/v), about 74% (w/v), about 75% (w/v), about 76% (w/v), about 77% (w/v), about 78% (w/v), about 79% (w/v), about 80% (w/v), about 81% (w/v), about 82% (w/v), about 83% (w/v), about 84% (w/v), about 85% (w/v), about 86% (w/v), about 87% (w/v), about 88% (w/v), about 89% (w/v), about 90% (w/v), about 91% (w/v), about 92% (w/v), about 93% (w/v), about 94% (w/v), about 95% (w/v), about 96% (w/v), about 97% (w/v), about 98% (w/v), about 99% (w/v), or about 100% (w/v).

Amino Acids

The present disclosure provides, in some embodiments, dispensable formulations, microneedles and/or microarray patches (MAPs) comprising an amino acid. In some embodiments, the amino acid can be selected from the group consisting of arginine-HCl, proline, histidine, methionine, aspartic acid, glutamic acid, and combinations thereof. In some embodiments, an amino acid may be present in a composition described herein at a concentration of about 0% (w/v) to about 100% (w/v). In some embodiments, the amino acid may be present in a composition, e.g., a dispensable formulation, at a concentration of about 0% (w/v), about 0.001% (w/v), about 0.01% (w/v), about 0.1% (w/v), about 0.2% (w/v), about 0.3% (w/v), about 0.4% (w/v), about 0.5% (w/v), about 0.6% (w/v), about 0.7% (w/v), about 0.8% (w/v), about 0.9% (w/v), about 1% (w/v), about 2% (w/v), about 3% (w/v), about 4% (w/V), about 5% (w/v), about 6% (w/v), about 7% (w/v), about 8% (w/v), about 9%

(w/v), about 10% (w/v), about 11% (w/v), about 12% (w/v), about 13% (w/v), about 14% (w/v), about 15% (w/v), about 16% (w/v), about 17% (w/v), about 18% (w/v), about 19% (w/v), about 20% (w/v), about 21% (w/v), about 22% (w/v), about 23% (w/v), about 24% (w/v), about 25% (w/v), about 26% (w/v), about 27% (w/v), about 28% (w/v), about 29% (w/v), about 30% (w/v), about 31% (w/V), about 32% (w/v), about 33% (w/v), about 34% (w/v), about 35% (w/v), about 36% (w/v), about 37% (w/v), about 38% (w/v), about 39% (w/v), about 40% (w/v), about 41% (w/v), about 42% (w/v), about 43% (w/v), about 44% (w/v), about 45% (w/v), about 46% (w/v), about 47% (w/v), about 48% (w/v), about 49% (w/v), about 50% (w/v), about 51% (w/v), about 52% (w/v), about 53% (w/v), about 54% (w/v), about 55% (w/v), about 56% (w/v), about 57% (w/v), about 58% (w/v), about 59% (w/v), about 60% (w/v), about 61% (w/v), about 62% (w/v), about 63% (w/v), about 64% (w/v), about 65% (w/v), about 66% (w/v), about 67% (w/v), about 68% (w/v), about 69% (w/v), about 70% (w/v), about 71% (w/v), about 72% (w/v), about 73% (w/v), about 74% (w/v), about 75% (w/v), about 76% (w/v), about 77% (w/v), about 78% (w/v), about 79% (w/v), about 80% (w/v), about 81% (w/v), about 82% (w/v), about 83% (w/v), about 84% (w/v), about 85% (w/v), about 86% (w/v), about 87% (w/v), about 88% (w/v), about 89% (w/v), about 90% (w/v), about 91% (w/v), about 92% (w/v), about 93% (w/v), about 94% (w/v), about 95% (w/v), about 96% (w/v), about 97% (w/v), about 98% (w/v), about 99% (w/v), or about 100% (w/v).

Antioxidants

The present disclosure provides, in some embodiments, dispensable formulations, microneedles and/or microarray patches (MAPs) comprising an antioxidant. In some embodiments, the antioxidant is selected from the group consisting of sodium metabisulfite, sodium pyruvate, sodium ascorbate, and combinations thereof. In some embodiments, an antioxidant may be present in a composition described herein at a concentration of about 0% (w/v) to about 100% (w/v). In some embodiments, the antioxidant may be present in a composition, e.g., a dispensable formulation, at a concentration of about 0% (w/v), about 0.001% (w/v), about 0.01% (w/v), about 0.1% (w/v), about 0.2% (w/v), about 0.3% (w/v), about 0.4% (w/v), about 0.5% (w/v), about 0.6% (w/v), about 0.7% (w/v), about 0.8% (w/v), about 0.9% (w/v), about 1% (w/v), about 2% (w/v), about 3% (w/v), about 4% (w/v), about 5% (w/v), about 6% (w/v), about 7% (w/v), about 8% (w/v), about 9% (w/v), about 10% (w/v), about 11% (w/v), about 12% (w/v), about 13% (w/v), about 14% (w/v), about 15% (w/v), about 16% (w/v), about 17% (w/v), about 18% (w/v), about 19% (w/v), about 20% (w/v), about 21% (w/v), about 22% (w/v), about 23% (w/v), about 24% (w/v), about 25% (w/v), about 26% (w/v), about 27% (w/v), about 28% (w/v), about 29% (w/v), about 30% (w/v), about 31% (w/v), about 32% (w/v), about 33% (w/v), about 34% (w/v), about 35% (w/v), about 36% (w/v), about 37% (w/v), about 38% (w/v), about 39% (w/v), about 40% (w/v), about 41% (w/v), about 42% (w/v), about 43% (w/v), about 44% (w/v), about 45% (w/v), about 46% (w/v), about 47% (w/v), about 48% (w/v), about 49% (w/v), about 50% (w/v), about 51% (w/v), about 52% (w/v), about 53% (w/v), about 54% (w/v), about 55% (w/v), about 56% (w/v), about 57% (w/v), about 58% (w/v), about 59% (w/v), about 60% (w/v), about 61% (w/v), about 62% (w/v), about 63% (w/v), about 64% (w/v), about 65% (w/v), about 66% (w/v), about 67% (w/v), about 68% (w/v), about 69% (w/v), about 70% (w/v), about 71% (w/v), about 72% (w/v), about 73% (w/v), about 74% (w/v), about 75% (w/v), about 76% (w/v), about 77% (w/v), about 78% (w/v), about 79% (w/v), about 80% (w/v), about 81% (w/v), about 82% (w/v), about 83% (w/v), about 84% (w/v), about 85% (w/v), about 86% (w/v), about 87% (w/v), about 88% (w/v), about 89% (w/v), about 90% (w/v), about 91% (w/v), about 92% (w/v), about 93% (w/v), about 94% (w/v), about 95% (w/v), about 96% (w/v), about 97% (w/v), about 98% (w/v), about 99% (w/v), or about 100% (w/v).

Buffers

The present disclosure provides, in some embodiments, dispensable formulations, microneedles and/or microarray patches (MAPs) comprising a buffer. In some embodiments, the buffer can be selected from the group consisting of Tris-HCl, PBS, TE, MOPS, Phosphate, Bis-tris, HEPES, and combinations thereof. In some embodiments, a buffer may be present in a composition described herein at a concentration of about 0% (w/v) to about 100% (w/v). In some embodiments, the sugar may be present in a composition, e.g., a dispensable formulation, at a concentration of about 0% (w/v), about 0.001% (w/v), about 0.01% (w/v), about 0.1% (w/v), about 0.2% (w/v), about 0.3% (w/v), about 0.4% (w/v), about 0.5% (w/v), about 0.6% (w/v), about 0.7% (w/v), about 0.8% (w/v), about 0.9% (w/v), about 1% (w/v), about 2% (w/v), about 3% (w/v), about 4% (w/v), about 5% (w/v), about 6% (w/v), about 7% (w/v), about 8% (w/v), about 9% (w/v), about 10% (w/v), about 11% (w/v), about 12% (w/v), about 13% (w/v), about 14% (w/v), about 15% (w/v), about 16% (w/v), about 17% (w/v), about 18% (w/v), about 19% (w/v), about 20% (w/v), about 21% (w/v), about 22% (w/v), about 23% (w/v), about 24% (w/v), about 25% (w/v), about 26% (w/v), about 27% (w/v), about 28% (w/v), about 29% (w/v), about 30% (w/v), about 31% (w/v), about 32% (w/v), about 33% (w/v), about 34% (w/v), about 35% (w/v), about 36% (w/v), about 37% (w/v), about 38% (w/v), about 39% (w/v), about 40% (w/v), about 41% (w/v), about 42% (w/v), about 43% (w/v), about 44% (w/v), about 45% (w/v), about 46% (w/v), about 47% (w/v), about 48% (w/v), about 49% (w/v), about 50% (w/v), about 51% (w/v), about 52% (w/v), about 53% (w/v), about 54% (w/v), about 55% (w/v), about 56% (w/v), about 57% (w/v), about 58% (w/v), about 59% (w/v), about 60% (w/v), about 61% (w/v), about 62% (w/v), about 63% (w/v), about 64% (w/v), about 65% (w/v), about 66% (w/v), about 67% (w/v), about 68% (w/v), about 69% (w/v), about 70% (w/v), about 71% (w/v), about 72% (w/v), about 73% (w/v), about 74% (w/v), about 75% (w/v), about 76% (w/v), about 77% (w/v), about 78% (w/v), about 79% (w/v), about 80% (w/v), about 81% (w/v), about 82% (w/v), about 83% (w/v), about 84% (w/v), about 85% (w/v), about 86% (w/v), about 87% (w/v), about 88% (w/v), about 89% (w/v), about 90% (w/v), about 91% (w/v), about 92% (w/v), about 93% (w/v), about 94% (w/v), about 95% (w/v), about 96% (w/v), about 97% (w/v), about 98% (w/v), about 99% (w/v), or about 100% (w/v).

Surfactants

The present disclosure provides, in some embodiments, dispensable formulations, microneedles and/or microarray patches (MAPs) comprising a surfactant. In some embodiments, the surfactant is selected from the group consisting of Kolliphor® EL, Kolliphor® HS 15, Pluronic® F-127 (Poloxamer 407), Pluronic® F-68 (Poloxamer 188), Tween® 20 (polysorbate 20), Tween® 80 (polysorbate 80), Soluplus®, P124, CHAPS, and combinations thereof. In some embodiments, a surfactant may be present in a composition described herein at a concentration of about 0% (w/v) to about 100% (w/v). In some embodiments, the surfactant may be present in a composition, e.g., a dispensable formulation, at a concentration of about 0% (w/v), about 0.001% (w/v), about 0.01% (w/v), about 0.1% (w/v), about 0.2% (w/v), about 0.3% (w/v), about 0.4% (w/v), about 0.5% (w/v), about 0.6% (w/v), about 0.7% (w/v), about 0.8% (w/v), about 0.9% (w/v), about 1% (w/v), about 2% (w/v), about 3% (w/v), about 4% (w/v), about 5% (w/v), about 6% (w/v), about 7% (w/v), about 8% (w/v), about 9% (w/v), about 10% (w/v), about 11% (w/v), about 12% (w/v), about 13% (w/v), about 14% (w/v), about 15% (w/v), about 16% (w/v), about 17% (w/v), about 18% (w/v), about 19% (w/v), about 20% (w/v), about 21% (w/v), about 22% (w/v), about 23% (w/v), about 24% (w/v), about 25% (w/v), about 26% (w/v), about 27% (w/v), about 28% (w/v), about 29% (w/v), about 30% (w/v), about 31% (w/v), about 32% (w/v), about 33% (w/v), about 34% (w/v), about 35% (w/v), about 36% (w/v), about 37% (w/v), about 38% (w/v), about 39% (w/v), about 40% (w/v), about 41% (w/v), about 42% (w/v), about 43% (w/v), about 44% (w/v), about 45% (w/v), about 46% (w/v), about 47% (w/v), about 48% (w/v), about 49% (w/v), about 50% (w/v), about 51% (w/v), about 52% (w/v), about 53% (w/v), about 54% (w/v), about 55% (w/v), about 56% (w/v), about 57% (w/v), about 58% (w/v), about 59% (w/v), about 60% (w/v), about 61% (w/v), about 62% (w/v), about 63% (w/v), about 64% (w/v), about 65% (w/v), about 66% (w/v), about 67% (w/v), about 68% (w/v), about 69% (w/v), about 70% (w/v), about 71% (w/v), about 72% (w/v), about 73% (w/v), about 74% (w/v), about 75% (w/v), about 76% (w/v), about 77% (w/v), about 78% (w/v), about 79% (w/v), about 80% (w/v), about 81% (w/v), about 82% (w/v), about 83% (w/v), about 84% (w/v), about 85% (w/v), about 86% (w/v), about 87% (w/v), about 88% (w/v), about 89% (w/v), about 90% (w/v), about 91% (w/v), about 92% (w/v), about 93% (w/v), about 94% (w/v), about 95% (w/v), about 96% (w/v), about 97% (w/v), about 98% (w/v), about 99% (w/v), or about 100% (w/v).

Salts

The present disclosure provides, in some embodiments, dispensable formulations, microneedles and/or microarray patches (MAPs) comprising a salt. In some embodiments, the salt is selected from the group consisting of NaCl, $CaCl_2$), $ZnCl_2$, $MgCl_2$, urea, and combinations thereof. In some embodiments, a salt may be present in a composition described herein at a concentration of about 0% (w/v) to about 100% (w/v). In some embodiments, the salt may be present in a composition, e.g., a dispensable formulation, at a concentration of about 0% (w/v), about 0.001% (w/v), about 0.01% (w/v), about 0.1% (w/v), about 0.2% (w/v), about 0.3% (w/v), about 0.4% (w/v), about 0.5% (w/v), about 0.6% (w/v), about 0.7% (w/v), about 0.8% (w/v), about 0.9% (w/v), about 1% (w/v), about 2% (w/v), about 3% (w/v), about 4% (w/v), about 5% (w/v), about 6% (w/v), about 7% (w/v), about 8% (w/v), about 9% (w/v), about 10% (w/v), about 11% (w/v), about 12% (w/v), about 13% (w/v), about 14% (w/v), about 15% (w/v), about 16% (w/v), about 17% (w/v), about 18% (w/v), about 19% (w/v), about 20% (w/v), about 21% (w/v), about 22% (w/v), about 23% (w/v), about 24% (w/v), about 25% (w/v), about 26% (w/v), about 27% (w/v), about 28% (w/v), about 29% (w/v), about 30% (w/v), about 31% (w/v), about 32% (w/v), about 33% (w/v), about 34% (w/v), about 35% (w/v), about 36% (w/v), about 37% (w/v), about 38% (w/v), about 39% (w/v), about 40% (w/v), about 41% (w/v), about 42% (w/v), about 43% (w/v), about 44% (w/v), about 45% (w/v), about 46% (w/v), about 47% (w/v), about 48% (w/v), about 49% (w/v), about 50% (w/v), about 51% (w/v), about 52% (w/v), about 53% (w/v), about 54% (w/v), about 55% (w/v), about 56% (w/v), about 57% (w/v), about 58% (w/v), about 59% (w/v), about 60% (w/v), about 61% (w/v), about 62% (w/v), about 63% (w/v), about 64% (w/v), about 65% (w/v), about 66% (w/v), about 67% (w/v), about 68% (w/v), about 69% (w/v), about 70% (w/v), about 71% (w/v), about 72% (w/v), about 73% (w/v), about 74% (w/v), about 75% (w/v), about 76% (w/v), about 77% (w/v), about 78% (w/v), about 79% (w/v), about 80% (w/v), about 81% (w/v), about 82% (w/v), about 83% (w/v), about 84% (w/v), about 85% (w/v), about 86% (w/v), about 87% (w/v), about 88% (w/v), about 89% (w/v), about 90% (w/v), about 91% (w/v), about 92% (w/v), about 93% (w/v), about 94% (w/v), about 95% (w/v), about 96% (w/v), about 97% (w/v), about 98% (w/v), about 99% (w/v), or about 100% (w/v).

The present disclosure provides, in some embodiments, dispensable formulations, microneedles and/or microarray patches (MAPs) comprising a formulations of Table A.

TABLE A

| Exemplary Dispensable Formulations, Microneedles, and Microarray Patches (MAPs) | | | |
|---|---|---|---|
| API | GLP-1 | mRNA/LNP | VLP |
| Tip: | PPS (Form 1): 180 mg/mL GLP-1 1% Povidone K 17 (PVP K17) 0.75% Proline 0.1% Kolliphor EL 0.9% NaCl 100 mM Tris-HCl buffer PHP (Form 2): 180 mg/mL GLP-1 1% Povidone K 17 (PVP K17) 3% Proline 0.1% Kolliphor ® EL 100 mM Tris-HCl buffer | 1% PVA 4-88 5% PVP K17 10% sucrose 1X TE buffer | 0.5% Fibroin 0.25% Tween-80 20 mM Tris 100 mM NaCl 4% Trehalose |
| Base: | 60% Povidone K 17 (PVP K17) 0.5% Polyvinyl alcohol (PVA) 4-88 1X TE Buffer | 0.5% PVA 60% PVP K17 1X TE buffer | 60% PVP K17 0.1% Triton |

The present disclosure provides, in some embodiments, dispensable formulations, microneedles and/or microarray patches (MAPs) comprising a component, a formulation, or characteristic as set forth in any one of Tables A-B and Tables 1-21. To the extent that the formulations provided in any one of Tables A-B and Tables 1-21 may refer to the inclusion of a dye (e.g., a AF-647 dye) or the like, one skilled in the art should understand that the present disclosure is intended to encompass embodiments in which the dye is not included in the formulations as set forth in any one of Tables A-B and Tables 1-21.

Methods of Use and Treatment

In one aspect, the present disclosure provides dispensable formulations, microneedles and/or the microarray patches (MAPs), comprising an active pharmaceutical ingredient (API) and a water soluble excipient, that can be configured and utilized for various applications, including, e.g., bio-medical applications, such as drug delivery, biosensing, biomolecular and cellular sampling, disease diagnosis, disease mitigation, disease treatment, disease prevention, and/or health monitoring; and cosmetic applications, such as nutrient and/or cosmeceutical delivery.

In one aspect, the present disclosure provides a method of administering an active pharmaceutical ingredient (API) (e.g., a therapeutically effective and/or prophylactically effective amount of an API) to a subject in need thereof. In some embodiments, the dispensable formulations, microneedles, and/or microarray patches (MAPs) comprising the API are useful for treating, delaying progression, delaying onset, slowing progression, preventing, providing remission, and/or improving the symptoms of a disease, disorder, and/or condition. In some embodiments, the methods comprise applying to the skin of a subject a microneedle and/or a microarray patch (MAP) described herein. In some embodiments, upon application of a microneedle and/or a microarray patch (MAP) to the skin of a subject, transdermal and/or intradermal delivery of the active pharmaceutical ingredient (API) occurs, e.g., to provide a systemic blood concentration of the API, or a metabolite thereof, that is bioequivalent to administration of the API parenterally, subcutaneously, intravenously, intramuscularly, and/or orally. In some embodiments, transdermally and/or intradermally administering the API using a microneedle and/or a microarray patch (MAP) described herein can reduce the number of and/or severity of adverse events as compared to administering a similar dose of the API parenterally, subcutaneously, intravenously, intramuscularly, and/or orally.

In one aspect, the present disclosure provides a method of administering a combination of active pharmaceutical ingredients (APIs) (e.g., two or more APIs) to a subject in need thereof.

By "a combination" or "in combination with," it is not intended to imply that the APIs or additional therapies may be administered at the same time and/or formulated for delivery together, although these methods of delivery are within the scope described herein. The APIs or additional therapies in the combination can be administered concurrently with, prior to, or subsequent to, one or more other APIs or additional therapies. The APIs or additional therapies can be administered in any order. In general, each API will be administered at a dose and/or on a time schedule determined for that API. It will further be appreciated that the APIs or additional therapies utilized in this combination may be administered together in a single composition or administered separately in different compositions. In general, it is expected that APIs or additional therapies utilized in combination may be utilized at levels that do not exceed the levels at which they are utilized individually. In some embodiments, the levels utilized in combination will be lower than those utilized individually.

In some embodiments, two or more APIs may be co-formulated in the same microneedle and/or MAP. Formulation compatibility may limit whether two or more given APIs can be co-formulated to be dispensed into the same microneedle and/or MAP. In case co-formulation is not possible, the manufacturing process can be adapted in order to dispense a first formulation into a portion of the needle array and then dispense a second formulation into a different portion of the needle array. Different formulations can also receive different process treatments after filling. For instance, if the first formulation may be for controlled-release or sustained-release and the formulation may be rendered less soluble, e.g., via specific components or processing, while the second formulation will be for immediate release, e.g., via different components or processing, the second formulation may be dispensed after the first. The manufacturing approach is flexible so other process sequences are possible.

In some embodiments, the disclosure also provides methods for combination therapies, wherein a microneedle and/or MAP can be fabricated to administer an API (e.g., a first API) and at least one additional API (e.g., a second API). Various forms of a therapeutic agent can be used which are capable of being released from the microneedles and/or MAPs described herein into adjacent tissues or fluids for local and/or systemic effects upon administration to a subject. In some embodiments, an additional therapeutic agent can be included within the consolidated microneedle tip and/or within the microneedle base. In some embodiments, a MAP may comprise a plurality of microneedles, wherein each microneedle independently comprises one or more APIs. In some embodiments, about 0% to about 100% of the microneedles present in a MAP may independently comprise a first API, while about 0% to about 100% of the microneedles present in the MAP independently comprise a second API, wherein the number of microneedles comprising the first API and the second API is equal to the total number of microneedles in the MAP.

In one aspect, the present disclosure provides a method of treating a disease, disorder, and/or condition in a subject in need thereof. In some embodiments, "treating" refers to the medical treatment of a subject in need thereof. The treatment may be preventive, prophylactic, palliative, symptomatic, and/or curative. In some embodiments, "treatment" refers to reducing, delaying or removing a symptom of the disease, disorder, and/or condition referred to. The timing, treatment dosage, and purpose of the treatment may vary from one subject to another, e.g., according to the status of the subject's health. The dispensable formulations, microneedles and/or the microarray patches (MAPs) can be configured to provide a treatment dosage of the active pharmaceutical ingredient (API) that is relevant to the disease, disorder, and/or condition. In some embodiments, the term "treatment dosage" refers to the dosage (e.g., amount and/or administration frequency) of the active pharmaceutical ingredient (API).

In one aspect, the present disclosure provides a method of suppressing a disease, disorder, and/or condition in a subject in need thereof. In one aspect, the present disclosure provides a method of stabilizing a disease, disorder, and/or condition in a subject in need thereof. In one aspect, the present disclosure provides a method of preventing a disease, disorder, and/or condition in a subject in need thereof. In one aspect, the present disclosure provides a method of preventing relapse of a disease, disorder, and/or condition in a subject in need thereof. In one aspect, the present disclosure provides a method of reducing the incidence of a disease, disorder, and/or condition in a subject in need thereof. In one aspect, the present disclosure provides a method of reducing the severity of a disease, disorder, and/or condition in a subject. In one aspect, the present disclosure provides a method of inhibiting the progression of a disease, disorder, and/or condition in a subject. In one aspect, the present disclosure provides a method of providing palliative care in a subject in need thereof. In one aspect, the present disclosure provides a method of increasing the survival (e.g., progression free survival) of a subject in need thereof.

In one aspect, the present disclosure provides a method of treating a disease, disorder, and/or condition in a subject in need thereof that has not responded adequately to a previous treatment and/or has progressed during a previous treatment. In one aspect, the present disclosure provides a method of treating a disease, disorder, and/or condition in a subject in need thereof that has not responded adequately to and/or has progressed during a previous treatment comprising the administration of the active pharmaceutical ingredient (API) via a non-transdermal and/or a non-intradermal route (e.g., via parenteral, subcutaneous, intravenous, intramuscular, and/or oral administration).

The methods of the present disclosure can be applied to various diseases, disorders, and/or conditions. Exemplary diseases, disorders, and/or conditions include, but are not limited to, an autoimmune or an immune-related disease, disorder, and/or condition; a bacterial disease, disorder, and/or condition; a blood disease, disorder, and/or condition; a bone disease, disorder, and/or condition; a cancer or a cancer-related disease, disorder, and/or condition; a cardiovascular disease, disorder, and/or condition; a circulatory disease, disorder, and/or condition; a childhood disease, disorder, and/or condition; a connective tissue disease, disorder, and/or condition; a digestive disease, disorder, and/or condition; an eating disease, disorder, and/or condition; an endocrine disease, disorder, and/or condition; an excretory disease, disorder, and/or condition; an eye disease, disorder, and/or condition; a fungal disease, disorder, and/or condition; a gastrointestinal tract disease, disorder, and/or condition; a genetic disease, disorder, and/or condition; a heart disease, disorder, and/or condition; an immune disease, disorder, and/or condition; an intestinal disease, disorder, and/or condition; an infectious disease, disorder, and/or condition; a kidney disease, disorder, and/or condition; a liver disease, disorder, and/or condition; a metabolic disease, disorder, and/or condition; a mitochondrial disease, disorder, and/or condition; a muscular disease, disorder, and/or condition; a neurological or neuropsychiatric disease, disorder, and/or condition; an ophthalmic disease, disorder, and/or condition; an oral disease, disorder, and/or condition; a prenatal or pregnancy-related disease, disorder, and/or condition; a protist disease, disorder, and/or condition; a reproductive disease, disorder, and/or condition; a respiratory disease, disorder, and/or condition; a skeletal disease, disorder, and/or condition; a skin disease, disorder, and/or condition; a systemic disease, disorder, and/or condition; a tumor; a viral disease, disorder, and/or condition; and combinations thereof.

In some embodiments, the subject has been diagnosed with the disease, disorder, and/or condition. As used herein, the term "diagnosis" generally refers to methods by which the skilled artisan can estimate and/or determine whether or not a subject is suffering from a given disease, disorder, and/or condition. In some embodiments, a diagnosis may be made on the basis of one or more diagnostic indicators, e.g., a marker, the presence, absence, amount, or change in amount of which is indicative of the presence, severity, or absence of the condition. In general, the disease, disorder, and/or condition can be diagnosed by conventional diagnostic techniques. In some embodiments, the methods of the present disclosure can be used together with any known diagnostic methods, such as physical inspection, visual inspection, biopsy, scanning, histology, radiology, imaging, ultrasound, use of a commercial kit, genetic testing, immunological testing, analysis of bodily fluids, or monitoring neural activity.

In some embodiments, the dispensable formulations, microneedles and/or the microarray patches (MAPs) described herein may be used for the administration of an effective amount of one or more active pharmaceutical ingredient (API) described herein, e.g., selected from the group consisting of amino acids, proteins, peptides, hormones, biologics, antibodies, growth factors, nucleic acids, such as DNA, RNA, and mRNA, gene constructs, and vectors, lipid nanoparticles (LNPs), sugars, antigens, vaccines, viruses, live attenuated viruses, inactivated viruses, adjuvanted vaccines, viral-like particles, enzymes, cells, small molecules, antibiotics, drugs, and any combination thereof. In some embodiments, the dispensable formulations, microneedles and/or the microarray patches (MAPs) described herein may be used for the administration of an effective amount of a polypeptide, a protein, a small molecule, an antibody, a fusion protein, or any combination thereof.

Type 2 Diabetes (T2D) and Obesity

Over 400 million adults worldwide are living with Type 2 diabetes (T2D). Despite significant advancements in effective treatments, T2D continues to rise at a concerning rate, and by 2035 it is projected that there will be >590 million patients diagnosed globally with this condition-making it one of the costliest chronic health conditions for patients and society. Glucagon-like peptide-1 receptor agonists (GLP-1 RA) have revolutionized the treatment of T2D because they provide substantial reductions in HbA1c as well as addressing the underlying metabolic dysfunction of obesity that both can cause and complicate the management of diabetes. Regimens that provide sustained plasma levels of GLP-1 RA provide optimal therapeutic effects and this has led to the development of formulations and/or modifications of the native sequence aimed at extending the peptide half-life. Semaglutide is a long acting GLP-1 analogue with low renal clearance and a long elimination half-life. This is achieved by engineering the peptide to avoid renal clearance and enzymatic degradation. While these modifications have reduced treatment frequency from daily to weekly, poor adherence linked to perceived treatment complexity and needle fear remains a general problem. These barriers highlight the need for new modes of GLP-1 RA delivery. The microneedles, MAPs, and systems described herein may be used to enable simple and effective GLP-1 RA delivery. The microneedles, MAPs, and systems described herein may also be used to enable effective GLP-1 RA delivery and/or combination treatments with various APIs relevant for T2D, obesity, NASH (Nonalcoholic steatohepatitis), MASH (Metabolic dysfunction-associated steatohepatitis), NAFLD (nonalcoholic fatty liver disease), short bowel syndrome, Alzheimer's, chronic heart failure, chronic kidney disease, osteoarthritis, obstructive sleep apnea, psoriasis and other inflammatory cutaneous diseases, and drug addiction.

Glucagon-like peptide-1 (GLP-1)

In some embodiments, the dispensable formulations, microneedles and/or the microarray patches (MAPs) described herein may be used for the administration of an effective amount of a glucagon-like peptide-1 (GLP-1) polypeptide, such as a GLP-1 receptor agonist, a GLP-1 analogue, a GLP-1 derivative, and/or a salt thereof. In some embodiments, the dispensable formulation, the microneedle and/or the microarray patch (MAP) can comprise and/or can be administered in combination with a GLP-1 receptor agonist, e.g., selected from the group consisting of semaglutide; dulaglutide; exenatide; liraglutide; lixisenatide; tirzepatide; albiglutide; taspoglutide; pharmaceutically acceptable salts thereof; derivatives thereof; analogues thereof; and combinations thereof. In some embodiments, the dispensable formulations, microneedles and/or the microarray patches (MAPs) described herein may be used for the administration of an effective amount of semaglutide.

In some embodiments, the dispensable formulations, microneedles and/or the microarray patches (MAPs) described herein may be used in any medical treatments, which would benefit from delivery of an API using a microneedle and/or a microarray patches (MAPs).

In some embodiments, the dispensable formulations, microneedles and/or the microarray patches (MAPs) described herein may be used for the prevention and/or treatment of any form of diabetes, such as hyperglycemia, type 2 diabetes, impaired glucose tolerance, type 1 diabetes, non-insulin dependent diabetes, MODY (maturity onset diabetes of the young), gestational diabetes, and/or for reduction of HbA1c. In some embodiments, the dispensable formulations, microneedles and/or the microarray patches (MAPs) described herein may be used for delaying or preventing diabetic disease progression, such as for delaying or preventing the progression in type 2 diabetes, for delaying or preventing the progression of impaired glucose tolerance (IGT) to insulin requiring type 2 diabetes, and/or for delaying or preventing the progression of non-insulin requiring type 2 diabetes to insulin requiring type 2 diabetes. In some embodiments, the dispensable formulations, microneedles and/or the microarray patches (MAPs) described herein may be used for the prevention and/or treatment of an eating disorder, such as obesity, e.g., by decreasing food intake, reducing body weight, preventing regain of weight, promoting weight maintenance, suppressing appetite, and/or inducing satiety.

In some embodiments, the dispensable formulations, microneedles and/or the microarray patches (MAPs) described herein may be used for the prevention and/or treatment of an eating disorder, such as binge eating disorder, bulimia nervosa, and/or obesity induced by administration of an antipsychotic or a steroid. In some embodiments, the dispensable formulations, microneedles and/or the microarray patches (MAPs) described herein may be used for the reduction of gastric motility; and/or delaying gastric emptying.

In some embodiments, the dispensable formulations, microneedles and/or the microarray patches (MAPs) described herein may be used for the prevention and/or treatment of a cardiovascular disease, such as delaying or reducing development of a major adverse cardiovascular event (MACE) selected from the group consisting of cardiovascular death, non-fatal myocardial infarction, non-fatal stroke, revascularization, hospitalization for unstable angina pectoris, and hospitalization for heart failure.

In some embodiments, the dispensable formulations, microneedles and/or the microarray patches (MAPs) described herein may be used for the prevention and/or treatment of nonalcoholic steatohepatitis or NASH.

In some embodiments, the dispensable formulations, microneedles and/or the microarray patches (MAPs) described herein may be used for the prevention and/or treatment of Alzheimer's disease.

In some embodiments, the dispensable formulations, microneedles and/or the microarray patches (MAPs) described herein may be used for type 2 diabetes and/or obesity.

Overweight and obesity may be defined as abnormal or excessive fat accumulation that presents a risk to health. A body mass index (BMI) over 25 can be considered overweight, and a BMI over 30 can be considered obese. Generally, all subjects suffering from obesity are also considered to be suffering from overweight. In some embodiments the invention relates to a method for treatment or prevention of obesity. In some embodiments the invention relates to use of the composition for treatment or prevention of obesity. In some embodiments the subject suffering from obesity is human, such as an adult human or a pediatric human (including infants, children, and adolescents). Body mass index (BMI) is a measure of body fat based on height and weight. The formula for calculation is BMI=weight in kilograms/[height in meters] 2. A human subject suffering from obesity may have a BMI of ≥30; this subject may also be referred to as obese. In some embodiments the human subject suffering from obesity may have a BMI of ≥35 or a BMI in the range of >30 to <40. In some embodiments the obesity is severe obesity or morbid obesity, wherein the human subject may have a BMI of ≥40.

In some embodiments the invention relates to a method for treatment or prevention of overweight, optionally in the presence of at least one weight-related comorbidity. In some embodiments the invention relates to use of the composition for treatment or prevention of overweight, optionally in the presence of at least one weight-related comorbidity. In some embodiments the subject suffering from overweight is human, such as an adult human or a pediatric human (including infants, children, and adolescents). In some embodiments a human subject suffering from overweight may have a BMI of ≥25 such as a BMI of ≥27. In some embodiments a human subject suffering from overweight has a BMI in the range of 25 to <30 or in the range of 27 to <30. In some embodiments the weight-related comorbidity is selected from the group consisting of hypertension, diabetes (such as type 2 diabetes), dyslipidemia, high cholesterol, and obstructive sleep apnea.

In some embodiments the invention relates to a method for reduction of body weight. In some embodiments the invention relates to use of the composition for reduction of body weight. A human to be subjected to reduction of body weight according to the present invention may have a BMI of ≥25 such as a BMI of ≥27 or a BMI of ≥30. In some embodiments the human to be subjected to reduction of body weight according to the present invention may have a BMI of ≥35 or a BMI of ≥40. The term "reduction of body weight" may include treatment or prevention of obesity and/or overweight.

In some embodiments the method or use comprises prevention, treatment, reduction and/or induction in one or more diseases or conditions defined herein or known in the art.

According to some embodiments, the disclosure provides methods that further comprise administering an additional agent to a subject. In some embodiments, the disclosure pertains to co-administration and/or co-formulation of one or more APIs.

EXAMPLES

Example 1: Evaluation of MIMIX MAP Tip Formulations for GLP-1 Receptor Agonist Delivery Overview of Microneedle Array Patches (MAPs) and the MIMIX MAP Platform Microneedle array patches, or MAPs, are a minimally invasive alternative to needle and syringe for delivery of vaccines and therapeutics to the skin. MAPs comprise an array of microprojections attached to a backing that can be applied to the skin with finger pressure or an applicator. They generally are categorized into four main types, hollow, solid/coated, swellable and dissolving.

MAPs have several potential logistical advantages including reduced costs for transport and distribution (due to their thermostability), easier and safer administration (no need for reconstitution), and greater acceptability and potentially less hesitancy by end-users due to the perception of being less painful, as they are needle-free.

Figure 1:
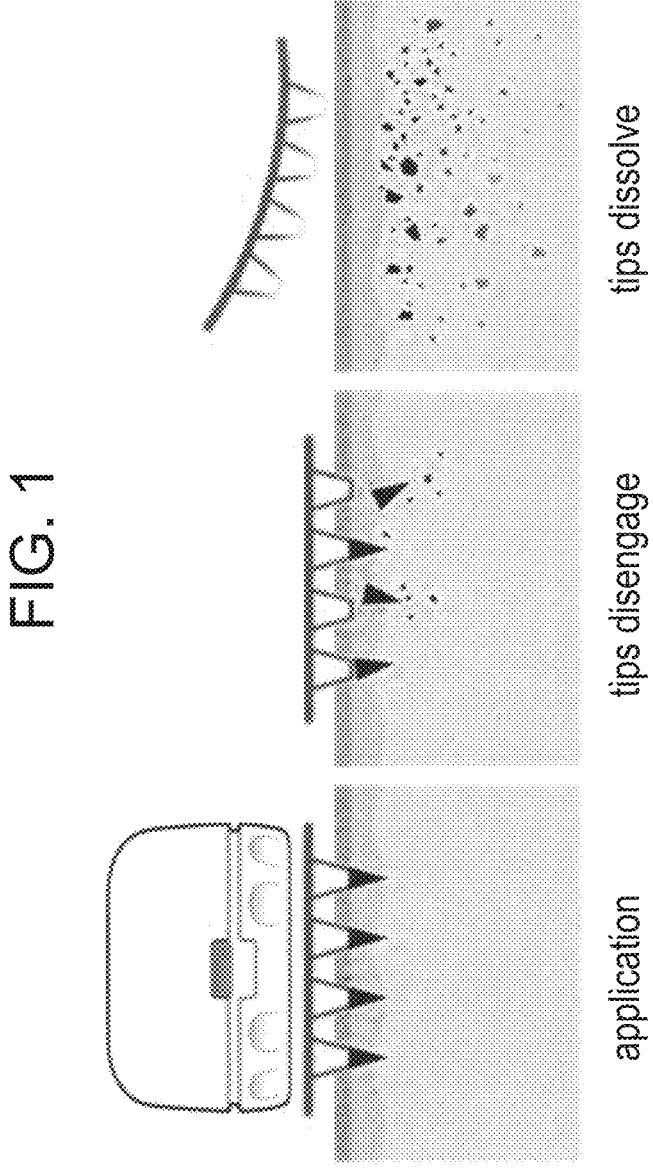
FIG. 1 shows a schematic of MIMIX MAP delivery and microneedle tip deployment. MIMIX MAPs are applied to the skin using a spring-loaded applicator. The moisture of the skin then dissolves the water-soluble base of each microneedle thereby deploying the tips. Deployed tips slowly dissolve and release the vaccine payload over time.

The MIMIX MAP is a novel type of dissolving MAP whereby specific combinations of polymers and excipients work collectively to stabilize and consolidate therapeutics or vaccine antigens to the tips of each microneedle. Use of a water-soluble pedestal, or base, for each microneedle is a second distinguishing feature of the MIMIX MAP that allows for deployment of the array's tips following application to the skin. Within minutes of placing the patch on the skin, the moisture of the skin dissolves the base, thereby delivering the array of tips to the dermis. Following application, the tips dissolve and release their payload over time (FIG. 1).

Figure 2:
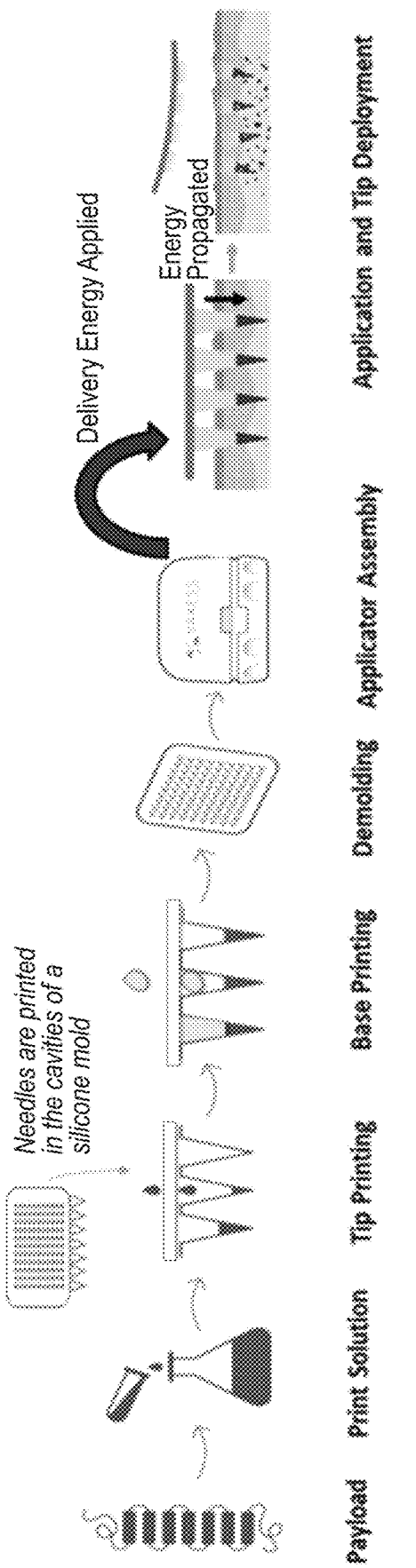
FIG. 2 shows a schematic of MIMIX MAP printing, demolding and delivery. The additive manufacturing process is shown. The process begins with a silicone mold with cavities that determine the length, shape and number of microneedles. Print solution containing the payload and specific excipients is dispensed first to form the Tip of each microneedle. After drying, the Base solution is printed and allowed to dry. An adhesive backing is added prior to demolding the MAP. A spring-loaded applicator is used to apply each MAP to the skin.

The Tip and Base components of the MIMIX MAP microneedles therefore serve specific functions in delivery of the payload to the dermis of the skin. These functions in turn dictate tip and base formulation requirements (FIG. 2). As shown in FIG. 2, MIMIX MAPs are produced by an additive manufacturing process. In a first step, a print solution containing the payload and formulation excipients is printed into the cavities of silicone molds that define the shape of each needle using a printing process likened to ink jet printing. The tips are allowed to dry. The base solution is then printed and allowed to dry. After applying an adhesive backing to the dried microneedle array it is removed, or 'demolded', from the mold. A spring-loaded applicator is used to apply the MAP to the skin and uses a defined delivery energy per needle (~2mJ per needle) to achieve a consistent, maximum depth of Tip delivery. This ensures full delivery of the payload. Because a force is applied to the MAP during its delivery it is important that both the Tip and the Base of each microneedle be sufficiently strong and stiff as to not deform during the application process. More specifically, propagation of energy through the Base and Tip of each needle allows for maximal depth of delivery of the Tips (FIG. 2).

It is important to note the size of each microneedle. Each MIMIX microneedle is a 1 mm long cone with a 30-degree included angle. The payload containing Tip is, ideally, less than 400 µm to ensure delivery below the surface of the skin. Volumetrically, this translates into a print solution dispense volume of 20-30 nL depending on the solids content of the solution, which is a function of the dose required for each payload. The total dose delivered by the MAP is determined by the amount of payload that can be loaded within each needle and the total number of microneedles. For example, if the desired clinical dose for a candidate product is 1 mg, and 5 µg per needle is the highest concentration that can be loaded per needle while maintaining the ideal <400 µm length of the Tip, then an array size of 200 microneedles would be used to deliver that dose. Smaller arrays are generally preferred in the clinic as they leave a smaller, self-resolving 'footprint' post application. Thus, in addition to conferring sufficient strength, a second goal for the MIMIX MAP Tip formulation is to stabilize the payload at the high concentrations required for manufacturing.

Printing small volumes of a highly concentrated solution creates additional challenges specific to MIMIX MAP manufacturing. The first is ensuring that the payload locates to the apex of the mold when printing.

FIG. 3 shows two extremes following subsequent drying of the dispensed print solution containing the payload. In one extreme the print solution 'pins' to the sides of the silicone mold and dries into a thin 'shell' on the cavity's walls. In the other extreme, the initial contact line formed by the liquid recedes as the Tip dries to allow for consolidation of the payload into the apex of the mold. Shells are undesirable because they typically are too long and are also structurally weak thereby precluding full delivery of the dose. They also present a higher risk of solubilizing when the Base solution is dispensed. A third goal of the MIMIX MAP Tip formulation therefore is to identify a combination of excipients that minimizes shell formation and promotes consolidation of the payload into the mold apex during Tip drying. A final consideration for the MIMIX MAP Tip formulation is 'printability'. A printer based on a piezo-actuated, dispensing valve is used for the small volume dispense that forms the Tip (and Base). With each dispense, Print Solution is 'jetted' into a mold cavity. Many of the same fluid properties such as density, viscosity, osmolality and surface tension that might be manipulated to achieve Tip consolidation can also affect this jetting process; and so, a fourth goal of the MIMIX MAP Tip formulation is to ensure fluid properties that allow for an accurate dispense. FIG. 4 depicts important processes and parameters that impact Tip drying and consolidation; surface tension and viscosity in particular, are also important considerations for the dispensing process.

In sum, MIMIX MAP Tip formulations must stabilize the payload at high concentrations, be amenable to the low volume jetting process used for printing, minimize shell formation, consolidate the payload to the apex of the mold during drying and lead to a sufficiently strong and stiff Tip that resists deformation following drying.

Development of MIMIX MAP Tip Formulations for GLP-1 Receptor Agonist Delivery

Glucagon-like peptide-1 (GLP-1) receptor agonists (also referred to herein as "GLP-1s") are now central to Type 2 diabetes (T2D) and obesity treatments. GLP-1 works in the gastrointestinal system and in appetite centers of the brain to control glucose homeostasis, energy homeostasis and satiety. Currently, the most effective obesity/T2D drugs, such as semaglutide, utilize the strategy of attaching a fatty acid moiety to the GLP-1 peptide that supports reversible binding to serum albumin and limits renal excretion. The MIMIX MAP platform has the potential to address several unmet needs associated with current delivery approaches of GLP-1s. These include treatment adherence and hesitancy associated with needle and syringe delivery and the low bioavailability associated with orally delivered GLP-1s.

A clinical feature of GLP-1s is the high dose required for obesity treatment relative to T2D treatment. For example, approximately twice the dose is required for semaglutide when used for obesity treatment vs T2D. This is believed to be due to the need to achieve high concentrations and longer residence times of GLP-1 in the appetite centers of the brain. To achieve a clinical dose of semaglutide delivered by MIMIX MAP, the experimentation has targeted 5-6 µg per needle and an array size of 400-480 microneedles for a total dose of 2.4 mg—the current highest dose of semaglutide for obesity treatment.

Initial Feasibility Studies

Initial feasibility studies evaluated Tip consolidation (overall length and morphology, e.g., presence of shells) for doses per needle ranging from 4-7 µg. MOPS was selected as a default buffer for initial evaluations of structural polymers and surfactants to facilitate Tip consolidation and printability.

Figure 5:
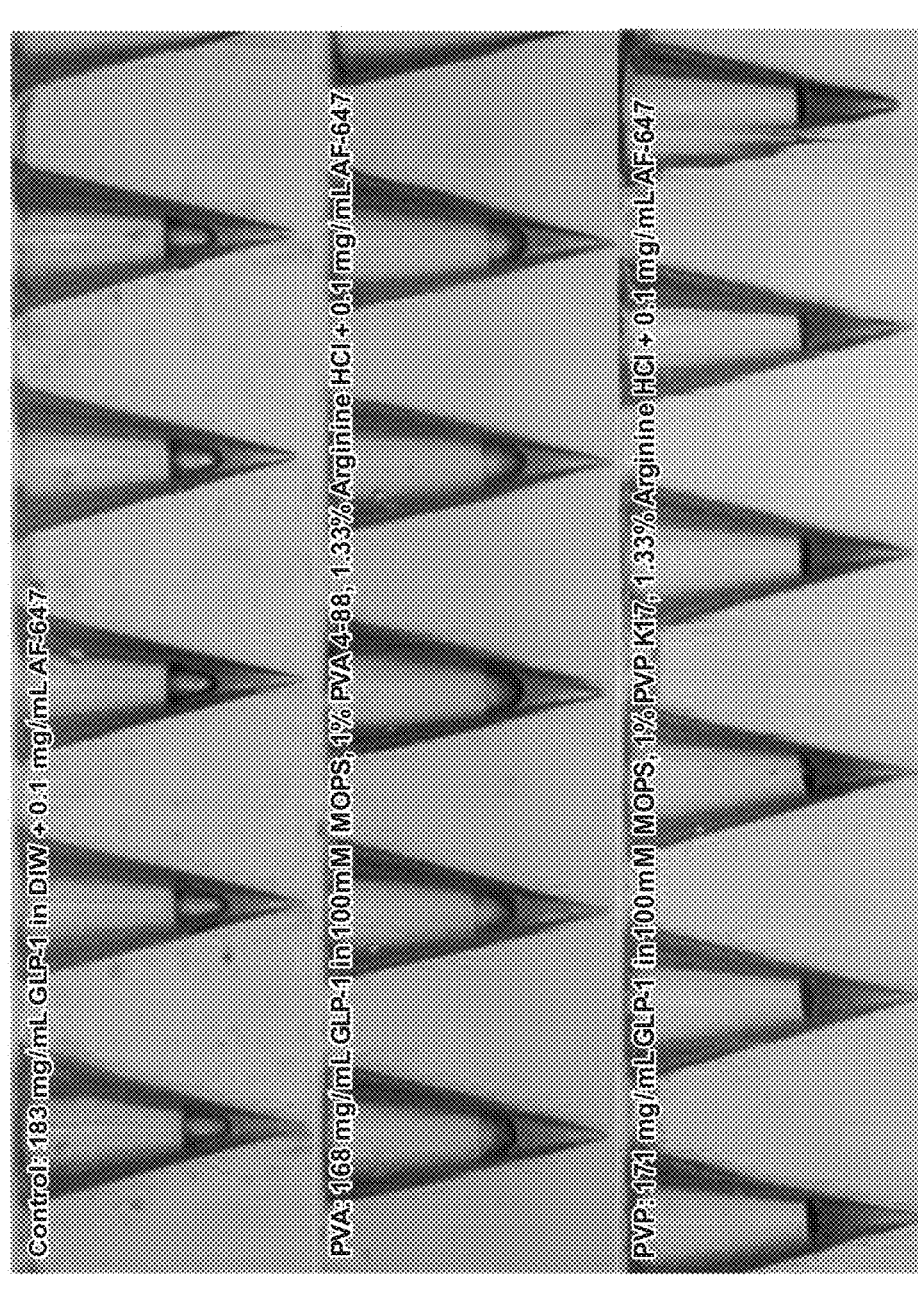
FIG. 5 shows that PVP K17 improves consolidation of GLP-1 containing Tips. Visible light micrograph of cross sectioned molds showing dried tips. Each needle cavity is about 1 mm long. For each condition 0.1 mg/mL of AF-647 was added to the print solution to aid visualization of the Tips.

In these early assessments the structural polymer polyvinylpyrrolidone K17 (PVP K17) was found to improve consolidation of Tips as measured by both the overall length of the Tip and the visual presence of shells (morphology). In experiment GLP-019, 121 microneedles were printed into silicone molds. As a control condition, inactive semaglutide (also referred to herein, e.g., as "GLP-1") was formulated in deionized water at a concentration of about 183 mg/mL. In one test condition, inactive semaglutide was formulated at a concentration of about 168 mg/ml a in 100 mM MOPS, 1% PVA 4-88 and 1.33% Arginine HCl. In a second test condition inactive semaglutide was formulated at a concentration of about 171 mg/mL in 100 mM MOPS, 1% PVP K17 and 1.33% Arginine HCL. The fluorescent dye, AF-647 was added to each condition at a concentration of 0.1 mg/mL. About twenty nanoliters were dispensed into each needle for all three conditions. The results in FIG. 5 show that the formulation including 1% PVP K17 improves the Tip consolidation.

Figure 6:
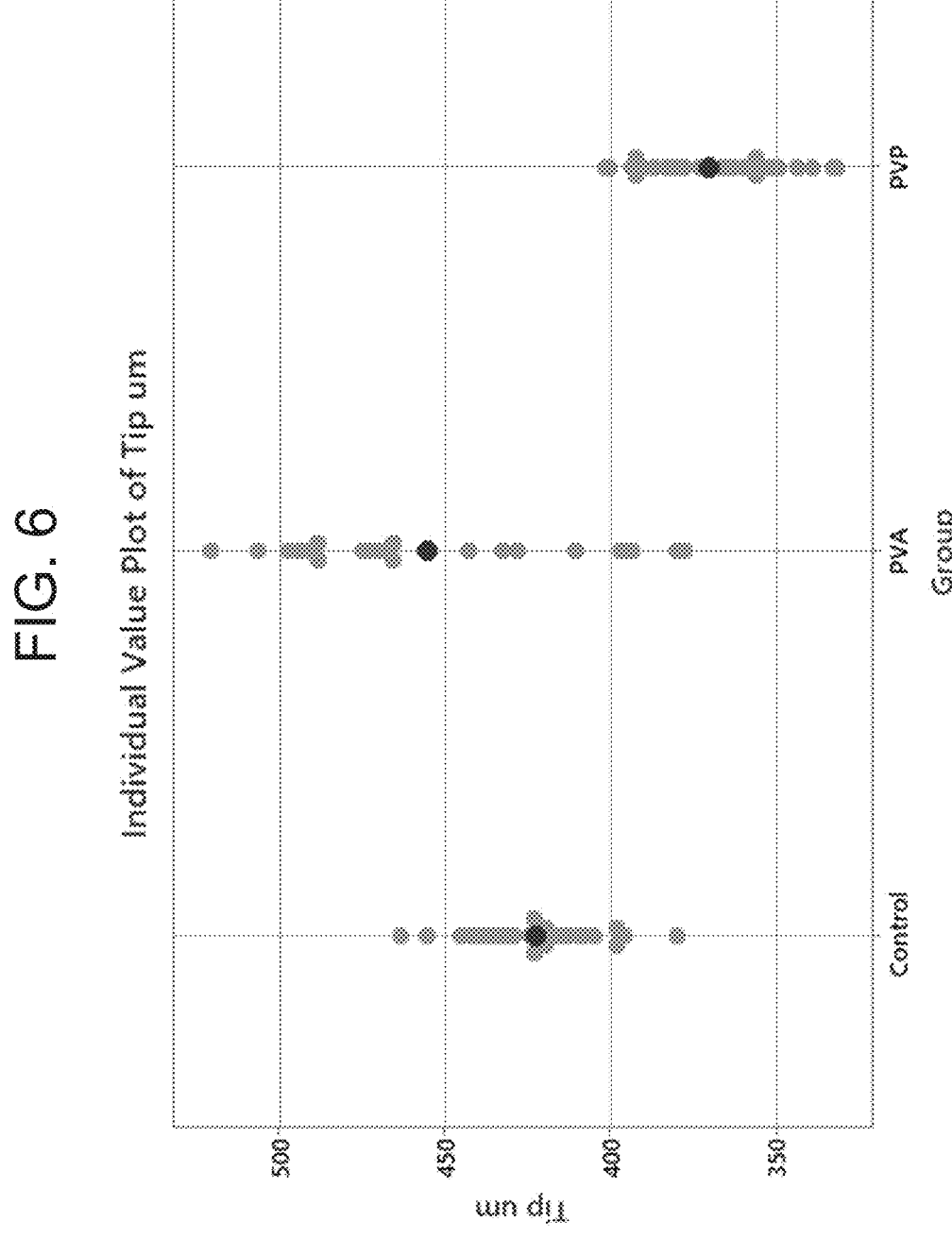
FIG. 6 shows that PVP K17 improves overall Tip Lengths. Dried Tips were measured in cross sectioned molds by image processing calibrated with a stage micrometer.

Overall Tip lengths reflect the improvement in consolidation in this experiment (FIG. 6).

In experiments GLP-022, GLP-032, GLP-045, and GLP-040, surfactants were evaluated for the ability to lower surface tension of the print solution and potentially to improve printability and yield. In GLP-045, various surfactants were compared in multiple criteria, with a background formulation of 180 mg/mL GLP-1+1% PVP K17+1.37% Arg-HCl+0.1 mg/mL AF-647 in 100 mM MOPS. From these results Kollipher EL was selected for further evaluation because it had a negligible impact on inactivated semaglutide recovery from films, because it presented good tip morphology in a macromold model system, and because it effectively reduced surface tension at a lower concentration compared to P188 (0.1% Kolliphor EL vs. 1% for P188).

In experiment GLP-040, Kollipher EL was found to modestly improve batch yields (89% without surfactant vs. 97% with surfactant) and therefore was included in the feasibility stage formulation (160-200 mg/mL GLP-1; 1% w/v PVP K17, 1.37% w/v Arginine HCl, 0.1% v/v Kolliphor EL, 100 mM MOPS buffer).

MAPs printed using this feasibility formulation were evaluated for API recovery-which measures dose recovered from a MAP as a percentage of the dose loaded; mean Tip length, API delivery-which measures the percentage of API remaining on a MAP post its ex vivo deployment onto pig skin and Tip strength as measured by the load at which it yields using an Instron crush test. The evaluations showed variability in Tip lengths and the presence of shells particularly at doses over 5 μg per Tip, variability in both API recovery and delivery and weaker tips than believed required (Table B). It was hypothesized that variation in payload delivery may be related to the Tip lengths and morphology (specifically the presence of shells) and insufficient strength of the Tips to achieve maximal delivery depth.

TABLE B

Summary of Feasibility Formulation Evaluations

| Programmatic Goal | Measurement feasibility formulation |
| --- | --- |
| 5-6 μg API per needle | 2-8 μg |
| API Recovery: >90% | 74-134% |
| Mean Tip Length: <400 um | 352 um-598 um |
| Shell length: minimize | 39 um-324 um |

TABLE B-continued

Summary of Feasibility Formulation Evaluations

| Programmatic Goal | Measurement feasibility formulation |
| --- | --- |
| API Delivery: >80% | 22-96% |
| Strength: >50N Yield | 30-70N |
| Load for 121 array >0.4N per needle | 0.24-0.58N/needle |

Example 2: Comparison of VX103 to GLP-1 Formulation

Figure 13A:
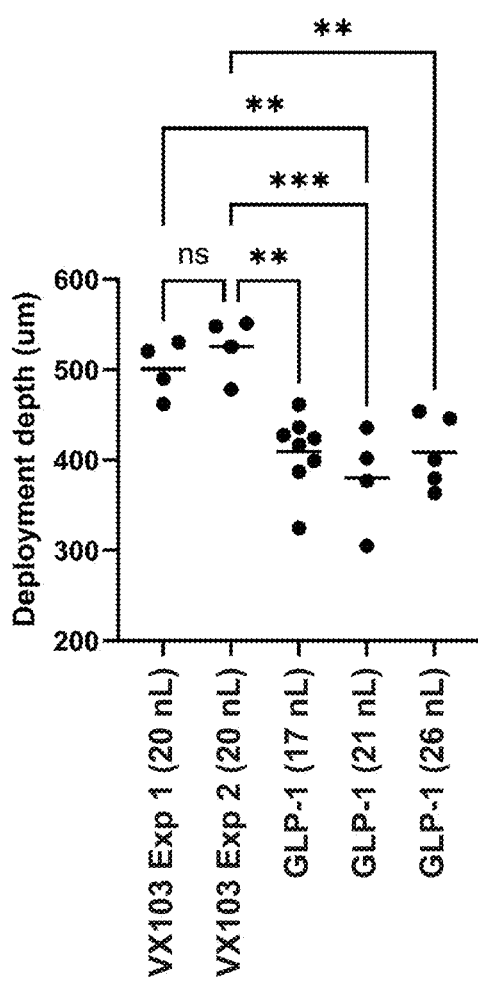
Figure 13B:
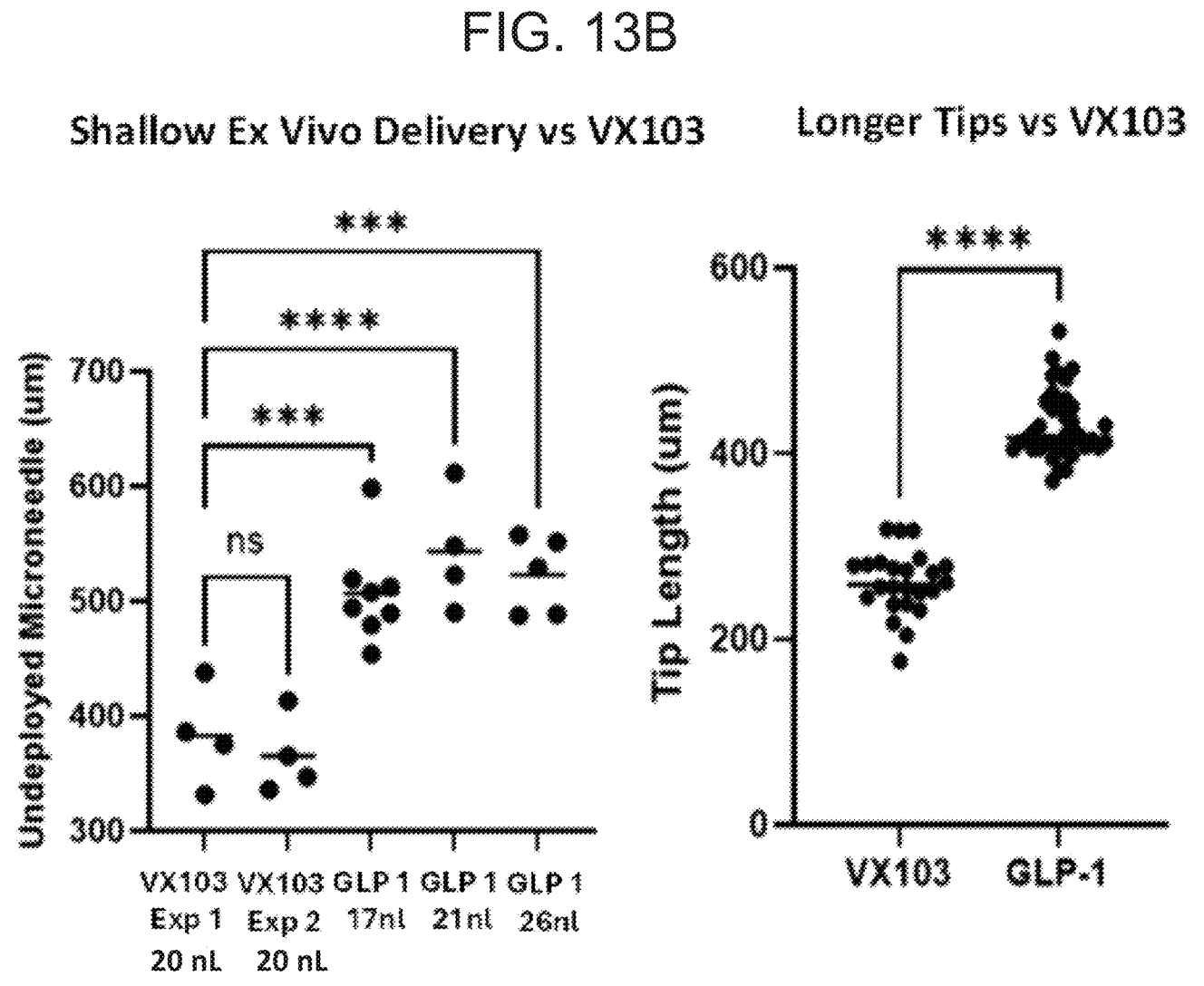
Figure 13C:
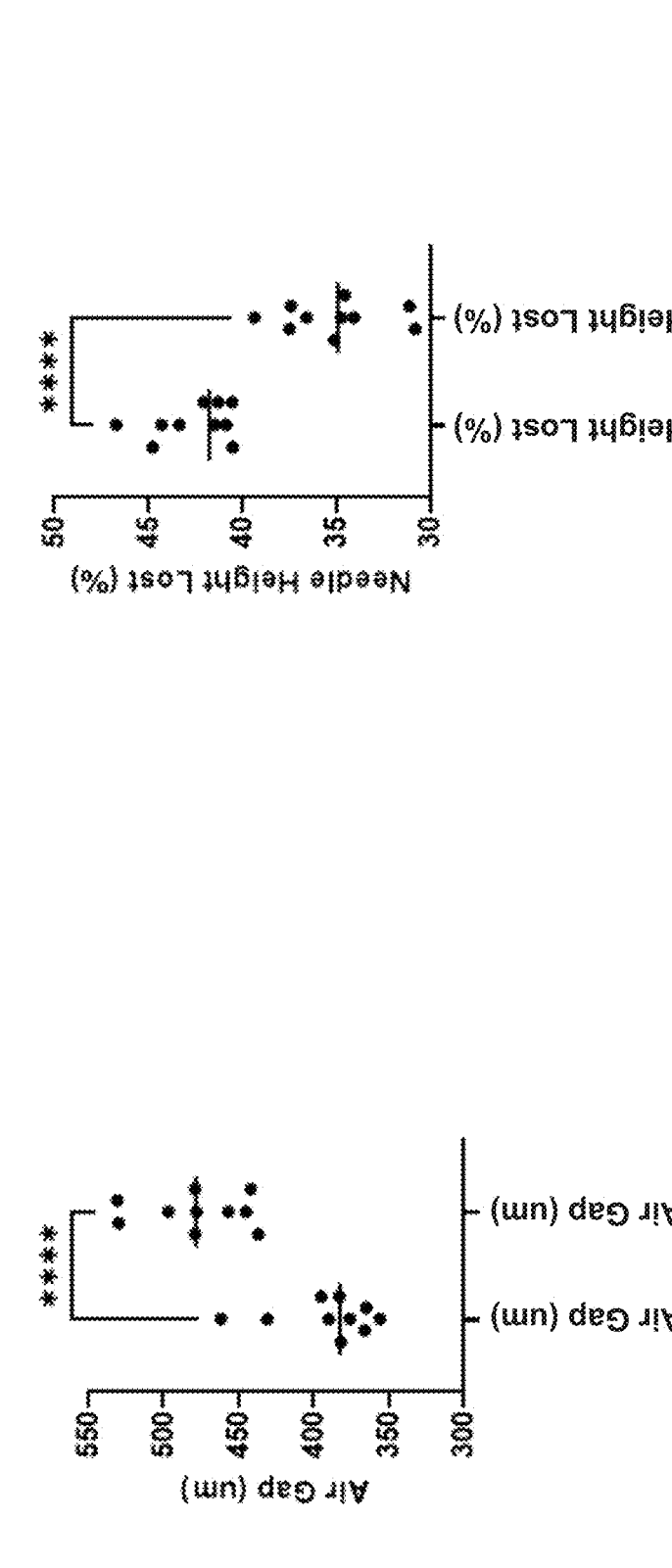

In study GLP-042, evaluations using Optical Coherence Tomography to evaluate the extent of microneedle delivery into pig skin ex vivo, showed that significantly more of the microneedle was delivered for VX-103, a clinical stage influenza vaccine containing MIMIX MAP, than for the GLP-1 containing microneedles; providing evidence for shallow delivery of the GLP-1 Tips that may be related to insufficient Tip strength for Tips formulated with the feasibility formulation (FIG. 13A-13C). FIG. 13A shows the ex vivo deployment results of the 3 separate ex vivo deployment sample sets of GLP-1 277 array MAPs compared to historical measurements of VX103 ex vivo deployments (VX103-245 and VX103-332, "2 drop" respectively). In a separate analysis, GLP-1 tip lengths (GLP-019-042) were compared against historical values for VX103 tip lengths. While the tip lengths are measured in two different ways, FIG. 13B, shows that there is a significant difference between the two groups. FIG. 13C shows a significant difference in Air Gap and Needle Height Lost deployment outcomes for 241-array VX103 and GLP-1 MAPs.

This early testing showed that other than tip length there may be other differences between the VX103 and GLP-1 MAPs that weren't well understood. This led to further investigation into MAP needle strength and stiffness, and delivery energy.

In study GLP-042, all VX103 tip length measurements used TM-402 the "wet tip length" measurement procedure where MAPs were dissolved in PBS and the resulting tips were imaged and measured. All GLP-1 microneedles used RTM-209 for tip length measurements, since GLP-1 tips are soluble in PBS. All ex vivo deployments were performed under RTM-206 (ex vivo deployment via OCT) and RTM-217 (PDIVR).

Crush Testing Comparison of Different MAP Types (MN-936)

Comparisons of deployment outcomes shows that GLP-1 air gaps are significantly larger than VX103, and the % needle height lost is significantly less than VX103. The % Undeployed release is also higher on average for GLP-1, but insufficient data is available to perform a statistical analysis. These results suggest that the GLP-1 MAPs are not deploying as efficiently as the VX103 MAPs. Many factors could contribute to the poor deployment outcomes of GLP-1 relative to VX103. Compression strength and stiffness could be contributing to the lower deployment efficiencies. Specifically, if the GLP-1 base and tips are significantly less stiff, the MAP's may not deploy as efficiently due to energy absorption of the cones, rather than energy transfer through the cones, during deployment. Study MN-936 compared the compression strengths of GLP-1 and VX103 MAPs. The study design is outlined in Table 1.

TABLE 1

| | | | Array and | | Sample | |
| Group | Tip | Base | Mold Size | Adhesive | Size | Dispense |
|---|---|---|---|---|---|---|
| MN-868-Control | 1% Fibroin; 0.5% Tween-20; 6.2 mg/mL 22-23 HA antigen; 3.1 mg/mL non-HA vaccine protein; 0.25X PBS without calcium and magnesium | 53% w/v PVP K17; 0.1% v/v Triton X-100 in water | 121 | 1510 | 4 | Normal |
| MN-929-121 | 53% w/v PVP K17; 0.1% v/v Triton X-100 in water | 53% w/v PVP K17; 0.1% v/v Triton X-100 in water | 277 | 1509 | 4 | Normal |
| GLP-027-PB | GLP-1* 180 mg/mL Inactive Semaglutide; 2.25% PVP K17; 0.607% Arg-HCl; in 90 mM MOPs buffer; 0.1 mg/mL AF-647 added to aid tip visualization | 60% PVP K17; 0.5% PVA 4-88; 1X TE Buffer | 121 | 1510 | 4 | Progressive Base |
| GLP-013- base only | 60% PVP K17; 0.5% PVA 4-88; 1X TE Buffer | 60% PVP K17; 0.5% PVA 4-88; 1X TE Buffer | 121 | 1510 | 4 | Progressive Base |

Figure 13D:
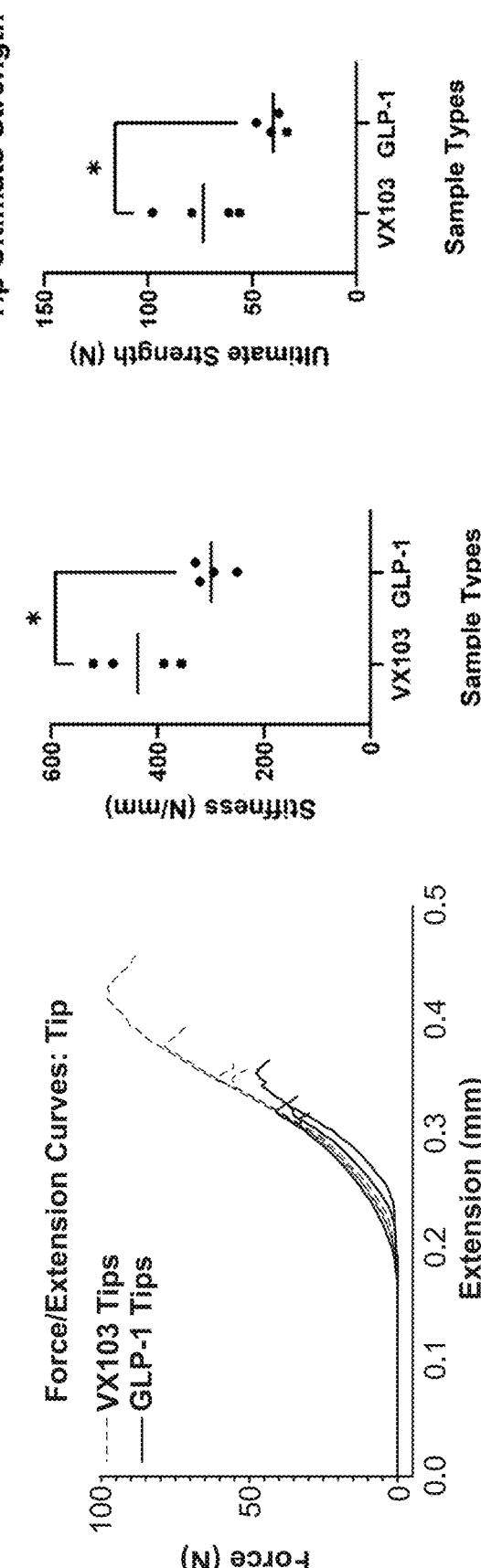
Figure 13E:
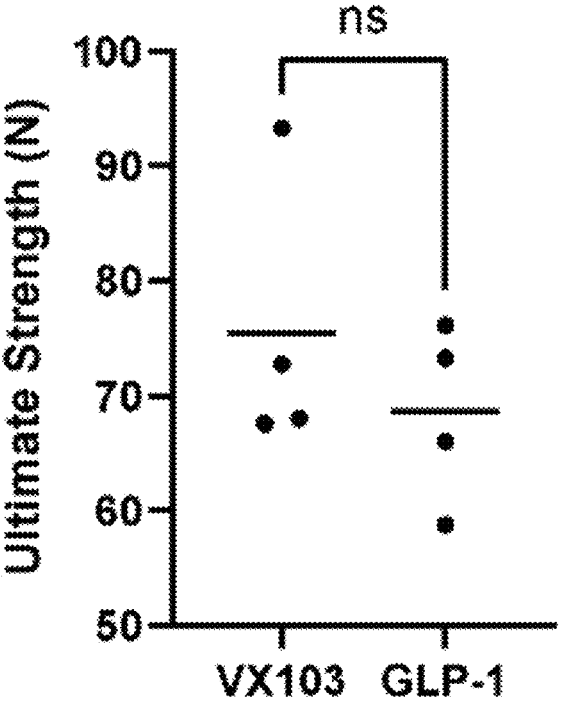

FIG. 13D shows the resultant load displacement curves of VX-103 MAPs compared to GLP-1 MAPs (left panel), and that the stiffness (middle panel) and ultimate strength (right panel) of the VX103 MAPs is higher than the GLP-1 MAPs. FIG. 13E shows the comparison of the compressive strengths of the MAPs constructed of the VX103 and GLP-1 base formulations only.

Since the tip and base formulations are different, a series of MAPs constructed with base material only were also tested in order to determine the contributions of the strengths from the individual components of the cones. A comparison of the compressive strengths of the MAPs constructed of the VX103 and GLP-1 base formulations only (FIG. 13E), recoveries from printed MAPs; have similar deliveries in the ex vivo delivery assay; and have similar Tip mechanical strengths and delivery metrics as measured by OCT assessments during ex vivo deployment.

Thus, AR and inactive material perform equivalently when formulated in the feasibility formulation. Based on the data from this experiment, GLP-1 sourced from Aminos research (AR) was used to develop suitable formulations for MAP delivered GLP-1.

In the formulation development effort, the excipients listed in Table 2 were evaluated for impact on Tip length/morphology and Tip strength.

TABLE 2

Exemplary Water-soluble Excipients Evaluated for Impact on Tip Strength and Consolidation

| Goal | Tip Strength | | Tip Consolidation | | |
|---|---|---|---|---|---|
| Category: | Polymers | Amino Acids | Buffers (at different pH and concentrations) | Surfactants | Salts, saccharides and sugar alcohols |
| Excipients: | PVPs; Cellulose derivatives; Dextran | Proline; Histidine | Tris-HCl; Phosphate; PBS | Tween 20; Kolliphor EL; F127; HS1S; P188 | NaCl; MgCl$_2$; Sucrose; Sorbitol | showed no significant differences, suggesting that the difference in strength between the GLP-1 and VX103 MAPs may stem from the difference in the tip strengths.

Example 3: Evaluation of Water-Soluble Excipients to Improve GLP-1 Tip Consolidation and Strength A formulation development effort was undertaken to improve GLP-1 Tip consolidation and strength and ultimately, the consistency and extent of GLP-1 delivery. The experiments of Example 3 utilized active semaglutide from Aminos Research (AR). Study GLP-060, compared recovery, delivery, Tip lengths and strengths for MAPs fabricated with the AR and inactive semaglutide. The study found that MAPs produced with the AR and inactive material: print similarly with the same print settings; have similar Tip lengths; have similar mechanical strengths; have similar API A modular approach was taken in which, for each category of excipient, different concentrations of that excipient as well as alternatives to that excipient were evaluated. Differing concentrations of PVP K17 and alternative structural polymers were evaluated first.

Step 1: Evaluate Higher Concentrations of PVP and Alternative Structural Polymers and Role in Tip Strength.

In experiment GLP-067, the compatibility of higher concentrations of PVP-K17 and alternative structural polymers with GLP-1 was evaluated using films which serve as tractable models of the MIMIX MAP. To assess compatibility, formulations with alternative polymers were cast on to polydimethylsiloxane (PDMS or silicone—the same material as used for MAP molds) as a thin film and allowed to dry. Films are reconstituted and the amount of GLP-1 quantified using RP-HPLC. Percent recovery is the amount recovered divided by the amount in the print solution used to create the film.

Figure 14:
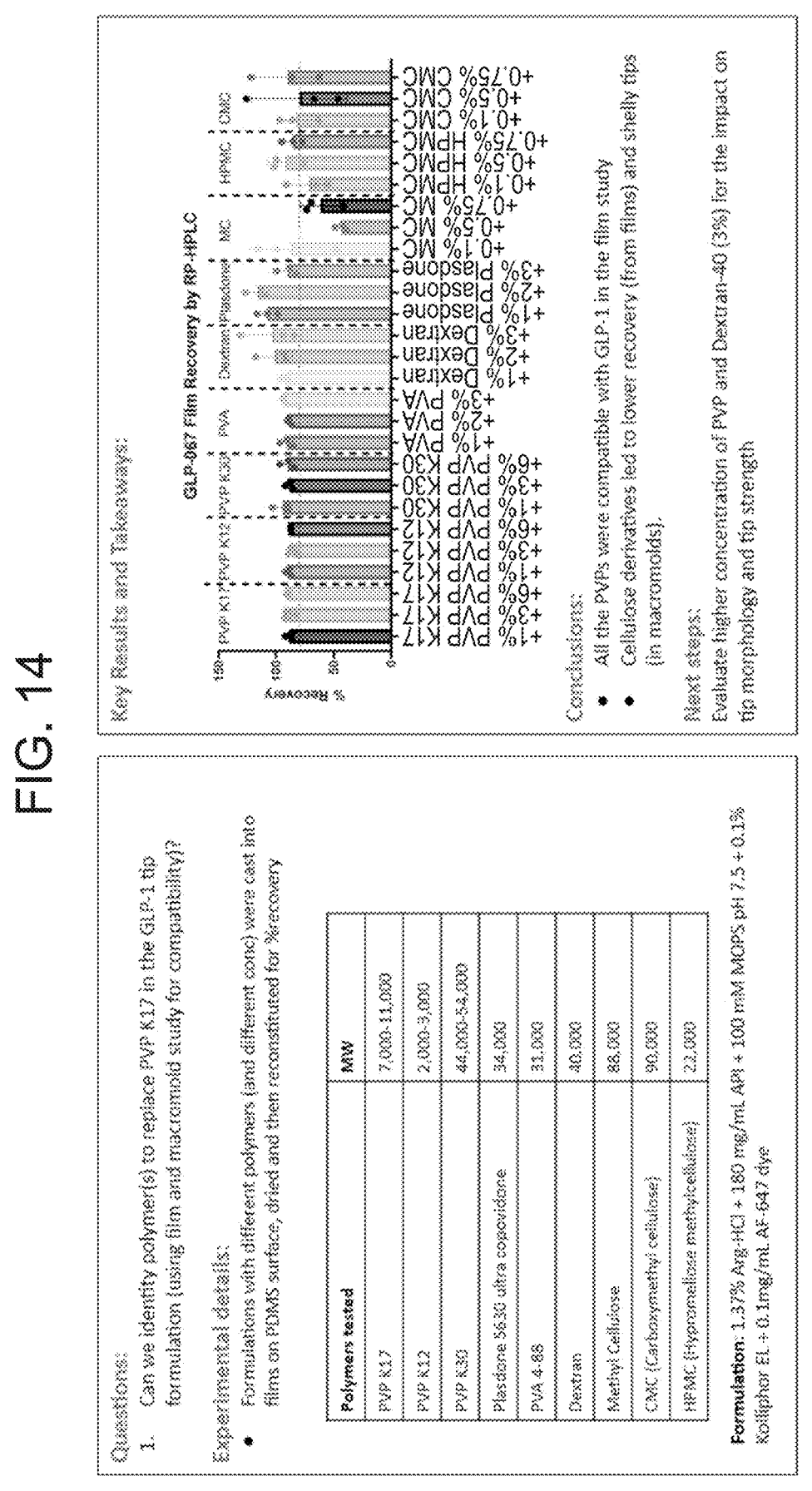

GLP-067 results, summarized in FIG. 14, show that higher concentrations of PVP K17 and 3% Dextran do not negatively impact GLP-1 recovery.

In experiment GLP-073, higher concentrations of PVP-K17 (6%) and 3% Dextran were evaluated for impact on Tip length/morphology and strength. The results shown in FIG. 15, showed that neither higher concentrations of PVP K17 or substitution of Dextran impacted the structural strength of the Tip. Dextran did lead to longer Tips and shells.

Figure 16:
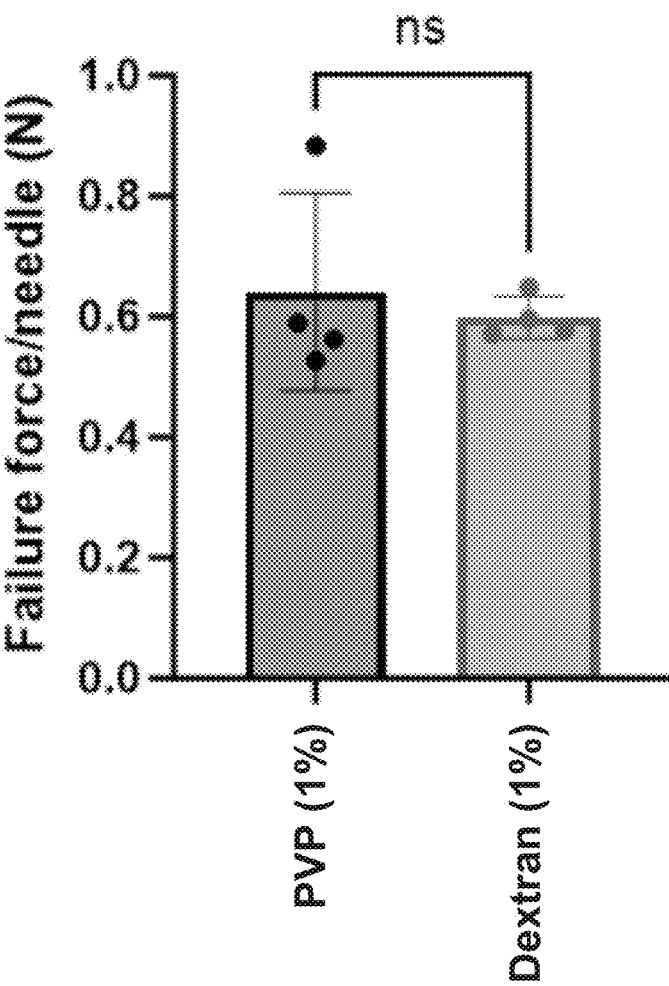
FIG. 16 shows tips formulated with 1% PVP K17 and 1% Dextran have comparable failure forces in the Instron crush test.

In a follow-on experiment, GLP-078, Tips containing 1% Dextran were comparable to Tips containing 1% PVP K17 in strength (FIG. 16). Tip lengths were comparable for both groups. From these studies 1% Dextran was selected as a backup to PVP K17 to mitigate potential risks of cutaneous reactions following repeat dosing of formulations containing PVP K17.

Step 2: Evaluate Tris HCl as a Suitable, More Commonly Used Buffer.

Figure 17:
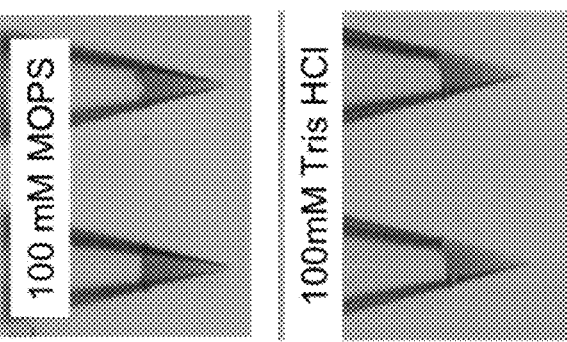
FIG. 17 shows tips formulated with Tris HCl are comparable to Tips formulated with MOPs in Tip lengths, percent consolidation and failure forces in the Instron compression test.

Although MOPS was found to be a suitable buffer in the feasibility studies, it is not a commonly used buffer for parenteral or ID delivery. In GLP-078. Tris-HCl, a more commonly used buffer, was found to be comparable to MOPS in terms of Tip length and strength (FIG. 17). Percent consolidation, which is the fraction of the Tip that is shell was comparable for the two buffer systems. Based on these data Tris-HCl was selected for further evaluation in the Tip formulation.

Step 3: Evaluate Alternative Amino Acids and Role in Bulking.

In studies with other payloads such as ovalbumin, Applicant has observed dislodgement of dried Tips during printing of the base. Addition of Arginine was found to prevent dislodgement of Tips carrying that payload and was included in the GLP-1 feasibility formulation by default. In Step 3 of the formulation optimization effort, alternative amino acids were evaluated for their impact on Tip lengths and strength. In experiment GLP-077, alternative amino acids to arginine were evaluated. The results, summarized in FIG. 18, somewhat surprisingly show that addition of 0.75% Proline significantly improves the mechanical strength of GLP-1 containing needles compared to control group containing Arginine-HCl. Batch yields which are based on the percentage of MAPs with no more than 10% defective needles were also higher for the Proline containing group.

A follow-on experiment (GLP-086) evaluated 0.75% vs 3% proline and demonstrated that increased levels of proline did improve Tip consolidation. The strength per needle was significantly lower for the higher concentration of Proline but still above the 0.6 N/needle typically observed for the feasibility (control) formulation (FIG. 19). Based on these data Proline was selected for further evaluation.

Step 4: Evaluate the Effect of Adding Salts or Divalent Metals.

Figure 20:
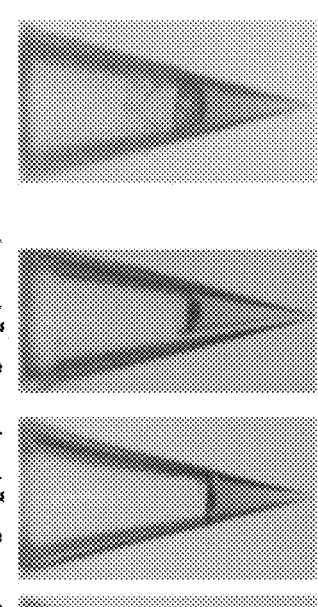
FIG. 20 shows incorporation of 0.9% NaCl improves Tip consolidation.

In GLP-1 070 and GLP-071, the effect of adding 0.9% NaCl, 1% $MgCl_2$ or 0.5% $MgCl_2$ on Tip length was evaluated. The addition of NaCl led to better consolidation of the Tips). Addition of $MgCl_2$ also improved Tip consolidation, however, higher concentrations of $MgCl_2$ led to precipitation and was therefore not pursued further. As shown in FIG. 20, incorporation of 0.9% NaCl improves Tip consolidation.

Figure 21:
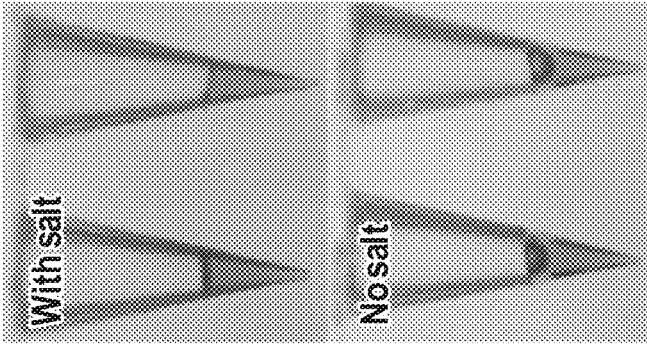
FIG. 21 shows addition of NaCl (0.9%) improves Tip consolidation

In experiment GLP-086, the effect of adding 0.9% NaCl to the updated formulation containing 0.75% proline and 100 mM Tris-HCl was evaluated. The addition of 0.9% NaCl to the Tip formulation significantly reduced the shell length and improved the % consolidation of the Tip (FIG. 21) while the Tip length and Tip strength were comparable.

Step 5: Evaluate the Combination of the Excipients

Figure 23A:
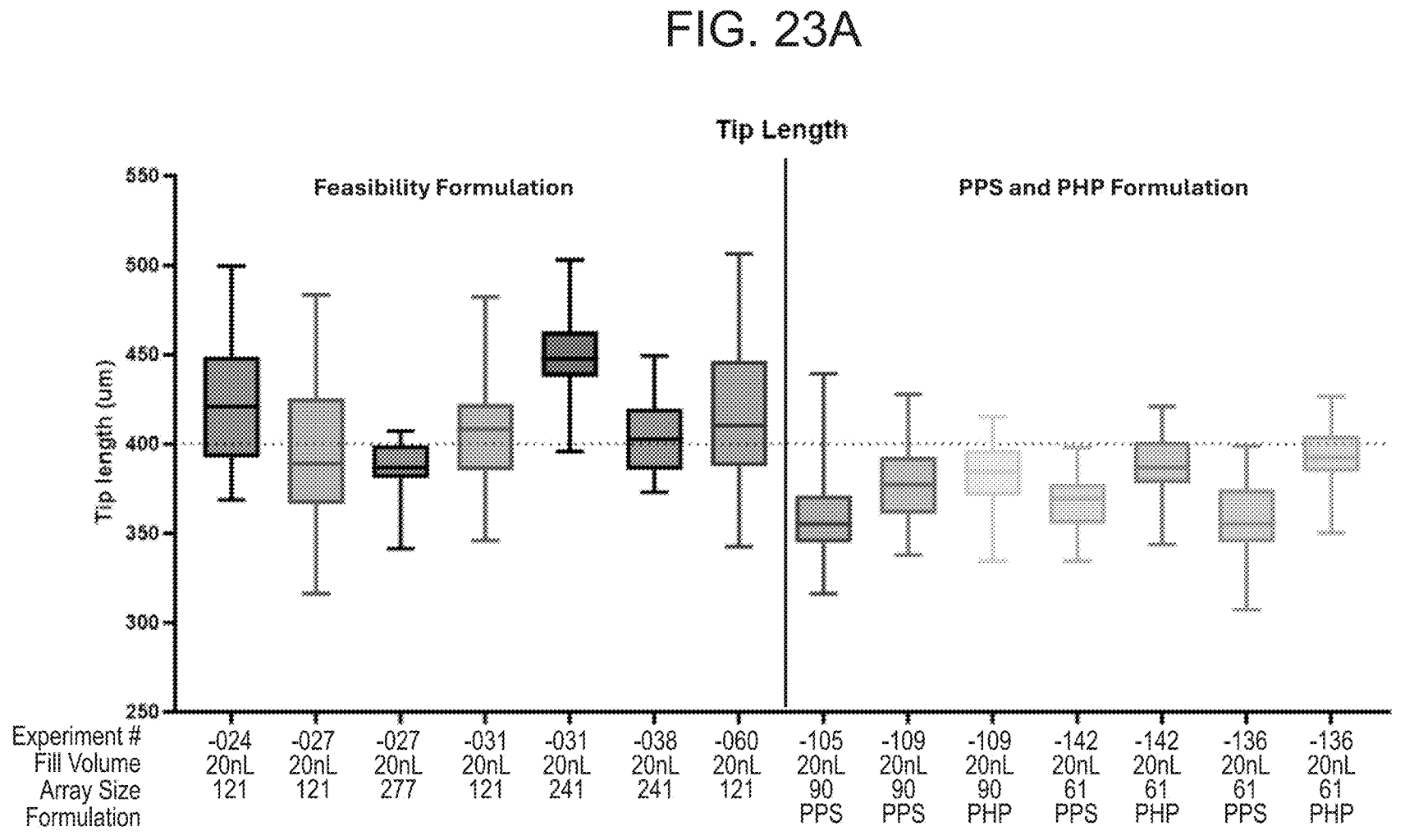
Figure 23B:
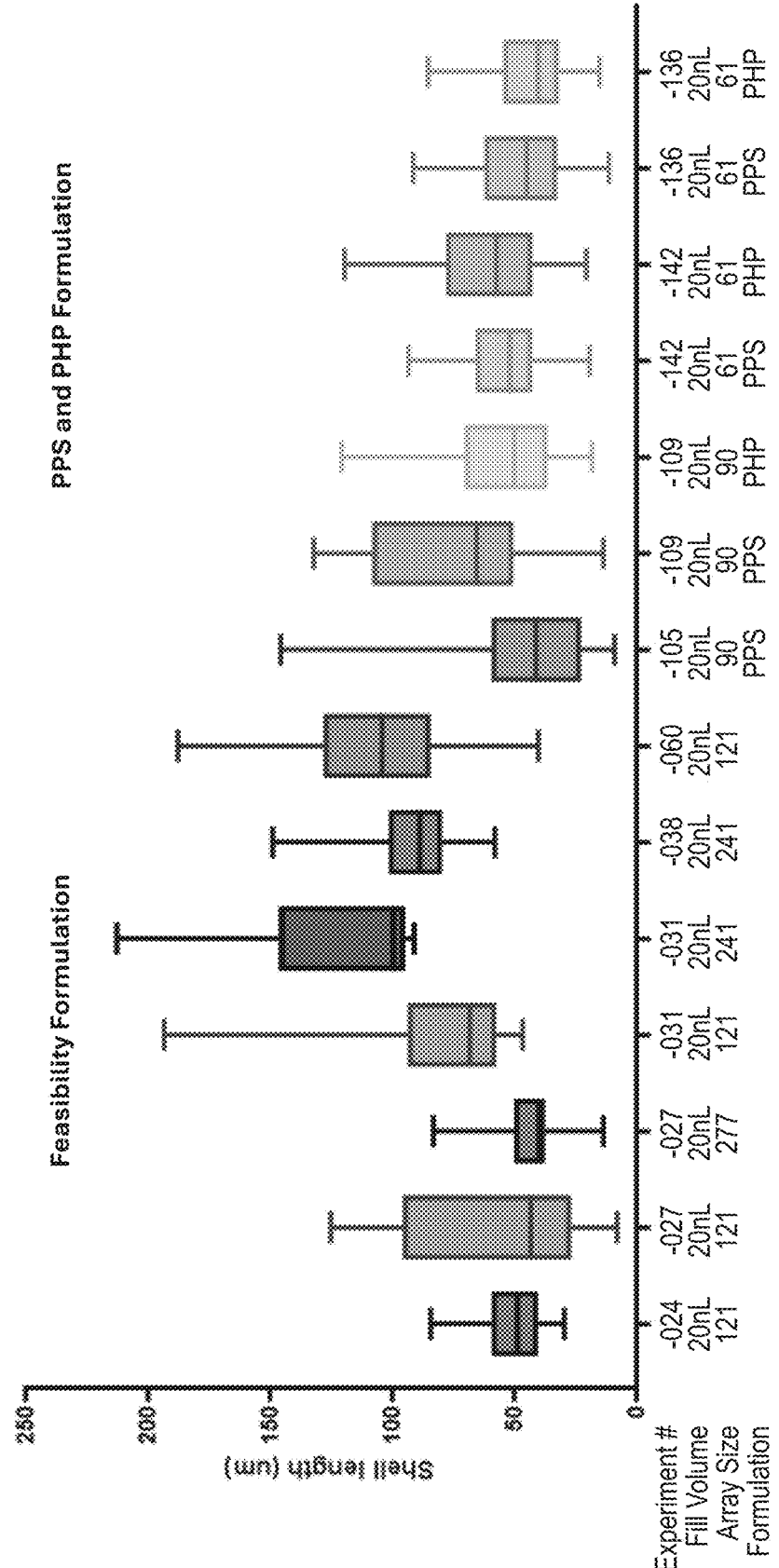

In GLP-136 and GLP-142, two different combinations of proline, and NaCl were evaluated along with Tri-HCl as the buffer (FIG. 22). The PPS formulation contains 180 mg/mL GLP-1, 1% PVP K17, 0.75% Proline, 0.1% Kolliphor EL, 0.9% NaCl, 0.1 mg/mL AF-647, and 100 mM Tris-HCl buffer. PHP formulation contains 180 mg/mL GLP-1, 1% PVP K17, 3% Proline, 0.1% Kolliphor EL, 0.1 mg/mL AF-647, and 100 mM Tris-HCl buffer. Formulation PPS contains 0.9% NaCl and leads to shorter Tips than the PHP formulation that does not contain any NaCl. In both groups the average Tip length was below the target 400 μM. Moreover, the tip strengths are comparable between the two formulation groups and higher than the values observed during the feasibility formulation. A longitudinal summary shows that both the PPS and PHP formulations led to reduced tip and shell lengths relative to the Feasibility Formulation (FIG. 23A-23B).

Figure 24:
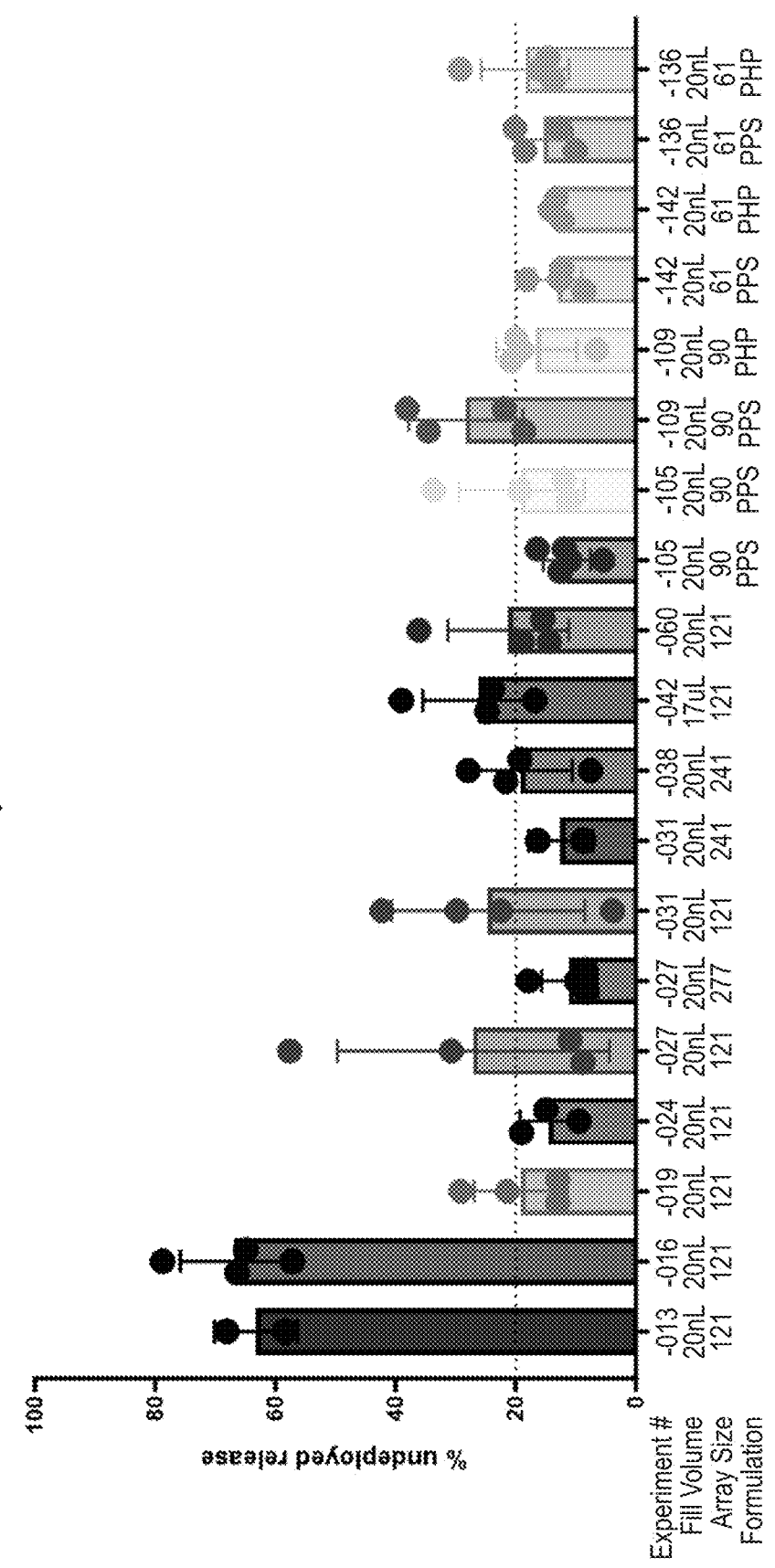
FIG. 24 shows that the PPS and PHP formulations lead to less variable delivery of the payload.

Finally, the intent of developing formulations that improved Tip length and strength was to improve the consistency of GLP-1 delivery into skin. Our goal has been to identify formulations that consistently deliver ≥80% of the payload. FIG. 24 shows the percent of payload remaining on the patch post ex vivo deployment into pig skin for experiments using the feasibility formulation (GLP-013-GLP-060) and PPS and PHS formulations optimized for tip length and strength (GLP-105-GLP-136). Percent undeployed release is calculated as the amount of GLP-1 remaining on the MAP post ex vivo deployment divided by the total amount of GLP-1 loaded onto the MAP and therefore is a measure of delivery. The data show that the PPS and PHP formulations are associated with more consistent delivery that meets the 80% delivery criteria.

Example 4: Evaluation of PPS and PHP Formulations in Pharmacokinetic (PK) Studies The PPS (Form 1) and PHP (Form 2) formulations were evaluated in 3 separate pharmacokinetic (PK) studies in the males Sprague Dawley rat model. The study designs for studies 1 and 2 are shown in Table 3.

TABLE 3

| Study designs for PK studies 1 and 2. | | | | | |
|---|---|---|---|---|---|
| MAP Configuration | Route | Array Configuration | Nominal Target Dose | Nominal Dose Per Needle | Group N |
| Study 1 | | | | | |
| 1 Form 1 60 MN | MAP | 60 Needles | 324 ug | 5.4 ug | 5 |
| 2 Form 1 90 MN | | 90 Needles | 324 ug | 3.6 ug | 5 |

TABLE 3-continued

| | | | | | | |
|---|---|---|---|---|---|---|
| MAP Configuration | Route | Array Configuration | Nominal Target Dose | Nominal Dose Per Needle | Group N | |

Study designs for PK studies 1 and 2.

| MAP Configuration | Route | Array Configuration | Nominal Target Dose | Nominal Dose Per Needle | Group N |
|---|---|---|---|---|---|
| Study 2 | | | | | |
| 1 Form 1 61 MN MAP | | 61 Needles | 324 ug | 5.4 | 5 |
| 2 Form 2 61 MN | | 61 Needles | 324 ug | 5.4 | 5 |
| 3 NA | SQ* | NA | 324 ug | NA | 5 |
| Timepoints: Blood Collection | | | | Pre-dose (Day 0), 3, 24, 72 hr post dose | |

*Purchased from Aminos Research, formulated in buffer and sterile filtered prior to injection.

Figure 25A:
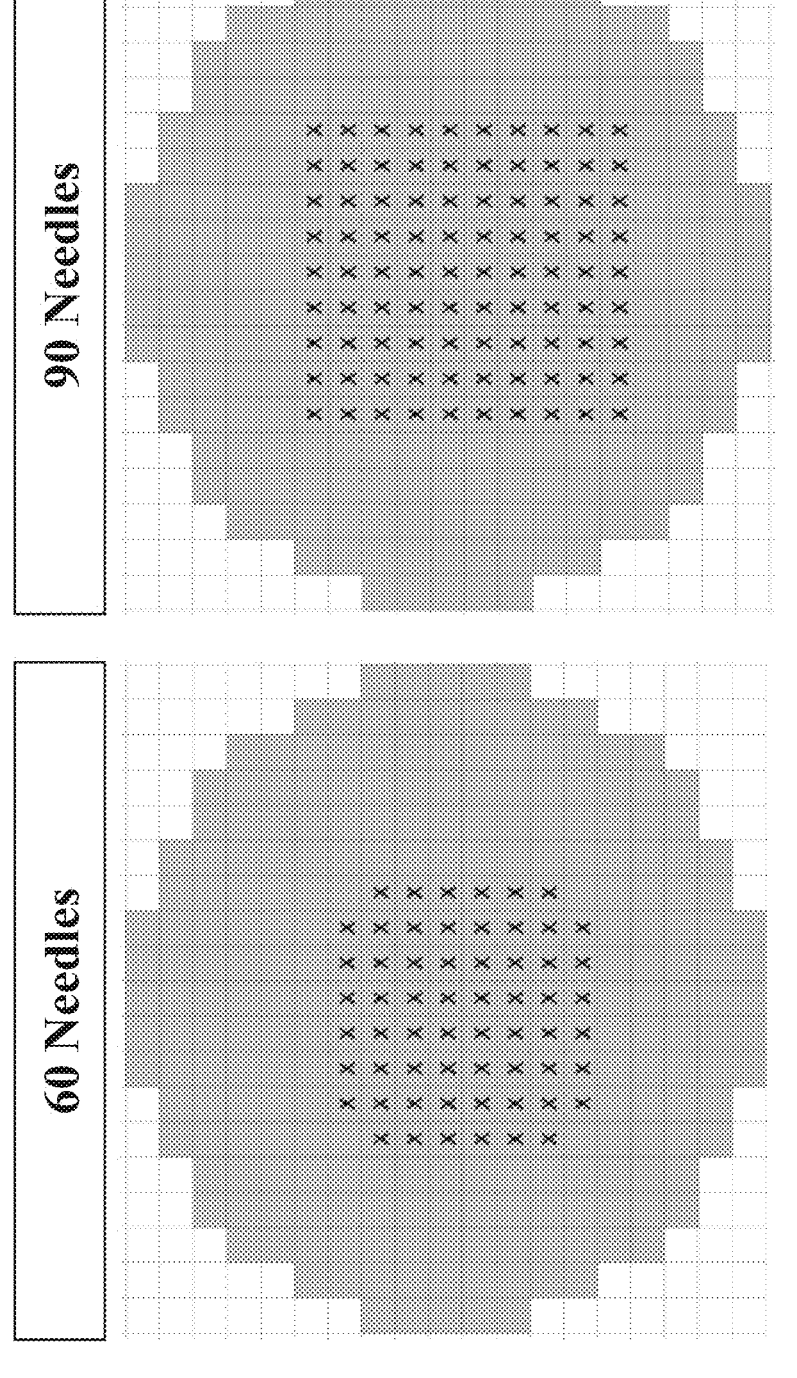
FIG. 25A shows exemplary 60-microneedle and 90-microneedle rectangular sub-arrays formulated with approximately 324 μg of GLP-1 each.
Figure 25B:
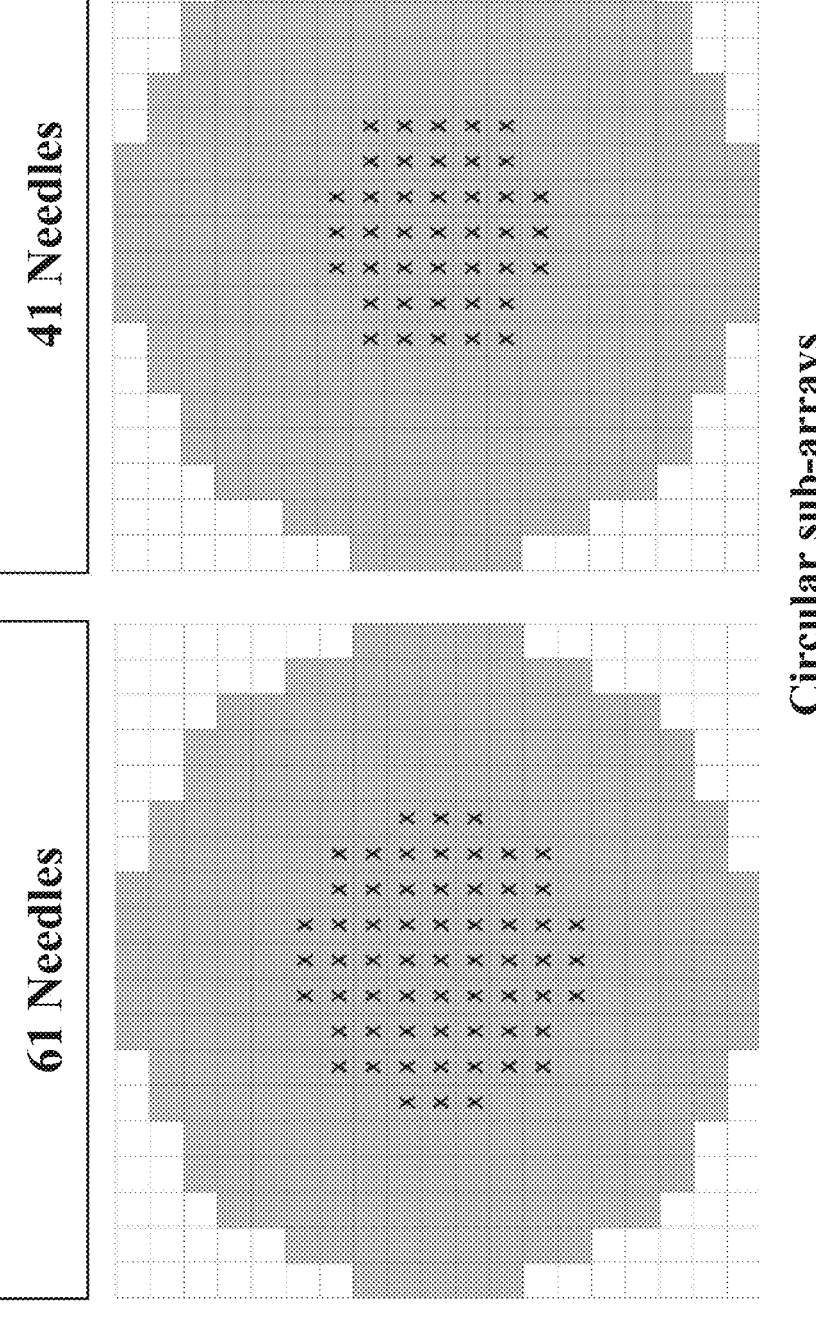
FIG. 25B shows exemplary 61-microneedle and 41-microneedle circular sub-arrays.

The first study was a pilot study evaluating the impact of array size and dose per needle on the PK profile. Approximately 324 μg of GLP-1 was formulated in Form 1 and delivered with a 60 vs a 90-microneedle array (FIG. 25A). The data (FIG. 25B, top panel) shows a comparable PK profile for both array sizes and dose loadings per needle. The second study was a pilot study evaluating ~5 μg per needle formulated in either Form 1 or Form 2 each delivered with a 61-microneedle array. A semaglutide sample formulated in 100 mM Tris pH 7.5, nominally matched for the intended dose, delivered subcutaneously was included as a comparator. The data (FIG. 25B, bottom panel) suggests both MAP delivered formulations performed similarly and may provide a higher relative bioavailability than subcutaneous delivery (FIG. 25B).

Figure 26A:
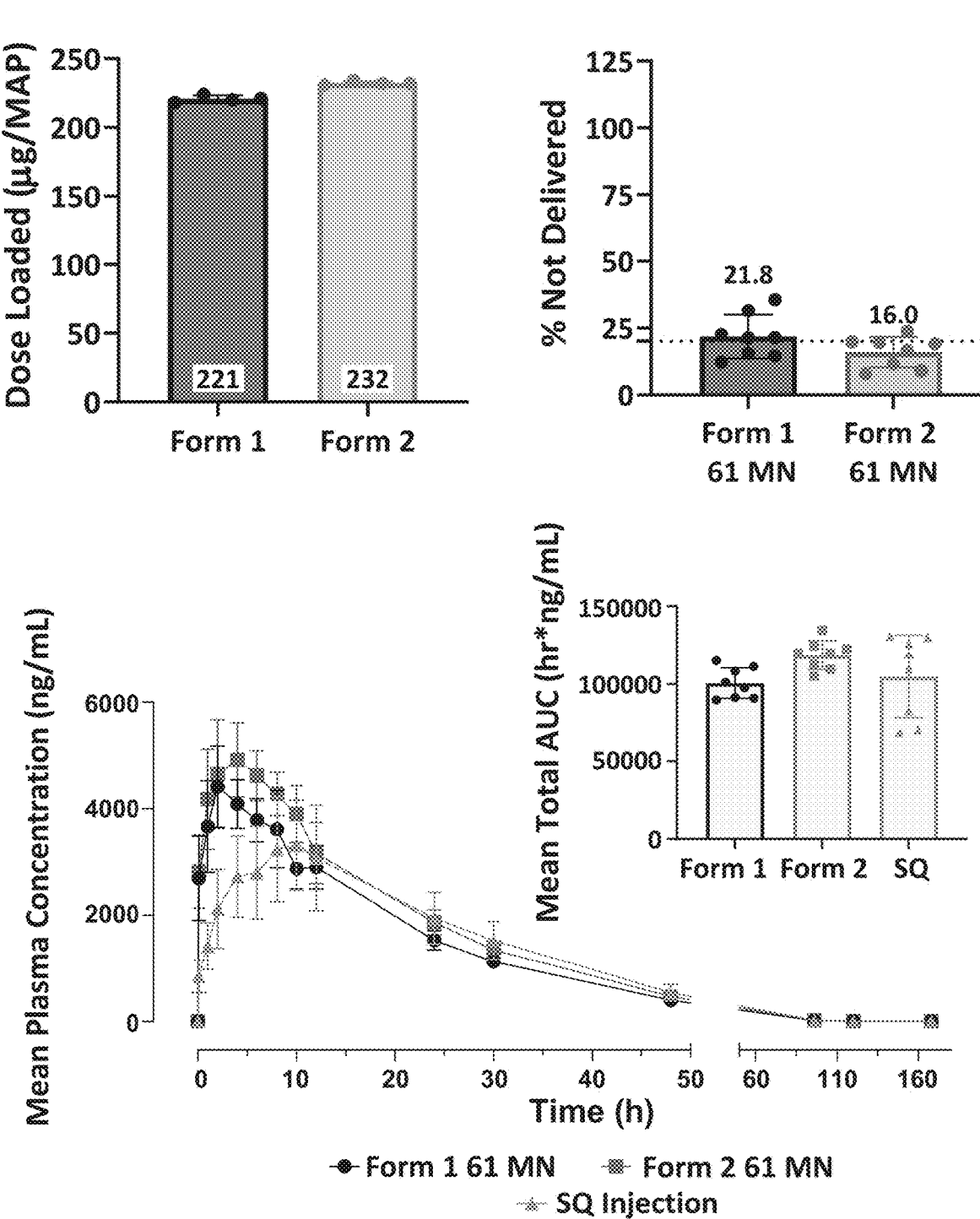
FIG. 26A shows a formal rat PK study evaluating the PPS (Form 1) and PHP (Form 2) formulations shows a faster Tmax and higher Cmax for MAP delivered semaglutide.
Figure 26B:
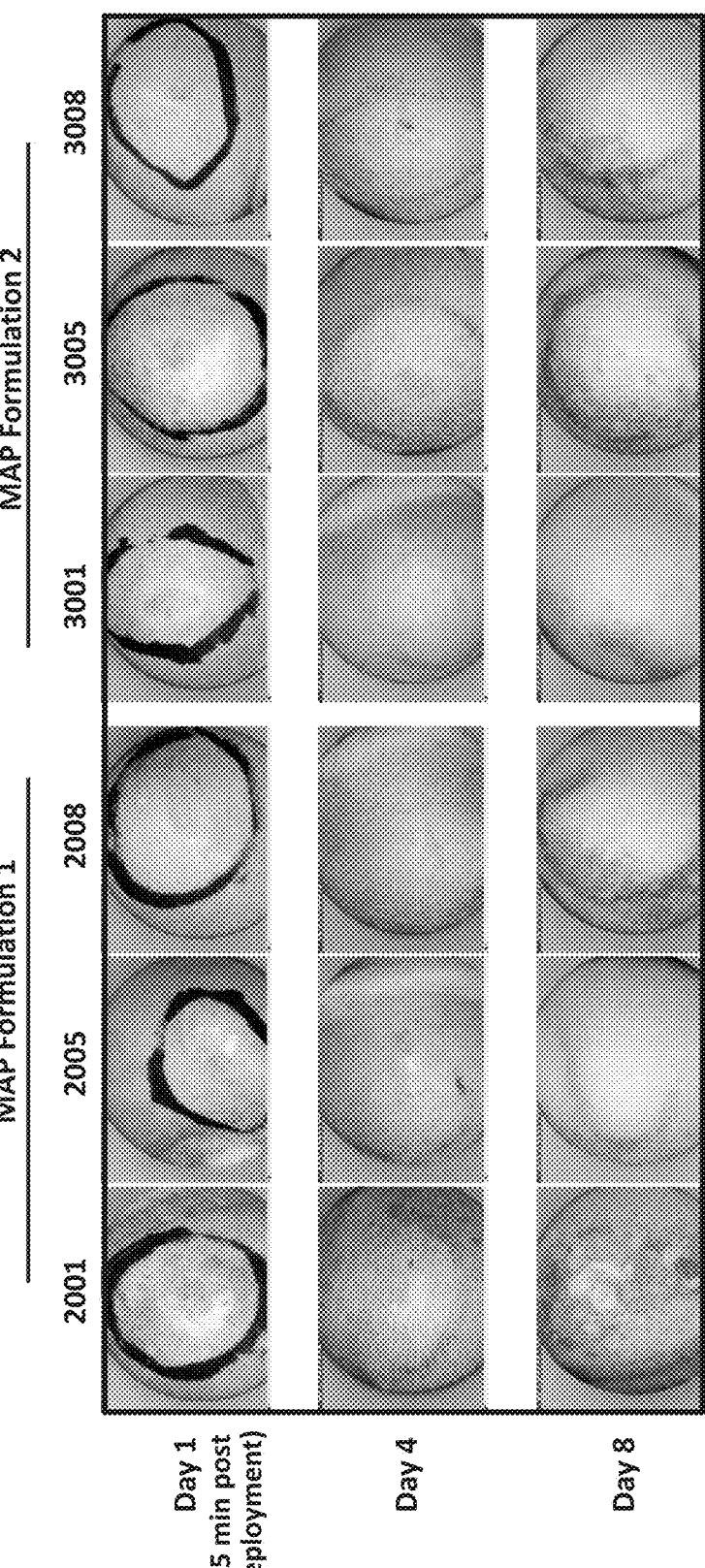
FIG. 26B shows images of MAP application sites showing a self-resolving light discoloration following MAP application.
Figure 26C:
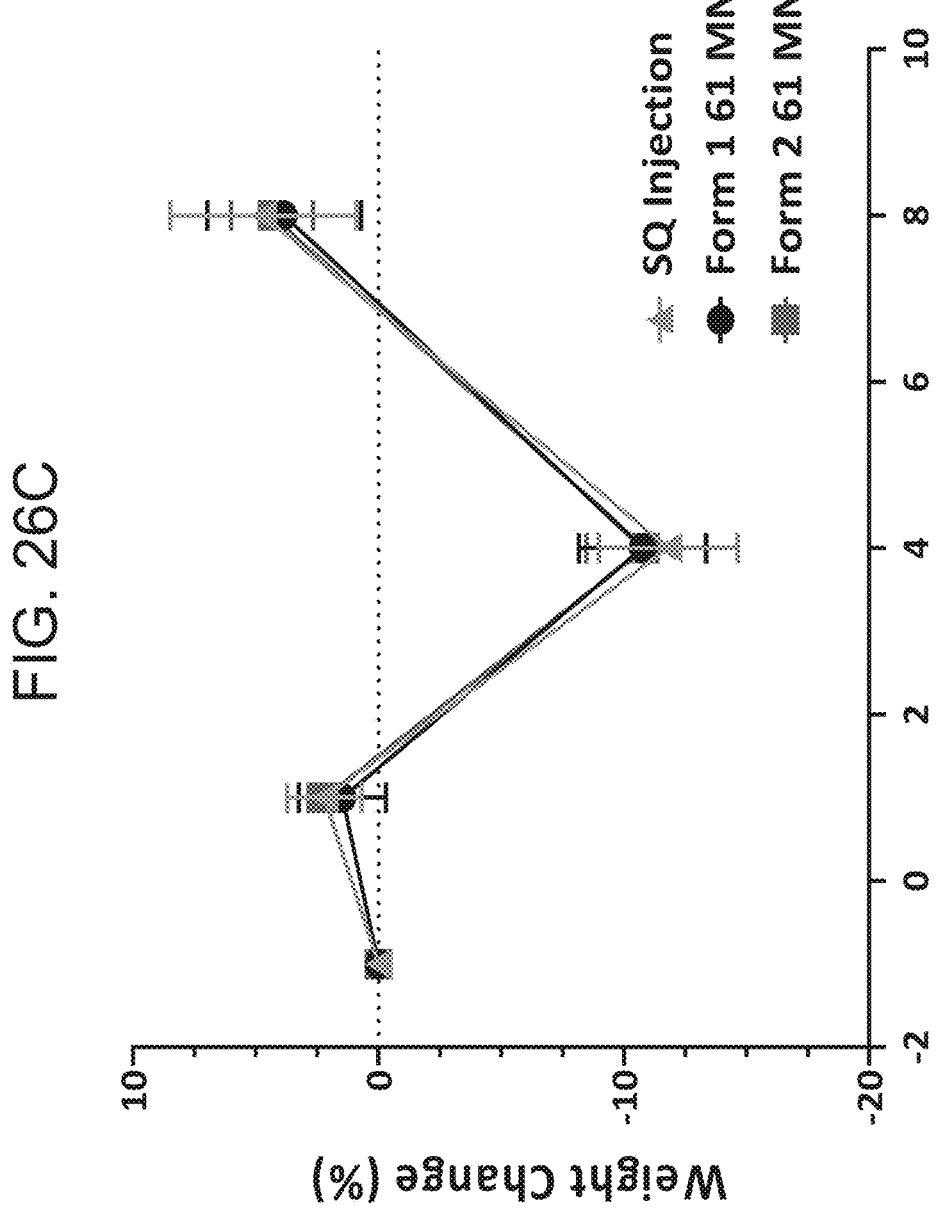
FIG. 26C shows MAP and subcutaneous delivery of GLP-1 led to ten percent weight loss by day 4 post dose.

A follow up PK study, with more extensive sampling, particularly in the first 48 hours, was carried out next. The study design is outlined in Table 4.

with the mechanism of action of GLP-1 (FIG. 26C). Finally, plots of the plasma concentration of semaglutide over time show a faster rise to higher peak concentrations for both MAP formulations relative to SQ delivered GLP-1 (FIG. 26A). The inset in FIG. 26A plots the total area under the curve (AUC) which is a measure of the total exposure to drug product for each animal, for each treatment group and serves as an estimate of bioavailability. While there is some variation in the AUC for SQ delivered GLP-1, perhaps due to variation in the injections, the BA for Form 2 appears modestly higher than SQ injection.

Full comparison of the PK parameters from this study (FIG. 27) further shows a comparable T1/2 (time to elimination), faster Tmax (time to peak concentration), higher Cmax (maximum concentration) and modestly higher AUC (bioavailability) suggesting that MAP delivery of GLP-1 could support either currently licensed dose levels of GLP-1 or MAP specific treatment regimens.

TABLE 4

Study design for PK study 3.

| Group Number | Group N | Test Article | Target Dose (mg/kg) | Route | Interim Blood Collection Time Points (Hours) | Individual Body Weights & Application Site Observations |
|---|---|---|---|---|---|---|
| 1 | 8 | Semaglutide* | 0.73 (220 ug per dose) | SQ | Pre–dose (Day –1), 0.5, 1, 2, 4, | Week –1, Day 1, 4, 8 |
| 2 | 8 | MAP Form 1 | 0.73 (220 ug per dose) | Intradermal Patch | 6, 8, 10, 12, 24, 30, 48, 96, 120 post | |
| 3 | 8 | MAP Form 2 | 0.73 (220 ug per dose) | | dose | |

*Purchased from Aminos Research, formulated in buffer and sterile filtered prior to injection Groups of 8 male Sprague Dawley rats received a 61-microneedle (61 MN) array delivering a target dose of 220 μg of semaglutide formulated in either Form 1 or Form 2. A dose matched sample formulated in Tris buffer delivered by the subcutaneous route was included as a comparator. MAP dose loading and delivery was confirmed by RP-HPLC (FIG. 26A, top panels). Images of the MAP application site taken prior to study start and on Study Days 1, 4 and 8 post application show a mild redness that largely resolves by Day 4 (FIG. 26B). Monitoring of weight shows a 10 percent weight loss by Day 4 in all 3 treatment groups, consistent Based on the formal rat PK study, Form 2 was selected for evaluation in the Gottingen minipig model. This study compared the pharmacokinetics of MAP delivered semaglutide to a SQ injection. A dose of 2 nmol per kg (220 μg total) was evaluated. Two MAP array sizes delivering the same nominal 220 μg dose were evaluated. One was a 61 MN array (loaded with 3.7 μg/needle) the other was a 41 MN array (loaded with 5.4 μg/needle). Tips for both arrays were formulated with Form 2. Ten animals randomized 4:3:3 across 2 cohorts received the 61 MN array, the 41 MN array, or semaglutide delivered by SQ injection as outlined in Table 5.

TABLE 5

| | | | | | |
|---|---|---|---|---|---|
| Minipig PK Study Design | | | | | |
| Group No. | Total Number Males | 04NOV Cohort 1 N | 06NOV Cohort 2 N | Test Article | Total Dose |
| 1 | 4 | 3 | 1 | MAP 61 MN | 220 µg |
| 2 | 3 | 2 | 1 | MAP 41 MN | 220 µg |
| 3 | 3 | 0 | 3 | SQ | 220 µg |

Plasma samples were taken at 0.5, 1, 2, 4, 6, 8, 10, 12, 24, 30, 48, 96, 120 and 168 hours post dosing and the concentration of semaglutide in the plasma quantified by RP-HPLC.

Figure 28A:
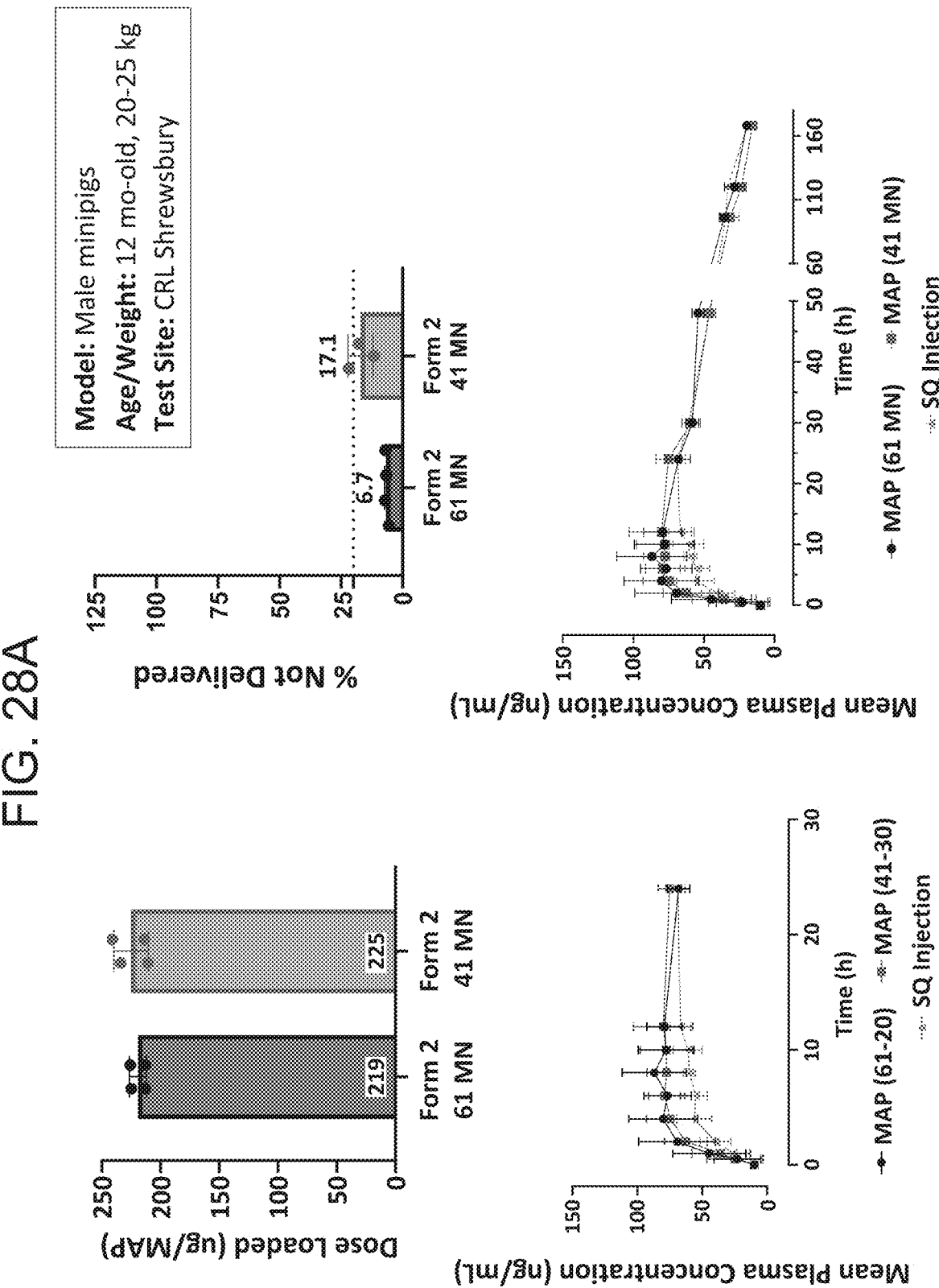
FIG. 28A shows minipig plasma concentration curves show modestly higher $C_{max}$ and comparable $T_{1/2}$ for MAP delivery relative to SQ delivery.

MAP dose loading and delivery was confirmed by RP-HPLC (FIG. 28A, Top panels). Plots of the plasma concentration of semaglutide over time show a modestly faster absorption, with a similar T1/2 and modestly higher Cmax for MAP delivery relative to SQ delivery. The formal PK analyses shown in FIG. 28B, confirm a modestly higher Cmax with a comparable Tmax and T1/2 for MAP versus SQ delivery. These data further demonstrate that MAP delivery of semaglutide could support either currently licensed dose levels or MAP specific treatment regimens.

Example 5: Evaluation of Longitudinal Deployment

A longitudinal analysis of deployment data is a useful tool in determining the effects of various formulations and other parameters on deployment efficiency and deployment depth. Table 6 shows a subset of deployment data where the applicator configuration and tip volumes were held constant across a series of 4 experiments. As is clear in this group of experiments, a direct inverse relationship is seen between penetration depth and % undeployed release (Avg % PD-IVR). Additionally, when comparing different formulations, for example such as in GLP-086, three formulations with different excipients showed similar deployment efficiency and depth, but with very different compression strength, all still above the minimum threshold of 0.4N/needle, however.

Example 6: GLP-1 Materials and Methods

TM—test method
RTM=research test method
MAP Inspection (TM-008): This method is used to visually inspect MAPs to quantify missing or defective Tips. A MAP with less than 10% defective/missing Tips passes inspection. Inspection is performed using a stereo microscope or digital microscope under at least 10× magnification. Exemplary defects are shown in (FIG. 28)

Figure 29B:
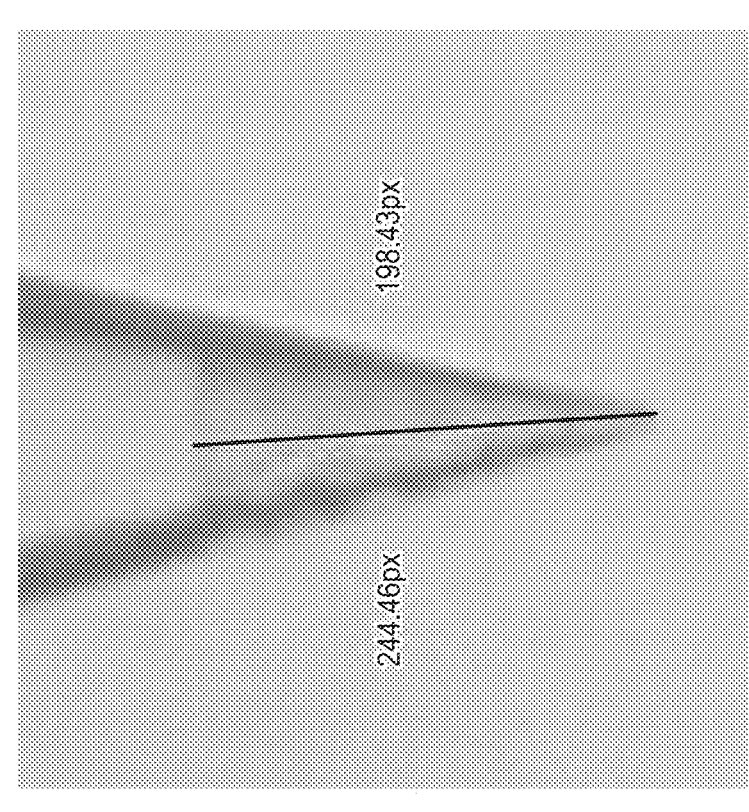
FIGS. 29B-29C shows exemplary tips measured by image processing.
Figure 29C:
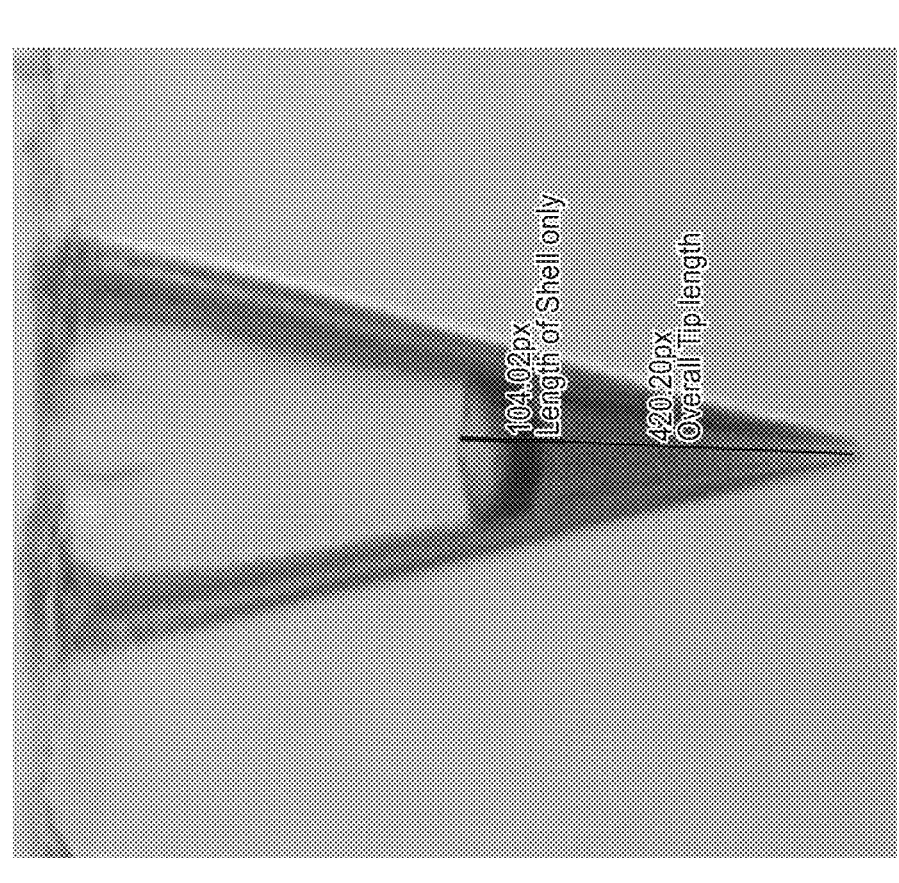

Mold Dissection for Tip Length (RTM-209): The mold dissection method uses magnified images of sectioned molds to obtain measurements and morphology of the dried tips in the molds. After tip printing and drying, a mold is cross-sectioned with a razor blade in between rows of needles. The dried tips are imaged within the needle cavities using a microscope. The tip overall length and shell length are measured by image processing. The image scale is calibrated using a stage micrometer, and lengths in micrometers are calculated from the lengths measured in pixels. Exemplary imaged tip with indicated tip length in pixels is shown in FIG. 29. The shell length as a portion of overall length is an indication of consolidation. Minimal shell length, corresponding to maximum consolidation, is preferred.

A280 for GLP-1 Quantification (TM-220): The spectrophotometric method uses absorbance at 280 nm to quantify GLP-1 in solution (stock and tip print solutions). Ten µL of solution is diluted into a tube containing 690 µL of 100 mM Tris buffer to create an intermediate solution, which is then further diluted to achieve a series of samples diluted by a factor of 300-700 fold (3-5 samples per dilution). One hundred µL of each sample is then loaded into a cuvette and the absorbance measured at 280 nm. GLP-1 concentration is calculated using an extinction coefficient at 280 nm for GLP-1 of 6990 M-1 cm-1 and a path length of 1 cm. The molecular weight of GLP-1, 4113.58 g/mol, is used to convert molarity to mass Reverse-phase HPLC for GLP-1 Content (TM-217): This UV-RP-HPLC method employs a C8 column (Symmetry C8 Sentry Guard Cartridge, 100 Å, 5 µm, 3.9 mm×20 mm, P/N WAT054250, Waters™) to quantify GLP-1 in solution using a gradient mobile phase of water and acetonitrile, each containing 0.1% trifluoroacetic acid (TFA). Samples, prepared at approximately 0.6667 mg/mL, are run for 5 minutes at a 2.0 mL/min flow rate with detection at 280 nm. The

TABLE 6

| Test Number | Applicator Configuration | Energy/ Needle [mJ] | Piston Velocity [m/s] | Tip Fill Volume [nL] | Pre-deployment needle height [um] | Air Gap [um] | Penetration Depth (Primary-Air Gap) [um] | Avg % PD-IVR By RP-HPLC |
|---|---|---|---|---|---|---|---|---|
| GLP-190 | ISA-019: (22)_0_S-1287_3gAl | 2.1 | 12.5 | 30 | 903 | 192 | 711 | 7.40% |
| GLP-NN-004-1 | ISA-019: (22)_0_S-1287_3gAl | 2.1 | 12.5 | 30 | 927 | 260 | 667 | 8.55% |
| GLP-NN-004-1 | ISA-019: (22)_0_S-1287_3gAl | 2.1 | 12.5 | 30 | 903 | 321 | 582 | 12.04% |
| GLP-NN-004-1 | ISA-019: (22)_0_S-1287_3gAl | 2.1 | 12.5 | 30 | 939 | 365 | 574 | 24.52% |
| GLP-NN-004-1 | ISA-019: (22)_0_S-1287_3gAl | 2.1 | 12.5 | 30 | 923 | 365 | 558 | 20.19% |

US 12,636,250 B2

135 column temperature is maintained at 35° C. with a 10 μL injection volume. The gradient begins at 30% mobile phase B for 0.08 minutes, ramps to 80% B by 2.50 minutes, holds at 80% B until 3.50 minutes, then returns to 30% B by 3.60 minutes, remaining at 30% B until the 5-minute mark. This assay is used to quantify the percentage release of GLP-1 from films and MAP samples or more specifically percent recovery.

Size Exclusion HPLC for GLP-1 Aggregation (TM-222): This size exclusion chromatography (SEC) method quantifies high molecular weight species of GLP-1 in solution using a Waters XBridge Protein BEH SEC column (125 Å, 2.5 μm, 7.8×300 mm, P/N 186006519). The mobile phase consists of 10% acetonitrile and 90% 100 mM sodium phosphate with 100 mM NaCl (pH 7.0), at a flow rate of 0.5 mL/min. Detection is carried out at 280 nm, with the column temperature maintained at 35° C.

Ex Vivo Deployment (TM-206): To test the functionality of MAPs for penetration of skin, dissolution, and delivery of dose, ex vivo porcine skin is used as a model substrate. The skin is harvested, excess fat and subcutaneous tissue is removed to produce a consistent thickness, hair is shaved, and the skin is frozen for storage. At the time of use, skin is thawed and equilibrated to room temperature. MAPs are applied to the skin using a spring-loaded applicator and left on the skin for 5 minutes. Various parameters including the initial and final height of needles before and after application and the depth of tip implantation into the skin are measured by Optical Coherence Tomography and used to determine the penetration depth. The residual GLP-1 remaining on the post deployed MAP is quantified using In Vitro Release (RTM-462) and Reverse-phase HPLC for GLP-1 Content (TM-217).

Exemplary measurements are summarized below.

Pre-Deployment Needle Height: The full height of undeployed needles.

Air Gap: The space between the bottom of the adhesive of the MAP backing and the skin surface, measured while the MAP is deployed.

Post-deployment Needle Height: The height of needles after the MAP has been removed from tissue following deployment.

Deployed Tip Depth: The length between the skin surface and the apex of a deployed tip in the skin, measured post-deployment after the MAP is removed.

Height Delivered: The difference between the pre-deployment needle height and post-deployment needle height measurements, representing the length of the needle that has been deployed and left behind.

In Vitro Release (RTM-462): To quantify GLP-1 loaded on a MAP and to assess purity and stability, MAPs are eluted in release media (distilled water, or DIW) and the eluate is assayed using HPLC methods. For elution, excess backing is removed and the microarray is submerged in 1 mL (for arrays of up to 121 microneedles (MN)) or 2 mL (for arrays >121 MN) of DIW in a tube and incubated at 25 C for 10 minutes (+/−5 minutes). Following incubation, tubes are centrifuged to pellet solids and 900 μl of supernatant is withdrawn. Eluted GLP-1 quantified by an HPLC method (TM-217).

Post Deployment In Vitro Release (RTM-462): GLP-1 remaining on the MAP following either ex vivo or in vivo deployment is quantified using the in vitro release assay. Following deployment MAPs are packaged and transferred for testing in the In Vitro Release assay with the following modifications. The excess backing is removed and trimmed patch is submerged in 0.5 mL or 1.0 mL of DIW for arrays up to 121 MN or >121 MN respectively. Following incubation at 25 C for 10 minutes (+/−5 minutes), 400 μl of supernatant is withdrawn for quantification by HPLC (TM-217).

Microneedle Mechanical Strength (TM-404): A compression assay is used to quantify the mechanical strength of sample MAPs. Using an Instron 5942 Single Column Test frame with a 500N load cell, the entire MAP is compressed between flat steel platens at a rate of 1 mm/min until failure is reached. The two readouts from this assay are failure force, defined as the peak maximum force that is followed by a >5% drop, and Young's modulus, determined from the slope of the load-displacement curve between 1N and failure force.

Rat and Minipig PK Studies. Male Sprague-Dawley rats (n≥5) of approximately 350-450 g and male Göttingen mini-pigs of 25-30 kg (n≥3) are used in pharmacokinetic studies. On study day 0, rats will receive a single dose of ~200-300 μg (or 150-225 nmol/kg) of GLP-1 delivered by the different MIMIX MAP formulations or by subcutaneous injection (s.c.) as a comparator. Minipigs will receive a single dose of 2 nmol/kg, or ~200-240 μg. For rats the MAP application and the s.c. injection is to the flank, for minipigs the s.c. injections and MAP applications will be given on the lower thorax. Blood samples will be collected into ice cooled EDTA tubes via the jugular vein or by venous catheter at 12 timepoints over 72 hours. Plasma will be processed at 4° C. and frozen. Semaglutide will be measured in plasma by ELISA or LC/MS. Individual animal plasma concentration-time values will be used to calculate plasma concentration-time data for each delivery route and analyzed by noncompartmental pharmacokinetics using standard PK software.

Example 7: MAP Study Using HA Encoding mRNA Encapsulated in LNPs

Microneedle Array Patches (MAPs) containing mRNA-LNPs encoding an H1 hemagglutinin (HA) antigen elicited more antigen-specific total binding and functional antibody titers compared to soluble injection of matched doses in the intradermal (ID) and intramuscular (IM) compartments. MAPs formed from print solutions containing 1% VA64 polymer (MAP Group 1) outperformed alternative formulations composed of 1% VA64/4% Arginine HCl (MAP Group 2) or 1% PVA 4-88/5% PVP K17/0.25% silk fibroin (MAP Group 3); however, Group 3 also elicited total anti-HA antibody titers comparable to soluble ID and IM injections. The rank order of MAP performance in vivo in rats reflected the rank order of in vitro QC testing, with Group 1 showing on average 79% encapsulation efficiency of the recovered LNP payload across both MAP lots used in the study. All MAPs in the study delivered the majority of the 1 μg loaded payload, with Form 1 showing on average 77.5% payload delivery between the prime and boost administrations.

Test Article Details:
Vaccine: In-house LNP encapsulating mRNA encoding HA antigen (10 mg scale)
Payload: Influenza HA (H1N1) (Strain: Guangdong-Maonan/SWL 1536/19)
Animals: Male, Sprague-Dawley rats (Charles River; 280-300g, 7-9 weeks old)

TABLE 7

| | mRNA-LNP Formulation | | | | | | |
|---|---|---|---|---|---|---|---|
| | Lipid mol % | | | Ionizable | Total Lipid/mRNA | | |
| Ionizable CKK-E12 | Cholesterol | DOPE | C14PEG2K | lipid/mRNA (w/w) | N/P Ratio | mass ratio % w/w | Final Buffer |
| 35 | 46.5 | 16 | 2.5 | 20 | 13 | 41 | 10% sucrose in 25 mM Tris HCl, pH 7.5 |

TABLE 8

| mRNA-LNP QC, Lot LNP-019 | |
|---|---|
| Concentration | 2.46 mg/ml |
| % Encapsulation Efficiency | 98.1% |
| Diameter (nm) | 84.2 nm |
| PDI | 0.167 |

TABLE 9

| Animal Study Assignments | | | | | | |
|---|---|---|---|---|---|---|
| | Prime | | Boost | | Dose | Rats/ |
| Group | Route | Formulation | Route | Formulation | (ug) | Group |
| | | | Injections | | | |
| 1 | IM | N/A | IM | N/A | 0.1 | 8/Group |
| 2 | | | | | 1 | 7/Group |
| 3 | ID | | ID | | 0.1 | 8/Group |
| 4 | | | | | 1 | 7/Group |
| | | | MAPs | | | |
| 5 | MAP | MAP Form 1 | MAP | MAP Form 1 | 1 | 10/Group |
| 6 | | MAP Form 2 | | MAP Form 2 | | 10/Group |
| 7 | | MAP Form 3 | | MAP Form 3 | | 10/Group |
| | | | | | Total | 60 |

TABLE 10

| MAP Groups for mRNA-LNP-026 MAP Lot | | | | | |
|---|---|---|---|---|---|
| Formulations (Printed in this order) | Tip Formulation | Tip Drying Conditions | Base | Base Drying Conditions | Rationale |
| 1 | 1% VA64 10% Sucrose 1X TE Buffer | 85% 30 min 60% 30 minutes at RT to 4C with desiccant overnight | 0.5% PVA, 60% PVP K17, 1X TE | 85% 5 min 60% 60 minutes at RT to 4C with desiccant 24 hrs | No fibroin tip formulation, highest in vitro and in vivo expression in films for certain mRNA-LNP lots |
| 2 | 1% VA64 4% Arginine HCl 10% Sucrose 1X TE Buffer | | | | No fibroin tip formulation, highest in vitro expression in films in certain mRNA-LNP lot, arginine can potentially prevent tip dislodging |
| 3 | 1% PVA 4-88 5% PVP K17 | | | | Fibroin tip formulation, second highest in vivo expression in films |

TABLE 10-continued

| MAP Groups for mRNA-LNP-026 MAP Lot | | | | | |
|---|---|---|---|---|---|
| Formulations (Printed in this order) | Tip Formulation | Tip Drying Conditions | Base | Base Drying Conditions | Rationale |
| | 0.25% Fibroin (B.R. lot) 10% Sucrose 1X TE Buffer | | | | with certain mRNA-LNP lot |

TABLE 11

| LNP-026 MAP Formulation Components | | | |
|---|---|---|---|
| Excipient | Vendor | Product # | Lot # |
| Kollidon VA64 | BASF | 50347977 | 03011336W0 |
| Kollidon PVP K17 | BASF | USP-EP-JP-BASF | 31784536W0 |
| PVA 4-88 | Sigma Aldrich | 1.41350.1000 | K53097650 128 |
| Arginine HCl | Sigma Aldrich | A6969 | SLCM9108 |
| Fibroin | Vaxess | N/A | B.R. |
| Sucrose | Sigma Aldrich | 84097 | BCCH2853 |
| TE Buffer | Thermo Fisher | T11493 | 2533879 |
| Tris HCl Buffer | Thermo Fisher | J62848.AK | W06J517 |
| EDTA | Invitrogen | 15575-038 | 2085657 |

Description of In-Life Procedures

Rats were immunized according to Table 9. Briefly, fresh aliquots of LNP-mRNA were thawed (−80C storage) and diluted with 1x Phosphate Buffered Saline prior to injection. All animals were anesthetized using 2-3% isoflurane to a stable plane prior to vaccine administrations. Sites of ID injection (rear flank, 1 inch off the spine) were shaved using an Oster 40 razor; sites of IM administration (right hind limb, quadricep) were swabbed with ethanol prior to injection. Sites of MAP administration were clipped and remaining hair removed with Nair, resulting in bare skin. MAPs were applied to rat using a mechanical applicator device and left on the skin for 5 minutes before removal.

Post-Administration Test Article Testing

MAPs deployed to rats were evaluated for the quality of deployments. Deployed MAPs were imaged using a microscope, and the number of intact needles on the MAP were counted. The number of intact needles on the array post-deployment was compared to the number of starting needles on the array to determine delivery efficiency (% Deployed Tips). Payload delivery was confirmed using the post-deploy in vitro release assay, whereby undeployed control MAPs and deployed MAPs were submerged in 1000 ul 1% Triton X-100 in 1X TE buffer release media and placed on a 25C shaker for 1 day. The release media was sampled and run on the Ribogreen assay to measure mRNA concentration. The concentration of mRNA recovered from deployed MAPs was normalized to the average mRNA concentration recovered from undeployed control MAPs and expressed as % undeployed release.

Figure 30:
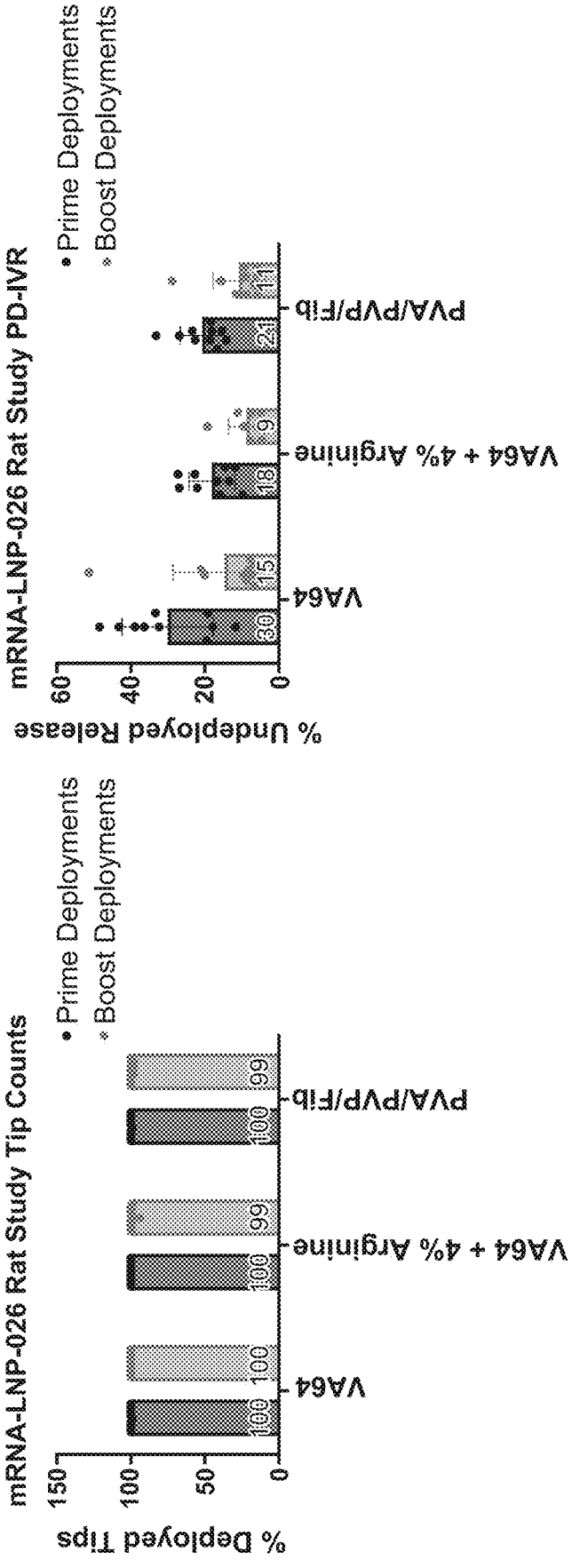
FIG. 30 shows LNP-026 MAP Deployments. The number of in-tact tips visible on the MAP after deployments was compared to the starting number of tips on the array as a measure of deployment (left). The concentration of mRNA recovered from deployed MAPs was normalized to the average mRNA concentration recovered from undeployed control MAPs and expressed as '% undeployed release' (right).

FIG. 30 shows LNP-026 MAP Deployments. The number of in-tact tips visible on the MAP after deployments was compared to the starting number of tips on the array as a measure of deployment (left). The concentration of mRNA recovered from deployed MAPs was normalized to the average mRNA concentration recovered from undeployed control MAPs and expressed as '% undeployed release' (right).

Animal Study Serological Assay Methods

Rat Anti-HA IgG ELISA. Concentration of anti-HA IgG in rat serum was determined using recombinant influenza hemagglutinin protein strain matched to the mRNA payload (Sino Biological, Cat: 40717-V08H) in a standard direct ELISA workflow. Briefly, 96-well maxisorp plates were coated with 1 μg/mL of the recombinant HA protein in a standard bicarbonate buffer and incubated overnight at 4C. This plate was washed three times with excess DPBS+ 0.05% Tween20 and then blocked with a 2% BSA solution in DPBS. Then, samples were diluted in DPBS containing 2% BSA and incubated for 2 hours in the blocked and washed maxisorp plate. The plates were washed using DPBS+0.05% Tween20 before probing with an anti-Rat HRP conjugate secondary antibody (Sigma, Cat: SAB3700541). After additional washes, the colorimetric substrate TMB (Sigma, Cat: T0440) was used to quantify the amount of retained HRP and the reaction was quenched with 2.0N sulfuric acid. The resulting stable yellow colorimetric substrate was quantified via absorbance at 450 nm using a 570 nm background subtraction read. A pool of rat sera containing high-titer anti-HA IgG antibodies was run in parallel and used as a reference standard after fitting to a 4-parameter logistic regression. Test samples were interpolated against the reference standard and given a titer value in AU/mL, which is roughly equivalent to its endpoint titer in the same assay.

Rat Hemagglutination Inhibition (HAI) Assay. The concentration of influenza-neutralizing antibodies in Rat sera was determined using a standard HAI assay adapted to rat sera. Briefly, Turkey red blood cells are washed and diluted in DPBS to a concentration of $2.5 \times 10^7$ cells/mL. In parallel, nonspecific inhibitors in the test sera was removed by a 20 min incubation with 10% kaolin (Fisher Scientific, Cat: K2-500). This inactivated sera is then pre-adsorbed with the diluted RBCs. The sera/RBC mixture is then mixed with influenza reference antigen (NIBSC) titrated to 8 hemagglutinin units (HAU) and the mixtures are allowed to incubate at room temperature for 45 minutes. Titer is determined by the highest reciprocal dilution of sera that is capable of preventing the characteristic lattice agglutination formation in the well (and thus driving formation of a much more consolidated RBC pellet).

Figure 31A:
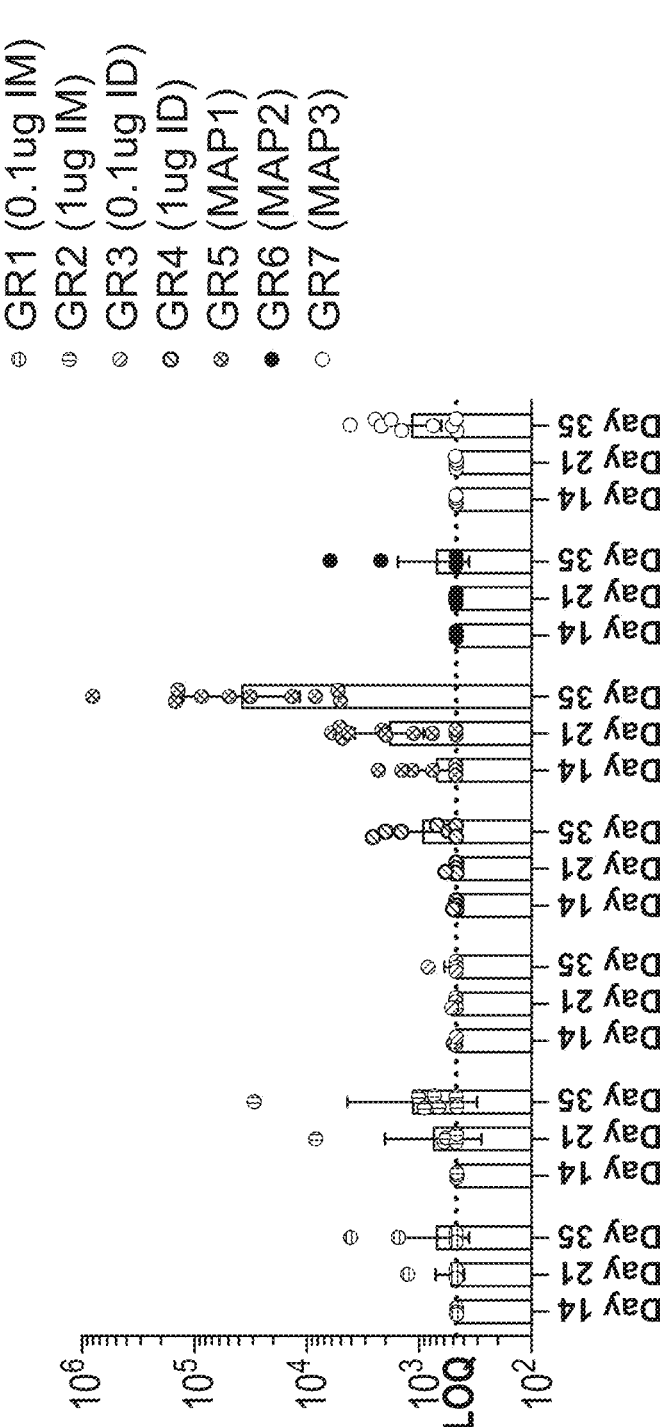
FIG. 31A shows a MAP delivering mRNA-LNP payload elicits anti-HA IgG titers superior to an equivalent dose of the same payload delivered via intramuscular or intradermal injection.
Figure 31B:
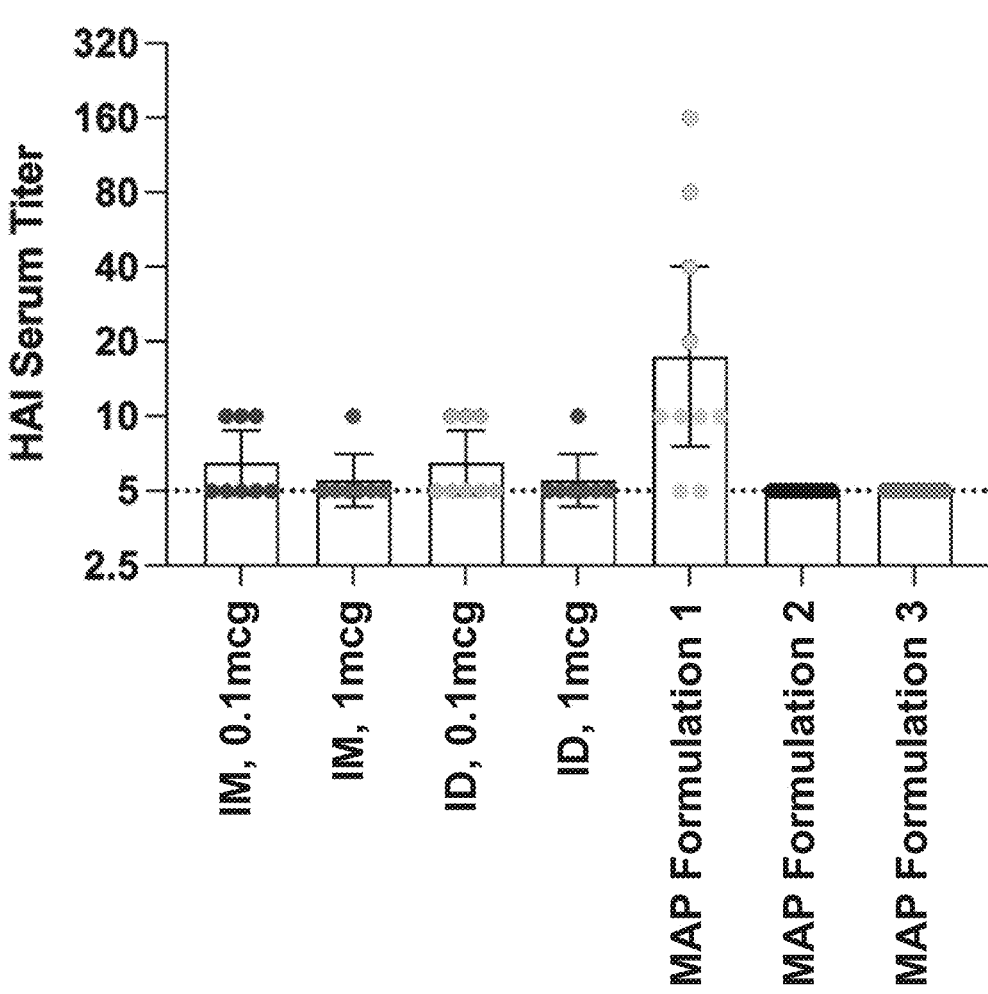
FIG. 31B shows an mRNA-LNP vaccine delivered via MAP elicits increased levels of neutralizing antibodies, e.g., hemagglutination inhibition antibodies when compared to an equivalent dose of mRNA-LNP delivered either intramuscularly or intradermally.

FIG. 31A shows a MAP delivering mRNA-LNP payload elicits anti-HA IgG titers superior to an equivalent dose of the same payload delivered via intramuscular or intradermal injection. FIG. 31B shows a mRNA-LNP vaccine delivered via MAP elicits increased levels of neutralizing antibodies, e.g., hemagglutination inhibition antibodies, when compared to an equivalent dose of mRNA-LNP delivered either intramuscularly or intradermally.

Example 8: MIMIX™ Dissolvable Microarray Patches (MAPs) as a Novel Drug Delivery Method for mRNA Overview Vaccines based on mRNA represent a promising alternative to conventional vaccines because mRNA vaccines can be rapidly developed and produced and possess high potency. However, mRNA vaccine instability and stringent requirements for cold chain transportation and storage remain significant challenges. MIMIX™ MAPs can potentially improve the shelf-stability and delivery of mRNA vaccines with simple, pain-free administration to the skin, while also eliminating dangerous sharps waste. Here, we report the development of a MAP for delivery of mRNA payloads formulated in Lipid Nanoparticles (LNP), along with quality assessments, in vitro and in vivo mRNA potency, and in vivo delivery efficiency.

MIMIX™ Platform Introduction

MIMIX™ is a clinically demonstrated microneedle array patch (MAP) technology that delivers a bioactive agent to the immunologically active dermal tissue. Further, the patch is applied with a preloaded applicator and removed after 5 minutes, which is convenient to use and would be broadly accessible, including in underdeveloped areas. FIG. 32A shows A) Simple four-step application of a MAP. 1) Open the pouch and take out the product 2) Deploy onto the skin using the applicator 3) wear the MAP for 5 minutes 4) peel off adhesive backing B) MIMIX system preloaded with a MAP C) Description of MIMIX components as tips could be modified.

Methodology—MAP Fabrication

An ink-jet printer dispenses a solution of prototype luciferase mRNA/LNP mixed with DiD label into a 121-microneedle mold to enable visualization. FIG. 32B shows A) Cartoon version of the whole MAP fabrication process B) Top-down view of a mold C) Side view and cross-sectioned mold throughout the process Methodology—MAP Characterization MAPs were then characterized using the following assays:

Tip consolidation: Fluorescent side view imaging.

mRNA encapsulation efficiency: Samples were incubated in the TE buffer, and then assayed via RiboGreen assay.

In vitro potency: Solubilized mRNA-LNPs MAPs were transfected into BHK-21 cells, and luciferase expression was measured via BrightGlo Luciferase Assay System (Promega) 24 hours later.

Deployment Efficiency: MAPs were deployed onto ex vivo pig skin, and deployment was assessed via fluorescent side view imaging of MAPs, fluorescent assessment of the skin where patches were deployed, and via fluorescent assay from the post-deployed MAPs.

In Vivo Potency: MAPs were deployed onto flanks of Sprague Dawley rats. After 24 hours, rats were injected with luciferin and imaged 30 min later using Luminescence In Vivo Imaging System (IVIS).

Capillary Electrophoresis (CE): RNA was purified from LNPs via spin columns and analyzed using an Agilent 5200 fragment analyzer.

FIG. 33 shows MAP in vivo potency IVIS workflow.

MAP Quality Assessment

FIG. 34 shows Fluorescence imaging was used to verify tip consolidation in a MAP and how the dried tip and base interact in a needle. The tips were filled at the distal end of needles, and the fluorescence was distributed evenly throughout the consolidated tips indicating the tips dried uniformly.

MAP Encapsulation Efficiency

FIG. 35A shows encapsulation efficiency was used to measure the stability of LNPs throughout the MAP drying process. N=4 MAPs from each of the two leading tip formulations were dissolved in buffer and subsequently assayed using the RiboGreen assay. The MIMIX platform was compatible with both leading tip formulations and different mRNA cargos (luciferase and hemagglutinin (HA)-encoding mRNA). FIG. 35B shows the data shown in FIG. 5 with additional labels indicating the formulation components evaluated. Formulation details are also summarized in Table 12.

TABLE 12

| | | | Tip Drying Conditions | Base Drying Conditions |
|---|---|---|---|---|
| | Tip | Base | | |
| Lead formulation 1 | 1% VA64 + 10% Sucrose + 1X TE buffer | 0.5% PVA + 60% PVP K17 + 1X TE buffer | 30 min at 85% RH | 5 min at 85% RH 60 min at Room Temp at 60% RH |
| Lead formulation 2 | 1% PVA 4-88 + 5% PVP K17 + 0.1% Fibroin (B.R.lot) + 10% Sucrose + 1X TE buffer | | 30 min at Room Temperature at 60% RH 4C desiccant box overnight (<10% RH) | 4C desiccant box overnight (<10% RH) |

| | Full name | Formulation |
|---|---|---|
| Luc | Luciferase LNP | 1.44 mg/ml mRNA, 10% sucrose in 25 mM Tris HCl, pH 7.4 |
| HA | Hemagglutinin (the influenza antigen) LNP | 1.79 mg/ml mRNA, 10% sucrose in 25 mM Tris HCl, pH 7.4 |

*Fibroin B.R means 180 minute (B.R lot): boil benchtop fibroin prep

MAP In Vitro Potency

FIG. 36A shows MAPs containing mRNA-LNPs encoding for luciferase were solubilized and eluate was transfected into BHK-21 cells to determine in vitro potency. Five different groups varying tip and base formulations and drying conditions were evaluated. Stepwise improvements to in vitro potency were observed with optimized formulations and drying conditions, from 3% to 21%, compared to the liquid control. FIG. 36B represents the data shown in FIG. 6 with additional labels indicating the formulation components evaluated. Formulation details are also summarized in Table 13.

TABLE 13

Formulation details related to FIG. 36A-36B

| Group | Tip Formulation | Tip drying conditions | Base Formulation (RT: Room temperature, O/N: Overnight) | Base drying conditions |
|---|---|---|---|---|
| A | 1% PVA 4-88/5% PVP K17/10% Sucrose/1X TE/0.413 ug/mL mRNA | 85% RH 30 min, 60% RH 30 min, 10% RH O/N (RT) | 17.7% PVA/ 17.7% PVP K17/17.7% Sucrose, nozzle temp 60 C. | 85% RH 5 min, 60% RH 30 min, 10% RH O/N (overnight drying) |
| B | 0.25% Fibroin/ 1% PVA 4-88/5% PVP K17/10% Sucrose/1X TE/ 0.413 ug/mL mRNA | 85% RH 30 min, 60% RH 30 min, 10% RH O/N (RT) | 17.7% PVA/ 17.7% PVP K17/17.7% Sucrose, nozzle temp 60 C. | 85% RH 5 min, 60% RH 30 min, 10% RH O/N (overnight drying) |
| C | 0.25% Fibroin/ 1% PVA 4-88/5% PVP K17/10% Sucrose/1X TE/ 0.413 ug/mL mRNA | 85% RH 30 min, 60% RH 30 min, 10% RH O/N (RT) | 50% PVP K12/0.5% PVA 4-88/ 1X TE, nozzle temp 25 C. | 85% RH 5 min, 60% RH 30 min, 10% RH O/N (overnight drying) |
| D | 0.25% Fibroin/ 1% PVA 4-88/5% PVP K17/10% Sucrose/1X TE/ 0.413 ug/mL mRNA | <10% RH immediate (4C) | 50% PVP K12/0.5% PVA 4-88/ 1X TE, nozzle temp 25 C. | 85% RH 5 min, 60% RH 30 min, 10% RH O/N (overnight drying) |
| E | 0.25% Fibroin/ 1% PVA 4-88/5% PVP K17/10% Sucrose/1X TE/ 0.413 ug/mL mRNA | <10% RH immediate (4C) | 50% PVP K12/0.5% PVA 4-88/ 1X TE, nozzle temp 25 C. | <10% RH immediate at 4C |

In Vitro Deployment Efficiency

FIG. 37 shows MAPs containing DiD-labelled LNP tip formulation and AlexaFluor 488 base formulation were fabricated, deployed into excised vivo porcine skin, and characterized to evaluate deployment efficiency. A) Fluorescent side-view imaging shows MAPs clearly deployed well, with little to no dye remaining in tip post-deployment. B) The deployed MAPs showed distinct and bright tips that were embedded within the skin, demonstrating compatibility of the labeled antigen with this method. C) Quantitative fluorescence revealed only an average of 9% DiD remaining on MAPs, indicating 91% of LNP was successfully delivered into the porcine skin.

TABLE 14

| | | | | | 5 |
|---|---|---|---|---|---|
| LNP | Final Tip Formulation concentration | Tip Drying Conditions | Base | Base Drying Conditions | |
| Phosphorex LNP; encoding for luciferase | Labeled (50% labeled, 50% unlabeled, 1 ug dose/MAP) 1% PVA 4-88 10% Sucrose 5% PVP K17 1X TE Buffer | 85% 30 min 60% 30 min 10% Overnight | Labeled 17.7% PVA 17.7% PVP K17 17.7% Sucrose | 5 min@85% RH 1 h@60% RH over-night@10% RH | 10 |
| Supplied at 0.54 mg/mL in 5% Sucrose, Tris buffer | *Tip fluorescently tagged with 2.5 mg/ml DiD in 100% EtOH | | *Base labeled with AlexaFluor 488 NHS Ester (not conjugated to anything) | | 15 |

<div align="center">Formulation details related to FIG. 37</div>

20

MAP In Vivo Potency

FIG. 38 shows the IVIS documented potency of MAPs in comparison to the same dose (Intramuscular) IM A) MAPs exhibited similar in vivo luciferase expression compared to IM. Delayed release kinetics from MAPs may also be attributed to differences in expression B) Representative IVIS images.

TABLE 15

Formulation details related to FIG. 38

| | Antigen | mRNA dosage (ug) | Final Tip Formulation concentration | Tip Drying Conditions | Base Formulation | Base Drying Conditions |
|---|---|---|---|---|---|---|
| IM | soluble antigen, Phosphorex LNP in diluted buffer (0.1% sucrose/ 0.2 mM tris in DPBS) | 1 | NA | NA | NA | NA |
| MAP | Phosphorex LNP (Supplied at 1 mg/mL in 5% Sucrose, Tris buffer) | 1 | 1% PVA 4-88 5% PVP K-17 0.1% Fibroin (B.R. Lot) 10% Sucrose 1X TE Buffer | 85% 30 min 60% 30 minutes at RT to 4 C. with desiccant overnight | 0.5% PVA 60% PVP K17 1X TE | 85% 5 min 60% 60 minutes at RT to 4 C. with desiccant 48 hrs |

MAP Stability

FIG. 39 shows HA-encoding mRNA MAPs were fabricated and stored for 1 month at 4C or 25C to determine mRNA stability via RiboGreen or CE. A) Encapsulation efficiency was retained in both liquid controls and MAPs at all temperature and time points, suggesting encapsulation efficiency likely not a good measure of mRNA stability. B) Significant loss in mRNA integrity observed in liquid format after 1 month storage. Largest contributor of degradation was due to mRNA aggregation/secondary structure formation. While there was some mRNA integrity loss through the manufacturing process, mRNA stored in the MAP format exhibited enhanced stability over liquid control, with no additional mRNA degradation observed after 1 month storage.

TABLE 16

Formulation details related to FIG. 39

| | Antigen | mRNA dosage (ug) | Final Tip Formulation concentration | Tip Drying Conditions | Base | Base Drying Conditions |
|---|---|---|---|---|---|---|
| Liquid | DS (Drug substance), HA LNP in 10% sucrose in 25 mM Tris HCl, pH 7.5 | 1 | NA | NA | NA | NA |
| MAP | mRNA-LNP-019-HA CKK-E12 HA LNPs: 2.46 mg/ml mRNA, 10% sucrose in 25 mM Tris HCl, pH 7.4 | 1 | 1% VA64 + 0.25% Fibroin (B.R. lot) + 10% sucrose + 1X TE buffer | 85% 30 min 60% 30 minutes at RT to 4 C. desiccant overnight | 0.5% PVA, 60% PVP K17, 1X TE | 85% 5 min 60% 60 minutes at RT to 4 C. desiccant overnight |

Conclusion and Future Studies

Applicant has demonstrated the feasibility of loading and delivering mRNA-based vaccines on the microarray patch (MAP) platform. High quality MAPs were shown to produce consolidated mRNA-LNP containing tips via fluorescence imaging that retain high encapsulation efficiency through manufacturing and good deployment into ex vivo porcine skin. Additionally, when stored in the MAP format, mRNA-LNPs exhibited a superior stability profile over liquid stored samples.

Future studies may evaluate different MAP manufacturing process including different drying conditions, and different tip/base formulations which may further improve in vitro and in vivo potency. Additionally, vaccine antigen-encoding mRNA can be used to evaluate immunogenicity of this payload and increased dose can be explored to further validate this platform.

Example 9: Summary of exemplary microneedle formulations characterized

Table 17 provides a summary of the exemplary microneedle formulations characterized herein with reference to the related figures.

Table 18 provides a summary of the exemplary microneedle formulations characterized herein with reference to experiment numbers.

Table 19 provides a summary of the exemplary microneedle formulations characterized herein with reference to the related figures.

Table 20 provides a summary of the exemplary mRNA-LNP formulation used for both HA and luciferase mRNA-LNP antigen.

Table 21 provides a longitudinal deployment data summary for the exemplary microneedle formulations characterized herein.

TABLE 17

| FIG. No. | Group name | Formulation conditions included (Tip) | Formulation conditions included (Base) |
|---|---|---|---|
| 5 | Control | GLP-1 (183 mg/mL), AF-647 (0.1 mg/mL) in DI-water | |

TABLE 17-continued

| FIG. No. | Group name | Formulation conditions included (Tip) | Formulation conditions included (Base) |
|---|---|---|---|
| | PVA | GLP-1 (168 mg/mL), PVA 4-88 (1%), Arginine HCL (1.33%), AF-647 (0.1 mg/mL), 100 mM MOPS buffer | |
| | PVP | GLP-1 (171 mg/mL), PVP K17 (1%), Arginine HCL (1.33%), AF-647 (0.1 mg/mL) in 100 mM MOPS buffer | |
| 6 | Control | GLP-1 (183 mg/mL), AF-647 (0.1 mg/mL) in DI-water | |
| | PVA | GLP-1 (168 mg/mL), PVA 4-88 (1%), Arginine HCl (1.33%), AF-647 (0.1 mg/mL), 100 mM MOPS buffer | |
| | PVP | GLP-1 (171 mg/mL), PVP K17 (1%), Arginine HCl (1.33%), AF-647 (0.1 mg/mL) in 100 mM MOPS buffer | |
| 7 | Control | GLP-1 (180 mg/mL), PVP K17 (1%), Arginine-HCl (1.37%), AF-647 (0.1 mg/mL), 100 mM MOPS buffer | |
| | + Kolliphor EL | GLP-1 (180 mg/mL), PVP K17 (1%), Arginine-HCl (1.37%), AF-647 (0.1 mg/mL), 100 mM MOPS buffer, Kolliphor EL (0.1% w/v) | |
| | + Kolliphor HS15 | GLP-1 (180 mg/mL), PVP K17 (1%), Arginine-HCl (1.37%), AF-647 (0.1 mg/mL), 100 mM MOPS buffer, Kolliphor HS-15 (0.1% w/v) | |
| | +F127 | GLP-1 (180 mg/mL), PVP K17 (1%), Arginine-HCl (1.37%), AF-647 (0.1 mg/mL), 100 mM MOPS buffer, Pluronic F-127 (0.7% w/v) | |
| | +P188 | GLP-1 (180 mg/mL), PVP K17 (1%), Arginine-HCl (1.37%), AF-647 (0.1 mg/mL), 100 mM MOPS buffer, Kolliphor P188 (0.1% w/v) | |
| | +Tween20 | GLP-1 (180 mg/mL), PVP K17 (1%), Arginine-HCl (1.37%), AF-647 (0.1 mg/mL), 100 mM MOPS buffer, Tween 20 (0.5% w/v) | |

TABLE 17-continued

| FIG. No. | Group name | Formulation conditions included (Tip) | Formulation conditions included (Base) |
|---|---|---|---|
| 8 | Control | GLP-1 (180 mg/mL), PVP K17 (1%), Arginine-HCl (1.37%), AF-647 (0.1 mg/mL), 100 mM MOPS buffer | |
| | +0.1% Kolliphor EL | GLP-1 (180 mg/mL), PVP K17 (1%), Arginine-HCl (1.37%), AF-647 (0.1 mg/mL), 100 mM MOPS buffer, Kolliphor EL (0.1% w/v) | |
| | +0.1% HS 15 | GLP-1 (180 mg/mL), PVP K17 (1%), Arginine-HCl (1.37%), AF-647 (0.1 mg/mL), 100 mM MOPS buffer, Kolliphor HS-15 (0.1% w/v) | |
| | +0.7% F127 | GLP-1 (180 mg/mL), PVP K17 (1%), Arginine-HCl (1.37%), AF-647 (0.1 mg/mL), 100 mM MOPS buffer, Pluronic F-127 (0.7% w/v) | |
| | +1% P188 | GLP-1 (180 mg/mL), PVP K17 (1%), Arginine-HCl (1.37%), AF-647 (0.1 mg/mL), 100 mM MOPS buffer, Kolliphor P188 (0.1% w/v) | |
| | +0.5% T20 | GLP-1 (180 mg/mL), PVP K17 (1%), Arginine-HCl (1.37%), AF-647 (0.1 mg/mL), 100 mM MOPS buffer, Tween 20 (0.5% w/v) | |
| 9 | Control | GLP-1 (180 mg/mL), PVP K17 (1%), Arginine-HCl (1.37%), AF-647 (0.1 mg/mL), 100 mM MOPS buffer | |
| | + Kolliphor EL | GLP-1 (180 mg/mL), PVP K17 (1%), Arginine-HCl (1.37%), AF-647 (0.1 mg/mL), 100 mM MOPS buffer, Kolliphor EL (0.1% w/v) | |
| | + HS15 | GLP-1 (180 mg/mL), PVP K17 (1%), Arginine-HCl (1.37%), AF-647 (0.1 mg/mL), 100 mM MOPS buffer, Kolliphor HS-15 (0.1% w/v) | |
| | + F127 | GLP-1 (180 mg/mL), PVP K17 (1%), Arginine-HCl (1.37%), AF-647 (0.1 mg/mL), 100 mM MOPS buffer, Pluronic F-127 (0.7% w/v) | |
| | + P188 | GLP-1 (180 mg/mL), PVP K17 (1%), Arginine-HCl (1.37%), AF-647 (0.1 mg/mL), 100 mM MOPS buffer, Kolliphor P188 (0.1% w/v) | |
| | + Tween20 | GLP-1 (180 mg/mL), PVP K17 (1%), Arginine-HCl (1.37%), AF-647 (0.1 mg/mL), 100 mM MOPS buffer, Tween 20 (0.5% w/v) | |
| 10 | GLP-013 20 nL | GLP-1 (192 mg/mL) in DI-water | |
| | GLP-013 40 nL | GLP-1 (192 mg/mL) in DI-water | |
| | GLP-016 10 nL | GLP-1 (183 mg/mL), AF-647 (0.1 mg/mL) in DI-water | |
| | GLP-016 30 nL | GLP-1 (183 mg/mL), AF-647 (0.1 mg/mL) in DI-water | |
| | GLP-019 Control | GLP-1 (183 mg/mL), AF-647 (0.1 mg/mL) in DI-water | |
| | GLP-019 PVP | GLP-1 (171 mg/mL), PVP K17 (1%), Arginine HCL (1.33%), AF-647 (0.1 mg/mL) in 100 mM MOPS buffer | |
| | GLP-024 Arg 30 nL | GLP-1 (171 mg/mL), Arginine-HCl (2.74%), AF-647 (0.1 mg/ml) in 100 mM MOPS buffer | |

TABLE 17-continued

| FIG. No. | Group name | Formulation conditions included (Tip) | Formulation conditions included (Base) |
|---|---|---|---|
| | GLP-024 PVP 30 nl | GLP-1 (171 mg/mL), PVP K17 (1%), Arginine-HCl (1.37%), AF-647 (0.1 mg/mL) in 100 mM MOPS buffer | |
| | GLP-027 Control (dial) | GLP-1 (171 mg/mL), PVP K17 (2.25%), Arginine-HCl (0.61%), AF-647 (0.1 mg/mL) in 100 mM MOPS buffer | |
| | GLP-027 PB 30 nl | GLP-1 (171 mg/mL), PVP K17 (2.25%), Arginine-HCl (0.61%), AF-647 (0.1 mg/mL) in 100 mM MOPS buffer | |
| | GLP-027 PB 30 nl 277 | GLP-1 (171 mg/mL), PVP K17 (2.25%), Arginine-HCl (0.61%), AF-647 (0.1 mg/mL) in 100 mM MOPS buffer | |
| | GLP-031 Control 30 nl | GLP-1 (171 mg/mL), PVP K17 (1%), Arginine-HCl (1.37%), AF-647 (0.1 mg/mL) in 100 mM MOPS buffer | |
| | GLP-031 PB 30 nl | GLP-1 (171 mg/mL), PVP K17 (1%), Arginine-HCl (1.37%), AF-647 (0.1 mg/mL) in 100 mM MOPS buffer | |
| | GLP-031 PB 30 nl 241 | GLP-1 (171 mg/mL), PVP K17 (1%), Arginine-HCl (1.37%), AF-647 (0.1 mg/mL) in 100 mM MOPS buffer | |
| | GLP-031 H20 nl 241 | GLP-1 (193 mg/mL), PVP K17 (1%), Arginine-HCl (1.37%), AF-647 (0.1 mg/mL) in 100 mM MOPS buffer | |
| | GLP-038 PB 20 nl | GLP-1 (171 mg/mL), PVP K17 (1%), Arginine-HCl (1.37%), AF-647 (0.1 mg/mL) in 100 mM MOPS buffer | |
| | GLP-038 PB 20 nl 241 | GLP-1 (171 mg/mL), PVP K17 (1%), Arginine-HCl (1.37%), AF-647 (0.1 mg/mL) in 100 mM MOPS buffer | |
| | GLP-038 H20 nl | GLP-1 (193 mg/mL), PVP K17 (1%), Arginine-HCl (1.37%), AF-647 (0.1 mg/mL) in 100 mM MOPS buffer | |
| | GLP-038 H20 nl 241 | GLP-1 (193 mg/mL), PVP K17 (1%), Arginine-HCl (1.37%), AF-647 (0.1 mg/mL) in 100 mM MOPS buffer | |
| | GLP-040 Control | GLP-1 (180 mg/mL), PVP K17 (1%), Arginine-HCl (1.37%), AF-647 (0.1 mg/mL) in 100 mM MOPS buffer | |
| | GLP-042 Low (17 ul) ISA-007 Backing | GLP-1 (180 mg/mL), PVP K17 (1%), Arginine-HCl (1.37%), AF-647 (0.1 mg/mL) in 100 mM MOPS buffer | |
| | GLP-042 High (26 ul) ISA-001 Backing | GLP-1 (180 mg/mL), PVP K17 (1%), Arginine-HCl (1.37%), AF-647 (0.1 mg/mL) in 100 mM MOPS buffer | |
| | GLP-042 Medium (21 ul) ISA-009 | GLP-1 (180 mg/mL), PVP K17 (1%), Arginine-HCl (1.37%), AF-647 (0.1 mg/mL) in 100 mM MOPS buffer | |
| | . . . | | |
| | GLP-060 NN | GLP-1 (180 mg/mL), PVP K17 (1%), Kolliphor EL (0.1%), Arginine-HCl (1.37%), AF-647 (0.1 mg/mL) in 100 mM MOPS buffer | |

TABLE 17-continued

| FIG. No. | Group name | Formulation conditions included (Tip) | Formulation conditions included (Base) |
|---|---|---|---|
| 11 | GLP-013 20 nL | GLP-1 (192 mg/mL) in DI-water | |
| | GLP-013 30 nL | GLP-1 (192 mg/mL) in DI-water | |
| | GLP-013 40 nL | GLP-1 (192 mg/mL) in DI-water | |
| | GLP-013 30 nL 277 | GLP-1 (192 mg/mL) in DI-water | |
| | GLP-016 10 nL | GLP-1 (183 mg/mL), AF-647 (0.1 mg/mL) in DI-water | |
| | GLP-016 20 nL | GLP-1 (183 mg/mL), AF-647 (0.1 mg/mL) in DI-water | |
| | GLP-016 30 nL | GLP-1 (183 mg/mL), AF-647 (0.1 mg/mL) in DI-water | |
| | GLP-016 20 nL (277) | GLP-1 (183 mg/mL), AF-647 (0.1 mg/mL) in DI-water | |
| | GLP-019 Control | GLP-1 (183 mg/mL), AF-647 (0.1 mg/mL) in DI-water | |
| | GLP-019 PVA | GLP-1 (168 mg/mL), PVA 4-88 (1%), Arginine HCL (1.33%), AF-647 (0.1 mg/mL), 100 mM MOPS buffer | |
| | GLP-019 PVP | GLP-1 (171 mg/mL), PVP K17 (1%), Arginine HCL (1.33%), AF-647 (0.1 mg/mL) in 100 mM MOPS buffer | |
| | GLP-019 SDB | GLP-1 (183 mg/mL), AF-647 (0.1 mg/mL) in DI-water | |
| | GLP-024 Arg | GLP-1 (171 mg/mL), Arginine-HCl (2.74%), AF-647 (0.1 mg/mL) in 100 mM MOPS buffer | |
| | GLP-024 Arg 30 nL | GLP-1 (171 mg/mL), Arginine-HCl (2.74%), AF-647 (0.1 mg/mL) in 100 mM MOPS buffer | |
| | GLP-024 PVP | GLP-1 (171 mg/mL), PVP K17 (1%), Arginine-HCl (1.37%), AF-647 (0.1 mg/mL) in 100 mM MOPS buffer | |
| | GLP-024 PVP 30 nl | GLP-1 (171 mg/mL), PVP K17 (1%), Arginine-HCl (1.37%), AF-647 (0.1 mg/mL) in 100 mM MOPS buffer | |
| | GLP-024 SDB | GLP-1 (171 mg/mL), PVP K17 (1%), Arginine-HCl (1.37%), AF-647 (0.1 mg/mL) in 100 mM MOPS buffer | |
| | GLP-024 PB | GLP-1 (171 mg/mL), PVP K17 (1%), Arginine-HCl (1.37%), AF-647 (0.1 mg/mL) in 100 mM MOPS buffer | |
| | GLP-027 Control (dial) | GLP-1 (171 mg/mL), PVP K17 (2.25%), Arginine-HCl (0.61%), AF-647 (0.1 mg/mL) in 100 mM MOPS buffer | |
| | GLP-027 Control . . . | GLP-1 (171 mg/mL), PVP K17 (2.25%), Arginine-HCl (0.61%), AF-647 (0.1 mg/mL) in 100 mM MOPS buffer | |
| | GLP-027 PB | GLP-1 (171 mg/mL), PVP K17 (2.25%), Arginine-HCl (0.61%), AF-647 (0.1 mg/mL) in 100 mM MOPS buffer | |
| | GLP-027 PB 30 nl | GLP-1 (171 mg/mL), PVP K17 (2.25%), Arginine-HCl (0.61%), AF-647 (0.1 mg/mL) in 100 mM MOPS buffer | |
| | GLP-027 PB 30 nl 277 | GLP-1 (171 mg/mL), PVP K17 (2.25%), Arginine-HCl (0.61%), AF-647 (0.1 mg/mL) in 100 mM MOPS buffer | |

TABLE 17-continued

| FIG. No. | Group name | Formulation conditions included (Tip) | Formulation conditions included (Base) |
|---|---|---|---|
| | GLP-031 Control | GLP-1 (171 mg/mL), PVP K17 (1%), Arginine-HCl (1.37%), AF-647 (0.1 mg/mL) in 100 mM MOPS buffer | |
| | GLP-031 Control 30 nl | GLP-1 (171 mg/mL), PVP K17 (1%), Arginine-HCl (1.37%), AF-647 (0.1 mg/mL) in 100 mM MOPS buffer | |
| | GLP-031 PB 20 nl | GLP-1 (171 mg/mL), PVP K17 (1%), Arginine-HCl (1.37%), AF-647 (0.1 mg/mL) in 100 mM MOPS buffer | |
| | GLP-031 PB 30 nl | GLP-1 (171 mg/mL), PVP K17 (1%), Arginine-HCl (1.37%), AF-647 (0.1 mg/mL) in 100 mM MOPS buffer | |
| | GLP-031 PB 20 nl 241 | GLP-1 (171 mg/mL), PVP K17 (1%), Arginine-HCl (1.37%), AF-647 (0.1 mg/mL) in 100 mM MOPS buffer | |
| | GLP-031 PB 30 nl 241 | GLP-1 (171 mg/mL), PVP K17 (1%), Arginine-HCl (1.37%), AF-647 (0.1 mg/mL) in 100 mM MOPS buffer | |
| | GLP-031 H20 nl | GLP-1 (193 mg/mL), PVP K17 (1%), Arginine-HCl (1.37%), AF-647 (0.1 mg/mL) in 100 mM MOPS buffer | |
| | GLP-031 H30 nl | GLP-1 (193 mg/mL), PVP K17 (1%), Arginine-HCl (1.37%), AF-647 (0.1 mg/mL) in 100 mM MOPS buffer | |
| | GLP-031 H20 nl 241 | GLP-1 (193 mg/mL), PVP K17 (1%), Arginine-HCl (1.37%), AF-647 (0.1 mg/mL) in 100 mM MOPS buffer | |
| | GLP-031 H30 nl 241 | GLP-1 (193 mg/mL), PVP K17 (1%), Arginine-HCl (1.37%), AF-647 (0.1 mg/mL) in 100 mM MOPS buffer | |
| | GLP-038 PB 20 nl | GLP-1 (171 mg/mL), PVP K17 (1%), Arginine-HCl (1.37%), AF-647 (0.1 mg/mL) in 100 mM MOPS buffer | |
| | GLP-038 PB 30 nl | GLP-1 (171 mg/mL), PVP K17 (1%), Arginine-HCl (1.37%), AF-647 (0.1 mg/mL) in 100 mM MOPS buffer | |
| | GLP-038 PB 20 nl 241 | GLP-1 (171 mg/mL), PVP K17 (1%), Arginine-HCl (1.37%), AF-647 (0.1 mg/mL) in 100 mM MOPS buffer | |
| | GLP-038 PB 30 nl 241 | GLP-1 (171 mg/mL), PVP K17 (1%), Arginine-HCl (1.37%), AF-647 (0.1 mg/mL) in 100 mM MOPS buffer | |
| | GLP-038 H20 nl | GLP-1 (193 mg/mL), PVP K17 (1%), Arginine-HCl (1.37%), AF-647 (0.1 mg/mL) in 100 mM MOPS buffer | |
| | GLP-038 H30 nl | GLP-1 (193 mg/mL), PVP K17 (1%), Arginine-HCl (1.37%), AF-647 (0.1 mg/mL) in 100 mM MOPS buffer | |
| | GLP-038 H20 nl 241 | GLP-1 (193 mg/mL), PVP K17 (1%), Arginine-HCl (1.37%), AF-647 (0.1 mg/mL) in 100 mM MOPS buffer | |
| | GLP-038 H30 nl 241 | GLP-1 (193 mg/mL), PVP K17 (1%), Arginine-HCl (1.37%), AF-647 (0.1 mg/mL) in 100 mM MOPS buffer | |

TABLE 17-continued

| FIG. No. | Group name | Formulation conditions included (Tip) | Formulation conditions included (Base) |
|---|---|---|---|
| | GLP-040 Control | GLP-1 (180 mg/mL), PVP K17 (1%), Arginine-HCl (1.37%), AF-647 (0.1 mg/mL) in 100 mM MOPS buffer | |
| | GLP-040 Surfactant | GLP-1 (192 mg/mL), PVP K17 (1%), Kolliphor EL (0.1% w/v), Arginine-HCl (1.37%), AF-647 (0.1 mg/mL) in 100 mM MOPS buffer | |
| | GLP-042 Low (17 ul) . . . | GLP-1 (180 mg/mL), PVP K17 (1%), Arginine-HCl (1.37%), AF-647 (0.1 mg/mL) in 100 mM MOPS buffer | |
| | GLP-042 Medium . . . | GLP-1 (180 mg/mL), PVP K17 (1%), Arginine-HCl (1.37%), AF-647 (0.1 mg/mL) in 100 mM MOPS buffer | |
| | GLP-042 High (26 ul) . . . | GLP-1 (180 mg/mL), PVP K17 (1%), Arginine-HCl (1.37%), AF-647 (0.1 mg/mL) in 100 mM MOPS buffer | |
| | GLP-042 Low (17 ul) . . . | GLP-1 (180 mg/mL), PVP K17 (1%), Arginine-HCl (1.37%), AF-647 (0.1 mg/mL) in 100 mM MOPS buffer | |
| | GLP-042 Medium | GLP-1 (180 mg/mL), PVP K17 (1%), Arginine-HCl (1.37%), AF-647 (0.1 mg/mL) in 100 mM MOPS buffer | |
| | GLP-042 High (26 ul) . . . | GLP-1 (180 mg/mL), PVP K17 (1%), Arginine-HCl (1.37%), AF-647 (0.1 mg/mL) in 100 mM MOPS buffer | |
| | GLP-060 NN | GLP-1 (180 mg/mL), PVP K17 (1% w/v), Kolliphor EL (0.1% w/v), Arginine-HCl (1.37%), AF-647 (0.1 mg/mL) in 100 mM MOPS buffer | |
| 12 | GLP-013 30 nL | GLP-1 (192 mg/mL) in DI-water | |
| | GLP-016 10 nL | GLP-1 (183 mg/mL), AF-647 (0.1 mg/mL) in DI-water | |
| | GLP-019 Control | GLP-1 (183 mg/mL), AF-647 (0.1 mg/mL) in DI-water | |
| | GLP-019 PVA | GLP-1 (168 mg/mL), PVA 4-88 (1%), Arginine HCL (1.33%), AF-647 (0.1 mg/mL), 100 mM MOPS buffer | |
| | GLP-019 PVP | GLP-1 (171 mg/mL), PVP K17 (1%), Arginine HCL (1.33%), AF-647 (0.1 mg/mL) in 100 mM MOPS buffer | |
| | GLP-027 PB | GLP-1 (171 mg/mL), PVP K17 (2.25%), Arginine-HCl (0.61%), AF-647 (0.1 mg/mL) in 100 mM MOPS buffer | |
| | GLP-040 Control | GLP-1 (180 mg/mL), PVP K17 (1%), Arginine-HCl (1.37%), AF-647 (0.1 mg/mL) in 100 mM MOPS buffer | |
| | GLP-040 Surfactant | GLP-1 (192 mg/mL), PVP K17 (1%), Kolliphor EL (0.1% w/v), Arginine-HCl (1.37%), AF-647 (0.1 mg/mL) in 100 mM MOPS buffer | |
| | GLP-060 NN | GLP-1 (180 mg/mL), PVP K17 (1% w/v), Kolliphor EL (0.1% w/v), Arginine-HCl (1.37%), AF-647 (0.1 mg/mL) in 100 mM MOPS buffer | |

TABLE 17-continued

| FIG. No. | Group name | Formulation conditions included (Tip) | Formulation conditions included (Base) |
|---|---|---|---|
| 13 | VX103 Exp (20 nL) | H1N1 (6.2 mg/mL), Tween 20 (0.5% v/v), Fibroin (1% w/v) in water | |
| | VX103 Exp 2 (20 nL | H1N1 (6.2 mg/mL), Tween 20 (0.5% v/v), Fibroin (1% w/v) in water | |
| | GLP-1 (17 nL) | GLP-1 (180 mg/mL), PVP K17 (1%), Arginine-HCl (1.37%), AF-647 (0.1 mg/mL) in 100 mM MOPS buffer | |
| | GLP-1 (21 nL) | GLP-1 (180 mg/mL), PVP K17 (1%), Arginine-HCl (1.37%), AF-647 (0.1 mg/mL) in 100 mM MOPS buffer | |
| | GLP-1 (26 nL) | GLP-1 (180 mg/mL), PVP K17 (1%), Arginine-HCl (1.37%), AF-647 (0.1 mg/mL) in 100 mM MOPS buffer | |
| 14 | +1% PVP K17 | GLP-1 (180 mg/mL), Kolliphor EL (0.1%), Arginine-HCl (1.37%), AF-647 (0.1 mg/mL) in 100 mM MOPS buffer, PVP K17 (1%) | |
| | +3% PVP K17 | GLP-1 (180 mg/mL), Kolliphor EL (0.1%), Arginine-HCl (1.37%), AF-647 (0.1 mg/mL) in 100 mM MOPS buffer, PVP K17 (3%) | |
| | +6% PVP K17 | GLP-1 (180 mg/mL), Kolliphor EL (0.1%), Arginine-HCl (1.37%), AF-647 (0.1 mg/mL) in 100 mM MOPS buffer, PVP K17 (6%) | |
| | +1% PVP K12 | GLP-1 (180 mg/mL), Kolliphor EL (0.1%), Arginine-HCl (1.37%), AF-647 (0.1 mg/mL) in 100 mM MOPS buffer, PVP K12 (1%) | |
| | +3% PVP K12 | GLP-1 (180 mg/mL), Kolliphor EL (0.1%), Arginine-HCl (1.37%), AF-647 (0.1 mg/mL) in 100 mM MOPS buffer, PVP K12 (3%) | |
| | +6% PVP K12 | GLP-1 (180 mg/mL), Kolliphor EL (0.1%), Arginine-HCl (1.37%), AF-647 (0.1 mg/mL) in 100 mM MOPS buffer, PVP K12 (6%) | |
| | +1% PVP K30 | GLP-1 (180 mg/mL), Kolliphor EL (0.1%), Arginine-HCl (1.37%), AF-647 (0.1 mg/mL) in 100 mM MOPS buffer, PVP K30 (1%) | |
| | +3% PVP K30 | GLP-1 (180 mg/mL), Kolliphor EL (0.1%), Arginine-HCl (1.37%), AF-647 (0.1 mg/mL) in 100 mM MOPS buffer, PVP K30 (3%) | |
| | +6% PVP K30 | GLP-1 (180 mg/mL), Kolliphor EL (0.1%), Arginine-HCl (1.37%), AF-647 (0.1 mg/mL) in 100 mM MOPS buffer, PVP K30 (6%) | |
| | +1% PVA | GLP-1 (180 mg/mL), Kolliphor EL (0.1%), Arginine-HCl (1.37%), AF-647 (0.1 mg/mL) in 100 mM MOPS buffer, PVA 4-88 (1%) | |
| | +2% PVA | GLP-1 (180 mg/mL), Kolliphor EL (0.1%), Arginine-HCl (1.37%), AF-647 (0.1 mg/mL) in 100 mM MOPS buffer, PVA 4-88 (2%) | |
| | +3% PVA | GLP-1 (180 mg/mL), Kolliphor EL (0.1%), Arginine-HCl (1.37%), AF-647 (0.1 mg/mL) in 100 mM MOPS buffer, PVA 4-88 (3%) | |
| | +1% Dextran | GLP-1 (180 mg/mL), Kolliphor EL (0.1%), Arginine-HCl (1.37%), AF-647 (0.1 mg/mL) in 100 mM MOPS buffer, Dextran (1%) | |
| | +2% Dextran | GLP-1 (180 mg/mL), Kolliphor EL (0.1%), Arginine-HCl (1.37%), AF-647 (0.1 mg/mL) in 100 mM MOPS buffer, Dextran (2%) | |
| | +3% | GLP-1 (180 mg/mL), Kolliphor | |

| FIG. No. | Group name | Formulation conditions included (Tip) | Formulation conditions included (Base) |
|---|---|---|---|
| | Dextran | EL (0.1%), Arginine-HCl (1.37%), AF-647 (0.1 mg/mL) in 100 mM MOPS buffer, Dextran (3%) | |
| | +1% Plasdone | GLP-1 (180 mg/mL), Kolliphor EL (0.1%), Arginine-HCl (1.37%), AF-647 (0.1 mg/mL) in 100 mM MOPS buffer, Plasdone S630 (1%) | |
| | +2% Plasdone | GLP-1 (180 mg/mL), Kolliphor EL (0.1%), Arginine-HCl (1.37%), AF-647 (0.1 mg/mL) in 100 mM MOPS buffer, Plasdone S630 (2%) | |
| | +3% Plasdone | GLP-1 (180 mg/mL), Kolliphor EL (0.1%), Arginine-HCl (1.37%), AF-647 (0.1 mg/mL) in 100 mM MOPS buffer, Plasdone S630 (3%) | |
| | +0.1% MC | GLP-1 (180 mg/mL), Kolliphor EL (0.1%), Arginine-HCl (1.37%), AF-647 (0.1 mg/mL) in 100 mM MOPS buffer, Methyl Cellulose (0.1%) | |
| | +0.5% MC | GLP-1 (180 mg/mL), Kolliphor EL (0.1%), Arginine-HCl (1.37%), AF-647 (0.1 mg/mL) in 100 mM MOPS buffer, Methyl Cellulose (0.5%) | |
| | +0.75% MC | GLP-1 (180 mg/mL), Kolliphor EL (0.1%), Arginine-HCl (1.37%), AF-647 (0.1 mg/mL) in 100 mM MOPS buffer, Methyl Cellulose (0.75%) | |
| | +0.1% HPMC | GLP-1 (180 mg/mL), Kolliphor EL (0.1%), Arginine-HCl (1.37%), AF-647 (0.1 mg/mL) in 100 mM MOPS buffer, Hypromellose methyl cell ulose (0.1%) | |
| | +0.5% HPMC | GLP-1 (180 mg/mL), Kolliphor EL (0.1%), Arginine-HCl (1.37%), AF-647 (0.1 mg/mL) in 100 mM MOPS buffer, Hypromellose methyl cell ulose (0.5%) | |
| | +0.75% HPMC | GLP-1 (180 mg/mL), Kolliphor EL (0.1%), Arginine-HCl (1.37%), AF-647 (0.1 mg/mL) in 100 mM MOPS buffer, Hypromellose methyl cell ulose (0.75%) | |
| | +0.1% CMC | GLP-1 (180 mg/mL), Kolliphor EL (0.1%), Arginine-HCl (1.37%), AF-647 (0.1 mg/mL) in 100 mM MOPS buffer, Carboxymethyl Cellulose (0.1%) | |
| | +0.5% CMC | GLP-1 (180 mg/mL), Kolliphor EL (0.1%), Arginine-HCl (1.37%), AF-647 (0.1 mg/mL) in 100 mM MOPS buffer, Carboxymethyl Cellulose (0.5%) | |
| | +0.75% CMC | GLP-1 (180 mg/mL), Kolliphor EL (0.1%), Arginine-HCl (1.37%), AF-647 (0.1 mg/mL) in 100 mM MOPS buffer, Carboxymethyl Cellulose(0.75%) | |
| 15 | Control: 1% PVP K17 | GLP-1 (180 mg/mL), Kolliphor EL (0.1%), Arginine-HCl (1.37%), AF-647 (0.1 mg/mL) in 100 mM MOPS buffer, PVP K17 (1%) | |
| | 3% Dextran | GLP-1 (180 mg/mL), Kolliphor EL (0.1%), Arginine-HCl (1.37%), AF-647 (0.1 mg/mL) in 100 mM MOPS buffer, Dextran (3%) | |
| | Higher PVP: 6% | GLP-1 (180 mg/mL), Kolliphor EL (0.1%), Arginine-HCl (1.37%), AF-647 (0.1 mg/mL) in 100 mM MOPS buffer, PVP K17 (6%) | |
| 16 | PVP (1%) | GLP-1 (180 mg/mL), Kolliphor EL (0.1%), Arginine-HCl (1.37%), AF-647 (0.1 mg/mL) in 100 mM MOPS buffer, PVP K17 (1%), NaCl (0.9%) | |
| | Dextran (1%) | GLP-1 (180 mg/mL), Kolliphor EL (0.1%), Arginine-HCl (1.37%), AF-647 (0.1 mg/mL) in 100 mM MOPS buffer, Dextran (1%), NaCl (0.9%) | |
| 17 | MOPS | GLP-1 (180 mg/mL), Kolliphor EL (0.1%), Arginine-HCl (1.37%), AF-647 (0.1 mg/mL) in 100 mM MOPS buffer, PVP K17 (1%), NaCl (0.9%) | |
| | Tris | GLP-1 (180 mg/mL), Kolliphor EL (0.1%), Arginine-HCl (1.37%), AF-647 (0.1 mg/mL) in 100 mM Tris-HCl buffer, PVP K17 (1%), NaCl (0.9%) | |
| 18 | GLP-077 Control | GLP-1 (180 mg/mL), Kolliphor EL (0.1%), Arginine-HCl (1.37%), AF-647 (0.1 mg/mL) in 100 mM MOPS buffer, PVP K17 (1%) | |
| | GLP-077 Histdine | GLP-1 (180 mg/mL), Kolliphor EL (0.1%), Histidine (0.5%), AF-647 (0.1 mg/mL) in 100 mM MOPS buffer, PVP K17 (1%) | |
| | GLP-077 Proline | GLP-1 (180 mg/mL), Kolliphor EL (0.1%), Proline (0.75%), AF-647 (0.1 mg/mL) in 100 mM MOPS buffer, PVP K17 (1%) | |
| 19 | 0.75% Proline or Proline (0.75%) 3% Proline or Proline (3%) | GLP-1 (180 mg/mL), Kolliphor EL (0.1%), Proline (0.75%), AF-647 (0.1 mg/mL) in 100 mM Tris-HCl buffer, PVP K17 (1%) GLP-1 (180 mg/mL), Kolliphor EL (0.1%), Proline (3%), AF-647 (0.1 mg/mL) in 100 mM Tris-HCl buffer, PVP K17 (1%) | |
| 20 | NaCl (0.9%) | GLP-1 (180 mg/mL), Kolliphor EL (0.1%), Arginine-HCl (1.37%), AF-647 (0.1 mg/mL) in 100 mM MOPS buffer, PVP K17 (1%), NaCl (0.9%) | |
| | MgCl2 (1%) | GLP-1 (180 mg/mL), Kolliphor EL (0.1%), Arginine-HCl (1.37%), AF-647 (0.1 mg/mL) in 100 mM MOPS buffer, PVP K17 (1%), MgC12 (1%) | |
| | MgCl2 (0.5%) | GLP-1 (180 mg/mL), Kolliphor EL (0.1%), Arginine-HCl (1.37%), AF-647 (0.1 mg/mL) in 100 mM MOPS buffer, PVP K17 (1%), MgCl2 (0.5%) | |
| | Control (GLP-060) | GLP-1 (180 mg/mL), PVP K17 (1% w/v), Kolliphor EL (0.1% w/v), Arginine-HCl (1.37%), AF-647 (0.1 mg/mL) in 100 mM MOPS buffer | |
| 21 | 0.75% Proline + 0.9% NaCl or With Salt 0.75% Proline or No salt | GLP-1 (180 mg/mL), Kolliphor EL (0.1%), Proline (0.75%), AF-647 (0.1 mg/mL) in 100 mM Tris-HCl buffer, PVP K17 (1%), NaCl (0.9%) GLP-1 (180 mg/mL), Kolliphor EL (0.1%), Proline (0.75%), AF-647 (0.1 mg/mL) in 100 mM Tris-HCl buffer, PVP K17 (1%) | |
| 22 | PPS-61-20 | GLP-1 (180 mg/mL), Kolliphor EL (0.1%), Proline (0.75%), AF-647 (0.1 mg/mL) in 100 mM Tris-HCl buffer, PVP K17 (1%), NaCl (0.9%) | |

TABLE 17-continued

| FIG. No. | Group name | Formulation conditions included (Tip) | Formulation conditions included (Base) |
|---|---|---|---|
| | PHP-61-20 | GLP-1 (180 mg/mL), Kolliphor EL (0.1%), Proline (3%), AF-647 (0.1 mg/mL) in 100 mM Tris-HCl buffer, PVP K17 (1%) | |
| 23A | -024 | GLP-1 (171 mg/mL), PVP K17 (1%), Arginine-HCl (1.37%), AF-647 (0.1 mg/mL) in 100 mM MOPS buffer | |
| | -027 | GLP-1 (171 mg/mL), PVP K17 (2.25%), Arginine-HCl (0.61%), AF-647 (0.1 mg/mL) in 100 mM MOPS buffer | |
| | -027 | GLP-1 (171 mg/mL), PVP K17 (2.25%), Arginine-HCl (0.61%), AF-647 (0.1 mg/mL) in 100 mM MOPS buffer | |
| | -031 | GLP-1 (171 mg/mL), PVP K17 (1%), Arginine-HCl (1.37%), AF-647 (0.1 mg/mL) in 100 mM MOPS buffer | |
| | -031 | GLP-1 (171 mg/mL), PVP K17 (1%), Arginine-HCl (1.37%), AF-647 (0.1 mg/mL) in 100 mM MOPS buffer | |
| | -038 | GLP-1 (171 mg/mL), PVP K17 (1%), Arginine-HCl (1.37%), AF-647 (0.1 mg/mL) in 100 mM MOPS buffer | |
| | -060 | GLP-1 (180 mg/mL), PVP K17 (1% w/v), Kolliphor EL (0.1% w/v), Arginine-HCl (1.37%), AF-647 (0.1 mg/mL) in 100 mM MOPS buffer | |
| | -105 (PPS) | GLP-1 (180 mg/mL), Kolliphor EL (0.1%), Proline (0.75%), AF-647 (0.1 mg/mL) in 100 mM Tris-HCl buffer, PVP K17 (1%), NaCl (0.9%) | |
| | -109 (PPS) | GLP-1 (180 mg/mL), Kolliphor EL (0.1%), Proline (0.75%), AF-647 (0.1 mg/mL) in 100 mM Tris-HCl buffer, PVP K17 (1%), NaCl (0.9%) | |
| | -109 (PHP) | GLP-1 (180 mg/mL), Kolliphor EL (0.1%), Proline (3%), AF-647 (0.1 mg/mL) in 100 mM Tris-HCl buffer, PVP K17 (1%) | |
| | -142 (PPS) | GLP-1 (180 mg/mL), Kolliphor EL (0.1%), Proline (0.75%), AF-647 (0.1 mg/mL) in 100 mM Tris-HCl buffer, PVP K17 (1%), NaCl (0.9%) | |
| | -142 (PHP) | GLP-1 (180 mg/mL), Kolliphor EL (0.1%), Proline (3%), AF-647 (0.1 mg/mL) in 100 mM Tris-HCl buffer, PVP K17 (1%) | |
| | -136 (PPS) | GLP-1 (180 mg/mL), Kolliphor EL (0.1%), Proline (0.75%), AF-647 (0.1 mg/mL) in 100 mM Tris-HCl buffer, PVP K17 (1%), NaCl (0.9%) | |
| | -136 (PHP) | GLP-1 (180 mg/mL), Kolliphor EL (0.1%), Proline (3%), AF-647 (0.1 mg/mL) in 100 mM Tris-HCl buffer, PVP K17 (1%) | |
| 23B | -024 | GLP-1 (171 mg/mL), PVP K17 (1%), Arginine-HCl (1.37%), AF-647 (0.1 mg/mL) in 100 mM MOPS buffer | |
| | -027 | GLP-1 (171 mg/mL), PVP K17 (2.25%), Arginine-HCl (0.61%), AF-647 (0.1 mg/mL) in 100 mM MOPS buffer | |
| | -027 | GLP-1 (171 mg/mL), PVP K17 (2.25%), Arginine-HCl (0.61%), | |

TABLE 17-continued

| FIG. No. | Group name | Formulation conditions included (Tip) | Formulation conditions included (Base) |
|---|---|---|---|
| | | AF-647 (0.1 mg/mL) in 100 mM MOPS buffer | |
| | -031 | GLP-1 (171 mg/mL), PVP K17 (1%), Arginine-HCl (1.37%), AF-647 (0.1 mg/mL) in 100 mM MOPS buffer | |
| | -031 | GLP-1 (171 mg/mL), PVP K17 (1%), Arginine-HCl (1.37%), AF-647 (0.1 mg/mL) in 100 mM MOPS buffer | |
| | -038 | GLP-1 (171 mg/mL), PVP K17 (1%), Arginine-HCl (1.37%), AF-647 (0.1 mg/mL) in 100 mM MOPS buffer | |
| | -060 | GLP-1 (180 mg/mL), PVP K17 (1% w/v), Kolliphor EL (0.1% w/v), Arginine-HCl (1.37%), AF-647 (0.1 mg/mL) in 100 mM MOPS buffer | |
| | -105 (PPS) | GLP-1 (180 mg/mL), Kolliphor EL (0.1%), Proline (0.75%), AF-647 (0.1 mg/mL) in 100 mM Tris-HCl buffer, PVP K17 (1%), NaCl (0.9%) | |
| | -109 (PPS) | GLP-1 (180 mg/mL), Kolliphor EL (0.1%), Proline (0.75%), AF-647 (0.1 mg/mL) in 100 mM Tris-HCl buffer, PVP K17 (1%), NaCl (0.9%) | |
| | -109 (PHP) | GLP-1 (180 mg/mL), Kolliphor EL (0.1%), Proline (3%), AF-647 (0.1 mg/mL) in 100 mM Tris-HCl buffer, PVP K17 (1%) | |
| | -142 (PPS) | GLP-1 (180 mg/mL), Kolliphor EL (0.1%), Proline (0.75%), AF-647 (0.1 mg/mL) in 100 mM Tris-HCl buffer, PVP K17 (1%), NaCl (0.9%) | |
| | -142 (PHP) | GLP-1 (180 mg/mL), Kolliphor EL (0.1%), Proline (3%), AF-647 (0.1 mg/mL) in 100 mM Tris-HCl buffer, PVP K17 (1%) | |
| | -136 (PPS) | GLP-1 (180 mg/mL), Kolliphor EL (0.1%), Proline (0.75%), AF-647 (0.1 mg/mL) in 100 mM Tris-HCl buffer, PVP K17 (1%), NaCl (0.9%) | |
| | -136 (PHP) | GLP-1 (180 mg/mL), Kolliphor EL (0.1%), Proline (3%), AF-647 (0.1 mg/mL) in 100 mM Tris-HCl buffer, PVP K17 (1%) | |
| 24 | -013 | GLP-1 (192 mg/mL) in DI-water | |
| | -016 | GLP-1 (183 mg/mL), AF-647 (0.1 mg/mL) in DI-water | |
| | -019 | GLP-1 (183 mg/mL), AF-647 (0.1 mg/mL) in DI-water | |
| | -024 | GLP-1 (171 mg/mL), PVP K17 (1%), Arginine-HCl (1.37%), AF-647 (0.1 mg/mL) in 100 mM MOPS buffer | |
| | -027 | GLP-1 (171 mg/mL), PVP K17 (2.25%), Arginine-HCl (0.61%), AF-647 (0.1 mg/mL) in 100 mM MOPS buffer | |
| | -027 | GLP-1 (171 mg/mL), PVP K17 (2.25%), Arginine-HCl (0.61%), AF-647 (0.1 mg/mL) in 100 mM MOPS buffer | |
| | -031 | GLP-1 (171 mg/mL), PVP K17 (1%), Arginine-HCl (1.37%), AF-647 (0.1 mg/mL) in 100 mM MOPS buffer | |

TABLE 17-continued

| FIG. No. | Group name | Formulation conditions included (Tip) | Formulation conditions included (Base) |
|---|---|---|---|
| | −031 | GLP-1 (171 mg/mL), PVP K17 (1%), Arginine-HCl (1.37%), AF-647 (0.1 mg/mL) in 100 mM MOPS buffer | |
| | −038 | GLP-1 (171 mg/mL), PVP K17 (1%), Arginine-HCl (1.37%), AF-647 (0.1 mg/mL) in 100 mM MOPS buffer | |
| | −042 | GLP-1 (180 mg/mL), PVP K17 (1%), Arginine-HCl (1.37%), AF-647 (0.1 mg/mL) in 100 mM MOPS buffer | |
| | −060 | GLP-1 (180 mg/mL), PVP K17 (1% w/v), Kolliphor EL (0.1% w/v), Arginine-HCl (1.37%), AF-647 (0.1 mg/mL) in 100 mM MOPS buffer | |
| | −105 (PPS) | GLP-1 (180 mg/mL), Kolliphor EL (0.1%), Proline (0.75%), AF-647 (0.1 mg/mL) in 100 mM Tris-HCl buffer, PVP K17 (1%), NaCl (0.9%) | |
| | −105 (PHP) | GLP-1 (180 mg/mL), Kolliphor EL (0.1%), Proline (3%), AF-647 (0.1 mg/mL) in 100 mM Tris-HCl buffer, PVP K17 (1%) | |
| | −109 (PPS) | GLP-1 (180 mg/mL), Kolliphor EL (0.1%), Proline (0.75%), AF-647 (0.1 mg/mL) in 100 mM Tris-HCl buffer, PVP K17 (1%), NaCl (0.9%) | |
| | −109 (PHP) | GLP-1 (180 mg/mL), Kolliphor EL (0.1%), Proline (3%), AF-647 (0.1 mg/mL) in 100 mM Tris-HCl buffer, PVP K17 (1%) | |
| | −142 (PPS) | GLP-1 (180 mg/mL), Kolliphor EL (0.1%), Proline (0.75%), AF-647 (0.1 mg/mL) in 100 mM Tris-HCl buffer, PVP K17 (1%), NaCl (0.9%) | |
| | −142 (PHP) | GLP-1 (180 mg/mL), Kolliphor EL (0.1%), Proline (3%), AF-647 (0.1 mg/mL) in 100 mM Tris-HCl buffer, PVP K17 (1%) | |
| | −136 (PPS) | GLP-1 (180 mg/mL), Kolliphor EL (0.1%), Proline (0.75%), AF-647 (0.1 mg/mL) in 100 mM Tris-HCl buffer, PVP K17 (1%), NaCl (0.9%) | |
| | −136 (PHP) | GLP-1 (180 mg/mL), Kolliphor EL (0.1%), Proline (3%), AF-647 (0.1 mg/mL) in 100 mM Tris-HCl buffer, PVP K17 (1%) | |
| 25C | Form 1 60 MN | GLP-1 (180 mg/mL), Kolliphor EL (0.1%), Proline (0.75%), AF-647 (0.1 mg/mL) in 100 mM Tris-HCl buffer, PVP K17 (1%), NaCl (0.9%) | |
| | Form 1 90 MN | GLP-1 (180 mg/mL), Kolliphor EL (0.1%), Proline (0.75%), AF-647 (0.1 mg/mL) in 100 mM Tris-HCl buffer, PVP K17 (1%), NaCl (0.9%) | |
| | Form 2 60 MN | GLP-1 (180 mg/mL), Kolliphor EL (0.1%), Proline (3%), AF-647 (0.1 mg/mL) in 100 mM Tris-HCl buffer, PVP K17 (1%) | |
| 26A | Form 1 or Form 1 61 MN | GLP-1 (180 mg/mL), Kolliphor EL (0.1%), Proline (0.75%), AF-647 (0.1 mg/mL) in 100 mM Tris-HCl buffer, PVP K17 (1%), NaCl (0.9%) | |

TABLE 17-continued

| FIG. No. | Group name | Formulation conditions included (Tip) | Formulation conditions included (Base) |
|---|---|---|---|
| | Form 2 or Form 2 61 MN | GLP-1 (180 mg/mL), Kolliphor EL (0.1%), Proline (3%), AF-647 (0.1 mg/mL) in 100 mM Tris-HCl buffer, PVP K17 (1%) | |
| | SQ or SQ injection | GLP-1 (1.1 mg/mL) in 10 mM Tri-HCl buffer | |
| 26B | MAP Formulation 1 | GLP-1 (180 mg/mL), Kolliphor EL (0.1%), Proline (0.75%), AF-647 (0.1 mg/mL) in 100 mM Tris-HCl buffer, PVP K17 (1%), NaCl (0.9%) | |
| | MAP Formulation 2 | GLP-1 (180 mg/mL), Kolliphor EL (0.1%), Proline (3%), AF-647 (0.1 mg/mL) in 100 mM Tris-HCl buffer, PVP K17 (1%) | |
| 26C | Form 1 61 MN | GLP-1 (180 mg/mL), Kolliphor EL (0.1%), Proline (0.75%), AF-647 (0.1 mg/mL) in 100 mM Tris-HCl buffer, PVP K17 (1%), NaCl (0.9%) | |
| | Form 2 61 MN | GLP-1 (180 mg/mL), Kolliphor EL (0.1%), Proline (3%), AF-647 (0.1 mg/mL) in 100 mM Tris-HCl buffer, PVP K17 (1%) | |
| | SQ injection | GLP-1 (1.1 mg/mL) in 10 mM Tri-HCl buffer | |
| 27 | Group 1 SC | GLP-1 (1.1 mg/mL) in 10 mM Tri-HCl buffer | |
| | Group 2 MAP Form 1 | GLP-1 (180 mg/mL), Kolliphor EL (0.1%), Proline (0.75%), AF-647 (0.1 mg/mL) in 100 mM Tris-HCl buffer, PVP K17 (1%), NaCl (0.9%) | |
| | MAP Form 2 | GLP-1 (180 mg/mL), Kolliphor EL (0.1%), Proline (3%), AF-647 (0.1 mg/mL) in 100 mM Tris-HCl buffer, PVP K17 (1%) | |
| 28A | Form 2 61 MN or MAP (61-20) | GLP-1 (180 mg/mL), Kolliphor EL (0.1%), Proline (3%), AF-647 (0.1 mg/mL) in 100 mM Tris-HCl buffer, PVP K17 (1%) | |
| | Form 2 41 MN or MAP (41-30) | GLP-1 (180 mg/mL), Kolliphor EL (0.1%), Proline (3%), AF-647 (0.1 mg/mL) in 100 mM Tris-HCl buffer, PVP K17 (1%) | |
| | SQ injection | GLP-1 (1.1 mg/mL) in 10 mM Tri-HCl buffer | |
| 30 | VA64 | HA mRNA-LNP (0.413 mg/ml), 1% VA64, 10% sucrose, 1X TE buffer | 0.5% PVA, 60% PVP K17, 1X TE buffer |
| 30 | VA64 + 4% Arginine | HA mRNA-LNP (0.413 mg/ml), 1% VA64, 4% arginine, 10% sucrose, 1X TE buffer | 0.5% PVA, 60% PVP K17, 1X TE buffer |
| 30 | PVA/ PVP/Fib | HA mRNA-LNP (0.413 mg/ml), 1% PVA 4-88, 5% PVP K17, 0.25% fibroin (B.R. lot), 10% sucrose, 1X TE buffer | 0.5% PVA, 60% PVP K17, 1X TE buffer |
| 31A-31B | 0.1 ug IM | HA mRNA-LNP (0.1 ug) diluted in PBS | N/A |
| 31A-31B | 1 ug IM | HA mRNA-LNP (1 ug) diluted in PBS | N/A |
| 31A-31B | 0.1 ug ID | HA mRNA-LNP (0.1 ug) diluted in PBS | N/A |
| 31A-31B | 1 ug ID | HA mRNA-LNP (1 ug) diluted in PBS | N/A |
| 31A-31B | MAP 1 | HA mRNA-LNP (0.413 mg/ml), 1% VA64, 10% sucrose, 1X TE buffer | 0.5% PVA, 60% PVP K17, 1X TE buffer |

TABLE 17-continued

| FIG. No. | Group name | Formulation conditions included (Tip) | Formulation conditions included (Base) |
|---|---|---|---|
| 31A-31B | MAP 2 | HA mRNA-LNP (0.413 mg/ml), 1% VA64, 4% arginine, 10% sucrose, 1X TE buffer | 0.5% PVA, 60% PVP K17, 1X TE buffer |
| 31A-31B | MAP 3 | HA mRNA-LNP (0.413 mg/ml), 1% PVA 4-88, 5% PVP K17, 0.25% fibroin (B.R. lot), 10% sucrose, 1X TE buffer | 0.5% PVA, 60% PVP K17, 1X TE buffer |
| 35A-35B | 1-Luc | Luciferase mRNA-LNP (0.413 mg/ml), 1% VA64, 10% sucrose, 1X TE buffer | 0.5% PVA, 60% PVP K17, 1X TE buffer |
| 35A-35B | 1-HA | HA mRNA-LNP (0.413 mg/ml), 1% VA64, 10% sucrose, 1X TE buffer | 0.5% PVA, 60% PVP K17, 1X TE buffer |
| 35A-35B | 2-Luc | Luciferase mRNA-LNP (0.413 mg/ml), 1% PVA 4-88, 5% PVP K17, 0.1% fibroin (B.R. lot), 10% sucrose, 1X TE buffer | 0.5% PVA, 60% PVP K17, 1X TE buffer |
| 35A-35B | 2-HA | HA mRNA-LNP (0.413 mg/ml), 1% PVA 4-88, 5% PVP K17, 0.1% fibroin (B.R. lot), 10% sucrose, 1X TE buffer | 0.5% PVA, 60% PVP K17, 1X TE buffer |
| 36A-36B | A | Luciferase mRNA-LNP (0.413 mg/ml), 1% PVA 4-88,5% PVP K17, 10% sucrose, 1X TE buffer | 17.7% PVA, 17.7% PVP K17, 17.7% sucrose |
| 36A-36B | B | Luciferase mRNA-LNP (0.413 mg/ml), 0.25% Fibroin, 1% PVA 4-88, 5% PVP K17, 10% sucrose, 1X TE buffer | 17.7% PVA, 17.7% PVP K17, 17.7% sucrose |
| 36A-36B | C | Luciferase mRNA-LNP (0.413 mg/ml), 0.25% Fibroin, 1% PVA 4-88, 5% PVP K17, 10% sucrose, 1X TE buffer | 0.5% PVA 4-88, 50% PVP K12, 1X TE buffer |
| 36A-36B | D | Luciferase mRNA-LNP (0.413 mg/ml), 0.25% Fibroin, 1% PVA 4-88, 5% PVP K17, 10% sucrose, 1X TE buffer | 0.5% PVA 4-88, 50% PVP K12, 1X TE buffer |
| 36A-36B | E | Luciferase mRNA-LNP (0.413 mg/ml), 0.25% Fibroin, 1% PVA 4-88, 5% PVP K17, 10% sucrose, 1X TE buffer | 0.5% PVA 4-88, 50% PVP K12, 1X TE buffer |
| 37 | MAP | Luciferase mRNA-LNP (0.413 mg/ml), 1% PVA 4-88, 5% PVP K17, 10% sucrose, 1X TE buffer | 17.7% PVA, 17.7% PVP K17, 17.7% sucrose (fluorescently labeled with AlexaFluor 488 NHS ester) |
| 38 | IM | Luciferase mRNA-LNP (1 ug) diluted in PBS | N/A |
| 38 | MAP | Luciferase mRNA-LNP (0.413 mg/ml), 1% PVA 4-88, 5% PVP K17, 0.1% Fibroin (B.R. Lot), 10% Sucrose, 1X TE Buffer | 0.5% PVA 4-88, 50% PVP K17, 1X TE buffer |
| 39 | Liquid | HA mRNA-LNP in 10% sucrose, 25 mM Tris-HCl | N/A |
| 39 | MAP | HA mRNA-LNP (0.413 mg/ml), 1% VA64, 0.25% Fibroin (B.R. lot), 10% sucrose, 1X TE buffer | 0.5% PVA 4-88, 50% PVP K17, 1X TE buffer |

TABLE 18

| Exp. No. | Formulation |
|---|---|
| GLP-060 | 1% PVP K17, 1.37% Arg-HCl, in 100 mM MOPS (pH 7.5) +0.1% Kolliphor EL with 0.1 mg/mL AF-647 + ~180 mg/mL NN GLP-1 |
| GLP-060 | 1% PVP K17, 1.37% Arg-HCl, in 100 mM MOPS (pH 7.5) +0.1% Kolliphor EL with 0.1 mg/mL AF-647 + ~180 mg/mL AR GLP-1 |
| GLP-068 | Control: 180 mg/mL GLP-1, 1% PVP K17, 1.37% Arg, 0.1% AF-647 dye, 0.1% Kolliphor EL in 100 mM MOPS |
| GLP-068 | High: 225 mg/mL GLP-1, 1% PVP K17, 1.37% Arg, 0.1% AF-647 dye, 0.1% Kolliphor EL in 100 mM MOPS |
| GLP-068 | Tris: 180 mg/mL GLP-1, 1% PVP K17, 1.37% Arg, 0.1% AF-647 dye, 0.1% Kolliphor EL in 100 mM Tris-HCl (pH 8.2) |
| GLP-070 Tip Only | Low Sucrose: 180 mg/mL GLP-1 (60 mM), 1% PVP K17, 1.37% Arg, 0.1% AF-647 dye, 0.1% Kolliphor EL in 100 mM MOPS with 2% Sucrose |
| GLP-070 Tip Only | High Sucrose: 180 mg/mL GLP-1 (60 mM), 1% PVP K17, 1.37% Arg, 0.1% AF-647 dye, 0.1% Kolliphor EL in 100 mM MOPS with 10% Sucrose |
| GLP-070 Tip Only | NaCl: 180 mg/mL GLP-1 (60 mM), 1% PVP K17, 1.37% Arg, 0.1% AF-647 dye, 0.1% Kolliphor EL in 100 mM MOPS with 0.9% NaCl |
| GLP-071 Tip Only | Low MgCl2: 180 mg/mL GLP-1 (60 mM), 1% PVP K17, 1.37% Arg, 0.1% AF-647 dye, 0.1% Kolliphor EL in 100 mM MOPS with 1% MgCl2 |
| GLP-071 Tip Only | Lower MgCl2: 180 mg/mL GLP-1 (60 mM), 1% PVP K17, 1.37% Arg, 0.1% AF-647 dye, 0.1% Kolliphor EL in 100 mM MOPS with 0.5% MgCl2 |
| GLP-071 Tip Only | Sorbitol: 180 mg/mL GLP-1 (60 mM), 1% PVP K17, 1.37% Arg, 0.1% AF-647 dye, 0.1% Kolliphor EL in 100 mM MOPS with 5% Sorbitol |
| GLP-073 | Control-PVP: 180 mg/mL GLP-1, 1% PVP K17, 1.37% Arg, 0.1% AF-647 dye, 0.1% Kolliphor EL in 100 mM MOPS |
| GLP-073 | Dextran: 180 mg/mL GLP-1, Dextran-40 (3%), 1.37% Arg, 0.1% AF-647 dye, 0.1% Kolliphor EL in 100 mM MOPS |
| GLP-073 | PVP K17 High: 180 mg/mL GLP-1, PVP K17 (6%), 1.37% Arg, 0.1% AF-647 dye, 0.1% Kolliphor EL in 100 mM Tris-HCl (pH 8.2) |
| GLP-077 | Control w/Arg: 180 mg/mL GLP-1, 1% PVP K17, 1.37% Arg, 0.1% AF-647 dye, 0.1% Kolliphor EL in 100 mM MOPS |
| GLP-077 | Proline: 180 mg/mL GLP-1, 1% PVP K17, 0.75% Proline, 0.1% AF-647 dye, 0.1% Kolliphor EL in 100 mM MOPS |
| GLP-077 | Histidine: 180 mg/mL GLP-1, 1% PVP K17, 1% Histidine, 0.1% AF-647 dye, 0.1% Kolliphor EL in 100 mM MOPS |
| GLP-078 | Low PVP with Salt: 180 mg/mL GLP-1, 1% PVP K17, 1.37% Arg, 0.1% AF-647 dye, 0.1% Kolliphor EL in 100 mM MOPS + 0.9% NaCl |
| GLP-078 | Tris: 180 mg/mL GLP-1, 1% PVP K17, 1.37% Arg, 0.1% AF-647 dye, 0.1% Kolliphor EL in 100 mM Tris + 0.9% NaCl |
| GLP-078 | Dextran: 180 mg/mL GLP-1, 3% Dextran, 1.37% Arg, 0.1% AF-647 dye, 0.1% Kolliphor EL in 100 mM MOPS + 0.9% NaCl |
| GLP-080 | Control w/NaCl: 180 mg/mL GLP-1, 1% PVP K17, 1.37% Arg, 0.1% AF-647 dye, 0.1% Kolliphor EL, 0.9% NaCl in 100 mM MOPS (NN GLP-1) |
| GLP-080 | Tween20: 180 mg/mL GLP-1, 1% PVP K17, 1.37% Arg, 0.1% AF-647 dye, 0.5% Tween 20, 0.9% NaCl in 100 mM MOPS (NN GLP-1) |
| GLP-080 | Diluted: Control Formulation Diluted 2x (NN GLP-1) |
| GLP-081 | Control w/Salt, Tris: 180 mg/mL GLP-1, 1% PVP K17, 1.37% Arg, 0.1% AF-647 dye, 0.1% Kolliphor EL, 0.9% NaCl in 100 mM Tris |
| GLP-081 | Proline: 180 mg/mL GLP-1, 1% PVP K17, 0.75% Proline, 0.1% AF-647 dye, 0.1% Kolliphor EL, 0.9% NaCl in 100 mM Tris |
| GLP-081 | Dextran: 180 mg/mL GLP-1, 3% Dextran, 0.75% Proline, 0.1% AF-647 dye, 0.1% Kolliphor EL, 0.9% NaCl in 100 mM Tris |
| GLP-086 | Repeat-081: 180 mg/mL GLP-1, 1% PVP K17, 0.75% Proline, 0.1% AF-647 dye, 0.1% Kolliphor EL, 0.9% NaCl in 100 mM Tris |
| GLP-086 | ProNoSalt: 180 mg/mL GLP-1, 1% PVP K17, 0.75% Proline, 0.1% AF-647 dye, 0.1% Kolliphor EL, 0% NaCl in 100 mM Tris |

TABLE 18-continued

| Exp. No. | Formulation |
|---|---|
| GLP-086 | HiProNoSalt: 180 mg/mL GLP-1, 1% PVP K17, 3% Proline, 0.1% AF-647 dye, 0.1% Kolliphor EL, 0% NaCl in 100 mM Tris |
| GLP-095 | −086 repeat: 180 mg/mL GLP-1, 1% PVP K17, 3% Proline, 0.1% AF-647 dye, 0.1% Kolliphor EL, 0% NaCl in 100 mM Tris |

TABLE 18-continued

| Exp. No. | Formulation |
|---|---|
| GLP-095 | −081 repeat: 180 mg/mL GLP-1, 1% PVP K17, 0.75% Proline, 0.1% AF-647 dye, 0.1% Kolliphor EL, 0.9% NaCl in 100 mM Tris |
| GLP-095 | Hiload:-081 repeat: 275 mg/mL GLP-1, 1% PVP K17, 0.75% Proline, 0.1% AF-647 dye, 0.1% Kolliphor EL, 0.9% NaCl in 100 mM Tris |

TABLE 19

| FIG. | Group Label | Antigen | Tip Formulation | Base Formulation | Tip Drying Conditions | Base Drying Conditions |
|---|---|---|---|---|---|---|
| 30 | VA64 | HA mRNA-LNP | 1% VA64, 10% sucrose, 1X TE buffer | 0.5% PVA, 60% PVP K17, 1X TE buffer | 85% RH 30 minutes, 60% RH 30 min at room temperature to 4 C. with desiccant overnight | 85% RH 5 minutes, 60% RH 60 minutes at room temperature to 4 C. with desiccant 24 hrs |
| 30 | VA64 + 4% Arginine | HA mRNA-LNP | 1% VA64, 4% arginine, 10% sucrose, 1X TE buffer | 0.5% PVA, 60% PVP K17, 1X TE buffer | 85% RH 30 minutes, 60% RH 30 min at room temperature to 4 C. with desiccant overnight | 85% RH 5 minutes, 60% RH 60 minutes at room temperature to 4 C. with desiccant 24 hrs |
| 30 | PVA/PVP/Fib | HA mRNA-LNP | 1% PVA 4-88, 5% PVP K17, 0.25% fibroin (B.R. lot), 10% sucrose, 1X TE buffer | 0.5% PVA, 60% PVP K17, 1X TE buffer | 85% RH 30 minutes, 60% RH 30 min at room temperature to 4 C. with desiccant overnight | 85% RH 5 minutes, 60% RH 60 minutes at room temperature to 4 C. with desiccant 24 hrs |
| 31A-31B | 0.1 ug IM | HA mRNA-LNP | N/A | N/A | N/A | N/A |
| 31A-31B | 1 ug IM | HA mRNA-LNP | N/A | N/A | N/A | N/A |
| 31A-31B | 0.1 ug ID | HA mRNA-LNP | N/A | N/A | N/A | N/A |
| 31A-31B | 1 ug ID | HA mRNA-LNP | N/A | N/A | N/A | N/A |
| 31A-31B | MAP 1 | HA mRNA-LNP | 1% VA64, 10% sucrose, 1X TE buffer | 0.5% PVA, 60% PVP K17, 1X TE buffer | 85% RH 30 minutes, 60% RH 30 minutes at room temperature to 4 C. with desiccant overnight | 85% RH 5 minutes, 60% RH 60 minutes at room temperature to 4 C. with desiccant overnight |
| 31A-31B | MAP 2 | HA mRNA-LNP | 1% VA64, 4% arginine, 10% sucrose, 1X TE buffer | 0.5% PVA, 60% PVP K17, 1X TE buffer | 85% RH 30 minutes, 60% RH 30 minutes at room temperature to 4 C. with desiccant overnight | 85% RH 5 minutes, 60% RH 60 minutes at room temperature to 4 C. with desiccant overnight |
| 31A-31B | MAP 3 | HA mRNA-LNP | 1% PVA 4-88, 5% PVP K17, 0.25% fibroin (B.R. lot), 10% sucrose, 1X TE buffer | 0.5% PVA, 60% PVP K17, 1X TE buffer | 85% RH 30 minutes, 60% RH 30 minutes at room temperature to 4 C. with desiccant overnight | 85% RH 5 minutes, 60% RH 60 minutes at room temperature to 4 C. with desiccant overnight |
| 35A-35B | 1 - Luc | Luciferase mRNA-LNP | 1% VA64, 10% sucrose, 1X TE buffer | 0.5% PVA, 60% PVP K17, 1X TE buffer | 85% RH 30 minutes, 60% RH 30 minutes at room temperature to 4 C. with desiccant overnight | 85% RH 5 minutes, 60% RH 60 minutes at room temperature to 4 C. with desiccant overnight |
| 35A-35B | 1 - HA | HA mRNA-LNP | 1% VA64, 10% sucrose, 1X TE buffer | 0.5% PVA, 60% PVP K17, 1X TE buffer | 85% RH 30 minutes, 60% RH 30 minutes at room temperature to 4 C. with desiccant overnight | 85% RH 5 minutes, 60% RH 60 minutes at room temperature to 4 C. with desiccant overnight |
| 35A-35B | 2 - Luc | Luciferase mRNA-LNP | 1% PVA 4-88, 5% PVP K17, 0.1% fibroin (B.R. lot), 10% sucrose, 1X TE buffer | 0.5% PVA, 60% PVP K17, 1X TE buffer | 85% RH 30 minutes, 60% RH 30 minutes at room temperature to 4 C. with desiccant overnight | 85% RH 5 minutes, 60% RH 60 minutes at room temperature to 4 C. with desiccant overnight |
| 35A-35B | 2 - HA | HA mRNA-LNP | 1% PVA 4-88, 5% PVP K17, 0.1% fibroin (B.R. lot), 10% sucrose, 1X TE buffer | 0.5% PVA, 60% PVP K17, 1X TE buffer | 85% RH 30 minutes, 60% RH 30 minutes at room temperature to 4 C. with desiccant overnight | 85% RH 5 minutes, 60% RH 60 minutes at room temperature to 4 C. with desiccant overnight |

TABLE 19-continued

| FIG. | Group Label | Antigen | Tip Formulation | Base Formulation | Tip Drying Conditions | Base Drying Conditions |
|---|---|---|---|---|---|---|
| 36A-36B | A | Luciferase mRNA-LNP | 1% PVA 4-88,5% PVP K17, 10% sucrose, 1X TE buffer | 17.7% PVA, 17.7% PVP K17, 17.7% sucrose | 85% RH 30 minutes, 60% RH 30 minutes at room temperature to 10% RH at room temperature overnight | 85% RH 5 minutes, 60% RH 30 minutes at room temperature to 10% RH at room temperature overnight |
| 36A-36B | B | Luciferase mRNA-LNP | 0.25% Fibroin, 1% PVA 4-88, 5% PVP K17, 10% sucrose, 1X TE buffer | 17.7% PVA, 17.7% PVP K17, 17.7% sucrose | 85% RH 30 minutes, 60% RH 30 minutes at room temperature to 10% RH at room temperature overnight | 85% RH 5 minutes, 60% RH 30 minutes at room temperature to 10% RH at room temperature overnight |
| 36A-36B | C | Luciferase mRNA-LNP | 0.25% Fibroin, 1% PVA 4-88, 5% PVP K17, 10% sucrose, 1X TE buffer | 0.5% PVA 4-88, 50% PVP K12, 1X TE buffer | 85% RH 30 minutes, 60% RH 30 minutes at room temperature to 10% RH at room temperature overnight | 85% RH 5 minutes, 60% RH 30 minutes at room temperature to 10% RH at room temperature overnight |
| 36A-36B | D | Luciferase mRNA-LNP | 0.25% Fibroin, 1% PVA 4-88, 5% PVP K17, 10% sucrose, 1X TE buffer | 0.5% PVA 4-88, 50% PVP K12, 1X TE buffer | 4 C. with desiccant overnight | 85% RH 5 minutes, 60% RH 30 minutes at room temperature to 10% RH at room temperature overnight |
| 36A-36B | E | Luciferase mRNA-LNP | 0.25% Fibroin, 1% PVA 4-88, 5% PVP K17, 10% sucrose, 1X TE buffer | 0.5% PVA 4-88, 50% PVP K12, 1X TE buffer | 4 C. with desiccant overnight | 4 C. with desiccant overnight |
| 37 | MAP | Luciferase mRNA-LNP (fluorescently labeled with 2.5 mg/ml DiD) | 1% PVA 4-88,5% PVP K17, 10% sucrose, 1X TE buffer | 17.7% PVA, 17.7% PVP K17, 17.7% sucrose (fluorescently labeled with AlexaFluor 488 NHS ester) | 85% RH 30 minutes, 60% RH 30 minutes at room temperature to 10% RH at room temperature overnight | 85% RH 5 minutes, 60% RH 60 minutes at room temperature to 10% RH at room temperature overnight |
| 38 | IM | Luciferase mRNA-LNP | N/A | N/A | N/A | N/A |
| 38 | MAP | Luciferase mRNA-LNP | 1% PVA 4-88, 5% PVP K17, 0.1% Fibroin (B.R. Lot), 10% Sucrose, 1X TE Buffer | 0.5% PVA 4-88, 50% PVP K17, 1X TE buffer | 85% RH 30 minutes, 60% RH 30 minutes at room temperature to 4 C. with desiccant overnight | 85% RH 5 minutes, 60% RH 60 minutes at room temperature to 4 C. with desiccant overnight |
| 39 | Liquid | HA mRNA-LNP | N/A | N/A | N/A | N/A |
| 39 | MAP | HA mRNA-LNP | 1% VA64, 0.25% Fibroin (B.R. lot), 10% sucrose, 1X TE buffer | 0.5% PVA 4-88, 50% PVP K17, 1X TE buffer | 85% RH 30 minutes, 60% RH 30 minutes at room temperature to 4 C. with desiccant overnight | 85% RH 5 minutes, 60% RH 60 minutes at room temperature to 4 C. with desiccant overnight |

45

In certain instances, the fibroin (B.R. lot) refers to a 180 minute boil benchtop fibroin preparation.

TABLE 20

| | | | | | | Total | |
| mRNA-LNP formulation used for both HA and luciferase mRNA-LNP antigen | | | | | | | |
| | Lipid mol % | | | Ionizable | | Lipid/mRNA | |
| Ionizable CKK-E12 | Cholesterol | DOPE | C14PEG2K | lipid/mRNA (w/w) | N/P Ratio | mass ratio % w/w | Final Buffer |
| 35 | 46.5 | 16 | 2.5 | 20 | 13 | 41 | 10% sucrose in 25 mM Tris HCl, pH 7.5 |

TABLE 21

Longitudinal Deployment Data Summary

| Lot Number (Group) | Array Size | Applicator (Configuration) | Energy/Needle [mJ] | Piston Velocity [m/s] | Backing (Adhesive) | Tip Fill Volume [nL] | Dose per Needle [nL] | Tip Length [um] | Pre-deployment needle height [um] | Air Gap [um] | Penetration Depth (Primary-Air Gap) [um] | Avg % PD-IVR By RP-HPLC | Dose delivered per needle [nL] | Instron - Force [N] | FF/ Needle [N] | Instron - YM [N/mm] | Cracks in base PD (Y/N) |
|---|---|---|---|---|---|---|---|---|---|---|---|---|---|---|---|---|---|
| GLP-006 (GLP-006) | 121 | Clinical (12 lbf/in) | 1.92 | 7 | 1509 | 20 | | 386 | 929 | 462 | 467 | | | | | | Y |
| GLP-013 (20 nL) | 121 | Clinical (12 lbf/in) | 1.92 | 7 | 1509 | 20 | | 385 | 910 | 516 | 297 | 63% | | | | | |
| GLP-013 (30 nL) | 121 | Clinical (12 lbf/in) | 1.92 | 7 | 1509 | 30 | | 442 | 903 | 485 | 348 | 57% | | 67 | | 382 | |
| GLP-013 (40 nL) | 121 | Clinical (12 lbf/in) | 1.92 | 7 | 1509 | 40 | | 598 | 902 | 482 | 313 | 76% | | | | | |
| GLP-013 (30 nL277) | 277 | DG15 (ISA-010: 22x22_3_S1287_3g) | 1.59 | 12.5 | 1509 | 30 | | 490 | 926 | 531 | 288 | 49% | | | | | |
| GLP-016 (10 nL) | 121 | Clinical (12 lbf/in) | 1.92 | 7 | 1509 | | | 352 | | | | | | | | | Y |
| GLP-016 (20 nL) | 121 | Clinical (12 lbf/in) | 1.92 | 7 | 1509 | 20 | | 444 | 907 | 407 | 500 | 67% | | 29 | | 219 | Y |
| GLP-016 (30 nL) | 121 | Clinical (12 lbf/in) | 1.92 | 7 | 1509 | 30 | | 485 | 905 | 425 | 479 | 61% | | 44 | | 301 | Y |
| GLP-016 (20 nL277) | 277 | Clinical (ISA-010: 22x22_3_S1287_3g) | 1.59 | 12.5 | 1509 | 20 | | 407 | 919 | 479 | 440 | 43% | | | | | Y |
| GLP-019 (Control) | 121 | Clinical (12 lbf/in) | 1.92 | 7 | 1509 | 20 | | 423 | 932 | 262 | 671 | 12% | | 29 | | 230 | Y |
| GLP-019 (SDB) | 121 | Clinical (12 lbf/in) | 1.92 | 7 | 1509 | 20 | | | 907 | 207 | 700 | 17% | | 35 | | 254 | Y |
| GLP-019 (PVP) | 121 | Clinical (12 lbf/in) | 1.92 | 7 | 1509 | 20 | | 438 | 943 | 263 | 680 | 6% | | 35 | | 237 | Y |
| GLP-019 (PVA) | 121 | | | | 1509 | 20 | | 370 | | | | | | 50 | | 352 | |
| GLP-024 (Arg) | 121 | Clinical (12 lbf/in) | 1.92 | 7 | 1510 | 20 | | 412 | 902 | 379 | 524 | 100% | | | | | Y |
| GLP-024 (Arg 30 nl) | 121 | Clinical (12 lbf/i7) | 1.92 | 7 | 1510 | 30 | | 486 | 922 | 284 | 638 | 20% | | | | | Y (smashed) |
| GLP-024 (PVP) | 121 | Clinical (12 lbf/in) | 1.92 | 7 | 1510 | 20 | | 395 | 894 | 326 | 568 | 26% | | | | | Y |
| GLP-024 (PVP 30 nl) | 121 | Clinical (12 lbf/in) | 1.92 | 7 | 1510 | 30 | | 448 | 894 | 374 | 521 | 41% | | | | | Y |
| GLP-024 (PVP-PB) | 121 | Clinical (12 lbf/in) | 1.92 | 7 | 1510 | 20 | | 456 | 912 | 271 | 642 | 10% | | | | | Y (smashed) |

TABLE 21-continued

Longitudinal Deployment Data Summary

| Lot Number (Group) | Array Size | Applicator (Configuration) | Energy/ Needle [mJ] | Piston Velocity [m/s] | Backing (Adhesive) | Tip Fill Volume [nL] | Dose per Needle [nL] | Tip Length [um] | Pre-deployment needle height [um] | Air Gap [um] | Penetration Depth (Primary-Air Gap) [um] | Avg % PD-IVR By RP-HPLC | Dose delivered per needle [nL] | Instron - Force [N] | FF/ Needle [N] | Instron - YM [N/mm] | Cracks in base PD (Y/N) |
|---|---|---|---|---|---|---|---|---|---|---|---|---|---|---|---|---|---|
| GLP-027 (Control (Dial)) | 121 | Clinical (12 lbf/in) | 1.92 | 7 | 1510 | 20 | | 415 | 915 | 364 | 551 | 15% | | | | | Y |
| GLP-027 (Control (Floor)) | 121 | Clinical (12 lbf/in) | 1.92 | 7 | 1510 | 20 | | 398 | 920 | 339 | 581 | 46% | | | | | Y |
| GLP-027 (PB) | 121 | Clinical (12 lbf/in) | 1.92 | 7 | 1510 | 20 | | | 892 | 265 | 627 | 31% | | | | | Y |
| GLP-027 (PB-30 nL) | 121 | Clinical (12 lbf/in) | 1.92 | 7 | 1510 | 30 | | 491 | 900 | 334 | 566 | 36% | | | | | Y |
| GLP-027 (PB277) | 277 | DG15 (22x22_0mm_S-1287_3g) | 1.95 | 14 | 1510 | 20 | | 406 | 890 | 372 | 518 | 7% | | | | | Y |
| GLP-027 (PB277-30 nL) | 277 | DG15 (22x22_0mm_S-1287_3g) | 1.95 | 14 | 1510 | 30 | | 430 | 897 | 387 | 510 | 22% | | | | | Y |
| GLP-031 (Control) | 121 | Clinical (12 lbf/in) | 1.92 | 7 | 1510 | 20 | | 429 | 891 | 383 | 509 | 18% | | | | | Y |
| GLP-031 (Control-30) | 121 | Clinical (12 lbf/in) | 1.92 | 7 | 1510 | 30 | | 480 | 896 | 340 | 556 | 24% | | | | | Y |
| GLP-031 (PB-20) | 121 | Clinical (12 lbf/in) | 1.92 | 7 | 1510 | 20 | | 407 | 894 | 382 | 512 | 25% | | | | | N |
| GLP-031 (PB-30) | 121 | Clinical (12 lbf/in) | 1.92 | 7 | 1510 | 30 | | 459 | 896 | 428 | 468 | 36% | | | | | N |
| GLP-031 (PB-20 241) | 241 | DG15 (ISA-010: 22x22_3_S1287_3g) | 1.83 | 12.5 | 1510 | 20 | | 450 | 892 | 442 | 450 | 13% | | | | | N |
| GLP-031 (PB-30 241) | 241 | DG15 (ISA-010: 22x22_3_S1287_3g) | 1.83 | 12.5 | 1510 | 30 | | 434 | 897 | 437 | 460 | 78% | | | | | N |
| GLP-031 (H2O 241) | 241 | DG15 (ISA-010: 22x22_3_S1287_3g) | 1.83 | 12.5 | 1510 | 20 | | 405 | 893 | 457 | 436 | 12% | | | | | N |
| GLP-031 (H3O 241) | 241 | DG15 (ISA-010: 22x22_3_S1287_3g) | 1.83 | 12.5 | 1510 | 30 | | 465 | 872 | 445 | 428 | 47% | | | | | N |
| GLP-038 (PB20 121) | 121 | Clinical (12 lbf/in) | 1.92 | 7 | ISA-008/ ISA-003 | 20 | | 419 | 910 | 414 | 496 | N/A | | | | | |
| GLP-038 (PB30 121) | 121 | Clinical (12 lbf/in) | 1.92 | 7 | ISA-008/ ISA-003 | 30 | | 502 | 886 | 426 | 460 | N/A | | | | | |

TABLE 21-continued

Longitudinal Deployment Data Summary

| Lot Number (Group) | Array Size | Applicator (Configuration) | Energy/ Needle [mJ] | Piston Velocity [m/s] | Backing (Adhesive) | Tip Fill Volume [nL] | Dose per Needle [nL] | Tip Length [um] | Pre-deployment needle height [um] | Air Gap [um] | Penetration Depth (Primary-Air Gap) [um] | Avg % PD-IVR By RP-HPLC | Dose delivered per needle [nL] | Instron - Force [N] | FF/ Needle [N] | Instron - YM [N/mm] | Cracks in base PD (Y/N) |
|---|---|---|---|---|---|---|---|---|---|---|---|---|---|---|---|---|---|
| GLP-038 (High30 121) | 121 | Clinical (12 lbf/in) | 1.92 | 7 | ISA-008/ ISA-003 | 30 | | 532 | 874 | 481 | 393 | N/A | | | | | Y |
| GLP-038 (PB20 241) | 241 | DG15 (ISA-010: 22x22_3_S1287_3g) | 1.83 | 12.5 | ISA-009/ ISA-007 | 20 | | 405 | 898 | 479 | 419 | 25% | | | | | Y |
| GLP-038 (PB30 241) | 241 | DG15 (ISA-010: 22x22_3_S1287_3g) | 1.83 | 12.5 | ISA-009/ ISA-007 | 30 | | 449 | 908 | 478 | 430 | 42% | | | | | Y |
| GLP-038 (H2O 241) | 241 | DG15 (ISA-010: 22x22_3_S1287_3g) | 1.83 | 12.5 | ISA-009/ ISA-007 | 20 | | 401 | 899 | 497 | 402 | 28% | | | | | Y |
| GLP-038 (H30 241) | 241 | DG15 (ISA-010: 22x22_3_S1287_3g) | 1.83 | 12.5 | ISA-009/ ISA-007 | 30 | | 483 | 893 | 530 | 363 | 44% | | | | | N |
| GLP-040 (Control) | 121 | Clinical (12 lbf/in) | 1.92 | 7 | ISA-008 | 20 | | 405 | 894 | 374 | 520 | 18% | | 59 | 0.49 | 562 | Y |
| GLP-040 | 121 | Clinical (12 lbf/in) | 1.92 | 7 | ISA-008 | 20 | | 403 | 901 | 379 | 523 | 20% | | 70 | 0.58 | 478 | Y |
| (Surfactant) GLP-040 (GLP-114 Surfactant) | 121 | | | | | | | | | | | | | 56 | 0.46 | 497 | |
| GLP-042 (17 nl ISA-009) | 241 | DG15 (ISA-010: 22x22_3_S1287_3g) | 1.83 | 12.5 | ISA-009 | 17 nL | | 382 | 916 | 516 | 400 | 26% | | 148 | 0.61 | 838 | Y |
| GLP-042 (17 nl ISA-007) | 241 | DG15 (ISA-010: 22x22_3_S1287_3g) | 1.83 | 12.5 | ISA-007 | 17 nL | | | 916 | 497 | 419 | 24% | | | | 838 | Y |
| GLP-042 (21 nl ISA-009) | 241 | DG15 (ISA-010: 22x22_3_S1287_3g) | 1.83 | 12.5 | ISA-009 | 21 nL | | 412 | 921 | 551 | 370 | 38% | | | | 838 | Y |
| GLP-042 (21 nl ISA-007) | 241 | DG15 (ISA-010: 22x22_3_S1287_3g) | 1.83 | 12.5 | ISA-007 | 21 nL | | | 925 | 536 | 389 | 36% | | | | 838 | Y |
| GLP-042 (26 nl ISA-009) | 241 | DG15 (ISA-010: 22x22_3_S1287_3g) | 1.83 | 12.5 | ISA-009 | 26 nL | | 415 | 931 | 532 | 399 | 35% | | | | 838 | Y |
| GLP-042 (26 nl ISA-007) | 241 | DG15 (ISA-010: 22x22_3_S1287_3g) | 1.83 | 12.5 | ISA-007 | 26 nL | | | 932 | 509 | 423 | 35% | | | | 838 | Y |
| GLP-060 (AR) | 121 | Clinical (12 lbf/in) | 1.92 | 7 | ISA-003 (1509) | 20 | | 415 | 885 | 455 | 430 | 21% | | 68 | 0.56 | 521 | N |

TABLE 21-continued

Longitudinal Deployment Data Summary

| Lot Number (Group) | Array Size | Applicator (Configuration) | Energy/ Needle [mJ] | Piston Velocity [m/s] | Backing (Adhesive) | Tip Fill Volume [nL] | Dose per Needle [nL] | Tip Length [um] | Pre-deployment needle height [um] | Air Gap [um] | Penetration Depth (Primary-Air Gap) [um] | Avg % PD-IVR By RP-HPLC | Dose delivered per needle [nL] | Instron - Force [N] | FF/ Needle [N] | Instron - YM [N/mm] | Cracks in base PD (Y/N) |
|---|---|---|---|---|---|---|---|---|---|---|---|---|---|---|---|---|---|
| GLP-060 (NN) | 121 | Clinical (12 lbf/in) | 1.92 | 7 | ISA-003 (1509) | 20 | | 422 | 892 | 434 | 457 | 28% | | 64 | 0.53 | 475 | N |
| GLP-061 (AR 121) | 121 | DG15 ((21x21)_0_75704_0g) | 2.5 | 16 | ISA-003 | 20 | | 415 | 885 | 340 | 544 | 24% | | 68 | 0.56 | 521 | |
| GLP-061 (AR 277) | 277 | DG15 (ISA-11: (22x22)_0_BI-69_3g) | 2.5 | 16 | ISA-007 (1509) | 20 | | 422 | 895 | 353 | 542 | 10% | | 64 | 0.23 | 475 | |
| GLP-061 (AR 277) | 277 | DG15 (ISA-11: (22x22)_0_BI-69_3g) | 2.5 | 16 | | 20 | | 379 | 891 | 373 | 518 | | | 163 | 0.59 | 1094 | |
| GLP-063 (base-only print (2 hr 10% RH LLA)) | 121 | Clinical (12 lbf/in) | 1.92 | 7 | ISA-008 | n/a - base only | | n/a - base only | 887 | 328 | 559 | n/a - base only | | 39 | 0.32 | 258 | Y |
| GLP-063 (base-only print (30% RH Overnight)) | 121 | Clinical () | 1.92 | 7 | ISA-008 | n/a - base only | | n/a - base only | 891 | 353 | 538 | n/a - base only | | 33 | 0.27 | 236 | Y |
| GLP-073 (Control) | 277 | DG15 (ISA-11: (22x22)_0_BI-69_3g) | 2.49 | 16 | 1509 | 20 | | 394 | 906 | 374 | 531 | 28% | | | | | N |
| GLP-073 (High PVP) | 277 | DG15 (ISA-11: (22x22)_0_BI-69_3g) | 2.49 | 16 | 1509 | 20 | | 389 | 898 | 394 | 505 | 17% | | | | | N |
| GLP-073 (Dextran) | 277 | DG15 (ISA-11: (22x22)_0_BI-69_3g) | 2.49 | 16 | 1509 | 20 | | 413 | 884 | 373 | 511 | 13% | | | | | N |
| GLP-077 (0.75% Proline) | 121 | DG15 ((21x21)_0_75704_0g) | 2.5 | 16 | 1509 | 20 | | 381 | 902 | 400 | 502 | 6% | | 96 | 0.79 | 602 | N |
| GLP-077 (1% Histidine) | 121 | DG15 ((21x21)_0_75704_0g) | 2.5 | 16 | 1509 | 20 | | 415 | 912 | 411 | 501 | 9% | | 104 | 0.86 | 650 | N |

TABLE 21-continued

Longitudinal Deployment Data Summary

| Lot Number (Group) | Array Size | Applicator (Configuration) | Energy/ Needle [mJ] | Piston Velocity [m/s] | Backing (Adhesive) | Tip Fill Volume [nL] | Dose per Needle [nL] | Tip Length [um] | Pre-deployment needle height [um] | Air Gap [um] | Penetration Depth (Primary-Air Gap) [um] | Avg % PD-IVR By RP-HPLC | Dose delivered per needle [nL] | Instron - Force [N] | FF/ Needle [N] | Instron - YM [N/mm] | Cracks in base PD (Y/N) |
|---|---|---|---|---|---|---|---|---|---|---|---|---|---|---|---|---|---|
| GLP-077 (Control - Arg) | 121 | DG15 ((21x21_0_75704_0g)) | 2.5 | 16 | 1509 | 20 | | | 922 | 414 | 509 | 12% | | 82 | 0.68 | 519 | N |
| GLP-078 (Low PVP) | 121 | DG15 ((21x21)_0_75704_0g) | 2.5 | 16 | ISA-003 (1509) | 20 | | 368 | 895 | 418 | 477 | 17% | | 78 | 0.64 | 578 | N |
| GLP-078 (Tris) | 121 | DG15 ((21x21)_0_75704_0g) | 2.5 | 16 | ISA-003 (1509) | 20 | | 366 | 895 | 502 | 393 | 19% | | 106 | 0.88 | 667 | N |
| GLP-078 (Dextran) | 121 | DG15 ((21x21)_0_75704_0g) | 2.5 | 16 | ISA-003 (1509) | 20 | | 368 | 902 | 477 | 425 | 13% | | 72 | 0.60 | 549 | N |
| GLP-080 (Control) | 121 | DG15 ((21x21_0_75704_0g)) | 2.5 | 16 | ISA-003 (1509) | 18 | | 358 | 892 | 411 | 481 | 8% | | 99 | 0.82 | 603 | N |
| GLP-080 (Diluted) | 121 | DG15 ((21x21)_0_75704_0g) | 2.5 | 16 | ISA-003 (1509) | 45 | | 450 | 906 | 374 | 532 | 7% | | 85 | 0.70 | 578 | N |
| GLP-080 (Tween 20) | 121 | DG15 ((21x21)_0_75704_0g) | 2.5 | 16 | ISA-003 (1509) | 18 | | 379 | 904 | 393 | 511 | 4% | | 97 | 0.80 | 591 | N |
| GLP-081 (Control + Salt + Tris) | 121 | Clinical (12 lbf/in) | 1.92 | 7 | ISA-003 (1509) | 18.5 | | 381 | 879 | 444 | 436 | 27% | | 86 | 0.71 | 645 | Y |
| GLP-081 (Proline) | 121 | Clinical (12 lbf/in) | 1.92 | 7 | ISA-003 (1509) | 18.73 | | 390 | 888 | 458 | 430 | 37% | | 100 | 0.83 | 656 | some |
| GLP-081 (Dextran) | 121 | Clinical (12 lbf/in) | 1.92 | 7 | ISA-003 (1509) | 17.38 | | 404 | 871 | 434 | 438 | 45% | | 87 | 0.72 | 594 | Y |
| GLP-081 Repeat (Control + Salt + Tris) | 121 | DG15 | | | | | | | | | | | | | | | |
| GLP-081 Repeat (Proline) | 121 | DG15 | | | | | | | | | | | | | | | |
| GLP-081 Repeat (Dextran) | 121 | DG15 | | | | | | | | | | | | | | | |
| GLP-086 (Repeat 81) | 121 | Clinical (12 lbf/in) | 1.92 | 7 | ISA-003 (1509) | 20.8 | | 381 | 929 | 305 | 624 | 15% | | 93 | 0.77 | 803 | N |
| GLP-086 (Pro No Salt) | 121 | Clinical (12 lbf/in) | 1.92 | 7 | ISA-003 (1509) | 21.25 | | 386 | 907 | 361 | 545 | 12% | | 108 | 0.90 | 851 | N |

TABLE 21-continued

Longitudinal Deployment Data Summary

| Lot Number (Group) | Array Size | Applicator (Configuration) | Energy/ Needle [mJ] | Piston Velocity [m/s] | Backing (Adhesive) | Tip Fill Volume [nL] | Dose per Needle [nL] | Tip Length [um] | Pre-deployment needle height [um] | Air Gap [um] | Penetration Depth (Primary-Air Gap) [um] | Avg % PD-IVR By RP-HPLC | Dose delivered per needle [nL] | Instron - Force [N] | FF/ Needle [N] | Instron - YM [N/mm] | Cracks in base PD (Y/N) |
|---|---|---|---|---|---|---|---|---|---|---|---|---|---|---|---|---|---|
| GLP-086 (HiPro No Salt) | 121 | Clinical (12 lbf/in) | 1.92 | 7 | ISA-003 (1509) | 19.93 | | 386 | 924 | 360 | 564 | 15% | | 62 | 0.52 | 668 | N |
| GLP-086 (GLP-114 Repeat 81) | 121 | | | | | | | | | | | | | 101 | 0.84 | 646 | |
| GLP-086 (GLP-114 HPNS) | 121 | | | | | | | | | | | | | 96 | 0.79 | 542 | |
| GLP-095 (Proline + NaCl) | 121 | DG15 (DG15(21x21)_0_ 75704_0g) | 2.5 | 16 | ISA-003 (1509) | 30 | 3.6 | 375 | 878 | 402 | 476 | 24% | 2.74 | 52 | 0.43 | 598 | N |
| GLP-095 (HiLoad) | 121 | DG15 (DG15(21x21)_0_ 75704_0g) | 2.5 | 16 | ISA-003 (1509) | 20 | | 521 | 926 | 396 | 529 | | | 77 | 0.64 | 607 | N |
| GLP-095 (HiPro + No Salt (20)) | 121 | DG15 (DG15(21x21)_0_ 75704_0g) | 2.5 | 16 | ISA-003 (1509) | 20 | 3.4 | 383 | 900 | 394 | 506 | 8% | 3.12 | 91 | 0.75 | 591 | N |
| GLP-095 (HiPro + No Salt (30)) | 121 | DG15 (DG15(21x21)_0_ 75704_0g) | 2.5 | 16 | ISA-003 (1509) | 30 | 5 | 451 | 928 | 388 | 540 | 21% | 3.95 | | | | |
| GLP-101 (HiPro-30) | 121 | DG15 ((21x21)_0_75704_0g) | 2.5 | 16 | ISA-003 (1509) | 30 | 5 | 473 | 917 | 494 | 423 | 62% | 1.90 | 70 | 0.58 | 486 | |
| GLP-101 (LoPro-30) | 121 | DG15 ((21x21)_0_75704_0g) | 2.5 | 16 | ISA-003 (1509) | 30 | 5 | 468 | 918 | 482 | 436 | 40% | 3.00 | 60 | 0.50 | 421 | |
| GLP-101 (NoPoly-30) | 121 | DG15 ((21x21)_0_75704_0g) | 2.5 | 16 | ISA-003 (1509) | 30 | 5.3 | 455 | 924 | 454 | 470 | 30% | 3.71 | 58 | 0.48 | 713 | |
| GLP-104 (HiProNoSalt) | 121 | DG15 ((21x21)_0_75704_0g) | 5.1 | 16 | ISA-003 (1509) | 20 | 3.4 | 389 | 895 | 457 | 438 | 26% | 2.52 | 112 | 0.92 | 665 | |
| GLP-104 (LoPro-w-Salt 20) | 121 | DG15 ((21x21)_0_75704_0g) | 5.1 | 16 | ISA-003 (1509) | 20 | 3.6 | 365 | 919 | 457 | 462 | 24% | 2.74 | 134 | 1.11 | 1042 | |

TABLE 21-continued

Longitudinal Deployment Data Summary

| Lot Number (Group) | Array Size | Applicator (Configuration) | Energy/ Needle [mJ] | Piston Velocity [m/s] | Backing (Adhesive) | Tip Fill Volume [nL] | Dose per Needle [nL] | Tip Length [um] | Pre-deployment needle height [um] | Air Gap [um] | Penetration Depth (Primary-Air Gap) [um] | Avg % PD-IVR By RP-HPLC | Dose delivered per needle [nL] | Instron - Force [N] | FF/ Needle [N] | Instron - YM [N/mm] | Cracks in base PD (Y/N) |
|---|---|---|---|---|---|---|---|---|---|---|---|---|---|---|---|---|---|
| GLP-104 (LoPro-w-Salt 30) | 121 | DG15 ((21x21)_0_75704_0g) | 3.4 | 16 | ISA-003 (1509) | 30 | 5.3 | 432 | 896 | 433 | 463 | 20% | 4.24 | 129 | 1.06 | 696 | |
| GLP-104 (LoPro-w-Salt 30-277) | 277 | | | | | 30 | | 432 | | | | | 0.00 | 348 | 1.26 | 1386 | |
| GLP-104 (NoPoly) | 121 | DG15 ((21x21)_0_75704_0g) | 3.4 | 16 | ISA-003 (1509) | 30 | | 509 | 904 | 437 | 467 | | 0.00 | 108 | 0.89 | 714 | |
| GLP-104 (GLP-114 HPNS-30) | 121 | | | | | | | | | | | | 0.00 | 137 | 1.14 | 721 | |
| GLP-104 (GLP-114 LPS-30) | 121 | | | | | | | | | | | | 0.00 | 115 | 0.95 | 649 | |
| GLP-105 (PPS-60-30-S) | 60 | DG15 ((21x21)_0_75704_0g) | 5.1 | 16 | ISA-003 (1509) | 30 | 5.3 | 403 | 871 | 340 | 531 | 30% | 3.71 | 50 | 0.84 | 485 | N |
| GLP-105 (PPS-60-30-B) | 60 | DG15 ((21x21)_0_75704_0g) | 5.1 | 16 | ISA-003 (1509) | 30 | | 401 | 865 | 393 | 472 | 27% | 0.00 | | | | N |
| GLP-105 (PPS-90-20-S) | 90 | DG15 ((21x21)_0_75704_0g) | 3.4 | 16 | ISA-003 (1509) | 20 | 3.8 | 349 | 887 | 448 | 439 | 19% | 3.08 | 91 | 1.01 | 560 | N |
| GLP-105 (PPS-90-20-B) | 90 | DG15 ((21x21)_0_75704_0g) | 3.4 | 16 | ISA-003 (1509) | 20 | | 380 | 833 | 391 | 442 | 22% | 0.00 | | | | N |
| GLP-105 (PPS-121-30) | 121 | | | | ISA-003 (1509) | 30 | | 442 | | | | | 0.00 | 98 | 0.81 | 529 | |
| GLP-105 (DPS-121-30) | 121 | DG15 ((21x21)_0_75704_0g) | 2.5 | 16 | ISA-003 (1509) | 30 | | 480 | 863 | 407 | 456 | | 0.00 | 92 | 0.76 | 416 | N |
| GLP-105 (DHP-121-30) | 121 | DG15 ((21x21)_0_75704_0g) | 2.5 | 16 | ISA-003 (1509) | 30 | | 434 | 936 | 436 | 500 | | 0.00 | | | | N |

TABLE 21-continued

Longitudinal Deployment Data Summary

| Lot Number (Group) | Array Size | Applicator (Configuration) | Energy/ Needle [mJ] | Piston Velocity [m/s] | Backing (Adhesive) | Tip Fill Volume [nL] | Dose per Needle [nL] | Tip Length [um] | Pre-deployment needle height [um] | Air Gap [um] | Penetration Depth (Primary Air Gap) [um] | Avg % PD-IVR By RP-HPLC | Dose delivered per needle [nL] | Instron - Force [N] | FF/ Needle [N] | Instron - YM [N/mm] | Cracks in base PD (Y/N) |
|---|---|---|---|---|---|---|---|---|---|---|---|---|---|---|---|---|---|
| GLP-105 (PPS-60-30-S) | 60 | Clinical (12 lbf/in) | 3.8 | 7 | ISA-003 (1509) | 30 | 5.3 | 403 | 898 | 382 | 516 | 40% | 3.18 | 50 | 0.84 | 485 | N |
| GLP-105 (PPS-60-30-B) | 60 | Clinical (12 lbf/in) | 3.8 | 7 | ISA-003 (1509) | 30 | | 401 | 858 | 476 | 382 | 55% | 0.00 | | | | N |
| GLP-105 (PPS-90-20-S) | 90 | Clinical (12 lbf/in) | 2.6 | 7 | ISA-003 (1509) | 20 | 3.8 | 349 | 909 | 440 | 469 | 35% | 2.47 | 91 | 1.01 | 560 | N |
| GLP-105 (PPS-90-20-B) | 90 | Clinical (12 lbf/in) | 2.6 | 7 | ISA-003 (1509) | 20 | | 380 | 868 | 451 | 417 | 39% | 0.00 | | | | N |
| GLP-108 (60) | 60 | | | | ISA-003 (1509) | 30 | | 465 | | | | | | 34 | 0.56 | 274 | |
| GLP-108 (121) | 121 | | | | ISA-003 (1509) | 30 | | 426 | | | | | | 63 | 0.52 | 542 | |
| GLP-108 (241) | 241 | | | | ISA-007 (1509) | 30 | | 407 | | | | | | 133 | 0.55 | 854 | |
| GLP-108 (277) | 277 | | | | ISA-007 (1509) | 30 | | 437 | | | | | | 118 | 0.42 | 645 | |
| GLP-109 (PPS-60-30) | 60 | Clinical (12 lbf/in) | 3.8 | 7 | ISA-003 (1509) | 30 | 5.4 | 466 | 924 | 370 | 554 | 28% | 3.90 | 51 | 0.85 | 321 | N |
| GLP-109 (PPS-90-20) | 90 | Clinical (12 lbf/in) | 2.6 | 7 | ISA-003 (1509) | 20 | 3.6 | 377 | 932 | 457 | 475 | 17% | 3.00 | 89 | 0.99 | 528 | N |
| GLP-109 (PHP-60-30) | 60 | Clinical (12 lbf/in) | 3.8 | 7 | ISA-003 (1509) | 30 | 5.1 | 440 | 914 | 319 | 595 | 23% | 3.93 | 50 | 0.83 | 301 | Y |
| GLP-109 (PHP-90-20) | 90 | Clinical (12 lbf/in) | 2.6 | 7 | ISA-003 (1509) | 20 | 3.6 | 383 | 919 | 445 | 474 | 17% | 2.99 | 79 | 0.88 | 477 | Y |
| GLP-113 (PPS-60-30) | 60 | Clinical (12 lbf/in) | 3.8 | 7 | ISA-003 (1509) | 30 | 5.2 | 411 | 892 | 352 | 540 | 19% | 4.21 | 32 | 0.54 | 343 | N |
| GLP-113 (PPS-90-20) | 90 | Clinical (12 lbf/in) | 2.6 | 7 | ISA-003 (1509) | 20 | 3.4 | 359 | 918 | 370 | 548 | 16% | 2.86 | 47 | 0.53 | 411 | N |

TABLE 21-continued

Longitudinal Deployment Data Summary

| Lot Number (Group) | Array Size | Applicator (Configuration) | Energy/ Needle [mJ] | Piston Velocity [m/s] | Backing (Adhesive) | Tip Fill Volume [nL] | Dose per Needle [nL] | Tip Length [um] | Pre-deployment needle height [um] | Air Gap [um] | Penetration Depth (Primary-Air Gap) [um] | Avg % PD-IVR By RP-HPLC | Dose delivered per needle [nL] | Instron - Force [N] | FF/ Needle [N] | Instron - YM [N/mm] | Cracks in base PD (Y/N) |
|---|---|---|---|---|---|---|---|---|---|---|---|---|---|---|---|---|---|
| GLP-113 (PHP-60-30) | 60 | Clinical (12 lbf/in) | 3.8 | 7 | ISA-003 (1509) | 30 | 5.1 | 433 | 904 | 317 | 587 | 28% | 3.67 | 32 | 0.54 | 279 | N |
| GLP-113 (PHP-90-20) | 90 | Clinical (12 lbf/in) | 2.6 | 7 | ISA-003 (1509) | 20 | 3.5 | 375 | 917 | 500 | 417 | 25% | 2.63 | 44 | 0.49 | 391 | N |
| GLP-115 (Control-121) | 121 | DG15 ((21x21)_0_75704_0g) | 2.5 | 16 | 1509 | 30 | 4.5 | 426 | 925 | 412 | 513 | 14% | 3.88 | 55 | 0.45 | 982 | N |
| GLP-115 (Control-277) | 277 | DG15 (ISA-11: (22x22)_0_BI-69_3g) | 2.49 | 16 | 1509 | 30 | 4.5 | 445 | 861 | 386 | 475 | 12% | 3.98 | 174 | 0.63 | 1131 | N |
| GLP-115 (No55-277) | 277 | DG15 (ISA-11: (22x22)_0_BI-69_3g) | 2.49 | 16 | 1509 | 30 | 4.5 | 419 | 902 | 444 | 458 | 16% | 3.78 | | | | N |
| GLP-115 (NoPB-277) | 277 | DG15 (ISA-11: (22x22)_0_BI-69_3g) | 2.49 | 16 | 1509 | 30 | 4.5 | 413 | 909 | 403 | 506 | 18% | 3.68 | | | | N |
| GLP-126 (Control-277) | 277 | DG15 (ISA-11: (22x22)_0_BI-69_3g) | 2.49 | 16 | 1509 | 30 | 5.8 | 461 | 916 | 393 | 523 | 15% | 4.93 | 214 | 0.77 | 1128 | N |
| GLP-126 (Gentle PB2-277) | 277 | DG15 (ISA-11: (22x22)_0_BI-69_3g) | 2.49 | 16 | 1509 | 30 | 5.8 | 457 | 906 | 348 | 558 | 9% | 5.28 | 179 | 0.65 | 1106 | N |
| GLP-126 (Long85-277) | 277 | DG15 (ISA-11: (22x22)_0_BI-69_3g) | 2.49 | 16 | 1509 | 30 | 5.8 | 441 | 913 | 410 | 503 | 22% | 4.52 | 155 | 0.56 | 1037 | N |
| GLP-126 (Int50-277) | 277 | DG15 (ISA-11: (22x22)_0_BI-69_3g) | 2.49 | 16 | 1509 | 30 | 5.8 | 460 | 914 | 415 | 499 | 26% | 4.29 | 155 | 0.56 | 1046 | N |
| GLP-126 (Control-60) | 277 | | | | | | | | | | | | 0.00 | 30 | 0.11 | 269 | |
| GLP-126 (Gentle-PB2-60) | 277 | | | | | | | | | | | | 0.00 | 179 | 0.65 | 1106 | |

TABLE 21-continued

Longitudinal Deployment Data Summary

| Lot Number (Group) | Array Size | Applicator (Configuration) | Energy/ Needle [mJ] | Piston Velocity [m/s] | Backing (Adhesive) | Tip Fill Volume [nL] | Dose per Needle [nL] | Tip Length [um] | Pre-deployment needle height [um] | Air Gap [um] | Penetration Depth (Primary-Air Gap) [um] | Avg % PD-IVR By RP-HPLC | Dose delivered per needle [nL] | Instron - Force [N] | FF/ Needle [N] | Instron - YM [N/mm] | Cracks in base PD (Y/N) |
|---|---|---|---|---|---|---|---|---|---|---|---|---|---|---|---|---|---|
| GLP-128 (Lot 1 - std PB) | 277 | DG15 (ISA-11: (22x22)_0_BI-69_3g) | 2.49 | 16 | ISA-007 (1509) | 30 | 6.1 | 451 | 826 | 376 | 450 | 15% | 5.18 | 135 | 0.49 | 911 | N |
| GLP-128 (Lot 1 - 61) | 61 | DG15 ((21x21)_0_75704_0g) | 5.0 | 16 | ISA-003 (1509) | 30 | 6.2 | 447 | 890 | 221 | 669 | 20% | 4.93 | 31 | 0.50 | 279 | Y |
| GLP-128 (Lot 2 - std PB) | 277 | DG15 (ISA-11: (22x22)_0_BI-69_3g) | 2.49 | 16 | ISA-007 (1509) | 30 | 6.1 | 417 | 903 | 436 | 467 | 26% | 4.54 | 148 | 0.53 | 969 | N |
| GLP-128 (Lot 2-No55-PB1) | 277 | DG15 (ISA-11: (22x22)_0_BI-69_3g) | 2.49 | 16 | ISA-007 (1509) | 30 | 6.1 | 434 | 911 | 352 | 559 | 17% | 5.05 | 148 | 0.54 | 1008 | N |
| GLP-128 (Lot3-No55-PB1) | 277 | DG15 (ISA-11: (22x22)_0_BI-69_3g) | 2.49 | 16 | ISA-007 (1509) | 30 | 6 | 441 | 891 | 427 | 464 | 32% | 4.08 | 168 | 0.61 | 985 | N |
| GLP-128 (Lot3-277) | 277 | DG15 (ISA-11: (22x22)_0_BI-69_3g) | 2.49 | 16 | ISA-007 (1509) | 30 | 6 | 439 | 900 | 391 | 509 | 19% | 4.85 | 123 | 0.44 | 907 | N |
| GLP-136 (T = 0) (PPS-61-20) | 61 | Clinical (12 lbf/in) | 3.8 | 7 | ISA-003 (1509) | 20 | 3.5 | 358 | 890 | 356 | 534 | 15% | 2.98 | 36 | 0.59 | 344 | N |
| GLP-136 (T = 0) (PHP-61-20) | 61 | Clinical (12 lbf/in) | 3.8 | 7 | ISA-003 (1509) | 20 | 3.4 | 392 | 907 | 399 | 508 | 18% | 2.79 | 37 | 0.61 | 318 | N |
| GLP-136 (T = 2 wk) (PPS-61-20) | 61 | Clinical (12 lbf/in) | 3.8 | 7 | ISA-003 (1509) | 20 | | 358 | 888 | 339 | | | 0.00 | | | | N |
| GLP-136 (T = 2 wk) (PHP-61-20) | 61 | Clinical (12 lbf/in) | 3.8 | 7 | ISA-003 (1509) | 20 | | 392 | 911 | 373 | | | 0.00 | | | | N |
| GLP-136 (PPS-277-30-IML) | 277 | DG15 (ISA-11: (22x22)_0_BI-69_3g) | 2.49 | 16 | ISA-007 (1509) | 30 | 5.2 | 450 | 828 | 356 | 472 | 24% | 3.95 | 253 | 0.91 | 1313 | N |

TABLE 21-continued

Longitudinal Deployment Data Summary

| Lot Number (Group) | Array Size | Applicator (Configuration) | Energy/ Needle [mJ] | Piston Velocity [m/s] | Backing (Adhesive) | Tip Fill Volume [nL] | Dose per Needle [nL] | Tip Length [um] | Pre-deployment needle height [um] | Air Gap [um] | Penetration Depth (Primary-Air Gap) [um] | Avg % PD-IVR By RP-HPLC | Dose delivered per needle [nL] | Instron - Force [N] | FF/ Needle [N] | Instron - YM [N/mm] | Cracks in base PD (Y/N) |
|---|---|---|---|---|---|---|---|---|---|---|---|---|---|---|---|---|---|
| GLP-136 (PPS-277-30-IMM) | 277 | DG15 (ISA-11: (22x22)_0_BI-69_3g) | 2.49 | 16 | ISA-007 (1509) | 30 | 5.2 | 431 | 887 | 477 | 410 | 26% | 3.85 | 158 | 0.57 | 1147 | N |
| GLP-140 (PPS-60-20 (SQ)) | 60 | Clinical (12 lbf/in) | 3.8 | 7 | ISA-003 (1509) | 20 | 3.2 | 360 | 902 | 408 | 494 | 21% | 2.53 | 39 | 0.64 | 319 | N |
| GLP-140 (PPS-61-20 (ROU, Aligned only)) | 61 | Clinical (12 lbf/in) | 3.8 | 7 | ISA-003 (1509) | 20 | 3.2 | 352 | 897 | 377 | 520 | 16% | 2.69 | 46 | 0.75 | 323 | N |
| GLP-140 (PPS-61-30 (ROU, Aligned only)) | 61 | Clinical (12 lbf/in) | 3.8 | 7 | ISA-003 (1509) | 30 | 4.9 | 438 | 909 | 398 | 511 | 26% | 3.61 | 42 | 0.68 | 334 | N |
| GLP-142 (277) (PPS-277-30) | 277 | | | | | | | | | | | | | 230 | 0.83 | 1267 | |
| GLP-142 (T=0) (PPS-61-20) | 61 | Clinical (12 lbf/in) | 3.8 | 7 | ISA-003 (1509) | 20 | 3.6 | 366 | 894 | 345 | 549 | 13% | 3.13 | 50 | 0.83 | 354 | N |
| GLP-142 (T=0) (PHP-61-20) | 61 | Clinical (12 lbf/in) | 3.8 | 7 | ISA-003 (1509) | 20 | 3.7 | 389 | 890 | 334 | 556 | 12% | 3.26 | 43 | 0.71 | 358 | N |
| GLP-142(T=2 wk) (PPS-61-20) | 61 | Clinical (12 lbf/in) | 3.8 | 7 | ISA-003 (1509) | 20 | | 366 | 895 | 349 | 546 | | 0.00 | 54 | 0.89 | 390 | |
| GLP-142(T=2 wk) (PHP-61-20) | 61 | Clinical (12 lbf/in) | 3.8 | 7 | ISA-003 (1509) | 20 | | 389 | 891 | 396 | 495 | | 0.00 | 54 | 0.89 | 358 | |

TABLE 21-continued

Longitudinal Deployment Data Summary

| Lot Number (Group) | Array Size | Applicator (Configuration) | Energy/ Needle [mJ] | Piston Velocity [m/s] | Backing (Adhesive) | Tip Fill Volume [nL] | Dose per Needle [nL] | Tip Length [um] | Pre-deployment needle height [um] | Air Gap [um] | Penetration Depth (Primary-Air Gap) [um] | Avg % PD-IVR By RP-HPLC | Dose delivered per needle [nL] | Instron - Force [N] | FF/ Needle [N] | Instron - YM [N/mm] | Cracks in base PD (Y/N) |
|---|---|---|---|---|---|---|---|---|---|---|---|---|---|---|---|---|---|
| GLP-143 (PPS-007) | 277 | | | | ISA-007 | | | 417 | | | | | 0.00 | 267 | 0.97 | 1294 | |
| GLP-143 (PPS-015) | 277 | | | | ISA-015 | | | 417 | | | | | 0.00 | 267 | 0.97 | 1294 | |
| GLP-143 (PHP-007) | 277 | | | | ISA-007 | | | 435 | | | | | 0.00 | 243 | 0.88 | 1271 | |
| GLP-122 (Thorax) | 277 | | | | | 30 | 5 | | | | | 10% | 4.49 | | | | |
| GLP-122 (Thorax) | 277 | | | | | 30 | 5 | | | | | 15% | 4.25 | | | | |
| GLP-122 (Thorax) | 277 | | | | | 30 | 5 | | | | | 10% | 4.50 | | | | |
| GLP-122 (Thorax) | 277 | | | | | 30 | 5 | | | | | 13% | 4.35 | | | | |
| GLP-122 (Back) | 277 | | | | | 30 | 5 | | | | | 28% | 3.58 | | | | |
| GLP-122 (Back) | 121 | Clinical (12 lbf/in) | 1.9 | 7 | | 30 | 5.1 | | | | | 23% | 3.92 | | | | |
| GLP-122 (Back) | 277 | | | | | 30 | 5 | | | | | 40% | 3.02 | | | | |
| GLP-146 (PPS) | 61 | Clinical | | | | 20 | 3.6 | | | | | | | | | | |
| GLP-146 (PPS) | 277 | DG16 | | | | 30 | 5.3 | | | | | | | | | | |
| GLP-146 (PHP) | 61 | Clinical | | | | 20 | 3.7 | | | | | | | | | | |

189                                                                        190

INCORPORATION BY REFERENCE

All publications, patents, and patent applications mentioned herein are hereby incorporated by reference in their entirety as if each individual publication, patent, or patent application was specifically and individually indicated to be incorporated by reference. In case of conflict, the present application, including any definitions herein, will control.

EQUIVALENTS

Those skilled in the art will recognize, or be able to ascertain using no more than routine experimentation, many equivalents to the specific embodiments of the invention described herein. Such equivalents are intended to be encompassed by the following claims.

8. The MAP of claim 1, wherein proline is present in the dispensable tip formulation at a concentration of about 3% (w/v).

9. The MAP of claim 1, wherein proline is present in the dispensable tip formulation at a concentration of about 0.75% (w/v).

10. The MAP of claim 1, wherein the dispensable tip formulation further comprises a water-soluble excipient selected from the group consisting of a surfactant, a salt, a polymer, a buffer, and combinations thereof.

11. The MAP of claim 10, wherein the surfactant is present in the dispensable tip formulation at a concentration of about 0.01% (w/v) to about 1% (w/v).

12. The MAP of claim 10, wherein the surfactant comprises a polyoxyl 35 castor oil surfactant, or a derivative thereof.

The invention claimed is:

1. A microarray patch (MAP), comprising a plurality of microneedles, wherein the microneedles comprise a consolidated microneedle tip formed from a dispensable tip formulation comprising:
(i) a glucagon-like peptide-1 (GLP-1) receptor agonist at a concentration of greater than about 100 mg/mL; and
(ii) proline,
wherein the microneedles are characterized by a primary needle height of about 700 μm to about 1,250 μm and a consolidated microneedle tip length of about 200 μm to about 500 μm,
wherein the GLP-1 receptor agonist is present in an amount of at least about 2 μg per consolidated microneedle tip, and
wherein the microneedles have a needle strength of at least about 0.3 N/needle.

2. The MAP of claim 1, wherein the GLP-1 receptor agonist is present in the dispensable tip formulation at a concentration of about 150 mg/mL to about 300 mg/mL.

3. The MAP of claim 1, wherein the GLP-1 receptor agonist is present in an amount of about 2 μg to about 20 μg per consolidated microneedle tip.

4. The MAP of claim 1, wherein the MAP comprises a total dose of about 0.01 mg to about 10 mg of the GLP-1 receptor agonist.

5. The MAP of claim 1, wherein the GLP-1 receptor agonist comprises semaglutide, a pharmaceutically acceptable salt thereof, or a derivative thereof.

6. The MAP of claim 5, wherein the MAP comprises a total dose of about 0.25 mg to about 2.4 mg of semaglutide, a pharmaceutically acceptable salt thereof, or a derivative thereof.

7. The MAP of claim 1, wherein proline is present in the dispensable tip formulation at a concentration of about 0.1% (w/v) to about 6% (w/v).

13. The MAP of claim 10, wherein the salt is present in the dispensable tip formulation at a concentration of about 0.5% (w/v) to about 5% (w/v).

14. The MAP of claim 10, wherein the salt is selected from the group consisting of a NaCl salt, a ZnCl$_2$ salt, a MgCl$_2$ salt, and combinations thereof.

15. The MAP of claim 10, wherein the salt comprises a NaCl salt.

16. The MAP of claim 10, wherein the polymer is present in the dispensable tip formulation at a concentration of about 0.5% (w/v) to about 6% (w/v).

17. The MAP of claim 10, wherein the polymer is selected from the group consisting of a povidone polymer, a polysaccharide polymer, and combinations thereof.

18. The MAP of claim 10, wherein the polymer is selected from the group consisting of a povidone K 17 (PVP K17) polymer, a dextran polymer, and combinations thereof.

19. The MAP of claim 10, wherein the buffer is present in the dispensable tip formulation at a concentration of about 5 mM to about 150 mM and is selected from the group consisting of a Tris-HCl buffer, a 3-(N-Morpholino) propanesulfonic acid (MOPS) buffer, and combinations thereof.

20. The MAP of claim 1, wherein the microneedles further comprise a microneedle base formed from a dispensable base formulation comprising at least one water-soluble excipient selected from the group consisting of a polymer, a surfactant, a buffer, and combinations thereof.

21. The MAP of claim 20, wherein the polymer is present in the dispensable base formulation at a concentration of about 30% (w/v) to about 90% (w/v).

22. The MAP of claim 20, wherein the surfactant is present in the dispensable base formulation at a concentration of about 0.1% (w/v) to about 3% (w/v).

23. The MAP of claim 20, wherein the water-soluble excipient is selected from the group consisting of polysorbate 20, polaxomer 188, Polyoxyl 35 Castor Oil, Polyoxyl 15 Hydrostearate, PVP K17, polyvinyl alcohol (PVA) 4-88, and combinations thereof.

24. The MAP of claim 1, wherein the microneedles have a consolidated microneedle tip length of greater than about 300 μm, and/or wherein no more than about 10% of the plurality of microneedles have a consolidated microneedle tip length of greater than about 400 μm.

25. The MAP of claim 1, wherein no more than about 20% of the plurality of microneedles comprises a manufacturing defect.

26. The MAP of claim 1, wherein the microneedles have a needle strength of at least about 0.4 N/needle and/or at least about 0.5 N/needle.

27. The MAP of claim 1, wherein the consolidated microneedle tip is characterized by a meniscus having contact angles of about 60 degrees to about 120 degrees.

28. The MAP of claim 1, which is configured for deployment onto the skin of a subject by using an applicator configured to apply impact energy to the plurality of microneedles to achieve deployment of at least about 70% of the consolidate microneedle tips in the MAP to a delivery depth of at least about 300 μm or at least about 400 μm below the surface of the subject's skin.

29. The MAP of claim 1, wherein the consolidated microneedle tip is characterized by a consolidated tip diameter of about 1 μm to about 15 μm.

30. The MAP of claim 1, wherein the dispensable tip formulation further comprises PVP K17 and Polyoxyl 35 Castor Oil.

* * * * *